United States Patent
Blake et al.

(10) Patent No.: US 9,133,187 B2
(45) Date of Patent: Sep. 15, 2015

(54) SERINE/THREONINE KINASE INHIBITORS

(75) Inventors: James F. Blake, Boulder, CO (US); Huifen Chen, South San Francisco, CA (US); Mark Joseph Chicarelli, Boulder, CO (US); Jason Demeese, Boulder, CO (US); Rustam Garrey, Boulder, CO (US); John J. Gaudino, Boulder, CO (US); Robert J. Kaus, Boulder, CO (US); Gabrielle R. Kolakowski, Boulder, CO (US); Allison L. Marlow, Boulder, CO (US); Peter J. Mohr, Boulder, CO (US); Li Ren, Boulder, CO (US); Jacob Schwarz, South San Francisco, CA (US); Christopher S. Siedem, Boulder, CO (US); Allen A. Thomas, Boulder, CO (US); Eli Wallace, Boulder, CO (US); Steven Mark Wenglowsky, Boulder, CO (US); Steven Boyd, Boulder, CO (US)

(73) Assignees: ARRAY BIOPHARMA INC., Boulder, CO (US); GENENTECH, INC., South San Francisco, CA (US)

( * ) Notice: Subject to any disclaimer, the term of this patent is extended or adjusted under 35 U.S.C. 154(b) by 0 days.

(21) Appl. No.: 14/002,079

(22) PCT Filed: Feb. 28, 2012

(86) PCT No.: PCT/US2012/027009
§ 371 (c)(1),
(2), (4) Date: Aug. 28, 2013

(87) PCT Pub. No.: WO2012/118850
PCT Pub. Date: Sep. 7, 2012

(65) Prior Publication Data
US 2013/0338140 A1   Dec. 19, 2013

Related U.S. Application Data

(60) Provisional application No. 61/447,587, filed on Feb. 28, 2011.

(51) Int. Cl.
| | | |
|---|---|---|
| *A01N 43/90* | (2006.01) | |
| *A61K 31/519* | (2006.01) | |
| *C07D 487/00* | (2006.01) | |
| *C07D 471/04* | (2006.01) | |
| *C07D 491/052* | (2006.01) | |
| *A61K 45/06* | (2006.01) | |

(52) U.S. Cl.
CPC ............ *C07D 471/04* (2013.01); *A61K 31/519* (2013.01); *A61K 45/06* (2013.01); *C07D 491/052* (2013.01)

(58) Field of Classification Search
None
See application file for complete search history.

(56) References Cited

U.S. PATENT DOCUMENTS

| | | | |
|---|---|---|---|
| 8,697,715 | B2 | 4/2014 | Blake et al. |
| 2009/0246198 | A1 | 10/2009 | Dong et al. |
| 2013/0252934 | A1 | 9/2013 | Blake et al. |
| 2014/0066453 | A1 | 3/2014 | Blake et al. |

FOREIGN PATENT DOCUMENTS

| | | |
|---|---|---|
| WO | WO 95/09847 A1 | 4/1995 |
| WO | WO 95/09851 A1 | 4/1995 |
| WO | WO 98/24780 A2 | 6/1998 |
| WO | WO 01/42241 A1 | 6/2001 |
| WO | WO 01/62233 A2 | 8/2001 |
| WO | WO 02/087513 A2 | 11/2002 |
| WO | WO 03/030909 A1 | 4/2003 |
| WO | WO 03/099808 A1 | 12/2003 |
| WO | WO 2004/007468 A1 | 1/2004 |
| WO | WO 2005/066139 A2 | 7/2005 |
| WO | WO 2005/099711 A1 | 10/2005 |
| WO | WO 2005/123680 A1 | 12/2005 |
| WO | WO 2006/021458 A2 | 3/2006 |
| WO | WO 2006/030032 A1 | 3/2006 |
| WO | WO 2006/070208 A1 | 7/2006 |
| WO | WO 2006/113704 A2 | 10/2006 |

(Continued)

OTHER PUBLICATIONS

Ashton et al., "Design and synthesis of novel amide AKT1 inhibitors with selectivity over CDK2", *Bioorganic & Medicinal Chemistry Letters*, vol. 21 (18), 5191-5196 (2011).
McIntyre et al., "Pyridazine Based Inhibitors of p38 MAPK", *Bioorganic & Medicinal Chemistry Letters 12*, 689-692 (2002).
Stanetty et al., "Novel and Efficient Access to Phenylaminopyrimidine Type Protein Kinase C Inhibitors Utilizing a Negishi Cross-Coupling Strategy", *Journal of Organic Chemistry 70*, 5215-5220 (2005).
Traynor et al., *Drugs of Today*, 40(8), 697-710, 698 (2004).
Burkhard et al., "Development of Extracellular Signal-Regulated Kinase Inhibitors", *Curr Top Med Chem* 9(8), 678-689 (2009).
Kohno et al., "Pharmacological inhibitors of the ERK signaling pathway: application as anticancer drugs", *Prog Cell Cycle Res.*, 5, 219-224 (2003).

(Continued)

*Primary Examiner* — Jeffrey H Murray
(74) *Attorney, Agent, or Firm* — Viksnins Harris & Padys PLLP

(57) ABSTRACT

Compounds having the formula I wherein Z, $Z^1$ $Z^2$ $Z^3$, $R^{3a}$, $R^{3b}$ and $R^b$ and as defined herein are inhibitors of ERK kinase. Also disclosed are compositions and methods for treating hyperproliferative disorders.

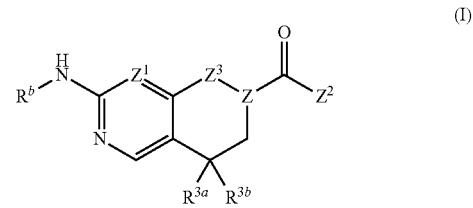

20 Claims, No Drawings

(56) References Cited

FOREIGN PATENT DOCUMENTS

| WO | WO 2007/071348 A1 | 6/2007 |
|---|---|---|
| WO | WO 2007/097937 A1 | 8/2007 |
| WO | WO 2007/125405 A2 | 11/2007 |
| WO | WO 2008/023239 A1 | 2/2008 |
| WO | WO 2008/039882 A1 | 4/2008 |
| WO | WO 2008/079933 A1 | 7/2008 |
| WO | WO 2008/014889 A1 | 12/2008 |
| WO | WO 2009/032861 A1 | 3/2009 |
| WO | WO 2009/061761 A2 | 5/2009 |
| WO | WO 2009/156484 A2 | 12/2009 |
| WO | WO 2009/158571 A1 | 12/2009 |
| WO | WO 2010/077275 A1 | 7/2010 |
| WO | WO 2012/118850 A1 | 9/2012 |
| WO | WO 2013/020062 A1 | 2/2013 |

OTHER PUBLICATIONS

Ma et al., "The ERK/MAPK pathway, as a target for the treatment of neuropathic pain", *Expert Opin Ther Targets*, 9(4), 699-713 (2005).

Patent Cooperation Treaty, International Searching Authority, Search Report and Written Opinion for PCT/US2012/027009, 9 pages, May 7, 2012.

Sommer et al., "Resolvins and inflammatory pain", *F1000 Medicine Reports*, 3:19, 6 pages (2011).

Yap et al., "Small Molecule Inhibitors of the ERK Signalling Pathway: Towards Novel Anti-cancer Therapeutics", *ChemMedChem*, 6(1), 38-48 (2011).

SERINE/THREONINE KINASE INHIBITORS

CROSS-REFERENCE TO PRIOR APPLICATIONS

This application is a 371 National Stage Application of International Application Number PCT/US2012/027009, filed Feb. 28, 2012, which claims priority to U.S. Provisional Application No. 61/447,587 that was filed on Feb. 28, 2011.

FIELD ON THE INVENTION

The present invention relates to compounds which inhibit kinases and which are useful for treating hyperproliferative and neoplastic diseases by inhibiting signal transduction pathways which commonly are overactive or overexpressed in cancerous tissue. The present compounds are selective inhibitors of ERK. The present invention further relates to methods for treating cancer or hyperproliferative diseases with compounds within the scope of the present invention

BACKGROUND OF THE INVENTION

The processes involved in tumor growth, progression, and metastasis are mediated by signaling pathways that are activated in cancer cells. The ERK pathway plays a central role in regulating mammalian cell growth by relaying extracellular signals from ligand-bound cell surface receptor tyrosine kinase (RTK's) such as erbB family, PDGF, FGF, and VEGF receptor tyrosine kinase. Activation of an RTK induces a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signaling pathway is an attractive pathway for anticancer therapies in a broad spectrum of human tumors. (M. Hohno and J. Pouyssegur, *Prog. in Cell Cycle Res.* 2003 5:219)

The ERK pathway has also been cited as a promising therapeutic target for the treatment of pain and inflammation (Ma, Weiya and Remi Quirion. "The ERK/MAPK pathway, as a target for the treatment of neuropathic pain" *Expert Opin. Ther. Targets.* 2005 9(4):699-713, and Sommer, Claudia and Frank Birklein. "Resolvins and inflammatory pain" F1000 *Medicine Reports* 20113:19).

Therefore, small-molecular inhibitors of ERK activity (i.e., ERK1 and ERK2 activity) would be useful for treating a broad spectrum of cancers, such as, for example, melanoma, pancreatic cancer, thyroid cancer, colorectal cancer, lung cancer, breast cancer, and ovarian cancer, as well as a treatment for pain and inflammation, such as arthritis, low back pain, inflammatory bowel disease, and rheumatism. Such a contribution is provided by this invention.

SUMMARY OF THE INVENTION

There is a continuing need for new and novel therapeutic agents which can be used for cancer and hyperproliferative conditions. The Raf/MEK/ERK pathway is an important signaling pathway which is frequently overexpressed and/or overactive in many cancerous tissues. Design and development of new pharmaceutical compounds is essential. In one aspect of the present invention there is provided a compound according to formula I wherein:

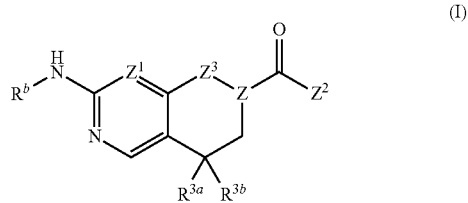
(I)

$Z$ is N and $Z^3$ is $CH_2$ or C=O; or, Z is $CR^g$ and $Z^3$ is O; $Z^1$ is independently CH or N;

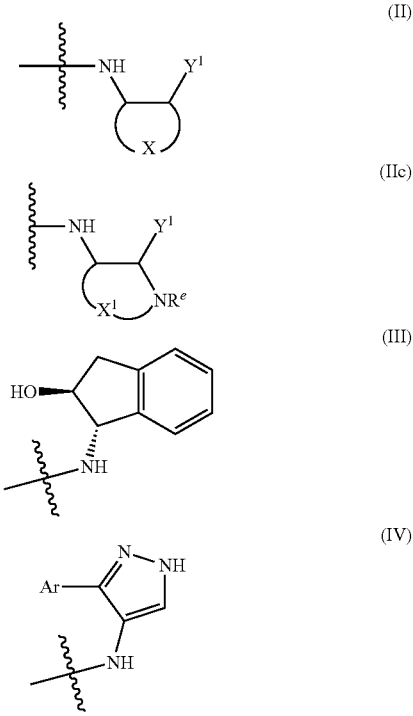

$Z^2$ is (a) $NR^aCR^1R^2Y$; (b) formula II wherein X is O, $(CH_2)_{1-3}$ or $CH_2NR^eCH_2$; (c) $CH_2CR^1R^2Y$; (d) formula III; (e) $CH_2CH(NR^fR^i)Ar$; (f) $CH_2NR^jAr$ wherein $R^j$ is $C_{1-6}$ alkyl or $C_{1-6}$ hydroxyalkyl and Ar is optionally substituted phenyl; (g) formula IV; (h) $CH_2NR^hR^i$ or (i) formula IIc wherein $X^1$ is $(CH_2)_{2-3}$;

$R^e$ is hydrogen, $C_{1-3}$ alkyl, $C_{1-3}$ hydroxyalkyl, $C_{1-3}$ alkoxy-$C_{1-3}$ alkyl, $C_{1-3}$ haloalkyl, $C_{1-3}$ acyl, benzyl, $C_{1-3}$ cyanoalkyl or $C_{1-3}$ alkylsulfonyl;

Y is $C_{3-6}$ cycloalkyl, aryl, $C_{1-3}$ aralkyl, phenoxymethyl, or heteroaryl wherein said heteroaryl is selected from the group consisting of benzoxazolyl, benzothiazolyl, benzimidazolyl, indolyl, N—$C_{1-3}$ alkyl-indolyl, pyrimidinyl, pyridinyl, oxazolyl and thiazolyl;

$Y^1$ is —Ar, —OAr, —S(O)$_{0-2}$Ar or —NR$^g$Ar wherein Ar is optionally substituted phenyl;

$R^1$ and $R^2$ are independently selected from the group consisting of (a) hydrogen, (b) $C_{1-10}$-alkyl, (c) $C_{1-6}$ haloalkyl, (d) $C_{3-7}$ cycloalkyl, (e) $C_{1-10}$ heteroalkyl optionally further substituted by aryl or benzyl, (f) (CH$_2$)$_{1-3}$OC(=O)R$^f$ wherein R$^f$ is $C_{1-6}$ alkyl, $C_{1-6}$ heteroalkyl or $C_{1-3}$ alkoxy-$C_{1-3}$ alkyl, (g) (CH$_2$)$_{1-3}$NR$^c$R$^d$ wherein R$^c$ and R$^d$ are independently hydrogen, $C_{1-6}$ alkyl, C(=O)R$^g$, S(=O)$_2$C$_{1-3}$ alkyl, $C_{2-4}$ hydroxyalkyl, $C_{1-3}$ alkoxy-$C_{1-3}$ alkyl, $C_{3-7}$ cycloalkyl-$C_{1-3}$ alkyl, pyridinyl, or pyrimidinyl, (h) cyano-$C_{1-3}$ alkyl, (i) $C_{1-3}$ alkylsulfonyl-$C_{1-3}$ alkyl, (j) carbamoyl, (k) N—$C_{1-3}$ alkyl-carbamoyl, (l) N,N—$C_{1-3}$ alkylcarbamoyl, (m) optionally substituted heteroaryl or heteroaryl-$C_{1-3}$ alkyl wherein said heteroaryl is selected from the group consisting of pyridinyl, 2-oxo-1,2-dihydropyridinyl, 6-oxo-1,6-dihydropyridinyl, pyrimidinyl, pyrazinyl, pyridazinyl, pyrazolyl, N—$C_{1-3}$ alkyl-pyrazolyl, imidazolyl, oxazolyl, isoxazolyl, thiazolyl, isothiazolyl, oxadiazolyl, indolyl, benzoxazolyl, benzothiazolyl, triazolyl, N—$C_{1-3}$ alkyl-triazolyl, and triazinyl, (n) heterocyclyl or heterocyclyl-$C_{1-3}$ alkyl wherein said heterocyclyl is selected from the group consisting of pyrrolidinyl, N—$C_{1-3}$ alkyl-pyrrolidinyl, N—$C_{1-3}$ acyl-pyrrolidinyl, azetidinyl, N—$C_{1-3}$ alkyl-azetidinyl, morpholinyl, piperidinyl and N—$C_{1-3}$ alkyl-piperidinyl wherein said heterocyclyl is optionally substituted by 1 to 3 groups independently selected from $C_{1-6}$ alkyl, halogen, hydroxyl, phenyl and oxo; $R^1$ and $R^2$ together with the carbon to which they are attached form a cyclic amine optionally substituted by 1 to 3 $C_{1-6}$ alkyl groups; or $R^1$ and $R^a$ together with the atoms to which they are attached form a cyclic amine optionally substituted by 1 to 3 groups independently selected from $C_{1-6}$ alkyl, halogen, hydroxyl, phenyl, benzyl or oxo, and (o) (2-methoxyethoxy)methyl;

$R^{3a}$ and $R^{3b}$ are independently hydrogen, halogen or hydroxyl;

$R^a$ is (a) hydrogen or $C_{1-3}$ alkyl or (b) $R^1$ and $R^a$ together with the atoms to which they are attached form a cyclic amine optionally substituted by 1 to 3 groups independently selected from the group consisting of $C_{1-6}$ alkyl, halogen, hydroxyl, phenyl, benzyl and oxo;

$R^b$ is selected from the group consisting of (a) hydrogen, (b) $C_{1-10}$ alkyl, (c) $C_{1-6}$ haloalkyl, (d) optionally substituted aryl or aryl-$C_{1-6}$ alkyl, (e) optionally substituted heteroaryl or heteroaryl-$C_{1-6}$ alkyl wherein said heteroaryl is selected from the group consisting of isoxazole, pyridinyl, pyridone, N—$C_{1-3}$ alkyl-pyridone, pyrimidinyl, pyrazinyl, pyrazole, N—$C_{1-6}$ alkyl-pyrazolyl, N-benzylpyrazolyl, thiazolyl, N—$C_{1-6}$ alkyl triazolyl and 2-oxo-tetrahydroquinolin-6-yl, (f) heterocyclyl or heterocyclyl-$C_{1-6}$ alkyl wherein said heterocyclyl is selected from the group consisting of tetrahydropyranyl, tetrahydrofuranyl, oxetanyl, piperidinyl, pyrrolidinyl, morpholinyl, N—$C_{1-6}$ alkyl piperidinyl and N—$C_{1-6}$ alkyl-2-oxo-pyrrolidinyl, (g) $C_{3-7}$ cycloalkyl or $C_{3-7}$ cycloalkyl-$C_{1-6}$ alkyl wherein said cycloalkyl is optionally substituted by hydroxyl or halo, (h) $C_{1-6}$ heteroalkyl, (i) $C_{1-6}$ acyl and (j) $C_{1-6}$ hydroxyalkyl;

each R$^g$ is independently hydrogen or $C_{1-3}$ alkyl;

each R$^h$ and R$^i$ together with the nitrogen atom to which they are attached form a pyrrolidinyl, piperidinyl, piperazinyl, N-methyl-piperazinyl or morpholinyl ring each optionally substituted with phenyl ring which phenyl ring is optionally substituted with halogen or $C_{1-3}$ haloalkyl;

each said aryl and each said heteroaryl is optionally substituted by 1 to 5 groups independently selected from $C_{1-6}$ alkyl, $C_{1-6}$ haloalkyl, $C_{1-6}$ alkoxy, $C_{3-6}$ cycloalkyl, halogen, hydroxyl, $C_{1-6}$ haloalkoxy, $C_{1-16}$ alkylthio, $C_{1-6}$ haloalkylthio, $C_{1-6}$ acylamino, cyano, nitro, optionally substituted aryloxy or $C_{1-3}$ cyanoalkyl;

each said heterocyclyl is optionally substituted with $C_{1-6}$ alkyl, $C_{1-6}$ haloalkyl, $C_{1-3}$ hydroxyalkyl or halogen;

each said cycloalkyl is optionally substituted by one to four groups independently selected from $C_{1-6}$ alkyl, $C_{1-6}$ alkoxy, halogen, cyano or oxo; and each said heteroalkyl is optionally substituted by phenyl, benzyl or $C_{1-3}$ haloalkyl.

The present invention further relates to tautomers, stereoisomers and pharmaceutically acceptable salts of compounds as described above.

The present invention also relates to a method for treating a hyperproliferative disorder by administering a therapeutically effective quantity of a compound according to formula I to a patient in need thereof. The compound can be administered alone or co-administered with other anti-hyperproliferative or chemotherapeutic compounds.

The present invention also relates to a method for inhibiting ERK protein kinase activity in a cell comprising treating a cell with a compound according to formula I in an amount effective to attenuate or eliminate ERK kinase activity.

The present invention also relates to a pharmaceutical composition comprising a compound according to formula I and at least one pharmaceutically acceptable carrier, diluent or excipient.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

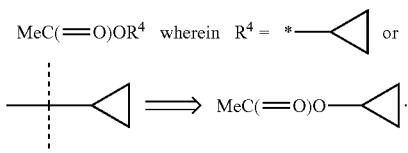

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings. The present invention encompasses all tautomeric forms of the compounds described herein.

It will be appreciated by the skilled artisan that some of the compounds of formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the skilled artisan that substitution of the tropane ring can be in either endo- or exo-configuration, and the present invention covers both configurations. The present invention includes all the individual stereoisomers (e.g., enantiomers), racemic mixtures or partially resolved mixtures of the compounds of formula I and, where appropriate, the individual tautomeric forms thereof.

The compounds of formula I may contain a basic center and suitable acid addition salts are formed from acids which form non-toxic salts. Examples of salts of inorganic acids include the hydrochloride, hydrobromide, hydroiodide, chloride, bromide, iodide, sulfate, bisulfate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.*, 1977 66:1-19 and G. S. Paulekuhn et al. *J. Med. Chem.* 2007 50:6665.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10th Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatises such as *Fieser and Fieser's Reagents for Organic Synthesis*; Wiley & Sons: New York, Volumes 1-21; R. C. LaRock, *Comprehensive Organic Transformations,* 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40 and will be familiar to those skilled in the art.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl and phenylethyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar) alkyl refers to either an unsubstituted alkyl or an aralkyl group. The term (hetero)aryl or (het)aryl refers to a moiety that is either an aryl or a heteroaryl group.

The term "alkyl" as used herein alone or in combination with other groups, denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-6}$ alkyl" as used herein refers to an alkyl composed of 1 to 6 carbons. Examples of alkyl groups include, but are not limited to methyl, ethyl, propyl, i-propyl, n-butyl, i-butyl, t-butyl, neopentyl, hexyl, and octyl.

The term "haloalkyl" as used herein denotes an unbranched or branched chain alkyl group as defined above, wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 2-fluoroethyl, 2-chloroethyl, 2-bromoethyl, 2,2-dichloroethyl, 3-bromopropyl or 2,2,2-trifluoroethyl.

The term "$C_{1-6}$ fluoroalkyl" as used herein denotes an unbranched or branched chain alkyl group as defined above, wherein 1, 2, 3 or more hydrogen atoms are substituted by a fluorine.

The term "haloalkoxy" as used herein refers to a group —OR, where R is haloalkyl as defined herein. The term "haloalkylthio" as used herein refers to a group —SR where R is haloalkyl as defined herein.

The term "halogen" or "halo" as used herein means fluorine, chlorine, bromine, or iodine.

The terms "hydroxyalkyl" and "alkoxyalkyl" as used herein denotes alkyl radical as herein defined, wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy is the oxygen atom.

The term "alkylthio" or "alkylsulfanyl" means an —S-alkyl group, wherein alkyl is as herein defined, such as methylthio, ethylthio, n-propylthio, i-propylthio, n-butylthio, hexylthio, including their isomers. "Lower alkylthio" as used herein denotes an alkylthio group with a "lower alkyl" group as previously defined. "$C_{1-10}$ alkylthio" as used herein refers to an —S-alkyl, wherein alkyl is $C_{1-10}$. "Arylthio" means an —S-aryl group, wherein aryl is as defined herein. "Phenylthio" is an "arylthio" moiety, wherein aryl is phenyl.

The terms "alkylsulfonyl" and "arylsulfonyl" as used herein denotes a group of formula —S(=O)$_2$R wherein R is alkyl or aryl respectively, and alkyl and aryl are as defined herein. The term $C_{1-3}$ alkylsulfonylamido as used herein refers to a group RSO$_2$NH—, wherein R is a $C_{1-3}$ alkyl group as defined herein.

The term "alkylsulfonylalkyl" as used herein denotes the radical R'R"—, wherein R' is an alkylsulfonyl moiety as defined herein, and R" is an alkylene radical as defined herein with the understanding that the attachment point of the arylalkyl moiety will be on the alkylene radical.

The term "heteroalkyl" as used herein means an alkyl radical as defined herein wherein one or two hydrogen atoms have been replaced with a substituent independently selected from the group consisting of —OR$^a$ and —NR$^b$R$^c$, with the understanding that the point of attachment of the heteroalkyl radical is through a carbon atom. R$^a$ is hydrogen or alkyl and R$^b$ and R$^c$ are independently of each other hydrogen, acyl, alkyl, or R$^b$ and R$^c$ together with the nitrogen to which they are attached form a cyclic amine. Hydroxyalkyl, alkoxyalkyl, aminoalkyl, alkylaminoalkyl and dialkylaminoalkyl moieties are subgenera encompassed by the term "heteroalkyl". Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-methylaminopropyl, and the like.

The term "cyclic amine" denotes a saturated carbon ring, containing from 3 to 6 carbon atoms, wherein at least one of the carbon atoms is replaced by a heteroatom selected from the group consisting of N, O and S, for example, piperidine, piperazine, morpholine, thiomorpholine, di-oxo-thiomorpholine, pyrrolidine, pyrazoline, imidazolidine and azetidine, wherein the cyclic carbon atoms are optionally substituted by one or more substituents, selected from the group consisting of halogen, hydroxy, phenyl, lower alkyl, lower alkoxy or 2-hydrogen atoms on a carbon are both replaced by oxo (=O). When the cyclic amine is a piperazine, one nitrogen atom can be optionally substituted by $C_{1-6}$ alkyl, $C_{1-6}$ acyl, or $C_{1-6}$ alkylsulfonyl.

The term "cycloalkyl" as used herein denotes a saturated carbocyclic ring containing 3 to 8 carbon atoms, i.e., cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "cycloalkylalkyl" as used herein refers to the radical R'R"—, wherein R' is a cycloalkyl radical as defined herein, and R" is an alkylene radical as defined herein, with the understanding that the attachment point of the cycloalkylalkyl moiety will be on the alkylene radical. Examples of cycloalkylalkyl radicals include, but are not limited to, cyclopropylmethyl, cyclohexylmethyl, or cyclopentylethyl. $C_{3-7}$ cycloalkyl-$C_{1-3}$ alkyl refers to the radical R'R" where R' is $C_{3-7}$ cycloalkyl and R" is $C_{1-3}$ alkylene as defined herein.

The term "aryl" as used herein denotes a monovalent aromatic carbocyclic radical containing 6 to 10 carbon atoms consisting of one individual ring, or one or more fused rings in which at least one ring is aromatic in nature. An aryl group can optionally be substituted with one or more, preferably one to three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, dialkylaminoalkyl, alkylsulfonyl, arylsulfinyl, alkylaminosulfonyl, arylaminosulfonyl, alkylsulfonylamido, arylsulfonylamido, carbamoyl, alkylcarbamoyl, dialkylcarbamoyl, arylcarbamoyl, alkylcarbonylamino and arylcarbonylamino, unless otherwise indicated. Alternatively two adjacent atoms of the aryl ring may be substituted with a methylenedioxy or ethylenedioxy group. Examples of aryl radicals include, but are not limited to, phenyl, naphthyl, indanyl, anthraquinolyl, tetrahydronaphthyl, 3,4-methylenedioxyphenyl, 1,2,3,4-tetrahydroquinolin-7-yl, 1,2,3,4-tetrahydroisoquinoline-7-yl, and the like. The point of attachment of bicyclic aryl substituents is on the carbocyclic aromatic ring.

The term "arylalkyl" or "aralkyl" as used herein denotes the radical R'R"—, wherein R' is an aryl radical as defined herein, and R" is an alkylene radical as defined herein, with the understanding that the attachment point of the arylalkyl moiety will be on the alkylene radical. "Optionally substituted aryl-$C_{1-3}$ alkyl" refers to a compound where the alkylene chain is 1 to 3 carbons and the aryl is optionally substituted. The term "benzyl" as used herein refers to a $C_6H_5CH_2$ radical.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. $C_{0-4}$ alkylene refers to a linear or branched saturated divalent hydrocarbon radical comprising 1-4 carbon atoms or, in the case of $C_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene and 2-ethylbutylene.

The terms "amino", "alkylamino" and "dialkylamino" as used herein refer to —NH$_2$, —NHR and —NR$_2$ respectively, and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to $NH_2(alkylene)_n$-, $RHN(alkylene)_n$-, and $R_2N(alkylene)_n$- respectively wherein R is alkyl, and both alkylene and alkyl are as defined herein and n is the number of carbon atoms in the alkylene chain. "$C_{1-10}$ alkylamino" as used herein refers to an alkylamino moiety, wherein alkyl is $C_{1-10}$. "$C_{1-10}$ alkyl-amino-$C_{2-6}$ alkyl" as used herein refers to a $C_{1-10}$ alkylamino(alkylene)$_{2-6}$ wherein alkyl is $C_{1-10}$ and the alkylene is $(CH_2)_{2-6}$. When the alkylene group contains three or more carbon atoms, the alkylene can be linear, e.g., —(CH$_2$)$_4$— or branched, e.g., —(CMe$_2$CH$_2$)—. The term "phenylamino" as used herein refers to —NHPh wherein Ph represents an optionally substituted phenyl group.

The term "acyl" or "alkanoyl" as used herein denotes a group of formula —C(=O)R wherein R is hydrogen or lower alkyl as defined herein. The term "alkylcarbonyl" as used herein denotes a group of formula C(=O)R, wherein R is alkyl as defined herein. The term $C_{1-6}$ acyl or "alkanoyl" refers to a group —C(=O)R containing 1 to 6 carbon atoms. The $C_1$ acyl or "alkanoyl" group is the formyl group wherein R=H and a $C_6$ acyl group refers to hexanoyl when the alkyl chain is unbranched. The term "arylcarbonyl" or "aroyl" as used herein means a group of formula C(=O)R wherein R is an aryl group; the term "benzoyl" as used herein is an "arylcarbonyl" or "aroyl" group wherein R is phenyl.

The term "acylamino" as used herein denotes a group of formula —NHC(=O)R, wherein R is hydrogen or lower alkyl as defined herein. $C_{1-6}$ acyl-amino refers to an acylamino group, wherein the C(=O)R moiety contains 1 to 6 carbon atoms.

The term cyano-$C_{1-3}$ alkyl refers to a $C_{1-3}$ alkyl moiety in which a hydrogen atom is replaced by cyano.

The term "carbamoyl" as used herein means the radical —CONH$_2$. The prefix "N-alkylcarbamoyl" and "N,N-dialkylcarbamoyl" means a the radical CONHR' or CONR'R", respectively, wherein the R' and R" groups are independently alkyl as defined herein. The prefix N-arylcarbamoyl" denotes the radical CONHR', wherein R' is an aryl radical as defined herein.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, unless specifically limited, pyridinyl, pyrimidinyl, pyrazinyl, pyrrolyl, pyrazolyl, imidazolyl, oxazolyl, isoxazolyl, thiazolyl, isothiazolyl, triazolinyl, thiadiazolyl and oxadiaxolinyl, which can optionally be substituted with one or more, preferably one or two substituents selected from hydroxy, cyano, $C_{1-6}$ alkyl, aryl, $C_{1-3}$ aralkyl, $C_{1-6}$ alkoxy, thio, lower haloalkoxy, $C_{1-6}$ alkylthio, halo, $C_{1-6}$ haloalkyl, $C_{1-6}$ alkylsulfinyl, $C_{1-6}$ alkylsulfonyl, halogen, amino, $C_{1-6}$ alkylamino, $C_{1-6}$ dialkylamino, amino-$C_{1-3}$ alkyl, $C_{1-3}$ alkylaminoalkyl, $C_{1-3}$ dialkylamino-$C_{1-3}$ alkyl, nitro, $C_{1-6}$ alkoxycarbonyl, carbamoyl, $C_{1-3}$ alkylcarbamoyl, $C_{1-3}$ dialkylcarbamoyl, arylcarbamoyl, $C_{1-6}$ alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring.

The term "heteroarylalkyl" or "heteroaralkyl" means the radical of the formula R'R"—, wherein R' is an optionally substituted heteroaryl radical as defined herein, and R" is an alkylene radical as defined herein, with the understanding that the attachment point of the heteroaryl radical will be on the alkylene radical. Examples of heteroarylalky radicals include, but are not limited to, 2-imidazolylmethyl, 3-pyrrolylethyl, 4-pyridinylmethyl and 5-pyrimidinylmethyl.

The term "heterocyclyl" or "heterocycle" as used herein denotes a monovalent saturated cyclic radical, consisting of one or more rings, preferably one to two rings, of three to eight atoms per ring, incorporating one or more ring heteroatoms (chosen from N, O or S(=O)$_{0-2}$) with the remaining ring atoms being carbon. The heterocyclyl moiety can optionally be independently substituted with one or more, preferably one or two substituents selected from hydroxy, oxo, cyano, lower alkyl, lower alkoxy, lower haloalkoxy, $C_{1-6}$ alkylthio, halo, $C_{1-6}$ haloalkyl, $C_{1-6}$ hydroxyalkyl, nitro, $C_{1-6}$ alkoxycarbonyl, $C_{1-6}$ acyl, amino, $C_{1-6}$ alkylamino, $C_{1-6}$ alkylsulfonyl, arylsulfonyl, $C_{1-6}$ alkylaminosulfonyl, arylaminosulfonyl, $C_{1-6}$ alkylsulfonylamido, arylsulfonylamido, $C_{1-6}$ alkylaminocarbonyl, arylaminocarbonyl, $C_{1-6}$ alkylcarbonylamino, or arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl unless specifically limited.

The term "heterocycloalkyl" (or "heterocyclylalkyl") denotes the radical of the formula R'R"—, wherein R' is a heterocyclic radical as defined herein, and R" is an alkylene radical as defined herein, and the attachment point of the heterocycloalkyl radical will be on the alkylene radical. Examples of heterocycloalkyl radicals include, but are not limited to, 1-piperazinylmethyl, or 2-morpholinomethyl.

The term "oxo" as used herein refers to "=O" (i.e., a doubly bonded oxygen affording a carbonyl group when attached to a carbon atom) wherein it is further understood that this is equivalent to two hydroxyl groups attached to the same carbon are equivalent The terms "treat" and "treatment" refer to therapeutic treatment wherein the object is to slow down (lessen) an undesired physiological change or disorder, such as the spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®, Novartis), fmasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; (ix) anti-angiogenic agents such as bevacizumab (AVASTIN®), Genentech); and (x) pharmaceutically acceptable salts, acids and derivatives of any of the above.

In one embodiment of the present invention there is provided a compound according to formula I wherein Z is N and $Z^3$ is CH or C=O; or, Z is $CR^g$ and $Z^3$ is O; $Z^1$ is

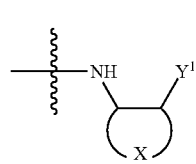

(II)

independently CH or N; $Z^2$ is (a) $NR^aCR^1R^2Y$; (b) formula II wherein X is $(CH_2)_{1-3}$ or $CH_2NR^eCH_2$; or (c) $CH_2CR^1R^2Y$; $R^e$ is hydrogen, $C_{1-3}$ alkyl, $C_{1-3}$ hydroxyalkyl, $C_{1-3}$ haloalkyl, $C_{1-3}$ acyl or $C_{1-3}$ alkylsulfonyl; Y is $C_{3-6}$ cycloalkyl, aryl, $C_{1-3}$ aralkyl or heteroaryl wherein said heteroaryl is selected from the group consisting of benzoxazolyl, benzothiazolyl, benzimidazolyl, indolyl, N—$C_{1-3}$ alkyl-indolyl, pyrimidinyl, pyridinyl, oxazolyl and thiazolyl; $Y^1$ is —Ar, —OAr, —S(O)$_{0-2}$Ar or —NR$^g$Ar wherein Ar is optionally substituted phenyl; $R^1$ and $R^2$ are independently selected from the group consisting of (a) hydrogen, (b) $C_{1-10}$ alkyl, (c) $C_{1-6}$ haloalkyl, (d) $C_{3-7}$ cycloalkyl, (e) $C_{1-10}$ heteroalkyl optionally further substituted by aryl or benzyl, (f) $(CH_2)_{1-3}OC(=O)R^f$ wherein $R^f$ is $C_{1-6}$ alkyl, $C_{1-6}$ heteroalkyl or $C_{1-3}$ alkoxy-$C_{1-3}$ alkyl, (g) $(CH_2)_{1-3}NR^cR^d$ wherein $R^c$ and $R^d$ are independently hydrogen, $C_{1-6}$ alkyl, C(=O)$R^g$, S(=O)$_2C_{1-3}$ alkyl, $C_{2-4}$ hydroxyalkyl, $C_{1-3}$ alkoxy-$C_{1-3}$ alkyl, $C_{3-7}$ cycloalkyl-$C_{1-3}$ alkyl, pyridinyl, or pyrimidinyl, (h) cyano-$C_{1-3}$ alkyl, (i) $C_{1-3}$ alkylsulfonyl-$C_{1-3}$ alkyl, (j) carbamoyl, (k) N—$C_{1-3}$ alkyl-carbamoyl, (l) N,N—$C_{1-3}$ alkylcarbamoyl; (m) optionally substituted heteroaryl or heteroaryl-$C_{1-3}$ alkyl wherein said heteroaryl is selected from the group consisting of pyridinyl, 2-oxo-1,2-dihydropyridinyl, 6-oxo-1,6-dihydropyridinyl, pyrimidinyl, pyrazinyl, pyridazinyl, pyrazolyl, N—$C_{1-3}$ alkyl-pyrazolyl, imidazolyl, oxazolyl, isoxazolyl, thiazolyl, isothiazolyl, oxadiazolyl, indolyl, benzoxazolyl, benzothiazolyl, triazolyl, N—$C_{1-3}$ alkyl-triazolyl and triazinyl, and (n) heterocycle or heterocyclyl-$C_{1-3}$ alkyl said heterocyclyl selected from the group consisting of pyrrolidinyl, N—$C_{1-3}$ alkyl-pyrrolidinyl, N—$C_{1-3}$ acyl-pyrrolidinyl, azetidinyl, N—$C_{1-3}$ alkyl-azetidinyl, morpholinyl, piperidinyl and N—$C_{1-3}$ alkyl-piperidinyl and wherein said heterocycle is optionally substituted by 1 to 3 groups independently selected from $C_{1-6}$ alkyl, halogen, hydroxyl, phenyl and oxo; or $R^1$ and $R^2$ together with the carbon to which they are attached form a cyclic amine optionally substituted by 1 to 3 $C_{1-6}$ alkyl groups; or $R^1$ and $R^a$ together with the atoms to which they are attached form a cyclic amine optionally substituted by 1 to 3 groups independently selected from $C_{1-6}$ alkyl, halogen, hydroxyl phenyl, benzyl or oxo; $R^{3a}$ and $R^{3b}$ are independently hydrogen, halogen or hydroxyl; $R^a$ is (a) hydrogen or $C_{1-3}$ alkyl or (b) $R^1$ and $R^a$ together with the atoms to which they are attached form a cyclic amine optionally substituted by 1 to 3 groups independently selected from $C_{1-6}$ alkyl, halogen, hydroxyl, phenyl, benzyl or oxo; $R^b$ is selected from the group consisting of (a) hydrogen, (b) $C_{1-10}$ alkyl, (c) $C_{1-6}$ haloalkyl, (d) optionally substituted aryl or aryl-$C_{1-6}$ alkyl, (e) optionally substituted heteroaryl or heteroaryl-$C_{1-6}$ alkyl wherein said heteroaryl is selected from the group consisting of isoxazole, pyridinyl, pyridone, pyrimidinyl, pyrazinyl, pyrazole, N-alkyl-pyrazolyl, N-benzylpyrazolyl, thiazolyl, N—$C_{1-6}$ alkyl triazolyl and 2-oxo-tetrahydroquinolin-6-yl, (f) heterocyclyl or heterocyclyl-$C_{1-6}$ alkyl wherein said heterocyclyl is selected from the group consisting of tetrahydropyranyl, tetrahydrofuranyl, oxetanyl, piperidinyl, pyrrolidinyl, morpholinyl, N—$C_{1-6}$ alkyl piperidinyl and N—$C_{1-6}$ alkyl-2-oxo-pyrrolidinyl, (g) $C_{3-7}$ cycloalkyl or $C_{3-7}$ cycloalkyl-$C_{1-6}$ alkyl wherein said cycloalkyl is optionally substituted by hydroxyl or halo, (h) $C_{1-6}$ heteroalkyl, (i) $C_{1-6}$ acyl and (j) $C_{1-6}$ hydroxyalkyl; each $R^g$ is independently hydrogen or $C_{1-3}$ alkyl; wherein: each said aryl and each said heteroaryl is optionally substituted by 1 to 5 groups independently selected from $C_{1-6}$ alkyl, $C_{1-6}$ haloalkyl, $C_{1-6}$ alkoxy, $C_{3-6}$ cycloalkyl, halogen, hydroxyl, $C_{1-6}$ haloalkoxy, $C_{1-6}$ alkylthio, $C_{1-6}$ haloalkylthio, $C_{1-6}$ acylamino, cyano, nitro or optionally substituted aryloxy; each said heterocyclyl is optionally substituted with $C_{1-6}$ alkyl, $C_{1-6}$ haloalkyl, $C_{1-3}$ hydroxyalkyl or halogen; each said cycloalkyl is optionally substituted by one to four groups independently selected from $C_{1-6}$ alkyl, $C_{1-6}$ alkoxy, halogen, cyano or oxo; each said heteroalkyl is optionally substituted by phenyl, benzyl or $C_{1-3}$ haloalkyl; or, a tautomer, stereoisomer or pharmaceutically acceptable salt thereof.

In one embodiment of the present invention there is provided a compound according to formula I wherein $R^1$, $R^2$, $R^{3a}$, $R^{3b}$, $R^a$, $R^b$, $R^c$, $R^d$, $R^e$, $R^f$, $R^g$, Y, $Y^1$, Z, $Z^1$, $Z^2$, $Z^3$ are as defined herein above or a tautomer, stereoisomer or pharmaceutically acceptable salt thereof.

In another embodiment of the present invention there is provided a compound according to formula I wherein Z and $Z^1$ are N; $Z^2$ is $NR^aCR^1R^2Ar$; $Z^3$ is $CH_2$; Ar is optionally substituted phenyl; $R^1$, $R^{3a}$, $R^{3b}$, and $R^a$ are hydrogen; $R^2$ is hydrogen, $C_{1-10}$ alkyl, $C_{1-6}$ haloalkyl, $C_{1-6}$ hydroxyalkyl, $C_{1-3}$ alkoxy-$C_{1-6}$ alkyl, $(CH_2)_{1-3}NR^cR^d$, pyrrolidin-2-yl, N—$C_{1-3}$ alkyl, pyrrolidin-2-yl or heteroaryl; and, $R^b$ is (a) $C_{1-10}$ alkyl, (b) $C_{1-6}$ haloalkyl, (c) $C_{1-6}$ hydroxyalkyl, (d) $C_{4-6}$ cycloalkyl optionally substituted by a hydroxy or (e) heterocyclyl; or, a tautomer, stereoisomer or pharmaceutically acceptable salt thereof.

In another embodiment of the present invention there is provided a compound according to formula I wherein Z and $Z^1$ are N; $Z^2$ is $NR^aCR^1R^2Ar$; $Z^3$ is $CH_2$; Ar is optionally substituted phenyl; $R^1$, $R^{3a}$, $R^{3b}$ and $R^a$ are hydrogen; $R^2$ is pyrazolyl, N—$C_{1-3}$ alkyl pyrazolyl, oxadiazolyl or N—$C_{1-3}$ alkyl triazolyl; and, $R^b$ is (a) $C_{1-10}$ alkyl, (b) $C_{1-6}$ haloalkyl, (c) $C_{1-6}$ hydroxyalkyl, (d) $C_{4-6}$ cycloalkyl optionally substituted by a hydroxy or (e) heterocyclyl; or, a tautomer, stereoisomer or pharmaceutically acceptable salt thereof.

In another embodiment of the present invention there is provided a compound according to formula I wherein Z and $Z^1$ are N; $Z^2$ is $NR^aCR^1R^2Ar$; $Z^3$ is $CH_2$; Ar is optionally substituted phenyl; $R^1$, $R^{3a}$, $R^{3b}$ and $R^a$ are hydrogen; $R^2$ is pyrazolyl, N—$C_{1-3}$ alkyl pyrazolyl, oxadiazolyl, triazolyl or N—$C_{1-3}$ triazolyl; and, $R^b$ is tetrahydropyranyl, $C_{1-6}$ hydroxyalkyl or $C_{1-6}$ haloalkyl; or, a tautomer, stereoisomer or, a pharmaceutically acceptable salt thereof.

In another embodiment of the present invention there is provided a compound according to formula I wherein Z and $Z^1$ are N; $Z^2$ is $NR^aCR^1R^2Ar$; $Z^3$ is $CH_2$; Ar is phenyl substituted by one to three groups selected from halogen, $C_{1-6}$ haloalkyl, $C_{1-6}$ alkoxy or $C_{1-6}$ haloalkoxy; $R^1$, $R^{3a}$, $R^{3b}$ and $R^a$ are hydrogen; $R^2$ is pyrazolyl, N—$C_{1-3}$ alkyl pyrazolyl, oxadiazolyl, triazolyl or N—$C_{1-3}$ triazolyl; and, $R^b$ is tetrahydropyranyl, $C_{1-6}$ hydroxyalkyl or $C_{1-6}$ haloalkyl; or, a tautomer, stereoisomer or, a pharmaceutically acceptable salt thereof.

In another embodiment of the present invention there is provided a compound according to formula I wherein Z and $Z^1$ are N; $Z^2$ is $NR^aCR^1R^2Ar$; $Z^3$ is $CH_2$; Ar is optionally substituted phenyl; $R^1$, $R^{3a}$, $R^{3b}$ and $R^a$ are hydrogen; $R^2$ pyrrolidinyl or N—$C_{1-3}$ alkyl-pyrrolidinyl; $R^b$ is (a) $C_{1-10}$ alkyl, (b) $C_{1-6}$ haloalkyl, (c) $C_{1-6}$ hydroxyalkyl, (d) $C_{4-6}$ cycloalkyl optionally substituted by a hydroxy or (e) heterocyclyl; or, a tautomer, stereoisomer or pharmaceutically acceptable salt thereof.

In another embodiment of the present invention there is provided a compound according to formula I wherein Z and $Z^1$ are N; $Z^2$ is $NR^aCR^1R^2Ar$; $Z^3$ is $CH_2$; Ar is optionally substituted phenyl; $R^1$, $R^{3a}$, $R^{3b}$ and $R^a$ are hydrogen; $R^2$ pyrrolidinyl or N—$C_{1-3}$ alkyl-pyrrolidinyl optionally substituted with one to three groups independently selected from $C_{1-6}$ alkyl, halogen, hydroxyl and oxo; and, $R^b$ is (a) $C_{1-10}$ alkyl, (b) $C_{1-6}$ haloalkyl, (c) $C_{1-6}$ hydroxyalkyl, (d) $C_{4-6}$ cycloalkyl optionally substituted by a hydroxy or (e) heterocyclyl; or, a tautomer, stereoisomer or pharmaceutically acceptable salt thereof.

In another embodiment of the present invention there is provided a compound according to formula I, wherein Z and $Z^1$ are N; $Z^2$ is $NR^aCR^1R^2Ar$; $Z^3$ is $CH_2$; Ar is optionally substituted phenyl; $R^1$, $R^{3a}$, $R^{3b}$ and $R^a$ are hydrogen; $R^2$ pyrrolidinyl or N—$C_{1-3}$ alkyl-pyrrolidinyl; $R^b$ is tetrahydropyranyl, $C_{1-6}$ hydroxyalkyl or $C_{1-6}$ haloalkyl; or, a tautomer, stereoisomer or a pharmaceutically acceptable salt thereof.

In another embodiment of the present invention there is provided a compound according to formula I wherein Z and $Z^1$ are N; $Z^2$ is $NR^aCR^1R^2Ar$; $Z^3$ is $CH_2$; Ar is phenyl substituted by one to three groups selected from halogen, $C_{1-6}$ haloalkyl, $C_{1-6}$ alkoxy or $C_{1-6}$ haloalkoxy; $R^1$, $R^{3a}$, $R^{3b}$ and $R^a$ are hydrogen; $R^2$ pyrrolidinyl or N—$C_{1-3}$ alkyl-pyrrolidinyl; $R^b$ is tetrahydropyranyl, $C_{1-6}$ hydroxyalkyl or $C_{1-6}$ haloalkyl; or, a tautomer, stereoisomer or a pharmaceutically acceptable salt thereof.

In a another embodiment of the present invention there is provided a compound according to formula I wherein Z and $Z^1$ are N; $Z^2$ is $NR^aCR^1R^2Ar$; $Z^3$ is $CH_2$; Ar is optionally substituted heteroaryl; $R^1$, $R^{3a}$, $R^{3b}$ and $R^a$ are hydrogen; $R^2$ is hydrogen, $C_{1-10}$ alkyl, $C_{1-6}$ haloalkyl, $C_{1-6}$ hydroxyalkyl, $C_{1-3}$ alkoxy-$C_{1-6}$ alkyl, $(CH_2)_{1-3}$ $NR^cR^d$, pyrrolidin-2-yl, N—$C_{1-3}$ alkyl, pyrrolidin-2-yl or heteroaryl, wherein said heteroaryl is selected from the group consisting of pyridinyl, 2-oxo-1,2-dihydropyridinyl, pyrimidinyl, pyrazinyl, pyridazinyl, pyrazolyl, N—$C_{1-3}$ alkyl-pyrazole, imidazolyl, oxazolyl, isoxazolyl, thiazolyl, isothiazolyl, oxadiazole, indolyl, benzoxazole, benzothiazole, triazolyl and triazinyl; and, $R^b$ is (a) $C_{1-10}$ alkyl, (b) $C_{1-6}$ haloalkyl, (c) $C_{1-6}$ hydroxyalkyl, (d) $C_{4-6}$ cycloalkyl optionally substituted by a hydroxy or (e) heterocyclyl; or, a tautomer, stereoisomer or pharmaceutically acceptable salt thereof.

In another embodiment of the present invention there is provided a compound according to formula I wherein Z and $Z^1$ are N; $Z^2$ is $NR^aCR^1R^2Ar$; $Z^3$ is $CH_2$; Ar is optionally substituted heteroaryl, wherein said heteroaryl is selected from the group consisting of pyridinyl, 2-oxo-1,2-dihydropyridinyl, pyrimidinyl, pyrazinyl, pyridazinyl, pyrazolyl, N—$C_{1-3}$ alkyl-pyrazole, imidazolyl, oxazolyl, isoxazolyl, thiazolyl, isothiazolyl, oxadiazole, indolyl, benzoxazole, benzothiazole, triazolyl and triazinyl; $R^1$, $R^{3a}$, $R^{3b}$ and $R^a$ are hydrogen; $R^2$ is hydrogen, $C_{1-10}$ alkyl, $C_{1-6}$ haloalkyl, $C_{1-6}$ hydroxyalkyl, $C_{1-3}$ alkoxy-$C_{1-6}$ alkyl, $(CH_2)_{1-3}NR^cR^d$, pyrrolidin-2-yl, N—$C_{1-3}$ alkyl, pyrrolidin-2-yl or heteroaryl; and, $R^b$ is $C_{1-10}$ alkyl, $C_{1-6}$ haloalkyl, $C_{1-6}$ hydroxyalkyl or tetrahydropyranyl; or, a tautomer, stereoisomer or a pharmaceutically acceptable salt thereof.

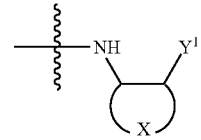

(II)

In another embodiment of the present invention there is provided a compound according to formula I wherein Z and $Z^1$ are N; $Z^2$ is formula II; $Y^1$ is —Ar, —OAr, —$S(O)_{0-2}$Ar or —$NR^gAr$ wherein Ar is optionally substituted phenyl; $Z^3$ is $CH_2$; $R^{3a}$ and $R^{3b}$ are hydrogen; or, a tautomer, stereoisomer or pharmaceutically acceptable salt thereof.

In another embodiment of the present invention there is provided a compound according to formula I wherein Z and $Z^1$ are N; $Z^2$ is formula II; X is $CH_2NR^eCH_2$; $R^e$ is hydrogen or $C_{1-6}$ alkyl; $Y^1$ is Ar; Ar is optionally substituted phenyl; $Z^3$ is $CH_2$; $R^{3a}$ and $R^{3b}$ are hydrogen; and, $R^b$ is (a) $C_{1-10}$ alkyl, (b) $C_{1-6}$ haloalkyl, (c) $C_{1-6}$ hydroxyalkyl, (d) $C_{4-6}$ cycloalkyl optionally substituted by a hydroxy or (e) heterocyclyl; or, a tautomer, stereoisomer or pharmaceutically acceptable salt thereof.

In another embodiment of the present invention there is provided a compound according to formula I wherein Z and Z' are N; $Z^2$ is formula II; X is $CH_2NR^eCH_2$; $R^e$ is hydrogen or $C_{1-6}$ alkyl; $Y^1$ is Ar; Ar is optionally substituted phenyl; $Z^3$ is $CH_2$; $R^{3a}$ and $R^{3b}$ are hydrogen; and, $R^b$ is $C_{1-10}$ alkyl, $C_{1-10}$ haloalkyl, $C_{1-6}$ hydroxyalkyl or tetrahydropyranyl; or, a tautomer, stereoisomer or a pharmaceutically acceptable salt thereof.

In another embodiment of the present invention there is provided a compound according to formula I wherein Z and Z' are N; $Z^2$ is formula II; X is $CH_2NR^eCH_2$; $R^e$ is hydrogen or $C_{1-6}$ alkyl; $Y^1$ is Ar; Ar is phenyl substituted by one to three groups selected from halogen, $C_{1-6}$ haloalkyl, $C_{1-6}$ alkoxy or $C_{1-6}$ haloalkoxy; $Z^3$ is $CH_2$; $R^{3a}$ and $R^{3b}$ are hydrogen; and, $R^b$ is $C_{1-10}$ alkyl, $C_{1-6}$ haloalkyl, $C_{1-6}$ hydroxyalkyl or tetrahydropyranyl; or, a pharmaceutically acceptable salt thereof.

In another embodiment of the present invention there is provided a compound according to formula I wherein Z and $Z^1$ are N; $Z^2$ is formula II; X is $CH_2NR^eCH_2$; $R^e$ is hydrogen or $C_{1-6}$ alkyl; $Y^1$ is —OAr; Ar is optionally substituted phenyl;

$Z^3$ is $CH_2$; $R^{3a}$ and $R^{3b}$ are hydrogen; and, $R^b$ is (a) $C_{1-10}$ alkyl, (b) $C_{1-6}$ haloalkyl, (c) $C_{1-6}$ hydroxyalkyl, (d) $C_{4-6}$ cycloalkyl optionally substituted by a hydroxy or (e) heterocyclyl; or, a tautomer, stereoisomer or pharmaceutically acceptable salt thereof.

In another embodiment of the present invention there is provided a compound according to formula I wherein Z and $Z^1$ are N; $Z^2$ is formula II; X is $CH_2NR^eCH_2$; $R^e$ is hydrogen or $C_{1-6}$ alkyl; $Y^1$ is —OAr; Ar is optionally substituted phenyl; $Z^3$ is $CH_2$; $R^{3a}$ and $R^{3b}$ are hydrogen; and, $R^b$ is $C_{1-10}$ alkyl, $C_{1-6}$ haloalkyl, $C_{1-6}$ hydroxyalkyl, or tetrahydropyranyl; or, a tautomer, stereoisomer or a pharmaceutically acceptable salt thereof.

In another embodiment of the present invention there is provided a compound according to formula I wherein Z and $Z^1$ are N; $Z^2$ is formula II; X is $CH_2NR^eCH_2$; $R^e$ is hydrogen or $C_{1-6}$ alkyl; $Y^1$ is —$S(O)_{0-2}$Ar; Ar is optionally substituted phenyl; $Z^3$ is $CH_2$; $R^{3a}$ and $R^{3b}$ are hydrogen; and, $R^b$ is $C_{1-6}$ alkyl, $C_{1-6}$ haloalkyl, $C_{1-6}$ hydroxyalkyl, or tetrahydropyranyl; or, a tautomer, stereoisomer or a pharmaceutically acceptable salt thereof.

In another embodiment of the present invention there is provided a compound according to formula I wherein Z and $Z^1$ are N; $Z^2$ is formula II; X is $CH_2NR^eCH_2$; $R^e$ is hydrogen or $C_{1-6}$ alkyl; $Y^1$ is —SAr; Ar is optionally substituted phenyl; $Z^3$ is $CH_2$; $R^{3a}$ and $R^{3b}$ are hydrogen; $R^b$ is $C_{1-10}$ alkyl, $C_{1-6}$ haloalkyl, $C_{1-6}$ hydroxyalkyl, or tetrahydropyranyl; or, a tautomer, stereoisomer or a pharmaceutically acceptable salt thereof.

In another embodiment of the present invention there is provided a compound according to formula I wherein Z and $Z^1$ are N; $Z^2$ is formula II; X is $CH_2NR^eCH_2$; $R^e$ is hydrogen or $C_{1-6}$ alkyl; $Y^1$ is —$NR^g$Ar; Ar is optionally substituted phenyl; $Z^3$ is $CH_2$; $R^{3a}$ and $R^{3b}$ are hydrogen; and, $R^b$ is $C_{1-10}$ alkyl, $C_{1-6}$ haloalkyl, $C_{1-6}$ hydroxyalkyl, or tetrahydropyranyl; or, a tautomer, stereoisomer or a pharmaceutically acceptable salt thereof.

In another embodiment of the present invention there is provided a compound according to formula I wherein Z and $Z^1$ are N; $Z^2$ is formula II; X is $CH_2NR^eCH_2$; $R^e$ is hydrogen or $C_{1-6}$ alkyl; $Y^1$ is —$NR^g$Ar; $R^g$ is hydrogen; Ar is optionally substituted phenyl; $Z^3$ is $CH_2$; $R^{3a}$ and $R^{3b}$ are hydrogen; and, $R^b$ is $C_{1-10}$ alkyl, $C_{1-6}$ haloalkyl, $C_{1-6}$ hydroxyalkyl, or tetrahydropyranyl; or, a tautomer, stereoisomer or a pharmaceutically acceptable salt thereof.

In another embodiment of the present invention there is provided a compound according to formula I wherein Z and $Z^1$ are N; $Z^2$ is formula II; X is $(CH_2)_{1-34}$; $Z^3$ is $CH_2$; $Y^1$ is Ar; Ar is optionally substituted phenyl; $R^{3a}$ and $R^{3b}$ are hydrogen; and, $R^b$ is $C_{1-10}$ alkyl, $C_{1-6}$ haloalkyl, $C_{1-6}$ hydroxyalkyl, or tetrahydropyranyl; or, a tautomer, stereoisomer or a pharmaceutically acceptable salt thereof.

In another embodiment of the present invention there is provided a compound according to formula I wherein Z and $Z^1$ are N; $Z^2$ is formula II; $Z^3$ is $CH_2$; X is $(CH_2)_3$; $Y^1$ is Ar; Ar is optionally substituted phenyl; $R^{3a}$ and $R^{3b}$ are hydrogen; and, $R^b$ is (a) $C_{1-10}$ alkyl, (b) $C_{1-6}$ haloalkyl, (c) $C_{1-6}$ hydroxyalkyl, (d) $C_{4-6}$ cycloalkyl optionally substituted by a hydroxy or (e) heterocyclyl; or, a tautomer, stereoisomer or pharmaceutically acceptable salt thereof.

In another embodiment of the present invention there is provided a compound according to formula I wherein Z and $Z^1$ are N; $Z^2$ is formula II; $Z^3$ is $CH_2$; X is $(CH_2)_3$; $Y^1$ is —OAr; Ar is optionally substituted phenyl; $R^{3a}$ and $R^{3b}$ are hydrogen; $R^b$ is (a) $C_{1-10}$ alkyl, (b) $C_{1-6}$ haloalkyl, (c) $C_{1-6}$ hydroxyalkyl, (d) $C_{4-6}$ cycloalkyl optionally substituted by a hydroxy or (e) heterocyclyl; or, a tautomer, stereoisomer or pharmaceutically acceptable salt thereof.

In another embodiment of the present invention there is provided a compound according to formula I wherein Z is N and $Z^1$ is CH; or, a tautomer, stereoisomer or a pharmaceutically acceptable salt thereof.

In another embodiment of the present invention there is provided a compound according to formula I wherein Z is N; $Z^1$ is CH; and $Z^2$ is $NR^aCR^1R^2$Ar; or, a tautomer, stereoisomer or a pharmaceutically acceptable salt thereof.

In another embodiment of the present invention there is provided a compound according to formula I wherein Z is N; $Z^1$ is CH; $Z^2$ is formula II; X is $CH_2NR^eCH_2$; and, $R^e$ is hydrogen or $C_{1-6}$ alkyl; or, a tautomer, stereoisomer or a pharmaceutically acceptable salt thereof.

In another embodiment of the present invention there is provided a compound according to formula I wherein Z is N; $Z^1$ is CH and $Z^2$ is $CH_2CR^1R^2Y$; or, a tautomer, stereoisomer or a pharmaceutically acceptable salt thereof.

In another embodiment of the present invention there is provided a compound according to formula I wherein Z is N; $Z^1$ is CH; $Z^2$ is $NR^aCR^1R^2$Ar; $Z^3$ is $CH_2$; Ar is optionally substituted phenyl; $R^1$, $R^{3a}$, $R^{3b}$ and $R^a$ are hydrogen; $R^2$ is hydrogen, $C_{1-10}$ alkyl, $C_{1-6}$ haloalkyl, $C_{1-6}$ hydroxyalkyl, $C_{1-3}$ alkoxy-$C_{1-6}$ alkyl, $(CH_2)_{1-3}NR^cR^d$, pyrrolidin-2-yl, N—$C_{1-3}$ alkyl, pyrrolidin-2-yl or heteroaryl, wherein said heteroaryl is selected from the group consisting of pyridinyl, 2-oxo-1,2-dihydropyridinyl, pyrimidinyl, pyrazinyl, pyridazinyl, pyrazolyl, N—$C_{1-3}$ alkyl-pyrazole, imidazolyl, oxazolyl, isoxazolyl, thiazolyl, isothiazolyl, oxadiazole, indolyl, benzoxazole, benzothiazole, triazolyl and triazinyl; and, $R^b$ is (a) $C_{1-10}$ alkyl, (b) $C_{1-6}$ haloalkyl, (c) $C_{1-6}$ hydroxyalkyl, (d) $C_{4-6}$ cycloalkyl optionally substituted by a hydroxy or (e) heterocyclyl; or, a tautomer, stereoisomer or pharmaceutically acceptable salt thereof.

In another embodiment of the present invention there is provided a compound according to formula I wherein Z is N; $Z^1$ is CH; $Z^2$ is $NR^aCR^1R^2$Ar; $Z^3$ is $CH_2$; Ar is optionally substituted phenyl; $R^1$, $R^{3a}$, $R^{3b}$ and $R^a$ are hydrogen; $R^2$ is hydrogen, $C_{1-10}$ alkyl, $C_{1-6}$ haloalkyl, $C_{1-6}$ hydroxyalkyl, $C_{1-3}$ alkoxy-$C_{1-6}$ alkyl, $(CH_2)_{1-3}NR^cR^d$, pyrrolidin-2-yl, N—$C_{1-3}$ alkyl, pyrrolidin-2-yl or heteroaryl, wherein said heteroaryl is selected from the group consisting of pyridinyl, 2-oxo-1,2-dihydropyridinyl, pyrimidinyl, pyrazinyl, pyridazinyl, pyrazolyl, N—$C_{1-3}$ alkyl-pyrazole, imidazolyl, oxazolyl, isoxazolyl, thiazolyl, isothiazolyl, oxadiazole, indolyl, benzoxazole, benzothiazole, triazolyl and triazinyl; and, $R^b$ is $C_{1-10}$ alkyl, $C_{1-6}$ haloalkyl, $C_{1-6}$ hydroxyalkyl, or tetrahydropyranyl; or, a tautomer, stereoisomer or a pharmaceutically acceptable salt thereof.

In another embodiment of the present invention there is provided a compound according to formula I wherein $Z^3$ is O; Z is $CR^g$; and, $R^{3a}$ and $R^{3b}$ are hydrogen, or, a tautomer, stereoisomer or a pharmaceutically acceptable salt thereof.

In another embodiment of the present invention there is provided a compound according to formula I wherein $Z^3$ is O; Z is $CR^g$; $Z^1$ is N; $Z^2$ is $NR^aCR^1R^2$Ar; $R^{3a}$, $R^{3b}$ and $R^g$ are hydrogen; $R^2$ is $C_{1-10}$ alkyl, $C_{1-6}$ haloalkyl or $C_{1-6}$ hydroxyalkyl; Ar is optionally substituted phenyl; and, $R^b$ is (a) $C_{1-10}$ alkyl, (b) $C_{1-6}$ haloalkyl, (c) $C_{1-6}$ hydroxyalkyl, (d) $C_{4-6}$ cycloalkyl optionally substituted by a hydroxy or (e) heterocyclyl; or, a tautomer, stereoisomer or pharmaceutically acceptable salt thereof.

In another embodiment of the present invention there is provided a compound according to formula I wherein $Z^3$ is O; Z is $CR^g$; $R^{3a}$, $R^{3b}$ and $R^g$ are hydrogen; $Z^1$ is N; $Z^2$ is formula II; X is $CH_2NR^eCH_2$; Ar is optionally substituted phenyl; and, $R^b$ is (a) $C_{1-10}$ alkyl, (b) $C_{1-6}$ haloalkyl, (c) $C_{1-6}$ hydroxyalkyl, (d) $C_{4-6}$ cycloalkyl optionally substituted by a hydroxy or (e) heterocyclyl; or, a tautomer, stereoisomer or pharmaceutically acceptable salt thereof.

In another embodiment, Z is N and $Z^3$ is CH.

In another embodiment, Z is CH and $Z^3$ is O.

In another embodiment, Z is N and $Z^3$ is C=O.

In another embodiment, Z is selected from CH and N. In another embodiment, Z is CH. In another embodiment, Z is N.

In another embodiment, $Z^1$ is selected from CH and N. In another embodiment, $Z^1$ is CH. In another embodiment, $Z^1$ is N.

In another embodiment, $R^{3a}$ and $R^{3b}$ are independently selected from hydrogen, halogen and hydroxyl. In another embodiment, $R^{3a}$ and $R^{3b}$ are hydrogen. In another embodiment, $R^{3a}$ is hydrogen and $R^{3b}$ is hydroxyl. In another embodiment, $R^{3a}$ and $R^{3b}$ are F.

In another embodiment, $Z^2$ is $NR^aCR^1R^2Y$. In certain embodiments, $R^a$ is hydrogen or methyl. In certain embodiments, $R^1$ is selected from hydrogen, $C_{1-10}$ alkyl, $C_{3-7}$ cycloalkyl, $(CH_2)_{1-3}OC(=O)R^f$, $(CH_2)_{1-3}NR^cR^d$, cyano-$C_{1-3}$ alkyl, $C_{1-3}$ alkylsulfonyl-$C_{1-3}$ alkyl, N—$C_{1-3}$ alkyl-carbamoyl, optionally substituted heteroaryl or heteroaryl-$C_{1-3}$ alkyl wherein said heteroaryl is selected from the group consisting of pyridinyl, 6-oxo-1,6-dihydropyridinyl, pyrazolyl, oxazolyl, isoxazolyl, oxadiazolyl, benzoxazolyl, benzothiazolyl and triazolyl, and optionally substituted heterocyclyl or heterocyclyl-$C_{1-3}$ alkyl wherein said heterocyclyl is selected from the group consisting of pyrrolidinyl, morpholinyl and piperidinyl, wherein the alkyl, heterocyclyl and heteroaryl are optionally substituted with halogen, OH, acetyl, $C_{1-3}$ alkyl or $C_{1-3}$ alkoxy, and wherein the alkoxy is optionally substituted with $C_{1-3}$ alkoxy. In certain embodiments, $R^c$ and $R^d$ are independently selected from hydrogen, $C_{1-6}$ alkyl, $C(=O)R^e$, $S(=O)_2C_{1-3}$ alkyl, $C_{1-3}$ alkoxy-$C_{1-3}$ alkyl, $C_{3-7}$ cycloalkyl-$C_{1-3}$ alkyl and pyrimidinyl, wherein the alkyl is optionally substituted with OH. In certain embodiments, $R^e$ is $C_{1-3}$ alkyl. In certain embodiments, $R^e$ is methyl. In certain embodiments, $R^e$ and $R^d$ are independently selected from hydrogen, methyl, ethyl, isobutyl, 2-hydroxyethyl, 2-methoxyethyl, $C(=O)CH_3$, $S(=O)_2CH_3$, cyclopropylmethyl, pyrimidin-2-yl and pyrimidin-4-yl. In certain embodiments, $R^f$ is selected from $C_{1-6}$ alkyl and $C_{1-3}$ alkoxy-$C_{1-3}$ alkyl, wherein the alkyl is optionally substituted with $NH_2$. In certain embodiments, $R^f$ is selected from methyl, $CH(NH_2)CH(CH_3)_2$ and methoxymethyl. In certain embodiments, $R^1$ is in the (S) configuration. In certain embodiments, $R^1$ is in the (R) configuration. In certain embodiments, $R^1$ is selected from hydrogen, methyl, ethyl, isopropyl, $CH_2CF_3$, $CF_3$, $CH_2OH$, $CH(OH)CH_3$, $CH_2CH_2OH$, $CH_2OCH_3$, $C(CH_3)_2OH$, $CH_2OCH_2CH_2OCH_3$, $CH(OH)CH_2CH_3$, $CH_2OCH_2CH_3$, $CH_2OCH(CH_3)_2$, $CH(OH)CH_2OH$, $CH_2CH_2OCH_3$, $CH(CH_3)OCH_3$, cyclopropyl, cyclopentyl, $CH_2OC(=O)CH_3$, $CH_2OC(=O)C(CH_3)_3$, $CH_2C(=O)CH(NH_2)CH(CH_3)_2$, $CH_2C(=O)CH_2OCH_3$, $CH_2CH_2NH_2$, $CH_2NH_2$, $CH_2CH_2NHCH_3$, $CH_2NHCH_3$, $CH_2NHCH_2CH_3$, $CH_2NHCH_2CH(CH_3)_2$, $CH_2NHCH_2CH_2OH$, $CH_2NHCH_2CH_2OCH_3$, $CH_2NHC(=O)CH_3$, $CH_2NHS(=O)_2CH_3$, $CH_2NHCH_2(cyclopropyl)$, $CH_2NH(pyrimidin-4-yl)$, $CH_2CH_2NHC(=O)CH_3$, $CH_2CH_2CN$, $CH_2CN$, $CH_2CH_2SO_2CH_3$, $C(=O)NHCH_3$, 6-oxo-1,6-dihydropyridin-2-yl, 6-methoxypyridin-2-yl, 2H-pyrazol-3-yl, 2-methyl-2H-pyrazol-3-yl, 1-methyl-1H-pyrazol-4-yl, 1-methyl-1H-pyrazol-3-yl, 1H-pyrazol-4-yl, benzooxazol-2-yl, benzothiazol-2-yl, oxazol-4-yl, oxazol-5-yl, 2-methyloxazol-5-yl, isoxazol-5-yl, oxadiazol-2-yl, [1,3,4]oxadiazol-2-yl, 5-methyl-[1,3,4]oxadiazol-2-yl, 3-methyl-[1,3,4]oxadiazol-5-yl (4H-[1,2,4]triazol-3-yl)methyl, pyrrolidin-2-yl, pyrrolidin-1-ylmethyl, 1-methylpyrrolidin-2-yl, 5,5-dimethylpyrrolidin-2-yl, 1-acetyl-pyrrolidin-2-yl, pyrrolidin-2-ylmethyl, morpholin-2-yl, piperidin-2-yl, piperidin-2-ylmethyl and piperidin-4-yl. In certain embodiments, $R^2$ is hydrogen or $C_{1-10}$ alkyl. In certain embodiments, $R^2$ is in the (S) configuration. In certain embodiments, $R^2$ is in the (R) configuration. In certain embodiments, $R^2$ is hydrogen or methyl. In certain embodiments, $R^1$ and $R^2$ together with the carbon to which they are attached form a cyclic amine optionally substituted by 1 to 3 $C_{1-6}$ alkyl groups. In certain embodiments, $R^1$ and $R^2$ together with the carbon to which they are attached form a cyclic amine optionally substituted by 1 to 3 $C_{1-6}$ alkyl groups, wherein the cyclic amine is selected from piperidinyl and pyrrolidinyl. In certain embodiments, $R^1$ and $R^2$ together with the carbon to which they are attached form a cyclic amine optionally substituted by 1 to 3 $C_{1-6}$ alkyl groups, wherein the cyclic amine is selected from piperidin-4-yl, pyrrolidin-3-yl and 1-methylpiperidin-4-yl. In certain embodiments, $R^1$ and $R^a$ together with the carbon to which they are attached form a cyclic amine, wherein the cyclic amine is selected from pyrrolidinyl, azetidinyl, morpholinyl, piperidinyl and piperazinyl.

In certain embodiments, Y is aryl or heteroaryl optionally substituted with $C_{1-6}$ alkyl, $C_{1-6}$ haloalkyl, $C_{1-6}$ alkoxy, halogen, $C_{1-6}$ haloalkoxy, $C_{1-6}$ alkylthio, $C_{1-6}$ haloalkylthio, $C_{1-6}$ acylamino and cyano, wherein the heteroaryl is selected from the group consisting of benzothiazolyl, benzoimidazolyl, indolyl, pyrimidinyl, pyridinyl, oxazolyl and thiazolyl. In certain embodiments, Y is aryl or heteroaryl optionally substituted with halogen, methyl, $CF_3$, $OCH_3$, $OCF_3$, $OCHF_2$, $OCH_3CF_3$, $SCH_3$, $SCF_3$, $NHC(=O)CH_3$, $C(CH_3)_2CN$ or CN, wherein the heteroaryl is selected from the group consisting of benzothiazolyl, benzoimidazolyl, indolyl, pyrimidinyl, pyridinyl, oxazolyl and thiazolyl. In certain embodiments, Y is aryl optionally substituted with F, Cl, methyl, $CF_3$, $OCH_3$, $OCF_3$, $OCHF_2$, $SCH_3$, $SCF_3$, $NHC(=O)CH_3$, $C(CH_3)_2CN$ or CN. In certain embodiments, Y is heteroaryl optionally substituted with methyl, F, Cl, $OCH_3$ or $CF_3$, wherein the heteroaryl is selected from the group consisting of benzothiazolyl, benzoimidazolyl, indolyl, pyrimidinyl, pyridinyl, oxazolyl and thiazolyl. In certain embodiments, Y is selected from phenyl, 3-chloro-4-fluorophenyl, 3,4-dichlorophenyl, 4-chloro-3-fluorophenyl, 4-chlorophenyl, 3-chlorophenyl, 4-trifluoromethylphenyl, 4-fluorophenyl, 3-fluoro-4-trifluoromethylphenyl, 3,4-difluorophenyl, 2-fluoro-3-trifluoromethylphenyl, 3,4,5-trifluorophenyl, 3-chloro-5-fluorophenyl, 4-chloro-3-trifluoromethoxyphenyl, 2,4-dichlorophenyl, 4-chloro-3-trifluoromethylphenyl, 4-trifluoromethylphenyl, 4-chloro-2-fluorophenyl, 2,3-dichlorophenyl, 3-chloro-4-trifluoromethoxyphenyl, 4-chloro-2,5-difluorophenyl, 3-chloro-4-trifluoromethylphenyl, 2-chloro-4-trifluoromethylphenyl, 4-chloro-3-methylphenyl, 4-trifluoromethylsulfanylphenyl, 3-chloro-4-methoxyphenyl, 3-chloro-4-methylphenyl, 4-difluoromethoxyphenyl, 3-acetylaminophenyl, 4-cyanophenyl, 4-methylsulfanylphenyl, 3-fluoro-4-methoxyphenyl, 4-methyl-3-trifluoromethylphenyl, 4-(cyano-dimethyl-methyl)phenyl, 4-chloro-3-methoxyphenyl, 3-fluoro-4-trifluoromethoxyphenyl, 2-fluoro-4-trifluoromethylphenyl, 4-cyano-3-fluorophenyl, 4-fluoro-3-methoxyphenyl, 3-cyano-4-fluorophenyl, 3-cyanophenyl, 2,5-difluorophenyl, 2,2,2-trifluoroethoxyphenyl, 3-chloro-4-cyanophenyl, 4-cyano-3-trifluoromethylphenyl, 3,4-dicyanophenyl, 4-cyano-3-methylphenyl, 1H-indol-6-yl, 1H-indol-2-yl, 1H-indol-5-yl, 1H-indol-7-yl, 1-methyl-1H-indol-6-yl, 5-fluoro-1H-indol-2-yl, 1H-benzoimidazol-2-yl, 1-benzothiazol-2-yl, 2-trifluoromethylpyrimidin-5-yl, 5-chloropyrimidin-2-yl, pyrimidin-5-yl, pyridin-3-yl, pyridin-2-yl, pyridin-4-yl, 6-methoxypyridin-3-yl, 5-fluoropyridin-3-yl, 6-trifluoromethylpyridin-3-yl, 6-methoxypyridin-2-yl, 6-methylpyridin-3-yl, oxazol-5-yl, and thiazol-2-yl. In certain embodiments, Y is selected from phenyl, 3-chloro-4-fluorophenyl, 3,4-dichlorophenyl, 4-chloro-3-fluorophenyl, 4-chlorophenyl, 3-chlorophenyl, 4-trifluoromethylphenyl, 4-fluorophenyl, 3-fluoro-4-trifluoromethylphenyl, 3,4-difluorophenyl, 2-fluoro-3-trifluoromethylphenyl, 3,4,5-trifluorophenyl, 3-chloro-5-fluorophenyl, 4-chloro-3-trifluoromethoxyphenyl, 2,4-dichlorophenyl, 4-chloro-3-trifluoromethylphenyl, 4-trifluoromethylphenyl, 4-chloro-2-fluorophenyl, 2,3-dichlorophenyl, 3-chloro-4-trifluoromethoxyphenyl, 4-chloro-2,5-difluorophenyl, 3-chloro-4-trifluoromethylphenyl, 2-chloro-4-trifluoromethylphenyl, 4-chloro-3-methylphenyl, 4-trifluoromethylsulfanylphenyl, 3-chloro-4-methoxyphenyl, 3-chloro-4-methylphenyl, 4-difluoromethoxyphenyl, 3-acetylaminophenyl, 4-cyanophenyl, 4-methylsulfanylphenyl, 3-fluoro-4-methoxyphenyl, 4-methyl-3-trifluoromethylphenyl, 4-(cyano-dimethyl-methyl)phenyl, 4-chloro-3-methoxyphenyl, 3-fluoro-4-trifluoromethoxyphenyl, 2-fluoro-4-trifluoromethylphenyl, 4-cyano-3-fluorophenyl, 4-fluoro-3-methoxyphenyl, 3-cyano-4-fluorophenyl, 3-cyanophenyl, 2,5-difluorophenyl, 2,2,2-trifluoroethoxyphenyl, 3-chloro-4-cyanophenyl, 4-cyano-3-trifluoromethylphenyl, 3,4-dicyanophenyl and 4-cyano-3-methylphenyl. In certain embodiments, Y is selected from 1H-indol-6-yl, 1H-indol-2-yl, 1H-indol-5-yl, 1H-indol-7-yl, 1-methyl-1H-indol-6-yl, 5-fluoro-1H-indol-2-yl, 1H-benzoimidazol-2-yl, 1-benzothiazol-2-yl, 2-trifluoromethylpyrimidin-5-yl, 5-chloropyrimidin-2-yl, pyrimidin-5-yl, pyridin-3-yl, pyridin-2-yl, pyridin-4-yl, 6-methoxypyridin-3-yl, 5-fluoropyridin-3-yl, 6-trifluoromethylpyridin-3-yl, 6-methoxypyridin-2-yl, 6-methylpyridin-3-yl, oxazol-5-yl, and thiazol-2-yl.

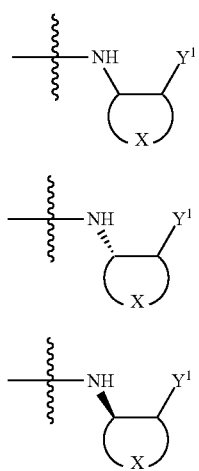

In another embodiment, $Z^2$ is formula (II), wherein X is $(CH_2)_{1-3}$ or $CH_2NR^eCH_2$. In certain embodiments, X is $CH_2$. In certain embodiments, X is $CH_2NR^eCH_2$. In certain embodiments, $R^e$ is selected from hydrogen, $C_{1-3}$ alkyl, $C_{1-3}$ hydroxyalkyl and $C_{1-3}$ haloalkyl. In certain embodiments, $R^e$ is selected from hydrogen, methyl, ethyl, 2-hydroxyethyl, 2,2,2-trifluoroethyl and 2,2-difluoroethyl. In certain embodiments, $Y^1$ is selected from phenyl, 4-trifluoromethylphenyl, 4-chlorophenyl, 3,4-dichlorophenyl, 3,4-difluorophenyl, 3-fluoro-4-trifluoromethylphenyl, 3-fluorophenyl, 4-chloro-3-fluorophenyl and 4-difluoromethoxyphenyl. In certain embodiments, $Y^1$ is in the (S) configuration. In certain embodiments, $Y^1$ is in the (R) configuration. In another embodiment, $Z^2$ is formula (IIa). In another embodiment, $Z^2$ is formula (IIb).

In another embodiment, $Z^2$ is $CH_2CR^1R^2Y$. In certain embodiments, $R^1$ is selected from hydrogen, $C_{1-10}$ alkyl and $(CH_2)_{1-3}NR^cR^d$. In certain embodiments, $R^c$ and $R^d$ are hydrogen. In certain embodiments, $R^1$ is selected from hydrogen, methyl, propyl and $CH_2NH_2$. In certain embodiments, $R^2$ is hydrogen. In certain embodiments, Y is selected from 3,4-dichlorophenyl, 2,4-dichlorophenyl, 4-fluorophenyl, 3-fluorophenyl, 4-chloro-2-fluorophenyl, 3,4-difluorophenyl, 4-chlorophenyl, 4-chloro-3-fluorophenyl, 3-chloro-4-fluorophenyl, 4-trifluoromethylphenyl and 3-fluoro-4-trifluoromethylphenyl.

In another embodiment, $Z^3$ is selected from CH and O. In another embodiment, $Z^3$ is CH. In another embodiment, $Z^3$ is O.

In another embodiment, $R^b$ is selected from hydrogen, $C_{1-10}$ alkyl, optionally substituted aryl or aryl-$C_{1-6}$ alkyl, optionally substituted heteroaryl or heteroaryl-$C_{1-6}$ alkyl, wherein said heteroaryl is selected from the group consisting of isoxazole, pyridinyl, pyridone, pyrimidinyl, pyrazinyl, pyrazole, thiazolyl, triazolyl, N—$C_{1-6}$ alkyl-pyrazolyl, N-benzylpyrazolyl, N—$C_{1-6}$ alkyl triazolyl and 2-oxo-tetrahydroquinolin-6-yl; heterocyclyl or heterocyclyl-$C_{1-6}$ alkyl, wherein said heterocyclyl is selected from the group consisting of tetrahydropyranyl, tetrahydrofuranyl, piperidinyl, pyrrolidinyl, morpholinyl, N—$C_{1-6}$ alkyl-piperidinyl and N—$C_{1-6}$ alkyl-2-oxo-pyrrolidinyl; and $C_{3-7}$ cycloalkyl or $C_{3-7}$ cycloalkyl-$C_{1-6}$ alkyl; wherein the alkyl, aryl, heteroaryl, heterocyclyl and cycloalkyl are optionally substituted with OH, oxo (except not on aromatic rings), halogen, CN, $C_{1-4}$ alkyl, $C_{1-4}$ hydroxyalkyl, $C_{1-6}$ alkoxy, benzyl, phenyl, $C_{3-7}$ cycloalkyl, 3 to 6 membered heterocyclyl or 5 to 6 membered heteroaryl, wherein the phenyl, cycloalkyl, heterocyclyl and heteroaryl are optionally substituted with halogen or $C_{1-4}$ alkyl. In another embodiment, $R^b$ is in the (S) configuration. In another embodiment, $R^b$ is in the (R) configuration. In another embodiment, $R^b$ is selected from hydrogen, methyl, ethyl, isopropyl, tert-butyl, isobutyl, 2-hydroxyethyl, 1-hydroxymethylpropyl, 2-hydroxy-1-methyl-ethyl, 2-methoxy-1-methyl-ethyl, 2-hydroxypropyl, 2-hydroxy-1-hydroxymethyl-ethyl, acetyl, 2,2,2-trifluoro-1-methyl-ethyl, 2,2,2-trifluoro-1-hydroxymethyl-ethyl, 2-fluoro-1-methyl-ethyl, 2-fluoro-1-fluoromethyl-ethyl, 2,2,2-trifluoroethyl, 3,3,3-trifluoropropyl, cyclopropylmethyl, 2-morpholin-4-yl-ethyl, 2,2-difluoro-1-methyl-ethyl, 4-fluorophenyl, 3-chloro-4-fluorophenyl, 4-chloro-3-fluorophenyl, 2-o-tolyl, 4-fluoro-2-methylphenyl, 2-chlorophenyl, 2-chloro-4-fluorophenyl, 4-fluoro-2-trifluoromethylphenyl, 4-cyano-2-fluorophenyl, pyrimidin-5-yl, 4-methylpyrimidin-5-yl, 2-methylpyrimidin-4-yl, 6-methylpyrimidin-4-yl, 2-oxo-1,2,3,4-tetrahydroquinolin-6-yl, 3,5-dimethylisoxazol-4-yl, 2-methylpyridin-4-yl, 4-chloropyridin-2-yl, 2-methylpyridin-3-yl, 2-methylpyridin-4-yl, 2-ethoxypyridin-4-yl, 2-cyclopropylpyridin-4-yl, 1-methyl-1H-pyrazol-4-yl, 1-ethyl-1H-pyrazol-4-yl, 1-methyl-1H-pyrazol-3-yl, 2-ethyl-2H-pyrazol-3-yl, 1-benzyl-1H-pyrazol-4-yl, 2-methyl-2H-pyrazol-3-yl, 2-isopropyl-2H-pyrazol-3-yl, 1-methyl-1H-pyrazol-5-yl, 1-methyl-6-oxo-1,6-dihydropyridin-3-yl, 4-methylthiazol-2-yl, 1-methyl-1H-[1,2,4]triazol-3-yl, 5-chloropyrazin-2-yl, tetrahydropyran-4-yl, tetrahydropyran-3-yl, 2-methyl-tetrahydropyran-4-yl, 2,2-dimethyl-tetrahydropyran-4-yl, 2-hydroxymethyltetrahydropyran-4-yl, 3-fluorotetrahydropyran-4-yl, 1-methylpiperidin-4-yl, 1-methyl-5-oxo-pyrrolidin-3-yl, tetrahydrofuran-3-yl, cyclopentyl, 3-hydroxycyclopentyl, 3,3-difluorocyclopentyl, 4-hydroxycyclohexyl, 3,3-difluorocyclohexyl, 3-hydroxycyclobutyl and 4,4-difluorocyclohexyl. In another embodiment, $R^b$ is (S)-2-hydroxy-1-methyl-ethyl. In another embodiment, $R^b$ is (S)-1-hydroxymethyl-propyl. In another embodiment, $R^b$ is (1S,3S)-3-hydroxycyclopentyl. In another embodiment, $R^b$ is tetrahydropyran-4-yl. In another embodiment, $R^b$ is selected from (S)-2-hydroxy-1-methyl-ethyl, (S)-1-hydroxymethyl-propyl, (1S,3S)-3-hydroxycyclopentyl and tetrahydropyran-4-yl.

In another embodiment of the present invention there is provided a compound selected from TABLE I or II or a pharmaceutically acceptable salt of a compound from TABLE I or II.

In another embodiment of the present invention there is provided a compound selected from TABLE I or a pharmaceutically acceptable salt thereof.

In another embodiment of the present invention there is provided a compound selected from TABLE II or a pharmaceutically acceptable salt thereof.

In another embodiment of the present invention there is provided a compound according to formula I selected from the following compounds:

2-(2-fluoro-1-methyl-ethylamino)-5,8-dihydro-6H-pyrido[3,4-d]pyrimidine-7-carboxylic acid [1-(3,4-dichloro-phenyl)-2-hydroxy-ethyl]-amide, 2-(3,3,3-trifluoro-propylamino)-5,8-dihydro-6H-pyrido[3,4-d]pyrimidine-7-carboxylic acid 4-cyano-3-fluoro-benzylamide, 2-isopropylamino-5,8-dihydro-6H-pyrido[3,4-d]pyrimidine-7-carboxylic acid [(1S,2R)-1-(3-chloro-4-fluoro-phenyl)-2-hydroxy-propyl]-amide, 2-(3-hydroxy-cyclobutylamino)-5,8-dihydro-6H-pyrido[3,4-d]pyrimidine-7-carboxylic acid [1-(3,4-dichloro-phenyl)-ethyl]-amide, 2-isopropylamino-5,8-dihydro-6H-pyrido[3,4-d]pyrimidine-7-carboxylic acid [4-(3,4-difluoro-phenyl)-1-methyl-pyrrolidin-3-yl]-amide, 2-(tetrahydro-pyran-4-ylamino)-5,8-dihydro-6H-pyrido[3,4-d]pyrimidine-7-carboxylic acid [(S)-1-(4-fluoro-phenyl)-ethyl]-amide;

(R)-2-(tetrahydro-pyran-4-ylamino)-5,6,7,8-tetrahydro-quinazoline-7-carboxylic acid [(R)-1-(3,4-dichloro-phenyl)-ethyl]-amide;

(S)-2-(tetrahydro-pyran-4-ylamino)-5,6,7,8-tetrahydro-quinazoline-7-carboxylic acid [(R)-1-(3,4-dichloro-phenyl)-ethyl]-amide;

2-(tetrahydro-pyran-4-ylamino)-5,6,7,8-tetrahydro-quinazoline-7-carboxylic acid [1-(4-chloro-3-fluoro-phenyl)-ethyl]-amide;

7-(tetrahydro-pyran-4-ylamino)-3,4-dihydro-1H-[2,6]naphthyridine-2-carboxylic acid [(S)-1-(3,4-dichloro-phenyl)-2-hydroxy-ethyl]-amide;

7-(tetrahydro-pyran-4-ylamino)-3,4-dihydro-1H-[2,6]naphthyridine-2-carboxylic acid [(S)-1-(4-chloro-3-fluoro-phenyl)-2-hydroxy-ethyl]-amide;

7-(tetrahydro-pyran-4-ylamino)-3,4-dihydro-1H-[2,6]naphthyridine-2-carboxylic acid [(S)-1-(3-chloro-4-fluoro-phenyl)-2-hydroxy-ethyl]-amide;

(R)-2-(tetrahydro-pyran-4-ylamino)-5,6,7,8-tetrahydro-quinazoline-7-carboxylic acid [(S)-1-(4-chloro-3-fluoro-phenyl)-2-hydroxy-ethyl]-amide;

(S)-2-(tetrahydro-pyran-4-ylamino)-5,6,7,8-tetrahydro-quinazoline-7-carboxylic acid [(S)-1-(4-chloro-3-fluoro-phenyl)-2-hydroxy-ethyl]-amide;

(R)-2-(tetrahydro-pyran-4-ylamino)-6,7-dihydro-5H-pyrano[2,3-d]pyrimidine-7-carboxylic acid [(R)-1-(4-chloro-3-fluoro-phenyl)-propyl]-amide;

(R)-2-(tetrahydro-pyran-4-ylamino)-6,7-dihydro-5H-pyrano[2,3-d]pyrimidine-7-carboxylic acid [(S)-1-(4-difluoromethoxy-phenyl)-2-hydroxy-ethyl]-amide;

2-(4,4-difluoro-cyclohexylamino)-5,8-dihydro-6H-pyrido[3,4-d]pyrimidine-7-carboxylic acid [(R)-1-(3,4-dichloro-phenyl)-ethyl]-amide;

2-(tetrahydro-pyran-4-ylamino)-5,8-dihydro-6H-pyrido[3,4-d]pyrimidine-7-carboxylic acid methyl-(1-phenyl-ethyl)-amide;

2-(2-methyl-tetrahydro-pyran-4-ylamino)-5,8-dihydro-6H-pyrido[3,4-d]pyrimidine-7-carboxylic acid [1-(3,4-dichloro-phenyl)-ethyl]-amide;

2-(tetrahydro-pyran-4-ylamino)-5,8-dihydro-6H-pyrido[3,4-d]pyrimidine-7-carboxylic acid [(S)-1-(4-fluoro-phenyl)-propyl]-amide;

2-(4,4-difluoro-cyclohexylamino)-5,8-dihydro-6H-pyrido[3,4-d]pyrimidine-7-carboxylic acid [(S)-1-(4-chloro-3-fluoro-phenyl)-2-hydroxy-ethyl]-amide;

2-(4,4-difluoro-cyclohexylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-(2-methyl-tetrahydro-pyran-4-ylamino)-5,8-dihydro-6H-pyrido[3,4-d]pyrimidine-7-carboxylic acid [1-(4-chloro-3-fluoro-phenyl)-2-hydroxy-ethyl]-amide;

2-(2-methyl-tetrahydro-pyran-4-ylamino)-5,8-dihydro-6H-pyrido[3,4-d]pyrimidine-7-carboxylic acid [1-(3-chloro-4-fluoro-phenyl)-2-hydroxy-ethyl]-amide;

2-(tetrahydro-pyran-4-ylamino)-5,8-dihydro-6H-pyrido[3,4-d]pyrimidine-7-carboxylic acid [(S)-1-(4-difluoromethoxy-phenyl)-2-hydroxy-ethyl]-amide;

2-isopropylamino-5,8-dihydro-6H-pyrido[3,4-d]pyrimidine-7-carboxylic acid (4-phenyl-piperidin-4-yl)-amide;

2-isopropylamino-5,8-dihydro-6H-pyrido[3,4-d]pyrimidine-7-carboxylic acid [4-(4-chloro-3-fluoro-phenyl)-piperidin-4-yl]-amide;

2-(tetrahydro-pyran-4-ylamino)-5,8-dihydro-6H-pyrido[3,4-d]pyrimidine-7-carboxylic acid [(R)-1-(3-chloro-4-cyano-phenyl)-ethyl]-amide;

2-(1-methyl-6-oxo-1,6-dihydro-pyridin-3-ylamino)-5,8-dihydro-6H-pyrido[3,4-d]pyrimidine-7-carboxylic acid [(R)-1-(3,4-dichloro-phenyl)-ethyl]-amide;

2-(tetrahydro-pyran-4-ylamino)-5,8-dihydro-6H-pyrido[3,4-d]pyrimidine-7-carboxylic acid [(R)-1-(4-cyano-3-fluoro-phenyl)-ethyl]-amide;

2-(tetrahydro-pyran-4-ylamino)-5,8-dihydro-6H-pyrido[3,4-d]pyrimidine-7-carboxylic acid 3,4-dicyano-benzylamide;

7-methyl-2-(tetrahydro-pyran-4-ylamino)-5,6,7,8-tetrahydro-quinazoline-7-carboxylic acid [1-(3,4-dichloro-phenyl)-ethyl]-amide;

7-(tetrahydro-pyran-4-ylamino)-3,4-dihydro-1H-[2,6]naphthyridine-2-carboxylic acid [(R)-1-(3,4-dichloro-phenyl)-3-hydroxy-propyl]-amide;

7-methyl-2-(tetrahydro-pyran-4-ylamino)-5,6,7,8-tetrahydro-quinazoline-7-carboxylic acid [1-(4-chloro-3-fluoro-phenyl)-2-hydroxy-ethyl]-amide;

(R)-2-(tetrahydro-pyran-4-ylamino)-6,7-dihydro-5H-pyrano[2,3-d]pyrimidine-7-carboxylic acid [(R)-1-(3-fluoro-4-methoxy-phenyl)-propyl]-amide;

(R)-2-(tetrahydro-pyran-4-ylamino)-6,7-dihydro-5H-pyrano[2,3-d]pyrimidine-7-carboxylic acid [(R)-1-(3-fluoro-4-trifluoromethoxy-phenyl)-propyl]-amide;

2-(2,2-dimethyl-tetrahydro-pyran-4-ylamino)-5,8-dihydro-6H-pyrido[3,4-d]pyrimidine-7-carboxylic acid [1-(4-chloro-3-fluoro-phenyl)-2-hydroxy-ethyl]-amide;

2-(2,2-dimethyl-tetrahydro-pyran-4-ylamino)-5,8-dihydro-6H-pyrido[3,4-d]pyrimidine-7-carboxylic acid [1-(3-chloro-4-fluoro-phenyl)-2-hydroxy-ethyl]-amide;

2-(tetrahydro-pyran-4-ylamino)-5,8-dihydro-6H-pyrido[3,4-d]pyrimidine-7-carboxylic acid [(S)-1-(4-difluoromethoxy-phenyl)-propyl]-amide;

2-(tetrahydro-pyran-4-ylamino)-5,8-dihydro-6H-pyrido[3,4-d]pyrimidine-7-carboxylic acid [(R)-1-(3-fluoro-4-trifluoromethoxy-phenyl)-propyl]-amide;

2-isopropylamino-5,8-dihydro-6H-pyrido[3,4-d]pyrimidine-7-carboxylic acid [4-(3,4-dichloro-phenyl)-1-methyl-piperidin-4-yl]-amide;

2-isopropylamino-5,8-dihydro-6H-pyrido[3,4-d]pyrimidine-7-carboxylic acid [(R)-(4-chloro-3-fluoro-phenyl)-(R)-piperidin-2-yl-methyl]-amide;

2-(tetrahydro-pyran-4-ylamino)-5,8-dihydro-6H-pyrido[3,4-d]pyrimidine-7-carboxylic acid [(R)-1-(4-cyano-3-methyl-phenyl)-ethyl]-amide;

2-(tetrahydro-pyran-4-ylamino)-5,8-dihydro-6H-pyrido[3,4-d]pyrimidine-7-carboxylic acid [(R)-1-(3-chloro-4-cyano-phenyl)-propyl]-amide;

2-(tetrahydro-pyran-4-ylamino)-5,8-dihydro-6H-pyrido[3,4-d]pyrimidine-7-carboxylic acid [(R)-1-(4-cyano-3-fluoro-phenyl)-propyl]-amide;

2-(tetrahydro-pyran-4-ylamino)-5,8-dihydro-6H-pyrido[3,4-d]pyrimidine-7-carboxylic acid [(R)-1-(4-cyano-2-fluoro-phenyl)-propyl]-amide;

2-(1-methyl-6-oxo-1,6-dihydro-pyridin-3-ylamino)-5,8-dihydro-6H-pyrido[3,4-d]pyrimidine-7-carboxylic acid [(R)-1-(3-fluoro-4-trifluoromethyl-phenyl)-ethyl]-amide;

(R)-2-(tetrahydro-pyran-4-ylamino)-5,6,7,8-tetrahydro-quinazoline-7-carboxylic acid [(R)-1-(4-difluoromethoxy-phenyl)-propyl]-amide;

(S)-2-(tetrahydro-pyran-4-ylamino)-5,6,7,8-tetrahydro-quinazoline-7-carboxylic acid [(R)-1-(4-difluoromethoxy-phenyl)-propyl]-amide;

(R)-2-(tetrahydro-pyran-4-ylamino)-5,6,7,8-tetrahydro-quinazoline-7-carboxylic acid [(R)-1-(3-fluoro-4-trifluoromethoxy-phenyl)-propyl]-amide;

(S)-2-(tetrahydro-pyran-4-ylamino)-5,6,7,8-tetrahydro-quinazoline-7-carboxylic acid [(R)-1-(3-fluoro-4-trifluoromethoxy-phenyl)-propyl]-amide;

2-(tetrahydro-pyran-4-ylamino)-5,8-dihydro-6H-pyrido[3,4-d]pyrimidine-7-carboxylic acid {(R)-1-[4-(2,2,2-trifluoro-ethoxy)-phenyl]-propyl}-amide;

2-isopropylamino-5,8-dihydro-6H-pyrido[3,4-d]pyrimidine-7-carboxylic acid [(R)-1-(4-chloro-3-fluoro-phenyl)-2-(R)-piperidin-2-yl-ethyl]-amide;

2-(tetrahydro-pyran-4-ylamino)-5,8-dihydro-6H-pyrido[3,4-d]pyrimidine-7-carboxylic acid [(R)-1-(4-cyano-3-methyl-phenyl)-propyl]-amide;

2-((S)-2-hydroxy-1-methyl-ethylamino)-5,8-dihydro-6H-pyrido[3,4-d]pyrimidine-7-carboxylic acid [(R)-1-(4-chloro-3-fluoro-phenyl)-2-(R)-piperidin-2-yl-ethyl]-amide;

2-isopropylamino-5,8-dihydro-6H-pyrido[3,4-d]pyrimidine-7-carboxylic acid [(S)-(3-fluoro-4-trifluoromethyl-phenyl)-(6-oxo-1,6-dihydro-pyridin-2-yl)-methyl]-amide;

2-((1S,3S)-3-hydroxy-cyclopentylamino)-5,8-dihydro-6H-pyrido[3,4-d]pyrimidine-7-carboxylic acid [(R)-(3-chloro-4-fluoro-phenyl)-cyclopropyl-methyl]-amide;

2-(tetrahydro-furan-3-ylamino)-5,8-dihydro-6H-pyrido[3,4-d]pyrimidine-7-carboxylic acid [4-(3-fluoro-4-trifluoromethyl-phenyl)-1-methyl-pyrrolidin-3-yl]-amide;

2-((1S,3S)-3-hydroxy-cyclopentylamino)-5,8-dihydro-6H-pyrido[3,4-d]pyrimidine-7-carboxylic acid [(R)-(3-chloro-4-fluoro-phenyl)-cyclopentyl-methyl]-amide;

(2-Pyridin-2-yl-pyrrolidin-1-yl)-[2-(tetrahydro-pyran-4-ylamino)-5,8-dihydro-6H-pyrido[3,4-d]pyrimidin-7-yl]-methanone;

2-(tetrahydro-pyran-4-ylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide;

7-(tetrahydro-pyran-4-ylamino)-3,4-dihydro-1H-[2,6]naphthyridine-2-carboxylic acid [(3S,4R)-4-(4-chloro-3-fluoro-phenyl)-pyrrolidin-3-yl]-amide;

(R)-2-(tetrahydro-pyran-4-ylamino)-6,7-dihydro-5H-pyrano[2,3-d]pyrimidine-7-carboxylic acid [(S)-(4-chloro-3-fluoro-phenyl)-(R)-pyrrolidin-2-yl-methyl]-amide;

3-{1-[2-(tetrahydro-pyran-4-ylamino)-5,8-dihydro-6H-pyrido[3,4-d]pyrimidine-7-carbonyl]-pyrrolidin-2-yl}-benzonitrile;

2-(tetrahydro-pyran-4-ylamino)-5,8-dihydro-6H-pyrido[3,4-d]pyrimidine-7-carboxylic acid [(S)-(3,4-dichloro-phenyl)-(S)-pyrrolidin-2-yl-methyl]-amide;

2-(tetrahydro-pyran-4-ylamino)-5,8-dihydro-6H-pyrido[3,4-d]pyrimidine-7-carboxylic acid [(R)-(4-chloro-3-fluoro-phenyl)-(S)-morpholin-2-yl-methyl]-amide;

2-(tetrahydro-pyran-4-ylamino)-5,8-dihydro-6H-pyrido[3,4-d]pyrimidine-7-carboxylic acid [(R)-(4-chloro-3-fluoro-phenyl)-(R)-morpholin-2-yl-methyl]-amide;

2-(tetrahydro-pyran-4-ylamino)-5,8-dihydro-6H-pyrido[3,4-d]pyrimidine-7-carboxylic acid [(R)-(4-chloro-3-fluoro-phenyl)-(R)-morpholin-2-yl-methyl]-amide;

2-(tetrahydro-pyran-4-ylamino)-5,8-dihydro-6H-pyrido[3,4-d]pyrimidine-7-carboxylic acid [(S)-(4-chloro-3-fluoro-phenyl)-(R)-morpholin-2-yl-methyl]-amide;

2-(tetrahydro-pyran-4-ylamino)-5,8-dihydro-6H-pyrido[3,4-d]pyrimidine-7-carboxylic acid [(R)-(4-chloro-3-fluoro-phenyl)-(R)-piperidin-2-yl-methyl]-amide;

2-(tetrahydro-pyran-4-ylamino)-5,8-dihydro-6H-pyrido[3,4-d]pyrimidine-7-carboxylic acid [(3-chloro-4-fluoro-phenyl)-piperidin-4-yl-methyl]-amide;

2-(tetrahydro-pyran-4-ylamino)-5,8-dihydro-6H-pyrido[3,4-d]pyrimidine-7-carboxylic acid [(R)-1-(4-chloro-3-fluoro-phenyl)-2-(R)-piperidin-2-yl-ethyl]-amide;

2-(1-methyl-1H-[1,2,4]triazol-3-ylamino)-5,8-dihydro-6H-pyrido[3,4-d]pyrimidine-7-carboxylic acid [(R)-1-(3,4-dichloro-phenyl)-ethyl]-amide;

2-(4-methyl-thiazol-2-ylamino)-5,8-dihydro-6H-pyrido[3,4-d]pyrimidine-7-carboxylic acid [(R)-1-(3,4-dichloro-phenyl)-ethyl]-amide;

2-(1-methyl-1H-pyrazol-3-ylamino)-5,8-dihydro-6H-pyrido[3,4-d]pyrimidine-7-carboxylic acid [(R)-1-(3,4-dichloro-phenyl)-ethyl]-amide;

2-(2-methyl-2H-pyrazol-3-ylamino)-5,8-dihydro-6H-pyrido[3,4-d]pyrimidine-7-carboxylic acid [(R)-1-(3,4-dichloro-phenyl)-ethyl]-amide;

2-(1-methyl-1H-pyrazol-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-(1-methyl-1H-pyrazol-4-ylamino)-3,4-dihydro-1H-[2,6]naphthyridine-2-carboxylic acid [(R)-1-(3,4-dichloro-phenyl)-ethyl]-amide;

2-isopropylamino-5,8-dihydro-6H-pyrido[3,4-d]pyrimidine-7-carboxylic acid [(R)-(4-chloro-3-fluoro-phenyl)-oxazol-4-yl-methyl]-amide;

2-isopropylamino-5,8-dihydro-6H-pyrido[3,4-d]pyrimidine-7-carboxylic acid [(S)-(4-chloro-3-fluoro-phenyl)-oxazol-4-yl-methyl]-amide;

2-(3,5-dimethyl-isoxazol-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-isopropylamino-5,8-dihydro-6H-pyrido[3,4-d]pyrimidine-7-carboxylic acid [(3,4-dichloro-phenyl)-(2H-pyrazol-3-yl)-methyl]-amide;

2-(2-Ethyl-2H-pyrazol-3-ylamino)-5,8-dihydro-6H-pyrido[3,4-d]pyrimidine-7-carboxylic acid [(R)-1-(3,4-dichloro-phenyl)-ethyl]-amide;

2-(2-hydroxy-1-methyl-ethylamino)-5,8-dihydro-6H-pyrido[3,4-d]pyrimidine-7-carboxylic acid [(3,4-dichloro-phenyl)-(2H-pyrazol-3-yl)-methyl]-amide;

2-(3,5-dimethyl-isoxazol-4-ylamino)-5,8-dihydro-6H-pyrido[3,4-d]pyrimidine-7-carboxylic acid [3-amino-1-(3,4-dichloro-phenyl)-propyl]-amide;

2-(2-hydroxy-1-methyl-ethylamino)-5,8-dihydro-6H-pyrido[3,4-d]pyrimidine-7-carboxylic acid [(4-chloro-3-fluoro-phenyl)-(1-methyl-1H-pyrazol-4-yl)-methyl]-amide;

2-(2-isopropyl-2H-pyrazol-3-ylamino)-5,8-dihydro-6H-pyrido[3,4-d]pyrimidine-7-carboxylic acid [(S)-1-(4-chloro-3-fluoro-phenyl)-2-hydroxy-ethyl]-amide;

2-(2-isopropyl-2H-pyrazol-3-ylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-(3,5-dimethyl-isoxazol-4-ylamino)-5,8-dihydro-6H-pyrido[3,4-d]pyrimidine-7-carboxylic acid [(S)-1-(3-chloro-4-fluoro-phenyl)-2-methylamino-ethyl]-amide;

2-(tetrahydro-pyran-4-ylamino)-5,8-dihydro-6H-pyrido[3,4-d]pyrimidine-7-carboxylic acid [(R)-(4-chloro-3-fluoro-phenyl)-[1,3,4]oxadiazol-2-yl-methyl]-amide;

2-(tetrahydro-pyran-4-ylamino)-5,8-dihydro-6H-pyrido[3,4-d]pyrimidine-7-carboxylic acid [(S)-(4-chloro-3-fluoro-phenyl)-[1,3,4]oxadiazol-2-yl-methyl]-amide;

2-(tetrahydro-pyran-4-ylamino)-5,8-dihydro-6H-pyrido[3,4-d]pyrimidine-7-carboxylic acid [(3,4-dichloro-phenyl)-oxazol-5-yl-methyl]-amide;

2-(tetrahydro-pyran-4-ylamino)-5,8-dihydro-6H-pyrido[3,4-d]pyrimidine-7-carboxylic acid [(4-chloro-3-fluoro-phenyl)-oxazol-5-yl-methyl]-amide;

2-(tetrahydro-pyran-4-ylamino)-5,8-dihydro-6H-pyrido[3,4-d]pyrimidine-7-carboxylic acid [(R)-(4-chloro-3-fluoro-phenyl)-oxazol-5-yl-methyl]-amide;

2-(tetrahydro-pyran-4-ylamino)-5,8-dihydro-6H-pyrido[3,4-d]pyrimidine-7-carboxylic acid [(S)-(4-chloro-3-fluoro-phenyl)-isoxazol-5-yl-methyl]-amide;

2-(tetrahydro-pyran-4-ylamino)-5,8-dihydro-6H-pyrido[3,4-d]pyrimidine-7-carboxylic acid [(3,4-dichloro-phenyl)-(2H-pyrazol-3-yl)-methyl]-amide;

2-(tetrahydro-pyran-4-ylamino)-5,8-dihydro-6H-pyrido[3,4-d]pyrimidine-7-carboxylic acid [(4-chloro-3-fluoro-phenyl)-(5-methyl-[1,3,4]oxadiazol-2-yl)-methyl]-amide;

2-(tetrahydro-pyran-4-ylamino)-5,8-dihydro-6H-pyrido[3,4-d]pyrimidine-7-carboxylic acid [(4-chloro-3-fluoro-phenyl)-(3-methyl-[1,2,4]oxadiazol-5-yl)-methyl]-amide;

2-(tetrahydro-pyran-4-ylamino)-5,8-dihydro-6H-pyrido[3,4-d]pyrimidine-7-carboxylic acid [(R)-1-(3,4-dichloro-phenyl)-2-(4H-[1,2,4]triazol-3-yl)-ethyl]-amide;

2-(tetrahydro-pyran-4-ylamino)-5,8-dihydro-6H-pyrido[3,4-d]pyrimidine-7-carboxylic acid [(4-chloro-3-fluoro-phenyl)-(2-methyl-oxazol-5-yl)-methyl]-amide;

(R)-2-(tetrahydro-pyran-4-ylamino)-6,7-dihydro-5H-pyrano[2,3-d]pyrimidine-7-carboxylic acid [(S)-(4-chloro-3-fluoro-phenyl)-(1-methyl-1H-pyrazol-4-yl)-methyl]-amide;

2-(tetrahydro-pyran-4-ylamino)-5,8-dihydro-6H-pyrido[3,4-d]pyrimidine-7-carboxylic acid [(3-fluoro-4-trifluoromethoxy-phenyl)-oxazol-5-yl-methyl]-amide;

2-(tetrahydro-pyran-4-ylamino)-5,8-dihydro-6H-pyrido[3,4-d]pyrimidine-7-carboxylic acid [(S)-(3-fluoro-4-trifluoromethoxy-phenyl)-oxazol-5-yl-methyl]-amide;

2-(tetrahydro-pyran-4-ylamino)-5,8-dihydro-6H-pyrido[3,4-d]pyrimidine-7-carboxylic acid [(R)-(4-chloro-3-fluoro-phenyl)-(1-methyl-1H-pyrazol-4-yl)-methyl]-amide;

2-(tetrahydro-pyran-4-ylamino)-5,8-dihydro-6H-pyrido[3,4-d]pyrimidine-7-carboxylic acid [(4-chloro-3-fluoro-phenyl)-(2-methyl-2H-pyrazol-3-yl)-methyl]-amide;

2-(tetrahydro-pyran-4-ylamino)-5,8-dihydro-6H-pyrido[3,4-d]pyrimidine-7-carboxylic acid [(R)-(4-chloro-3-fluoro-phenyl)-(2-methyl-2H-pyrazol-3-yl)-methyl]-amide;

2-(5-chloro-pyrazin-2-ylamino)-5,8-dihydro-6H-pyrido[3,4-d]pyrimidine-7-carboxylic acid [(R)-1-(3,4-dichloro-phenyl)-ethyl]-amide;

2-(Pyrimidin-5-ylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-(5-chloro-pyrazin-2-ylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-(4-chloro-pyridin-2-ylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-(2-methyl-pyrimidin-4-ylamino)-5,8-dihydro-6H-pyrido[3,4-d]pyrimidine-7-carboxylic acid [(R)-1-(3,4-dichloro-phenyl)-ethyl]-amide;

2-(6-methyl-pyrimidin-4-ylamino)-5,8-dihydro-6H-pyrido[3,4-d]pyrimidine-7-carboxylic acid [(S)-1-(4-chloro-3-fluoro-phenyl)-2-hydroxy-ethyl]-amide;

2-(6-methyl-pyrimidin-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-(2-methyl-pyrimidin-4-ylamino)-5,8-dihydro-6H-pyrido[3,4-d]pyrimidine-7-carboxylic acid [(S)-1-(4-chloro-3-fluoro-phenyl)-2-hydroxy-ethyl]-amide;

2-(2-methyl-pyrimidin-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-(4-methyl-pyrimidin-5-ylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-(2-chloro-phenylamino)-5,8-dihydro-6H-pyrido[3,4-d]pyrimidine-7-carboxylic acid [(S)-1-(4-chloro-3-fluoro-phenyl)-2-hydroxy-ethyl]-amide;

2-(4-fluoro-phenylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-(4-chloro-3-fluoro-phenylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-(3-chloro-4-fluoro-phenylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-(2-chloro-4-fluoro-phenylamino)-5,8-dihydro-6H-pyrido[3,4-d]pyrimidine-7-carboxylic acid [(S)-1-(4-chloro-3-fluoro-phenyl)-2-hydroxy-ethyl]-amide;

2-(2-methyl-pyridin-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-(2-methyl-pyridin-3-ylamino)-5,8-dihydro-6H-pyrido[3,4-d]pyrimidine-7-carboxylic acid [(S)-1-(3-chloro-4-fluoro-phenyl)-2-hydroxy-ethyl]-amide;

7-(4-fluoro-phenylamino)-3,4-dihydro-1H-[2,6]naphthyridine-2-carboxylic acid [(S)-1-(3-chloro-4-fluoro-phenyl)-2-hydroxy-ethyl]-amide;

7-(2-methyl-pyridin-4-ylamino)-3,4-dihydro-1H-[2,6]naphthyridine-2-carboxylic acid [(R)-1-(3,4-dichloro-phenyl)-ethyl]-amide;

2-o-Tolylamino-5,8-dihydro-6H-pyrido[3,4-d]pyrimidine-7-carboxylic acid [(S)-1-(4-chloro-3-fluoro-phenyl)-2-hydroxy-ethyl]-amide;

2-(4-fluoro-2-methyl-phenylamino)-5,8-dihydro-6H-pyrido[3,4-d]pyrimidine-7-carboxylic acid [(S)-1-(4-chloro-3-fluoro-phenyl)-2-hydroxy-ethyl]-amide;

2-(4-fluoro-phenylamino)-5,8-dihydro-6H-pyrido[3,4-d]pyrimidine-7-carboxylic acid [(1S,2S)-1-(3-chloro-4-fluoro-phenyl)-2-hydroxy-propyl]-amide;

2-(4-fluoro-phenylamino)-5,8-dihydro-6H-pyrido[3,4-d]pyrimidine-7-carboxylic acid [3-amino-1-(3,4-dichloro-phenyl)-propyl]-amide;

2-(4-fluoro-phenylamino)-5,8-dihydro-6H-pyrido[3,4-d]pyrimidine-7-carboxylic acid [(S)-1-(3-chloro-4-fluoro-phenyl)-2-methylamino-ethyl]-amide;

2-(4-cyano-2-fluoro-phenylamino)-5,8-dihydro-6H-pyrido[3,4-d]pyrimidine-7-carboxylic acid [(S)-1-(4-chloro-3-fluoro-phenyl)-2-hydroxy-ethyl]-amide;

2-isopropylamino-5,8-dihydro-6H-pyrido[3,4-d]pyrimidine-7-carboxylic acid [(S)-1-(3-chloro-4-fluoro-phenyl)-2-(pyrimidin-4-ylamino)-ethyl]-amide;

2-isopropylamino-5,8-dihydro-6H-pyrido[3,4-d]pyrimidine-7-carboxylic acid [(S)-(3-fluoro-4-trifluoromethyl-phenyl)-(6-methoxy-pyridin-2-yl)-methyl]-amide;

7-(2-cyclopropyl-pyridin-4-ylamino)-3,4-dihydro-1H-[2,6]naphthyridine-2-carboxylic acid [(R)-1-(3,4-dichloro-phenyl)-ethyl]-amide;

2-(4-fluoro-phenylamino)-5,8-dihydro-6H-pyrido[3,4-d]pyrimidine-7-carboxylic acid [3-(4-chloro-phenyl)-pyrrolidin-3-yl]-amide;

2-(2-chloro-4-fluoro-phenylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide;

2-(4-fluoro-2-methyl-phenylamino)-5,8-dihydro-6H-pyrido[3,4-d]pyrimidine-7-carboxylic acid [(3S,4R)-4-(3-fluoro-phenyl)-pyrrolidin-3-yl]-amide;

2-o-tolylamino-5,8-dihydro-6H-pyrido[3,4-d]pyrimidine-7-carboxylic acid [(3S,4R)-4-(3,4-difluoro-phenyl)-pyrrolidin-3-yl]-amide;

2-(4-fluoro-2-methyl-phenylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide;

2-(2-chloro-4-fluoro-phenylamino)-5,8-dihydro-6H-pyrido[3,4-d]pyrimidine-7-carboxylic acid [(S)-(4-chloro-3-fluoro-phenyl)-(S)-pyrrolidin-2-yl-methyl]-amide;

2-(2-chloro-4-fluoro-phenylamino)-5,8-dihydro-6H-pyrido[3,4-d]pyrimidine-7-carboxylic acid [(3S,4R)-4-(4-chloro-3-fluoro-phenyl)-1-methyl-pyrrolidin-3-yl]-amide;

2-(4-fluoro-phenylamino)-5,8-dihydro-6H-pyrido[3,4-d]pyrimidine-7-carboxylic acid [(3S,4R)-4-(3-fluoro-4-trifluoromethyl-phenyl)-pyrrolidin-3-yl]-amide;

2-(4-fluoro-2-trifluoromethyl-phenylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide;

2-(2-oxo-1,2,3,4-tetrahydro-quinolin-6-ylamino)-5,8-dihydro-6H-pyrido[3,4-d]pyrimidine-7-carboxylic acid [(S)-1-(3-chloro-4-fluoro-phenyl)-2-hydroxy-ethyl]-amide;

2-(1-benzyl-1H-pyrazol-4-ylamino)-5,8-dihydro-6H-pyrido[3,4-d]pyrimidine-7-carboxylic acid [(R)-1-(3,4-dichloro-phenyl)-ethyl]-amide;

2-((S)-2-hydroxy-1-methyl-ethylamino)-5,8-dihydro-6H-pyrido[3,4-d]pyrimidine-7-carboxylic acid (benzothiazol-2-ylmethyl)-amide;

2-((S)-2-hydroxy-1-methyl-ethylamino)-5,8-dihydro-6H-pyrido[3,4-d]pyrimidine-7-carboxylic acid (benzooxazol-2-ylmethyl)-amide;

2-((S)-2-hydroxy-1-methyl-ethylamino)-5,8-dihydro-6H-pyrido[3,4-d]pyrimidine-7-carboxylic acid (1H-benzoimidazol-2-ylmethyl)-amide;

2-isopropylamino-5,8-dihydro-6H-pyrido[3,4-d]pyrimidine-7-carboxylic acid (1H-indol-2-ylmethyl)-amide;

2-isopropylamino-5,8-dihydro-6H-pyrido[3,4-d]pyrimidine-7-carboxylic acid (1H-indol-6-ylmethyl)-amide;

2-isopropylamino-5,8-dihydro-6H-pyrido[3,4-d]pyrimidine-7-carboxylic acid (5-fluoro-1H-indol-2-ylmethyl)-amide;

2-isopropylamino-5,8-dihydro-6H-pyrido[3,4-d]pyrimidine-7-carboxylic acid (1-benzothiazol-2-yl-ethyl)-amide;

2-((S)-2-hydroxy-1-methyl-ethylamino)-5,8-dihydro-6H-pyrido[3,4-d]pyrimidine-7-carboxylic acid (1H-indol-6-ylmethyl)-amide;

2-((S)-2-hydroxy-1-methyl-ethylamino)-5,8-dihydro-6H-pyrido[3,4-d]pyrimidine-7-carboxylic acid (1H-indol-5-ylmethyl)-amide;

2-((S)-2-hydroxy-1-methyl-ethylamino)-5,8-dihydro-6H-pyrido[3,4-d]pyrimidine-7-carboxylic acid (1H-indol-7-ylmethyl)-amide;

2-isopropylamino-5,8-dihydro-6H-pyrido[3,4-d]pyrimidine-7-carboxylic acid [1-(1H-benzoimidazol-2-yl)-ethyl]-amide;

2-((S)-2-hydroxy-1-methyl-ethylamino)-5,8-dihydro-6H-pyrido[3,4-d]pyrimidine-7-carboxylic acid (1-methyl-1H-indol-6-ylmethyl)-amide;

2-(tetrahydro-pyran-4-ylamino)-5,8-dihydro-6H-pyrido[3,4-d]pyrimidine-7-carboxylic acid (1H-indol-6-ylmethyl)-amide;

2-(tetrahydro-pyran-4-ylamino)-5,8-dihydro-6H-pyrido[3,4-d]pyrimidine-7-carboxylic acid (5-fluoro-1H-indol-2-ylmethyl)-amide;

2-(tetrahydro-pyran-4-ylamino)-5,8-dihydro-6H-pyrido[3,4-d]pyrimidine-7-carboxylic acid [(R)-1-(1H-indol-6-yl)-ethyl]-amide;

2-(tetrahydro-pyran-4-ylamino)-5,8-dihydro-6H-pyrido[3,4-d]pyrimidine-7-carboxylic acid [(S)-1-(1H-indol-6-yl)-ethyl]-amide;

2-(4-fluoro-phenylamino)-5,8-dihydro-6H-pyrido[3,4-d]pyrimidine-7-carboxylic acid (1-benzothiazol-2-yl-ethyl)-amide;

2-(4-fluoro-phenylamino)-5,8-dihydro-6H-pyrido[3,4-d]pyrimidine-7-carboxylic acid [1-(1H-benzoimidazol-2-yl)-ethyl]-amide;

(R)-2-(tetrahydro-pyran-4-ylamino)-6,7-dihydro-5H-pyrano[2,3-d]pyrimidine-7-carboxylic acid [(S)-(4-chloro-3-fluoro-phenyl)-(1-methyl-1H-pyrazol-4-yl)-methyl]-amide;

(R)-2-(tetrahydro-pyran-4-ylamino)-6,7-dihydro-5H-pyrano[2,3-d]pyrimidine-7-carboxylic acid [(R)-1-(3-fluoro-4-methoxy-phenyl)-propyl]-amide;

2-(tetrahydro-pyran-4-ylamino)-5,8-dihydro-6H-pyrido[3,4-d]pyrimidine-7-carboxylic acid [(3R,4R)-4-(4-chloro-3-fluoro-phenoxy)-1-methyl-pyrrolidin-3-yl]-amide;

2-(tetrahydro-pyran-4-ylamino)-5,8-dihydro-6H-pyrido[3,4-d]pyrimidine-7-carboxylic acid [(3S,4S)-4-(4-chloro-3-fluoro-phenoxy)-1-methyl-pyrrolidin-3-yl]-amide;

or a tautomer, stereoisomer or a pharmaceutically acceptable salt thereof.

In another embodiment of the present invention there is provided a method of inhibiting ERK protein kinase activity in a cell comprising treating the cell with a compound according to formula I wherein $R^1$, $R^2$, $R^{3a}$, $R^{3b}$, $R^a$, $R^b$, $R^c$, $R^d$, $R^e$, $R^f$, $R^g$, Y, $Y^1$, Z, $Z^1$, $Z^2$, $Z^3$ are as defined herein above or a tautomer, stereoisomer or a pharmaceutically acceptable salt thereof.

In another embodiment of the present invention there is provided a method of inhibiting ERK protein kinase activity in a patient in need thereof comprising the step of administering to said patient a compound according to formula I, wherein $R^1$, $R^2$, $R^{3a}$, $R^{3b}$, $R^a$, $R^b$, $R^c$, $R^d$, $R^e$, $R^f$, $R^g$, Y, $Y^1$, Z, $Z^1$, $Z^2$, $Z^3$ are as defined herein above or a tautomer, stereoisomer or a pharmaceutically acceptable salt thereof.

In another embodiment of the present invention there is provided a method of treating or ameliorating the severity of a hyperproliferative disorder in a patient in need thereof comprising administering to said patient a compound according to formula I wherein $R^1$, $R^2$, $R^{3a}$, $R^{3b}$, $R^a$, $R^b$, $R^c$, $R^d$, $R^e$, $R^f$, $R^g$, $Y^1$, Z, $Z^1$, $Z^2$, $Z^3$ are as defined herein above or a pharmaceutically acceptable salt thereof.

In another embodiment of the present invention there is provided a method of treating or ameliorating the severity of a hyperproliferative disorder comprising administering a compound according to formula I, or a pharmaceutically acceptable salt thereof, wherein in said hyperproliferative disorder is selected from the group consisting of adenoma, bladder cancer, brain cancer, breast cancer, colon cancer, epidermal carcinoma, follicular carcinoma, cancer of the genitourinary tract, glioblastoma, Hodgkin's disease, head and neck cancers, hepatoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer, and undifferentiated carcinoma.

In another embodiment the hyperproliferative disorder is melanoma.

In another embodiment the hyperproliferative disorder is pancreatic cancer.

In another embodiment the hyperproliferative disorder is thyroid cancer.

In another embodiment the hyperproliferative disorder is colorectal cancer.

In another embodiment the hyperproliferative disorder is lung cancer.

In another embodiment the hyperproliferative disorder is breast cancer.

In another embodiment the hyperproliferative disorder is ovarian cancer.

In another embodiment the hyperproliferative disorder is acute myelogenous leukemia.

In another embodiment the hyperproliferative disorder is chronic myelomonocytic leukemia.

In another embodiment the hyperproliferative disorder is chronic myelogenous leukemia.

In another embodiment the hyperproliferative disorder is multiple myeloma.

In another embodiment the hyperproliferative disorder is myeloid leukemia.

In another embodiment of the present invention there is provided a method of treating or ameliorating the severity of a hyperproliferative disorder comprising co-administering a compound according to formula I, or a pharmaceutically acceptable salt thereof, with at least one other chemotherapeutic agent used to treat or ameliorate a hyperproliferative disorder.

In another embodiment of the present invention there is provided a method of treating or ameliorating the severity of an inflammatory disorder comprising administering a compound according to formula I, or a pharmaceutically acceptable salt thereof.

In another embodiment of the present invention there is provided a method of treating or ameliorating the severity of pain comprising administering a compound according to formula I, or a pharmaceutically acceptable salt thereof.

In certain embodiments, the inflammatory disorder may be selected from arthritis, low back pain, inflammatory bowel disease, and rheumatism.

In another embodiment of the present invention there is provided a composition comprising a compound according to formula I, or a pharmaceutically acceptable salt thereof, and at least one pharmaceutically acceptable carrier, excipient or diluent.

Commonly used abbreviations include: acetyl (Ac), aqueous (aq.), atmospheres (Atm), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), diphenylphosphoryl azide (DPPA), N,N-dimethyl acetamide (DMA), 4-N,N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-hydroxy-7-aza-benzotriazole (HOAt), 1-N-hydroxybenzotriazole (HOBt), high pressure liquid chromatography (HPLC), isopropanol (IPA), lithium diisopropylamide (LDA), methanol (MeOH), melting point (mp), $MeSO_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), saturated (satd.), tert-butyldimethylsilyl or t-$BuMe_2Si$ (TBDMS), tetrabutyl ammonium fluoride (TBAF), triethylamine (TEA or $Et_3N$), triflate or $CF_3SO_2$— (Tf), trifluoroacetic acid (TFA), O-benzotriazol-1-yl-N,N,N', N'-tetramethyluronium tetrafluoroborate (TBTU), thin layer chromatography (TLC), tetrahydrofuran (THF), tetramethylethylenediamine (TMEDA), trimethylsilyl or $Me_3Si$ (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n-), iso (i-), secondary (sec-), tertiary (tert-) and neo- have their customary meaning when used with an alkyl moiety. (J. Rigaudy and D. P. Klesney, Nomenclature in Organic Chemistry, IUPAC 1979 Pergamon Press, Oxford.).

Compounds and Preparation

Examples of representative compounds within the scope of the invention are provided in the following Tables. These examples and preparations which follow are provided to enable those skilled in the art to more clearly understand and to practice the present invention. They should not be considered as limiting the scope of the invention, but merely as being illustrative and representative thereof.

If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. The following numbering system is used herein.

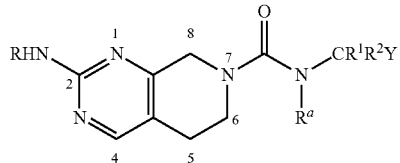

TABLE 1

| | | |
|---|---|---|
| I-1 | 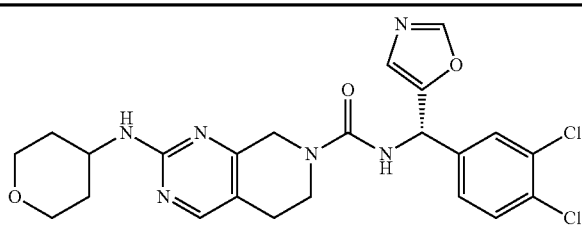 | 2-(Tetrahydro-pyran-4-ylamino)-5,8-dihydro-6H-pyrido[3,4-d]pyrimidine-7-carboxylic acid [(S)-(3,4-dichloro-phenyl)-oxazol-5-yl-methyl]-amide |
| I-2 | 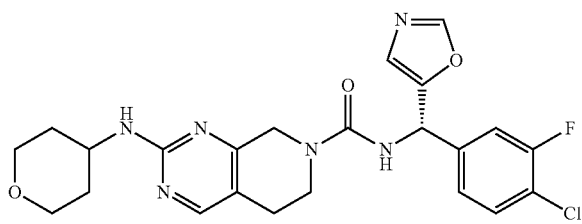 | 2-(Tetrahydro-pyran-4-ylamino)-5,8-dihydro-6H-pyrido[3,4-d]pyrimidine-7-carboxylic acid [(S)-(4-chloro-3-fluoro-phenyl)-oxazol-5-yl-methyl]amide |
| I-3 | 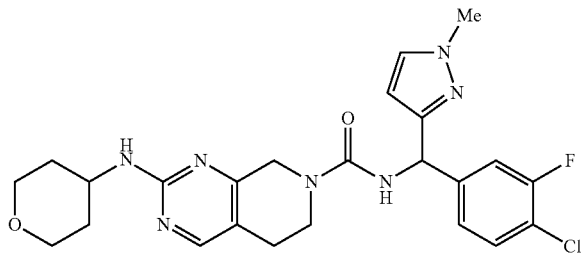 | 2-(Tetrahydro-pyran-4-ylamino)-5,8-dihydro-6H-pyrido[3,4-d]pyrimidine-7-carboxylic acid [(4-chloro-3-fluoro-phenyl)-(1-methyl-1H-pyrazol-3-yl)-methyl]-amide |
| I-4 | 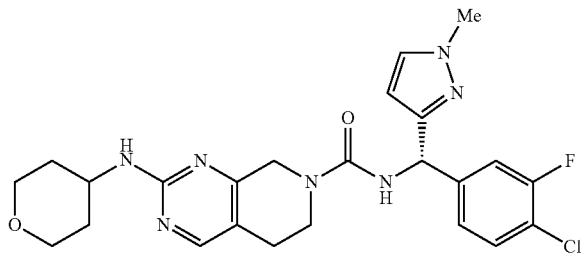 [SMILES: Cn1ccc(C(NC(=O)N2CCc3cnc(NC4CCOCC4)nc3C2)c2ccc(Cl)c(F)c2)n1] | 2-(Tetrahydro-pyran-4-ylamino)-5,8-dihydro-6H-pyrido[3,4-d]pyrimidine-7-carboxylic acid [(S)-(4-chloro-3-fluoro-phenyl)-(1-methyl-1H-pyrazol-3-yl)-methyl]-amide |
| I-5 | 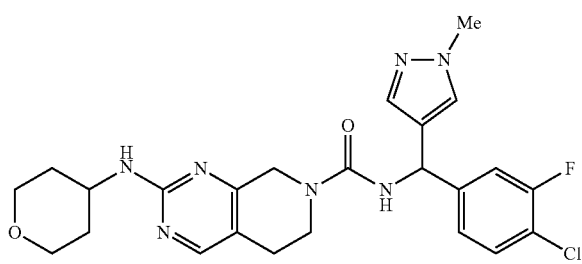 [SMILES: Cn1cc(C(NC(=O)N2CCc3cnc(NC4CCOCC4)nc3C2)c2ccc(Cl)c(F)c2)cn1] | 2-(Tetrahydro-pyran-4-ylamino)-5,8-dihydro-6H-pyrido[3,4-d]pyrimidine-7-carboxylic acid [(4-chloro-3-fluoro-phenyl)-(1-methyl-1H-pyrazol-4-yl)-methyl]-amide |

TABLE 1-continued

| | | |
|---|---|---|
| I-6 | 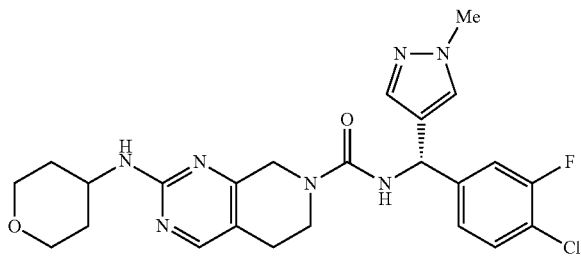 [SMILES: Cn1cc([C@@H](NC(=O)N2CCc3cnc(NC4CCOCC4)nc3C2)c2ccc(Cl)c(F)c2)cn1] | 2-(Tetrahydro-pyran-4-ylamino)-5,8-dihydro-6H-pyrido[3,4-d]pyrimidine-7-carboxylic acid [(S)-(4-chloro-3-fluoro-phenyl)-(1-methyl-1H-pyrazol-4-yl)-methyl]-amide |
| I-7 | 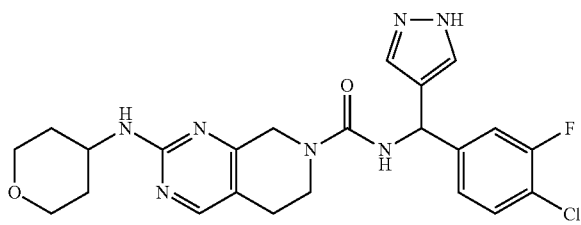 | 2-(Tetrahydro-pyran-4-ylamino)-5,8-dihydro-6H-pyrido[3,4-d]pyrimidine-7-carboxylic acid [(4-chloro-3-fluoro-phenyl)-(1H-pyrazol-4-yl)-methyl]-amide |
| I-8 | 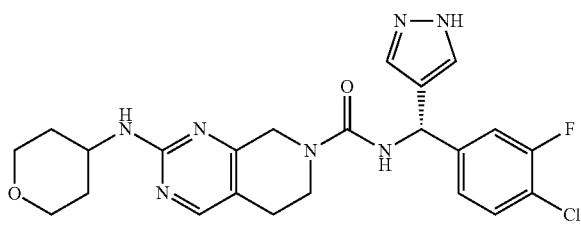 [SMILES: O=C(NC(c1cn[nH]c1)c1ccc(Cl)c(F)c1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(S)-(4-chloro-3-fluoro-phenyl)-(1H-pyrazol-4-yl)-methyl]-amide |
| I-9 | 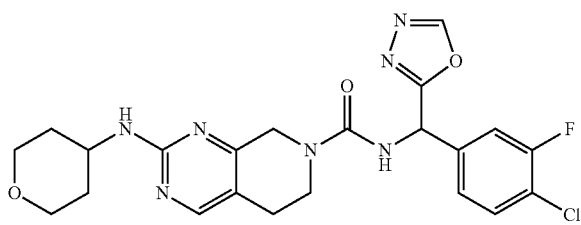 [SMILES: O=C(NC(c1ccc(Cl)c(F)c1)c1nnco1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(4-chloro-3-fluoro-phenyl)-[1,3,4]oxadiazol-2-yl-methyl]-amide |
| I-10 | 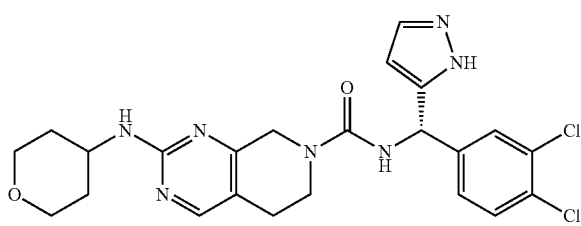 [SMILES: O=C(N[C@@H](c1ccc(Cl)c(Cl)c1)c1ccn[nH]1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(R)-(3,4-dichloro-phenyl)-(2H-pyrazol-3-yl)-methyl]-amide |
| I-11 | 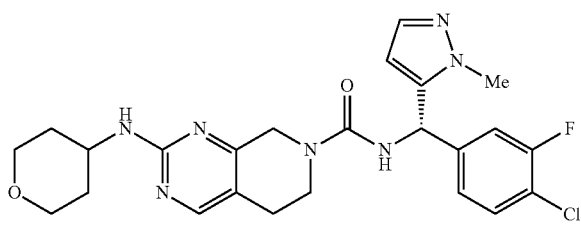 [SMILES: Cn1nccc1[C@@H](NC(=O)N1CCc2cnc(NC3CCOCC3)nc2C1)c1ccc(Cl)c(F)c1] | 2-(Tetrahydro-pyran-4-ylamino)-5,8-dihydro-6H-pyrido[3,4-d]primidine-7-carboxylic acid [(S)-(4-chloro-3-fluoro-phenyl)-(2-methyl-2H-pyrazol-3-yl)-methyl]-amide |
| I-12 | 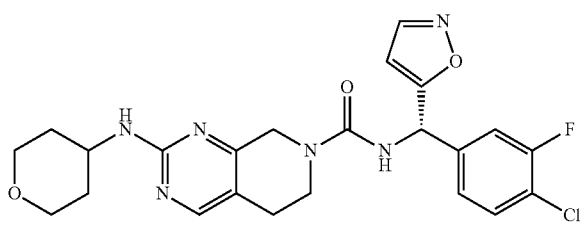 [SMILES: O=C(N[C@@H](c1ccc(Cl)c(F)c1)c1ccno1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(4-chloro-3-fluoro-phenyl)-isoxazol-5-yl-methyl]-amide |

TABLE 1-continued

| | | |
|---|---|---|
| I-13 | | 2-(Tetrahydro-pyran-4-ylamino)-5,8-dihydro-6H-pyrido[3,4-d]pyrimidine-7-carboxylic acid [(R)-(3-fluoro-4-trifluoromethoxy-phenyl)-oxazol-5-yl-methyl]-amide |
| I-14 | | 2-(Tetrahydro-pyran-4-ylamino)-5,8-dihydro-6H-pyrido[3,4-d]pyrimidine-7-carboxylic acid [(S)-1-(4-chloro-3-fluoro-phenyl)-2-hydroxy-ethyl]-amide |
| I-15 | | 2-Isopropylamino-5,8-dihydro-6H-pyrido[3,4-d]pyrimidine-7-carboxylic acid [(S)-(3-fluoro-4-trifluoromethyl-phenyl)-(R)-pyrrolidin-2-yl-methyl]-amide |
| I-16 | | 2-Isopropylamino-5,8-dihydro-6H-pyrido[3,4-d]pyrimidine-7-carboxylic acid [(S)-1-(3,4-dichloro-phenyl)-2-hydroxy-ethyl]-amide |
| I-17 | | (S)-3-(4-Chloro-3-fluoro-phenyl)-1-(2-isopropylamino-5,8-dihydro-6H-pyrido[3,4-d]pyrimidin-7-yl)-4-methylamino-butan-1-one |
| I-18 | | 2-Isopropylamino-5,8-dihydro-6H-pyrido[3,4-d]pyrimidine-7-carboxylic acid [(1S,2S)-1-(2-fluoro-3-trifluoromethyl-phenyl)-2-hydroxy-propyl]-amide |
| I-19 | | 2-Isopropylamino-5,8-dihydro-6H-pyrido[3,4-d]pyrimidine-7-carboxylic acid [(1S,2R)-1-(2-fluoro-3-trifluoromethyl-phenyl)-2-hydroxy-propyl]-amide |

TABLE 1-continued

| | | |
|---|---|---|
| I-20 | 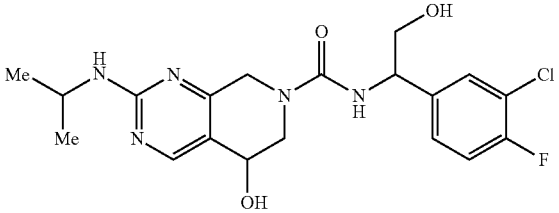 [SMILES: CC(C)Nc1ncc2c(n1)CN(C(=O)NC(CO)c1ccc(F)c(Cl)c1)CC2O] | 5-Hydroxy-2-isopropylamino-5,8-dihydro-6H-pyrido[3,4-d]pyrimidine-7-carboxylic acid [1-(3-chloro-4-fluoro-phenyl)-2-hydroxy-ethyl]-amide |
| I-21 | 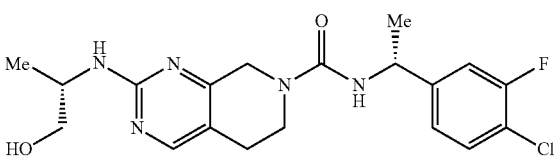 | 2-((S)-2-Hydroxy-1-methyl-ethylamino)-5,8-dihydro-6H-pyrido[3,4-d]primidine-7-carboxylic acid [(R)-1-(4-chloro-3-fluoro-phenyl)-ethyl]-amide |
| I-22 | 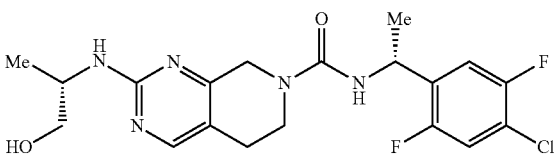 [SMILES: C[C@@H](CO)Nc1ncc2c(n1)CN(C(=O)N[C@H](C)c1cc(F)c(Cl)cc1F)CC2] | 2-((S)-2-Hydroxy-1-methyl-ethylamino)-5,8-dihydro-6H-pyrido[3,4-d]pyrimidine-7-carboxylic acid [(R)-1-(4-chloro-2,5-difluoro-phenyl)-ethyl]-amide |
| I-23 | 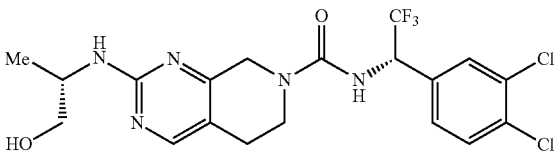 [SMILES: C[C@@H](CO)Nc1ncc2c(n1)CN(C(=O)N[C@@H](c1ccc(Cl)c(Cl)c1)C(F)(F)F)CC2] | 2-(S)-2-Hydroxy-1-methyl-ethylamino)-5,8-dihydro-6H-pyrido[3,4-d]pyrimidine-7-carboxylic acid [(S)-1-(3,4-dichloro-phenyl)-2,2,2-trifluoro-ethyl]-amide |
| I-24 | 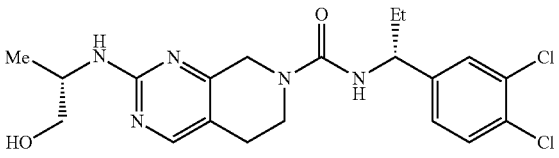 [SMILES: CC[C@@H](NC(=O)N1CCc2cnc(N[C@@H](C)CO)nc2C1)c1ccc(Cl)c(Cl)c1] | 2-((S)-2-Hydroxy-1-methyl-ethylamino)-5,8-dihydro-6H-pyrido[3,4-d]pyrimidine-7-carboxylic acid [(R)-1-(3,4-dichloro-phenyl)-propyl]-amide |
| I-25 | 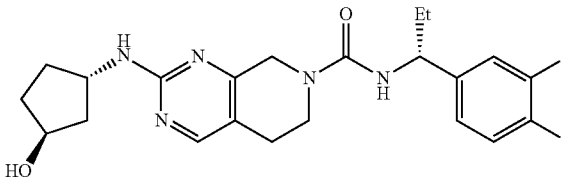 | 2-((1S,3S)-3-Hydroxy-cyclopentylamino)-5,8-dihydro-6H-pyrido[3,4-d]pyrimidine-7-carboxylic acid [(R)-1-(3,4-dichloro-phenyl)-propyl]-amide |
| I-26 | 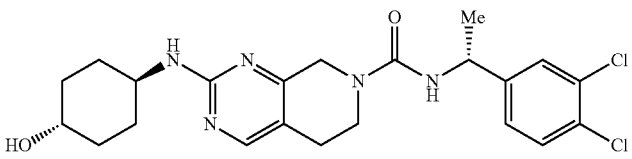 [SMILES: C[C@@H](NC(=O)N1CCc2cnc(N[C@H]3CC[C@H](O)CC3)nc2C1)c1ccc(Cl)c(Cl)c1] | 2-(4-Hydroxy-cyclohexylamino)-5,8-dihydro-6H-pyrido[3,4-d]pyrimidine-7-carboxylic acid [(R)-1-(3,4-dichloro-phenyl)-ethyl]-amide |
| I-27 | 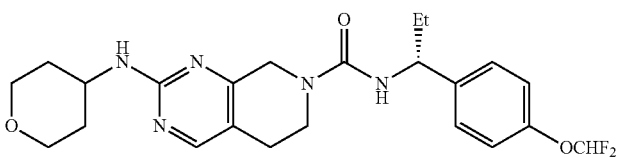 [SMILES: CC[C@@H](NC(=O)N1CCc2cnc(NC3CCOCC3)nc2C1)c1ccc(OC(F)F)cc1] | 2-(Tetrahydro-pyran-4-ylamino)-5,8-dihydro-6H-pyrido[3,4-d]pyrimidine-7-carboxylic acid [(R)-1-(4-difluoromethoxy-phenyl)-propyl]-amide |
| I-28 | 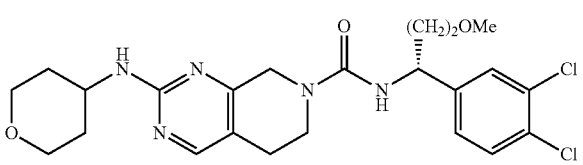 | 2-(Tetrahydro-pyran-4-ylamino)-5,8-dihydro-6H-pyrido[3,4-d]pyrimidine-7-carboxylic acid [(R)-1-(3,4-dichloro-phenyl)-3-methoxy-propyl]-amide |

TABLE 1-continued

| | | |
|---|---|---|
| I-29 | | 2-(2-Methyl-2H-pyrazol-3-ylamino)-5,8-dihydro-6H-pyrido[3,4-d]pyrimidine-7-carboxylic acid [(R)-1-(3,4-dichloro-phenyl)-ethyl]-amide |
| I-30 | | 2-(1-Ethyl-1H-pyrazol-4-ylamino)-5,8-dihydro-6H-pyrido[3,4-d]pyrimidine-7-carboxylic acid [(R)-1-(3,4-dichloro-phenyl)-ethyl]-amide |
| I-31 | | 2-(1-Methyl-1H-pyrazol-4-ylamino)-5,8-dihydro-6H-pyrido[3,4-d]pyrimidine-7-carboxylic acid [(R)-1-(3,4-dichloro-phenyl)-ethyl]-amide |
| I-32 | | 2-((S)-2-Hydroxy-1-methyl-ethylamino)-5,8-dihydro-6H-pyrido[3,4-d]pyrimidine-7-carboxylic acid [(R)-1-(3,4-dichloro-phenyl)-2-methyl-propyl]-amide |
| I-33 | | 2-((S)-2-Hydroxy-1-methyl-ethylamino)-5,8-dihydro-6H-pyrido[3,4-d]pyrimidine-7-carboxylic acid [(R)-1-(3,4-dichloro-phenyl)-3-hydroxy-propyl]-amide |
| I-34 | | 2-((S)-2-Hydroxy-1-methyl-ethylamino)-5,8-dihydro-6H-pyrido[3,4-d]pyrimidine-7-carboxylic acid [1-(3,4-dichloro-phenyl)-3,3,3-trifluoro-propyl]-amide |
| I-35 | | 2-(2-Ethoxy-pyridin-4-ylamino)-5,8-dihydro-6H-pyrido[3,4-d]pyrimidine-7-carboxylic acid [(R)-1-(3,4-dichloro-phenyl)-ethyl]-amide |
| I-36 | | 2-(2-Methyl-pyridin-4-ylamino)-5,8-dihydro-6H-pyrido[3,4-d]pyrimidine-7-carboxylic acid [(R)-1-(3,4-dichloro-phenyl)-ethyl]-amide |
| I-37 | | 2-((1S,3S)-3-Hydroxy-cyclopentylamino)-5,8-dihydro-6H-pyrido[3,4-d]pyrimidine-7-carboxylic acid [(R)-1-(3-fluoro-4-trifluoromethyl-phenyl)-propyl]-amide |

TABLE 1-continued

| ID | Structure | Name |
|---|---|---|
| I-38 | 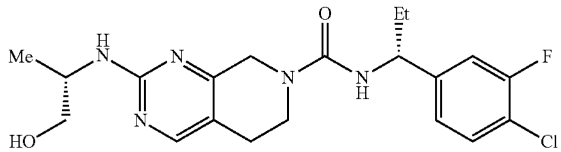 [SMILES: CC[C@@H](NC(=O)N1CCc2cnc(N[C@@H](C)CO)nc2C1)c1ccc(Cl)c(F)c1] | 2-((S)-2-Hydroxy-1-methyl-ethylamino)-5,8-dihydro-6H-pyrido[3,4-d]pyrimidine-7-carboxylic acid [(R)-1-(4-chloro-3-fluoro-phenyl)-propyl]-amide |
| I-39 | 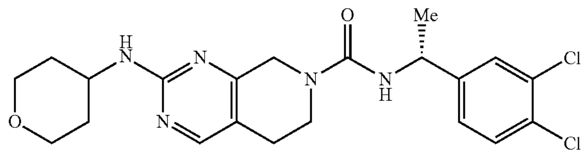 [SMILES: C[C@@H](NC(=O)N1CCc2cnc(NC3CCOCC3)nc2C1)c1ccc(Cl)c(Cl)c1] | 2-(Tetrahydro-pyran-4-ylamino)-5,8-dihydro-6H-pyrido[3,4-d]pyrimidine-7-carboxylic acid [(R)-1-(3,4-dichloro-phenyl)-ethyl]-amide |
| I-40 | 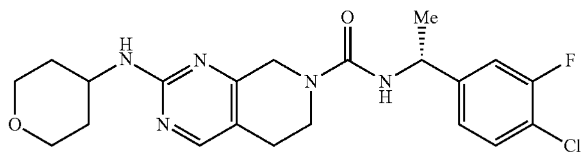 [SMILES: C[C@@H](NC(=O)N1CCc2cnc(NC3CCOCC3)nc2C1)c1ccc(Cl)c(F)c1] | 2-(Tetrahydro-pyran-4-ylamino)-5,8-dihydro-6H-pyrido[3,4-d]pyrimidine-7-carboxylic acid [(R)-1-(4-chloro-3-fluoro-phenyl)-ethyl]-amide |
| I-41 | 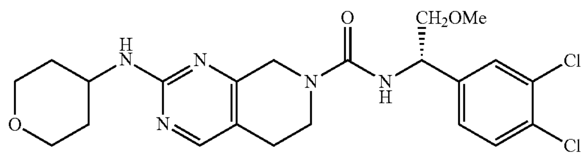 | 2-(Tetrahydro-pyran-4-ylamino)-5,8-dihydro-6H-pyrido[3,4-d]pyrimidine-7-carboxylic acid [(S)-1-(3,4-dichloro-phenyl)-2-methoxy-ethyl]-amide |
| I-42 | 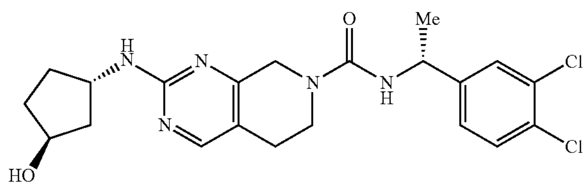 [SMILES: C[C@@H](NC(=O)N1CCc2cnc(N[C@H]3CC[C@H](O)C3)nc2C1)c1ccc(Cl)c(Cl)c1] | 2-((1S,3S)-3-Hydroxy-cyclopentylamino)-5,8-dihydro-6H-pyrido[3,4-d]pyrimidine-7-carboxylic acid [(R)-1-(3,4-dichloro-phenyl)-ethyl]-amide |
| I-43 | 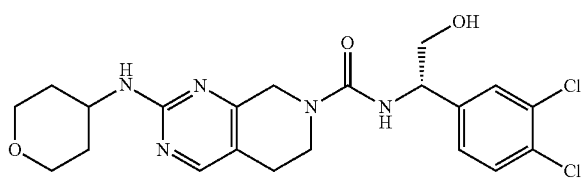 [SMILES: O=C(N[C@H](CO)c1ccc(Cl)c(Cl)c1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(S)-1-(3,4-dichloro-phenyl)-2-hydroxy-ethyl]-amide |
| I-44 | 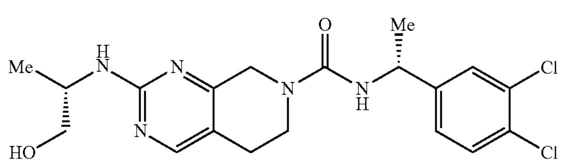 [SMILES: C[C@@H](CO)Nc1ncc2c(n1)CN(C(=O)N[C@H](C)c1ccc(Cl)c(Cl)c1)CC2] | 2-((S)-2-Hydroxy-1-methyl-ethylamino)-5,8-dihydro-6H-pyrido[3,4-d]pyrimidine-7-carboxylic acid [(R)-1-(3,4-dichloro-phenyl)-ethyl]-amide |
| I-45 | 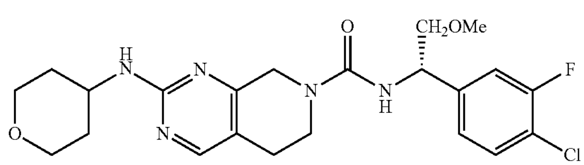 | 2-(Tetrahydro-pyran-4-ylamino)-5,8-dihydro-6H-pyrido[3,4-d]pyrimidine-7-carboxylic acid [(S)-1-(4-chloro-3-fluoro-phenyl)-2-methoxy-ethyl]-amide |
| I-46 | 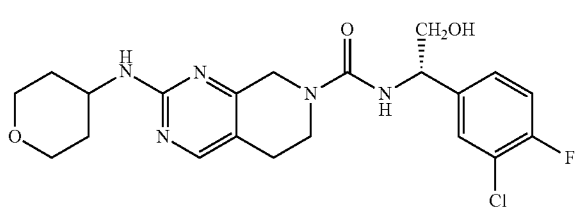 [SMILES: O=C(N[C@H](CO)c1ccc(F)c(Cl)c1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide |

TABLE 1-continued

| | | |
|---|---|---|
| I-47 | | Acetic acid (S)-2-(3-chloro-4-fluoro-phenyl)-2-{[2-(tetrahydro-pyran-4-ylamino)-5,8-dihydro-6H-pyrido[3,4-d]pyrimidine-7-carbonyl]-amino}-ethyl ester |
| I-48 | | 2-((S)-2-Hydroxy-1-methyl-ethylamino)-5,8-dihydro-6H-pyrido[3,4-d]pyrimidine-7-carboxylic acid [(S)-1-(3,4-dichloro-phenyl)-2-methoxy-ethyl]-amide |
| I-49 | | 2-Isopropylamino-5,8-dihydro-6H-pyrido[3,4-d]pyrimidine-7-carboxylic acid [(S)-(3,4-dichloro-phenyl)-(R)-pyrrolidin-2-yl-methyl]-amide |
| I-50 | | 5,5-Difluoro-2-(tetrahydro-pyran-4-ylamino)-5,8-dihydro-6H-pyrido[3,4-d]pyrimidine-7-carboxylic acid [(R)-1-(3,4-dichloro-phenyl)-ethyl]-amide |
| I-51 | | 5,5-Difluoro-2-(tetrahydro-pyran-4-ylamino)-5,8-dihydro-6H-pyrido[3,4-d]pyrimidine-7-carboxylic acid [(S)-1-(4-chloro-3-fluoro-phenyl)-2-methoxy-ethyl]-amide |
| I-52 | | 2-((1S,3S)-3-Hydroxy-cyclopentylamino)-5,8-dihydro-6H-pyrido[3,4-d]pyrimidine-7-carboxylic acid [(R)-1-(3-fluoro-4-trifluoromethyl-phenyl)-ethyl]-amide |
| I-53 | | 5,5-Difluoro-2-(tetrahydro-pyran-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide |

TABLE 1-continued

| ID | Structure | Name |
|---|---|---|
| I-54 | 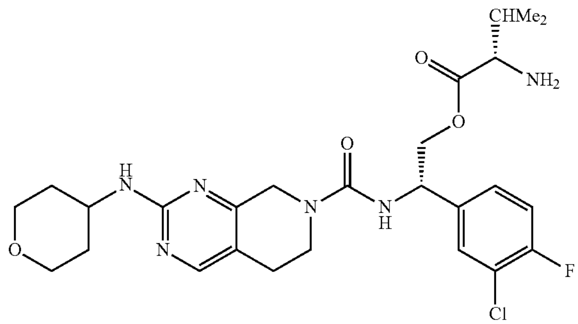 | (S)-2-Amino-3-methyl-butyric acid (S)-2-(3-chloro-4-fluoro-phenyl)-2-{[2-(tetrahydro-pyran-4-ylamino)-5,8-dihydro-6H-pyrido[3,4-d]pyrimidine-7-carbonyl]-amino}-ethyl ester |
| I-55 | 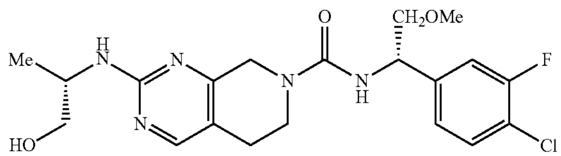 | 2-((S)-2-Hydroxy-1-methyl-ethylamino)-5,8-dihydro-6H-pyrido[3,4-d]pyrimidine-7-carboxylic acid [(S)-1-(4-chloro-3-fluoro-phenyl)-2-methoxy-ethyl]-amide |
| I-56 | 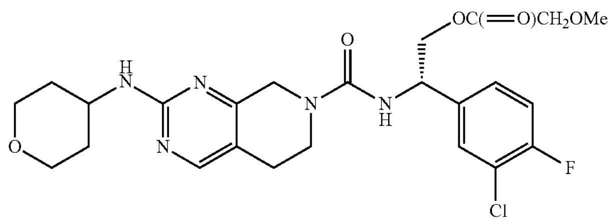 | Methoxy-acetic acid (S)-2-(3-chloro-4-fluoro-phenyl)-2-{[2-(tetrahydro-pyran-4-ylamino)-5,8-dihydro-6H-pyrido[3,4-d]pyrimidine-7-carbonyl]-amino}-ethyl ester |
| I-57 | 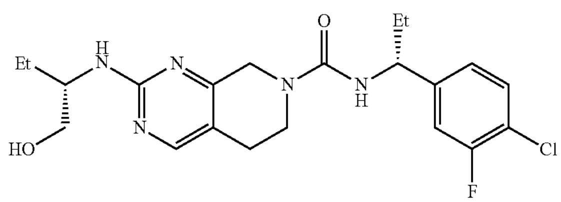 [SMILES: CC[C@@H](CO)Nc1ncc2c(n1)CN(C(=O)N[C@H](CC)c1ccc(Cl)c(F)c1)CC2] | 2-((S)-1-Hydroxymethyl-propylamino)-5,8-dihydro-6H-pyrido[3,4-d]pyrimidine-7-carboxylic acid [(R)-1-(4-chloro-3-fluoro-phenyl)-propyl]-amide |
| I-58 | 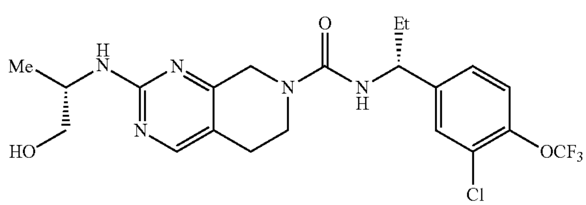 [SMILES: CC[C@@H](NC(=O)N1CCc2cnc(N[C@@H](C)CO)nc2C1)c1ccc(OC(F)(F)F)c(Cl)c1] | 2-((S)-2-Hydroxy-1-methyl-ethylamino)-5,8-dihydro-6H-pyrido[3,4-d]pyrimidine-7-carboxylic acid [(R)-1-(3-chloro-4-trifluoromethoxy-phenyl)-propyl]-amide |
| I-59 | 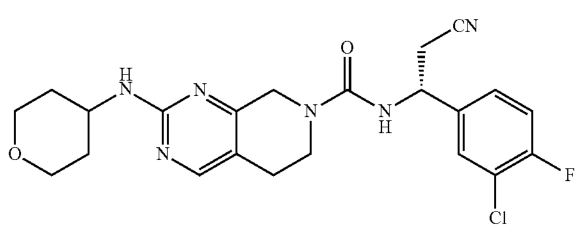 [SMILES: N#CC[C@@H](NC(=O)N1CCc2cnc(NC3CCOCC3)nc2C1)c1ccc(F)c(Cl)c1] | 2-(Tetrahydro-pyran-4-ylamino)-5,8-dihydro-6H-pyrido[3,4-d]pyrimidine-7-carboxylic acid [(R)-1-(3-chloro-4-fluoro-phenyl)-2-cyano-ethyl]-amide |
| I-60 | 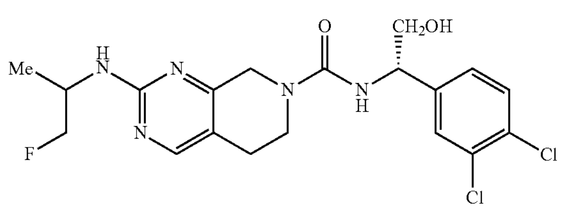 [SMILES: CC(CF)Nc1ncc2c(n1)CN(C(=O)N[C@H](CO)c1ccc(Cl)c(Cl)c1)CC2] | 2-((R)-2-Fluoro-1-methyl-ethylamino)-5,8-dihydro-6H-pyrido[3,4-d]pyrimidine-7-carboxylic acid [(S)-1-(3,4-dichloro-phenyl)-2-hydroxy-ethyl]-amide |

TABLE 1-continued

| | | |
|---|---|---|
| I-61 | 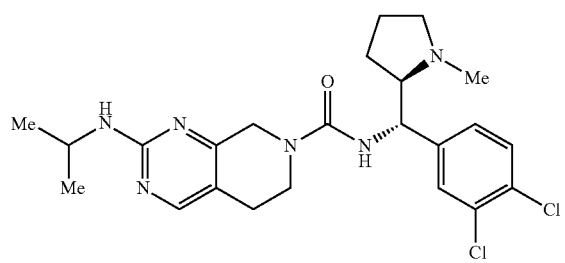 [SMILES: CC(C)Nc1ncc2c(n1)CN(C(=O)N[C@@H](c1ccc(Cl)c(Cl)c1)[C@H]1CCCN1C)CC2] | 2-Isopropylamino-5,8-dihydro-6H-pyrido[3,4-d]pyrimidine-7-carboxylic acid [(S)-(3,4-dichloro-phenyl)-((R)-1-methyl-pyrrolidin-2-yl)-methyl]-amide |
| I-62 | 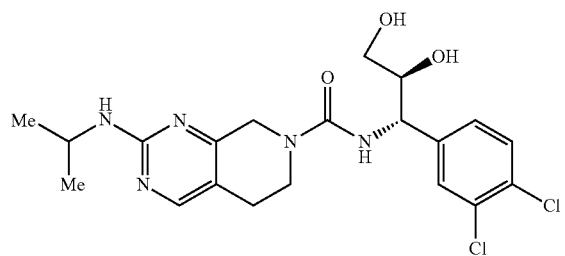 [SMILES: CC(C)Nc1ncc2c(n1)CN(C(=O)N[C@@H](c1ccc(Cl)c(Cl)c1)[C@H](O)CO)CC2] | 2-Isopropylamino-5,8-dihydro-6H-pyrido[3,4-d]pyrimidine-7-carboxylic acid [(1S,2S)-1-(3,4-dichloro-phenyl)-2,3-dihydroxy-propyl]-amide |
| I-63 | 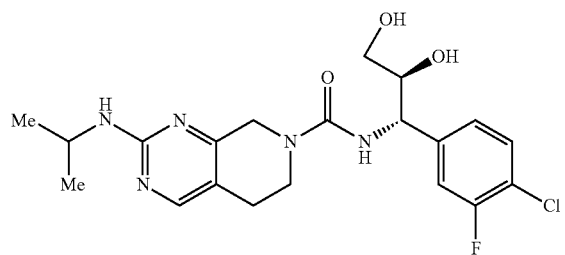 | 2-Isopropylamino-5,8-dihydro-6H-pyrido[3,4-d]pyrimidine-7-carboxylic acid [(1S,2S)-1-(4-chloro-3-fluoro-phenyl)-2,3-dihydroxy-propyl]-amide |
| I-64 | 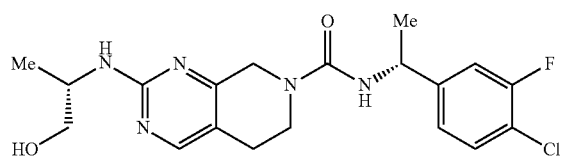 [SMILES: C[C@@H](CO)Nc1ncc2c(n1)CN(C(=O)N[C@H](C)c1ccc(Cl)c(F)c1)CC2] | 2-((S)-2-Hydroxy-1-methyl-ethylamino)-5,8-dihydro-6H-pyrido[3,4-d]pyrimidine-7-carboxylic acid [(R)-1-(3-fluoro-4-trifluoromethyl-phenyl)-ethyl]-amide |
| I-65 | 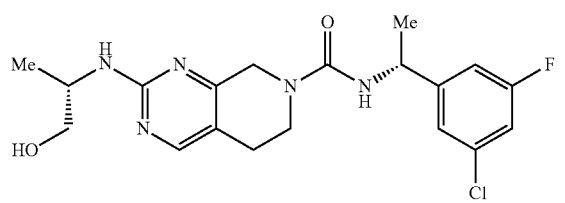 [SMILES: C[C@@H](CO)Nc1ncc2c(n1)CN(C(=O)N[C@H](C)c1cc(F)cc(Cl)c1)CC2] | 2-((S)-2-Hydroxy-1-methyl-ethylamino)-5,8-dihydro-6H-pyrido[3,4-d]pyrimidine-7-carboxylic acid [(R)-1-(3-chloro-5-fluoro-phenyl)-ethyl]-amide |
| I-66 | 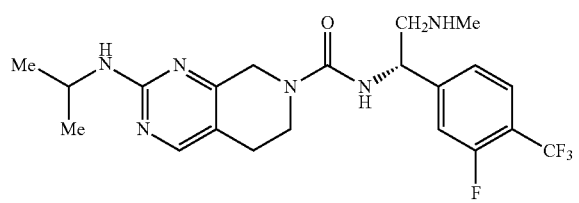 | 2-Isopropylamino-5,8-dihydro-6H-pyrido[3,4-d]pyrimidine-7-carboxylic acid [(S)-1-(3-fluoro-4-trifluoromethyl-phenyl)-2-methylamino-ethyl]-amide |
| I-67 | 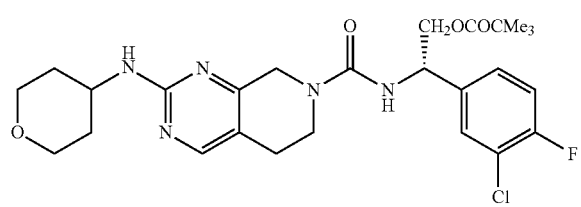 | 2,2-Dimethyl-propionic acid (S)-2-(3-chloro-4-fluoro-phenyl)-2-{[2-(tetrahydro-pyran-4-ylamino)-5,8-dihydro-6H-pyrido[3,4-d]pyrimidine-7-carbonyl]-amino}-ethyl ester |

TABLE 1-continued

| | | |
|---|---|---|
| I-68 | 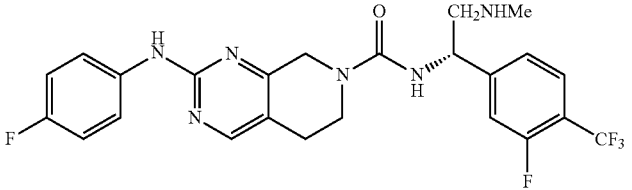 | 2-(4-Fluoro-phenylamino)-5,8-dihydro-6H-pyrido[3,4-d]pyrimidine-7-carboxylic acid [(S)-1-(3-fluoro-4-trifluoromethyl-phenyl)-2-methylamino-ethyl]-amide |
| I-69 | 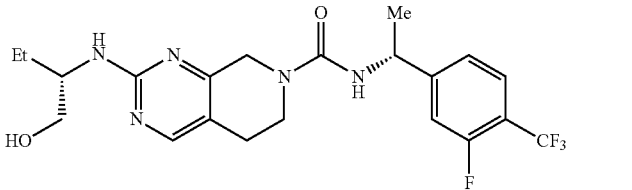 [SMILES: CC[C@@H](CO)Nc1ncc2c(n1)CN(C(=O)N[C@H](C)c1ccc(C(F)(F)F)c(F)c1)CC2] | 2-((S)-1-Hydroxymethyl-propylamino)-5,8-dihydro-6H-pyrido[3,4-d]pyrimidine-7-carboxylic acid [(R)-1-(3-fluoro-4-trifluoromethyl-phenyl)-ethyl]-amide |
| I-70 | 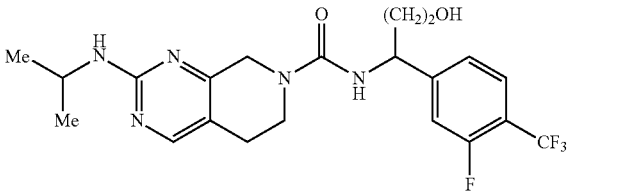 | 2-Isopropylamino-5,8-dihydro-6H-pyrido[3,4-d]pyrimidine-7-carboxylic acid [1-(3-fluoro-4-trifluoromethyl-phenyl)-3-hydroxy-propyl]-amide |
| I-71 | 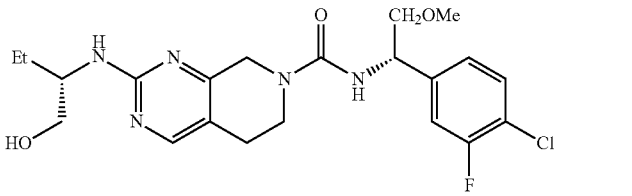 | 2-((S)-1-Hydroxymethyl-propylamino)-5,8-dihydro-6H-pyrido[3,4-d]pyrimidine-7-carboxylic acid [(S)-1-(4-chloro-3-fluoro-phenyl)-2-methoxy-ethyl]-amide |
| I-72 | 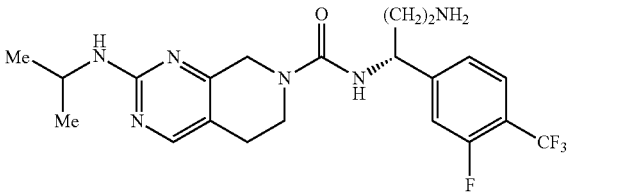 | 2-Isopropylamino-5,8-dihydro-6H-pyrido[3,4-d]pyrimidine-7-carboxylic acid [(R)-3-amino-1-(3-fluoro-4-trifluoromethyl-phenyl)-propyl]-amide |
| I-73 | 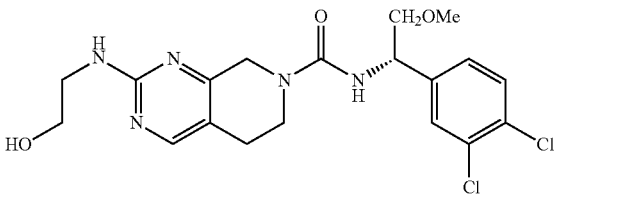 | 2-(2-Hydroxy-ethylamino)-5,8-dihydro-6H-pyrido[3,4-d]pyrimidine-7-carboxylic acid [(S)-1-(3,4-dichloro-phenyl)-2-methoxy-ethyl]-amide |
| I-74 | 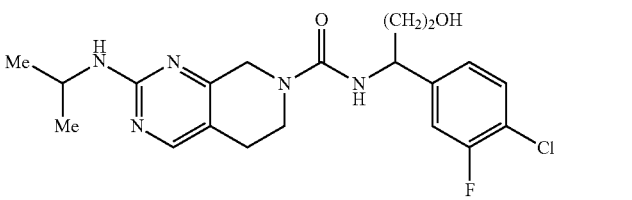 | 2-Isopropylamino-5,8-dihydro-6H-pyrido[3,4-d]pyrimidine-7-carboxylic acid [1-(4-chloro-3-fluoro-phenyl)-3-hydroxy-propyl]-amide |
| I-75 | 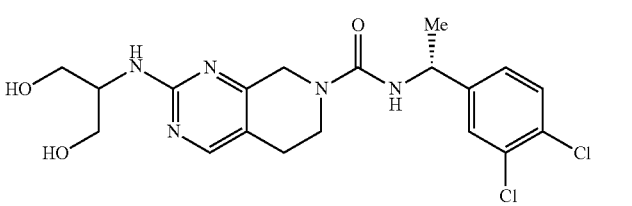 [SMILES: C[C@@H](NC(=O)N1CCc2cnc(NC(CO)CO)nc2C1)c1ccc(Cl)c(Cl)c1] | 2-(2-Hydroxy-1-hydroxymethyl-ethylamino)-5,8-dihydro-6H-pyrido[3,4-d]pyrimidine-7-carboxylic acid [(R)-1-(3,4-dichloro-phenyl)-ethyl]-amide |

TABLE 1-continued

| | | |
|---|---|---|
| I-76 | | 2-(2,2,2-Trifluoro-1-methyl-ethylamino)-5,8-dihydro-6H-pyrido[3,4-d]pyrimidine-7-carboxylic acid [1-(3,4-dichloro-phenyl)-2-hydroxy-ethyl]-amide |
| I-77 | | 2-Isopropylamino-5,8-dihydro-6H-pyrido[3,4-d]pyrimidine-7-carboxylic acid [1-(3,4-difluoro-phenyl)-3-hydroxy-propyl]-amide |
| I-78 | | 2-Isopropylamino-5,8-dihydro-6H-pyrido[3,4-d]pyrimidine-7-carboxylic acid [1-(4-chloro-3-fluoro-phenyl)-3-methylamino-propyl]-amide |
| I-79 | | 2-((S)-1-Hydroxymethyl-propylamino)-5,8-dihydro-6H-pyrido[3,4-d]pyrimidine-7-carboxylic acid [(S)-1-(3-fluoro-4-trifluoromethyl-phenyl)-2-methoxy-ethyl]-amide |
| I-80 | | 2-((S)-2-Hydroxy-1-methyl-ethylamino)-5,8-dihydro-6H-pyrido[3,4-d]pyrimidine-7-carboxylic acid [(S)-1-(3-fluoro-4-trifluoromethyl-phenyl)-2-methylamino-ethyl]-amide |
| I-81 | | 2-Isopropylamino-5,8-dihydro-6H-pyrido[3,4-d]pyrimidine-7-carboxylic acid [(R)-1-(4-fluoro-phenyl)-ethyl]-amide |
| I-82 | | 2-(2-Hydroxy-1-hydroxymethyl-ethylamino)-5,8-dihydro-6H-pyrido[3,4-d]pyrimidine-7-carboxylic acid [(R)-1-(3-fluoro-4-trifluoromethyl-phenyl)-ethyl]-amide |
| I-83 | | 2-(1-Methyl-piperidin-4-ylamino)-5,8-dihydro-6H-pyrido[3,4-d]primidine-7-carboxylic acid [(R)-1-(3,4-dichloro-phenyl)-ethyl]-amide |

TABLE 1-continued

| | | |
|---|---|---|
| I-84 | [structure] | 2-(2,2,2-Trifluoro-1-methyl-ethylamino)-5,8-dihydro-6H-pyrido[3,4-d]pyrimidine-7-carboxylic acid [(4-chloro-3-fluoro-phenyl)-oxazol-5-yl-methyl]-amide |
| I-85 | [structure] | 2-Isopropylamino-5,8-dihydro-6H-pyrido[3,4-d]pyrimidine-7-carboxylic acid [(R)-3-acetylamino-1-(3-fluoro-4-trifluoromethyl-phenyl)-propyl]-amide |
| I-86 | [structure] | 2-(Tetrahydro-pyran-4-ylamino)-5,8-dihydro-6H-pyrido[3,4-d]pyrimidine-7-carboxylic acid [(S)-((S)-5,5-dimethyl-pyrrolidin-2-yl)-(2-fluoro-4-trifluoromethyl-phenyl)-methyl]-amide |
| I-87 | [structure] | 2-Isopropylamino-5,8-dihydro-6H-pyrido[3,4-d]pyrimidine-7-carboxylic acid [(S)-((S)-1-acetyl-pyrrolidin-2-yl)-(4-chloro-3-fluoro-phenyl)-methyl]-amide |
| I-88 | [structure] | 2-(2-Morpholin-4-yl-ethylamino)-5,8-dihydro-6H-pyrido[3,4-d]pyrimidine-7-carboxylic acid [(R)-1-(3,4-dichloro-phenyl)-ethyl]-amide |
| I-89 | [structure] | 2-Isopropylamino-5,8-dihydro-6H-pyrido[3,4-d]pyrimidine-7-carboxylic acid [(1S,2S)-1-(3-chloro-4-fluoro-phenyl)-2-hydroxy-propyl]-amide |
| I-90 | [structure] | 2-((S)-2-Hydroxy-1-methyl-ethylamino)-5,8-dihydro-6H-pyrido[3,4-d]pyrimidine-7-carboxylic acid 3,4-dichloro-benzylamide |

TABLE 1-continued

| ID | Structure | Name |
|---|---|---|
| I-91 | 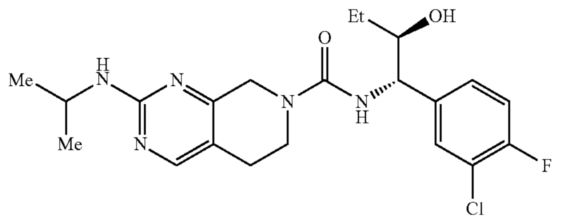 [SMILES: CC[C@@H](O)[C@@H](NC(=O)N1CCc2cnc(NC(C)C)nc2C1)c1ccc(F)c(Cl)c1] | 2-Isopropylamino-5,8-dihydro-6H-pyrido[3,4-d]pyrimidine-7-carboxylic acid [(1S,2R)-1-(3-chloro-4-fluoro-phenyl)-2-hydroxy-butyl]-amide |
| I-92 | 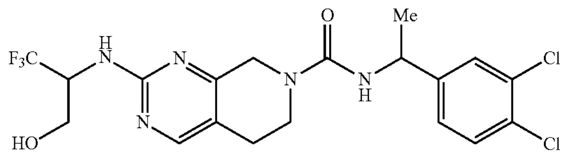 [SMILES: CC(NC(=O)N1CCc2cnc(NC(CO)C(F)(F)F)nc2C1)c1ccc(Cl)c(Cl)c1] | 2-(2,2,2-Trifluoro-1-hydroxymethyl-ethylamino)-5,8-dihydro-6H-pyrido[3,4-d]pyrimidine-7-carboxylic acid [1-(3,4-dichloro-phenyl)-ethyl]-amide |
| I-93 | 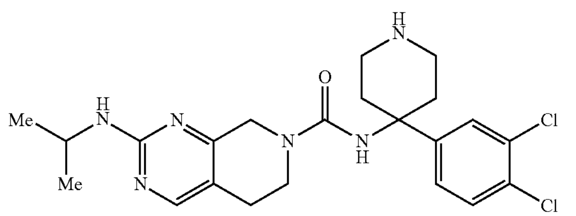 [SMILES: CC(C)Nc1ncc2c(n1)CN(C(=O)NC1(c3ccc(Cl)c(Cl)c3)CCNCC1)CC2] | 2-Isopropylamino-5,8-dihydro-6H-pyrido[3,4-d]pyrimidine-7-carboxylic acid [4-(3,4-dichloro-phenyl)-piperidin-4-yl]-amide |
| I-94 | 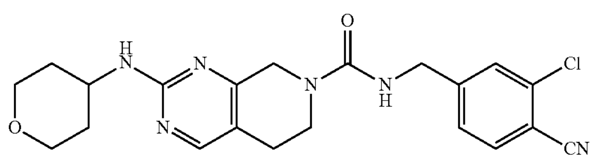 [SMILES: N#Cc1ccc(CNC(=O)N2CCc3cnc(NC4CCOCC4)nc3C2)cc1Cl] | 2-(Tetrahydro-pyran-4-ylamino)-5,8-dihydro-6H-pyrido[3,4-d]pyrimidine-7-carboxylic acid 3-chloro-4-cyano-benzylamide |
| I-95 | 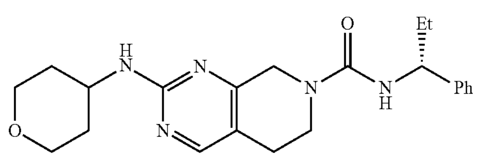 [SMILES: CC[C@@H](NC(=O)N1CCc2cnc(NC3CCOCC3)nc2C1)c1ccccc1] | 2-(Tetrahydro-pyran-4-ylamino)-5,8-dihydro-6H-pyrido[3,4-d]pyrimidine-7-carboxylic acid ((R)-1-phenyl-propyl)-amide |
| I-96 | 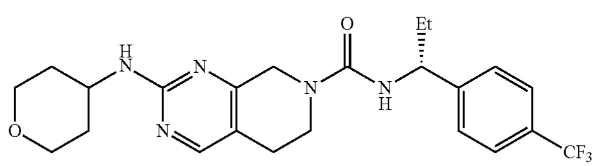 [SMILES: CC[C@@H](NC(=O)N1CCc2cnc(NC3CCOCC3)nc2C1)c1ccc(C(F)(F)F)cc1] | 2-(Tetrahydro-pyran-4-ylamino)-5,8-dihydro-6H-pyrido[3,4-d]pyrimidine-7-carboxylic acid [(R)-1-(4-trifluoromethyl-phenyl)-propyl]-amide |
| I-97 | 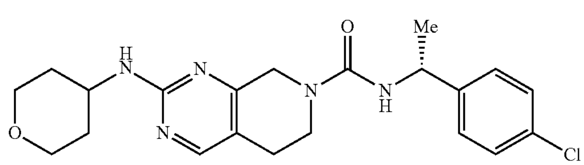 [SMILES: C[C@@H](NC(=O)N1CCc2cnc(NC3CCOCC3)nc2C1)c1ccc(Cl)cc1] | 2-(Tetrahydro-pyran-4-ylamino)-5,8-dihydro-6H-pyrido[3,4-d]pyrimidine-7-carboxylic acid [(R)-1-(4-chloro-phenyl)-ethyl]-amide |
| I-98 | 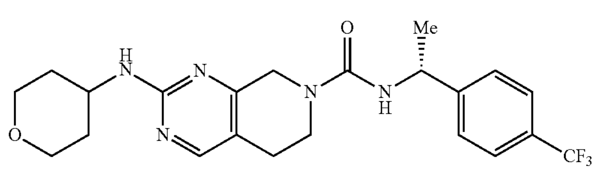 | 2-(Tetrahydro-pyran-4-ylamino)-5,8-dihydro-6H-pyrido[3,4-d]pyrimidine-7-carboxylic acid [(R)-1-(4-trifluoromethyl-phenyl)-ethyl]-amide |
| I-99 | 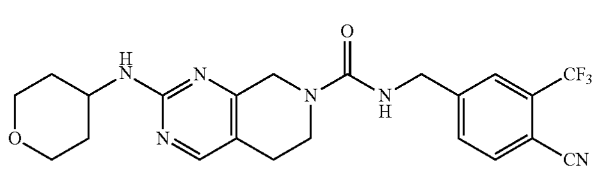 [SMILES: N#Cc1ccc(CNC(=O)N2CCc3cnc(NC4CCOCC4)nc3C2)cc1C(F)(F)F] | 2-(Tetrahydro-pyran-4-ylamino)-5,8-dihydro-6H-pyrido[3,4-d]pyrimidine-7-carboxylic acid 4-cyano-3-trifluoromethyl-benzylamide |

TABLE 1-continued

| ID | Name |
|---|---|
| I-100 | 2-(Tetrahydro-pyran-4-ylamino)-5,8-dihydro-6H-pyrido[3,4-d]pyrimidine-7-carboxylic acid [(R)-1-(4-fluoro-phenyl)-propyl]-amide |
| I-101 | 2-(Tetrahydro-pyran-4-ylamino)-5,8-dihydro-6H-pyrido[3,4-d]pyrimidine-7-carboxylic acid [(R)-1-(4-fluoro-phenyl)-ethyl]-amide |
| I-102 | 2-(Tetrahydro-pyran-4-ylamino)-5,8-dihydro-6H-pyrido[3,4-d]pyrimidine-7-carboxylic acid ((R)-1-phenyl-ethyl)-amide |
| I-103 | 2-(Tetrahydro-pyran-4-ylamino)-5,8-dihydro-6H-pyrido[3,4-d]pyrimidine-7-carboxylic acid [(R)-3-cyano-1-(3,4-dichloro-phenyl)-propyl]-amide |
| I-104 | 2-Isopropylamino-5,8-dihydro-6H-pyrido[3,4-d]pyrimidine-7-carboxylic acid [(R)-3-cyano-1-(3,4-dichloro-phenyl)-propyl]-amide |
| I-105 | 2-(Tetrahydro-pyran-4-ylamino)-5,8-dihydro-6H-pyrido[3,4-d]pyrimidine-7-carboxylic acid [(R)-1-(3,4-dichloro-phenyl)-3-methanesulfonyl-propyl]-amide |
| I-106 | 2-Isopropylamino-5,8-dihydro-6H-pyrido[3,4-d]pyrimidine-7-carboxylic acid [(R)-1-(3,4-dichloro-phenyl)-3-methanesulfonyl-propyl]-amide |
| I-107 | 2-(Tetrahydro-pyran-4-ylamino)-5,8-dihydro-6H-pyrido[3,4-d]pyrimidine-7-carboxylic acid [1-(1H-indol-6-yl)-ethyl]-amide |
| I-108 | 2-(Tetrahydro-pyran-4-ylamino)-5,8-dihydro-6H-pyrido[3,4-d]pyrimidine-7-carboxylic acid [(R)-3-cyano-1-(4-difluoromethoxy-phenyl)-propyl]-amide |
| I-109 | 2-((S)-2-Hydroxy-1-methyl-ethylamino)-5,8-dihydro-6H-pyrido[3,4-d]pyrimidine-7-carboxylic acid (2-trifluoromethyl-pyrimidin-5-ylmethyl)-amide |

TABLE 1-continued

| ID | Structure | Name |
|---|---|---|
| I-110 | (structure with (CH₂)₂NH₂ substituent, 3,4-dichlorophenyl) | 2-Isopropylamino-5,8-dihydro-6H-pyrido[3,4-d]pyrimidine-7-carboxylic acid [3-amino-1-(3,4-dichloro-phenyl)-propyl]-amide |
| I-111 | (structure with (CH₂)₂NHMe substituent, 3,4-dichlorophenyl) | 2-Isopropylamino-5,8-dihydro-6H-pyrido[3,4-d]pyrimidine-7-carboxylic acid [1-(3,4-dichloro-phenyl)-3-methylamino-propyl]-amide |
| I-112 | (structure with CH₂OH substituent, 3-chloro-4-fluorophenyl, ketone linkage) | 3-(3-Chloro-4-fluoro-phenyl)-4-hydroxy-1-(2-isopropylamino-5,8-dihydro-6H-pyrido[3,4-d]pyrimidin-7-yl)-butan-1-one |
| I-113 | (structure with CH₂NHMe substituent, 4-chlorophenyl, (S) stereochemistry) | (S)-3-(4-Chloro-phenyl)-1-(2-isopropylamino-5,8-dihydro-6H-pyrido[3,4-d]pyrimidin-7-yl)-4-methylamino-butan-1-one |
| I-114 | (structure with tetrahydropyran-4-ylamino group and indol-2-ylmethyl amide) | 2-(Tetrahydro-pyran-4-ylamino)-5,8-dihydro-6H-pyrido[3,4-d]pyrimidine-7-carboxylic acid (1H-indol-2-ylmethyl)-amide |
| I-115 | (structure with (CH₂)₂OH substituent, 3,4-dichlorophenyl) | 2-Isopropylamino-5,8-dihydro-6H-pyrido[3,4-d]pyrimidine-7-carboxylic acid [1-(3,4-dichloro-phenyl)-3-hydroxy-propyl]-amide |
| I-116 | (structure with (CH₂)₂NH₂ substituent, 4-chlorophenyl, (R) stereochemistry) | 2-Isopropylamino-5,8-dihydro-6H-pyrido[3,4-d]pyrimidine-7-carboxylic acid [(R)-3-amino-1-(4-chloro-phenyl)-propyl]-amide |
| I-117 | (structure with (CH₂)₂NHMe substituent, 4-chlorophenyl, (R) stereochemistry) | 2-Isopropylamino-5,8-dihydro-6H-pyrido[3,4-d]pyrimidine-7-carboxylic acid [(R)-1-(4-chloro-phenyl)-3-methylamino-propyl]-amide |
| I-118 | (structure with (CH₂)₂NH₂ substituent, 3-chlorophenyl, (R) stereochemistry) | 2-Isopropylamino-5,8-dihydro-6H-pyrido[3,4-d]pyrimidine-7-carboxylic acid [(R)-3-amino-1-(3-chloro-phenyl)-propyl]-amide |
| I-119 | (structure with (CH₂)₂NH₂ substituent, 4-trifluoromethylphenyl, (R) stereochemistry) | 2-Isopropylamino-5,8-dihydro-6H-pyrido[3,4-d]pyrimidine-7-carboxylic acid [(R)-3-amino-1-(4-trifluoromethyl-phenyl)-propyl]-amide |

TABLE 1-continued

| | | |
|---|---|---|
| I-120 | 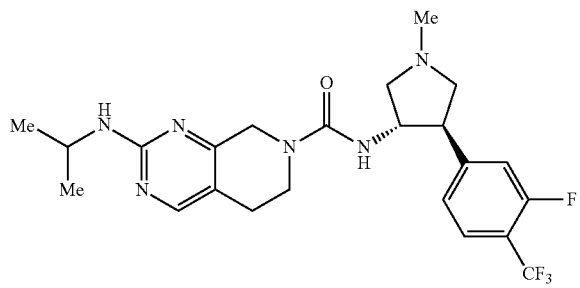 [SMILES: CC(C)Nc1ncc2c(n1)CN(C(=O)N[C@@H]1CN(C)C[C@H]1c1ccc(C(F)(F)F)c(F)c1)CC2] | 2-Isopropylamino-5,8-dihydro-6H-pyrido[3,4-d]pyrimidine-7-carboxylic acid [(3S,4R)-4-(3-fluoro-4-trifluoromethyl-phenyl)-1-methyl-pyrrolidin-3-yl]-amide |
| I-121 | 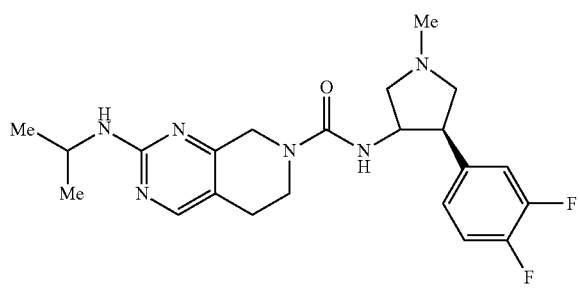 [SMILES: CC(C)Nc1ncc2c(n1)CN(C(=O)NC1CN(C)C[C@H]1c1ccc(F)c(F)c1)CC2] | 2-Isopropylamino-5,8-dihydro-6H-pyrido[3,4-d]pyrimidine-7-carboxylic acid [(3S,4R)-4-(3,4-difluoro-phenyl)-1-methyl-pyrrolidin-3-yl]-amide |
| I-122 | 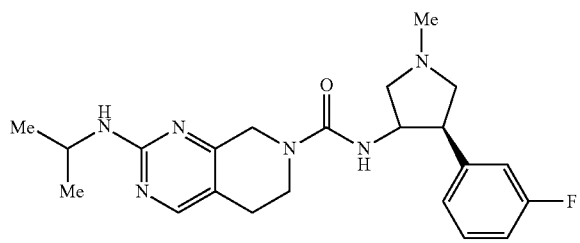 [SMILES: CC(C)Nc1ncc2c(n1)CN(C(=O)NC1CN(C)C[C@H]1c1cccc(F)c1)CC2] | 2-Isopropylamino-5,8-dihydro-6H-pyrido[3,4-d]pyrimidine-7-carboxylic acid [(3S,4R)-4-(3-fluoro-phenyl)-1-methyl-pyrrolidin-3-yl]-amide |
| I-123 | 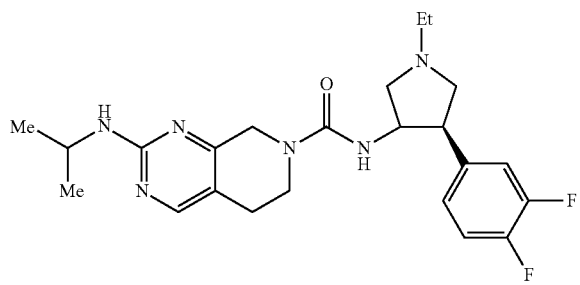 [SMILES: CCN1CC(NC(=O)N2CCc3cnc(NC(C)C)nc3C2)[C@H](c2ccc(F)c(F)c2)C1] | 2-Isopropylamino-5,8-dihydro-6H-pyrido[3,4-d]pyrimidine-7-carboxylic acid [(3S,4R)-4-(3,4-difluoro-phenyl)-1-ethyl-pyrrolidin-3-yl]-amide |
| I-124 | 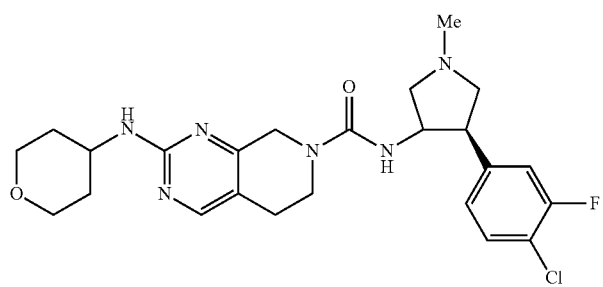 | 2-(Tetrahydro-pyran-4-ylamino)-5,8-dihydro-6H-pyrido[3,4-d]pyrimidine-7-carboxylic acid [(3S,4R)-4-(4-chloro-3-fluoro-phenyl)-1-methyl-pyrrolidin-3-yl]-amide |

TABLE 1-continued

| I-125 | 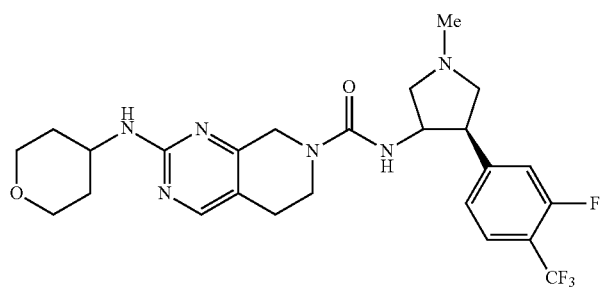 [SMILES: CN1CC(NC(=O)N2CCc3cnc(NC4CCOCC4)nc3C2)[C@H](c2ccc(C(F)(F)F)c(F)c2)C1] | 2-(Tetrahydro-pyran-4-ylamino)-5,8-dihydro-6H-pyrido[3,4-d]pyrimidine-7-carboxylic acid [(3S,4R)-4-(3-fluoro-4-trifluoromethyl-phenyl)-1-methyl-pyrrolidin-3-yl]-amide |
|---|---|---|
| I-126 | 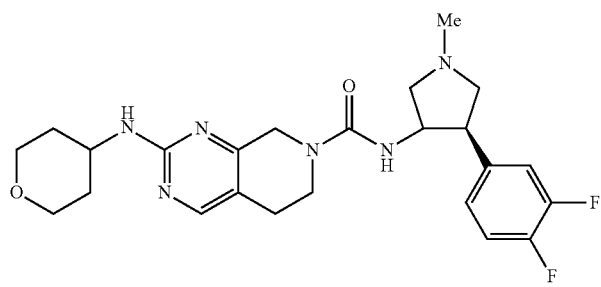 [SMILES: CN1CC(NC(=O)N2CCc3cnc(NC4CCOCC4)nc3C2)[C@H](c2ccc(F)c(F)c2)C1] | 2-(Tetrahydro-pyran-4-ylamino)-5,8-dihydro-6H-pyrido[3,4-d]pyrimidine-7-carboxylic acid [(3S,4R)-4-(3,4-difluoro-phenyl)-1-methyl-pyrrolidin-3-yl]-amide |
| I-127 | 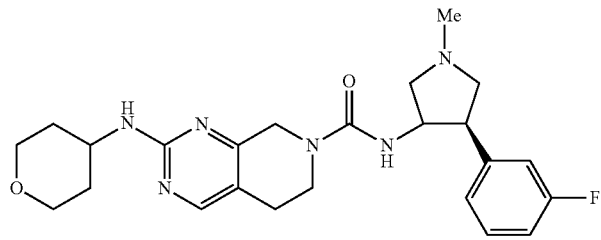 [SMILES: CN1CC(NC(=O)N2CCc3cnc(NC4CCOCC4)nc3C2)[C@H](c2cccc(F)c2)C1] | 2-(Tetrahydro-pyran-4-ylamino)-5,8-dihydro-6H-pyrido[3,4-d]pyrimidine-7-carboxylic acid [(3S,4R)-4-(3-fluoro-phenyl)-1-methyl-pyrrolidin-3-yl]-amide |
| I-128 | 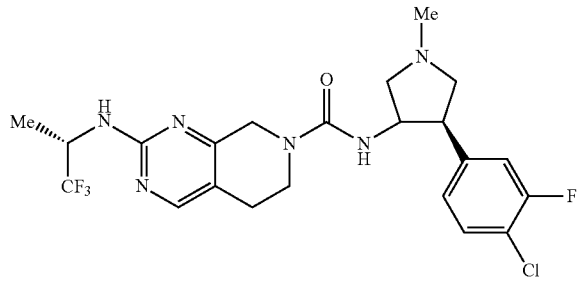 [SMILES: C[C@H](Nc1ncc2c(n1)CN(C(=O)NC1CN(C)C[C@H]1c1ccc(Cl)c(F)c1)CC2)C(F)(F)F] | 2-((S)-2,2,2-Trifluoro-1-methyl-ethylamino)-5,8-dihydro-6H-pyrido[3,4-d]pyrimidine-7-carboxylic acid [(3S,4R)-4-(4-chloro-3-fluoro-phenyl)-1-methyl-pyrrolidin-3-yl]-amide |
| I-129 | 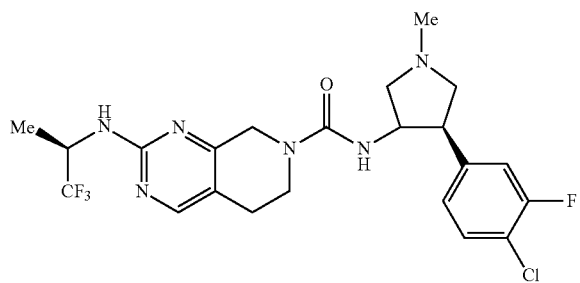 [SMILES: C[C@@H](Nc1ncc2c(n1)CN(C(=O)NC1CN(C)C[C@H]1c1ccc(Cl)c(F)c1)CC2)C(F)(F)F] | 2-((R)-2,2,2-Trifluoro-1-methyl-ethylamino)-5,8-dihydro-6H-pyrido[3,4-d]pyrimidine-7-carboxylic acid [(3S,4R)-4-(4-chloro-3-fluoro-phenyl)-1-methyl-pyrrolidin-3-yl]-amide |
| I-130 | 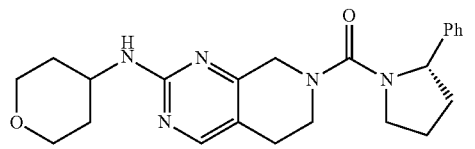 [SMILES: O=C(N1CCc2cnc(NC3CCOCC3)nc2C1)N1CCC[C@H]1c1ccccc1] | ((S)-2-Phenyl-pyrrolidin-1-yl)-[2-(tetrahydro-pyran-4-ylamino)-5,8-dihydro-6H-pyrido[3,4-d]pyrimidin-7-yl]-methanone |

TABLE 1-continued

| | | |
|---|---|---|
| I-131 | | ((R)-2-Phenyl-pyrrolidin-1-yl)-[2-(tetrahydro-pyran-4-ylamino)-5,8-dihydro-6H-pyrido[3,4-d]pyrimidin-7-yl]-methanone |
| I-132 | | [2-(4-Chloro-phenyl)-pyrrolidin-1-yl]-2-(tetrahydro-pyran-4-ylamino)-5,8-dihydro-6H-pyrido[3,4-d]pyrimidin-7-yl]-methanone |
| I-133 | | [2-(3-Chloro-phenyl)-pyrrolidin-1-yl]-[2-(tetrahydro-pyran-4-ylamino)-5,8-dihydro-6H-pyrido[3,4-d]pyrimidin-7-yl]-methanone |
| I-134 | | [2-(4-Fluoro-phenyl)-pyrrolidin-1-yl]-[2-(tetrahydro-pyran-4-ylamino)-5,8-dihydro-6H-pyrido[3,4-d]pyrimidin-7-yl]-methanone |
| I-135 | | (2-Phenyl-azetidin-1-yl)-[2-(tetrahydro-pyran-4-ylamino)-5,8-dihydro-6H-pyrido[3,4-d]pyrimidin-7-yl]-methanone |
| I-136 | | [(R)-2-(2,5-Difluoro-phenyl)-pyrrolidin-1-yl]-[2-(tetrahydro-pyran-4-ylamino)-5,8-dihydro-6H-pyrido[3,4-d]pyrimidin-7-yl]-methanone |
| I-137 | | (2-Benzyl-pyrrolidin-1-yl)-[2-(tetrahydro-pyran-4-ylamino)-5,8-dihydro-6H-pyrido[3,4-d]ppimidin-7-yl]-methanone |

TABLE 1-continued

| I-138 | 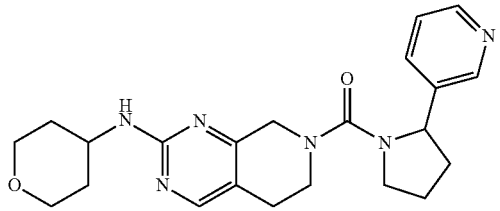 [SMILES: O=C(N1CCc2cnc(NC3CCOCC3)nc2C1)N1CCCC1c1cccnc1] | (2-Pyridin-3-yl-pyrrolidin-1-yl)-[2-(tetrahydro-pyran-4-ylamino)-5,8-dihydro-6H-pyrido[3,4-d]pyrimidin-7-yl]-methanone |
| I-139 | 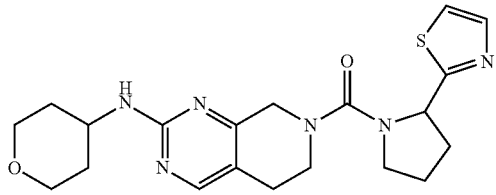 [SMILES: O=C(N1CCc2cnc(NC3CCOCC3)nc2C1)N1CCCC1c1nccs1] | [2-(Tetrahydro-pyran-4-ylamino)-5,8-dihydro-6H-pyrido[3,4-d]pyrimidin-7-yl]-(2-thiazol-2-yl-pyrrolidin-1-yl)-methanone |
| I-140 | 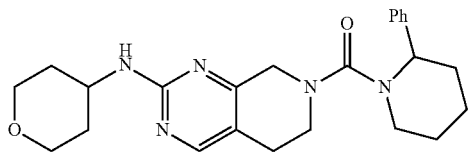 [SMILES: O=C(N1CCc2cnc(NC3CCOCC3)nc2C1)N1CCCCC1c1ccccc1] | (2-Phenyl-piperidin-1-yl)-[2-(tetrahydro-pyran-4-ylamino)-5,8-dihydro-6H-pyrido[3,4-d]pyrimidin-7-yl]-methanone |
| I-141 | 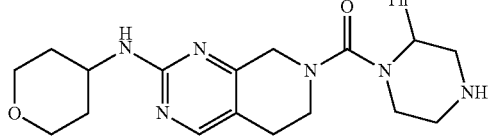 | (2-Phenyl-piperazin-1-yl)-[2-(tetrahydro-pyran-4-ylamino)-5,8-dihydro-6H-pyrido[3,4-d]pyrimidin-7-yl]-methanone |
| I-142 | 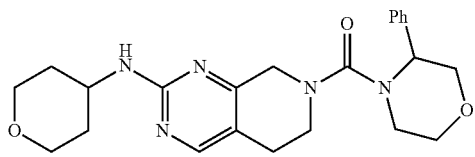 [SMILES: O=C(N1CCc2cnc(NC3CCOCC3)nc2C1)N1CCOCC1c1ccccc1] | (3-Phenyl-morpholin-4-yl)-[2-(tetrahydro-pyran-4-ylamino)-5,8-dihydro-6H-pyrido[3,4-d]pyrimidin-7-yl]-methanone |
| I-143 | 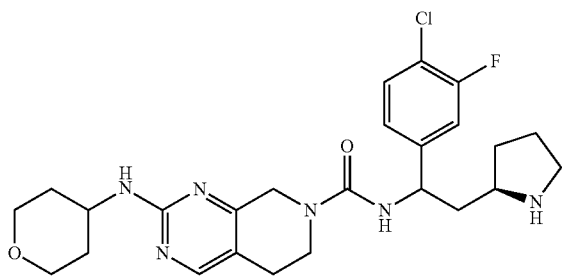 [SMILES: O=C(NC(C[C@H]1CCCN1)c1ccc(Cl)c(F)c1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [1-(3-chloro-4-fluoro-phenyl)-2-pyrrolidin-2-yl-ethyl]-amide |
| I-144 | 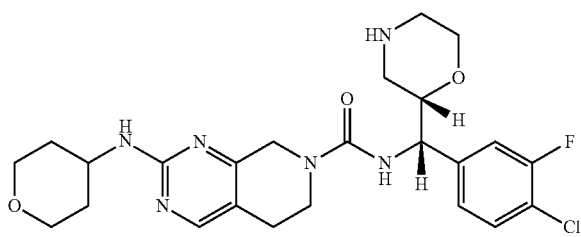 [SMILES: O=C(N[C@@H](c1ccc(Cl)c(F)c1)[C@@H]1CNCCO1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(R)-(4-chloro-3-fluoro-phenyl)-(R)-morpholin-2-yl-methyl]-amide |

TABLE 1-continued

| ID | Name |
|---|---|
| I-145 | 2-(4-Fluoro-2-methyl-phenylamino)-5,8-dihydro-6H-pyrido[3,4-d]pyrimidine-7-carboxylic acid [(3S,4R)-4-(4-chloro-3-fluoro-phenyl)-1-methyl-pyrrolidin-3-yl]-amide |
| I-146 | 2-(4-Fluoro-2-methyl-phenylamino)-5,8-dihydro-6H-pyrido[3,4-d]pyrimidine-7-carboxylic acid [(3S,4R)-4-(3-fluoro-phenyl)-1-methyl-pyrrolidin-3-yl]-amide |
| I-147 | 2-((S)-2-Hydroxy-1-methyl-ethylamino)-5,8-dihydro-6H-pyrido[3,4-d]pyrimidine-7-carboxylic acid [(R)-1-(3-chloro-4-fluoro-phenyl)-ethyl]-amide |
| I-148 | 2-Isopropylamino-5,8-dihydro-6H-pyrido[3,4-d]pyrimidine-7-carboxylic acid [(3S,4R)-4-(3-fluoro-4-trifluoromethyl-phenyl)-pyrrolidin-3-yl]-amide |
| I-149 | 7-((S)-2-Hydroxy-1-methyl-ethylamino)-3,4-dihydro-1H-[2,6]naphthyridine-2-carboxylic acid [(R)-1-(3,4-dichloro-phenyl)-ethyl]-amide |
| I-150 | (R)-2-(Tetrahydro-pyran-4-ylamino)-6,7-dihydro-5H-pyrano[2,3-d]pyrimidine-7-carboxylic acid [(S)-1-(4-chloro-3-fluoro-phenyl)-2-hydroxy-ethyl]-amide |
| I-151 | 2-(Tetrahydro-pyran-4-ylamino)-5,8-dihydro-6H-pyrido[3,4-d]pyrimidine-7-carboxylic acid [4-(4-chloro-3-fluoro-phenoxy)-1-methyl-pyrrolidin-3-yl]-amide |

TABLE 1-continued

| | | |
|---|---|---|
| I-152 | [structure] | 2-(Tetrahydro-pyran-4-ylamino)-5,8-dihydro-6H-pyrido[3,4-d]pyrimidine-7-carboxylic acid [4-(3-chloro-4-fluoro-phenoxy)-1-methyl-pyrrolidin-3-yl]-amide |
| I-153 | [structure] | 2-(Tetrahydro-pyran-4-ylamino)-5,8-dihydro-6H-pyrido[3,4-d]pyrimidine-7-carboxylic acid [4-(3,4-difluoro-phenoxy)-1-methyl-pyrrolidin-3-yl]-amide |
| I-154 | [structure] | 2-Isopropylamino-5,8-dihydro-6H-pyrido[3,4-d]pyrimidine-7-carboxylic acid [(R)-1-(4-chloro-phenyl)-3-hydroxy-propyl]-amide |
| I-155 | [structure] | N-((R)-1-(3,4-dichlorophenyl)ethyl)-2-((2S,4R)-2-(hydroxymethyl)tetrahydro-2H-pyran-4-ylamino)-5,6-dihydropyrido[3,4-d]pyrimidine-7(8H)-carboxamide |
| I-156 | [structure] | N-((S)-(3,4-dichlorophenyl)(oxazol-5-yl)methyl)-2-((3S,4S)-3-fluorotetrahydro-2H-pyran-4-ylamino)-5,6-dihydropyrido[3,4-d]pyrimidine-7(8H)-carboxamide |

Other representative compounds within the scope of the present invention are compiled in TABLE II. Compounds in TABLE II are prepared using methodology extensively described in the examples which follow.

TABLE II

| | Structure | Name | MS |
|---|---|---|---|
| II-1 | [structure] | 4-Amino-3-(4-chloro-phenyl)-1-(2-isopropylamino-5,8-dihydro-6H-pyrido[3,4-d]pyrimidin-7-yl)-butan-1-one | 388.1 |

TABLE II-continued

| | Structure | Name | MS |
|---|---|---|---|
| II-2 | 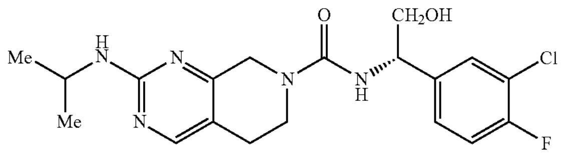 [SMILES: CC(C)Nc1ncc2c(n1)CN(C(=O)N[C@H](CO)c1ccc(F)c(Cl)c1)CC2] | 2-Isopropylamino-5,8-dihydro-6H-pyrido[3,4-d]pyrimidine-7-carboxylic acid [(S)-1-(3-chloro-4-fluoro-phenyl)-2-hydroxy-ethyl]-amide | 408.1 |
| II-3 | 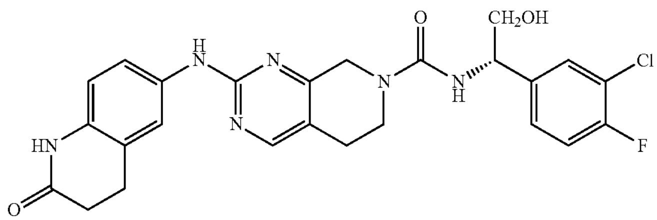 [SMILES: O=C1CCc2cc(Nc3ncc4c(n3)CN(C(=O)N[C@H](CO)c3ccc(F)c(Cl)c3)CC4)ccc2N1] | 2-(2-Oxo-1,2,3,4-tetrahydro-quinolin-6-ylamino)-5,8-dihydro-6H-pyrido[3,4-d]pyrimidine-7-carboxylic acid [(S)-1-(3-chloro-4-fluoro-phenyl)-2-hydroxy-ethyl]-amide | 511.5 |
| II-4 | 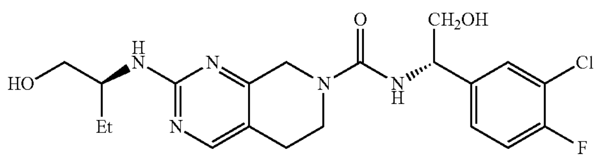 [SMILES: CC[C@@H](CO)Nc1ncc2c(n1)CN(C(=O)N[C@H](CO)c1ccc(F)c(Cl)c1)CC2] | 2-((S)-1-Hydroxymethyl-propylamino)-5,8-dihydro-6H-pyrido[3,4-d]pyrimidine-7-carboxylic acid [(S)-1-(3-chloro-4-fluoro-phenyl)-2-hydroxy-ethyl]-amide | 438.1 |
| II-5 | 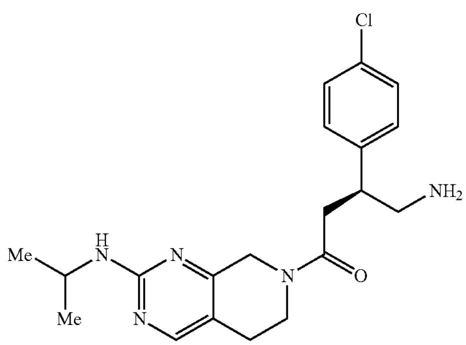 [SMILES: CC(C)Nc1ncc2c(n1)CN(C(=O)C[C@H](CN)c1ccc(Cl)cc1)CC2] | (S)-4-Amino-3-(4-chloro-phenyl)-1-(2-isopropylamino-5,8-dihydro-6H-pyrido[3,4-d]pyrimidin-7-yl)-butan-1-one | 388.1 |
| II-6 | 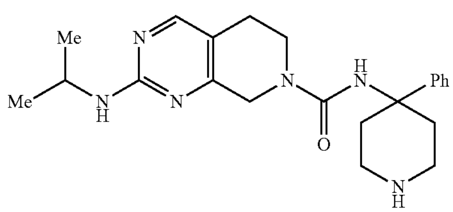 [SMILES: CC(C)Nc1ncc2c(n1)CN(C(=O)NC1(c3ccccc3)CCNCC1)CC2] | 2-Isopropylamino-5,8-dihydro-6H-pyrido[3,4-d]pyrimidine-7-carboxylic acid (4-phenyl-piperidin-4-yl)-amide | 395.2 |
| II-7 | 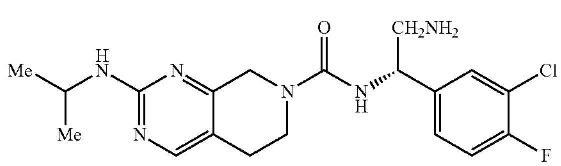 | 2-Isopropylamino-5,8-dihydro-6H-pyrido[3,4-d]pyrimidine-7-carboxylic acid [(S)-2-amino-1-(3-chloro-4-fluoro-phenyl)-ethyl]-amide | 407.0 |
| II-8 | 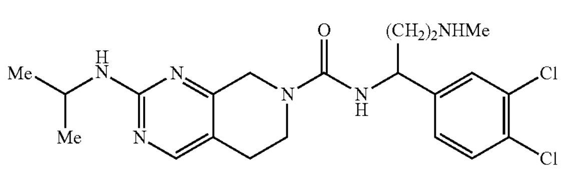 | 2-Isopropylamino-5,8-dihydro-6H-pyrido[3,4-d]pyrimidine-7-carboxylic acid [1-(3,4-dichloro-phenyl)-3-methylamino-propyl]-amide | 451.4 |

TABLE II-continued

| | Structure | Name | MS |
|---|---|---|---|
| II-9 | 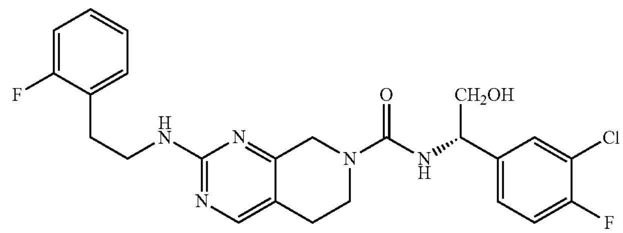 [SMILES: O=C(N[C@H](CO)c1ccc(F)c(Cl)c1)N1CCc2cnc(NCCc3ccccc3F)nc2C1] | 2-[2-(2-Fluoro-phenyl)-ethylamino]-5,8-dihydro-6H-pyrido[3,4-d]pyrimidine-7-carboxylic acid [(S)-1-(3-chloro-4-fluoro-phenyl)-2-hydroxy-ethyl]-amide | 488.1 |
| II-10 | 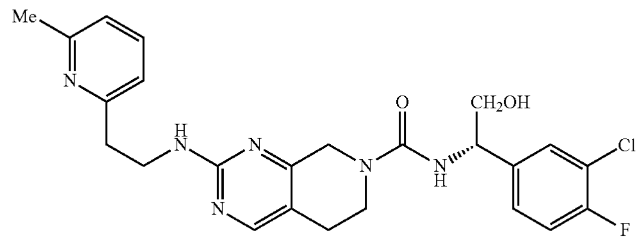 [SMILES: Cc1cccc(CCNc2ncc3c(n2)CN(C(=O)N[C@H](CO)c2ccc(F)c(Cl)c2)CC3)n1] | 2-[2-(6-Methyl-pyridin-2-yl)-ethylamino]-5,8-dihydro-6H-pyrido[3,4-d]pyrimidine-7-carboxylic acid [(S)-1-(3-chloro-4-fluoro-phenyl)-2-hydroxy-ethyl]-amide | 485.2 |
| II-11 | 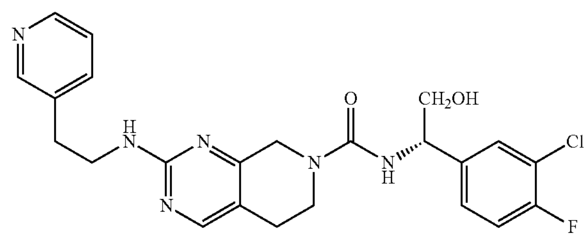 [SMILES: O=C(N[C@H](CO)c1ccc(F)c(Cl)c1)N1CCc2cnc(NCCc3cccnc3)nc2C1] | 2-(2-Pyridin-3-yl-ethylamino)-5,8-dihydro-6H-pyrido[3,4-d]pyrimidine-7-carboxylic acid [(S)-1-(3-chloro-4-fluoro-phenyl)-2-hydroxy-ethyl]-amide | 471.0 |
| II-12 | 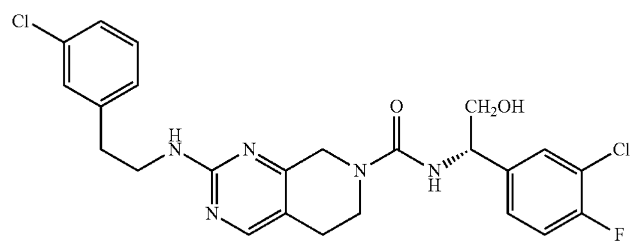 [SMILES: O=C(N[C@H](CO)c1ccc(F)c(Cl)c1)N1CCc2cnc(NCCc3cccc(Cl)c3)nc2C1] | 2-[2-(3-Chloro-phenyl)-ethylamino]-5,8-dihydro-6H-pyrido[3,4-d]pyrimidine-7-carboxylic acid [(S)-1-(3-chloro-4-fluoro-phenyl)-2-hydroxy-ethyl]-amide | 504.1 |
| II-13 | 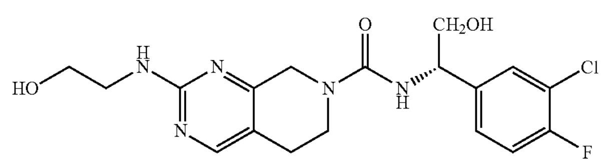 [SMILES: O=C(N[C@H](CO)c1ccc(F)c(Cl)c1)N1CCc2cnc(NCCO)nc2C1] | 2-(2-Hydroxy-ethylamino)-5,8-dihydro-6H-pyrido[3,4-d]pyrimidine-7-carboxylic acid [(S)-1-(3-chloro-4-fluoro-phenyl)-2-hydroxy-ethyl]-amide | 410.1 |
| II-14 | 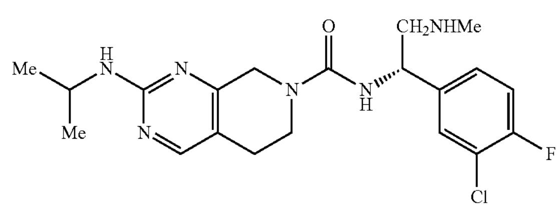 | 2-Isopropylamino-5,8-dihydro-6H-pyrido[3,4-d]pyrimidine-7-carboxylic acid [(S)-1-(3-chloro-4-fluoro-phenyl)-2-methylamino-ethyl]-amide | 421.3 |
| II-15 | 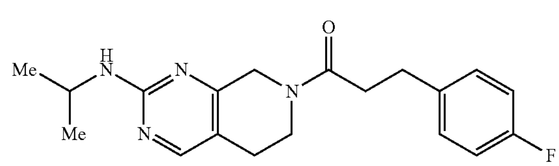 [SMILES: CC(C)Nc1ncc2c(n1)CN(C(=O)CCc1ccc(F)cc1)CC2] | 3-(4-Fluoro-phenyl)-1-(2-isopropylamino-5,8-dihydro-6H-pyrido[3,4-d]pyrimidin-7-yl)-propan-1-one | 343.2 |

TABLE II-continued

| | Structure | Name | MS |
|---|---|---|---|
| II-16 | 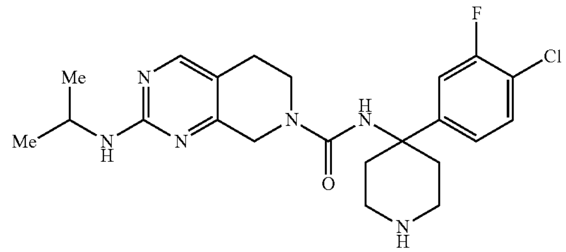 [SMILES: CC(C)Nc1ncc2c(n1)CN(C(=O)NC1(c3ccc(Cl)c(F)c3)CCNCC1)CC2] | 2-Isopropylamino-5,8-dihydro-6H-pyrido[3,4-d]pyrimidine-7-carboxylic acid [4-(4-chloro-3-fluoro-phenyl)-piperidin-4-yl]-amide | 447.4 |
| II-17 | 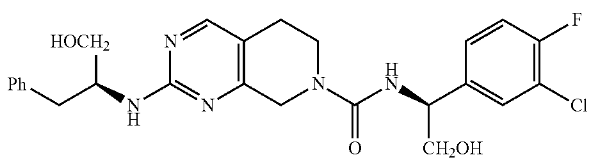 | 2-((S)-1-Hydroxymethyl-2-phenyl-ethylamino)-5,8-dihydro-6H-pyrido[3,4-d]pyrimidine-7-carboxylic acid [(S)-1-(3-chloro-4-fluoro-phenyl)-2-hydroxy-ethyl]-amide | 500.6 |
| II-18 | 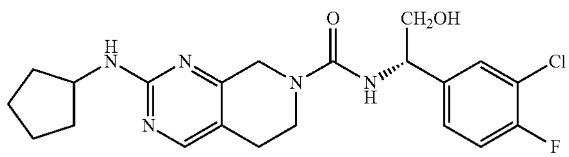 [SMILES: O=C(N[C@H](CO)c1ccc(F)c(Cl)c1)N1CCc2cnc(NC3CCCC3)nc2C1] | 2-Cyclopentylamino-5,8-dihydro-6H-pyrido[3,4-d]pyrimidine-7-carboxylic acid [(S)-1-(3-chloro-4-fluoro-phenyl)-2-hydroxy-ethyl]-amide | 434.1 |
| II-19 | 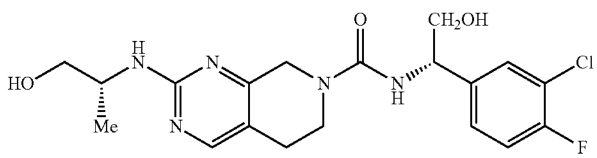 [SMILES: C[C@H](CO)Nc1ncc2c(n1)CN(C(=O)N[C@H](CO)c1ccc(F)c(Cl)c1)CC2] | 2-((R)-2-Hydroxy-1-methyl-ethylamino)-5,8-dihydro-6H-pyrido[3,4-d]pyrimidine-7-carboxylic acid [(S)-1-(3-chloro-4-fluoro-phenyl)-2-hydroxy-ethyl]-amide | 424.1 |
| II-20 | 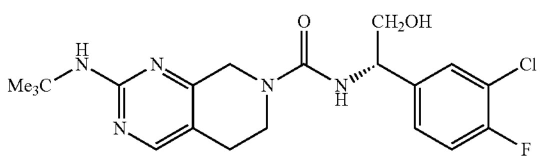 | 2-tert-Butylamino-5,8-dihydro-6H-pyrido[3,4-d]pyrimidine-7-carboxylic acid [(S)-1-(3-chloro-4-fluoro-phenyl)-2-hydroxy-ethyl]-amide | 4221 |
| II-21 | 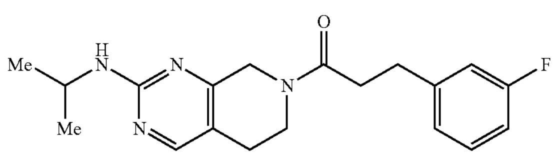 [SMILES: CC(C)Nc1ncc2c(n1)CN(C(=O)CCc1cccc(F)c1)CC2] | 3-(3-Fluoro-phenyl)-1-(2-isopropylamino-5,8-dihydro-6H-pyrido[3,4-d]pyrimidin-7-yl)-propan-1-one | 343.2 |
| II-22 | 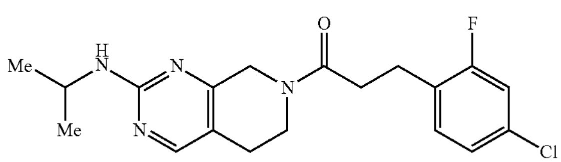 [SMILES: CC(C)Nc1ncc2c(n1)CN(C(=O)CCc1ccc(Cl)cc1F)CC2] | 3-(4-Chloro-2-fluoro-phenyl)-1-(2-isopropylamino-5,8-dihydro-6H-pyrido[3,4-d]pyrimidin-7-yl)-propan-1-one | 377.2 |
| II-23 | 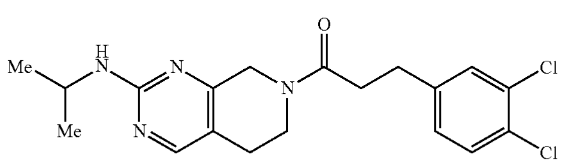 [SMILES: CC(C)Nc1ncc2c(n1)CN(C(=O)CCc1ccc(Cl)c(Cl)c1)CC2] | 3-(3,4-Dichloro-phenyl)-1-(2-isopropylamino-5,8-dihydro-6H-pyrido[3,4-d]pyrimidin-7-yl)-propan-1-one | 393.4 |
| II-24 | 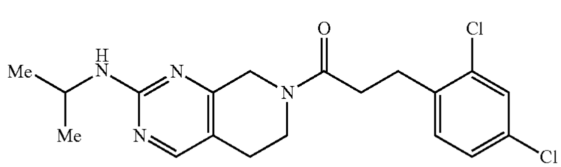 [SMILES: CC(C)Nc1ncc2c(n1)CN(C(=O)CCc1ccc(Cl)cc1Cl)CC2] | 3-(2,4-Dichloro-phenyl)-1-(2-isopropylamino-5,8-dihydro-6H-pyrido[3,4-d]pyrimidin-7-yl)-propan-1-one | 393.4 |

TABLE II-continued

| | Name | MS |
|---|---|---|
| II-25 | 3-(3,4-Difluoro-phenyl)-1-(2-isopropylamino-5,8-dihydro-6H-pyrido[3,4-d]pyrimidin-7-yl)-propan-1-one | 361.2 |
| II-26 | 2-Isopropylamino-5,8-dihydro-6H-pyrido[3,4-d]pyrimidine-7-carboxylic acid [(3-chloro-4-fluoro-phenyl)-methylcarbamoyl-methyl]-amide | 435.0 |
| II-27 | 2-Isopropylamino-5,8-dihydro-6H-pyrido[3,4-d]pyrimidine-7-carboxylic acid [(S)-1-(3-chloro-4-fluoro-phenyl)-2-ethylamino-ethyl]-amide | 435.1 |
| II-28 | 2-Isopropylamino-5,8-dihydro-6H-pyrido[3,4-d]pyrimidine-7-carboxylic acid [(S)-1-(3-chloro-4-fluoro-phenyl)-2-(2-hydroxy-ethylamino)-ethyl]-amide | 451.0 |
| II-29 | 2-Isopropylamino-5,8-dihydro-6H-pyrido[3,4-d]pyrimidine-7-carboxylic acid [(S)-1-(3-chloro-4-fluoro-phenyl)-2-isobutylamino-ethyl]-amide | 463.1 |
| II-30 | 2-Methylamino-5,8-dihydro-6H-pyrido[3,4-d]pyrimidine-7-carboxylic acid [(S)-1-(3-chloro-4-fluoro-phenyl)-2-hydroxy-ethyl]-amide | 380.0 |
| II-31 | 2-[2-(4-Chloro-phenyl)-1-methyl-ethylamino]-5,8-dihydro-6H-pyrido[3,4-d]pyrimidine-7-carboxylic acid [1-(3-chloro-4-fluoro-phenyl)-2-hydroxy-ethyl]-amide | 518.1 |
| II-32 | 2-Isobutylamino-5,8-dihydro-6H-pyrido[3,4-d]pyrimidine-7-carboxylic acid [(S)-1-(3-chloro-4-fluoro-phenyl)-2-hydroxy-ethyl]-amide | 422.1 |
| II-33 | 2-((S)-2-Methoxy-1-methyl-ethylamino)-5,8-dihydro-6H-pyrido[3,4-d]pyrimidine-7-carboxylic acid [(S)-1-(3-chloro-4-fluoro-phenyl)-2-hydroxy-ethyl]-amide | 438.1 |

TABLE II-continued

| | Structure | Name | MS |
|---|---|---|---|
| II-34 | 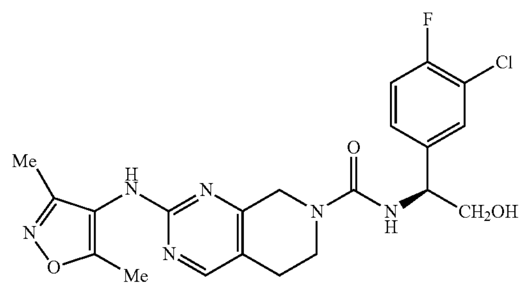 [SMILES: Cc1noc(C)c1Nc1ncc2c(n1)CN(C(=O)N[C@H](CO)c1ccc(F)c(Cl)c1)CC2] | 2-(3,5-Dimethyl-isoxazol-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide | 461.0 |
| II-35 | 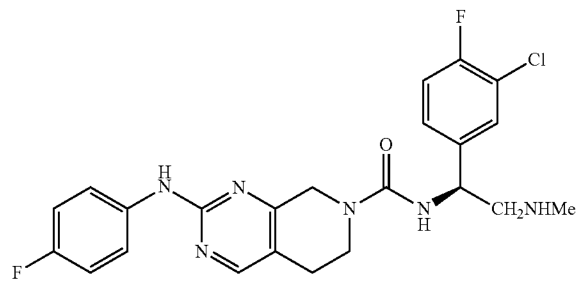 | 2-(4-Fluoro-phenylamino)-5,8-dihydro-6H-pyrido[3,4-d]pyrimidine-7-carboxylic acid [(S)-1-(3-chloro-4-fluoro-phenyl)-2-methylamino-ethyl]-amide | 473.0 |
| II-36 | 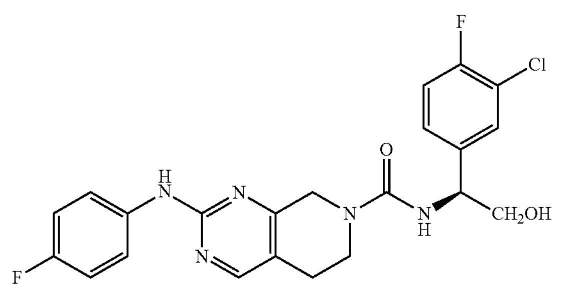 [SMILES: O=C(N[C@H](CO)c1ccc(F)c(Cl)c1)N1CCc2cnc(Nc3ccc(F)cc3)nc2C1] | 2-(4-Fluoro-phenylamino)-5,8-dihydro-6H-pyrido[3,4-d]pyrimidine-7-carboxylic acid [(S)-1-(3-chloro-4-fluoro-phenyl)-2-hydroxy-ethyl]-amide | 460.1 |
| II-37 | 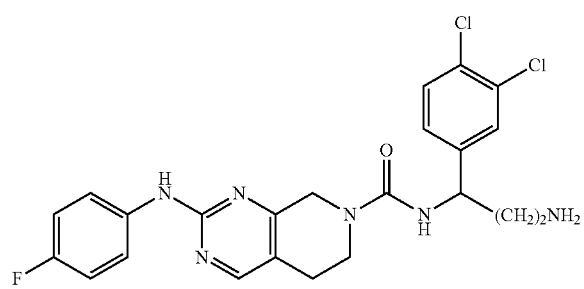 | 2-(4-Fluoro-phenylamino)-5,8-dihydro-6H-pyrido[3,4-d]pyrimidine-7-carboxylic acid [3-amino-1-(3,4-dichloro-phenyl)-propyl]-amide | 490.8 |
| II-38 | 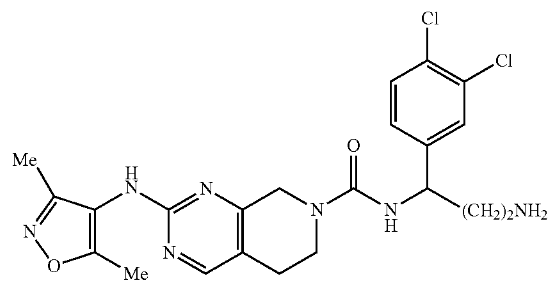 | 2-(3,5-Dimethyl-isoxazol-4-ylamino)-5,8-dihydro-6H-pyrido[3,4-d]pyrimidine-7-carboxylic acid [3-amino-1-(3,4-dichloro-phenyl)-propyl]-amide | 491.8 |

TABLE II-continued

| | Structure | Name | MS |
|---|---|---|---|
| II-39 | 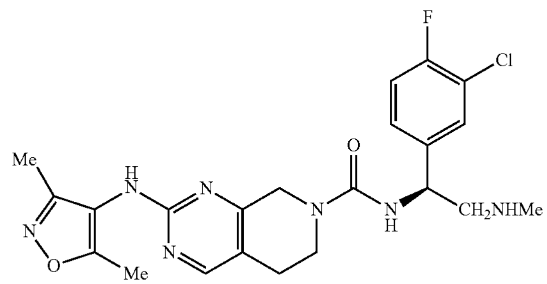 | 2-(3,5-Dimethyl-isoxazol-4-ylamino)-5,8-dihydro-6H-pyrido[3,4-d]pyrimidine-7-carboxylic acid [(S)-1-(3-chloro-4-fluoro-phenyl)-2-methylamino-ethyl]-amide | 474.0 |
| II-40 | 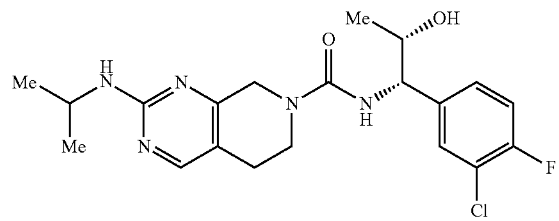 [SMILES: CC(C)Nc1ncc2c(n1)CN(C(=O)N[C@@H](c1ccc(F)c(Cl)c1)[C@H](C)O)CC2] | 2-Isopropylamino-5,8-dihydro-6H-pyrido[3,4-d]pyrimidine-7-carboxylic acid [(1S,2S)-1-(3-chloro-4-fluoro-phenyl)-2-hydroxy-propyl]-amide | 422.4 |
| II-41 | 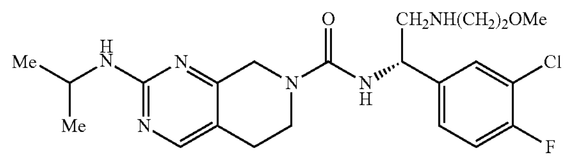 | 2-Isopropylamino-5,8-dihydro-6H-pyrido[3,4-d]pyrimidine-7-carboxylic acid [(S)-1-(3-chloro-4-fluoro-phenyl)-2-(2-methoxy-ethylamino)-ethyl]-amide | 465.1 |
| II-42 | 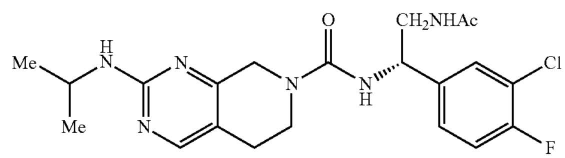 | 2-Isopropylamino-5,8-dihydro-6H-pyrido[3,4-d]pyrimidine-7-carboxylic acid [(S)-2-acetylamino-1-(3-chloro-4-fluoro-phenyl)-ethyl]-amide | 449.0 |
| II-43 | 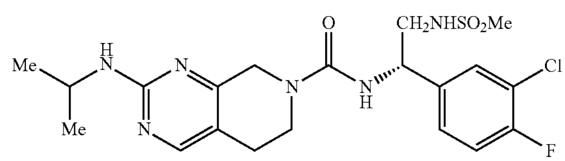 | 2-Isopropylamino-5,8-dihydro-6H-pyrido[3,4-d]pyrimidine-7-carboxylic acid [(S)-1-(3-chloro-4-fluoro-phenyl)-2-methanesulfonylamino-ethyl]-amide | 485.1 |
| II-44 | 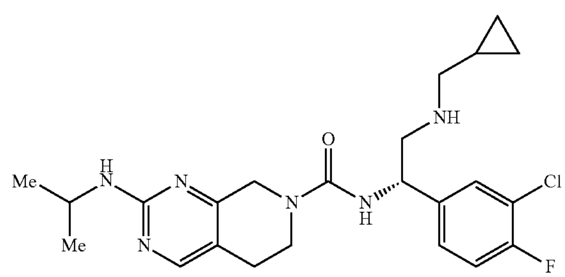 [SMILES: CC(C)Nc1ncc2c(n1)CN(C(=O)N[C@H](CNCC1CC1)c1ccc(F)c(Cl)c1)CC2] | 2-Isopropylamino-5,8-dihydro-6H-pyrido[3,4-d]pyrimidine-7-carboxylic acid [(S)-1-(3-chloro-4-fluoro-phenyl)-2-(cyclopropylmethyl-amino)-ethyl]-amide | 461.0 |
| II-45 | 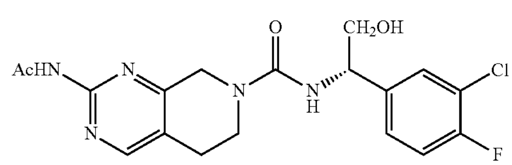 [SMILES: CC(=O)Nc1ncc2c(n1)CN(C(=O)N[C@H](CO)c1ccc(F)c(Cl)c1)CC2] | 2-Acetylamino-5,8-dihydro-6H-pyrido[3,4-d]pyrimidine-7-carboxylic acid [(S)-1-(3-chloro-4-fluoro-phenyl)-2-hydroxy-ethyl]-amide | no parent |
| II-46 | 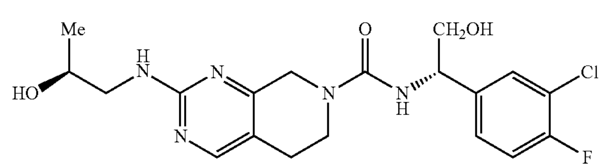 [SMILES: C[C@H](O)CNc1ncc2c(n1)CN(C(=O)N[C@H](CO)c1ccc(F)c(Cl)c1)CC2] | 2-((S)-2-Hydroxy-propylamino)-5,8-dihydro-6H-pyrido[3,4-d]pyrimidine-7-carboxylic acid [(S)-1-(3-chloro-4-fluoro-phenyl)-2-hydroxy-ethyl]-amide | 424.0 |

TABLE II-continued

| | Name | MS |
|---|---|---|
| II-47 | 2-Amino-5,8-dihydro-6H-pyrido[3,4-d]pyrimidine-7-carboxylic acid [(S)-1-(3-chloro-4-fluoro-phenyl)-2-hydroxy-ethyl]-amide | 366.0 |
| II-48 | 4-Amino-3-(4-chloro-3-fluoro-phenyl)-1-(2-isopropylamino-5,8-dihydro-6H-pyrido[3,4-d]pyrimidin-7-yl)-butan-1-one | 406.3 |
| II-49 | 4-Amino-3-(3-chloro-4-fluoro-phenyl)-1-(2-isopropylamino-5,8-dihydro-6H-pyrido[3,4-d]pyrimidin-7-yl)-butan-1-one | 406.3 |
| II-50 | 2-Isopropylamino-5,8-dihydro-6H-pyrido[3,4-d]pyrimidine-7-carboxylic acid [(S)-1-(3-chloro-4-fluoro-phenyl)-2-(pyrimidin-2-ylamino)-ethyl]-amide | 485.0 |
| II-51 | 2-Isopropylamino-5,8-dihydro-6H-pyrido[3,4-d]pyrimidine-7-carboxylic acid [(S)-1-(3-chloro-4-fluoro-phenyl)-2-(pyrimidin-4-ylamino)-ethyl]-amide | 485.1 |
| II-52 | 2-(4-Fluoro-phenylamino)-5,8-dihydro-6H-pyrido[3,4-d]pyrimidine-7-carboxylic acid [(1S,2S)-1-(3-chloro-4-fluoro-phenyl)-2-hydroxy-propyl]-amide | 474.5 |
| II-53 | 2-Isopropylamino-5,8-dihydro-6H-pyrido[3,4-d]pyrimidine-7-carboxylic acid [(S)-(4-chloro-3-fluoro-phenyl)-(S)-pyrrolidin-2-yl-methyl]-amide | 447.4 |

TABLE II-continued

| | Structure | Name | MS |
|---|---|---|---|
| II-54 | 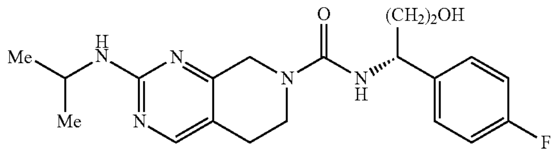 | 2-Isopropylamino-5,8-dihydro-6H-pyrido[3,4-d]pyrimidine-7-carboxylic acid [(R)-1-(4-fluoro-phenyl)-3-hydroxy-propyl]-amide | 388.0 |
| II-55 | 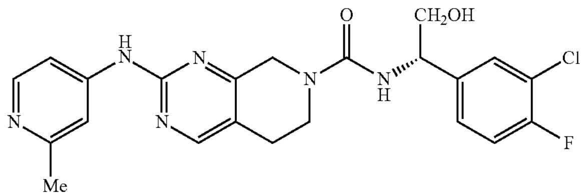 [SMILES: Cc1cc(Nc2ncc3c(n2)CN(C(=O)N[C@H](CO)c2ccc(F)c(Cl)c2)CC3)ccn1] | 2-(2-Methyl-pyridin-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide | 457.2 |
| II-56 | 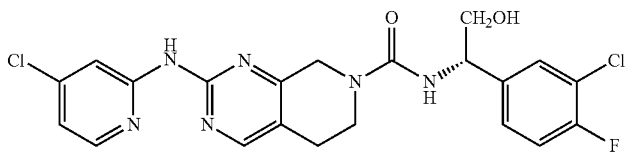 [SMILES: O=C(N[C@H](CO)c1ccc(F)c(Cl)c1)N1CCc2cnc(Nc3cc(Cl)ccn3)nc2C1] | 2-(4-Chloro-pyridin-2-ylamino)-5,8-dihydro-6H-pyrido[3,4-d]pyrimidine-7-carboxylic acid [(S)-1-(3-chloro-4-fluoro-phenyl)-2-hydroxy-ethyl]-amide | 477.0 |
| II-57 | 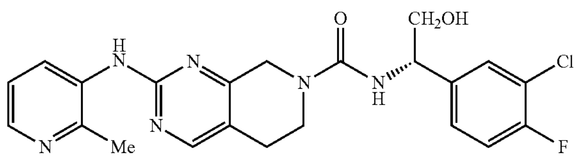 [SMILES: Cc1ncccc1Nc1ncc2c(n1)CN(C(=O)N[C@H](CO)c1ccc(F)c(Cl)c1)CC2] | 2-(2-Methyl-pyridin-3-ylamino)-5,8-dihydro-6H-pyrido[3,4-d]pyrimidine-7-carboxylic acid [(S)-1-(3-chloro-4-fluoro-phenyl)-2-hydroxy-ethyl]-amide | 457.0 |
| II-58 | 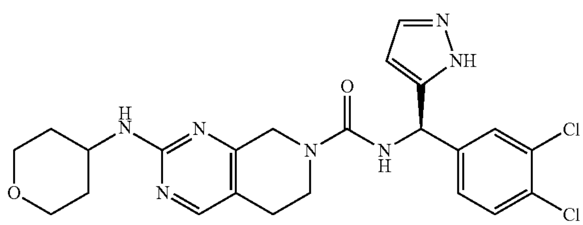 [SMILES: O=C(N[C@H](c1ccc(Cl)c(Cl)c1)c1ccn[nH]1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(S)-(3,4-dichloro-phenyl)-(2H-pyrazol-3-yl)-methyl]-amide | 502.2 |
| II-59 | 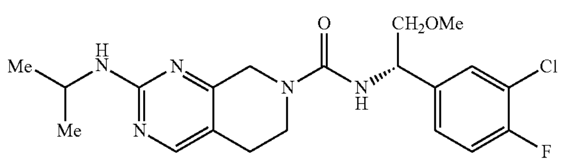 | 2-Isopropylamino-5,8-dihydro-6H-pyrido[3,4-d]pyrimidine-7-carboxylic acid [(S)-1-(3-chloro-4-fluoro-phenyl)-2-methoxy-ethyl]-amide | 422.1 |
| II-60 | 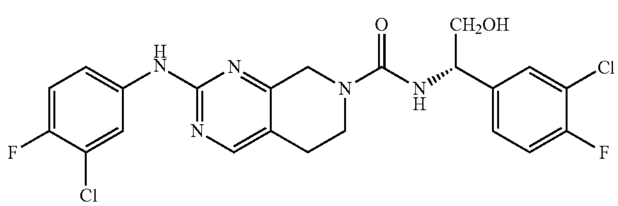 [SMILES: O=C(N[C@H](CO)c1ccc(F)c(Cl)c1)N1CCc2cnc(Nc3ccc(F)c(Cl)c3)nc2C1] | 2-(3-Chloro-4-fluoro-phenylamino)-5,8-dihydro-6H-pyrido[3,4-d]pyrimidine-7-carboxylic acid [(S)-1-(3-chloro-4-fluoro-phenyl)-2-hydroxy-ethyl]-amide | 494.5 |
| II-61 | 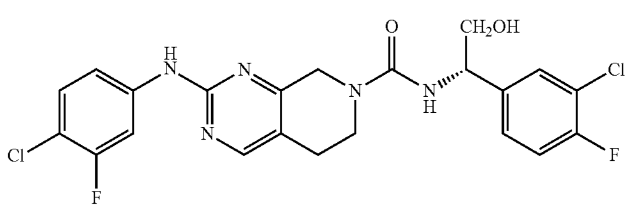 [SMILES: O=C(N[C@H](CO)c1ccc(F)c(Cl)c1)N1CCc2cnc(Nc3ccc(Cl)c(F)c3)nc2C1] | 2-(4-Chloro-3-fluoro-phenylamino)-5,8-dihydro-6H-pyrido[3,4-d]pyrimidine-7-carboxylic acid [(S)-1-(3-chloro-4-fluoro-phenyl)-2-hydroxy-ethyl]-amide | 494.5 |

TABLE II-continued

| | Structure | Name | MS |
|---|---|---|---|
| II-62 | 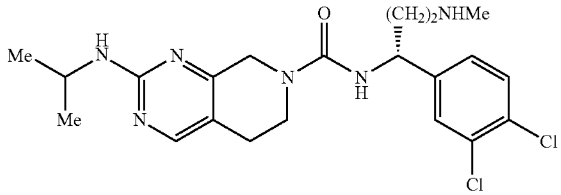 | 2-Isopropylamino-5,8-dihydro-6H-pyrido[3,4-d]pyrimidine-7-carboxylic acid [(R)-1-(3,4-dichloro-phenyl)-3-methylamino-propyl]-amide | 451.1 |
| II-63 | 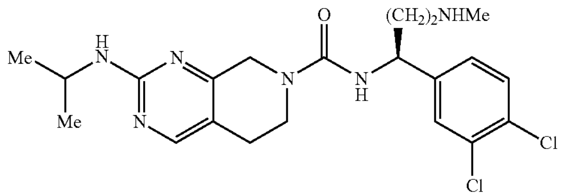 | 2-Isopropylamino-5,8-dihydro-6H-pyrido[3,4-d]pyrimidine-7-carboxylic acid [(S)-1-(3,4-dichloro-phenyl)-3-methylamino-propyl]-amide | 451.1 |
| II-64 | 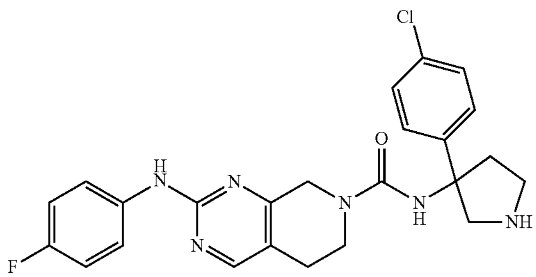 [SMILES: O=C(NC1(c2ccc(Cl)cc2)CCNC1)N1CCc2cnc(Nc3ccc(F)cc3)nc2C1] | 2-(4-Fluoro-phenylamino)-5,8-dihydro-6H-pyrido[3,4-d]pyrimidine-7-carboxylic acid [3-(4-chloro-phenyl)-pyrrolidin-3-yl]-amide | 467.4 |
| II-65 | 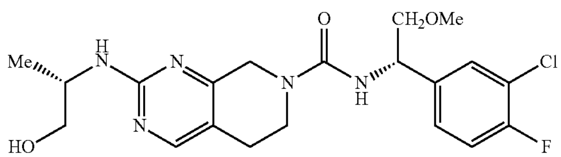 | 2-((S)-2-Hydroxy-1-methyl-ethylamino)-5,8-dihydro-6H-pyrido[3,4-d]pyrimidine-7-carboxylic acid [(S)-1-(3-chloro-4-fluoro-phenyl)-2-methoxy-ethyl]-amide | 438.0 |
| II-66 | 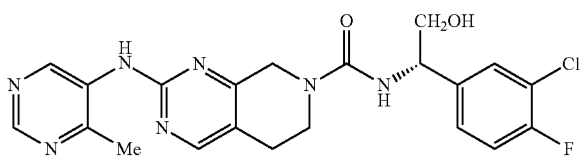 [SMILES: Cc1ncncc1Nc1ncc2c(n1)CN(C(=O)N[C@H](CO)c1ccc(F)c(Cl)c1)CC2] | 2-(4-Methyl-pyrimidin-5-ylamino)-5,8-dihydro-6H-pyrido[3,4-d]pyrimidine-7-carboxylic acid [(S)-1-(3-chloro-4-fluoro-phenyl)-2-hydroxy-ethyl]-amide | 458.1 |
| II-67 | 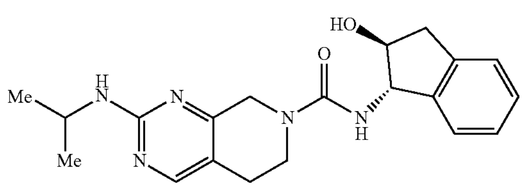 [SMILES: CC(C)Nc1ncc2c(n1)CN(C(=O)N[C@H]1c3ccccc3C[C@@H]1O)CC2] | 2-Isopropylamino-5,8-dihydro-6H-pyrido[3,4-d]pyrimidine-7-carboxylic acid ((1S,2S)-2-hydroxy-indan-1-yl)-amide | 368.3 |
| II-68 | 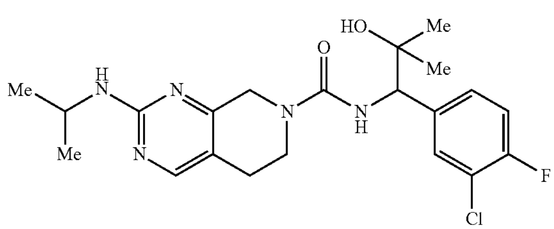 [SMILES: CC(C)Nc1ncc2c(n1)CN(C(=O)NC(c1ccc(F)c(Cl)c1)C(C)(C)O)CC2] | 2-Isopropylamino-5,8-dihydro-6H-pyrido[3,4-d]pyrimidine-7-carboxylic acid [1-(3-chloro-4-fluoro-phenyl)-2-hydroxy-2-methyl-propyl]-amide | 436.1 |
| II-69 | 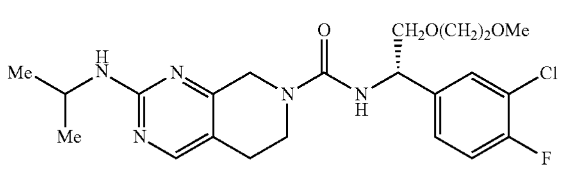 | 2-Isopropylamino-5,8-dihydro-6H-pyrido[3,4-d]pyrimidine-7-carboxylic acid [(S)-1-(3-chloro-4-fluoro-phenyl)-2-(2-methoxy-ethoxy)-ethyl]-amide | 466.1 |

TABLE II-continued

| | Structure | Name | MS |
|---|---|---|---|
| II-70 | 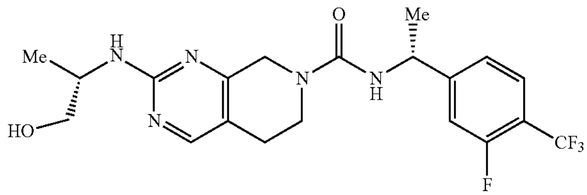 [SMILES: C[C@@H](CO)Nc1ncc2c(n1)CN(C(=O)N[C@H](C)c1ccc(C(F)(F)F)c(F)c1)CC2] | 2-((S)-2-Hydroxy-1-methyl-ethylamino)-5,8-dihydro-6H-pyrido[3,4-d]pyrimidine-7-carboxylic acid [(R)-1-(3-fluoro-4-trifluoromethyl-phenyl)-ethyl]-amide | 442.5 |
| II-71 | 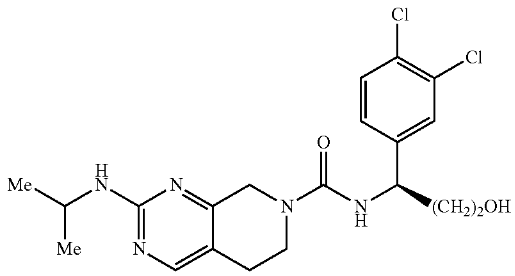 | 2-Isopropylamino-5,8-dihydro-6H-pyrido[3,4-d]pyrimidine-7-carboxylic acid [(R)-1-(3,4-dichloro-phenyl)-3-hydroxy-propyl]-amide | 438.1 |
| II-72 | 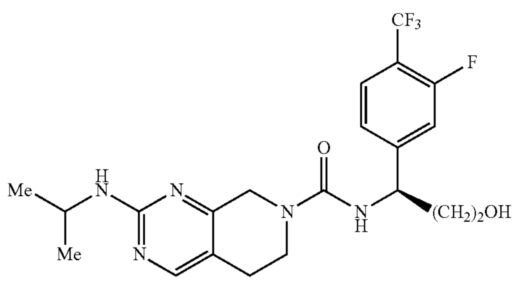 | 2-Isopropylamino-5,8-dihydro-6H-pyrido[3,4-d]pyrimidine-7-carboxylic acid [(R)-1-(3-fluoro-4-trifluoromethyl-phenyl)-3-hydroxy-propyl]-amide | 456.2 |
| II-73 | 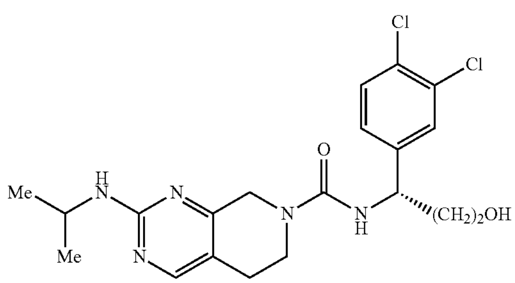 | 2-Isopropylamino-5,8-dihydro-6H-pyrido[3,4-d]pyrimidine-7-carboxylic acid [(S)-1-(3,4-dichloro-phenyl)-3-hydroxy-propyl]-amide | 438.1 |
| II-74 | 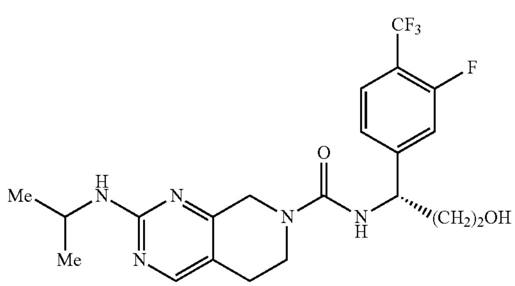 | 2-Isopropylamino-5,8-dihydro-6H-prido[3,4-d]pyrimidine-7-carboxylic acid [(S)-1-(3-fluoro-4-trifluoromethyl-phenyl)-3-hydroxy-propyl]-amide | 456.2 |
| II-75 | 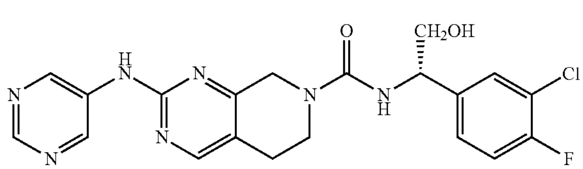 [SMILES: O=C(N[C@H](CO)c1ccc(F)c(Cl)c1)N1CCc2cnc(Nc3cncnc3)nc2C1] | 2-(Pyrimidin-5-ylamino)-5,8-dihydro-6H-pyrido[3,4-d]pyrimidine-7-carboxylic acid [(S)-1-(3-chloro-4-fluoro-phenyl)-2-hydroxy-ethyl]-amide | 444.1 |

TABLE II-continued

| | Structure | Name | MS |
|---|---|---|---|
| II-76 | 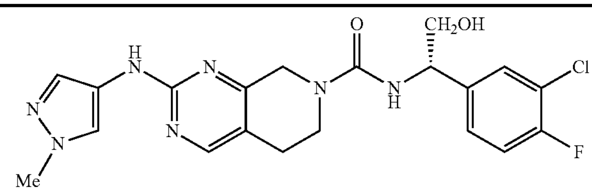 | 2-(1-Methyl-1H-pyrazol-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide | 446.2 |
| II-77 | 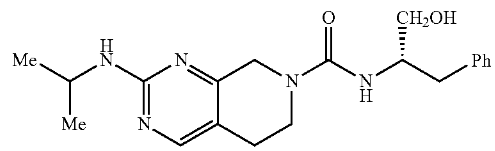 [SMILES: CC(C)Nc1ncc2c(n1)CN(C(=O)N[C@H](CO)Cc1ccccc1)CC2] | 2-Isopropylamino-5,8-dihydro-6H-pyrido[3,4-d]pyrimidine-7-carboxylic acid ((S)-1-hydroxymethyl-2-phenyl-ethyl)-amide | 370.4 |
| II-78 | 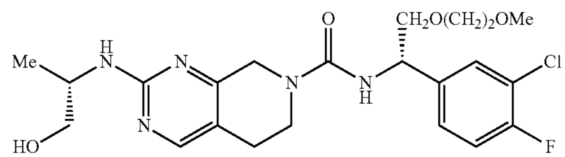 | 2-((S)-2-Hydroxy-1-methyl-ethylamino)-5,8-dihydro-6H-pyrido[3,4-d]pyrimidine-7-carboxylic acid [(S)-1-(3-chloro-4-fluoro-phenyl)-2-(2-methoxy-ethoxy)-ethyl]-amide | 482.2 |
| II-79 | 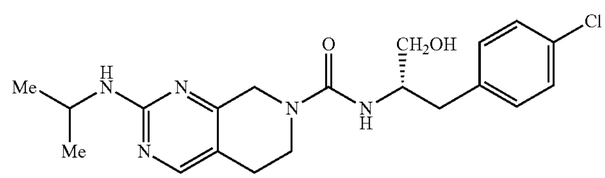 [SMILES: CC(C)Nc1ncc2c(n1)CN(C(=O)N[C@H](CO)Cc1ccc(Cl)cc1)CC2] | 2-Isopropylamino-5,8-dihydro-6H-pyrido[3,4-d]pyrimidine-7-carboxylic acid [(S)-2-(4-chloro-phenyl)-1-hydroxymethyl-ethyl]-amide | 404.4 |
| II-80 | 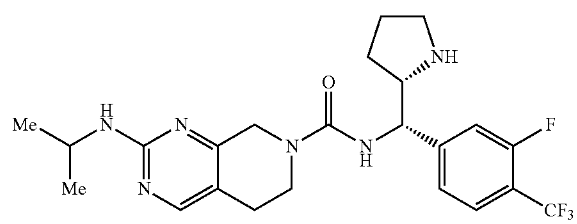 [SMILES: CC(C)Nc1ncc2c(n1)CN(C(=O)N[C@@H](c1ccc(C(F)(F)F)c(F)c1)[C@@H]1CCCN1)CC2] | 2-Isopropylamino-5,8-dihydro-6H-pyrido[3,4-d]pyrimidine-7-carboxylic acid [(S)-(3-fluoro-4-trifluoromethyl-phenyl)-(S)-pyrrolidin-2-yl-methyl]-amide | 481.1 |
| II-81 | 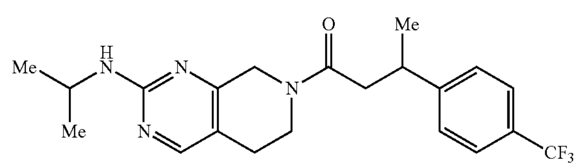 [SMILES: CC(C)Nc1ncc2c(n1)CN(C(=O)CC(C)c1ccc(C(F)(F)F)cc1)CC2] | 1-(2-Isopropylamino-5,8-dihydro-6H-pyrido[3,4-d]pyrimidin-7-yl)-3-(4-trifluoromethyl-phenyl)-butan-1-one | 407.2 |
| II-82 | 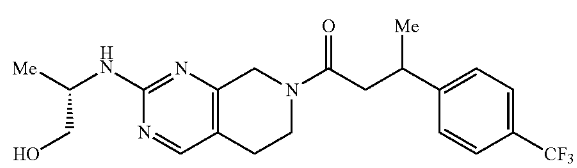 [SMILES: CC(CC(=O)N1CCc2cnc(N[C@@H](C)CO)nc2C1)c1ccc(C(F)(F)F)cc1] | 1-[2-(2-Hydroxy-1-methyl-ethylamino)-5,8-dihydro-6H-pyrido[3,4-d]pyrimidin-7-yl]-3-(4-trifluoromethyl-phenyl)-butan-1-one | 423.3 |
| II-83 | 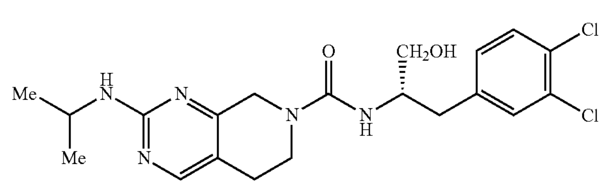 [SMILES: CC(C)Nc1ncc2c(n1)CN(C(=O)N[C@H](CO)Cc1ccc(Cl)c(Cl)c1)CC2] | 2-Isopropylamino-5,8-dihydro-6H-pyrido[3,4-d]pyrimidine-7-carboxylic acid [(S)-2-(3,4-dichloro-phenyl)-1-hydroxymethyl-ethyl]-amide | 438.5 |
| II-84 | 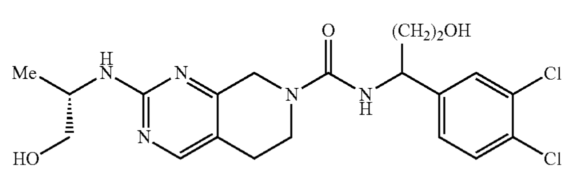 | 2-(2-Hydroxy-1-methyl-ethylamino)-5,8-dihydro-6H-pyrido[3,4-d]pyrimidine-7-carboxylic acid [1-(3,4-dichloro-phenyl)-3-hydroxy-propyl]-amide | 454.1 |

TABLE II-continued

| | Structure | Name | MS |
|---|---|---|---|
| II-85 | 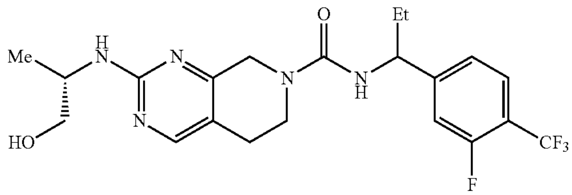 [SMILES: CCC(NC(=O)N1CCc2cnc(N[C@@H](C)CO)nc2C1)c1ccc(C(F)(F)F)c(F)c1] | 2-(2-Hydroxy-1-methyl-ethylamino)-5,8-dihydro-6H-pyrido[3,4-d]pyrimidine-7-carboxylic acid [1-(3-fluoro-4-trifluoromethyl-phenyl)-propyl]-amide | 456.2 |
| II-86 | 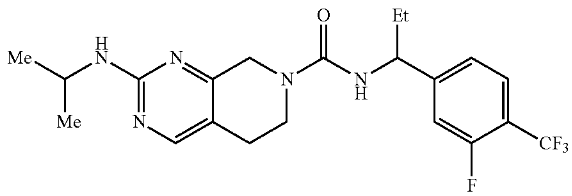 [SMILES: CCC(NC(=O)N1CCc2cnc(NC(C)C)nc2C1)c1ccc(C(F)(F)F)c(F)c1] | 2-Isopropylamino-5,8-dihydro-6H-pyrido[3,4-d]pyrimidine-7-carboxylic acid [1-(3-fluoro-4-trifluoromethyl-phenyl)-propyl]-amide | 440.2 |
| II-87 | 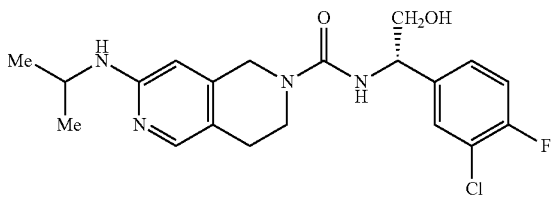 [SMILES: CC(C)Nc1cc2c(cn1)CCN(C(=O)N[C@H](CO)c1ccc(F)c(Cl)c1)C2] | 7-Isopropylamino-3,4-dihydro-1H-[2,6]naphthyridine-2-carboxylic acid [(S)-1-(3-chloro-4-fluoro-phenyl)-2-hydroxy-ethyl]-amide | 407.1 |
| II-88 | 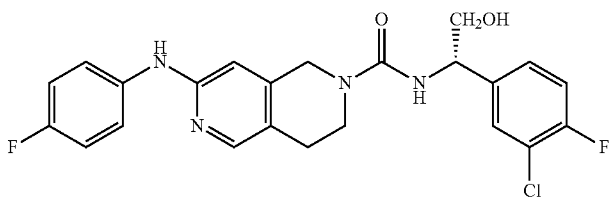 [SMILES: O=C(N[C@H](CO)c1ccc(F)c(Cl)c1)N1CCc2cnc(Nc3ccc(F)cc3)cc2C1] | 7-(4-Fluoro-phenylamino)-3,4-dihydro-1H-[2,6]naphthyridine-2-carboxylic acid [(S)-1-(3-chloro-4-fluoro-phenyl)-2-hydroxy-ethyl]-amide | 459.6 |
| II-89 | 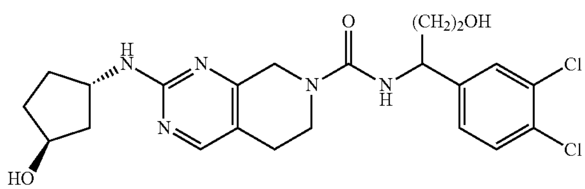 | 2-(3-Hydroxy-cyclopentylamino)-5,8-dihydro-6H-pyrido[3,4-d]pyrimidine-7-carboxylic acid [1-(3,4-dichloro-phenyl)-3-hydroxy-propyl]-amide | 480.1 |
| II-90 | 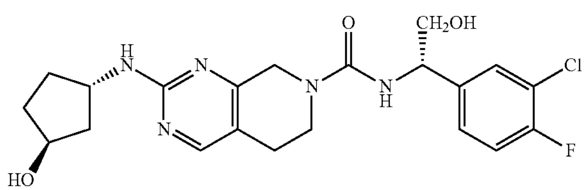 [SMILES: O=C(N[C@H](CO)c1ccc(F)c(Cl)c1)N1CCc2cnc(N[C@H]3CC[C@H](O)C3)nc2C1] | 2-((1S,3S)-3-Hydroxy-cyclopentylamino)-5,8-dihydro-6H-pyrido[3,4-d]pyrimidine-7-carboxylic acid [(S)-1-(3-chloro-4-fluoro-phenyl)-2-hydroxy-ethyl]-amide | 450.2 |
| II-91 | 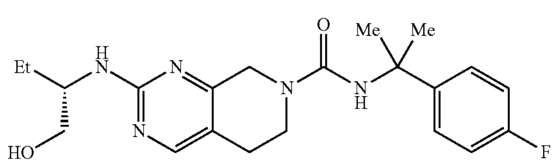 [SMILES: CC[C@@H](CO)Nc1ncc2c(n1)CN(C(=O)NC(C)(C)c1ccc(F)cc1)CC2] | 2-((S)-1-Hydroxymethyl-propylamino)-5,8-dihydro-6H-pyrido[3,4-d]pyrimidine-7-carboxylic acid [1-(4-fluoro-phenyl)-1-methyl-ethyl]-amide | 402.2 |
| II-92 | 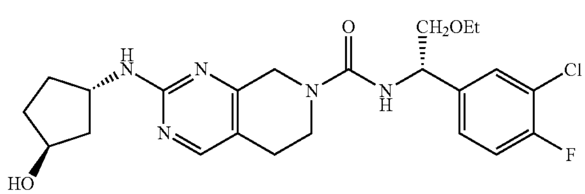 | 2-((1S,3S)-3-Hydroxy-cyclopentylamino)-5,8-dihydro-6H-pyrido[3,4-d]pyrimidine-7-carboxylic acid [(S)-1-(3-chloro-4-fluoro-phenyl)-2-ethoxy-ethyl]-amide | 478.2 |

TABLE II-continued

| | Name | MS |
|---|---|---|
| II-93 | 2-((S)-2-Hydroxy-1-methyl-ethylamino)-5,8-dihydro-6H-pyrido[3,4-d]pyrimidine-7-carboxylic acid [(S)-1-(3-chloro-4-fluoro-phenyl)-2-isopropoxy-ethyl]-amide | 466.2 |
| II-94 | 2-((S)-2-Hydroxy-1-methyl-ethylamino)-5,8-dihydro-6H-pyrido[3,4-d]pyrimidine-7-carboxylic acid [(S)-1-(3-chloro-4-fluoro-phenyl)-2-ethoxy-ethyl]-amide | 452.1 |
| II-95 | 2-((1S,3S)-3-Hydroxy-cyclopentylamino)-5,8-dihydro-6H-pyrido[3,4-d]pyrimidine-7-carboxylic acid [(S)-1-(3-chloro-4-fluoro-phenyl)-2-isopropoxy-ethyl]-amide | 492.3 |
| I-96 | 2-Isopropylamino-8-oxo-5,8-dihydro-6H-pyrido[3,4-d]pyrimidine-7-carboxylic acid [(S)-(4-chloro-3-fluoro-phenyl)-(S)-pyrrolidin-2-yl-methyl]-amide | 461.2 |
| II-97 | 3-(3-Fluoro-4-trifluoromethyl-phenyl)-1-[2-(2-hydroxy-1-methyl-ethylamino)-5,8-dihydro-6H-pyrido[3,4-d]pyrimidin-7-yl]-hexan-1-one | 469.3 |
| II-98 | 3-(3-Fluoro-4-trifluoromethyl-phenyl)-1-(2-isopropylamino-5,8-dihydro-6H-pyrido[3,4-d]pyrimidin-7-yl)-hexan-1-one | 453.3 |
| II-99 | 2-Isopropylamino-5,8-dihydro-6H-pyrido[3,4-d]pyrimidine-7-carboxylic acid [(S)-(3-fluoro-4-trifluoromethyl-phenyl)-(6-oxo-1,6-dihydro-pyridin-2-yl)-methyl]-amide | 506.1 |
| II-100 | 2-Isopropylamino-5,8-dihydro-6H-pyrido[3,4-d]pyrimidine-7-carboxylic acid [(S)-(3-fluoro-4-trifluoromethyl-phenyl)-(6-methoxy-pyridin-2-yl)-methyl]-amide | 519.0 |

TABLE II-continued

| | Structure | Name | MS |
|---|---|---|---|
| II-101 | 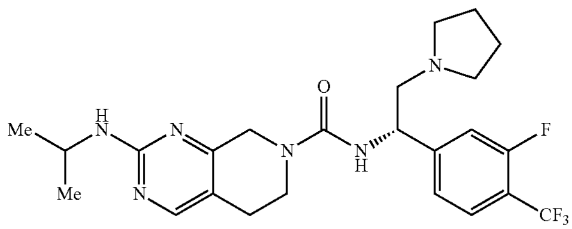 [SMILES: CC(C)Nc1ncc2c(n1)CN(C(=O)N[C@H](CN1CCCC1)c1ccc(C(F)(F)F)c(F)c1)CC2] | 2-Isopropylamino-5,8-dihydro-6H-pyrido[3,4-d]pyrimidine-7-carboxylic acid [(S)-1-(3-fluoro-4-trifluoromethyl-phenyl)-2-pyrrolidin-1-yl-ethyl]amide | 495.2 |
| II-102 | 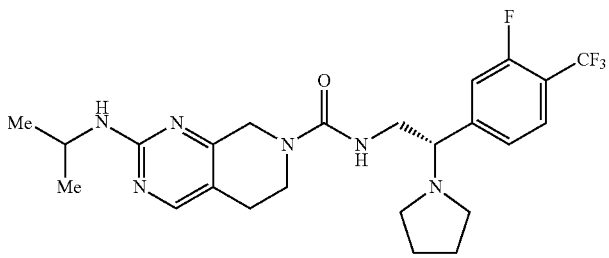 [SMILES: CC(C)Nc1ncc2c(n1)CN(C(=O)NC[C@H](c1ccc(C(F)(F)F)c(F)c1)N1CCCC1)CC2] | 2-Isopropylamino-5,8-dihydro-6H-pyrido[3,4-d]pyrimidine-7-carboxylic acid [(S)-2-(3-fluoro-4-trifluoromethyl-phenyl)-2-pyrrolidin-1-yl-ethyl]-amide | 49532 |
| II-103 | 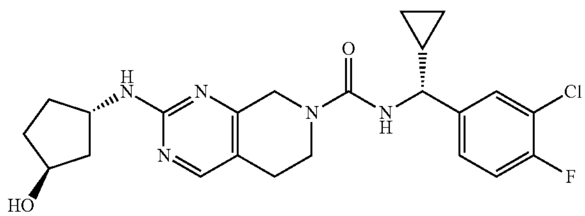 [SMILES: O=C(N[C@@H](c1ccc(F)c(Cl)c1)C1CC1)N1CCc2cnc(N[C@H]3CC[C@H](O)C3)nc2C1] | 2-((1S,3S)-3-Hydroxy-cyclopentylamino)-5,8-dihydro-6H-pyrido[3,4-d]pyrimidine-7-carboxylic acid [(R)-(3-chloro-4-fluoro-phenyl)-cyclopropyl-methyl]-amide | 460.1 |
| II-104 | 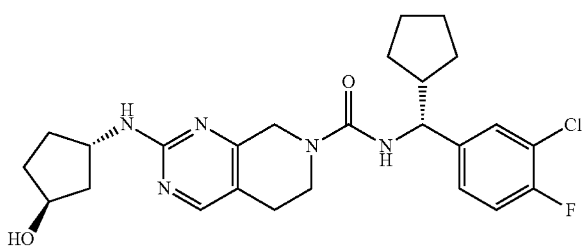 [SMILES: O=C(N[C@@H](c1ccc(F)c(Cl)c1)C1CCCC1)N1CCc2cnc(N[C@H]3CC[C@H](O)C3)nc2C1] | 2-((1S,3S)-3-Hydroxy-cyclopentylamino)-5,8-dihydro-6H-pyrido[3,4-d]pyrimidine-7-carboxylic acid [(R)-(3-chloro-4-fluoro-phenyl)-cyclopentyl-methyl]-amide | 4882 |
| II-105 | 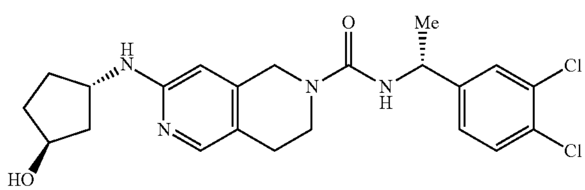 [SMILES: C[C@@H](NC(=O)N1CCc2cnc(N[C@H]3CC[C@H](O)C3)cc2C1)c1ccc(Cl)c(Cl)c1] | 7-(3-Hydroxy-cyclopentylamino)-3,4-dihydro-1H-[2,6]naphthyridine-2-carboxylic acid [1-(3,4-dichloro-phenyl)-ethyl]-amide | 449.6 |
| II-106 | 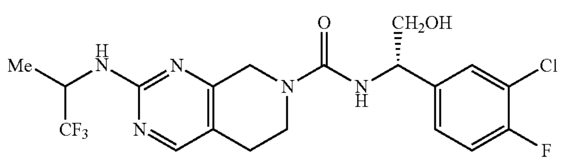 [SMILES: CC(Nc1ncc2c(n1)CN(C(=O)N[C@H](CO)c1ccc(F)c(Cl)c1)CC2)C(F)(F)F] | 2-(2,2,2-Trifluoro-1-methyl-ethylamino)-5,8-dihydro-6H-pyrido[3,4-d]pyrimidine-7-carboxylic acid [1-(3-chloro-4-fluoro-phenyl)-2-hydroxy-ethyl]-amide | 462.4 |
| II-107 | 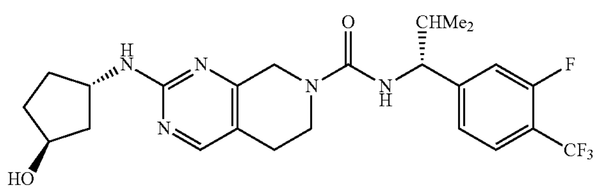 | 2-((1S,3S)-3-Hydroxy-cyclopentylamino)-5,8-dihydro-6H-pyrido[3,4-d]pyrimidine-7-carboxylic acid [(R)-1-(3-fluoro-4-trifluoromethyl-phenyl)-2-methyl-propyl]-amide | 496.3 |

TABLE II-continued

| | Structure | Name | MS |
|---|---|---|---|
| II-108 | 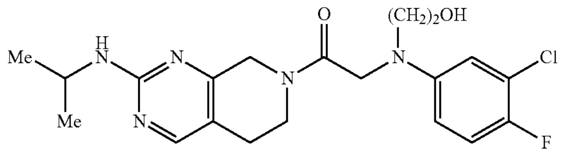 | 2-[(3-Chloro-4-fluoro-phenyl)-(2-hydroxy-ethyl)-amino]-1-(2-isopropylamino-5,8-dihydro-6H-pyrido[3,4-d]pyrimidin-7-yl)-ethanone | 422.4 |
| II-109 | 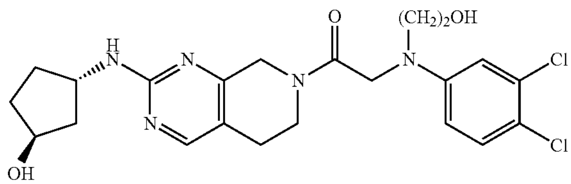 | 2-((1S,3S)-3-Hydroxy-cyclopentylamino)-5,8-dihydro-6H-pyrido[3,4-d]pyrimidine-7-carboxylic acid [(R)-1-(3,4-dichloro-phenyl)-3-hydroxy-propyl]-amide | 480.1 |
| II-110 | 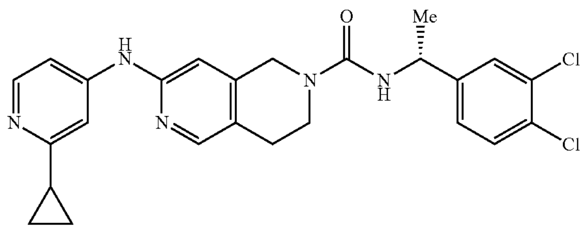 [SMILES: C[C@@H](NC(=O)N1CCc2cnc(Nc3ccnc(C4CC4)c3)cc2C1)c1ccc(Cl)c(Cl)c1] | 7-(2-Cyclopropyl-pyridin-4-ylamino)-3,4-dihydro-1H-[2,6]naphthyridine-2-carboxylic acid [(R)-1-(3,4-dichloro-phenyl)-ethyl]-amide | 484.2 |
| II-111 | 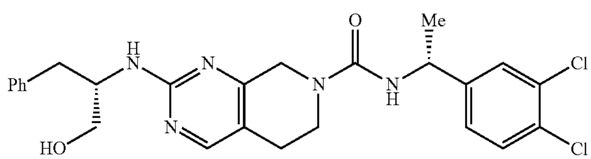 [SMILES: C[C@@H](NC(=O)N1CCc2cnc(N[C@H](CO)Cc3ccccc3)nc2C1)c1ccc(Cl)c(Cl)c1] | 2-((S)-1-Hydroxymethyl-2-phenyl-ethylamino)-5,8-dihydro-6H-pyrido[3,4-d]pyrimidine-7-carboxylic acid [(R)-1-(3,4-dichloro-phenyl)-ethyl]-amide | 500.6 |
| II-112 | 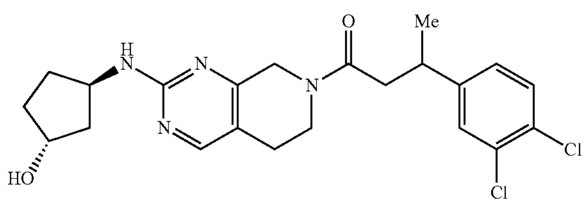 [SMILES: CC(CC(=O)N1CCc2cnc(N[C@@H]3CC[C@@H](O)C3)nc2C1)c1ccc(Cl)c(Cl)c1] | 3-(3,4-Dichloro-phenyl)-1-[2-(3-hydroxy-cyclopentylamino)-5,8-dihydro-6H-pyrido[3,4-d]pyrimidin-7-yl]-butan-1-one | 449.2 |
| II-113 | 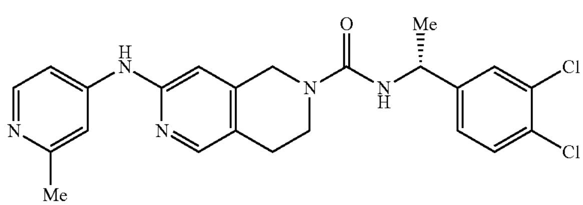 [SMILES: Cc1cc(Nc2cc3c(cn2)CCN(C(=O)N[C@H](C)c2ccc(Cl)c(Cl)c2)C3)ccn1] | 7-(2-Methyl-pyridin-4-ylamino)-3,4-dihydro-1H-[2,6]naphthyridine-2-carboxylic acid [(R)-1-(3,4-dichloro-phenyl)-ethyl]-amide | 456.1 |
| II-114 | 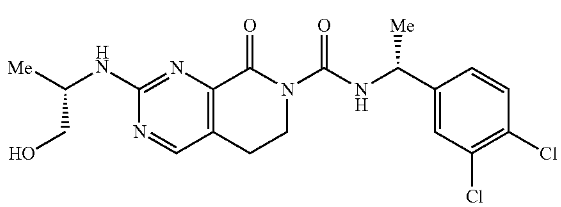 [SMILES: C[C@@H](CO)Nc1ncc2c(n1)C(=O)N(C(=O)N[C@H](C)c1ccc(Cl)c(Cl)c1)CC2] | 2-((S)-2-Hydroxy-1-methyl-ethylamino)-8-oxo-5,8-dihydro-6H-pyrido[3,4-d]pyrimidine-7-carboxylic acid [(R)-1-(3,4-dichloro-phenyl)-ethyl]-amide | N/A |
| II-115 | 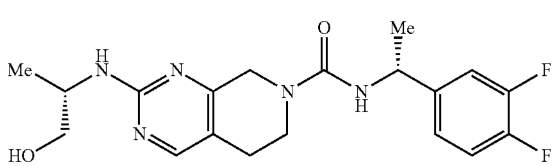 [SMILES: C[C@@H](CO)Nc1ncc2c(n1)CN(C(=O)N[C@H](C)c1ccc(F)c(F)c1)CC2] | 2-((S)-2-Hydroxy-1-methyl-ethylamino)-5,8-dihydro-6H-pyrido[3,4-d]pyrimidine-7-carboxylic acid [(R)-1-(3,4-difluoro-phenyl)-ethyl]-amide | 392.1 |

TABLE II-continued

| | Structure | Name | MS |
|---|---|---|---|
| II-116 | 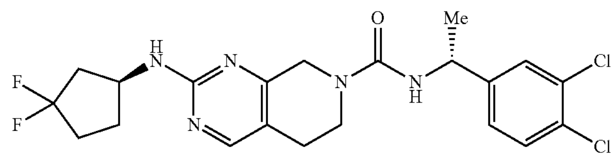 [SMILES: C[C@@H](NC(=O)N1CCc2cnc(N[C@H]3CCC(F)(F)C3)nc2C1)c1ccc(Cl)c(Cl)c1] | 2-((S)-3,3-Difluoro-cyclopentylamino)-5,8-dihydro-6H-pyrido[3,4-d]pyrimidine-7-carboxylic acid [(R)-1-(3,4-dichloro-phenyl)-ethyl]-amide | 470.2 |
| II-117 | 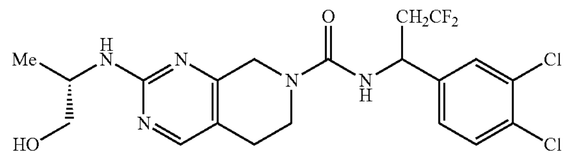 | 2-(2-Hydroxy-1-methyl-ethylamino)-5,8-dihydro-6H-pyrido[3,4-d]pyrimidine-7-carboxylic acid [1-(3,4-dichloro-phenyl)-3,3,3-trifluoro-propyl]-amide | 492.2 |
| II-118 | 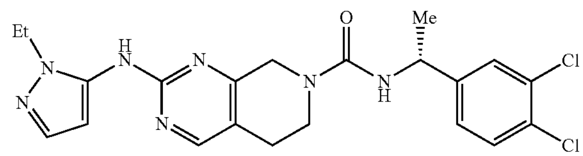 [SMILES: CCn1nccc1Nc1ncc2c(n1)CN(C(=O)N[C@H](C)c1ccc(Cl)c(Cl)c1)CC2] | 2-(2-Ethyl-2H-pyrazol-3-ylamino)-5,8-dihydro-6H-pyrido[3,4-d]pyrimidine-7-carboxylic acid [(R)-1-(3,4-dichloro-phenyl)-ethyl]-amide | 460.1 |
| II-119 | 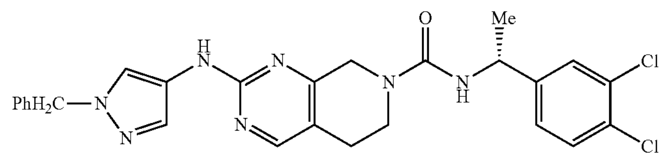 | 2-(1-Benzyl-1H-pyrazol-4-ylamino)-5,8-dihydro-6H-pyrido[3,4-d]pyrimidine-7-carboxylic acid [(R)-1-(3,4-dichloro-phenyl)-ethyl]-amide | 522.1 |
| II-120 | 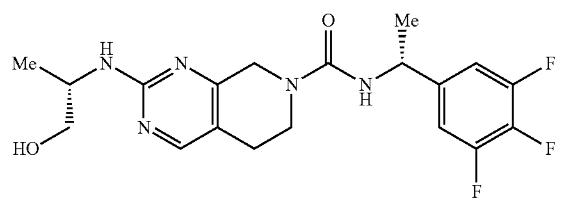 [SMILES: C[C@@H](CO)Nc1ncc2c(n1)CN(C(=O)N[C@H](C)c1cc(F)c(F)c(F)c1)CC2] | 2-((S)-2-Hydroxy-1-methyl-ethylamino)-5,8-dihydro-6H-pyrido[3,4-d]pyrimidine-7-carboxylic acid [(R)-1-(3,4,5-trifluoro-phenyl)-ethyl]-amide | 410.1 |
| II-121 | 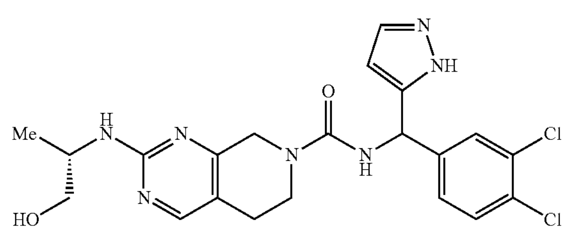 [SMILES: C[C@@H](CO)Nc1ncc2c(n1)CN(C(=O)NC(c1ccc(Cl)c(Cl)c1)c1ccn[nH]1)CC2] | 2-(2-Hydroxy-1-methyl-ethylamino)-5,8-dihydro-6H-pyrido[3,4-d]pyrimidine-7-carboxylic acid [(3,4-dichloro-phenyl)-(2H-pyrazol-3-yl)-methyl]-amide | 476.0 |
| II-122 | 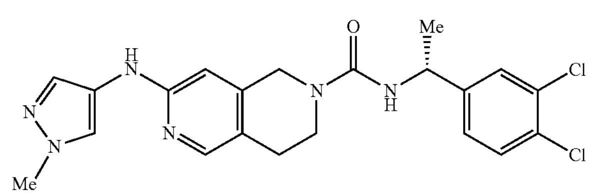 [SMILES: C[C@@H](NC(=O)N1CCc2cnc(Nc3cnn(C)c3)cc2C1)c1ccc(Cl)c(Cl)c1] | 7-(1-Methyl-1H-pyrazol-4-ylamino)-3,4-dihydro-1H-[2,6]naphthyridine-2-carboxylic acid [(R)-1-(3,4-dichloro-phenyl)-ethyl]-amide | 445.2 |
| II-123 | 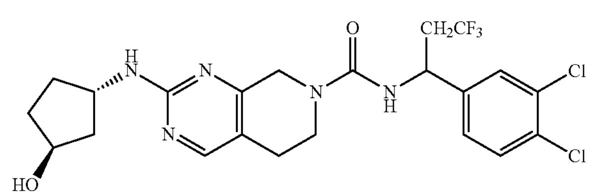 | 2-(3-Hydroxy-cyclopentylamino)-5,8-dihydro-6H-pyrido[3,4-d]pyrimidine-7-carboxylic acid [1-(3,4-dichloro-phenyl)-3,3,3-trifluoro-propyl]-amide | 518.1 |

TABLE II-continued

| | Name | MS |
|---|---|---|
| II-124 | 7-(2-Hydroxy-1-methyl-ethylamino)-3,4-dihydro-1H-[2,6]naphthyridine-2-carboxylic acid [1-(3,4-dichloro-phenyl)-3,3,3-trifluoro-propyl]-amide | 491.2 |
| II-125 | 7-((S)-2-Hydroxy-1-methyl-ethylamino)-3,4-dihydro-1H-[2,6]naphthyridine-2-carboxylic acid [(R)-1-(3,4-dichloro-phenyl)-propyl]-amide | 437.2 |
| II-126 | 2-(2-Methyl-pyrimidin-4-ylamino)-5,8-dihydro-6H-pyrido[3,4-d]pyrimidine-7-carboxylic acid [(R)-1-(3,4-dichloro-phenyl)-ethyl]-amide | 458.1 |
| II-127 | 2-(2-Hydroxy-1-methyl-ethylamino)-5,8-dihydro-6H-pyrido[3,4-d]pyrimidine-7-carboxylic acid [1-(3,4-dichloro-phenyl)-2-methyl-propyl]-amide | 452.1 |
| II-128 | 7-((S)-2-Hydroxy-1-methyl-ethylamino)-3,4-dihydro-1H-[2,6]naphthyridine-2-carboxylic acid [(S)-1-(3,4-dichloro-phenyl)-2-methoxy-ethyl]-amide | 453.2 |
| II-129 | 2-((S)-2-Hydroxy-1-methyl-ethylamino)-5,8-dihydro-6H-pyrido[3,4-d]pyrimidine-7-carboxylic acid [(R)-1-(3,4-dichloro-phenyl)-3,3,3-trifluoro-propyl]-amide | 494.2 |
| II-130 | 2-((S)-2-Hydroxy-1-methyl-ethylamino)-5,8-dihydro-6H-pyrido[3,4-d]pyrimidine-7-carboxylic acid [(S)-1-(3,4-dichloro-phenyl)-3,3,3-trifluoro-propyl]-amide | 492.1 |
| II-131 | 7-((S)-2-Hydroxy-1-methyl-ethylamino)-3,4-dihydro-1H-[2,6]naphthyridine-2-carboxylic acid [(R)-1-(3,4-dichloro-phenyl)-3-hydroxy-propyl]-amide | 453.2 |
| II-132 | 2-(2-Hydroxy-1-methyl-ethylamino)-5,8-dihydro-6H-pyrido[3,4-d]pyrimidine-7-carboxylic acid [2-(4-chloro-3-fluoro-phenyl)-1-methyl-ethyl]-amide | 422.2 |

TABLE II-continued

| | Structure | Name | MS |
|---|---|---|---|
| II-133 | 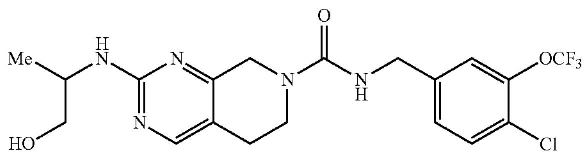 [SMILES: CC(CO)Nc1ncc2c(n1)CN(C(=O)NCc1ccc(Cl)c(OC(F)(F)F)c1)CC2] | 2-(2-Hydroxy-1-methyl-ethylamino)-5,8-dihydro-6H-pyrido[3,4-d]pyrimidine-7-carboxylic acid 4-chloro-3-trifluoromethoxy-benzylamide | 460.2 |
| II-134 | 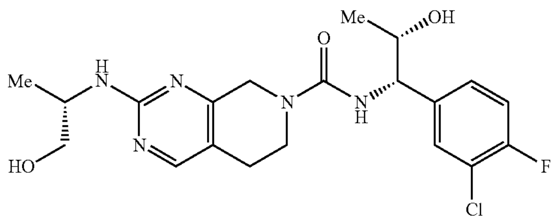 [SMILES: C[C@H](O)[C@@H](NC(=O)N1CCc2cnc(N[C@@H](C)CO)nc2C1)c1ccc(F)c(Cl)c1] | 2-(2-Hydroxy-1-methyl-ethylamino)-5,8-dihydro-6H-pyrido[3,4-d]pyrimidine-7-carboxylic acid [(1S,2S)-1-(3-chloro-4-fluoro-phenyl)-2-hydroxy-propyl]-amide | 438.1 |
| II-135 | 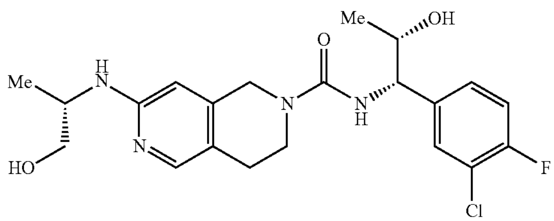 [SMILES: C[C@H](O)[C@@H](NC(=O)N1CCc2cnc(N[C@@H](C)CO)cc2C1)c1ccc(F)c(Cl)c1] | 7-((S)-2-Hydroxy-1-methyl-ethylamino)-3,4-dihydro-1H-[2,6]naphthyridine-2-carboxylic acid [(1S,2S)-1-(3-chloro-4-fluoro-phenyl)-2-hydroxy-propyl]-amide | 437.2 |
| II-136 | 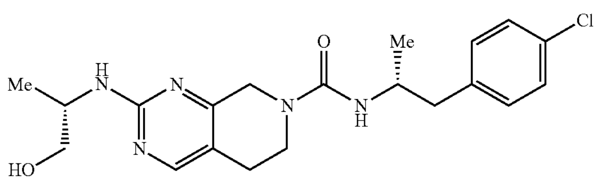 [SMILES: C[C@H](Cc1ccc(Cl)cc1)NC(=O)N1CCc2cnc(N[C@@H](C)CO)nc2C1] | 2-(2-Hydroxy-1-methyl-ethylamino)-5,8-dihydro-6H-pyrido[3,4-d]pyrimidine-7-carboxylic acid [2-(4-chloro-phenyl)-1-methyl-ethyl]-amide | 404.1 |
| II-137 | 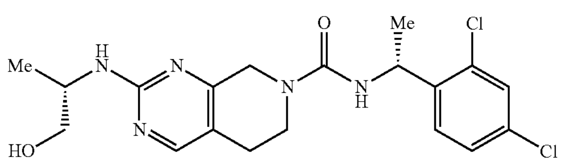 [SMILES: C[C@@H](CO)Nc1ncc2c(n1)CN(C(=O)N[C@H](C)c1ccc(Cl)cc1Cl)CC2] | 2-((S)-2-Hydroxy-1-methyl-ethylamino)-5,8-dihydro-6H-pyrido[3,4-d]pyrimidine-7-carboxylic acid [(R)-1-(2,4-dichloro-phenyl)-ethyl]-amide | 424.1 |
| II-138 | 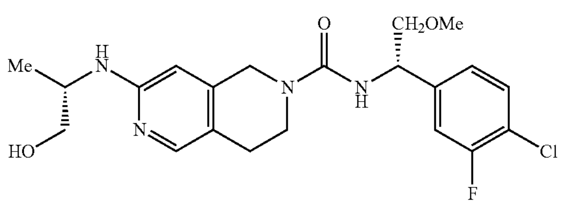 | 7-((S)-2-Hydroxy-1-methyl-ethylamino)-3,4-dihydro-1H-[2,6]naphthyridine-2-carboxylic acid [(S)-1-(4-chloro-3-fluoro-phenyl)-2-methoxy-ethyl]-amide | 437.2 |
| II-139 | 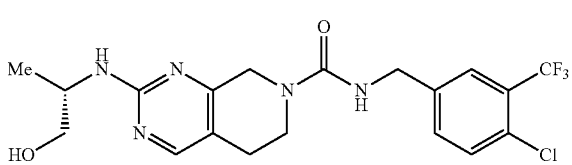 [SMILES: C[C@@H](CO)Nc1ncc2c(n1)CN(C(=O)NCc1ccc(Cl)c(C(F)(F)F)c1)CC2] | 2-((S)-2-Hydroxy-1-methyl-ethylamino)-5,8-dihydro-6H-pyrido[3,4-d]pyrimidine-7-carboxylic acid 4-chloro-3-trifluoromethyl-benzylamide | 444.1 |
| II-140 | 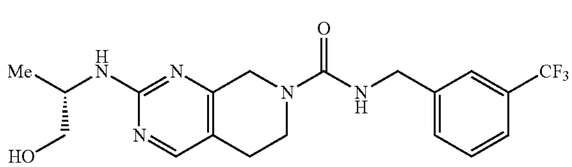 [SMILES: C[C@@H](CO)Nc1ncc2c(n1)CN(C(=O)NCc1cccc(C(F)(F)F)c1)CC2] | 2-((S)-2-Hydroxy-1-methyl-ethylamino)-5,8-dihydro-6H-pyrido[3,4-d]pyrimidine-7-carboxylic acid 3-trifluoromethyl-benzylamide | 410.2 |

TABLE II-continued

| | Structure | Name | MS |
|---|---|---|---|
| II-141 | 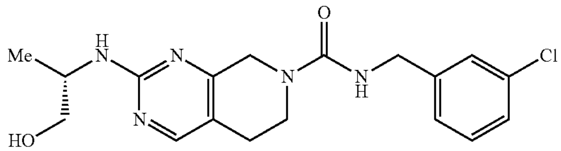 [SMILES: C[C@@H](CO)Nc1ncc2c(n1)CN(C(=O)NCc1cccc(Cl)c1)CC2] | 2-((S)-2-Hydroxy-1-methyl-ethylamino)-5,8-dihydro-6H-pyrido[3,4-d]pyrimidine-7-carboxylic acid 3-chloro-benzylamide | 376.1 |
| II-142 | 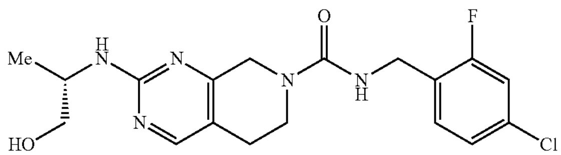 [SMILES: C[C@@H](CO)Nc1ncc2c(n1)CN(C(=O)NCc1ccc(Cl)cc1F)CC2] | 2-((S)-2-Hydroxy-1-methyl-ethylamino)-5,8-dihydro-6H-pyrido[3,4-d]pyrimidine-7-carboxylic acid 4-chloro-2-fluoro-benzylamide | 394.1 |
| II-143 | 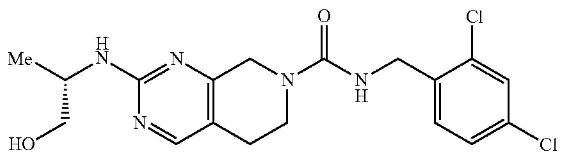 [SMILES: C[C@@H](CO)Nc1ncc2c(n1)CN(C(=O)NCc1ccc(Cl)cc1Cl)CC2] | 2-((S)-2-Hydroxy-1-methyl-ethylamino)-5,8-dihydro-6H-pyrido[3,4-d]pyrimidine-7-carboxylic acid 2,4-dichloro-benzylamide | 410.1 |
| II-144 | 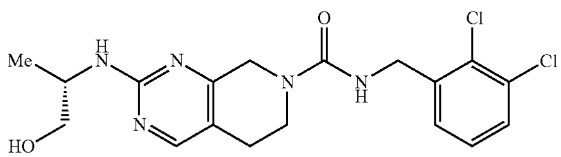 [SMILES: C[C@@H](CO)Nc1ncc2c(n1)CN(C(=O)NCc1cccc(Cl)c1Cl)CC2] | 2-((S)-2-Hydroxy-1-methyl-ethylamino)-5,8-dihydro-6H-pyrido[3,4-d]pyrimidine-7-carboxylic acid 2,3-dichloro-benzylamide | 410.1 |
| II-145 | 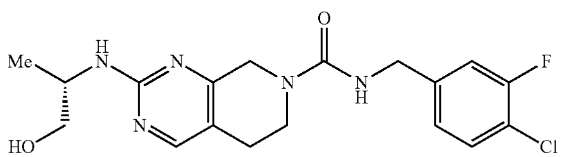 [SMILES: C[C@@H](CO)Nc1ncc2c(n1)CN(C(=O)NCc1ccc(Cl)c(F)c1)CC2] | 2-((S)-2-Hydroxy-1-methyl-ethylamino)-5,8-dihydro-6H-pyrido[3,4-d]pyrimidine-7-carboxylic acid 4-chloro-3-fluoro-benzylamide | 394.2 |
| II-146 | 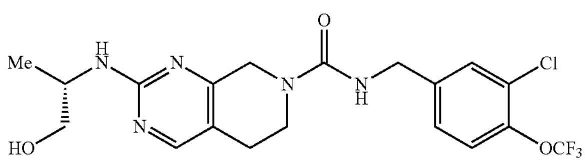 [SMILES: C[C@@H](CO)Nc1ncc2c(n1)CN(C(=O)NCc1ccc(OC(F)(F)F)c(Cl)c1)CC2] | 2-((S)-2-Hydroxy-1-methyl-ethylamino)-5,8-dihydro-6H-pyrido[3,4-d]pyrimidine-7-carboxylic acid 3-chloro-4-trifluoromethoxy-benzylamide | 460.1 |
| II-147 | 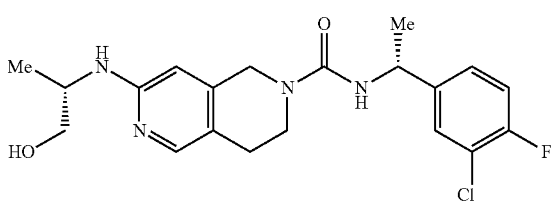 [SMILES: C[C@@H](CO)Nc1cc2c(cn1)CCN(C(=O)N[C@H](C)c1ccc(F)c(Cl)c1)C2] | 7-((S)-2-Hydroxy-1-methyl-ethylamino)-3,4-dihydro-1H-[2,6]naphthyridine-2-carboxylic acid [(R)-1-(3-chloro-4-fluoro-phenyl)-ethyl]-amide | 407.5 |
| II-148 | 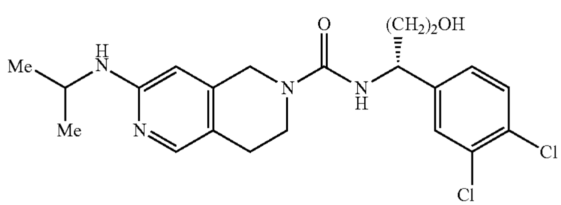 | 7-Isopropylamino-3,4-dihydro-1H-[2,6]naphthyridine-2-carboxylic acid [(R)-1-(3,4-dichloro-phenyl)-3-hydroxy-propyl]-amide | 437.1 |
| II-149 | 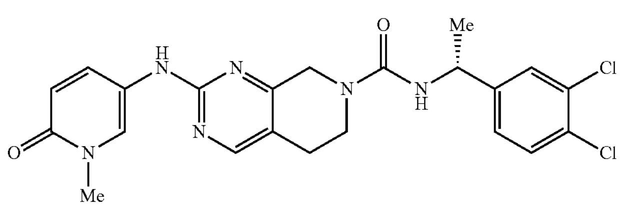 [SMILES: C[C@@H](NC(=O)N1CCc2cnc(Nc3ccc(=O)n(C)c3)nc2C1)c1ccc(Cl)c(Cl)c1] | 2-(1-Methyl-6-oxo-1,6-dihydro-pyridin-3-ylamino)-5,8-dihydro-6H-pyrido[3,4-d]pyrimidine-7-carboxylic acid [(R)-1-(3,4-dichloro-phenyl)-ethyl]-amide | 473.1 |

TABLE II-continued

| | Name | MS |
|---|---|---|
| II-150 | 2-(1-Methyl-6-oxo-1,6-dihydro-pyridin-3-ylamino)-5,8-dihydro-6H-pyrido[3,4-d]pyrimidine-7-carboxylic acid [(R)-1-(3-fluoro-4-trifluoromethyl-phenyl)-ethyl]-amide | 491.2 |
| II-151 | 2-((S)-2-Hydroxy-1-methyl-ethylamino)-5,8-dihydro-6H-pyrido[3,4-d]pyrimidine-7-carboxylic acid (benzooxazol-2-ylmethyl)-amide | 383.4 |
| II-152 | 2-((S)-2-Hydroxy-1-methyl-ethylamino)-5,8-dihydro-6H-pyrido[3,4-d]pyrimidine-7-carboxylic acid (benzothiazol-2-ylmethyl)-amide | 399.3 |
| II-153 | 2-((S)-2-Hydroxy-1-methyl-ethylamino)-5,8-dihydro-6H-pyrido[3,4-d]pyrimidine-7-carboxylic acid [(S)-1-(3,4-dichloro-phenyl)-2-methyl-propyl]-amide | 452.1 |
| II-154 | 2-((S)-2-Hydroxy-1-methyl-ethylamino)-5,8-dihydro-6H-pyrido[3,4-d]pyrimidine-7-carboxylic acid [(S)-(3-fluoro-4-trifluoromethyl-phenyl)-(S)-pyrrolidin-2-yl-methyl]-amide | 497.1 |
| II-155 | 2-((S)-2-Hydroxy-1-methyl-ethylamino)-5,8-dihydro-6H-pyrido[3,4-d]pyrimidine-7-carboxylic acid [(S)-(4-chloro-3-fluoro-phenyl)-(S)-pyrrolidin-2-yl-methyl]-amide | 463.1 |
| II-156 | 2-(2-Hydroxy-1-methyl-ethylamino)-5,8-dihydro-6H-pyrido[3,4-d]pyrimidine-7-carboxylic acid (2-phenyl-cyclopropyl)-amide | 368.2 |
| II-157 | 2-Isopropylamino-5,8-dihydro-6H-pyrido[3,4-d]pyrimidine-7-carboxylic acid (2-phenyl-cyclopropyl)-amide | 352.1 |

TABLE II-continued

| | Structure | Name | MS |
|---|---|---|---|
| II-158 | 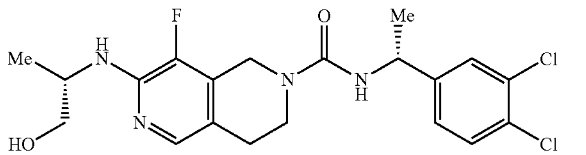 [SMILES: C[C@@H](CO)Nc1ncc2c(c1F)CN(C(=O)N[C@H](C)c1ccc(Cl)c(Cl)c1)CC2] | 8-Fluoro-7-((S)-2-hydroxy-1-methyl-ethylamino-3,4-dihydro-1H-[2,6]naphthyridine-2-carboxylic acid [(R)-1-(3,4-dichloro-phenyl)-ethyl]-amide | 443.5 |
| II-159 | 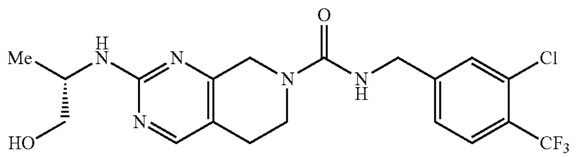 [SMILES: C[C@@H](CO)Nc1ncc2c(n1)CN(C(=O)NCc1ccc(C(F)(F)F)c(Cl)c1)CC2] | 2-((S)-2-Hydroxy-1-methyl-ethylamino)-5,8-dihydro-6H-pyrido[3,4-d]pyrimidine-7-carboxylic acid 3-chloro-4-trifluoromethyl-benzylamide | 444.1 |
| II-160 | 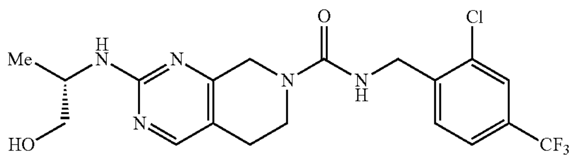 [SMILES: C[C@@H](CO)Nc1ncc2c(n1)CN(C(=O)NCc1ccc(C(F)(F)F)cc1Cl)CC2] | 2-((S)-2-Hydroxy-1-methyl-ethylamino)-5,8-dihydro-6H-pyrido[3,4-d]pyrimidine-7-carboxylic acid 2-chloro-4-trifluoromethyl-benzylamide | 444.1 |
| II-161 | 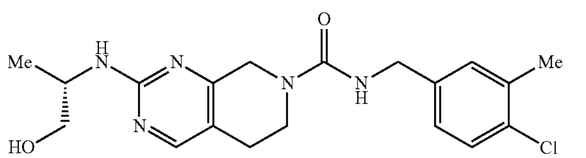 [SMILES: Cc1cc(CNC(=O)N2CCc3cnc(N[C@@H](C)CO)nc3C2)ccc1Cl] | 2-((S)-2-Hydroxy-1-methyl-ethylamino)-5,8-dihydro-6H-pyrido[3,4-d]pyrimidine-7-carboxylic acid 4-chloro-3-methyl-benzylamide | 390.2 |
| II-162 | 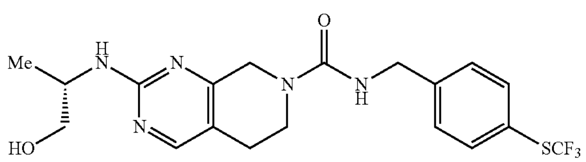 | 2-((S)-2-Hydroxy-1-methyl-ethylamino)-5,8-dihydro-6H-pyrido[3,4-d]pyrimidine-7-carboxylic acid 4-trifluoromethylsulfanyl-benzylamide | 442.2 |
| II-163 | 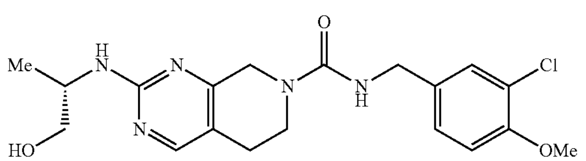 [SMILES: COc1ccc(CNC(=O)N2CCc3cnc(N[C@@H](C)CO)nc3C2)cc1Cl] | 2-((S)-2-Hydroxy-1-methyl-ethylamino)-5,8-dihydro-6H-pyrido[3,4-d]pyrimidine-7-carboxylic acid 3-chloro-4-methoxy-benzylamide | 406.1 |
| II-164 | 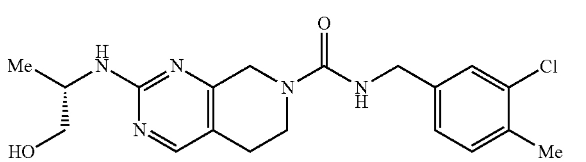 [SMILES: Cc1ccc(CNC(=O)N2CCc3cnc(N[C@@H](C)CO)nc3C2)cc1Cl] | 2-((S)-2-Hydroxy-1-methyl-ethylamino)-5,8-dihydro-6H-pyrido[3,4-d]pyrimidine-7-carboxylic acid 3-chloro-4-methyl-benzylamide | 390.1 |
| II-165 | 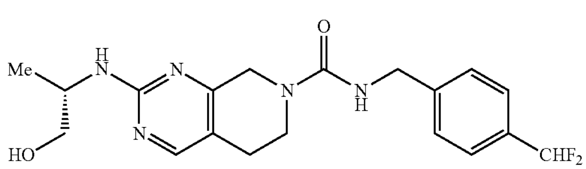 [SMILES: C[C@@H](CO)Nc1ncc2c(n1)CN(C(=O)NCc1ccc(C(F)F)cc1)CC2] | 2-((S)-2-Hydroxy-1-methyl-ethylamino)-5,8-dihydro-6H-pyrido[3,4-d]pyrimidine-7-carboxylic acid 4-difluoromethoxy-benzylamide | 408.2 |
| II-166 | 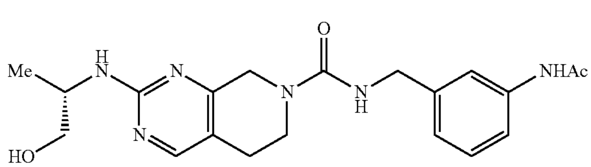 [SMILES: CC(=O)Nc1cccc(CNC(=O)N2CCc3cnc(N[C@@H](C)CO)nc3C2)c1] | 2-((S)-2-Hydroxy-1-methyl-ethylamino)-5,8-dihydro-6H-pyrido[3,4-d]pyrimidine-7-carboxylic acid 3-acetylamino-benzylamide | 399.2 |

TABLE II-continued

| | Structure | Name | MS |
|---|---|---|---|
| II-167 | 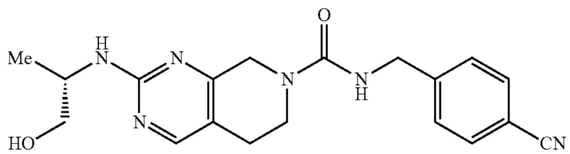 [SMILES: C[C@@H](CO)Nc1ncc2c(n1)CN(C(=O)NCc1ccc(C#N)cc1)CC2] | 2-((S)-2-Hydroxy-1-methyl-ethylamino)-5,8-dihydro-6H-pyrido[3,4-d]pyrimidine-7-carboxylic acid 4-cyano-benzylamide | 367.2 |
| II-168 | 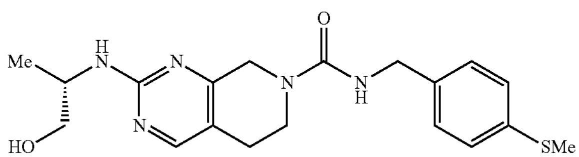 [SMILES: CSc1ccc(CNC(=O)N2CCc3cnc(N[C@@H](C)CO)nc3C2)cc1] | 2-((S)-2-Hydroxy-1-methyl-ethylamino)-5,8-dihydro-6H-pyrido[3,4-d]pyrimidine-7-carboxylic acid 4-methylsulfanyl-benzylamide | 388.1 |
| II-169 | 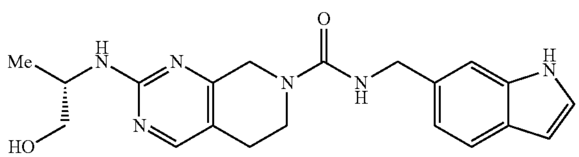 [SMILES: C[C@@H](CO)Nc1ncc2c(n1)CN(C(=O)NCc1ccc3cc[nH]c3c1)CC2] | 2-((S)-2-Hydroxy-1-methyl-ethylamino)-5,8-dihydro-6H-pyrido[3,4-d]pyrimidine-7-carboxylic acid (1H-indol-6-ylmethyl)-amide | 381.1 |
| II-170 | 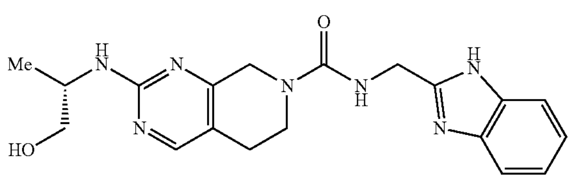 [SMILES: C[C@@H](CO)Nc1ncc2c(n1)CN(C(=O)NCc1nc3ccccc3[nH]1)CC2] | 2-((S)-2-Hydroxy-1-methyl-ethylamino)-5,8-dihydro-6H-pyrido[3,4-d]pyrimidine-7-carboxylic acid (1H-benzoimidazol-2-ylmethyl)-amide | 382.4 |
| II-171 | 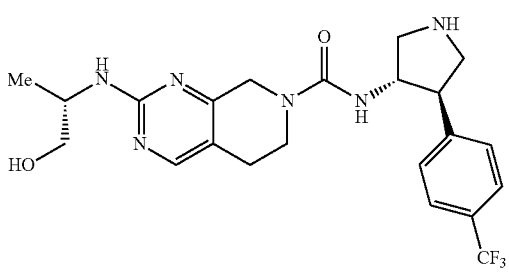 [SMILES: C[C@@H](CO)Nc1ncc2c(n1)CN(C(=O)N[C@@H]1CNC[C@H]1c1ccc(C(F)(F)F)cc1)CC2] | 2-(2-Hydroxy-1-methyl-ethylamino)-5,8-dihydro-6H-pyrido[3,4-d]pyrimidine-7-carboxylic acid [4-(4-trifluoromethyl-phenyl)-pyrrolidin-3-yl]-amide | N/A[1] |
| II-172 | 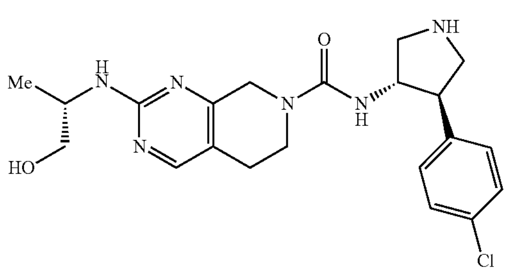 [SMILES: C[C@@H](CO)Nc1ncc2c(n1)CN(C(=O)N[C@@H]1CNC[C@H]1c1ccc(Cl)cc1)CC2] | 2-(2-Hydroxy-1-methyl-ethylamino)-5,8-dihydro-6H-pyrido[3,4-d]pyrimidine-7-carboxylic acid [4-(4-chloro-phenyl)-pyrrolidin-3-yl]-amide | N/A[1] |
| II-173 | 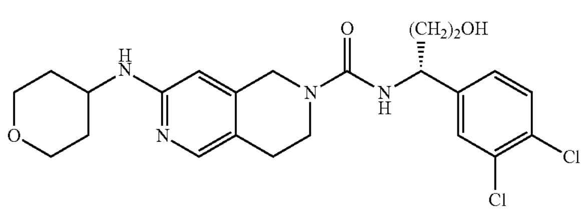 | 7-(Tetrahydro-pyran-4-ylamino)-3,4-dihydro-1H-[2,6]naphthyridine-2-carboxylic acid [(R)-1-(3,4-dichloro-phenyl)-3-hydroxy-propyl]-amide | 479.2 |

TABLE II-continued

| | Structure | Name | MS |
|---|---|---|---|
| II-174 | 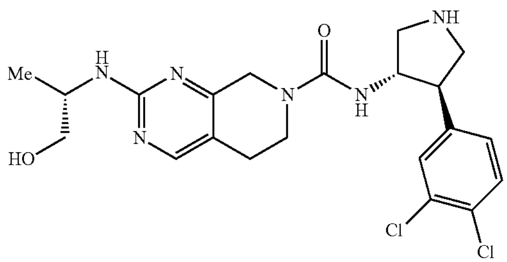 [SMILES: C[C@@H](CO)Nc1ncc2c(n1)CN(C(=O)N[C@@H]1CNC[C@H]1c1ccc(Cl)c(Cl)c1)CC2] | 2-(2-Hydroxy-1-methyl-ethylamino)-5,8-dihydro-6H-pyrido[3,4-d]pyrimidine-7-carboxylic acid [4-(3,4-dichloro-phenyl)-pyrrolidin-3-yl]-amide | 465.1[1] |
| II-175 | 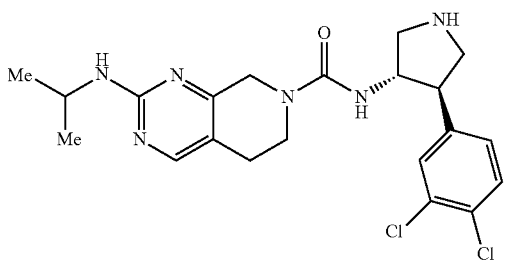 [SMILES: CC(C)Nc1ncc2c(n1)CN(C(=O)N[C@@H]1CNC[C@H]1c1ccc(Cl)c(Cl)c1)CC2] | 2-Isopropylamino-5,8-dihydro-6H-pyrido[3,4-d]pyrimidine-7-carboxylic acid [4-(3,4-dichloro-phenyl)-pyrrolidin-3-yl]-amide | 449.2[1] |
| II-176 | 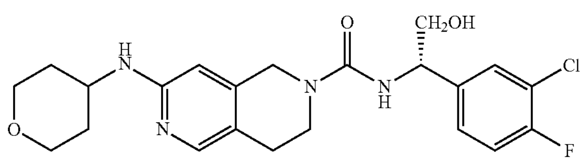 [SMILES: O=C(N[C@H](CO)c1ccc(F)c(Cl)c1)N1CCc2cnc(NC3CCOCC3)cc2C1] | 7-(Tetrahydro-pyran-4-ylamino)-3,4-dihydro-1H-[2,6]naphthyridine-2-carboxylic acid [(S)-1-(3-chloro-4-fluoro-phenyl)-2-hydroxy-ethyl]-amide | 449.2 |
| II-177 | 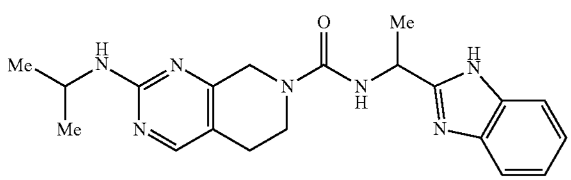 [SMILES: CC(C)Nc1ncc2c(n1)CN(C(=O)NC(C)c1nc3ccccc3[nH]1)CC2] | 2-Isopropylamino-5,8-dihydro-6H-pyrido[3,4-d]pyrimidine-7-carboxylic acid [1-(1H-benzoimidazol-2-yl)-ethyl]-amide | 380.3 |
| II-178 | 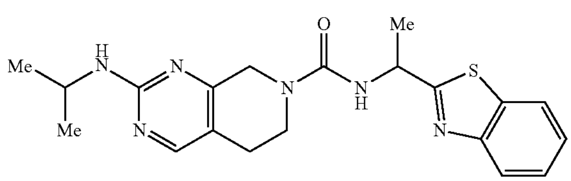 [SMILES: CC(C)Nc1ncc2c(n1)CN(C(=O)NC(C)c1nc3ccccc3s1)CC2] | 2-Isopropylamino-5,8-dihydro-6H-pyrido[3,4-d]pyrimidine-7-carboxylic acid (1-benzothiazol-2-yl-ethyl)-amide | 397.3 |
| II-179 | 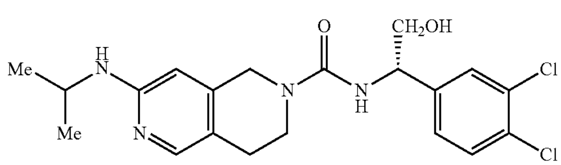 [SMILES: CC(C)Nc1cc2c(cn1)CCN(C(=O)N[C@H](CO)c1ccc(Cl)c(Cl)c1)C2] | 7-Isopropylamino-3,4-dihydro-1H-[2,6]naphthyridine-2-carboxylic acid [(S)-1-(3,4-dichloro-phenyl)-2-hydroxy-ethyl]-amide | 423.5 |
| II-180 | 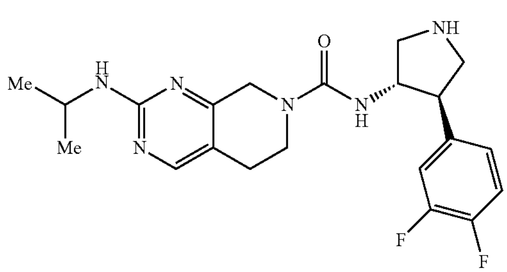 [SMILES: CC(C)Nc1ncc2c(n1)CN(C(=O)N[C@@H]1CNC[C@H]1c1ccc(F)c(F)c1)CC2] | 2-Isopropylamino-5,8-dihydro-6H-pyrido[3,4-d]pyrimidine-7-carboxylic acid [4-(3,4-difluoro-phenyl)-pyrrolidin-3-yl]amide | 417.2[1] |

TABLE II-continued

| | Structure | Name | MS |
|---|---|---|---|
| II-181 | 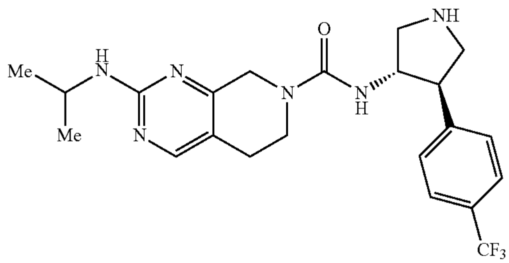 [SMILES: CC(C)Nc1ncc2c(n1)CN(C(=O)N[C@@H]1CNC[C@H]1c1ccc(C(F)(F)F)cc1)CC2] | 2-Isopropylamino-5,8-dihydro-6H-pyrido[3,4-d]pyrimidine-7-carboxylic acid [4-(4-trifluoromethyl-phenyl)-pyrrolidin-3-yl]-amide | 449.2[1] |
| II-182 | 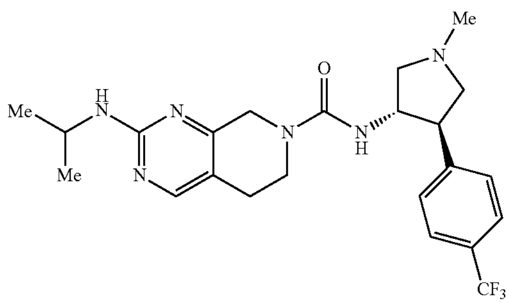 | 2-Isopropylamino-5,8-dihydro-6H-pyrido[3,4-d]pyrimidine-7-carboxylic acid [1-methyl-4-(4-trifluoromethyl-phenyl)-pyrrolidin-3-yl]-amide | 463.2[1] |
| II-183 | 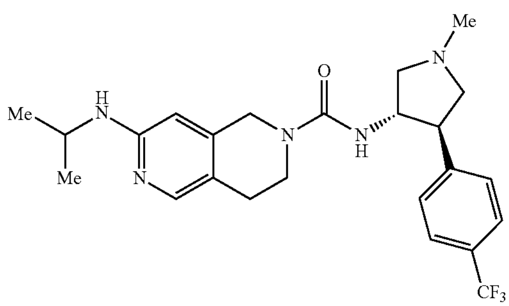 [SMILES: CC(C)Nc1ncc2c(n1)CN(C(=O)N[C@@H]1CN(C)C[C@H]1c1ccc(C(F)(F)F)cc1)CC2] | 7-Isopropylamino-3,4-dihydro-1H-[2,6]naphthyridine-2-carboxylic acid [4-(4-trifluoromethyl-phenyl)-pyrrolidin-3-yl]-amide | 448.2[1] |
| II-184 | 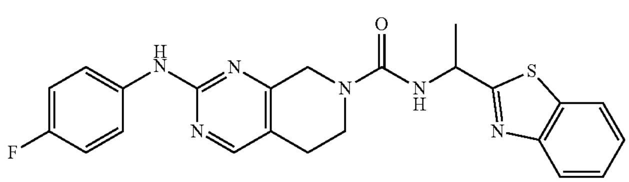 [SMILES: CC(NC(=O)N1CCc2cnc(Nc3ccc(F)cc3)nc2C1)c1nc2ccccc2s1] | 2-(4-Fluoro-phenylamino)-5,8-dihydro-6H-pyrido[3,4-d]pyrimidine-7-carboxylic acid (1-benzothiazol-2-yl-ethyl)-amide | 449.3 |
| II-185 | 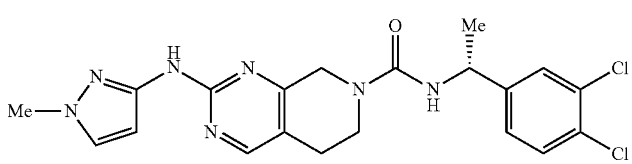 [SMILES: C[C@@H](NC(=O)N1CCc2cnc(Nc3ccn(C)n3)nc2C1)c1ccc(Cl)c(Cl)c1] | 2-(1-Methyl-1H-pyrazol-3-ylamino)-5,8-dihydro-6H-pyrido[3,4-d]pyrimidine-7-carboxylic acid [(R)-1-(3,4-dichloro-phenyl)-ethyl]-amide | 446.1 |
| II-186 | 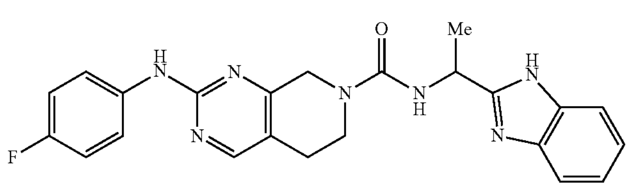 [SMILES: CC(NC(=O)N1CCc2cnc(Nc3ccc(F)cc3)nc2C1)c1nc2ccccc2[nH]1] | 2-(4-Fluoro-phenylamino)-5,8-dihydro-6H-pyrido[3,4-d]pyrimidine-7-carboxylic acid [1-(1H-benzoimidazol-2-yl)-ethyl]-amide | 432.3 |

TABLE II-continued

| Structure | Name | MS |
|---|---|---|
| II-187 | 2-Isopropylamino-5,8-dihydro-6H-pyrido[3,4-d]pyrimidine-7-carboxylic acid [(R)-(4-chloro-3-fluoro-phenyl)-oxazol-4-yl-methyl]-amide | 445.3 |
| II-188 | 2-Isopropylamino-5,8-dihydro-6H-pyrido[3,4-d]pyrimidine-7-carboxylic acid [(S)-(4-chloro-3-fluoro-phenyl)-oxazol-4-yl-methyl]-amide | 445.4 |
| II-189 | 2-((S)-2-Hydroxy-1-methyl-ethylamino)-5,8-dihydro-6H-pyrido[3,4-d]pyrimidine-7-carboxylic acid 3-fluoro-4-methoxy-benzylamide | 390.1 |
| II-190 | 2-((S)-2-Hydroxy-1-methyl-ethylamino)-5,8-dihydro-6H-pyrido[3,4-d]pyrimidine-7-carboxylic acid 4-methyl-3-trifluoromethyl-benzylamide | 424.2 |
| II-191 | 2-((S)-2-Hydroxy-1-methyl-ethylamino)-5,8-dihydro-6H-pyrido[3,4-d]pyrimidine-7-carboxylic acid [(R)-1-(3,4-dichloro-phenyl)-3-methoxy-propyl]-amide | 4681 |
| II-192 | 2-((S)-2-Hydroxy-1-methyl-ethylamino)-5,8-dihydro-6H-pyrido[3,4-d]pyrimidine-7-carboxylic acid 4-(cyano-dimethyl-methyl)-benzylamide | 409.2 |
| II-193 | 2-(4-Methyl-thiazol-2-ylamino)-5,8-dihydro-6H-pyrido[3,4-d]pyrimidine-7-carboxylic acid [(R)-1-(3,4-dichloro-phenyl)-ethyl]-amide | 463.1 |

TABLE II-continued

| | Structure | Name | MS |
|---|---|---|---|
| II-194 | 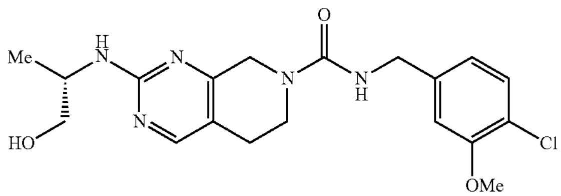 [SMILES: COc1cc(CNC(=O)N2CCc3cnc(N[C@@H](C)CO)nc3C2)ccc1Cl] | 2-((S)-2-Hydroxy-1-methyl-ethylamino)-5,8-dihydro-6H-pyrido[3,4-d]pyrimidine-7-carboxylic acid 4-chloro-3-methoxy-benzylamide | 407.1 |
| II-195 | 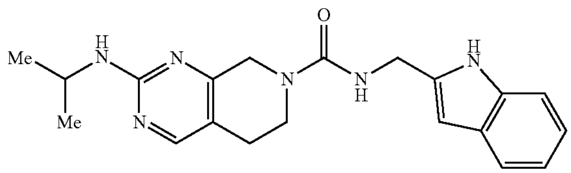 [SMILES: CC(C)Nc1ncc2c(n1)CN(C(=O)NCc1cc3ccccc3[nH]1)CC2] | 2-Isopropylamino-5,8-dihydro-6H-pyrido[3,4-d]pyrimidine-7-carboxylic acid (1H-indol-2-ylmethyl)-amide | 365.3 |
| II-196 | 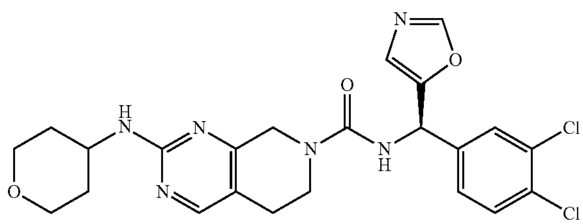 [SMILES: O=C(N[C@H](c1ccc(Cl)c(Cl)c1)c1cnco1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(R)-(3,4-dichloro-phenyl)-oxazol-5-yl-methyl]-amide | 505.5 |
| II-197 | 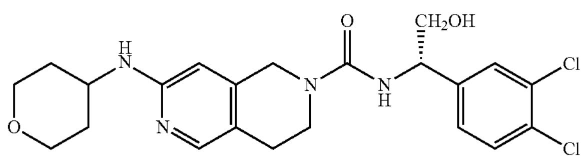 [SMILES: O=C(N[C@H](CO)c1ccc(Cl)c(Cl)c1)N1CCc2cnc(NC3CCOCC3)cc2C1] | 7-(Tetrahydro-pyran-4-ylamino)-3,4-dihydro-1H-[2,6]naphthyridine-2-carboxylic acid [(S)-1-(3,4-dichloro-phenyl)-2-hydroxy-ethyl]-amide | 465.2 |
| II-198 | 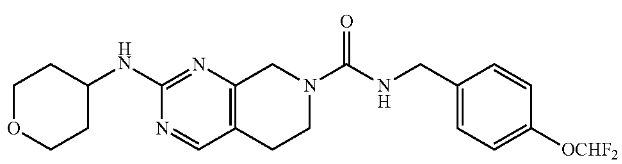 [SMILES: O=C(NCc1ccc(OC(F)F)cc1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid 4-difluoromethoxy-benzylamide | 434.2 |
| II-199 | 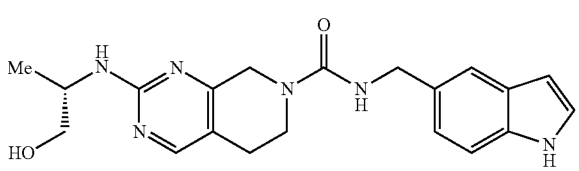 [SMILES: C[C@@H](CO)Nc1ncc2c(n1)CN(C(=O)NCc1ccc3[nH]ccc3c1)CC2] | 2-((S)-2-Hydroxy-1-methyl-ethylamino)-5,8-dihydro-6H-pyrido[3,4-d]pyrimidine-7-carboxylic acid (1H-indol-5-ylmethyl)-amide | 381.1 |
| II-200 | 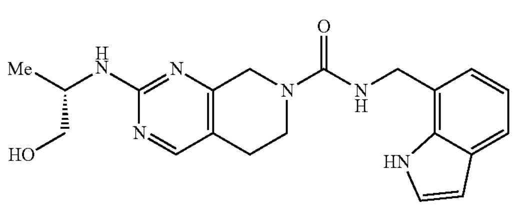 [SMILES: C[C@@H](CO)Nc1ncc2c(n1)CN(C(=O)NCc1cccc3cc[nH]c13)CC2] | 2-((S)-2-Hydroxy-1-methyl-ethylamino)-5,8-dihydro-6H-pyrido[3,4-d]pyrimidine-7-carboxylic acid (1H-indol-7-ylmethyl)-amide | 381.1 |
| II-201 | 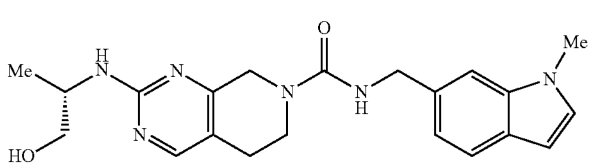 [SMILES: C[C@@H](CO)Nc1ncc2c(n1)CN(C(=O)NCc1ccc3ccn(C)c3c1)CC2] | 2-((S)-2-Hydroxy-1-methyl-ethylamino)-5,8-dihydro-6H-pyrido[3,4-d]pyrimidine-7-carboxylic acid (1-methyl-1H-indol-6-ylmethyl)-amide | 395.1 |

TABLE II-continued

| Structure | Name | MS |
|---|---|---|
| II-202 | 2-Isopropylamino-5,8-dihydro-6H-pyrido[3,4-d]pyrimidine-7-carboxylic acid (1H-indol-6-ylmethyl)-amide | 365.1 |
| II-203 | 2-(1-Methyl-1H-[1,2,4]triazol-3-ylamino)-5,8-dihydro-6H-pyrido[3,4-d]pyrimidine-7-carboxylic acid [(R)-1-(3,4-dichloro-phenyl)-ethyl]-amide | 447.1 |
| II-204 | 2-Isopropylamino-5,8-dihydro-6H-pyrido[3,4-d]pyrimidine-7-carboxylic acid [(3S,4R)-1-benzyl-4-(3,4-difluoro-phenyl)-pyrrolidin-3-yl]-amide | 507.3 |
| II-205 | 2-(2-Hydroxy-1-methyl-ethylamino)-5,8-dihydro-6H-pyrido[3,4-d]pyrimidine-7-carboxylic acid [1-(5-chloro-pyrimidin-2-yl)-ethyl]-amide | 392.0 |
| II-206 | 2-Isopropylamino-5,8-dihydro-6H-pyrido[3,4-d]pyrimidine-7-carboxylic acid [(3,4-dichloro-phenyl)-(2H-pyrazol-3-yl)-methyl]-amide | 462.3 |
| II-207 | 2-((S)-2-Hydroxy-1-methyl-ethylamino)-5,8-dihydro-6H-pyrido[3,4-d]pyrimidine-7-carboxylic acid [(1R,2R)-1-(3,4-dichloro-phenyl)-2-methoxy-propyl]-amide | 468.1 |
| II-208 | 2-(Tetrahydro-pyran-4-ylamino)-5,8-dihydro-6H-pyrido[3,4-d]pyrimidine-7-carboxylic acid [(S)-1-(4-difluoromethoxy-phenyl)-propyl]-amide | 462.2 |

TABLE II-continued

| | Structure | Name | MS |
|---|---|---|---|
| II-209 | 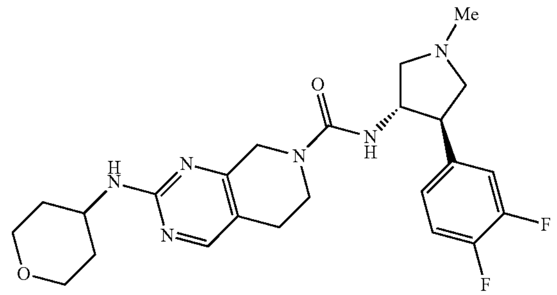 [SMILES: CN1C[C@@H](NC(=O)N2CCc3cnc(NC4CCOCC4)nc3C2)[C@H](c2ccc(F)c(F)c2)C1] | 2-(Tetrahydro-pyran-4-ylamino)-5,8-dihydro-6H-pyrido[3,4-d]pyrimidine-7-carboxylic acid [(3S,4R)-4-(3,4-difluoro-phenyl)-1-methyl-pyrrolidin-3-yl]-amide | no MS |
| II-210 | 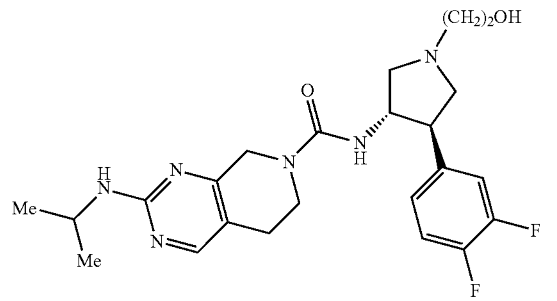 | 2-Isopropylamino-5,8-dihydro-6H-pyrido[3,4-d]pyrimidine-7-carboxylic acid [(3S,4R)-4-(3,4-difluoro-phenyl)-1-(2-hydroxy-ethyl)-pyrrolidin-3-yl]-amide | 461.2 |
| II-211 | 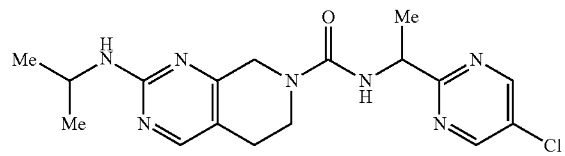 [SMILES: CC(C)Nc1ncc2c(n1)CN(C(=O)NC(C)c1ncc(Cl)cn1)CC2] | 2-Isopropylamino-5,8-dihydro-6H-pyrido[3,4-d]pyrimidine-7-carboxylic acid [1-(5-chloro-pyrimidin-2-yl)-ethyl]-amide | 376.0 |
| II-212 | 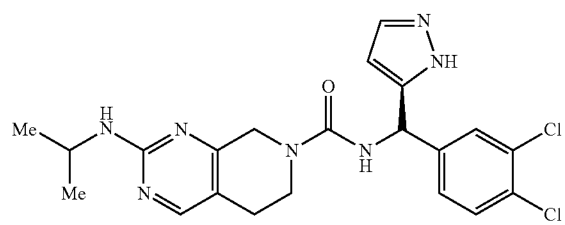 | 2-Isopropylamino-5,8-dihydro-6H-pyrido[3,4-d]pyrimidine-7-carboxylic acid [(S)-(3,4-dichloro-phenyl)-(2H-pyrazol-3-yl)-methyl]-amide | 462.3 |
| II-213 | 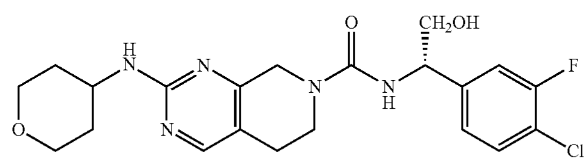 [SMILES: O=C(N[C@H](CO)c1ccc(Cl)c(F)c1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(S)-1-(4-chloro-3-fluoro-phenyl)-2-hydroxy-ethyl]-amide | 450.3 |
| II-214 | 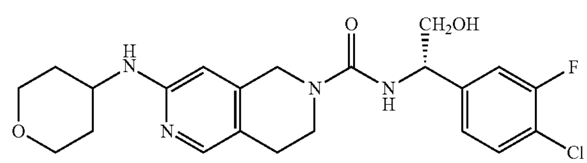 [SMILES: O=C(N[C@H](CO)c1ccc(Cl)c(F)c1)N1CCc2cnc(NC3CCOCC3)cc2C1] | 7-(Tetrahydro-pyran-4-ylamino)-3,4-dihydro-1H-[2,6]naphthyridine-2-carboxylic acid [(S)-1-(4-chloro-3-fluoro-phenyl)-2-hydroxy-ethyl]-amide | 449.6 |
| II-215 | 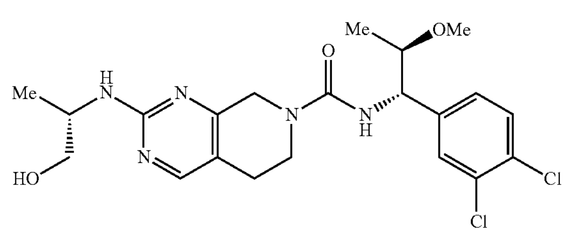 [SMILES: CO[C@H](C)[C@@H](NC(=O)N1CCc2cnc(N[C@@H](C)CO)nc2C1)c1ccc(Cl)c(Cl)c1] | 2-((S)-2-Hydroxy-1-methyl-ethylamino)-5,8-dihydro-6H-pyrido[3,4-d]pyrimidine-7-carboxylic acid [(1S,2R)-1-(3,4-dichloro-phenyl)-2-methoxy-propyl]-amide | 468.2 |

TABLE II-continued

| | Structure | Name | MS |
|---|---|---|---|
| II-216 | 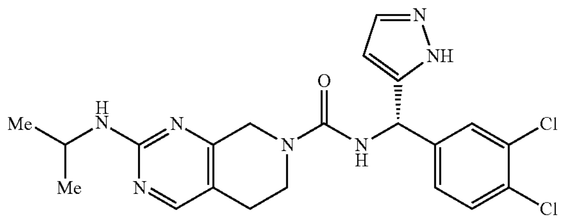 [SMILES: CC(C)Nc1ncc2c(n1)CN(C(=O)N[C@@H](c1ccc(Cl)c(Cl)c1)c1ccn[nH]1)CC2] | 2-Isopropylamino-5,8-dihydro-6H-pyrido[3,4-d]pyrimidine-7-carboxylic acid [(R)-(3,4-dichloro-phenyl)-(2H-pyrazol-3-yl)-methyl]-amide | 462.3 |
| II-217 | 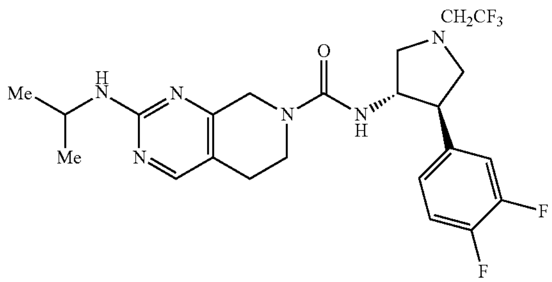 [SMILES: CC(C)Nc1ncc2c(n1)CN(C(=O)N[C@@H]1CNC[C@H]1c1ccc(F)c(F)c1)CC2 ; "CH2CF3"] | 2-Isopropylamino-5,8-dihydro-6H-pyrido[3,4-d]pyrimidine-7-carboxylic acid [(3S,4R)-4-(3,4-difluoro-phenyl)-1-(2,2,2-trifluoro-ethyl)-pyrrolidin-3-yl]-amide | 499.2 |
| II-218 | 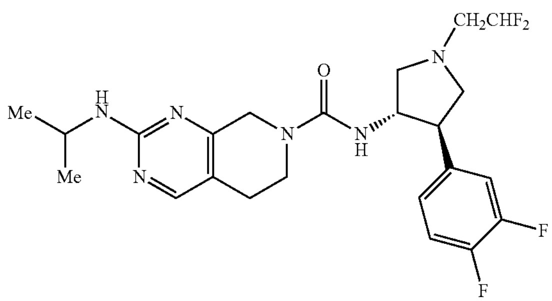 | 2-Isopropylamino-5,8-dihydro-6H-pyrido[3,4-d]pyrimidine-7-carboxylic acid [(3S,4R)-1-(2,2-difluoro-ethyl)-4-(3,4-difluoro-phenyl)-pyrrolidin-3-yl]-amide | 481.1 |
| II-219 | 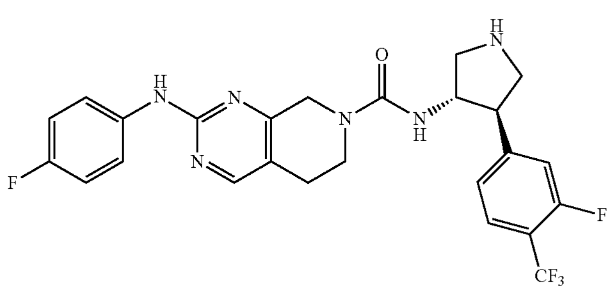 [SMILES: O=C(N[C@@H]1CNC[C@H]1c1ccc(C(F)(F)F)c(F)c1)N1CCc2cnc(Nc3ccc(F)cc3)nc2C1] | 2-(4-Fluoro-phenylamino)-5,8-dihydro-6H-pyrido[3,4-d]pyrimidine-7-carboxylic acid [(3S,4R)-4-(3-fluoro-4-trifluoromethyl-phenyl)-pyrrolidin-3-yl]-amide | 519.1 |
| II-220 | 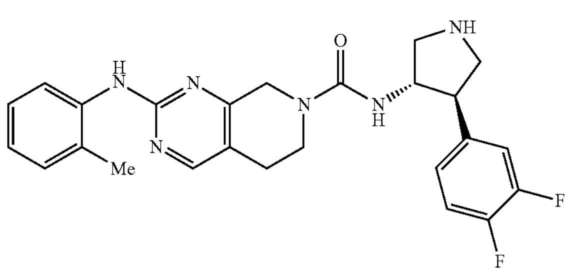 [SMILES: Cc1ccccc1Nc1ncc2c(n1)CN(C(=O)N[C@@H]1CNC[C@H]1c1ccc(F)c(F)c1)CC2] | 2-o-Tolylamino-5,8-dihydro-6H-pyrido[3,4-d]pyrimidine-7-carboxylic acid [(3S,4R)-4-(3,4-difluoro-phenyl)-pyrrolidin-3-yl]-amide | 465.1 |

TABLE II-continued

| | Structure | Name | MS |
|---|---|---|---|
| II-221 | 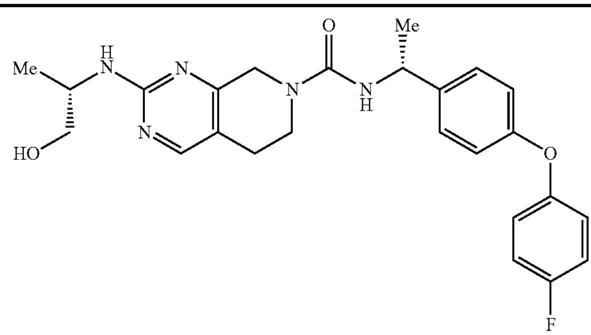 | 2-((S)-2-Hydroxy-1-methyl-ethylamino)-5,8-dihydro-6H-pyrido[3,4-d]pyrimidine-7-carboxylic acid {(R)-1-[4-(4-fluoro-phenoxy)-phenyl]-ethyl}-amide | 466.1 |
| II-222 | 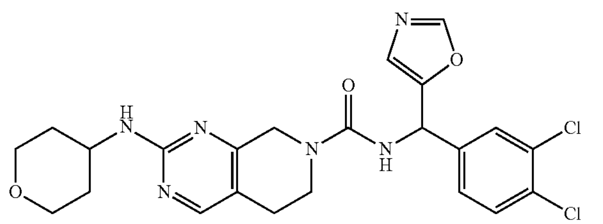 | 2-(Tetrahydro-pyran-4-ylamino)-5,8-dihydro-6H-pyrido[3,4-d]pyrimidine-7-carboxylic acid [(3,4-dichloro-phenyl)-oxazol-5-yl-methyl]-amide | 505.5 |
| II-223 | 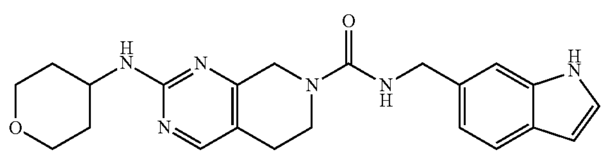 [SMILES: O=C(NCc1ccc2cc[nH]c2c1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid (1H-indol-6-ylmethyl)-amide | 407.1 |
| II-224 | 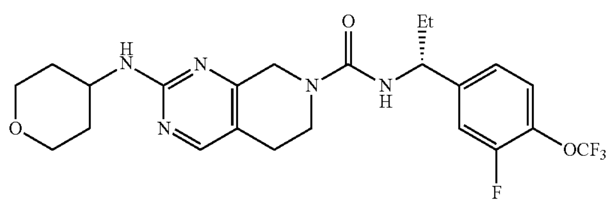 [SMILES: CC[C@@H](NC(=O)N1CCc2cnc(NC3CCOCC3)nc2C1)c1ccc(OC(F)(F)F)c(F)c1] | 2-(Tetrahydro-pyran-4-ylamino)-5,8-dihydro-6H-pyrido[3,4-d]pyrimidine-7-carboxylic acid [(R)-1-(3-fluoro-4-trifluoromethoxy-phenyl)-propyl]-amide | 498.2 |
| II-225 | 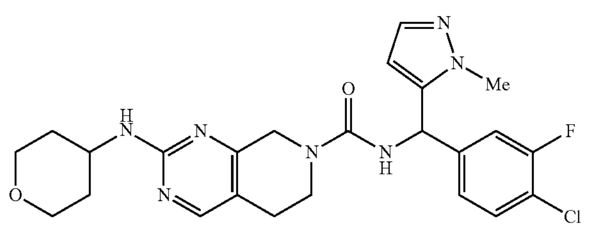 [SMILES: Cn1nccc1C(NC(=O)N1CCc2cnc(NC3CCOCC3)nc2C1)c1ccc(Cl)c(F)c1] | 2-(Tetrahydro-pyran-4-ylamino)-5,8-dihydro-6H-pyrido[3,4-d]pyrimidine-7-carboxylic acid [(4-chloro-3-fluoro-phenyl)-(2-methyl-2H-pyrazol-3-yl)-methyl]-amide | 501.4 |
| II-226 | 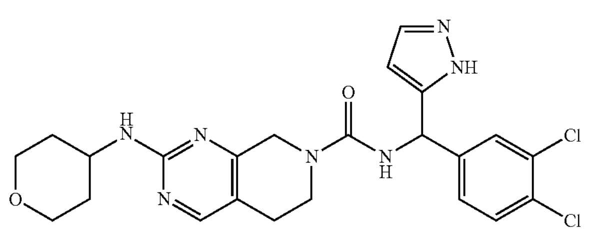 [SMILES: O=C(NC(c1ccc(Cl)c(Cl)c1)c1ccn[nH]1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(3,4-dichloro-phenyl)-(2H-pyrazol-3-yl)-methyl]amide | 504.4 |
| II-227 | 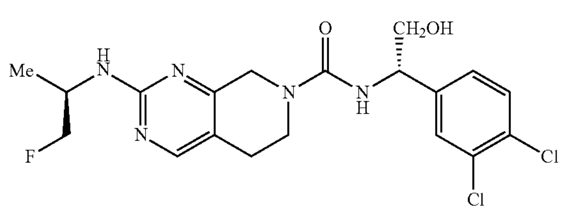 [SMILES: C[C@H](CF)Nc1ncc2c(n1)CN(C(=O)N[C@H](CO)c1ccc(Cl)c(Cl)c1)CC2] | 2-((R)-2-Fluoro-1-methyl-ethylamino)-5,8-dihydro-6H-pyrido[3,4-d]pyrimidine-7-carboxylic acid [(S)-1-(3,4-dichloro-phenyl)-2-hydroxy-ethyl]-amide | 442.1 |

TABLE II-continued

| | Structure | Name | MS |
|---|---|---|---|
| II-228 | 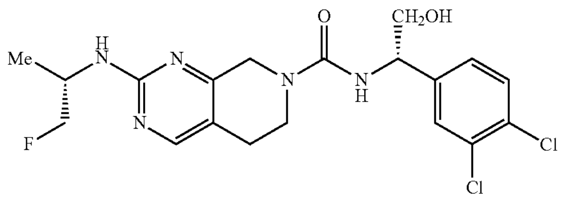 [SMILES: C[C@@H](CF)Nc1ncc2c(n1)CN(C(=O)N[C@H](CO)c1ccc(Cl)c(Cl)c1)CC2] | 2-((S)-2-Fluoro-1-methyl-ethylamino)-5,8-dihydro-6H-pyrido[3,4-d]pyrimidine-7-carboxylic acid [(S)-1-(3,4-dichloro-phenyl)-2-hydroxy-ethyl]-amide | 442.3 |
| II-229 | 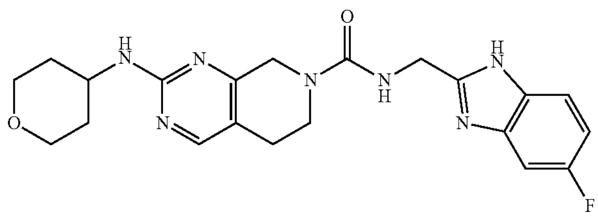 [SMILES: O=C(NCc1nc2cc(F)ccc2[nH]1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid (5-fluoro-1H-indol-2-ylmethyl)-amide | 425.1 |
| II-230 | 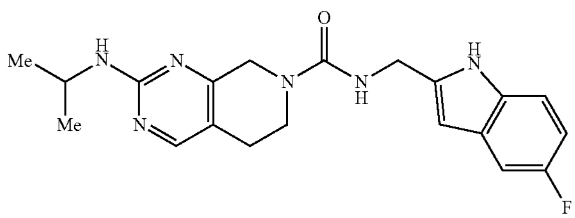 [SMILES: CC(C)Nc1ncc2c(n1)CN(C(=O)NCc1cc3cc(F)ccc3[nH]1)CC2] | 2-Isopropylamino-5,8-dihydro-6H-pyrido[3,4-d]pyrimidine-7-carboxylic acid (5-fluoro-1H-indol-2-ylmethyl)-amide | 383.1 |
| II-231 | 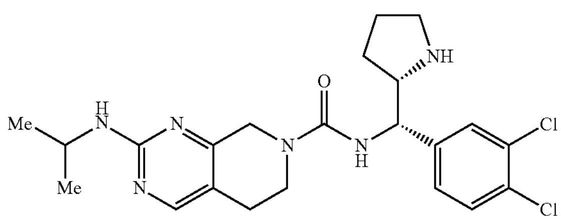 | 2-Isopropylamino-5,8-dihydro-6H-pyrido[3,4-d]pyrimidine-7-carboxylic acid [(S)-(3,4-dichloro-phenyl)-(S)-pyrrolidin-2-yl-methyl]-amide | 463.1 |
| II-232 | 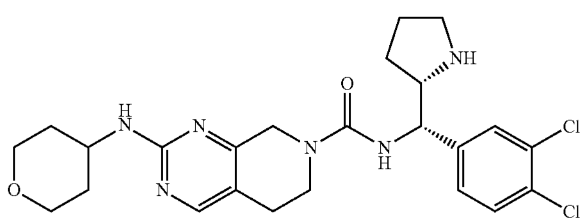 [SMILES: O=C(N[C@@H](c1ccc(Cl)c(Cl)c1)[C@@H]1CCCN1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(S)-(3,4-dichloro-phenyl)-(S)-pyrrolidin-2-yl-methyl]-amide | 505.1 |
| II-233 | 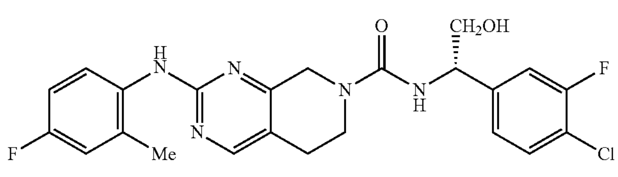 [SMILES: Cc1cc(F)ccc1Nc1ncc2c(n1)CN(C(=O)N[C@H](CO)c1ccc(Cl)c(F)c1)CC2] | 2-(4-Fluoro-2-methyl-phenylamino)-5,8-dihydro-6H-pyrido[3,4-d]pyrimidine-7-carboxylic acid [(S)-1-(4-chloro-3-fluoro-phenyl)-2-hydroxy-ethyl]-amide | 474.1 |
| II-234 | 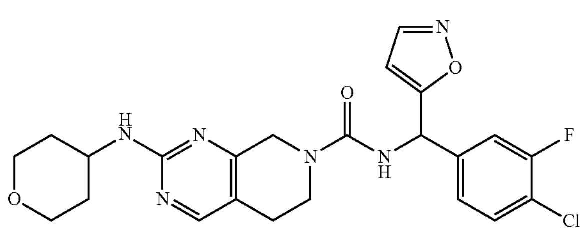 [SMILES: O=C(NC(c1ccc(Cl)c(F)c1)c1ccno1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(4-chloro-3-fluoro-phenyl)-isoxazol-5-yl-methyl]-amide | 487.2 |

TABLE II-continued

| | Structure | Name | MS |
|---|---|---|---|
| II-235 | 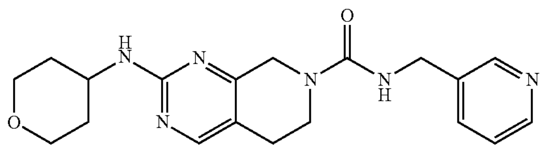 [SMILES: O=C(NCc1cccnc1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid (pyridin-3-ylmethyl)-amide | 369.1 |
| II-236 | 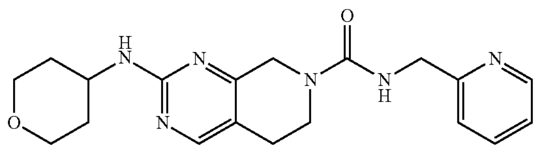 [SMILES: O=C(NCc1ccccn1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid (pyridin-2-ylmethyl)-amide | 369.2 |
| II-237 | 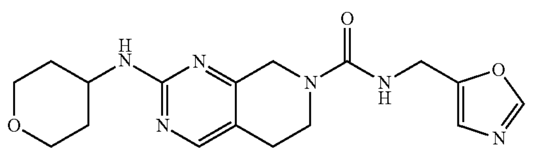 [SMILES: O=C(NCc1cnco1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid (oxazol-5-ylmethyl)-amide | 359.1 |
| II-238 | 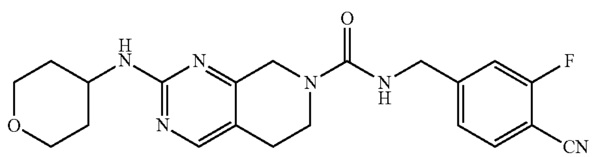 [SMILES: N#Cc1ccc(CNC(=O)N2CCc3cnc(NC4CCOCC4)nc3C2)cc1F] | 2-(Tetrahydro-pyran-4-ylamino)-5,8-dihydro-6H-pyrido[3,4-d]pyrimidine-7-carboxylic acid 4-cyano-3-fluoro-benzylamide | 411.2 |
| II-239 | 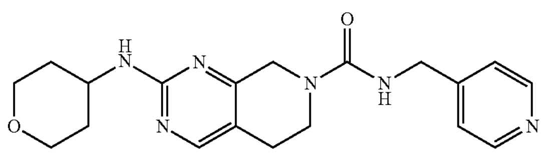 [SMILES: O=C(NCc1ccncc1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid (pyridin-4-ylmethyl)-amide | 369.1 |
| II-240 | 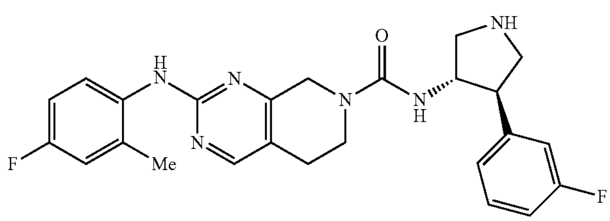 [SMILES: Cc1cc(F)ccc1Nc1ncc2c(n1)CN(C(=O)N[C@@H]1CNC[C@H]1c1cccc(F)c1)CC2] | 2-(4-Fluoro-2-methyl-phenylamino)-5,8-dihydro-6H-pyrido[3,4-d]pyrimidine-7-carboxylic acid [(3S,4R)-4-(3-fluoro-phenyl)-pyrrolidin-3-yl]-amide | 465.1 |
| II-241 | 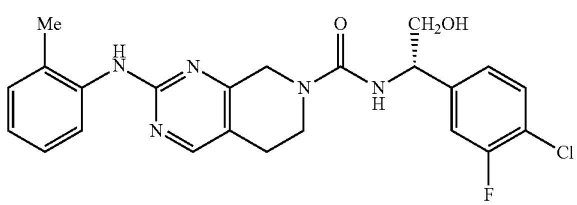 [SMILES: Cc1ccccc1Nc1ncc2c(n1)CN(C(=O)N[C@H](CO)c1ccc(Cl)c(F)c1)CC2] | 2-o-Tolylamino-5,8-dihydro-6H-pyrido[3,4-d]pyrimidine-7-carboxylic acid [(S)-1-(4-chloro-3-fluoro-phenyl)-2-hydroxy-ethyl]-amide | 456.1 |
| II-242 | 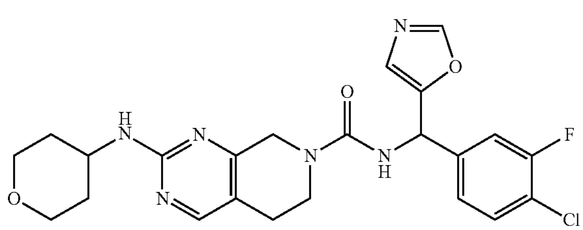 [SMILES: O=C(NC(c1ccc(Cl)c(F)c1)c1cnco1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(4-chloro-3-fluoro-phenyl)-oxazol-5-yl-methyl]-amide | 487.1 |
| II-243 | 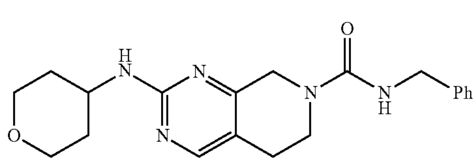 [SMILES: O=C(NCc1ccccc1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid benzylamide | 350.6 |

TABLE II-continued

| | Structure | Name | MS |
|---|---|---|---|
| II-244 | 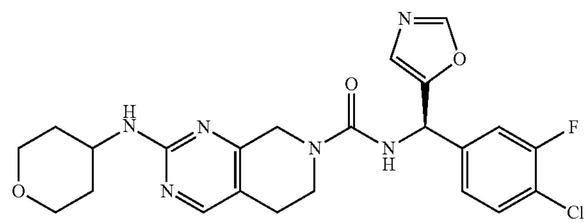 [SMILES: O=C(N[C@H](c1ccc(Cl)c(F)c1)c1cnco1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(R)-(4-chloro-3-fluoro-phenyl)-oxazol-5-yl-methyl]-amide | 487.1 |
| II-245 | 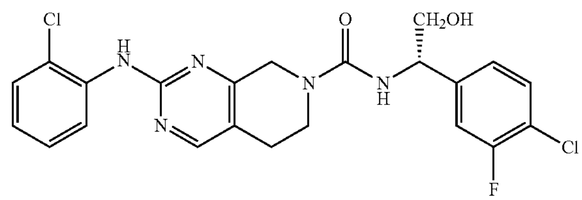 [SMILES: O=C(N[C@H](CO)c1ccc(Cl)c(F)c1)N1CCc2cnc(Nc3ccccc3Cl)nc2C1] | 2-(2-Chloro-phenylamino)-5,8-dihydro-6H-pyrido[3,4-d]pyrimidine-7-carboxylic acid [(S)-1-(4-chloro-3-fluoro-phenyl)-2-hydroxy-ethyl]-amide | 476.2 |
| II-246 | 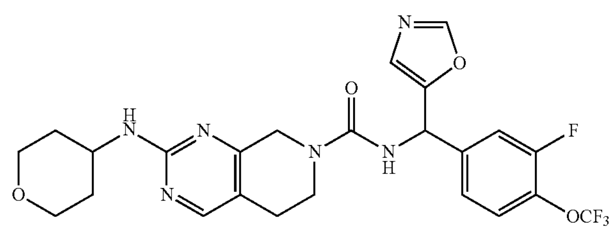 | 2-(Tetrahydro-pyran-4-ylamino)-5,8-dihydro-6H-pyrido[3,4-d]pyrimidine-7-carboxylic acid [(3-fluoro-4-trifluoromethoxy-phenyl)-oxazol-5-yl-methyl]-amide | 537.1 |
| II-247 | 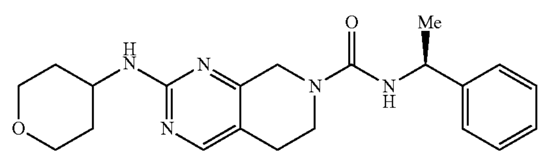 [SMILES: C[C@H](NC(=O)N1CCc2cnc(NC3CCOCC3)nc2C1)c1ccccc1] | 2-(Tetrahydro-pyran-4-ylamino)-5,8-dihydro-6H-pyrido[3,4-d]pyrimidine-7-carboxylic acid ((S)-1-phenyl-ethyl)-amide | 382.2 |
| II-248 | 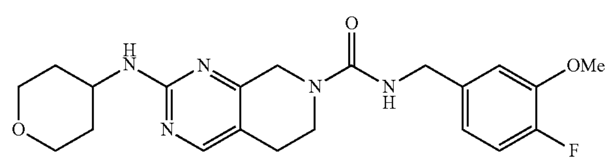 [SMILES: COc1cc(CNC(=O)N2CCc3cnc(NC4CCOCC4)nc3C2)ccc1F] | 2-(Tetrahydro-pyran-4-ylamino)-5,8-dihydro-6H-pyrido[3,4-d]pyrimidine-7-carboxylic acid 4-fluoro-3-methoxy-benzylamide | 416.2 |
| II-249 | 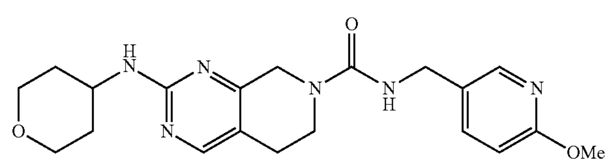 [SMILES: COc1ccc(CNC(=O)N2CCc3cnc(NC4CCOCC4)nc3C2)cn1] | 2-(Tetrahydro-pyran-4-ylamino)-5,8-dihydro-6H-pyrido[3,4-d]pyrimidine-7-carboxylic acid (6-methoxy-pyridin-3-ylmethyl)-amide | 399.2 |
| II-250 | 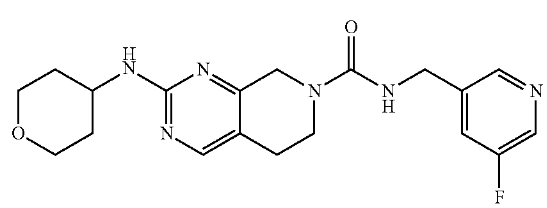 [SMILES: O=C(NCc1cncc(F)c1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid (5-fluoro-pyridin-3-ylmethyl)-amide | 387.1 |
| II-251 | 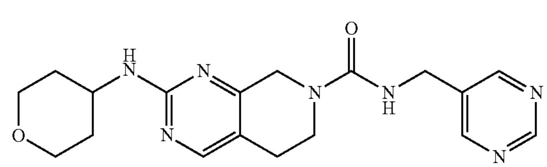 [SMILES: O=C(NCc1cncnc1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid (pyrimidin-5-ylmethyl)-amide | 370.2 |

TABLE II-continued

| | Structure | Name | MS |
|---|---|---|---|
| II-252 | 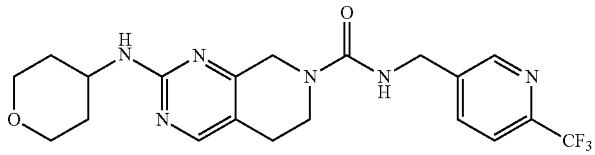 | 2-(Tetrahydro-pyran-4-ylamino)-5,8-dihydro-6H-pyrido[3,4-d]pyrimidine-7-carboxylic acid (6-trifluoromethyl-pyridin-3-ylmethyl)-amide | 437.2 |
| II-253 | 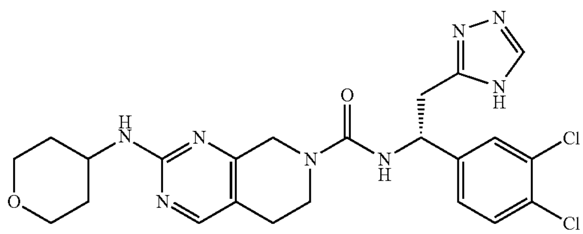 [SMILES: O=C(N[C@H](Cc1nnc[nH]1)c1ccc(Cl)c(Cl)c1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(R)-1-(3,4-dichloro-phenyl)-2-(4H-[1,2,4]triazol-3-yl)-ethyl]-amide | 517.0 |
| II-254 | 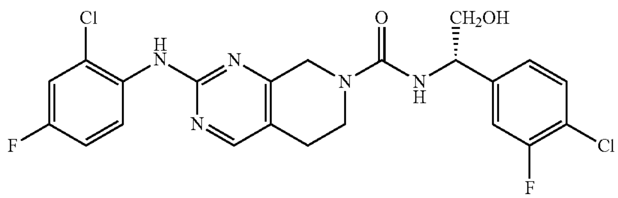 [SMILES: O=C(N[C@H](CO)c1ccc(Cl)c(F)c1)N1CCc2cnc(Nc3ccc(F)cc3Cl)nc2C1] | 2-(2-Chloro-4-fluoro-phenylamino)-5,8-dihydro-6H-pyrido[3,4-d]pyrimidine-7-carboxylic acid [(S)-1-(4-chloro-3-fluoro-phenyl)-2-hydroxy-ethyl]-amide | 494.0 |
| II-255 | 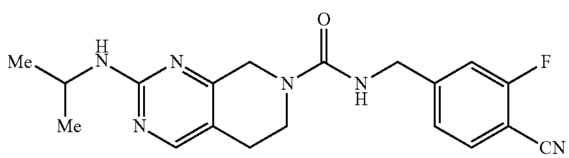 [SMILES: CC(C)Nc1ncc2c(n1)CN(C(=O)NCc1ccc(C#N)c(F)c1)CC2] | 2-Isopropylamino-5,8-dihydro-6H-pyrido[3,4-d]pyrimidine-7-carboxylic acid 4-cyano-3-fluoro-benzylamide | 369.1 |
| II-256 | 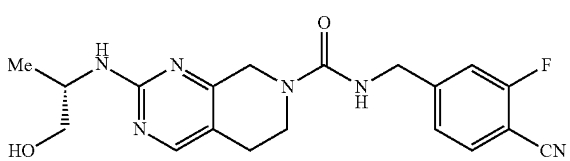 [SMILES: C[C@@H](CO)Nc1ncc2c(n1)CN(C(=O)NCc1ccc(C#N)c(F)c1)CC2] | 2-((S)-2-Hydroxy-1-methyl-ethylamino)-5,8-dihydro-6H-pyrido[3,4-d]pyrimidine-7-carboxylic acid 4-cyano-3-fluoro-benzylamide | 385.1 |
| II-257 | 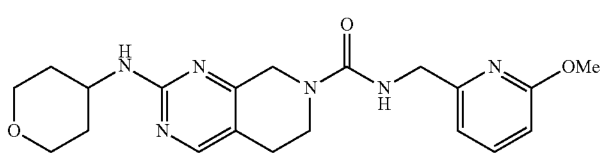 [SMILES: COc1cccc(CNC(=O)N2CCc3cnc(NC4CCOCC4)nc3C2)n1] | 2-(Tetrahydro-pyran-4-ylamino)-5,8-dihydro-6H-pyrido[3,4-d]pyrimidine-7-carboxylic acid (6-methoxy-pyridin-2-ylmethyl)-amide | 399.2 |
| II-258 | 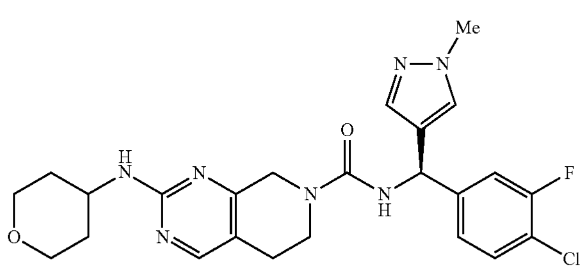 [SMILES: Cn1cc([C@H](NC(=O)N2CCc3cnc(NC4CCOCC4)nc3C2)c2ccc(Cl)c(F)c2)cn1] | 2-(Tetrahydro-pyran-4-ylamino)-5,8-dihydro-6H-pyrido[3,4-d]pyrimidine-7-carboxylic acid [(R)-(4-chloro-3-fluoro-phenyl)-(1-methyl-1H-pyrazol-4-yl)-methyl]-amide | 499.9 |
| II-259 | 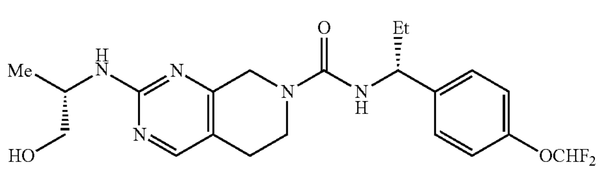 [SMILES: CC[C@@H](NC(=O)N1CCc2cnc(N[C@@H](C)CO)nc2C1)c1ccc(OC(F)F)cc1] | 2-((S)-2-Hydroxy-1-methyl-ethylamino)-5,8-dihydro-6H-pyrido[3,4-d]pyrimidine-7-carboxylic acid [(R)-1-(4-difluoromethoxy-phenyl)-propyl]-amide | 436.2 |

TABLE II-continued

| | Structure | Name | MS |
|---|---|---|---|
| II-260 | 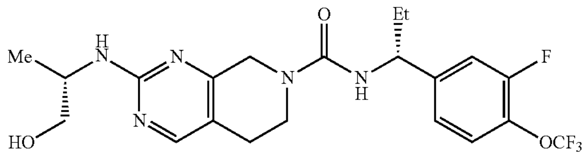 [SMILES: CC[C@@H](NC(=O)N1CCc2cnc(N[C@@H](C)CO)nc2C1)c1ccc(OC(F)(F)F)c(F)c1] | 2-((S)-2-Hydroxy-1-methyl-ethylamino)-5,8-dihydro-6H-pyrido[3,4-d]pyrimidine-7-carboxylic acid [(R)-1-(3-fluoro-4-trifluoromethoxy-phenyl)-propyl]-amide | 472.2 |
| II-261 | 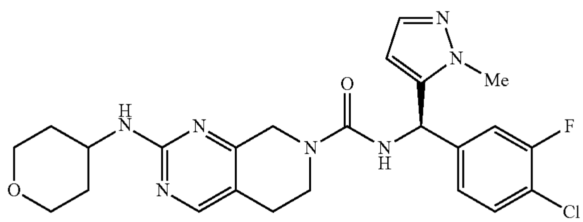 [SMILES: Cn1nccc1[C@H](NC(=O)N1CCc2cnc(NC3CCOCC3)nc2C1)c1ccc(Cl)c(F)c1] | 2-(Tetrahydro-pyran-4-ylamino)-5,8-dihydro-6H-pyrido[3,4-d]pyrimidine-7-carboxylic acid [(R)-(4-chloro-3-fluoro-phenyl)-(2-methyl-2H-pyrazol-3-yl)-methyl]-amide | 500.2 |
| II-262 | 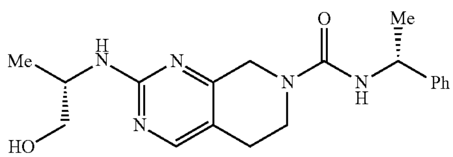 [SMILES: C[C@@H](CO)Nc1ncc2c(n1)CN(C(=O)N[C@H](C)c1ccccc1)CC2] | 2-((S)-2-Hydroxy-1-methyl-ethylamino)-5,8-dihydro-6H-pyrido[3,4-d]pyrimidine-7-carboxylic acid ((R)-1-phenyl-ethyl)-amide | 356.1 |
| II-263 | 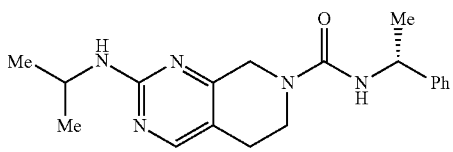 [SMILES: CC(C)Nc1ncc2c(n1)CN(C(=O)N[C@H](C)c1ccccc1)CC2] | 2-Isopropylamino-5,8-dihydro-6H-pyrido[3,4-d]pyrimidine-7-carboxylic acid ((R)-1-phenyl-ethyl)-amide | 340.2 |
| II-264 | 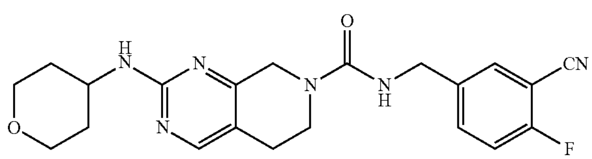 [SMILES: N#Cc1cc(CNC(=O)N2CCc3cnc(NC4CCOCC4)nc3C2)ccc1F] | 2-(Tetrahydro-pyran-4-ylamino)-5,8-dihydro-6H-pyrido[3,4-d]pyrimidine-7-carboxylic acid 3-cyano-4-fluoro-benzylamide | 411.1 |
| II-265 | 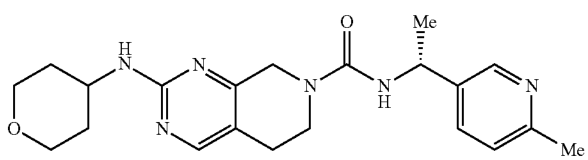 [SMILES: Cc1ccc([C@@H](C)NC(=O)N2CCc3cnc(NC4CCOCC4)nc3C2)cn1] | 2-(Tetrahydro-pyran-4-ylamino)-5,8-dihydro-6H-pyrido[3,4-d]pyrimidine-7-carboxylic acid [(R)-1-(6-methyl-pyridin-3-yl)-ethyl]-amide | 397.2 |
| II-266 | 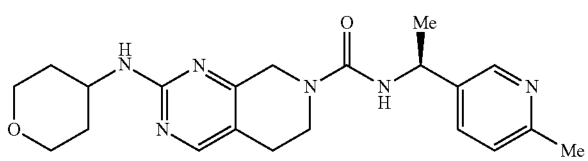 [SMILES: Cc1ccc([C@H](C)NC(=O)N2CCc3cnc(NC4CCOCC4)nc3C2)cn1] | 2-(Tetrahydro-pyran-4-ylamino)-5,8-dihydro-6H-pyrido[3,4-d]pyrimidine-7-carboxylic acid [(S)-1-(6-methyl-pyridin-3-yl)-ethyl]-amide | 397.2 |
| II-267 | 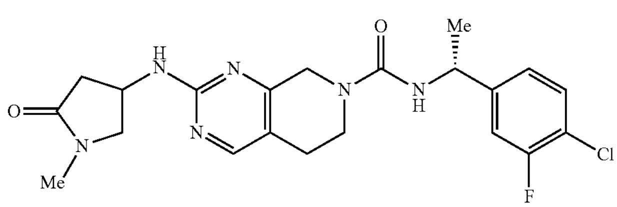 [SMILES: C[C@@H](NC(=O)N1CCc2cnc(NC3CC(=O)N(C)C3)nc2C1)c1ccc(Cl)c(F)c1] | 2-(1-Methyl-5-oxo-pyrrolidin-3-ylamino)-5,8-dihydro-6H-pyrido[3,4-d]pyrimidine-7-carboxylic acid [1-(4-chloro-3-fluoro-phenyl)-ethyl]-amide | 447.0 |
| II-268 | 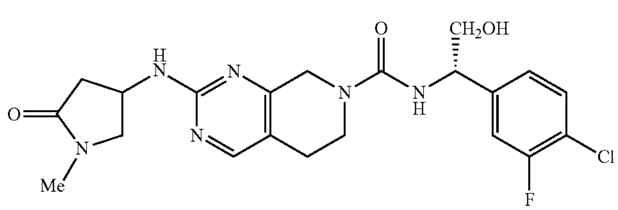 [SMILES: CN1CC(Nc2ncc3c(n2)CN(C(=O)N[C@H](CO)c2ccc(Cl)c(F)c2)CC3)CC1=O] | 2-(1-Methyl-5-oxo-pyrrolidin-3-ylamino)-5,8-dihydro-6H-pyrido[3,4-d]pyrimidine-7-carboxylic acid [1-(4-chloro-3-fluoro-phenyl)-2-hydroxy-ethyl]-amide | 463.0 |

TABLE II-continued

| | Structure | Name | MS |
|---|---|---|---|
| II-269 | 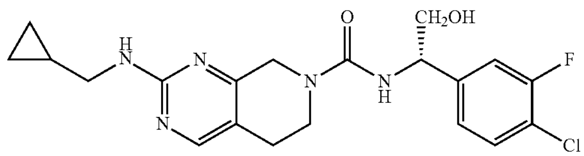 [SMILES: O=C(N[C@H](CO)c1ccc(Cl)c(F)c1)N1CCc2cnc(NCC3CC3)nc2C1] | 2-(Cyclopropylmethyl-amino)-5,8-dihydro-6H-pyrido[3,4-d]pyrimidine-7-carboxylic acid [(S)-1-(4-chloro-3-fluoro-phenyl)-2-hydroxy-ethyl]-amide | 420.2 |
| II-270 | 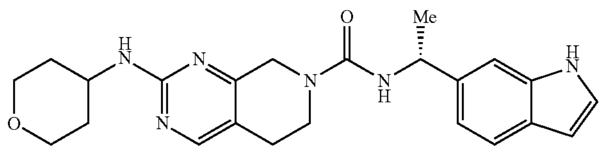 | 2-(Tetrahydro-pyran-4-ylamino)-5,8-dihydro-6H-pyrido[3,4-d]pyrimidine-7-carboxylic acid [(R)-1-(1H-indol-6-yl)-ethyl]-amide | 421.2 |
| II-271 | 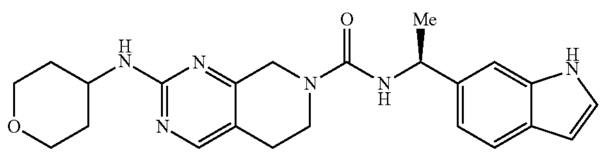 [SMILES: C[C@H](NC(=O)N1CCc2cnc(NC3CCOCC3)nc2C1)c1ccc2cc[nH]c2c1] | 2-(Tetrahydro-pyran-4-ylamino)-5,8-dihydro-6H-pyrido[3,4-d]pyrimidine-7-carboxylic acid [(S)-1-(1H-indol-6-yl)-ethyl]-amide | 421.2 |
| II-272 | 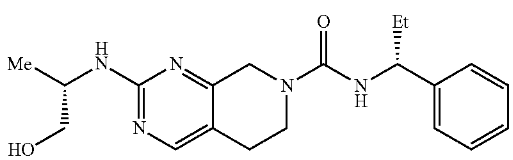 [SMILES: CC[C@@H](NC(=O)N1CCc2cnc(N[C@@H](C)CO)nc2C1)c1ccccc1] | 2-((S)-2-Hydroxy-1-methyl-ethylamino)-5,8-dihydro-6H-pyrido[3,4-d]pyrimidine-7-carboxylic acid ((R)-1-phenyl-propyl)-amide | 370.2 |
| II-273 | 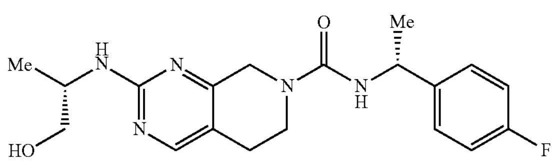 | 2-((S)-2-Hydroxy-1-methyl-ethylamino)-5,8-dihydro-6H-pyrido[3,4-d]pyrimidine-7-carboxylic acid [(S)-1-(4-fluoro-phenyl)-ethyl]-amide | 374.1 |
| II-274 | 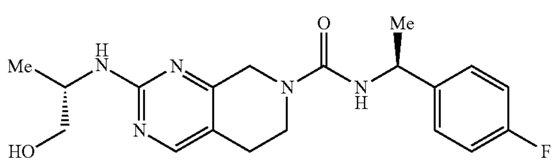 [SMILES: C[C@H](NC(=O)N1CCc2cnc(N[C@@H](C)CO)nc2C1)c1ccc(F)cc1] | 2-((S)-2-Hydroxy-1-methyl-ethylamino)-5,8-dihydro-6H-pyrido[3,4-d]pyrimidine-7-carboxylic acid [(R)-1-(4-fluoro-phenyl)-ethyl]-amide | 374.1 |
| II-275 | 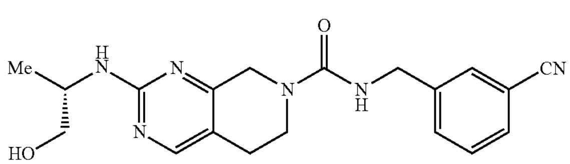 [SMILES: C[C@@H](CO)Nc1ncc2c(n1)CN(C(=O)NCc1cccc(C#N)c1)CC2] | 2-((S)-2-Hydroxy-1-methyl-ethylamino)-5,8-dihydro-6H-pyrido[3,4-d]pyrimidine-7-carboxylic acid 3-cyano-benzylamide | 367.1 |
| II-276 | 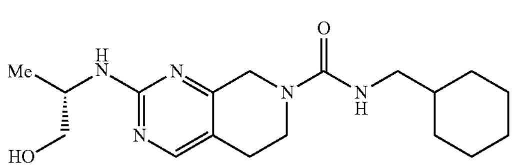 [SMILES: C[C@@H](CO)Nc1ncc2c(n1)CN(C(=O)NCC1CCCCC1)CC2] | 2-((S)-2-Hydroxy-1-methyl-ethylamino)-5,8-dihydro-6H-pyrido[3,4-d]pyrimidine-7-carboxylic acid cyclohexylmethyl-amide | 348.2 |
| II-277 | 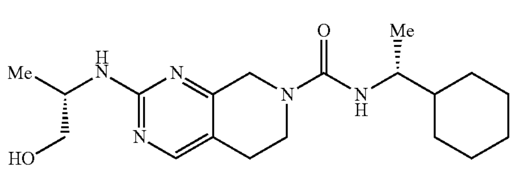 [SMILES: C[C@@H](CO)Nc1ncc2c(n1)CN(C(=O)N[C@H](C)C1CCCCC1)CC2] | 2-((S)-2-Hydroxy-1-methyl-ethylamino)-5,8-dihydro-6H-pyrido[3,4-d]pyrimidine-7-carboxylic acid ((R)-1-cyclohexyl-ethyl)-amide | 362.2 |

TABLE II-continued

| | Structure | Name | MS |
|---|---|---|---|
| II-278 | 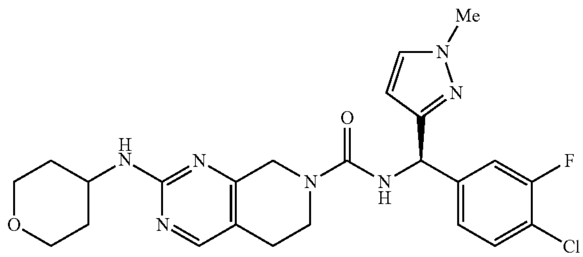 [SMILES: Cn1ccc([C@H](NC(=O)N2CCc3cnc(NC4CCOCC4)nc3C2)c2ccc(Cl)c(F)c2)n1] | 2-(Tetrahydro-pyran-4-ylamino)-5,8-dihydro-6H-pyrido[3,4-d]pyrimidine-7-carboxylic acid [(R)-(4-chloro-3-fluoro-phenyl)-(1-methyl-1H-pyrazol-3-yl)-methyl]-amide | 500.0 |
| II-279 | 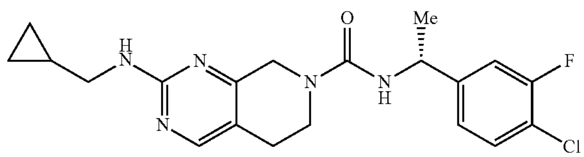 [SMILES: C[C@@H](NC(=O)N1CCc2cnc(NCC3CC3)nc2C1)c1ccc(Cl)c(F)c1] | 2-(Cyclopropylmethyl-amino)-5,8-dihydro-6H-pyrido[3,4-d]pyrimidine-7-carboxylic acid [(R)-1-(4-chloro-3-fluoro-phenyl)-ethyl]-amide | 404.2 |
| II-280 | 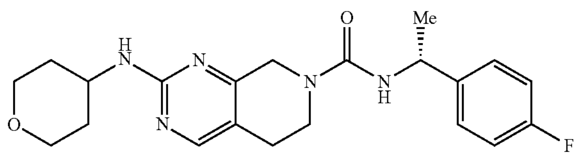 [SMILES: C[C@@H](NC(=O)N1CCc2cnc(NC3CCOCC3)nc2C1)c1ccc(F)cc1] | 2-(Tetrahydro-pyran-4-ylamino)-5,8-dihydro-6H-pyrido[3,4-d]pyrimidine-7-carboxylic acid [(R)-1-(4-fluoro-phenyl)-ethyl]-amide | 400.2 |
| II-281 | 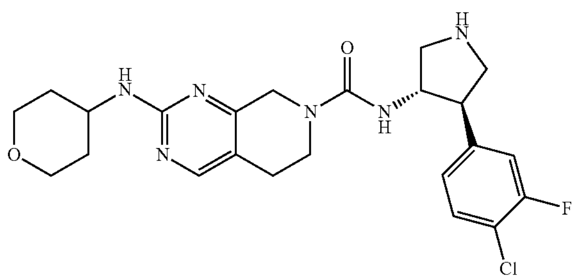 [SMILES: O=C(N[C@@H]1CNC[C@H]1c1ccc(Cl)c(F)c1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide | 475.0 |
| II-282 | 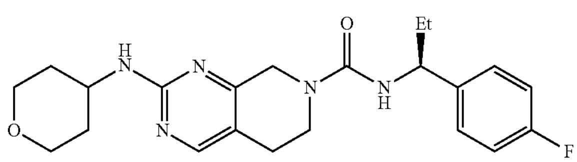 [SMILES: CC[C@H](NC(=O)N1CCc2cnc(NC3CCOCC3)nc2C1)c1ccc(F)cc1] | 2-(Tetrahydro-pyran-4-ylamino)-5,8-dihydro-6H-pyrido[3,4-d]pyrimidine-7-carboxylic acid [(S)-1-(4-fluoro-phenyl)-propyl]-amide | 414.2 |
| II-283 | 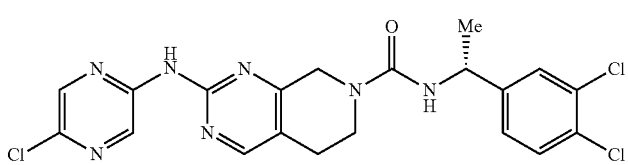 [SMILES: C[C@@H](NC(=O)N1CCc2cnc(Nc3cnc(Cl)cn3)nc2C1)c1ccc(Cl)c(Cl)c1] | 2-(5-Chloro-pyrazin-2-ylamino)-5,8-dihydro-6H-pyrido[3,4-d]pyrimidine-7-carboxylic acid [(R)-1-(3,4-dichloro-phenyl)-ethyl]-amide | 478.1 |
| II-284 | 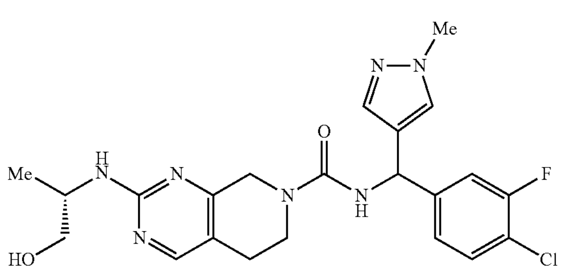 [SMILES: C[C@@H](CO)Nc1ncc2c(n1)CN(C(=O)NC(c1ccc(Cl)c(F)c1)c1cnn(C)c1)CC2] | 2-(2-Hydroxy-1-methyl-ethylamino)-5,8-dihydro-6H-pyrido[3,4-d]pyrimidine-7-carboxylic acid [(4-chloro-3-fluoro-phenyl)-(1-methyl-1H-pyrazol-4-yl)-methyl]-amide | 474.1 |

TABLE II-continued

| | Structure | Name | MS |
|---|---|---|---|
| II-285 | 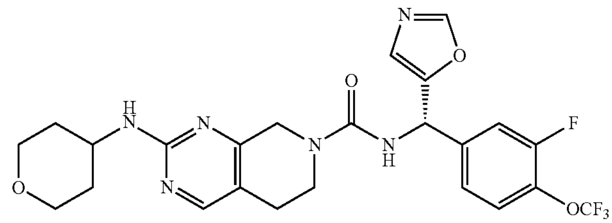 [SMILES: O=C(N[C@@H](c1ccc(OC(F)(F)F)c(F)c1)c1cnco1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(S)-(3-fluoro-4-trifluoromethoxy-phenyl)-oxazol-5-yl-methyl]-amide | 537.2 |
| II-286 | 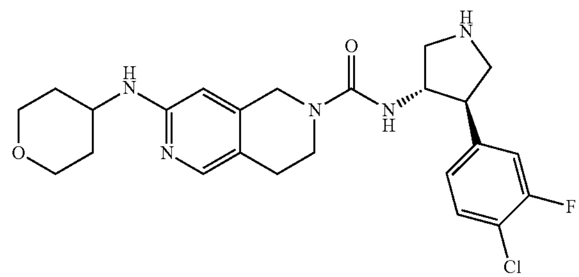 [SMILES: O=C(N[C@@H]1CNC[C@H]1c1ccc(Cl)c(F)c1)N1CCc2cnc(NC3CCOCC3)cc2C1] | 7-(Tetrahydro-pyran-4-ylamino)-3,4-dihydro-1H-[2,6]naphthyridine-2-carboxylic acid [(3S,4R)-4-(4-chloro-3-fluoro-phenyl)-pyrrolidin-3-yl]-amide | 474.3 |
| II-287 | 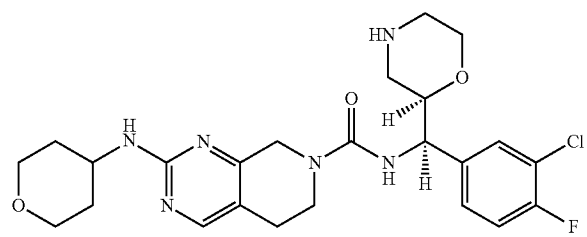 [SMILES: O=C(N[C@H](c1ccc(F)c(Cl)c1)[C@H]1CNCCO1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(4-chloro-3-fluoro-phenyl)-morpholin-2-yl-methyl]-amide | 505.3[1] |
| II-288 | 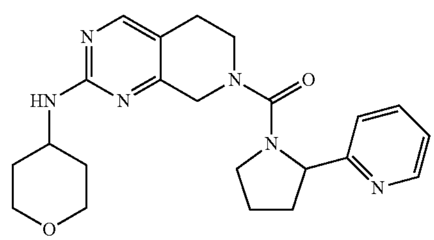 [SMILES: O=C(N1CCc2cnc(NC3CCOCC3)nc2C1)N1CCCC1c1ccccn1] | (2-Pyridin-2-yl-pyrrolidin-1-yl)-[2-(tetrahydro-pyran-4-ylamino)-5,8-dihydro-6H-pyrido[3,4-d]pyrimidin-7-yl]-methanone | 409.0 |
| II-289 | 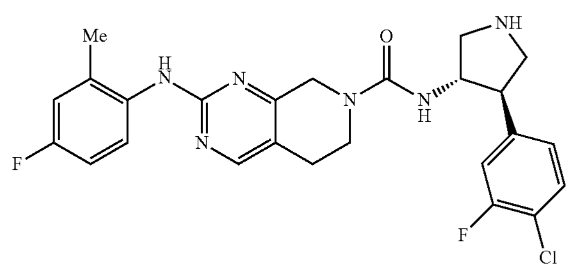 [SMILES: Cc1cc(F)ccc1Nc1ncc2c(n1)CN(C(=O)N[C@@H]1CNC[C@H]1c1ccc(Cl)c(F)c1)CC2] | 2-(4-Fluoro-2-methyl-phenylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide | 499.1 |
| II-290 | 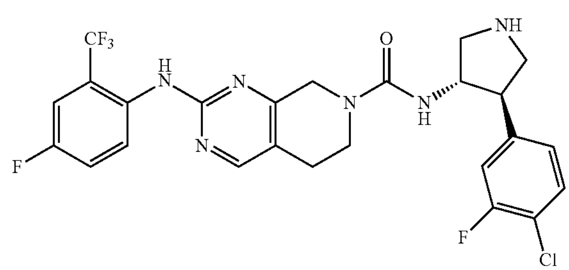 [SMILES: O=C(N[C@@H]1CNC[C@H]1c1ccc(Cl)c(F)c1)N1CCc2cnc(Nc3ccc(F)cc3C(F)(F)F)nc2C1] | 2-(4-Fluoro-2-trifluoromethyl-phenylamino)-5,8-dihydro-6H-pyrido[3,4-d]pyrimidine-7-carboxylic acid [(3S,4R)-4-(4-chloro-3-fluoro-phenyl)-pyrrolidin-3-yl]amide | 553.1 |

TABLE II-continued

| | Structure | Name | MS |
|---|---|---|---|
| II-291 | 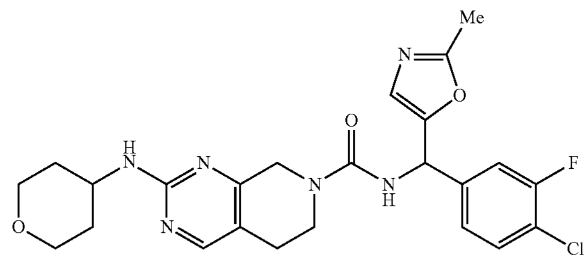 [SMILES: Cc1ncc(C(NC(=O)N2CCc3cnc(NC4CCOCC4)nc3C2)c2ccc(Cl)c(F)c2)o1] | 2-(Tetrahydro-pyran-4-ylamino)-5,8-dihydro-6H-pyrido[3,4-d]pyrimidine-7-carboxylic acid [(4-chloro-3-fluoro-phenyl)-(2-methyl-oxazol-5-yl)-methyl]-amide | 501.0 |
| II-292 | 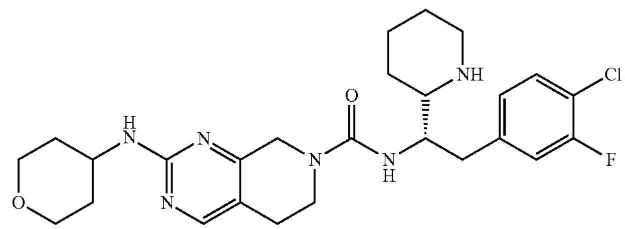 [SMILES: O=C(N[C@@H](Cc1ccc(Cl)c(F)c1)C1CCCCN1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(R)-(4-chloro-3-fluoro-phenyl)-(R)-piperidin-2-yl-methyl]-amide | 503.3 |
| II-293 | 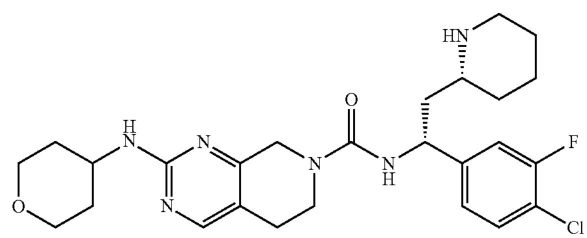 [SMILES: O=C(N[C@H](C[C@H]1CCCCN1)c1ccc(Cl)c(F)c1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(R)-1-(4-chloro-3-fluoro-phenyl)-2-(R)-piperidin-2-yl-ethyl]-amide | 547.3 |
| II-294 | 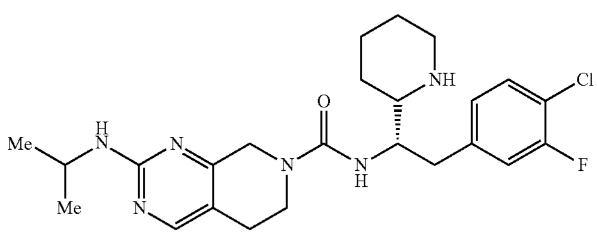 [SMILES: CC(C)Nc1ncc2c(n1)CN(C(=O)N[C@@H](Cc1ccc(Cl)c(F)c1)C1CCCCN1)CC2] | 2-Isopropylamino-5,8-dihydro-6H-pyrido[3,4-d]pyrimidine-7-carboxylic acid [(R)-(4-chloro-3-fluoro-phenyl)-(R)-piperidin-2-yl-methyl]-amide | 461.2 |
| II-295 | 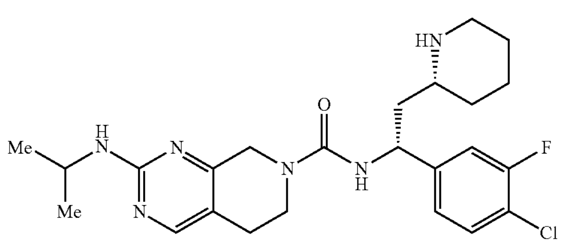 [SMILES: CC(C)Nc1ncc2c(n1)CN(C(=O)N[C@H](C[C@H]1CCCCN1)c1ccc(Cl)c(F)c1)CC2] | 2-Isopropylamino-5,8-dihydro-6H-pyrido[3,4-d]pyrimidine-7-carboxylic acid [(R)-1-(4-chloro-3-fluoro-phenyl)-2-(R)-piperidin-2-yl-ethyl]-amide | 475.3 |
| II-296 | 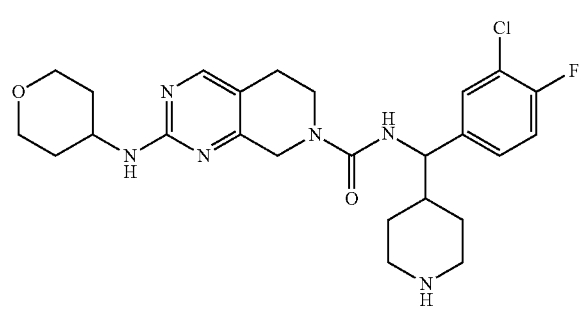 [SMILES: O=C(NC(c1ccc(F)c(Cl)c1)C1CCNCC1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(3-chloro-4-fluoro-phenyl)-piperidin-4-yl-methyl]-amide | 503.3 |

TABLE II-continued

| | Structure | Name | MS |
|---|---|---|---|
| II-297 | 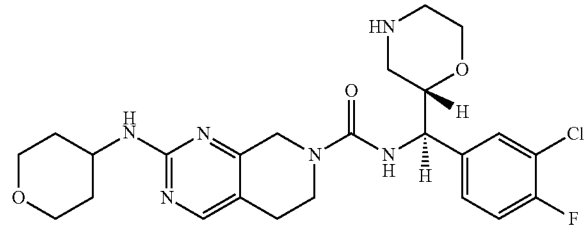 [SMILES: O=C(N[C@H](c1ccc(F)c(Cl)c1)[C@@H]1CNCCO1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(4-chloro-3-fluoro-phenyl)-morpholin-2-yl-methyl]-amide | 505.3[1] |
| II-298 | 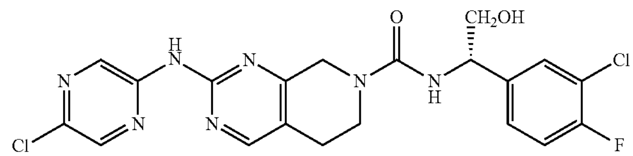 [SMILES: O=C(N[C@H](CO)c1ccc(F)c(Cl)c1)N1CCc2cnc(Nc3cnc(Cl)cn3)nc2C1] | 2-(5-Chloro-pyrazin-2-ylamino)-5,8-dihydro-6H-pyrido[3,4-d]pyrimidine-7-carboxylic acid [(S)-1-(3-chloro-4-fluoro-phenyl)-2-hydroxy-ethyl]-amide | 478.1 |
| II-299 | 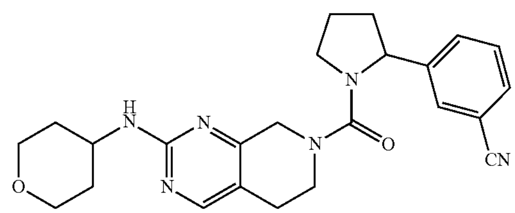 [SMILES: N#Cc1cccc(C2CCCN2C(=O)N2CCc3cnc(NC4CCOCC4)nc3C2)c1] | 3-{1-[2-(Tetrahydro-pyran-4-ylamino)-5,8-dihydro-6H-pyrido[3,4-d]pyrimidine-7-carbonyl]-pyrrolidin-2-yl}-benzonitrile | 433.3 |
| II-300 | 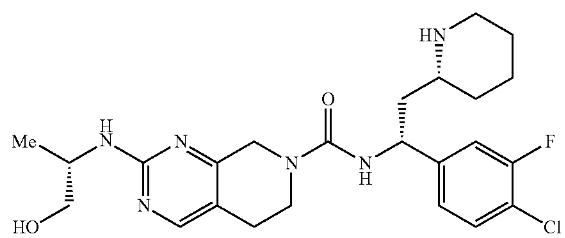 [SMILES: C[C@@H](CO)Nc1ncc2c(n1)CN(C(=O)N[C@H](C[C@H]1CCCCN1)c1ccc(Cl)c(F)c1)CC2] | 2-((S)-2-Hydroxy-1-methyl-ethylamino)-5,8-dihydro-6H-pyrido[3,4-d]pyrimidine-7-carboxylic acid [(R)-1-(4-chloro-3-fluoro-phenyl)-2-(R)-piperidin-2-yl-ethyl]-amide | 491.3 |
| II-301 | 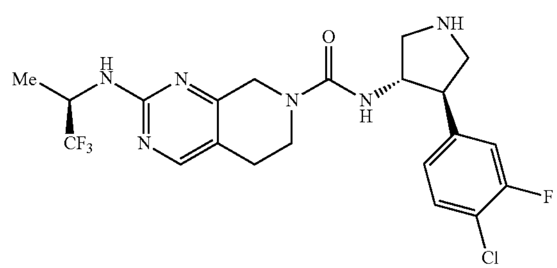 [SMILES: C[C@@H](Nc1ncc2c(n1)CN(C(=O)N[C@@H]1CNC[C@H]1c1ccc(Cl)c(F)c1)CC2)C(F)(F)F] | 2-((R)-2,2,2-Trifluoro-1-methyl-ethylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide | 487.1 |
| II-302 | 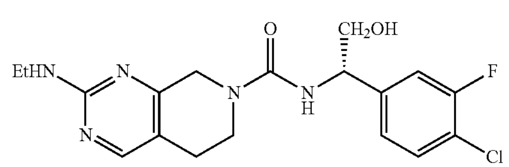 | 2-Ethylamino-5,8-dihydro-6H-pyrido[3,4-d]pyrimidine-7-carboxylic acid [(S)-1-(4-chloro-3-fluoro-phenyl)-2-hydroxy-ethyl]-amide | 394.2 |
| II-303 | 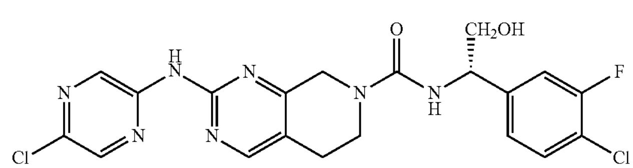 [SMILES: O=C(N[C@H](CO)c1ccc(Cl)c(F)c1)N1CCc2cnc(Nc3cnc(Cl)cn3)nc2C1] | 2-(5-Chloro-pyrazin-2-ylamino)-5,8-dihydro-6H-pyrido[3,4-d]pyrimidine-7-carboxylic acid [(S)-1-(4-chloro-3-fluoro-phenyl)-2-hydroxy-ethyl]-amide | 478.1 |
| II-304 | 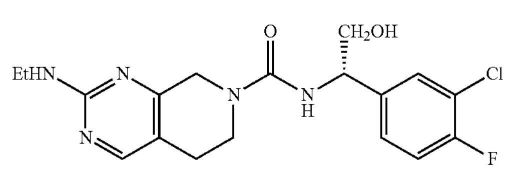 | 2-Ethylamino-5,8-dihydro-6H-pyrido[3,4-d]pyrimidine-7-carboxylic acid [(S)-1-(3-chloro-4-fluoro-phenyl)-2-hydroxy-ethyl]-amide | 393.8 |

TABLE II-continued

| | Structure | Name | MS |
|---|---|---|---|
| II-305 | 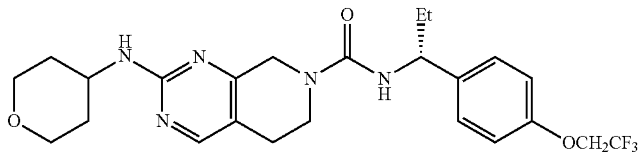 | 2-(Tetrahydro-pyran-4-ylamino)-5,8-dihydro-6H-pyrido[3,4-d]pyrimidine-7-carboxylic acid {(R)-1-[4-(2,2,2-trifluoro-ethoxy)-phenyl]-propyl}-amide | 494.1 |
| II-306 | 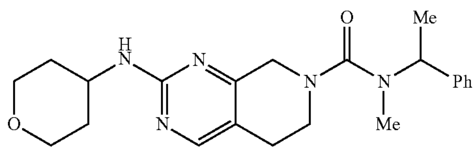 [SMILES: CC(c1ccccc1)N(C)C(=O)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid methyl-(1-phenyl-ethyl)-amide | 396.2 |
| II-307 | 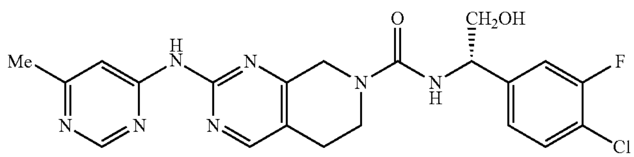 | 2-(6-Methyl-pyrimidin-4-ylamino)-5,8-dihydro-6H-pyrido[3,4-d]pyrimidine-7-carboxylic acid [(S)-1-(4-chloro-3-fluoro-phenyl)-2-hydroxy-ethyl]-amide | 500.1 |
| II-308 | 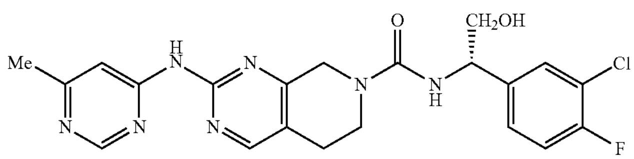 [SMILES: Cc1cc(Nc2ncc3c(n2)CN(C(=O)N[C@H](CO)c2ccc(F)c(Cl)c2)CC3)ncn1] | 2-(6-Methyl-pyrimidin-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide | 458.1 |
| II-309 | 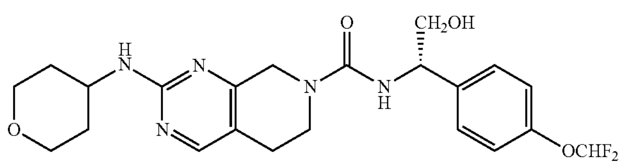 [SMILES: O=C(N[C@H](CO)c1ccc(OC(F)F)cc1)N1CCc2cnc(NC3CCOCC3)nc2C1] | 2-(Tetrahydro-pyran-4-ylamino)-5,8-dihydro-6H-pyrido[3,4-d]pymidine-7-carboxylic acid [(S)-1-(4-difluoromethoxy-phenyl)-2-hydroxy-ethyl]-amide | 464.1 |
| II-310 | 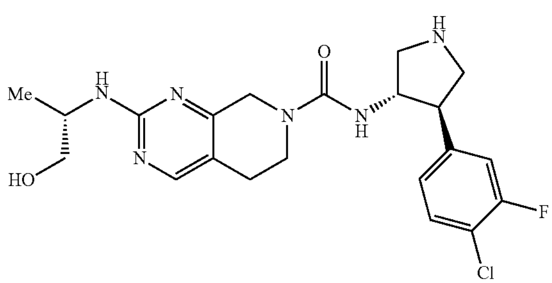 [SMILES: C[C@@H](CO)Nc1ncc2c(n1)CN(C(=O)N[C@@H]1CNC[C@H]1c1ccc(Cl)c(F)c1)CC2] | 2-((S)-2-Hydroxy-1-methyl-ethylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide | 450.3 |
| II-311 | 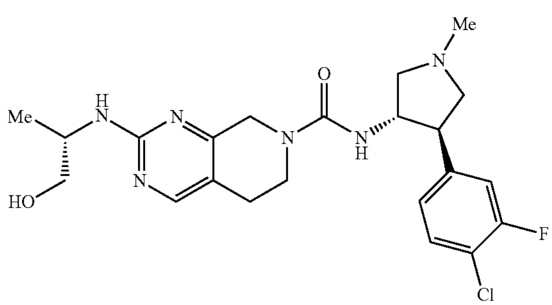 [SMILES: C[C@@H](CO)Nc1ncc2c(n1)CN(C(=O)N[C@@H]1CN(C)C[C@H]1c1ccc(Cl)c(F)c1)CC2] | 2-((S)-2-Hydroxy-1-methyl-ethylamino)-5,8-dihydro-6H-pyrido[3,4-d]pyrimidine-7-carboxylic acid [(3S,4R)-4-(4-chloro-3-fluoro-phenyl)-1-methyl-pyrrolidin-3-yl]-amide | 463.1 |

TABLE II-continued

| | Structure | Name | MS |
|---|---|---|---|
| II-312 | 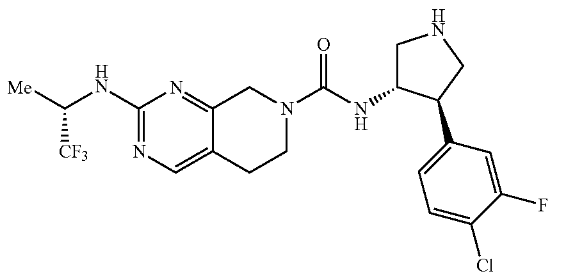 [SMILES: C[C@H](Nc1ncc2c(n1)CN(C(=O)N[C@@H]1CNC[C@H]1c1ccc(Cl)c(F)c1)CC2)C(F)(F)F] | 2-((S)-2,2,2-Trifluoro-1-methyl-ethylamino)-5,8-dihydro-6H-pyrido[3,4-d]pyrimidine-7-carboxylic acid [(3S,4R)-4-(4-chloro-3-fluoro-phenyl)-pyrrolidin-3-yl]amide | 486.9 |
| II-313 | 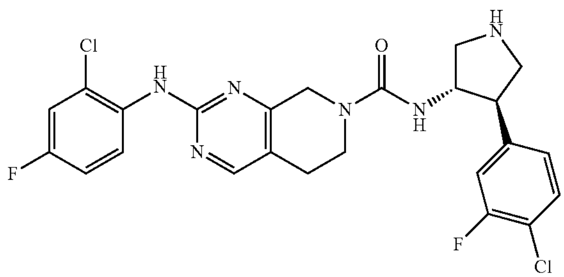 [SMILES: O=C(N[C@@H]1CNC[C@H]1c1ccc(Cl)c(F)c1)N1CCc2cnc(Nc3ccc(F)cc3Cl)nc2C1] | 2-(2-Chloro-4-fluoro-phenylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide | N/A |
| II-314 | 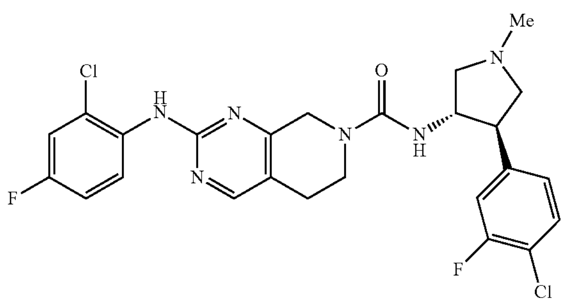 [SMILES: CN1C[C@@H](NC(=O)N2CCc3cnc(Nc4ccc(F)cc4Cl)nc3C2)[C@H](c2ccc(Cl)c(F)c2)C1] | 2-(2-Chloro-4-fluoro-phenylamino)-5,8-dihydro-6H-pyrido[3,4-d]pyrimidine-7-carboxylic acid [(3S,4R)-4-(4-chloro-3-fluoro-phenyl)-1-methyl-pyrrolidin-3-yl]-amide | N/A |
| II-315 | 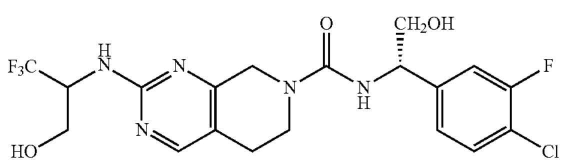 [SMILES: O=C(N[C@H](CO)c1ccc(Cl)c(F)c1)N1CCc2cnc(NC(CO)C(F)(F)F)nc2C1] | 2-(2,2,2-Trifluoro-1-hydroxymethyl-ethylamino)-5,8-dihydro-6H-pyrido[3,4-d]pyrimidine-7-carboxylic acid [1-(4-chloro-3-fluoro-phenyl)-2-hydroxy-ethyl]-amide | 478.0 |
| II-316 | 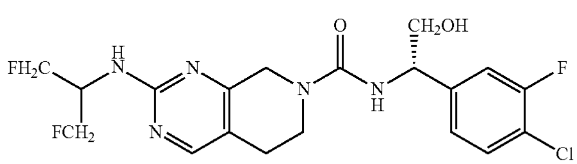 | 2-(2-Fluoro-1-fluoromethyl-ethylamino)-5,8-dihydro-6H-pyrido[3,4-d]pyrimidine-7-carboxylic acid [(S)-1-(4-chloro-3-fluoro-phenyl)-2-hydroxy-ethyl]-amide | N/A |
| II-317 | 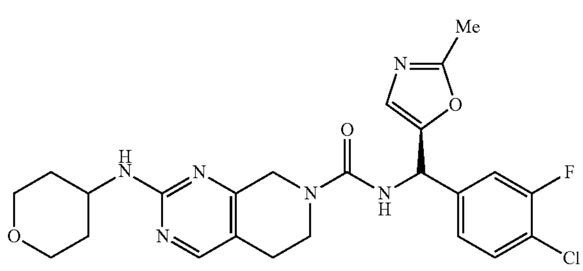 | 2-(Tetrahydro-pyran-4-ylamino)-5,8-dihydro-6H-pyrido[3,4-d]pyrimidine-7-carboxylic acid [(S)-(4-chloro-3-fluoro-phenyl)-(2-methyl-oxazol-5-yl)-methyl]-amide | 501.1 |

TABLE II-continued

| | Structure | Name | MS |
|---|---|---|---|
| II-318 | 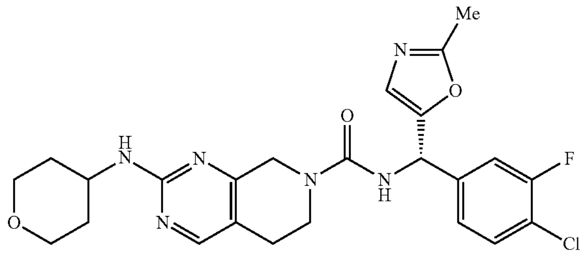 | 2-(Tetrahydro-pyran-4-ylamino)-5,8-dihydro-6H-pyrido[3,4-d]pyrimidine-7-carboxylic acid [(R)-(4-chloro-3-fluoro-phenyl)-(2-methyl-oxazol-5-yl)-methyl]-amide | 501.2 |
| II-319 | 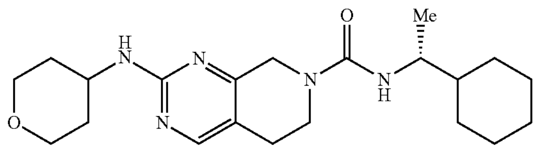 [SMILES: C[C@@H](NC(=O)N1CCc2cnc(NC3CCOCC3)nc2C1)C1CCCCC1] | 2-(Tetrahydro-pyran-4-ylamino)-5,8-dihydro-6H-pyrido[3,4-d]pyrimidme-7-carboxylic acid ((R)-1-cyclohexyl-ethyl)-amide | 388.2 |
| II-320 | 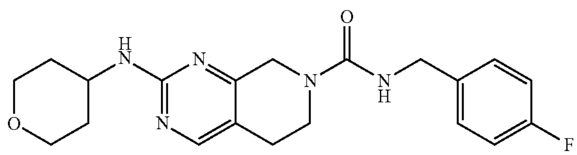 [SMILES: O=C(NCc1ccc(F)cc1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid 4-fluoro-benzylamide | 386.1 |
| II-321 | 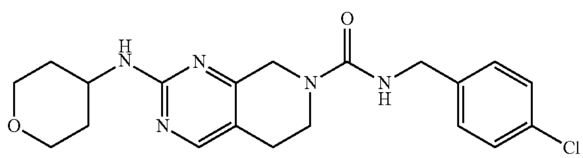 [SMILES: O=C(NCc1ccc(Cl)cc1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid 4-chloro-benzylamide | 402.1 |
| II-322 | 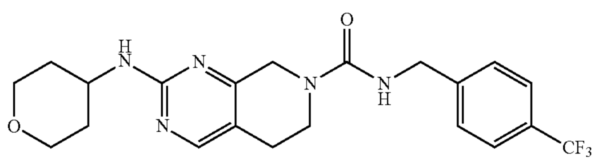 [SMILES: O=C(NCc1ccc(C(F)(F)F)cc1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid 4-trifluoromethyl-benzylamide | 436.1 |
| II-323 | 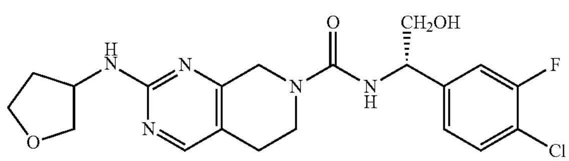 [SMILES: O=C(N[C@H](CO)c1ccc(Cl)c(F)c1)N1CCc2cnc(NC3CCOC3)nc2C1] | 2-(Tetrahydro-furan-3-ylamino)-5,8-dihydro-6H-pyrido[3,4-d]pyrimidine-7-carboxylic acid [1-(4-chloro-3-fluoro-phenyl)-2-hydroxy-ethyl]-amide | 458.1 |
| II-324 | 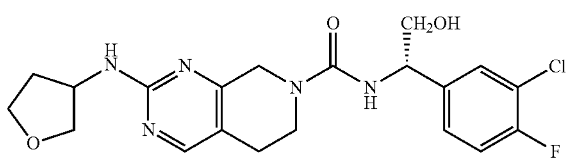 [SMILES: O=C(N[C@H](CO)c1ccc(F)c(Cl)c1)N1CCc2cnc(NC3CCOC3)nc2C1] | 2-(Tetrahydro-furan-3-ylamino)-5,8-dihydro-6H-pyrido[3,4-d]pyrimidine-7-carboxylic acid [1-(3-chloro-4-fluoro-phenyl)-2-hydroxy-ethyl]-amide | 436.2 |
| II-325 | 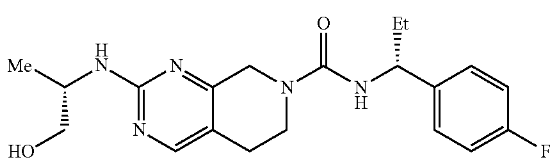 [SMILES: CC[C@@H](NC(=O)N1CCc2cnc(N[C@@H](C)CO)nc2C1)c1ccc(F)cc1] | 2-((S)-2-Hydroxy-1-methyl-ethylamino)-5,8-dihydro-6H-pyrido[3,4-d]pyrimidine-7-carboxylic acid [(R)-1-(4-fluoro-phenyl)-propyl]-amide | 388.2 |
| II-326 | 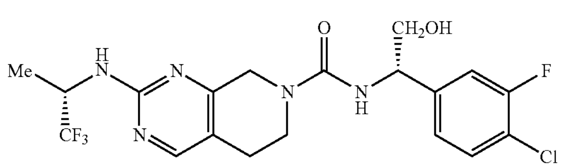 [SMILES: C[C@H](Nc1ncc2c(n1)CN(C(=O)N[C@H](CO)c1ccc(Cl)c(F)c1)CC2)C(F)(F)F] | 2-((S)-2,2,2-Trifluoro-1-methyl-ethylamino)-5,8-dihydro-6H-pyrido[3,4-d]pyrimidine-7-carboxylic acid [(S)-1-(4-chloro-3-fluoro-phenyl)-2-hydroxy-ethyl]-amide | 162.1 |

TABLE II-continued

| | Structure | Name | MS |
|---|---|---|---|
| II-327 | 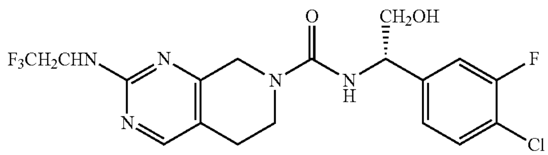 | 2-(2,2,2-Trifluoro-ethylamino)-5,8-dihydro-6H-pyrido[3,4-d]pyrimidine-7-carboxylic acid [(S)-1-(4-chloro-3-fluoro-phenyl)-2-hydroxy-ethyl]-amide | 448.2 |
| II-328 | 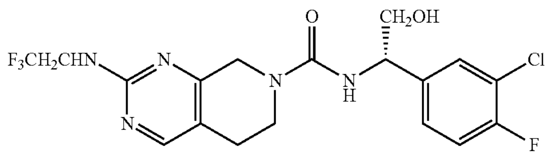 | 2-(2,2,2-Trifluoro-ethylamino)-5,8-dihydro-6H-pyrido[3,4-d]pyrimidine-7-carboxylic acid [(S)-1-(3-chloro-4-fluoro-phenyl)-2-hydroxy-ethyl]-amide | 448.1 |
| II-329 | 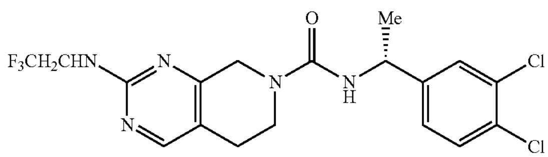 | 2-(2,2,2-Trifluoro-ethylamino)-5,8-dihydro-6H-pyrido[3,4-d]pyrimidine-7-carboxylic acid [(R)-1-(3,4-dichloro-phenyl)-ethyl]-amide | 449.0 |
| II-330 | 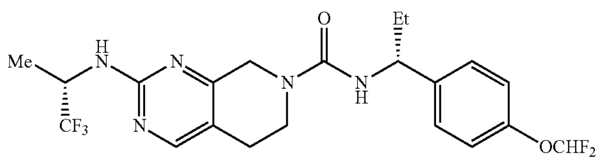 [SMILES: CC[C@@H](NC(=O)N1CCc2cnc(N[C@@H](C)C(F)(F)F)nc2C1)c1ccc(OC(F)F)cc1] | 2-((S)-2,2,2-Trifluoro-1-methyl-ethylamino)-5,8-dihydro-6H-pyrido[3,4-d]pyrimidine-7-carboxylic acid [(R)-1-(4-difluoromethoxy-phenyl)-propyl]-amide | 474.1 |
| II-331 | 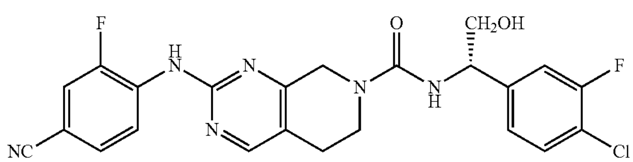 [SMILES: N#Cc1ccc(Nc2ncc3c(n2)CN(C(=O)N[C@H](CO)c2ccc(Cl)c(F)c2)CC3)c(F)c1] | 2-(4-Cyano-2-fluoro-phenylamino)-5,8-dihydro-6H-pyrido[3,4-d]pyrimidine-7-carboxylic acid [(S)-1-(4-chloro-3-fluoro-phenyl)-2-hydroxy-ethyl]-amide | No MS |
| II-332 | 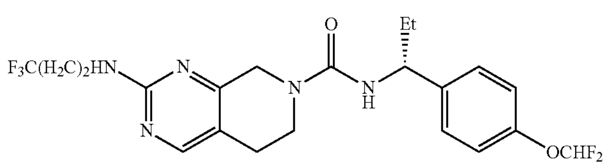 | 2-(3,3,3-Trifluoro-propylamino)-5,8-dihydro-6H-pyrido[3,4-d]pyrimidine-7-carboxylic acid [(R)-1-(4-difluoromethoxy-phenyl)-propyl]-amide | 474.2 |
| II-333 | 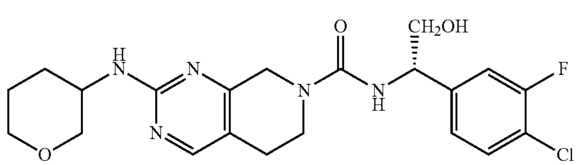 [SMILES: O=C(N[C@H](CO)c1ccc(Cl)c(F)c1)N1CCc2cnc(NC3CCCOC3)nc2C1] | 2-(Tetrahydro-pyran-3-ylamino)-5,8-dihydro-6H-pyrido[3,4-d]pyrimidine-7-carboxylic acid [1-(4-chloro-3-fluoro-phenyl)-2-hydroxy-ethyl]-amide | 450.2 |
| II-334 | 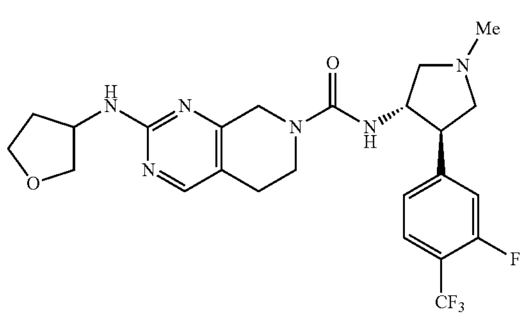 [SMILES: CN1C[C@@H](NC(=O)N2CCc3cnc(NC4CCOC4)nc3C2)[C@H](c2ccc(C(F)(F)F)c(F)c2)C1] | 2-(Tetrahydro-furan-3-ylamino)-5,8-dihydro-6H-pyrido[3,4-d]pyrimidine-7-carboxylic acid [4-(3-fluoro-4-trifluoromethyl-phenyl)-1-methyl-pyrrolidin-3-yl]-amide | 509.3 |
| II-335 | 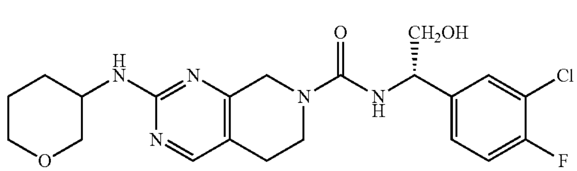 [SMILES: O=C(N[C@H](CO)c1ccc(F)c(Cl)c1)N1CCc2cnc(NC3CCCOC3)nc2C1] | 2-(Tetrahydro-pyran-3-ylamino)-5,8-dihydro-6H-pyrido[3,4-d]pyrimidine-7-carboxylic acid [1-(3-chloro-4-fluoro-phenyl)-2-hydroxy-ethyl]-amide | 451.1 |

TABLE II-continued

| | Name | MS |
|---|---|---|
| II-336 | 2-((S)-2,2,2-Trifluoro-1-methyl-ethylamino)-5,8-dihydro-6H-pyrido[3,4-d]pyrimidine-7-carboxylic acid (2-phenoxy-ethyl)-amide | 410.1 |
| II-337 | 2-(Tetrahydro-pyran-4-ylamino)-5,8-dihydro-6H-pyrido[3,4-d]pyrimidine-7-carboxylic acid [(4-chloro-3-fluoro-phenyl)-(3-methyl-[1,2,4]oxadiazol-5-yl)-methyl]-amide | 502.2 |
| II-338 | 2-(Tetrahydro-pyran-4-ylamino)-5,8-dihydro-6H-pyrido[3,4-d]pyrimidine-7-carboxylic acid [(4-chloro-3-fluoro-phenyl)-(5-methyl-[1,3,4]oxadiazol-2-yl)-methyl]-amide | 502.0 |
| II-339 | 2-(4,4-Difluoro-cyclohexylamino)-5,8-dihydro-6H-pyrido[3,4-d]pyrimidine-7-carboxylic acid [(S)-1-(4-chloro-3-fluoro-phenyl)-2-hydroxy-ethyl]-amide | 484.2 |
| II-340 | 2-(4,4-Difluoro-cyclohexylamino)-5,8-dihydro-6H-pyrido[3,4-d]pyrimidine-7-carboxylic acid [(S)-1-(3-chloro-4-fluoro-phenyl)-2-hydroxy-ethyl]-amide | 484.2 |
| II-341 | 2-(Tetrahydro-pyran-4-ylamino)-5,8-dihydro-6H-pyrido[3,4-d]pyrimidine-7-carboxylic acid [(3S,4R)-1-cyanomethyl-4-(3,4-difluoro-phenyl)-pyrrolidin-3-yl]-amide | 498.1 |
| II-342 | 2-((S)-2-Hydroxy-1-methyl-ethylamino)-5,8-dihydro-6H-pyrido[3,4-d]pyrimidine-7-carboxylic acid [(R)-1-(3,4-difluoro-phenyl)-propyl]-amide | 406.2 |

TABLE II-continued

| | Structure | Name | MS |
|---|---|---|---|
| II-343 | 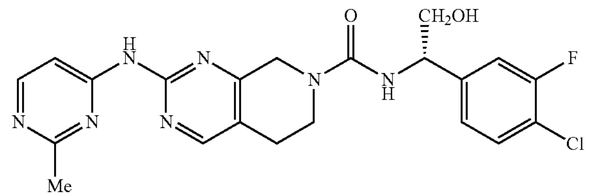 [SMILES: Cc1nccc(Nc2ncc3c(n2)CN(C(=O)N[C@H](CO)c2ccc(Cl)c(F)c2)CC3)n1] | 2-(2-Methyl-pyrimidin-4-ylamino)-5,8-dihydro-6H-pyrido[3,4-d]pyrimidine-7-carboxylic acid [(S)-1-(4-chloro-3-fluoro-phenyl)-2-hydroxy-ethyl]-amide | 458.2 |
| II-344 | 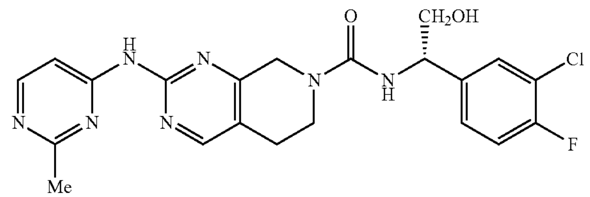 [SMILES: Cc1nccc(Nc2ncc3c(n2)CN(C(=O)N[C@H](CO)c2ccc(F)c(Cl)c2)CC3)n1] | 2-(2-Methyl-pyrimidin-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide | 458.2 |
| II-345 | 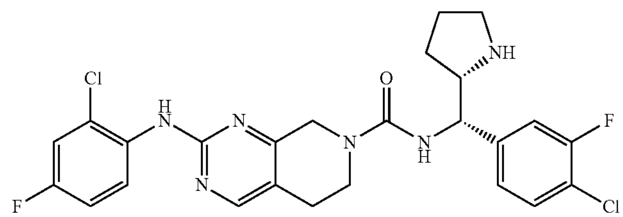 [SMILES: O=C(N[C@@H](c1ccc(Cl)c(F)c1)[C@@H]1CCCN1)N1CCc2cnc(Nc3ccc(F)cc3Cl)nc2C1] | 2-(2-Chloro-4-fluoro-phenylamino)-5,8-dihydro-6H-pyrido[3,4-d]pyrimidine-7-carboxylic acid [(S)-(4-chloro-3-fluoro-phenyl)-(S)-pyrrolidin-2-yl-methyl]-amide | 533.0 |
| II-346 | 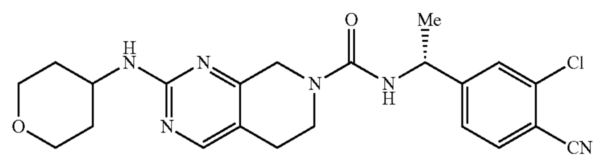 [SMILES: C[C@@H](NC(=O)N1CCc2cnc(NC3CCOCC3)nc2C1)c1ccc(C#N)c(Cl)c1] | 2-(Tetrahydro-pyran-4-ylamino)-5,8-dihydro-6H-pyrido[3,4-d]pyrimidine-7-carboxylic acid [(R)-1-(3-chloro-4-cyano-phenyl)-ethyl]-amide | 441.1 |
| II-347 | 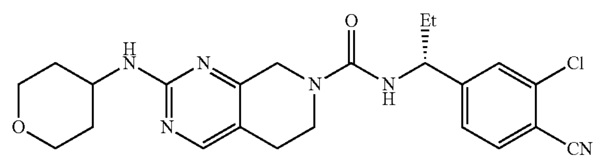 [SMILES: CC[C@@H](NC(=O)N1CCc2cnc(NC3CCOCC3)nc2C1)c1ccc(C#N)c(Cl)c1] | 2-(Tetrahydro-pyran-4-ylamino)-5,8-dihydro-6H-pyrido[3,4-d]pyrimidine-7-carboxylic acid [(R)-1-(3-chloro-4-cyano-phenyl)-propyl]-amide | 455.1 |
| II-348 | 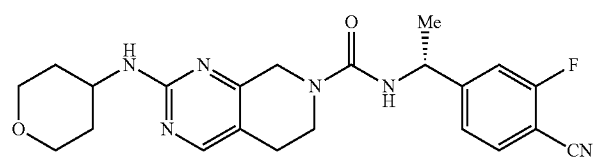 [SMILES: CC[C@@H](NC(=O)N1CCc2cnc(NC3CCOCC3)nc2C1)c1ccc(C#N)c(F)c1] | 2-(Tetrahydro-pyran-4-ylamino)-5,8-dihydro-6H-pyrido[3,4-d]pyrimidine-7-carboxylic acid [(R)-1-(4-cyano-3-fluoro-phenyl)-ethyl]-amide | 425.2 |
| II-349 | 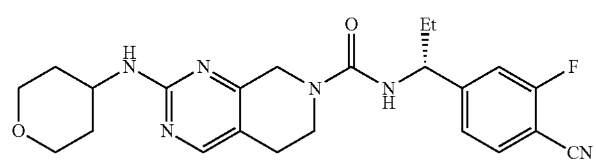 | 2-(Tetrahydro-pyran-4-ylamino)-5,8-dihydro-6H-pyrido[3,4-d]pyrimidine-7-carboxylic acid [(R)-1-(4-cyano-3-fluoro-phenyl)-propyl]-amide | 439.2 |
| II-350 | 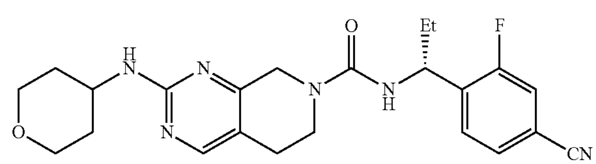 [SMILES: CC[C@@H](NC(=O)N1CCc2cnc(NC3CCOCC3)nc2C1)c1ccc(C#N)cc1F] | 2-(Tetrahydro-pyran-4-ylamino)-5,8-dihydro-6H-pyrido[3,4-d]pyrimidine-7-carboxylic acid [(R)-1-(4-cyano-2-fluoro-phenyl)-propyl]-amide | 439.2 |
| II-351 | 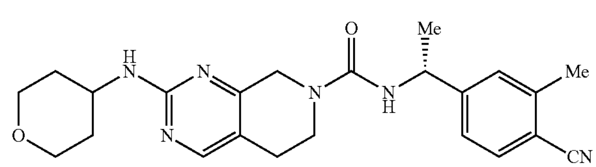 [SMILES: Cc1cc([C@@H](C)NC(=O)N2CCc3cnc(NC4CCOCC4)nc3C2)ccc1C#N] | 2-(Tetrahydro-pyran-4-ylamino)-5,8-dihydro-6H-pyrido[3,4-d]pyrimidine-7-carboxylic acid [(R)-1-(4-cyano-3-methyl-phenyl)-ethyl]-amide | 421.2 |

| | Name | MS |
|---|---|---|
| II-352 | 2-(Tetrahydro-pyran-4-ylamino)-5,8-dihydro-6H-pyrido[3,4-d]pyrimidine-7-carboxylic acid [(R)-1-(4-cyano-3-methyl-phenyl)-propyl]-amide | 435.2 |
| II-353 | 2-((S)-2-Hydroxy-1-methyl-ethylamino)-5,8-dihydro-6H-pyrido[3,4-d]pyrimidine-7-carboxylic acid [(R)-1-(3-chloro-4-cyano-phenyl)-propyl]-amide | 429.1 |
| II-354 | 2-((S)-2-Hydroxy-1-methyl-ethylamino)-5,8-dihydro-6H-pyrido[3,4-d]pyrimidine-7-carboxylic acid [(R)-1-(4-cyano-3-fluoro-phenyl)-propyl]-amide | 413.2 |
| II-355 | 2-(3,3-Difluoro-cyclobutylamino)-5,8-dihydro-6H-pyrido[3,4-d]pyrimidine-7-carboxylic acid [(R)-1-(3,4-dichloro-phenyl)-ethyl]-amide | 456.1 |
| II-356 | 2-Isopropylamino-5,8-dihydro-6H-pyrido[3,4-d]pyrimidine-7-carboxylic acid [4-(3,4-dichloro-phenyl)-1-methyl-piperidin-4-yl]-amide | N/A |
| II-357 | 2-((S)-2-Hydroxy-1-methyl-ethylamino)-5,8-dihydro-6H-pyrido[3,4-d]pyrimidine-7-carboxylic acid [(R)-1-(3-chloro-4-methoxy-phenyl)-propyl]-amide | 434.0 |
| II-358 | 2-((S)-2-Hydroxy-1-methyl-ethylamino)-5,8-dihydro-6H-pyrido[3,4-d]pyrimidine-7-carboxylic acid [(R)-1-(3-fluoro-4-methoxy-phenyl)-propyl]-amide | 418.2 |
| II-359 | 2-(Tetrahydro-pyran-4-ylamino)-5,8-dihydro-6H-pyrido[3,4-d]pyrimidine-7-carboxylic acid [(R)-(4-chloro-3-fluoro-phenyl)-[1,3,4]oxadiazol-2-yl-methyl]-amide | 488.1 |

TABLE II-continued

| | Structure | Name | MS |
|---|---|---|---|
| II-360 | 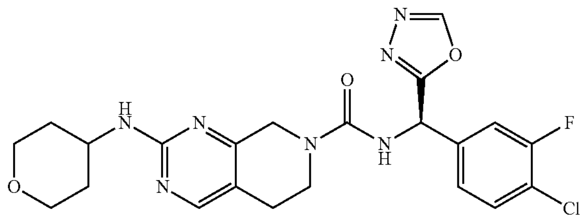 [SMILES: O=C(N[C@H](c1ccc(Cl)c(F)c1)c1nnco1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [(S)-(4-chloro-3-fluoro-phenyl)-[1,3,4]oxadiazol-2-yl-methyl]-amide | 488.1 |
| II-361 | 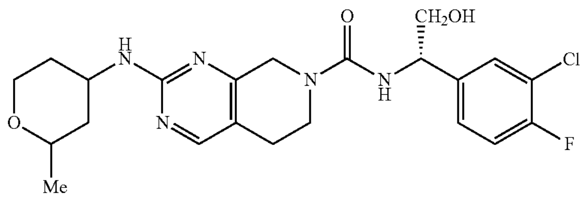 [SMILES: CC1CC(Nc2ncc3c(n2)CN(C(=O)N[C@H](CO)c2ccc(F)c(Cl)c2)CC3)CCO1] | 2-(2-Methyl-tetrahydro-pyran-4-ylamino)-5,8-dihydro-6H-pyrido[3,4-d]pyrimidine-7-carboxylic acid [1-(3-chloro-4-fluoro-phenyl)-2-hydroxy-ethyl]-amide | 464.1 |
| II-362 | 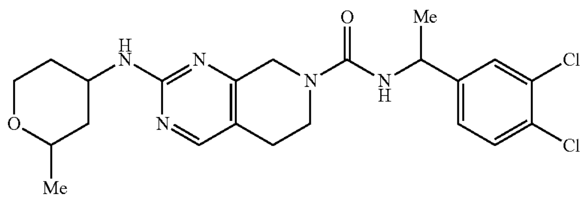 [SMILES: CC1CC(Nc2ncc3c(n2)CN(C(=O)NC(C)c2ccc(Cl)c(Cl)c2)CC3)CCO1] | 2-(2-Methyl-tetrahydro-pyran-4-ylamino)-5,8-dihydro-6H-pyrido[3,4-d]pyrimidine-7-carboxylic acid [1-(3,4-dichloro-phenyl)-ethyl]-amide | 464.2 |
| II-363 | 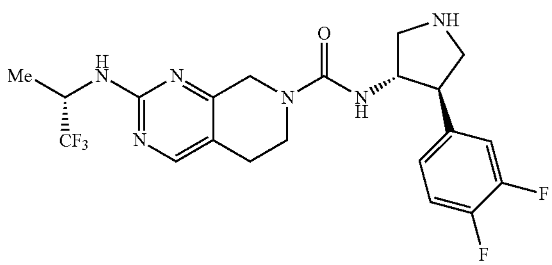 [SMILES: C[C@H](Nc1ncc2c(n1)CN(C(=O)N[C@@H]1CNC[C@H]1c1ccc(F)c(F)c1)CC2)C(F)(F)F] | 2-((S)-2,2,2-Trifluoro-1-methyl-ethylamino)-5,8-dihydro-6H-pyrido[3,4-d]pyrimidine-7-carboxylic acid [(3S,4R)-4-(3,4-difluoro-phenyl)-pyrrolidin-3-yl]-amide | 471.1 |
| II-364 | 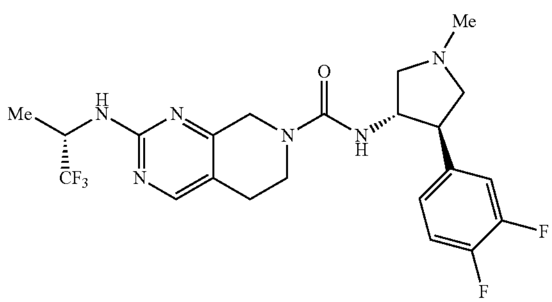 [SMILES: C[C@H](Nc1ncc2c(n1)CN(C(=O)N[C@@H]1CN(C)C[C@H]1c1ccc(F)c(F)c1)CC2)C(F)(F)F] | 2-((S)-2,2,2-Trifluoro-1-methyl-ethylamino)-5,8-dihydro-6H-pyrido[3,4-d]pyrimidine-7-carboxylic acid [(3S,4R)-4-(3,4-difluoro-phenyl)-1-methyl-pyrrolidin-3-yl]-amide | 485.3 |
| II-365 | 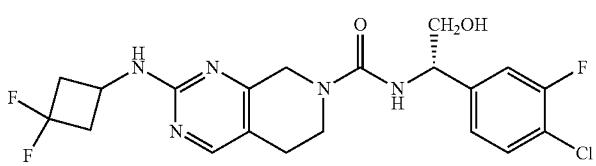 [SMILES: O=C(N[C@H](CO)c1ccc(Cl)c(F)c1)N1CCc2cnc(NC3CC(F)(F)C3)nc2C1] | 2-(3,3-Difluoro-1-cyclobutylamino)-5,8-dihydro-6H-pyrido[3,4-d]pyrimidine-7-carboxylic acid [(S)-1-(4-chloro-3-fluoro-phenyl)-2-hydroxy-ethyl]-amide | 456.2 |
| II-366 | 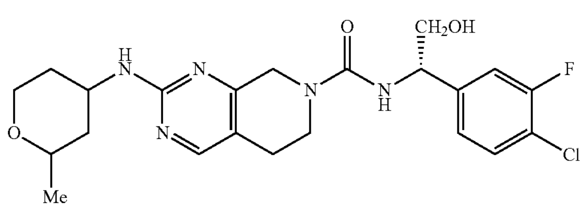 | 2-(2-Methyl-tetrahydro-pyran-4-ylamino)-5,8-dihydro-6H-pyrido[3,4-d]pyrimidine-7-carboxylic acid [1-(3,4-dichloro-fluoro-phenyl)-2-hydroxy-ethyl]-amide | 464.2 |

TABLE II-continued

| | Structure | Name | MS |
|---|---|---|---|
| II-367 | 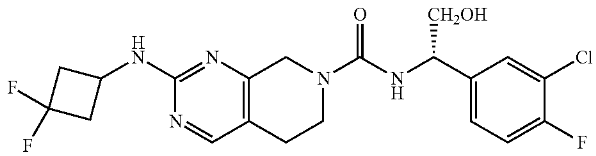 [SMILES: O=C(N[C@H](CO)c1ccc(F)c(Cl)c1)N1CCc2cnc(NC3CC(F)(F)C3)nc2C1] | 2-(3,3-Difluoro-cyclobutylamino)-5,8-dihydro-6H-pyrido[3,4-d]pyrimidine-7-carboxylic acid [1-(4-chloro-3-fluoro-phenyl)-2-hydroxy-ethyl]-amide | 456.2 |
| II-368 | 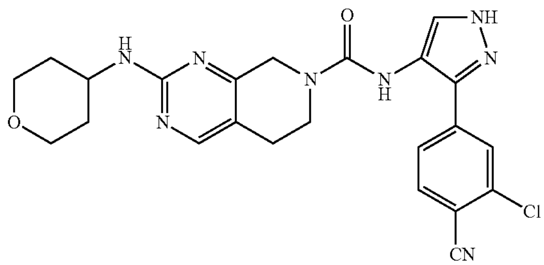 [SMILES: N#Cc1ccc(-c2n[nH]cc2NC(=O)N2CCc3cnc(NC4CCOCC4)nc3C2)cc1Cl] | 2-(Tetrahydro-pyran-4-ylamino)-5,8-dihydro-6H-pyrido[3,4-d]pyrimidine-7-carboxylic acid [3-(3-chloro-4-cyano-phenyl)-1H-pyrazol-4-yl]-amide | 479.1 |
| II-369 | 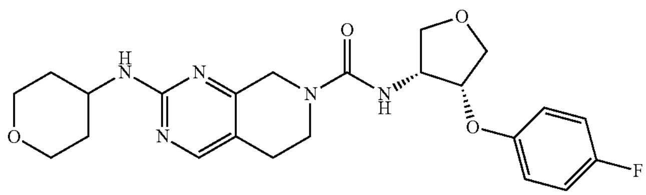 [SMILES: O=C(N[C@@H]1COC[C@@H]1Oc1ccc(F)cc1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [4-(4-fluoro-phenoxy)-tetrahydro-furan-3-yl]-amide | 458.4 |
| II-370 | 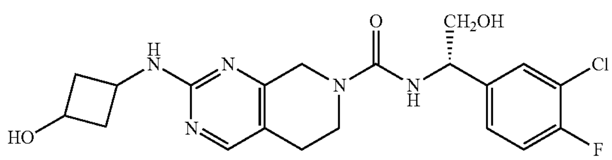 [SMILES: O=C(N[C@H](CO)c1ccc(F)c(Cl)c1)N1CCc2cnc(NC3CC(O)C3)nc2C1] | 2-(3-Hydroxy-cyclobutylamino)-5,8-dihydro-6H-pyrido[3,4-d]pyrimidine-7-carboxylic acid [1-(3-chloro-4-fluoro-phenyl)-2-hydroxy-ethyl]-amide | 436.1 |
| II-371 | 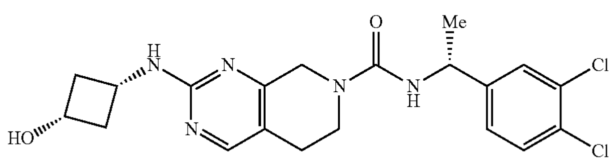 [SMILES: C[C@@H](NC(=O)N1CCc2cnc(N[C@H]3C[C@@H](O)C3)nc2C1)c1ccc(Cl)c(Cl)c1] | 2-((1S,3S)-3-Hydroxy-cyclobutylamino)-5,8-dihydro-6H-pyrido[3,4-d]pyrimidine-7-carboxylic acid [(R)-1-(3,4-dichloro-phenyl)-ethyl]amide | 436.1 |
| II-372 | 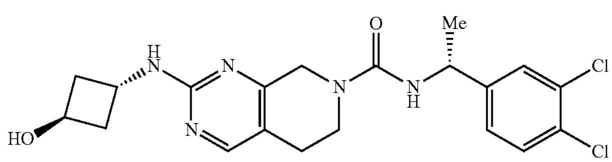 [SMILES: C[C@@H](NC(=O)N1CCc2cnc(N[C@H]3C[C@H](O)C3)nc2C1)c1ccc(Cl)c(Cl)c1] | 2-((1R,3R)-3-Hydroxy-cyclobutylamino)-5,8-dihydro-6H-pyrido[3,4-d]pyrimidine-7-carboxylic acid [(R)-1-(3,4-dichloro-phenyl)-ethyl]-amide | 436.1 |
| II-373 | 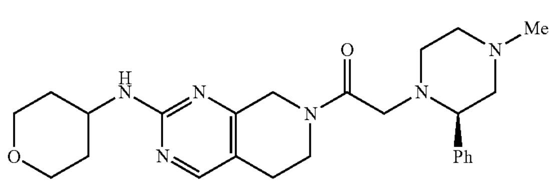 [SMILES: CN1CCN(CC(=O)N2CCc3cnc(NC4CCOCC4)nc3C2)[C@H](c2ccccc2)C1] | 2-(4-Methyl-2-phenyl-piperazin-1-yl)-1-[2-(tetrahydro-pyran-4-ylamino)-5,8-dihydro-6H-pyrido[3,4-d]pyrimidin-7-yl]-ethanone | 451.2 |
| II-374 | 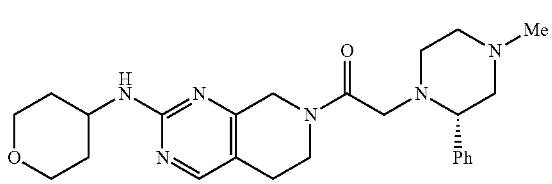 [SMILES: CN1CCN(CC(=O)N2CCc3cnc(NC4CCOCC4)nc3C2)[C@@H](c2ccccc2)C1] | 2-(4-Methyl-2-phenyl-piperazin-1-yl)-1-[2-(tetrahydro-pyran-4-ylamino)-5,8-dihydro-6H-pyrido[3,4-d]pyrimidin-7-yl]-ethanone | 451.2 |

TABLE II-continued

| | Structure | Name | MS |
|---|---|---|---|
| II-375 | 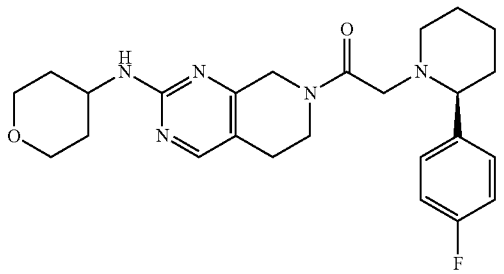 [SMILES: O=C(CN1CCCC[C@H]1c1ccc(F)cc1)N1CCc2cnc(NC3CCOCC3)nc2C1] | 2-[2-(4-Fluoro-phenyl)-piperidin-1-yl]-1-[2-(tetrahydro-pyran-4-ylamino)-5,8-dihydro-6H-pyrido[3,4-d]pyrimidin-7-yl]-ethanone | 454.1 |
| II-376 | 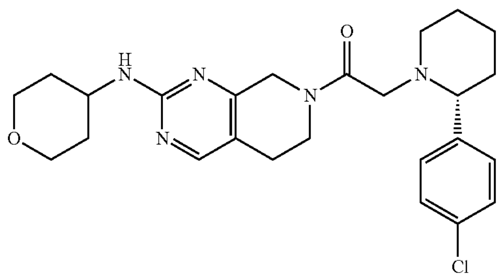 | 2-[2-(4-Chloro-phenyl)-piperazin-1-yl]-1-[2-(tetrahydro-pyran-4-ylamino)-5,8-dihydro-6H-pyrido[3,4-d]pyrimidin-7-yl]-ethanone | 471.1 |
| II-377 | 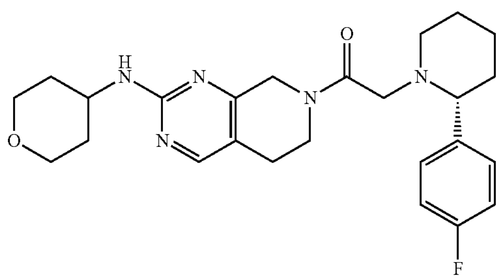 [SMILES: O=C(CN1CCCC[C@@H]1c1ccc(F)cc1)N1CCc2cnc(NC3CCOCC3)nc2C1] | 2-[2-(4-Fluoro-phenyl)-piperidin-1-yl]-1-[2-(tetrahydro-pyran-4-ylamino)-5,8-dihydro-6H-pyrido[3,4-d]pyrimidin-7-yl]-ethanone | 454.0 |
| II-378 | 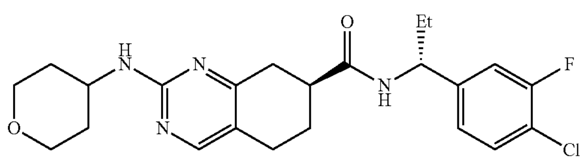 [SMILES: CC[C@@H](NC(=O)[C@H]1CCc2cnc(NC3CCOCC3)nc2C1)c1ccc(Cl)c(F)c1] | (R)-2-(Tetrahydro-pyran-4-ylamino)-6,7-dihydro-5H-pyrano[2,3-d]pyrimidine-7-carboxylic acid [(R)-1-(4-chloro-3-fluoro-phenyl)-propyl]-amide | 449.0 |
| II-379 | 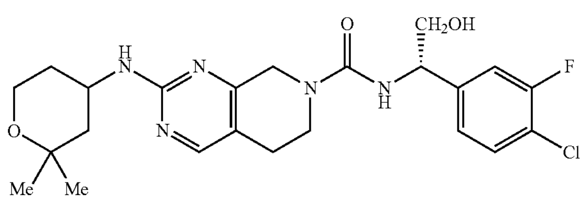 | 2-(2,2-Dimethyl-tetrahydro-pyran-4-ylamino)-5,8-dihydro-6H-pyrido[3,4-d]pyrimidine-7-carboxylic acid [1-(4-chloro-3-fluoro-phenyl)-2-hydroxy-ethyl]-amide | 478.3 |
| II-380 | 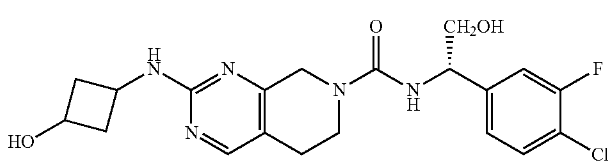 [SMILES: O=C(N[C@H](CO)c1ccc(Cl)c(F)c1)N1CCc2cnc(NC3CC(O)C3)nc2C1] | 2-(3-Hydroxy-cyclobutylamino)-5,8-dihydro-6H-pyrido[3,4-d]pyrimidine-7-carboxylic acid [1-(4-chloro-3-fluoro-phenyl)-2-hydroxy-ethyl]-amide | 436.1 |
| II-381 | 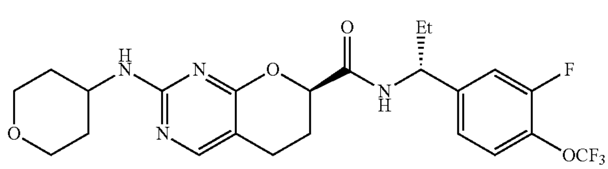 [SMILES: CC[C@@H](NC(=O)[C@H]1CCc2cnc(NC3CCOCC3)nc2O1)c1ccc(OC(F)(F)F)c(F)c1] | (R)-2-(Tetrahydro-pyran-4-ylamino)-6,7-dihydro-5H-pyrano[2,3-d]pyrimidine-7-carboxylic acid [(R)-1-(3-fluoro-4-trifluoromethoxy-phenyl)-propyl]-amide | 499.0 |

TABLE II-continued

| | Structure | Name | MS |
|---|---|---|---|
| II-382 | 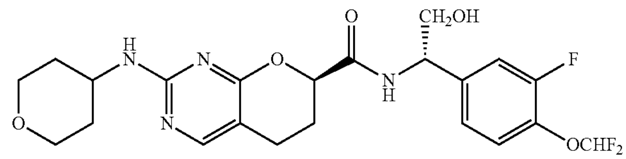 [SMILES: O=C(N[C@H](CO)c1ccc(OC(F)F)c(F)c1)[C@H]1CCc2cnc(NC3CCOCC3)nc2O1] | (R)-2-(Tetrahydro-pyran-4-ylamino)-6,7-dihydro-5H-pyrano[2,3-d]pyrimidine-7-carboxylic acid [(S)-1-(4-difluoromethoxy-phenyl)-2-hydroxy-ethyl]-amide | 465.0 |
| II-383 | 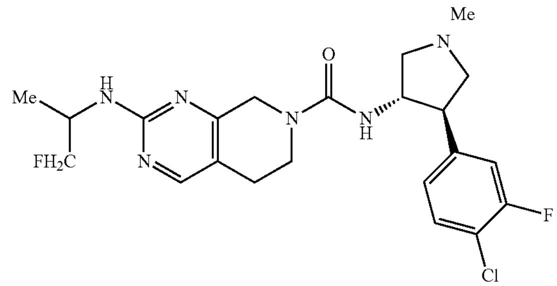 | 2-(2-Fluoro-1-methyl-ethylamino)-5,8-dihydro-6H-pyrido[3,4-d]pyrimidine-7-carboxylic acid [4-(4-chloro-3-fluoro-phenyl)-1-methyl-pyrrolidin-3-yl]-amide | 464.8 |
| II-384 | 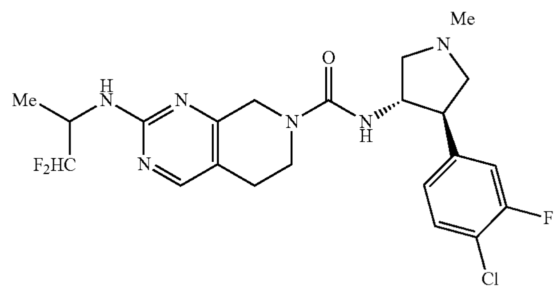 [SMILES: CC(Nc1ncc2c(n1)CN(C(=O)N[C@@H]1CNC[C@H]1c1ccc(Cl)c(F)c1)CC2)C(F)F] | 2-(2,2-Difluoro-1-methyl-ethylamino)-5,8-dihydro-6H-pyrido[3,4-d]pyrimidine-7-carboxylic acid [4-(4-chloro-3-fluoro-phenyl)-1-methyl-pyrrolidin-3-yl]-amide | 482.9 |
| II-385 | 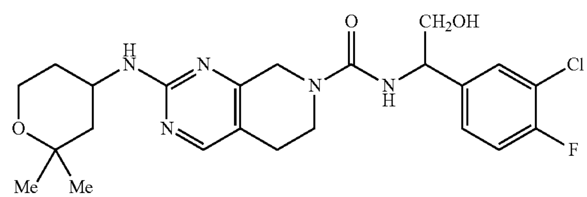 [SMILES: CC1(C)CC(Nc2ncc3c(n2)CN(C(=O)NC(CO)c2ccc(F)c(Cl)c2)CC3)CCO1] | 2-(2,2-Dimethyl-tetrahydro-pyran-4-ylamino)-5,8-dihydro-6H-pyrido[3,4-d]pyrimidine-7-carboxylic acid [1-(3-chloro-4-fluoro-phenyl)-2-hydroxy-ethyl]-amide | 478.3 |
| II-386 | 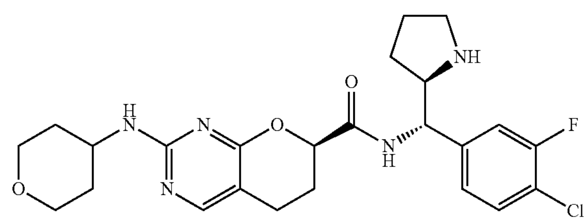 [SMILES: O=C(N[C@@H](c1ccc(Cl)c(F)c1)[C@H]1CCCN1)[C@H]1CCc2cnc(NC3CCOCC3)nc2O1] | (R)-2-(Tetrahydro-pyran-4-ylamino)-6,7-dihydro-5H-pyrano[2,3-d]pyrimidine-7-carboxylic acid [(S)-(4-chloro-3-fluoro-phenyl)-(R)-pyrrolidin-2-yl-methyl]-amide | 490.0 |
| II-387 | 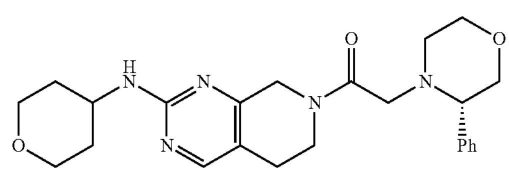 [SMILES: O=C(CN1CCOC[C@@H]1c1ccccc1)N1CCc2cnc(NC3CCOCC3)nc2C1] | 2-((S)-3-Phenyl-morpholin-4-yl)-1-[2-(tetrahydro-pyran-4-ylamino)-5,8-dihydro-6H-pyrido[3,4-d]pyrimidin-7-yl]-ethanone | 438.1 |
| II-388 | 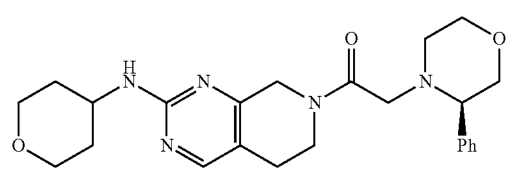 [SMILES: O=C(CN1CCOC[C@H]1c1ccccc1)N1CCc2cnc(NC3CCOCC3)nc2C1] | 2-((R)-3-Phenyl-morpholin-4-yl)-1-[2-(tetrahydro-pyran-4-ylamino)-5,8-dihydro-6H-pyrido[3,4-d]pyrimidin-7-yl]-ethanone | 438.1 |

TABLE II-continued

| | Structure | Name | MS |
|---|---|---|---|
| II-389 | 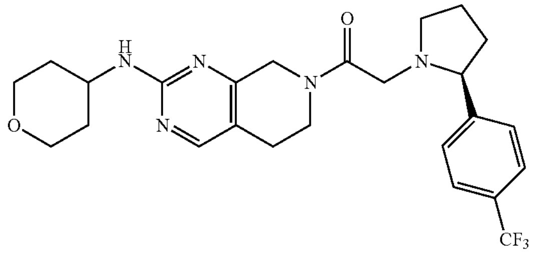 [SMILES: O=C(CN1CCC[C@H]1c1ccc(C(F)(F)F)cc1)N1CCc2cnc(NC3CCOCC3)nc2C1] | 1-[2-(Tetrahydro-pyran-4-ylamino)-5,8-dihydro-6H-pyrido[3,4-d]pyrimidin-7-yl]-2-[2-(4-trifluoromethyl-phenyl)-pyrrolidin-1-yl]-ethanone | 490.1 |
| II-390 | 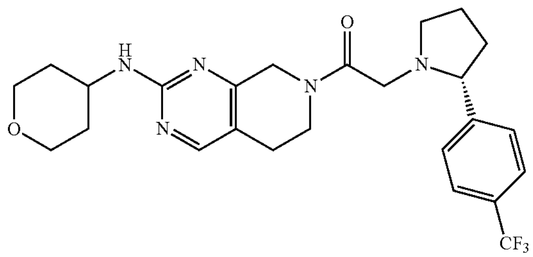 [SMILES: O=C(CN1CCC[C@@H]1c1ccc(C(F)(F)F)cc1)N1CCc2cnc(NC3CCOCC3)nc2C1] | 1-[2-(Tetrahydro-pyran-4-ylamino)-5,8-dihydro-6H-pyrido[3,4-d]pyrimidin-7-yl]-2-[2-(4-trifluoromethyl-phenyl)-pyrrolidin-1-yl]-ethanone | 490.1 |
| II-391 | 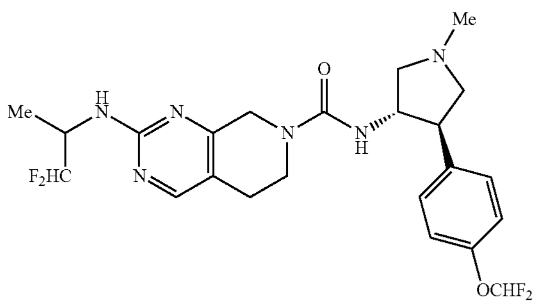 [SMILES: CC(Nc1ncc2c(n1)CN(C(=O)N[C@@H]1CN(C)C[C@H]1c1ccc(OC(F)F)cc1)CC2)C(F)F] | 2-(2,2-Difluoro-1-methyl-ethylamino)-5,8-dihydro-6H-pyrido[3,4-d]pyrimidine-7-carboxylic acid [4-(4-difluoromethoxy-phenyl)-1-methyl-pyrrolidin-3-yl]-amide | 496.9 |
| II-392 | 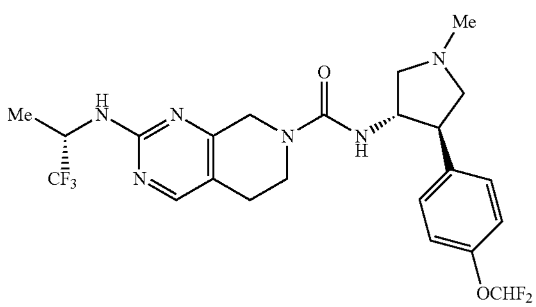 | 2((S)-2,2,2-Trifluoro-1-methyl-ethylamino)-5,8-dihydro-6H-pyrido[3,4-d]pyrimidine-7-carboxylic acid [(3S,4R)-4-(4-difluoromethoxy-phenyl)-1-methyl-pyrrolidin-3-yl]-amide | 515.0 |
| II-393 | 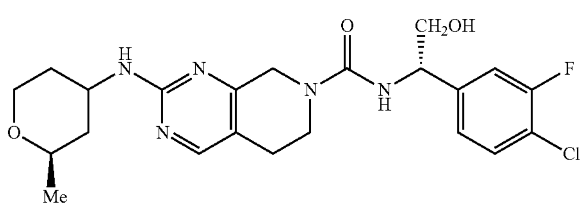 [SMILES: C[C@@H]1CC(Nc2ncc3c(n2)CN(C(=O)N[C@H](CO)c2ccc(Cl)c(F)c2)CC3)CCO1] | 2-(2-Methyl-tetrahydro-pyran-4-ylamino)-5,8-dihydro-6H-pyrido[3,4-d]pyrimidine-7-carboxylic acid [1-(4-chloro-3-fluoro-phenyl)-2-hydroxy-ethyl]-amide | 464.2 |
| II-394 | 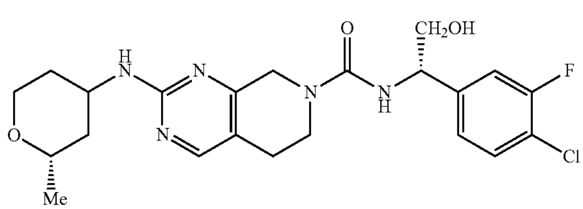 [SMILES: C[C@H]1CC(Nc2ncc3c(n2)CN(C(=O)N[C@H](CO)c2ccc(Cl)c(F)c2)CC3)CCO1] | 2-(2-Methyl-tetrahydro-pyran-4-ylamino)-5,8-dihydro-6H-pyrido[3,4-d]pyrimidine-7-carboxylic acid [1-(4-chloro-3-fluoro-phenyl)-2-hydroxy-ethyl]-amide | 464.2 |

TABLE II-continued

| | Name | MS |
|---|---|---|
| II-395 | 2-(Tetrahydro-pyran-4-ylamino)-5,8-dihydro-6H-pyrido[3,4-d]pyrimidine-7-carboxylic acid [2-(3,4-difluoro-phenyl)-1-methyl-pyrrolidin-3-yl]-amide | 473.2 |
| II-396 | 2-(Tetrahydro-pyran-4-ylamino)-5,8-dihydro-6H-pyrido[3,4-d]pyrimidine-7-carboxylic acid [4-(3-chloro-4-cyano-phenoxy)-1-methyl-pyrrolidin-3-yl]-amide | 512.3 |
| II-397 | 2-((S)-1-Hydroxymethyl-3-methoxy-propylamino)-5,8-dihydro-6H-pyrido[3,4-d]pyrimidine-7-carboxylic acid [(S)-1-(4-chloro-3-fluoro-phenyl)-2-hydroxy-ethyl]-amide | 468.2 |
| II-398 | 2-((S)-1-Hydroxymethyl-3-methoxy-propylamino)-5,8-dihydro-6H-pyrido[3,4-d]pyrimidine-7-carboxylic acid [(S)-1-(3-chloro-4-fluoro-phenyl)-2-hydroxy-ethyl]-amide | 468.0 |
| II-399 | 2-((S)-1-Hydroxymethyl-3-methoxy-propylamino)-5,8-dihydro-6H-pyrido[3,4-d]pyrimidine-7-carboxylic acid [(R)-1-(3,4-dichloro-phenyl)-ethyl]-amide | 468.1 |
| II-400 | (R)-2-((R)-1-Cyclopropyl-ethylamino)-6,7-dihydro-5H-pyrano[2,3-d]pyrimidine-7-carboxylic acid [(S)-1-(4-difluoromethoxy-phenyl)-2-hydroxy-ethyl]-amide | N/A |
| II-401 | (R)-2-((R)-1-Cyclopropyl-ethylamino)-6,7-dihydro-5H-pyrano[2,3-d]pyrimidine-7-carboxylic acid [(R)-3-cyano-1-(4-difluoromethoxy-phenyl)-propyl]-amide | 472.0 |
| II-402 | (S)-2-((R)-1-Cyclopropyl-ethylamino)-6,7-dihydro-5H-pyrano[2,3-d]pyrimidine-7-carboxylic acid [(S)-1-(4-difluoromethoxy-phenyl)-2-hydroxy-ethyl]-amide | 449.0 |

TABLE II-continued

| | Structure | Name | MS |
|---|---|---|---|
| II-403 | 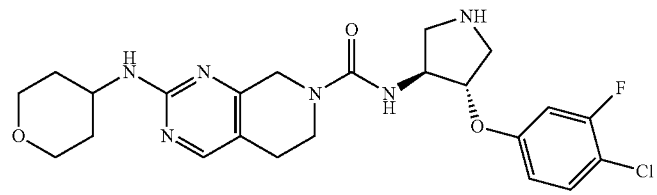 [SMILES: O=C(N[C@H]1CNC[C@@H]1Oc1ccc(Cl)c(F)c1)N1CCc2cnc(NC3CCOCC3)nc2C1] | 2-(Tetrahydro-pyran-4-ylamino)-5,8-dihydro-6H-pyrido[3,4-d]pyrimidine-7-carboxylic acid [4-(4-chloro-3-fluoro-phenoxy)-pyrrolidin-3-yl]-amide | 491.3 |
| II-404 | 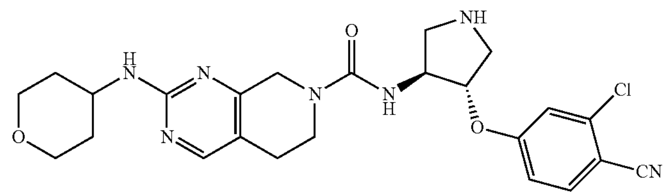 [SMILES: N#Cc1ccc(O[C@H]2CNC[C@@H]2NC(=O)N2CCc3cnc(NC4CCOCC4)nc3C2)cc1Cl] | 2-(Tetrahydro-pyran-4-ylamino)-5,8-dihydro-6H-pyrido[3,4-d]pyrimidine-7-carboxylic acid [4-(3-chloro-4-cyano-phenoxy)-pyrrolidin-3-yl]-amide | 498.2 |
| II-405 | 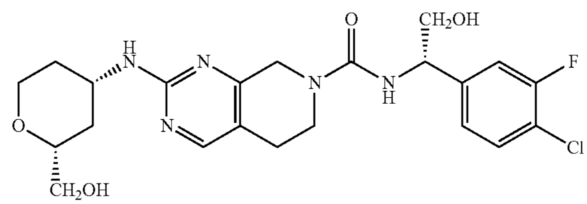 | 2-(2-Hydroxymethyl-tetrahydro-pyran-4-ylamino)-5,8-dihydro-6H-pyrido[3,4-d]pyrimidine-7-carboxylic acid [1-(4-chloro-3-fluoro-phenyl)-2-hydroxy-ethyl]-amide | 480.2 |
| II-406 | 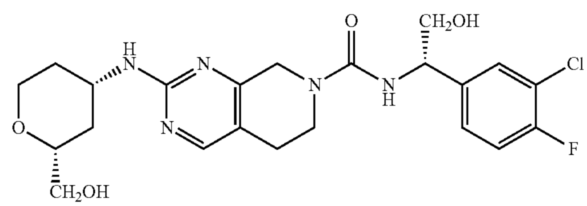 [SMILES: O=C(N[C@H](CO)c1ccc(F)c(Cl)c1)N1CCc2cnc(N[C@H]3CCO[C@@H](CO)C3)nc2C1] | 2-(2-Hydroxymethyl-tetrahydro-pyran-4-ylamino)-5,8-dihydro-6H-pyrido[3,4-d]pyrimidine-7-carboxylic acid [1-(3-chloro-4-fluoro-phenyl)-2-hydroxy-ethyl]-amide | 480.1 |
| II-407 | 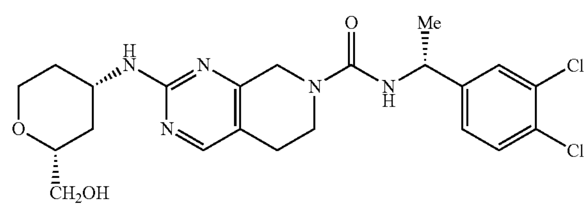 [SMILES: C[C@@H](NC(=O)N1CCc2cnc(N[C@H]3CCO[C@@H](CO)C3)nc2C1)c1ccc(Cl)c(Cl)c1] | 2-(2-Hydroxymethyl-tetrahydro-pyran-4-ylamino)-5,8-dihydro-6H-pyrido[3,4-d]pyrimidine-7-carboxylic acid [1-(3,4-dichloro-phenyl)-ethyl]-amide | 480.0 |
| II-408 | 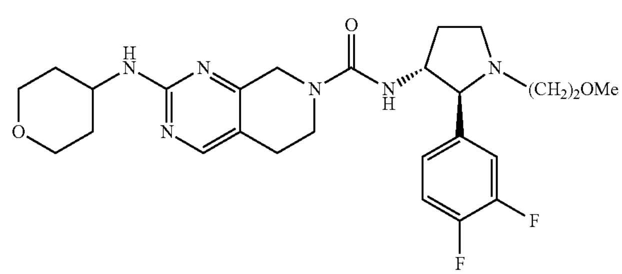 | 2-(Tetrahydro-pyran-4-ylamino)-5,8-dihydro-6H-pyrido[3,4-d]pyrimidine-7-carboxylic acid [2-(3,4-difluoro-phenyl)-1-(2-methoxy-ethyl)-pyrrolidin-3-yl]-amide | 517.3 |
| II-409 | 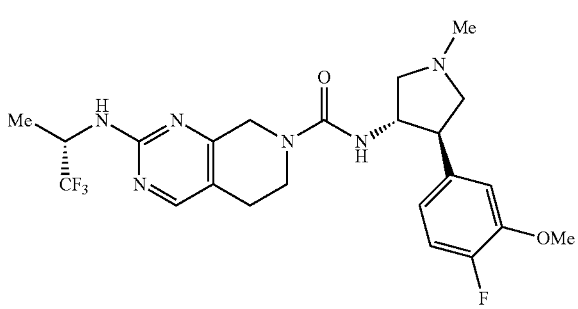 [SMILES: COc1cc([C@@H]2CN(C)C[C@H]2NC(=O)N2CCc3cnc(N[C@@H](C)C(F)(F)F)nc3C2)ccc1F] | 2-((S)-2,2,2-Trifluoro-1-methyl-ethylamino)-5,8-dihydro-6H-pyrido[3,4-d]pyrimidine-7-carboxylic acid [(3S,4R)-4-(4-fluoro-3-methoxy-phenyl)-1-methyl-pyrrolidin-3-yl]-amide | 497.1 |

TABLE II-continued

| | Structure | Name | MS |
|---|---|---|---|
| II-410 | 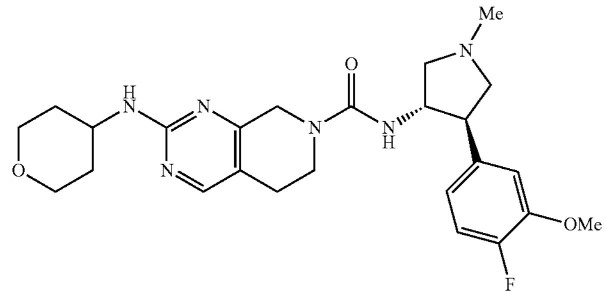 [SMILES: COc1cc([C@@H]2CN(C)C[C@H]2NC(=O)N2CCc3cnc(NC4CCOCC4)nc3C2)ccc1F] | 2-(Tetrahydro-pyran-4-ylamino)-5,8-dihydro-6H-pyrido[3,4-d]pyrimidine-7-carboxylic acid [(3S,4R)-4-(4-fluoro-3-methoxy-phenyl)-1-methyl-pyrrolidin-3-yl]-amide | 485.1 |
| II-411 | 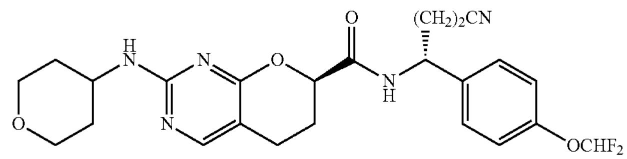 | (R)-2-(Tetrahydro-pyran-4-ylamino)-6,7-dihydro-5H-pyrano[2,3-d]pyrimidine-7-carboxylic acid [(R)-3-cyano-1-(4-difluoromethoxy-phenyl)-propyl]-amide | 488.0 |
| II-412 | 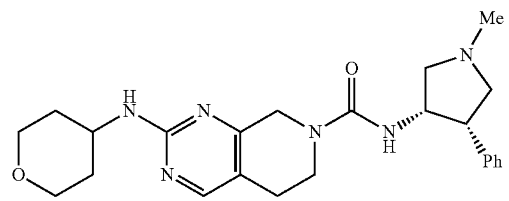 [SMILES: CN1C[C@H](c2ccccc2)[C@H](NC(=O)N2CCc3cnc(NC4CCOCC4)nc3C2)C1] | 2-(Tetrahydro-pyran-4-ylamino)-5,8-dihydro-6H-pyrido[3,4-d]pyrimidine-7-carboxylic acid (1-methyl-4-phenyl-pyrrolidin-3-yl)-amide | 437.3 |
| II-413 | 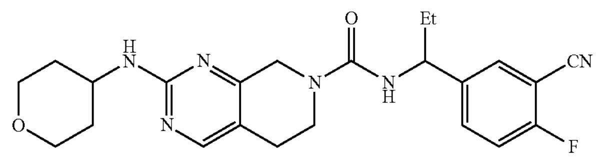 [SMILES: CCC(NC(=O)N1CCc2cnc(NC3CCOCC3)nc2C1)c1ccc(F)c(C#N)c1] | 2-(Tetrahydro-pyran-4-ylamino)-5,8-dihydro-6H-pyrido[3,4-d]pyrimidine-7-carboxylic acid [1-(3-cyano-4-fluoro-phenyl)-propyl]-amide | 439.0 |
| II-414 | 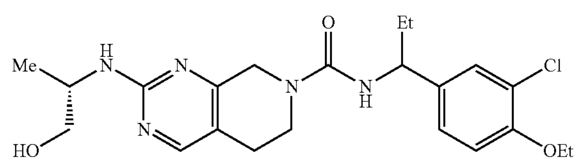 [SMILES: CCOc1ccc(C(CC)NC(=O)N2CCc3cnc(N[C@@H](C)CO)nc3C2)cc1Cl] | 2-(2-Hydroxy-1-methyl-ethylamino)-5,8-dihydro-6H-pyrido[3,4-d]pyrimidine-7-carboxylic acid [1-(3-chloro-4-ethoxy-phenyl)-propyl]-amide | 448.0 |
| II-415 | 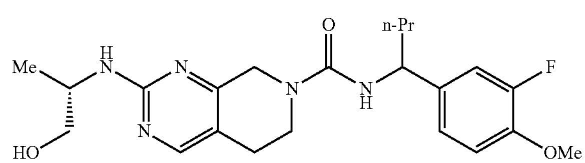 | 2-(2-Hydroxy-1-methyl-ethylamino)-5,8-dihydro-6H-pyrido[3,4-d]pyrimidine-7-carboxylic acid [1-(3-fluoro-4-methoxy-phenyl)-butyl]-amide | 432.2 |
| II-416 | 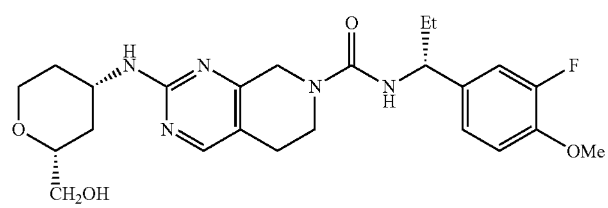 [SMILES: CC[C@@H](NC(=O)N1CCc2cnc(N[C@H]3CCO[C@@H](CO)C3)nc2C1)c1ccc(OC)c(F)c1] | 2-(2-Hydroxymethyl-tetrahydro-pyran-4-ylamino)-5,8-dihydro-6H-pyrido[3,4-d]pyrimidine-7-carboxylic acid [1-(3-fluoro-4-methoxy-phenyl)-propyl]-amide | 474.2 |
| II-417 | 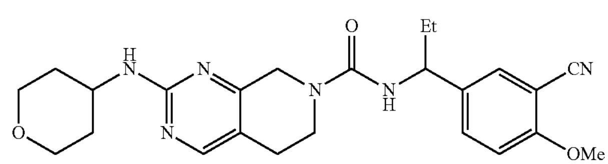 [SMILES: CCC(NC(=O)N1CCc2cnc(NC3CCOCC3)nc2C1)c1ccc(OC)c(C#N)c1] | 2-(Tetrahydro-pyran-4-ylamino)-5,8-dihydro-6H-pyrido[3,4-d]pyrimidine-7-carboxylic acid [1-(3-cyano-4-methoxy-phenyl)-propyl]-amide | 451.0 |

TABLE II-continued

| | Structure | Name | MS |
|---|---|---|---|
| II-418 | 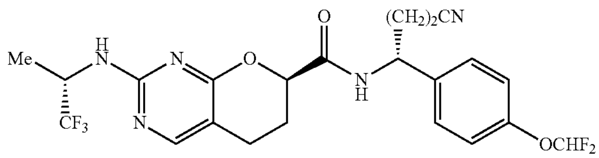 | (R)-2-((S)-2,2,2-Trifluoro-1-methyl-ethylamino)-6,7-dihydro-5H-pyrano[2,3-d]pyrimidine-7-carboxylic acid [(R)-3-cyano-1-(4-difluoromethoxy-phenyl)-propyl]-amide | 500.2 |
| II-419 | 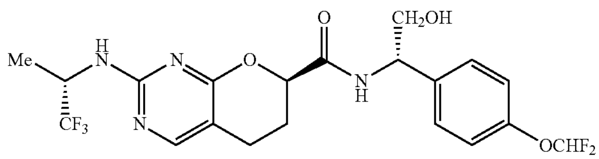 [SMILES: C[C@H](Nc1ncc2c(n1)O[C@@H](C(=O)N[C@H](CO)c1ccc(OC(F)F)cc1)CC2)C(F)(F)F] | (R)-2-((S)-2,2,2-Trifluoro-1-methyl-ethylamino)-6,7-dihydro-5H-pyro[2,3-d]pyrimidine-7-carboxylic acid [(S)-1-(4-difluoromethoxy-phenyl)-2-hydroxy-ethyl]-amide | 477.1 |
| II-420 | 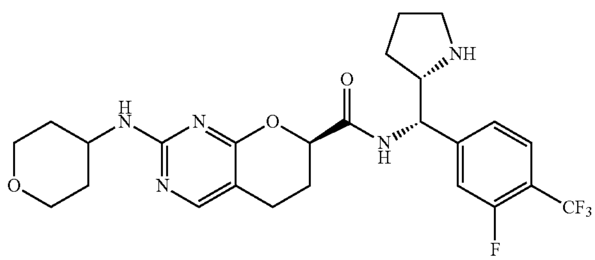 [SMILES: O=C(N[C@@H](c1ccc(C(F)(F)F)c(F)c1)[C@@H]1CCCN1)[C@H]1CCc2cnc(NC3CCOCC3)nc2O1] | (R)-2-(Tetrahydro-pyran-4-ylamino)-6,7-dihydro-5H-pyrano[2,3-d]pyrimidine-7-carboxylic acid [(S)-(3-fluoro-4-trifluoromethyl-phenyl)-(S)-pyrrolidin-2-yl-methyl]-amide | 524.2 |
| II-421 | 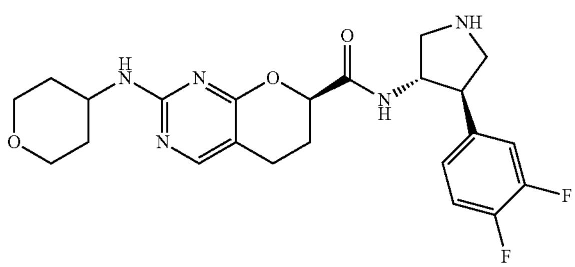 [SMILES: O=C(N[C@@H]1CNC[C@H]1c1ccc(F)c(F)c1)[C@H]1CCc2cnc(NC3CCOCC3)nc2O1] | (R)-2-(Tetrahydro-pyran-4-ylamino)-6,7-dihydro-5H-pyrano[2,3-d]pyrimidine-7-carboxylic acid [(3S,4R)-4-(3,4-difluoro-phenyl)-pyrrolidin-3-yl]-amide | 460.2 |
| II-422 | 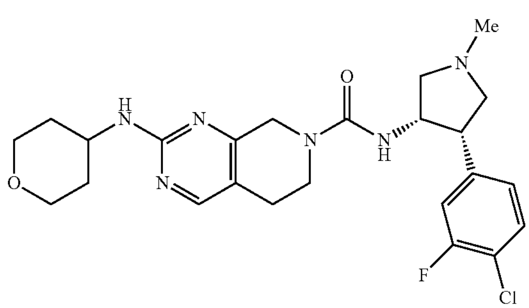 [SMILES: CN1C[C@H](c2ccc(Cl)c(F)c2)[C@H](NC(=O)N2CCc3cnc(NC4CCOCC4)nc3C2)C1] | 2-(Tetrahydro-pyran-4-ylamino)-5,8-dihydro-6H-pyrido[3,4-d]pyrimidine-7-carboxylic acid [4-(4-chloro-3-fluoro-phenyl)-1-methyl-pyrrolidin-3-yl]-amide | 489.2 |
| II-423 | 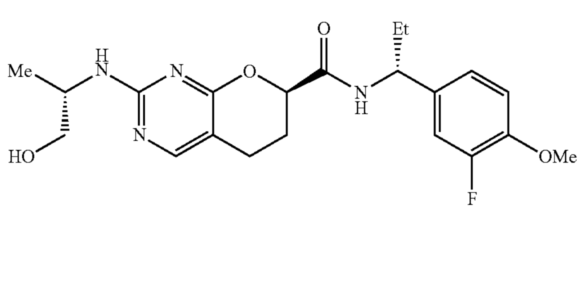 [SMILES: CC[C@@H](NC(=O)[C@H]1CCc2cnc(N[C@@H](C)CO)nc2O1)c1ccc(OC)c(F)c1] | (R)-2-((S)-2-Hydroxy-1-methyl-ethylamino)-6,7-dihydro-5H-pyrano[2,3-d]pyrimidine-7-carboxylic acid [(R)-1-(3-fluoro-4-methoxy-phenyl)-propyl]-amide | 419.2 |

TABLE II-continued

| Structure | Name | MS |
|---|---|---|
| II-424 | 2-(Tetrahydro-pyran-4-ylamino)-5,8-dihydro-6H-pyrido[3,4-d]pyrimidine-7-carboxylic acid [(S)-(3-chloro-4-fluoro-phenyl)-(1-methyl-1H-pyrazol-4-yl)-methyl]-amide | 500.2 |
| II-425 | 2-(Tetrahydro-pyran-4-ylamino)-5,8-dihydro-6H-pyrido[3,4-d]pyrimidine-7-carboxylic acid [4-(3,4-difluoro-phenyl)-1-methyl-pyrrolidin-3-yl]-amide | 473.3 |
| II-426 | 2-(Tetrahydro-pyran-4-ylamino)-5,8-dihydro-6H-pyrido[3,4-d]pyrimidine-7-carboxylic acid [4-(3-chloro-4-fluoro-phenyl)-1-methyl-pyrrolidin-3-yl]-amide | 489.2 |
| II-427 | 2-(Tetrahydro-pyran-4-ylamino)-5,8-dihydro-6H-pyrido[3,4-d]pyrimidine-7-carboxylic acid [(S)-(3-chloro-4-methoxy-phenyl)-(1-methyl-1H-pyrazol-4-yl)-methyl]-amide | 512.3 |
| II-428 | (R)-2-(Tetrahydro-pyran-4-ylamino)-6,7-dihydro-5H-pyrano[2,3-d]pyrimidine-7-carboxylic acid [(S)-(3-fluoro-4-methoxy-phenyl)-((R)-1-methyl-pyrrolidin-2-yl)-methyl]-amide | 500.3 |
| II-429 | 2-(Tetrahydro-pyran-4-ylamino)-5,8-dihydro-6H-pyrido[3,4-d]pyrimidine-7-carboxylic acid [(R)-(4-cyano-3-fluoro-phenyl)-(1-methyl-1H-pyrazol-4-yl)-methyl]-amide | 491.2 |

TABLE II-continued

| Structure | Name | MS |
|---|---|---|
| II-430 | 2-(Tetrahydro-pyran-4-ylamino)-5,8-dihydro-6H-pyrido[3,4-d]pyrimidine-7-carboxylic acid [(3-cyano-4-methoxy-phenyl)-(1-methyl-1H-pyrazol-4-yl)-methyl]-amide | 503.3 |
| II-431 | 2-(Tetrahydro-pyran-4-ylamino)-5,8-dihydro-6H-pyrido[3,4-d]pyrimidine-7-carboxylic acid [(3-cyano-4-methoxy-phenyl)-(1-methyl-1H-pyrazol-4-yl)-methyl]-amide | 503.2 |
| II-432 | 2-(Tetrahydro-pyran-4-ylamino)-5,8-dihydro-6H-pyrido[3,4-d]pyrimidine-7-carboxylic acid [(R)-(3-chloro-4-cyano-phenyl)-(1-methyl-1H-pyrazol-4-yl)-methyl]-amide | 507.3 |

[1]Mixture of two compounds

Compounds of the present invention can be made by a variety of methods depicted in the illustrative synthetic reaction schemes and examples described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diasteromeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., J. Chromatogr., 1975 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. (see, e.g., *Drug Stereochemistry, Analytical Methods and Pharmacology*, Irving W. Wainer, Ed., Marcel Dekker, Inc., New York 1993).

Under method (1), diastereomeric salts can be formed by reaction of enantiomerically pure chiral bases such as brucine, quinine, ephedrine, strychnine, α-methyl-. β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. Eliel and S. Wilen, *Stereochemistry of Organic Compounds*, John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. *J. Org. Chem.*, 1982 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" 1989 W. J. Lough, Ed., Chapman and Hall, New York; Okamoto, *J. Chromatogr.*, 1990 513:375-378). Enriched or purified enantiomers can be distinguished by methods used to distinguish other chiral molecules with asymmetric carbon atoms, such as optical rotation and circular dichroism.

Racemic mixtures were separated by supercritical fluid chromatography using a Mettler Toledo MG II chromatograph using a 5 μm AS-H SFC 21.2×250 mm column or AD-H SFC column using MeOH or IPA containing 0.1% TFA as a cosolvent. Typical conditions include a flow rate of 50 g/min, a column temperature of 40° Celsius. Run time was typically 5 to 10 min.

Some compounds in the following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

Compounds of the present invention are prepared by the general procedure depicted in SCHEME A. The requisite 5,6,7,8-tetrahydropyrido[3,4-d]pyrimidin-2-amine fragments A-3b are prepared by condensation of a substituted guanidine and tert-butyl 4-((dimethylamino)methylene)-3-oxo-piperidine-1-carboxylate (A-9) which is prepared by condensation of tert-butyl 3-oxo-piperidine-1-carboxylate (CASRN 98977-36-7) and tert-butoxy-N,N,N',N'-tetramethylmethanediamine (CASRN 5815-08-7). The 2-position of compounds of the present invention typically is substituted by a secondary amine and the ready availability of N-substituted guanidines afford the flexibility to incorporate the substituents contemplated in the present invention. The synthesis of A-2 is readily accomplished by treating 1H-pyrazole-1-carboximidamidate hydrochloride (A-1, R″=H) or the corresponding bis-CBZ derivative (A-1; R″=CBZ) with a primary amine. A structurally diverse collection of primary amines is readily available from commercial sources or by literature preparations allowing wide latitude in the substitution at the 2-position. After the condensation of A-2 and A-9 the Boc protecting group is removed under acidic conditions using standard protocols to afford a 5,6,7,8-tetrahydropyrido[3,4-d]pyrimidin-2-amine derivative (A-3b).

SCHEME A

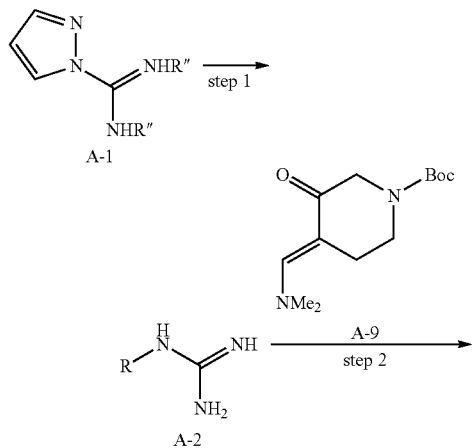

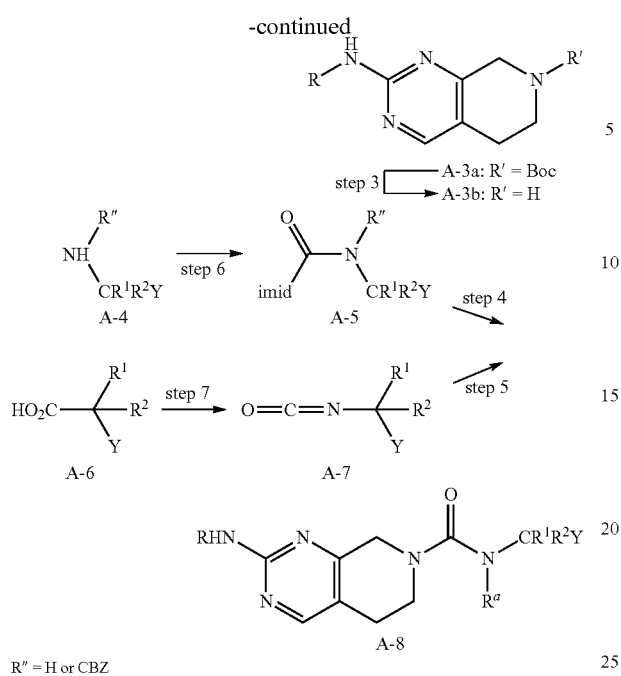

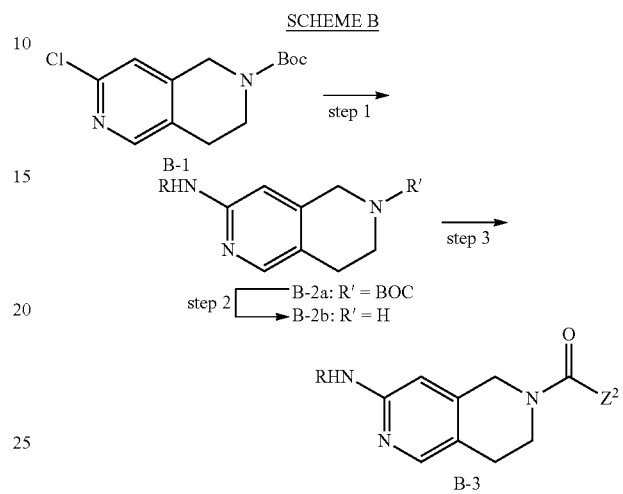

Acylation of the piperidine to afford a urea (A-3 R'=C(=O)NR$^a$CR$^1$R$^2$Y) can be accomplished by treating a primary or secondary amine (A-4) with CDI which affords a N-substituted 1H-pyrazole-1-carboxamide (A-5), which is subsequently treated with A-3b to afford the urea A-8. An alternative route to preparing an activated acylating agent is to convert an appropriately substituted carboxylic acid A-6 to the corresponding acyl azide with DPPA which can subsequently be converted to an isocyanate A-7 by a Curtius rearrangement. The reactive isocyanate will readily react with A-3b to afford the A-8. (K. Ninomiya et al. *Tetrahedron* 1974 30:2151; V. V. Sureshbabu et al. *Tetrahedron Lett.* 2008 49:1408).

Compounds within the scope of the present invention that are amides rather than ureas (A-3, R'=C(=O)CH$_2$CR$^1$R$^2$Y) can be prepared using activated carboxylic acid derivatives that have been developed and extensively utilized for peptide synthesis.

Activated carboxylic acids include acid chlorides or symmetrical or mixed acid anhydrides which react with amines in a solvent such as DMF, DCM, THF, with or without water as a co-solvent at temperatures between 0° C. and 60° C. generally in the presence of a base, such as Na$_2$CO$_3$, NaHCO$_3$, K$_2$CO$_3$, DIPEA, TEA or pyridine. Carboxylic acids are converted into their acid chlorides using standard reagents well known to someone skilled in the art, such as thionyl chloride, oxalyl chloride, phosphoryl chloride and the like. Those reagents can be used in presence of bases, such as DIPEA, TEA or pyridine.

Alternatively a carboxylic acid can be converted in situ into activated acids by treating the carboxylic acid with EDC, DCC, BOP, PyBrOP, or 2-fluoro-1-methylpyridinium p-toluenesulphonate (Mukaiyama's reagent) and the like, optionally in the presence of modifiers such as HOBt, with or without a base such as NMM, TEA or DIPEA in an inert solvent, such as DMF or DCM, at temperatures between 0° C. and 60° C. The reaction may alternatively be carried out in presence of HATU or HOAt and TEA or DIPEA in DMF, DCM or THF. Acylation of amines has been reviewed (J. March, supra pp. 417-425; H. G. Benz, *Synthesis of Amides and Related Compounds* in *Comprehensive Organic Synthesis*, E. Winterfeldt, ed., vol. 6, Pergamon Press, Oxford 1991 pp. 381-411; see R. C. Larock, *Comprehensive Organic Transformations—A Guide to Functional Group Preparations*, 1989, VCH Publishers Inc., New York; pp. 972-976).

Compounds within the scope of the present invention which are 5,6,7,8-tetrahydro-2,6-naphthyridin-3-amine are prepared from tert-butyl 7-chloro-3,4-dihydro-2,6-naphthyridine-2(1H)-carboxylate (B-1). (CASRN 1060816-50-3 purchased from Anichem Inc.) Introduction of the desired amine at the 3-position is accomplished by palladium catalyzed amination. Subsequent removal of the Boc affords the pyridine, which can be further elaborated as described above.

Introduction of primary or secondary amines by replacement of a leaving group on a (hetero)aryl ring can be accomplished by Buchwald-Hartwig palladium-catalyzed cross-coupling of an amine and B-1 (J. P. Wolfe and S. L. Buchwald *J. Org. Chem.* 2000 65:1144-1157 and *Acc. Chem. Res.* 1998 31:805-818; J. P. Wolfe et al. *J. Org. Chem.* 2000 65:1158; J. F. Hartwig *Angew. Chem. Int. Ed.* 1998 37:2046-2067). Typical conditions include Pd(dppf)Cl$_2$ in the presence of base, e.g. sodium tert-butoxide or Cs$_2$CO$_3$, and an aprotic solvent. Typical leaving groups include halogen and triflates and optimum leaving groups will depend on the precise reactant.

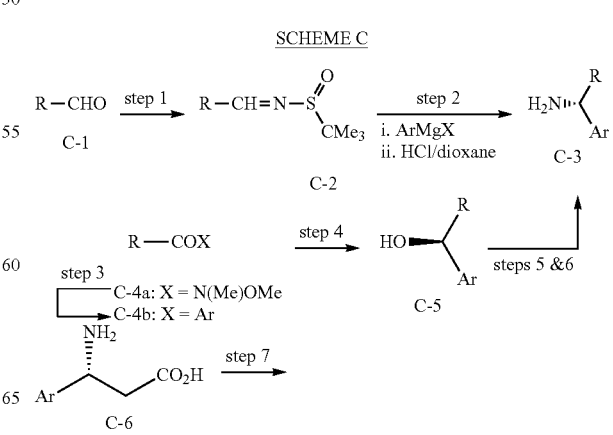

-continued

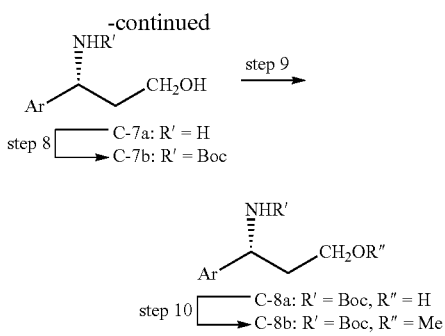

Compounds within the scope of the present invention require substituted amines A-4 which are optionally chiral. These amines can be prepared using general methods depicted in SCHEME C. Addition of an aryl Grignard or aryllithium reagent to chiral N-tert-butylsulfinyl imines (C-2) affords chiral amines (C-3) directly. (D. A. Cogan et al., *Tetrahedron* 1999 55:8883-8904). The imines are, in turn, available from the large pool of aldehydes which can be easily prepared or purchased. Alternatively, a 1-aryl-1-ethanone derivative (C-4b) can be subjected to chiral hydride reduction (step 4) with (R)-1-methyl-3,3-diphenylhexahydropyrrolo[1, 2-c][1,3,2]oxazaborole and borane diethylaniline (A. M. Salunkhe and E. R. Burkhardt *Tetrahedron Lett.* 1997 38(9) 1523-1526 and 38(9)1519-1522; and E. J. Corey et al., *J. Am. Chem. Soc.* 1987 109:5551) to afford a chiral alcohol, which is then converted to the corresponding amine via the Gabriel synthesis utilizing Mitsunobu conditions to introduce the phthalimide moiety (steps 5 & 6).

Mitsunobu conditions (D. L. Hughes, The Mitsunobu Reaction, in *Organic Reactions*, Volume 42, 1992, John Wiley & Sons, New York; pp. 335-656) comprise activating alcohols with a mixture of a phosphine, such as a trialkylphosphine like tributylphosphine ((n-Bu)$_3$P), triphenylphosphine (Ph$_3$P) and the like and a diazo-compound like DEAD, DIAD or di-tert-butyl-azodicarboxylate in an inert solvent commonly used for such transformations such as THF, toluene, DCM. There is no particular limitation on the nature of the solvent to be employed, provided that it has no adverse effect on the reaction or the reagents involved and that it can dissolve the reagents, at least to some extent. The reaction can take place over a wide range of temperatures ranging from ambient temperatures to the reflux temperature of the solvent employed.

Alternatively, useful chiral amino alcohol intermediates can be prepared by hydride reduction of amino acids (e.g., C-6). The ready availability of chiral amino acids provides a rich pool of synthetic fragments which can be incorporated into compounds within the scope of the present invention. (R. M. Williams, *Synthesis of optically Active α-Amino Acids*, Vol 7 of *Organic Chemistry Series*; Baldwin, J. E.; Magnus, P. D. (Eds.); Pergamon Press, Oxford 1989). The resulting amino alcohol (C-7a) can be either N- or O-protected to further modify the fragment. Condensation of O-silylated amines afford the hydroxylmethyl substituted derivatives within the scope of the present invention, and the deprotected alcohol allows for additional modification of the R$^1$ substituent. The examples which follow provide examples of further modification of the alcohol.

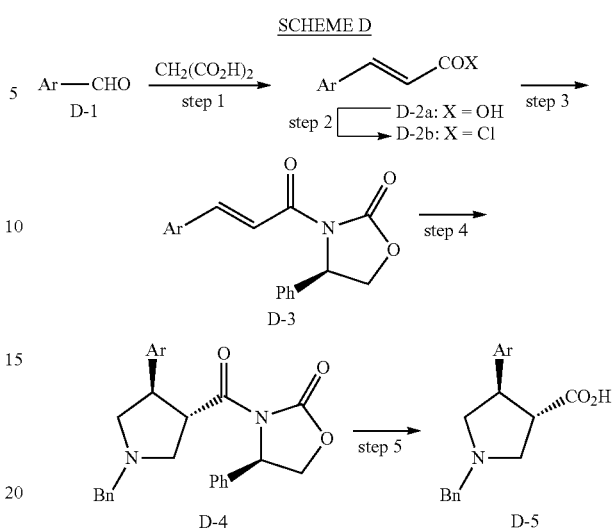

4-Aryl-1-benzyl-pyrrolin-3-carboxylic acids were prepared from readily available substituted benzaldeydes D-1 by Knoevenagel condensation with malonic acid to afford a substituted acrylic acid. Condensation of the corresponding acid chloride with (R)-4-phenyloxazolidin-2-one introduces a chiral auxiliary, which affords chiral D-4 after a 1,3-dipolar addition of an azomethine methylide. Hydrolysis of the amide affords a carboxylic acid, which can be converted to the isocyanate and condensed with an amine and deprotected to afford compounds within the scope of the present invention.

Compounds within the scope of the present invention in which Z$^2$ is a 3-amino-4-aryl-pyrrolidine derivative are conveniently prepared from a N-protected 4-aryl-pyrrolidine-3-carboxylic using the Schmidt rearrangement (see, e.g., example 68).

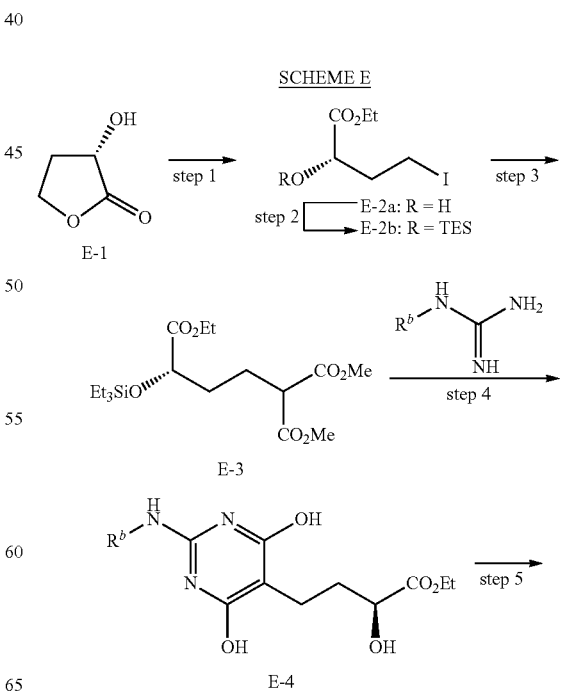

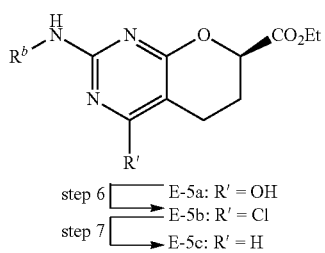

step 6 ⎯⎯ E-5a: R' = OH
⎯⎯▶ E-5b: R' = Cl
step 7 ⎯⎯▶ E-5c: R' = H 2-(Substituted)amino-6,7-dihydro-5H-pyrano[2,3-d]pyrimidine-7-carboxylic acids were prepared by the steps depicted in SCHEME E. (S)-4-Ethyl 1,1-dimethyl 4-(triethylsilyloxy)butane-1,1,4-tricarboxylate (E-2b) was prepared by ring-opening of E-1 with concomitant displacement of the terminal hydroxyl with iodide followed by displacement of the iodide with dimethyl malonate. The Principal synthesis affords an extremely general approach to preparing the pyrimidine ring which was utilized to prepare E-4. One fragment is a β-dicarbonyl compound. The carbonyls may be composed of ketones, aldehydes, carboxylic acid derivatives or nitriles. The second three atom segment is amidine, urea, thiourea or guanidine. The range of equivalents capable of undergoing this reaction affords significant flexibility in the preparation of substituted pyrimidines. (D. J. Brown, Pyrimidines and their benzo Derivatives in *Comprehensive Heterocyclic Chemistry*, A. J. Boulton and A. McKillop (ed) vol. 3 part 2b, chap. 2.13, Pergamon Press, Oxford 1984 pp. 57-157; D. J. Brown, The Pyrimidines, Supplement II in *The Chemistry of Heterocyclic Compounds*, A. Weissberger and E. C. Taylor (ed), Wiley Interscience, New York 1985, pp. 21-62).

Cyclization of E-4 to afford the desired 6,7-dihydro-5H-pyrano[2,3-d]pyrimidine skeletal was accomplished utilizing the Mitsunobu protocol. The residual hydroxyl substituent was removed by the two-step process of chlorination and hydrogenolytic cleavage to afford E-5c. Hydrolysis of the ester and conversion of the resulting acid to the desired amide was carried out as described above.

1-Alkyl-3-aryloxy-4-amino-pyrrolidines (F-6c) that are useful intermediates for some compounds within the scope of the invention are prepared from tert-butyl 2,5-dihydro-1H-pyrrole-1-carboxylate (F-1, CASRN 73286-70-1). Epoxidation of F-1 and subsequent ring-opening affords the trans hydroxyl ether F-3a. Inversion of the 3-hydroxy moiety was accomplished by oxidation and re-reduction with L-selectride to afford the requisite cis isomer F-3b. N-methylation can be accomplished by acid-catalyzed-deprotection of the Boc followed by reductive amination to introduce the alkyl substitution. Finally the 4-amino group was introduced by a three-step sequence consisting of mesylation of the alcohol, displacement of the mesyloxy substituent with azide and finally reduction of the azide. The latter reaction was conveniently accomplished utilizing the Staudinger protocol with $Ph_3P$ although other methodology can also be employed. One skilled in the art will recognize other methodology which can be adapted to prepare the desired intermediate. Incorporation of F-6c into the final product can be accomplished by procedures previously described. One skilled in the art will appreciate that the sequence can be used to prepare the corresponding thioether and their oxidization products by substituting a thiophenyl for the phenol in step 2. Similarly ring opening of F-2 with an azide and subsequent reduction and arylation of the resulting amine will afford the corresponding aryl amines.

The SCHEMES described above provide general procedures which have been applied to compounds encompassed in the present invention. The examples which follow containing additional details which are useful to introduce the various structural features found in specific compounds.

Biological Activity

Determination of the activity of ERK activity of a compound of formula I is possible by a number of direct and indirect detection methods. Certain exemplary compounds described herein were assayed for their ERK inhibition assay (Example 77). The range of ERK binding activities of Examples I-1 to I-150 was less than 1 nM (nanomolar) to about 10 μM (micromolar). A cell-based function assay (Ex-

SCHEME F

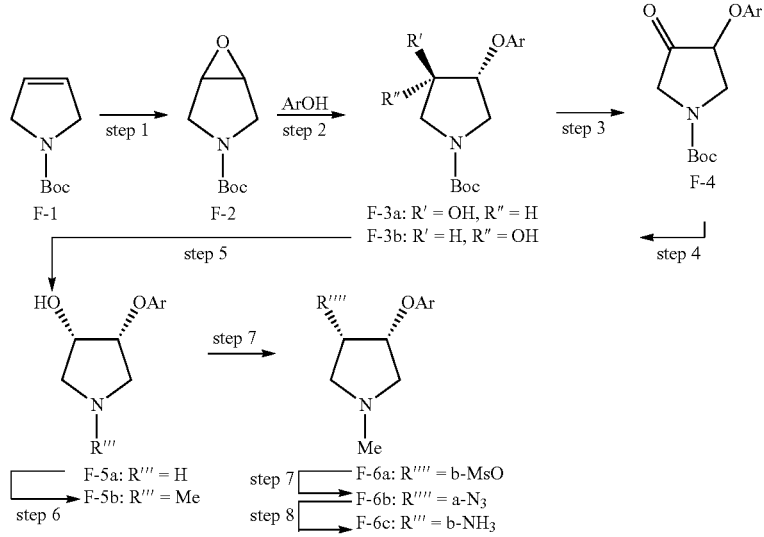

ample 79) was used to determine the effect of ERK inhibitors on down-stream signaling. Representative values for these assays can be found in TABLE 2 in example 77.

The cytotoxic or cytostatic activity of formula I exemplary compounds was measured by: establishing a proliferating mammalian tumor cell line in a cell culture medium, adding a formula I compound, culturing the cells for a period from about 6 h to about 5 d; and measuring cell viability (Example 78). Cell-based in vitro assays were used to measure viability, i.e. proliferation ($IC_{50}$), cytotoxicity ($EC_{50}$).

Dosage & Administration

The present invention provides pharmaceutical compositions or medicaments containing the compounds of the invention and at least one therapeutically inert carrier, diluent or excipient, as well as methods of using the compounds of the invention to prepare such compositions and medicaments. In one example, compounds of Formula I with the desired degree of purity may be formulated by mixing with physiologically acceptable carriers, i.e., carriers that are non-toxic to recipients at the dosages and concentrations employed into a dosage form at ambient temperature and at the appropriate pH. The pH of the formulation depends mainly on the particular use and the concentration of compound, but typically ranges anywhere from about 3 to about 8. In one example, a compound of Formula I is formulated in an acetate buffer, at pH 5. In another embodiment, the compounds of Formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the severity of the disorder, the particular patient being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit ERK activity. Typically such amount may be below the amount that s toxic to normal cells, or the patient as a whole.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Sustained-release preparations may be prepared. Suitable examples of sustained-release preparations include semipermeable matrices of solid hydrophobic polymers containing a compound of Formula I, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

A dose to treat human patients may range from about 0.1 mg to about 1000 mg of a compound of formula I. A typical dose may be about 1 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's *Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

For oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

An example of a suitable oral dosage form is a tablet containing about 25 mg, 50 mg, 100 mg, 250 mg or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

In one embodiment, the pharmaceutical composition also includes at least one additional anti-proliferative agent.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of formula I may be employed alone or in combination with other therapeutic agents for the treatment of a disease or disorder described herein, such as a hyperproliferative disorder (e.g., cancer). In certain embodiments, a compound of formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of formula I such that they do not adversely affect each other. The combination therapy may provide "synergy" and prove "synergistic", i.e., the effect achieved when the active ingredients used together is greater than the sum of the effects that results from using the compounds separately.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Suitable dosages for any of the above co-administered agents are those presently used and may be lowered due to the combined action (synergy) of the newly identified agent and other chemotherapeutic agents or treatments.

Combination therapies according to the present invention thus comprise the administration of at least one compound of formula I, or a stereoisomer, geometric isomer, tautomer, metabolite, or pharmaceutically acceptable salt and the use of at least one other cancer treatment method. The amounts of the compound(S) of formula I and the other pharmaceutically active chemotherapeutic agent(S) and the relative timings of administration will be selected in order to achieve the desired combined therapeutic effect.

Articles of Manufacture

In another embodiment of the invention, an article of manufacture, or "kit", containing materials useful for the treatment of the diseases and disorders described above is provided. In one embodiment, the kit comprises a container comprising a compound of formula I, or a stereoisomer, tautomer, or pharmaceutically acceptable salt thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of formula I or a formulation thereof which is effective for treating the condition and may have a sterile access port (for example, the container may be an intravenous solution bag or a vial having a stopper pierceable by a hypodermic injection needle). At least one active agent in the composition is a compound of formula I. Alternatively, or additionally, the article of manufacture may further comprise a second container comprising a pharmaceutically diluent, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, the kits are suitable for the delivery of solid oral forms of a compound of formula I, such as tablets or capsules. Such a kit can include a number of unit dosages. An example of such a kit is a "blister pack". Blister packs are well known in the packaging industry and are widely used for packaging pharmaceutical unit dosage forms.

According to one embodiment, a kit may comprise (a) a first container with a compound of formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Example 1

N-((3,4-dichlorophenyl)(oxazol-5-yl)methyl)-2-(tetrahydro-2H-pyran-4-ylamino)-5,6-dihydropyrido[3,4-d]pyrimidine-7(8H)-carboxamide (I-1)

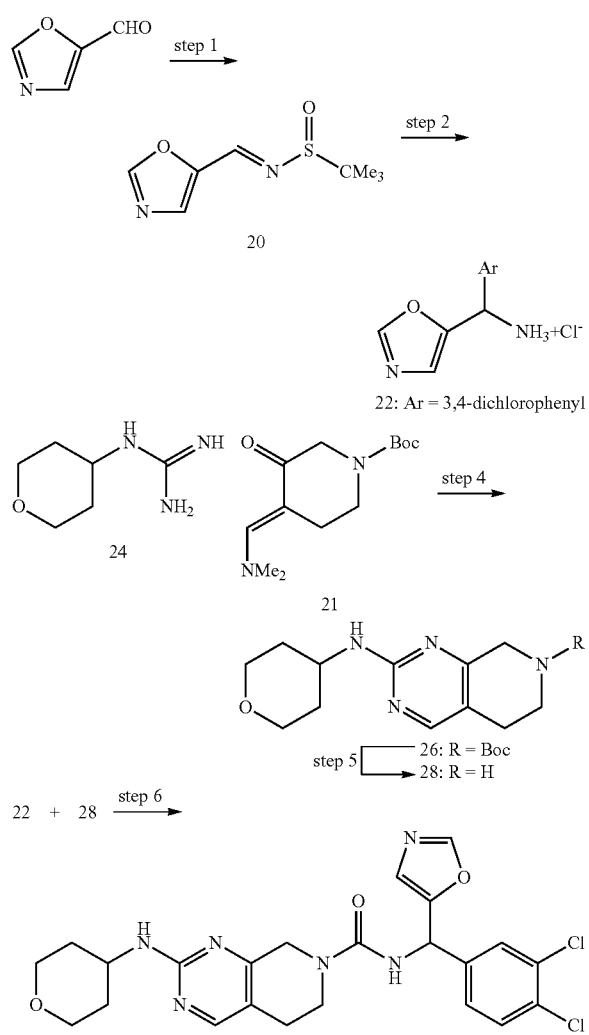

Step 1:

Oxazole-5-carbaldehyde (1.0 g, 10.30 mmol), 2-methylpropane-2-sulfinamide (2.247 g, 18.54 mmol; CASRN 146374-27-8), and tetraethoxytitanium (8.460 g, 37.09 mmol) were placed in THF (15 mL) and heated to 65° C. for 12 h. The reaction was cooled and poured onto water. The solids were filtered off and the filtrate was extracted with EtOAc. The layers were separated and the organic layer was concentrated. The resulting residue was purified by $SiO_2$ chromatography (20-25% EtOAc/hexane) to afford (E)-2-methyl-N-(oxazol-5-ylmethylene)propane-2-sulfinamide (20, 1.211 g, 6.047 mmol, 58.70% yield).

Step 2:

A dried-flask was charged with 20 (1.211 g, 6.047 mmol) and toluene (5 mL) was added. The reaction was cooled to −78° C. and (3,4-dichlorophenyl)magnesium bromide (18.14 mL, 9.071 mmol, 0.5 M in THF) was added. The reaction was warmed to −10° C. for 15 min. Saturated $NH_4Cl$ was added and the reaction was extracted with DCM. The organic layer was separated, dried, filtered, and concentrated. The resulting residue was dissolved in DCM (10 mL) then 4 N HCl in dioxane (15.12 mL, 60.47 mmol) was added and the solution was stirred for 30 min. The reaction mixture was added dropwise to a stirred solution of ether. The resulting solid was filtered and washed with ether to afford (3,4-dichlorophenyl)(oxazol-5-yl)methanamine hydrochloride (22, 1.24 g, 4.436 mmol, 73.35% yield).

Step 3:

To a stirred solution of 1H-pyrazole-1-carboximidamide hydrochloride (65.2 g, 445 mmol) in DMF (200 mL) at RT under nitrogen was added sequentially DIPEA (103 mL, 593 mmol) and tetrahydro-2H-pyran-4-amine (30 g, 297 mmol; CASRN 38041-19-9) and the reaction was stirred for 3 d. $Et_2O$ (100 mL) was added, and the reaction was stirred for 10 min then the reaction was allowed to settle and the ether layer was decanted. This process was repeated 3 times and a solid formed after allowing to settle for 30 min. The solid was filtered off and rinsed with $Et_2O$ and dried under high vacuum to afford 35 g, (95% purity, 78% yield) of 1-(tetrahydro-2H-pyran-4-yl)guanidine (24) as a light yellow solid: MS m/z (APCI-pos) M+1=144.1.

Step 4:

A solution of 24 (15.0 g, 105 mmol) and 21 (26.6 g, 105 mmol, CASRN 871726-72-6, see Z. Guo et al. WO2005/121130 for general procedure) and EtOH (150 mL) was stirred and heated to 45° C. Sodium ethoxide (78.2 mL, 210 mmol, 21 wt % in EtOH) was then added, and the reaction was stirred for 18 h at 45° C., cooled and concentrated. DCM (400 mL) was added and the mixture was washed with brine (200 mL). The organic fractions were isolated, dried ($Na_2SO_4$), filtered, and concentrated to afford 27 g (95% purity, 75% yield) of tert-butyl 2-(tetrahydro-2H-pyran-4-ylamino)-5,6-dihydropyrido[3,4-d]pyrimidine-7(8H)-carboxylate (26) as a viscous red oil: MS m/z (APCI-pos) M+1=335.0.

Step 5:

A round-bottom flask was charged with 26 (27.5 g, 82.2 mmol), DCM (100 mL) and MeOH (25 mL) and maintained under nitrogen. A 4N solution of HCl in dioxane (103 mL, 411 mmol) was added and the resulting solution stirred for 18 h. The reaction mixture was concentrated and re-suspended in DCM (150 mL). A methanolic $NH_3$ solution (25 mL, 7 N) and additional DCM (100 mL) was added. The precipitated salts were filtered and the filtrate concentrated to afford a brown solid which was stirred with $Et_2O$/MeOH (95:5) for 1 h. A fine light brown solid precipitated and recovered by filtration to afford 15 g, (99% purity, 77% yield) of N-(tetrahydro-2H-pyran-4-yl)-5,6,7,8-tetrahydropyrido[3,4-d]pyrimidin-2-amine (28): MS m/z (APCI-pos) M+1=235.2.

Step 6:

A solution of (3,4-dichlorophenyl)(oxazol-5-yl)methanamine hydrochloride (22, 183 mg, 0.779 mmol), TEA (326 μL, 2.34 mmol) and DCM (5 mL) was stirred at RT for 10 min. CDI (158 mg, 0.974 mmol) was added and the reaction was stirred at RT for 1 h. A solution of 28 (211 mg, 0.779 mmol), TEA (326 μL, 2.34 mmol) and THF (2 mL) was stirred for 10 min then added to the solution and the resulting mixture stirred for 2 h at RT. The reaction was poured into water, and extracted with DCM. The combined organic fractions were dried ($MgSO_4$), filtered, and concentrated. The crude product was purified by $SiO_2$ chromatography eluting with a MeOH/DCM gradient (2-5% MeOH/DCM). The recovered product was further purified by reverse phase column chromatography (SP4, 0-55% MeCN:water) to afford 82 mg (20.9%) of N-((3,4-dichlorophenyl)(oxazol-5-yl)methyl)-2-(tetrahydro-2H-pyran-4-ylamino)-5,6-dihydropyrido[3,4-d]pyrimidine-7(8H)-carboxamide (30): $^1$H NMR (400 MHz, CDCl₃) δ 8.09 (s, 1H), 7.86 (s, 1H), 7.43 (m, 2H), 7.17 (dd, 1H). 6.93 (s, 1H), 6.30 (d, 1H), 5.09 (d, 1H), 4.88 (d, 1H), 4.37 (s, 2H), 4.05-3.95 (m, 3H), 3.68 (m, 2H), 3.54 (t, 2H), 2.70 (t, 2H), 2.01 (d, 2H), 1.59-1.46 (m, 2H); LCMS (ACPI-pos) m/z 505.5 (M+H)+.

(I-1)

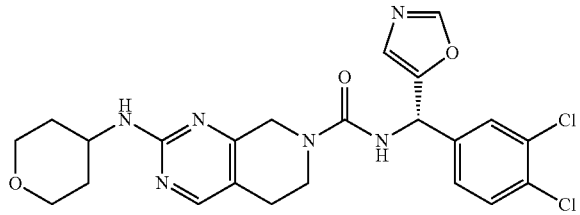

(S)—N-((3,4-dichlorophenyl)(oxazol-5-yl)methyl)-2-(tetrahydro-2H-pyran-4-ylamino)-5,6-dihydropyrido[3,4-d]pyrimidine-7(8H)-carboxamide (I-1) (81 mg, 0.16 mmol) was resolved by chromatography on a Chiral Tech IC column (4.6 mm×250 mm) eluting with 40% EtOH/hexane at a flow rate of 1 mL/min. The first peak was collected to afford 27 mg (33%) of I-1: ¹H NMR (400 MHz, CDCl₃) δ 8.09 (s, 1H), 7.86 (s, 1H), 7.43 (m, 2H), 7.17 (dd, 1H). 6.93 (s, 1H), 6.30 (d, 1H), 5.09 (d, 1H), 4.88 (d, 1H), 4.37 (s, 2H), 4.05-3.95 (m, 3H), 3.68 (m, 2H), 3.54 (t, 2H), 2.70 (t, 2H), 2.01 (d, 2H), 1.59-1.46 (m, 2H); LCMS (ACPI-pos) m/z 505.5 (M+H)+

N-((4-chloro-3-fluorophenyl)(oxazol-5-yl)methyl)-2-(tetrahydro-2H-pyran-4-γ amino)-5,6-dihydropyrido[3,4-d]pyrimidine-7(8H)-carboxamide (I-51) was prepared analogously except in step 2, (3,4-dichlorophenyl)magnesium bromide was replaced (4-chloro-3-fluorophenyl)magnesium bromide to afford 119 mg (32.4%) of I-51: ¹H NMR (400 MHz, CDCl₃) δ 8.09 (s, 1H), 7.86 (s, 1H), 7.39 (t, 1H), 7.14 (dd, 1H). 7.06 (d, 1H), 6.93 (s, 1H), 6.31 (d, 1H), 5.11 (d, 1H), 4.89 (d, 1H), 4.37 (s, 2H), 4.05-3.95 (m, 3H), 3.66 (m, 2H), 3.53 (dt, 2H), 2.69 (t, 2H), 2.01 (m, 2H), 1.59-1.46 (m, 2H); LCMS (ACPI-pos) m/z 487.1 (M+H)+.

(S)—N-((4-chloro-3-fluorophenyl)(oxazol-5-yl)methyl)-2-(tetrahydro-2H-pyran-4-ylamino)-5,6-dihydropyrido[3,4-d]pyrimidine-7(8H)-carboxamide (I-2) was prepared by chiral chromatography of N-((4-chloro-3-fluorophenyl)(oxazol-5-yl)methyl)-2-(tetrahydro-2H-pyran-4-ylamino)-5,6-dihydropyrido[3,4-d]pyrimidine-7(8H)-carboxamide (117 mg) on a Chiral Tech IA column (22 mm×250 mm) eluting with 40% EtOH/hexane at a flow rate of 22 mL/min. Collection of the first peak afforded 57 mg (48%) of I-2: ¹H NMR (400 MHz, CDCl₃) δ 8.09 (s, 1H), 7.86 (s, 1H), 7.39 (t, 1H), 7.14 (dd, 1H). 7.06 (d, 1H), 6.93 (s, 1H), 6.31 (d, 1H), 5.11 (d, 1H), 4.89 (d, 1H), 4.37 (s, 2H), 4.05-3.95 (m, 3H), 3.66 (m, 2H), 3.53 (dt, 2H), 2.69 (t, 2H), 2.01 (m, 2H), 1.59-1.46 (m, 2H); LCMS (ACPI-pos) m/z 487.1 (M+H)+.

(R)—N-(1-(3,4-dichlorophenyl)ethyl)-2-(tetrahydro-2H-pyran-4-ylamino)-5,6-dihydropyrido[3,4-d]pyrimidine-7(8H)-carboxamide (I-39) was prepared analogously except in step 6, 22 was replaced by 185. The crude product was purified by SiO₂ chromatography eluting with a DCM/MeOH gradient (500:7 to 500:18) to afford 0.120 g (36.1%) of I-39: MS m/z (APCI-pos) M+1=450.

(R)—N-(1-(4-chloro-3-fluorophenyl)ethyl)-2-(tetrahydro-2H-pyran-4-ylamino)-5,6-dihydropyrido[3,4-d]pyrimidine-7(8H)-carboxamide (I-40) was prepared analogously except in step 6, 22 was replaced by 140. The crude product was purified by SiO₂ chromatography eluting with a DCM/MeOH gradient (500:10 to 500:15) to afford 0.100 g (31.2%) of I-40: MS m/z (APCI-pos) M+1=434.

Example 2

N-((4-chloro-3-fluorophenyl)(1-methyl-1H-pyrazol-3-yl)methyl)-2-(tetrahydro-2H-pyran-4-ylamino)-5,6-dihydropyrido[3,4-d]pyrimidine-7(8H)-carboxamide (I-3)

(4-Chloro-3-fluoro-phenyl)-(1-methyl-1H-pyrazol-3-yl)-methylamine (32) was prepared from 1-methyl-1H-pyrazole-3-carbaldehyde (CASRN 27258-32-8) in accord with the procedure described in steps 1 and 2 of example 1 except (4-chloro-3-fluorophenyl)magnesium bromide was used in place of (3,4-dichlorophenyl)magnesium bromide in step 2.

N-((4-chloro-3-fluorophenyl)(1-methyl-1H-pyrazol-3-yl)methyl)-2-(tetrahydro-2H-pyran-4-ylamino)-5,6-dihydropyrido[3,4-d]pyrimidine-7(8H)-carboxamide was prepared from in accord with the procedure in steps 3 to 6 of example 1 except in step 6, 22 was replaced with 32 to afford 136 mg (20%) of I-3: ¹H NMR (400 MHz, CDCl₃) δ 8.08 (s, 1H), 7.30 (m, 2H), 7.15 (m, 2H), 5.98 (m, 3H), 4.87 (d, 1H), 4.43 (s, 2H), 4.07-3.95 (m, 3H), 3.89 (s, 3H), 3.75 (m, 1H), 3.66-3.51 (m, 3H), 2.68 (m, 2H), 2.03 (d, 2H), 1.53 (m, 2H); LCMS (ACPI-pos) m/z 500.0 (M+H)⁺.

(S)—N-((4-chloro-3-fluorophenyl)(1-methyl-1H-pyrazol-3-yl)methyl)-2-(tetrahydro-2H-pyran-4-ylamino)-5,6-dihydropyrido[3,4-d]pyrimidine-7(8H)-carboxamide (I-4) was prepared by resolution of I-3 on a Chiral Technologies AS-H SFC column (21.2×250 mm) eluting with 20% MeOH/hexanes at a flow rate of 50 mL/min to afford I-4: ¹H NMR (400 MHz, CDCl₃) δ 8.08 (s, 1H), 7.30 (m, 2H), 7.15 (m, 2H), 5.98 (m, 3H), 4.87 (d, 1H), 4.43 (s, 2H), 4.07-3.95 (m, 3H), 3.89 (s, 3H), 3.75 (m, 1H), 3.66-3.51 (m, 3H), 2.68 (m, 2H), 2.03 (d, 2H), 1.53 (m, 2H); LCMS (ACPI-pos) m/z 500.0 (M+H)⁺.

Example 3

N-((4-chloro-3-fluorophenyl)(1-methyl-1H-pyrazol-4-yl)methyl)-2-(tetrahydro-2H-pyran-4-ylamino)-5,6-dihydropyrido[3,4-d]pyrimidine-7(8H)-carboxamide (I-5)

The title compound was prepared in accord with the procedures in example 2 except (4-chloro-3-fluoro-phenyl)-(1-methyl-1H-pyrazol-4-yl)-methylamine (34) prepared from 1-methyl-1H-pyrazole-4-carbaldehyde (CASRN 25016-11-9) was used in place of 32 to afford 207 mg (35%) of I-5: ¹H NMR (400 MHz, CDCl₃) δ 8.09 (s, 1H), 7.35 (m, 2H), 7.14 (d, 1H), 7.09 (m, 2H), 6.05 (d, 1H), 4.90 (dd, 2H), 4.34 (s, 2H), 4.05-3.95 (m, 3H), 3.86 (s, 3H), 3.75-3.59 (m, 2H), 3.54 (t, 2H), 2.67 (t, 2H), 2.01 (d, 2H), 1.53 (m, 2H); LCMS (ACPI-pos) m/z 500.0 (M+H)⁺.

(S)—N-((4-chloro-3-fluorophenyl)(1-methyl-1H-pyrazol-4-yl)methyl)-2-(tetrahydro-2H-pyran-4-ylamino)-5,6-dihydropyrido[3,4-d]pyrimidine-7(8H)-carboxamide (I-6) was prepared by resolution of I-5 on a Chiral Tech IA column (22 mm×250 mm) eluting with 40% EtOH/hexane at a flow rate of 18 mL/min. The first peak afforded 88 mg (44%) of I-6: ¹H NMR (400 MHz, CDCl₃) δ 8.09 (s, 1H), 7.35 (m, 2H), 7.14 (d, 1H), 7.09 (m, 2H), 6.05 (d, 1H), 4.90 (dd, 2H), 4.34 (s, 2H), 4.05-3.95 (m, 3H), 3.86 (s, 3H), 3.75-3.59 (m, 2H), 3.54 (t, 2H), 2.67 (t, 2H), 2.01 (d, 2H), 1.53 (m, 2H); LCMS (ACPI-pos) m/z 500.0 (M+H)⁺.

Example 4

N-((4-chloro-3-fluorophenyl)(1H-pyrazol-4-yl)methyl)-2-(tetrahydro-2H-pyran-4-ylamino)-5,6-dihydropyrido[3,4-d]pyrimidine-7(8H)-carboxamide
(I-7)

Step 1:
N-((1H-pyrazol-4-yl)methylene)-2-methylpropane-2-sulfinamide (36, 2.58 g 62%) was prepared from 1H-pyrazole-4-carbaldehyde in accord with the procedure in step 1 of example 1.

Step 2:
To a solution of 36 (1.47 g, 7.378 mmol), Boc$_2$O (1.932 g, 8.852 mmol) and TEA (2.056 mL, 14.75 mmol) in MeCN (30 mL) was added DMAP (0.09012 g, 0.7377 mmol) and the resulting solution was stirred for 1 h. Water was added and the reaction was extracted with ether. The organic layer was separated, dried, filtered and concentrated. The crude residue was purified by SiO$_2$ eluting with 40% EtOAc/hexane to afford 2.14 g (96.9%) of (E)-tert-butyl 4-((tert-butylsulfinylimino)methyl)-1H-pyrazole-1-carboxylate (38).

Step 3:
(4-Chloro-3-fluorophenyl)(1H-pyrazol-4-yl)methanamine (40) was prepared from 38 in accord with the procedure in step 2 of example 1 except (3,4-dichlorophenyl)magnesium bromide was replaced with (4-chloro-3-fluorophenyl)magnesium bromide.

The title compound was prepared by condensation of 28 and 40 in accord with the procedure in step 6 of example 1 to afford 50 mg (4%) of I-7: $^1$H NMR (400 MHz, CDCl$_3$) δ 8.09 (s, 1H), 7.41 (s, 2H), 7.36 (t, 1H), 7.15 (d, 1H), 7.10 (d, 1H), 6.12 (d, 1H), 4.96 (d, 1H), 4.90 (s, 1H), 4.35 (m, 2H), 4.05-3.95 (m, 3H), 3.75-3.59 (m, 2H), 3.53 (dt, 2H), 2.69 (t, 2H), 2.01 (d, 2H), 1.54 (m, 2H); LCMS (ACPI-pos) m/z 486.4 (M+H)$^+$.

(S)—N-((4-chloro-3-fluorophenyl)(1H-pyrazol-4-yl)methyl)-2-(tetrahydro-2H-pyran-4-ylamino)-5,6-dihydropyrido[3,4-d]pyrimidine-7(8H)-carboxamide (I-8) was resolved by chromatography on a Chiral Tech IC column (4.6 mm×250 mm) eluting with 40% EtOH/hexane at a flow rate of 1 mL/min to afford 17 mg (35%) of I-8: $^1$H NMR (400 MHz, CDCl$_3$) δ 8.09 (s, 1H), 7.41 (s, 2H), 7.36 (t, 1H), 7.15 (d, 1H), 7.10 (d, 1H), 6.12 (d, 1H), 4.96 (d, 1H), 4.90 (s, 1H), 4.35 (m, 2H), 4.05-3.95 (m, 3H), 3.75-3.59 (m, 2H), 3.53 (dt, 2H), 2.69 (t, 2H), 2.01 (d, 2H), 1.54 (m, 2H); LCMS (ACPI-pos) m/z 486.4 (M+H)$^+$.

Example 5

N-((4-chloro-3-fluorophenyl)(1,3,4-oxadiazol-2-yl)methyl)-2-(tetrahydro-2H-pyran-4-ylamino)-5,6-dihydropyrido[3,4-d]pyrimidine-7(8H)-carboxamide
(I-9)

Step 1:
To a solution of 2-amino-2-(4-chloro-3-fluorophenyl)acetic acid (5.00 g, 24.56 mmol) in MeOH (30 mL) at 0° C. was added dropwise thionyl chloride (5.37 mL, 73.67 mmol) and the reaction was stirred for 18 h. The reaction mixture was concentrated and the solids were triturated with Et$_2$O to afford 6.580 g (105%) of methyl 2-amino-2-(4-chloro-3-fluorophenyl)acetate hydrochloride (42) which was used without further purification.

Step 2:
Methyl 2-(4-chloro-3-fluorophenyl)-2-(2-(tetrahydro-2H-pyran-4-ylamino)-5,6,7,8-tetrahydropyrido[3,4-d]pyrimidine-7-carboxamido)acetate (44) was prepared from 42 in accord with the procedure in step 6 of example to afford 650 mg (40%) of 44.

Step 3:
To a solution of 44 (610 mg, 1.28 mmol) and THF (5 mL) was added MeOH (1 mL) followed by the dropwise addition of 1M NaOH (5105 μL, 5.11 mmol). The reaction was stirred for 1 h, cooled to 0° C. and acidified to pH 3 with 1N HCl. The mixture was extracted twice with 10% MeOH in DCM (25 mL). The organic layers were combined and concentrated to afford 270 mg (45.6%) of 2-(4-chloro-3-fluorophenyl)-2-(2-(tetrahydro-2H-pyran-4-ylamino)-5,6,7,8-tetrahydropyrido[3,4-d]pyrimidine-7-carboxamido)acetic acid (46) which was used without further purification.

Step 4:
To a solution of 46 (270 mg, 0.582 mmol) and EDCI (139 mg, 0.728 mmol) and CHCl$_3$ (10 mL) was added formohydrazide (41.9 mg, 0.698 mmol) and the reaction was stirred at RT for 2 h. Water was added and the mixture was extracted with DCM. The organic layer was separated and concentrated. The crude residue was purified by SiO$_2$ chromatography eluting with a MeOH/DCM gradient (6 to 8% MeOH) to afford 119 mg (36.4%) of N-(1-(4-chloro-3-fluorophenyl)-2-(2-formylhydrazinyl)-2-oxoethyl)-2-(tetrahydro-2H-pyran-4-ylamino)-5,6-dihydropyrido[3,4-d]pyrimidine-7(8H)-carboxamide (48).

Step 5:
To a solution of 48 (119 mg, 0.212 mmol) and MeCN (2 mL) was added DIPEA (164 mg, 1.27 mmol) and PPh$_3$ (99.9 mg, 0.381 mmol) and the solution was stirred for 5 min. Perchloroethane (65.1 mg, 0.275 mmol) was added and the reaction was stirred for 3 h. The reaction mixture was concentrated and partitioned between EtOAc and H$_2$O. The organic layer was separated and the aqueous phase was extracted with EtOAc. The organic layers were combined and concentrated. The crude product was purified by reverse phase chromatography (SP4) eluting with a MeCN/H$_2$O gradient (5-95% MeCN) to afford 50.0 mg (48.4%) of I-9: $^1$H NMR (400 MHz, CDCl$_3$) δ 8.39 (s, 1H), 8.08 (s, 1H), 7.41 (t, 1H), 7.21 (dd, 1H), 7.14 (d, 1H), 6.35 (d, 1H), 5.83 (d, 1H), 4.90 (d, 1H), 4.43 (s, 2H), 4.05-3.95 (m, 3H), 3.77-3.60 (m, 2H), 3.55 (t, 2H), 2.70 (m, 2H), 2.03 (d, 2H), 1.53 (m, 2H); LCMS (ACPI-pos) m/z 488.2 (M+H)$^+$.

Example 6

(S)—N-((3,4-dichlorophenyl)(H-pyrazol-5-yl)methyl)-2-(tetrahydro-2H-pyran-4-ylamino)-5,6-dihydropyrido[3,4-d]pyrimidine-7(8H)-carboxamide
(I-10)

Step 1:
N-((3,4-dichlorophenyl)(1H-pyrazol-5-yl)methyl)-2-(tetrahydro-2H-pyran-4-ylamino)-5,6-dihydropyrido[3,4-d]pyrimidine-7(8H)-carboxamide (50) was prepared from 1-(tetrahydro-2H-pyran-2-yl)-1H-pyrazole-5-carbaldehyde (CASRN 957483-88-4) in accord with steps 1-6 of example 1 to afford 94 mg (14%) of 50.

Step 2:
The title compound was resolved by chromatography on a Chiral Technologies AS-H SFC (21.2×250 mm) column eluting with 20% MeOH/hexane at a flow rate of 50 mL/min to afford I-10: $^1$H NMR (400 MHz, CDCl$_3$) δ 8.07 (s, 1H), 7.57 (d, 1H), 7.45 (d, 1H), 7.24 (dd, 1H), 7.12 (s, 1H), 6.07 (m, 2H), 5.96 (bs, 1H), 4.90 (d, 1H), 4.41 (m, 2H), 4.08-3.95 (m, 3H), 3.74 (m, 1H), 3.63 (m, 1H), 3.54 (dt, 2H), 2.67 (m, 2H), 2.01 (d, 2H), 1.52 (m, 2H); LCMS (ACPI-pos) m/z 504.4 (M+H)$^+$.

Example 7

(S)—N-((4-chloro-3-fluorophenyl)(1-methyl-1H-pyrazol-5-yl)methyl)-2-(tetrahydro-2H-pyran-4-ylamino)-5,6-dihydropyrido[3,4-d]pyrimidine-7(8H)-carboxamide (I-11)

Step 1:

N-((4-chloro-3-fluorophenyl)(1-methyl-1H-pyrazol-5-yl)methyl)-2-(tetrahydro-2H-pyran-4-ylamino)-5,6-dihydropyrido[3,4-d]pyrimidine-7(8H)-carboxamide (52) was prepared from 1-methyl-1H-pyrazole-5-carbaldehyde in accord with the procedure described for steps 1 to 6 of example 1 except in step 2 (4-chloro-3-fluorophenyl)magnesium bromide was used instead of (3,4-dichlorophenyl)magnesium bromide to afford 190 mg (28%) of 52.

Step 2:

The title compound was resolved by chromatography on a Chiral Technologies AS-H SFC (21.2×250 mm) column eluting with 20% MeOH/hexane at a flow rate of 50 mL/min to afford I-11: $^1$H NMR (400 MHz, CDCl$_3$) δ 8.08 (s, 1H), 7.57 (m, 2H), 7.43 (dd, 1H), 7.28 (d, 1H), 7.25 (dd, 1H), 6.91 (d, 1H), 6.21 (d, 1H), 5.79 (d, 1H), 4.43 (q, 2H), 3.92-3.81 (m, 3H), 3.73 (s, 3H), 3.61 (m, 2H), 3.35 (dt, 2H), 2.55 (t, 2H), 1.79 (d, 2H), 1.47 (m, 2H); LCMS (ACPI-pos) m/z 500.5 (M+H)$^+$.

Example 8

(S)—N-((4-chloro-3-fluorophenyl)(isoxazol-5-yl)methyl)-2-(tetrahydro-2H-pyran-4-ylamino)-5,6-dihydropyrido[3,4-d]pyrimidine-7(8H)-carboxamide (I-12)

(4-Chloro-3-fluorophenyl)(oxazol-5-yl)methanamine was prepared from 5-isoxazolecarboxaldehyde (CASRN 16401-14-2) in accord with the procedures in steps 1 and 2 of example 1 except in step 2, (3,4-dichlorophenyl)magnesium bromide was replaced with 4-chloro-3-fluorophenyl)magnesium bromide (53). N-((4-chloro-3-fluorophenyl)(isoxazol-5-yl)methyl)-2-(tetrahydro-2H-pyran-4-ylamino)-5,6-dihydropyrido[3,4-d]pyrimidine-7(8H)-carboxamide (54) was prepared (204 mg, 51%) in accord with the procedure steps 1 to 6 of example 1 except 53 was used in place of 22: $^1$H NMR (400 MHz, CDCl$_3$) δ 8.24 (d, 1H), 8.09 (s, 1H), 7.39 (t, 2H), 7.15 (dd, 1H), 7.07 (d, 1H), 6.38 (d, 1H), 6.17 (d, 1H), 5.29 (d, 1H), 4.89 (d, 1H), 4.38 (s, 2H), 4.05-3.95 (m, 3H), 3.73 (m, 2H), 3.58 (dt, 2H), 2.69 (t, 2H), 2.02 (d, 2H), 1.54 (m, 2H); LCMS (ACPI-pos) m/z 487.2 (M+H)$^+$.

Step 2:

The title compound was resolved by chiral chromatography utilizing the procedure in example 2 to afford 41 mg (16%) of I-12: $^1$H NMR (400 MHz, CDCl$_3$) δ 8.24 (d, 1H), 8.09 (s, 1H), 7.39 (t, 2H), 7.15 (dd, 1H), 7.07 (d, 1H), 6.38 (d, 1H), 6.17 (d, 1H), 5.29 (d, 1H), 4.89 (d, 1H), 4.38 (s, 2H), 4.05-3.95 (m, 3H), 3.73 (m, 2H), 3.58 (dt, 2H), 2.69 (t, 2H), 2.02 (d, 2H), 1.54 (m, 2H); LCMS (ACPI-pos) m/z 487.2 (M+H)$^+$.

Example 9

(S)—N-((3-fluoro-4-(trifluoromethoxy)phenyl)(oxazol-5-yl)methyl)-2-(tetrahydro-2H-pyran-4-ylamino)-5,6-dihydropyrido[3,4-d]pyrimidine-7(8H)-carboxamide (I-13)

Step 1:

A suspension of 4-bromo-2-fluoro-1-(trifluoromethoxy)benzene (582 g, 2247 mmol), Mg (54.6 g, 2247 mmol) and iodine in THF (10 mL) was heated at reflux for 2 h. The reaction was cooled to 0° C. and added to a solution of (E)-2-methyl-N-(oxazol-5-ylmethylene)propane-2-sulfinamide (300 g, 1498 mmol, step 1 of example 1) in toluene (10 mL) cooled to 0° C. The reaction was stirred at 0° C. for 30 min. The reaction was quenched with water and extracted with DCM. The organic layer was concentrated to afford crude N-((3-fluoro-4-(trifluoromethoxy)phenyl)(oxazol-5-yl)methyl)-2-methylpropane-2-sulfinamide (55) which was used without further purification.

Step 2:

To a solution of 55 (570 g, 1.5 mol) and DCM (10 mL) was added HCl (3.74 mL, 1.5 mol) and the solution stirred for 30 min. The reaction mixture was added dropwise to a stirred solution of ether. The solids were filtered and washed with Et$_2$O to afford 223 mg (47.6%) of (3-fluoro-4-(trifluoromethoxy)phenyl)(oxazol-5-yl)methanamine hydrochloride (56).

Step 3:

N-((3-fluoro-4-(trifluoromethoxy)phenyl)(oxazol-5-yl)methyl)-2-(tetrahydro-2H-pyran-4-ylamino)-5,6-dihydropyrido[3,4-d]pyrimidine-7(8H)-carboxamide (58) was prepared from 56 in accord with the procedure in step 6 of example 1 to afford 78 mg (21%) of 58.

Step 4:

The title compound was resolved by chiral chromatography on a Chiral Technologies AS-H SFC (21.2×250 mm) column eluting with 20% MeOH/hexane at a flow rate of 50 mL/min. Collection of the first peak afforded I-13: $^1$H NMR (400 MHz, CDCl$_3$) δ 8.10 (s, 1H), 7.80 (s, 1H), 7.30 (t, 1H), 7.20 (d, 1H), 7.13 (d, 1H), 6.95 (s, 1H), 6.35 (d, 1H), 5.13 (d, 1H), 4.90 (d, 1H), 4.38 (s, 2H), 4.38 (s, 2H), 4.05-3.95 (m, 3H), 3.70 (m, 2H), 2.53 (t, 2H), 2.10 (t, 2H), 2.02 (d, 2H), 1.55 (m, 2H); LCMS (ACPI-pos) m/z 537.1 (M+H)$^+$.

Example 10

(S)—N-(1-(4-chloro-3-fluorophenyl)-2-hydroxyethyl)-2-(tetrahydro-2H-pyran-4-ylamino)-5,6-dihydropyrido[3,4-d]pyrimidine-7(8H)-carboxamide (I-14)

Step 1:

To a solution of ethyl 2-(tert-butyldimethylsilyloxy)acetate (59, 20.0 g, 91.59 mmol), N,O-dimethylhydroxylamine hydrochloride (18.76 g, 192.3 mmol) and THF (800 mL) cooled to 0° C. was added dropwise via addition funnel isopropylmagnesium chloride (183.2 mL, 366.4 mmol) and the reaction was stirred for 3 h. The reaction was quenched with saturated NH$_4$Cl and extracted with EtOAc. The organic layer was dried, filtered and concentrated. The crude product was purified by passage through a SiO$_2$ plug eluting with 20% EtOAc/hexane to afford 15.12 g (70.7%) of 2-(tert-butyldimethylsilyloxy)-N-methoxy-N-methylacetamide (60).

Step 2:

To a solution of 60 (15.12 g, 64.79 mmol) and THF (50 mL) cooled to 0° C. was added dropwise (4-chloro-3-fluorophenyl)magnesium bromide (226.8 mL, 113.4 mmol) and the solution was stirred at 0° C. for 2 h. Saturated NH₄Cl was added and the reaction was extracted with DCM. The organic layer was separated, dried, filtered and concentrated. The crude product was purified by passage through a SiO₂ plug eluting with 5% EtOAc/hexane to afford 18.36 g (93.6%) of 2-(tert-butyldimethylsilyloxy)-1-(4-chloro-3-fluorophenyl)ethanone (62).

Step 3:

A solution of (R)-1-methyl-3,3-diphenylhexahydropyrrolo[1,2-c][1,3,2]oxazaborole (4.861 mL, 4.861 mmol) and borane diethylaniline (8.615 mL, 48.61 mmol) in MTBE (325 mL) was prepared at RT then heated to 40° C. for 15 min. A MTBE (250 mL) solution of 62 (14.72 g, 48.61 mmol) was added dropwise over 15 min via addition funnel to the above solution and the reaction was stirred at 40° C. for 30 min. The reaction was cooled and MeOH (15 mL) was added dropwise followed by 1M HCl (50 mL). The reaction was poured into water (150 mL) and extracted with DCM (2×150 mL). The combined organic fractions were dried (MgSO₄), filtered and concentrated. The crude product was purified by SiO₂ chromatography (Biotoge 65) eluting with an EtOAc/hexane gradient (2 to 5% EtOAc) to afford 16.50 g (91.1%) of (R)-2-(tert-butyldimethylsilyloxy)-1-(4-chloro-3-fluorophenyl)ethanol (64).

Step 4:

To a solution of 64 (13.50 g, 44.28 mmol) and THF (150 mL) cooled to 0° C. was added isoindoline-1,3-dione (7.167 g, 48.71 mmol) and PPh₃ (17.42 g, 66.42 mmol) followed by the dropwise addition of a 40% solution DEAD (26.15 mL, 66.42 mmol) in toluene. The reaction was warmed to RT and stirred for 20 h. The reaction was concentrated and dissolved in Et₂O (might require sonication). The solids were filtered and the filtrate was concentrated. The crude residue was purified by SiO₂ chromatography (Biotage 65) eluting with 10% EtOAc/hexane to afford 14.35 g of (74.67%) (S)-2-(2-(tert-butyldimethylsilyloxy)-1-(4-chloro-3-fluorophenyl)ethyl)isoindoline-1,3-dione (66).

Step 5:

To a solution of 66 (14.35 g, 33.07 mmol) and THF/MeOH (1:1, 400 mL) was added hydrazine monohydrate (4.138 g, 82.67 mmol) and the reaction was heated to 60° C. for 3 h. The reaction was diluted with THF and filtered. The solid was discarded and the filtrate was concentrated and the residue dissolved in ether (200 mL). The organic layer was washed twice with water (100 mL). The organic layer was then dried, filtered and concentrated. The crude product was purified by SiO₂ (Biotage 65) eluting with an EtOAc/hexane gradient (30 to 40% EtOAc) to afford 8.85 g (88.1%) of (S)-2-(tert-butyldimethylsilyloxy)-1-(4-chloro-3-fluorophenyl)ethanamine (68).

Step 6:

(S)—N-(2-(tert-butyldimethylsilyloxy)-1-(4-chloro-3-fluorophenyl)ethyl)-2-(tetrahydro-2H-pyran-4-ylamino)-5,6-dihydropyrido[3,4-d]pyrimidine-7(8H)-carboxamide (70) was prepared from 68 in accord with the procedure described in step 6 of example 1 (1.236 g, 60%).

Step 7:

To a solution of 70 (1.236 g, 2.191 mmol) in 15% MeOH/DCM (75 mL) was added slowly HCl (2.19 mL, 8.763 mmol) and the reaction was stirred at RT for 20 min. Saturated NH₄Cl was added slowly and the resulting solution extracted with DCM. The organic layer was separated and concentrated. The crude residue was purified by SiO₂ chromatography eluting with an MeOH/DCM gradient (4 to 5% MeOH) to afford 0.841 g (85.3%) of I-14: ¹H NMR (400 MHz, CDCl₃) δ 8.09 (s, 1H), 7.38 (t, 1H), 7.14 (dd, 1H), 7.08 (d, 1H), 5.28 (d, 1H), 4.97 (m, 1H), 4.89 (d, 1H), 4.39 (s, 2H), 4.06-3.90 (m, 4H), 3.86 (m, 1H), 3.76-3.60 (m, 2H), 3.55 (dt, 2H), 2.69 (t, 2H), 2.26 (t, 1H), 2.02 (d, 2H), 1.53 (m, 2H); LCMS (ACPI-pos) m/z 450.0 (M+H)⁺.

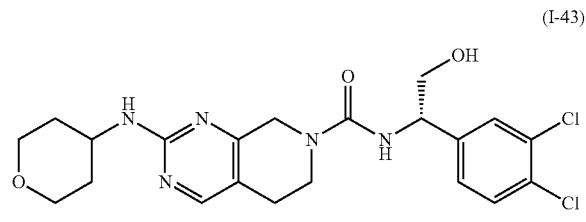 [SMILES: O=C(N[C@H](CO)c1ccc(Cl)c(Cl)c1)N1CCc2cnc(NC3CCOCC3)nc2C1]

(I-43)

(S)—N-(1-(3,4-dichlorophenyl)-2-hydroxyethyl)-2-(tetrahydro-2H-pyran-4-ylamino)-5,6-dihydropyrido[3,4-d]pyrimidine-7(8H)-carboxamide (I-43)

(R)-2-(tert-butyldimethylsilyloxy)-1-(3,4-dichlorophenyl)ethanol (69) was prepared from 59 in accord with the procedures in steps 1 to 5 except in step 2, (4-chloro-3-fluorophenyl)magnesium bromide was replaced with (3,4-dichlorophenyl)magnesium bromide. Condensation of 69 and 28 was carried out in accord with the procedure described in step 6 of example 1 to afford (S)—N-(2-(tert-butyldimethylsilyloxy)-1-(3,4-dichlorophenyl)ethyl)-2-(tetrahydro-2H-pyran-4-ylamino)-5,6-dihydropyrido[3,4-d]pyrimidine-7(8H)-carboxamide (69a).

To a solution of 69a (0.175 g, 0.301 mmol) and DCM (3 mL) was added 6M HCl (0.0110 g, 0.301 mmol) in IPA and the reaction was stirred for 2 h and then poured into satd. aq. Na₂CO₃ and extracted with DCM. The combined organic fractions were dried (MgSO₄), filtered and concentrated in vacuo. The crude product was purified by SiO₂ chromatography eluting with a DCM/MeOH gradient (500:30 to 500:45) to afford 0.030 g (21.3%) of I-43: MS m/z (APCI-pos) M+1=466.

Example 11

N—((S)-(3-fluoro-4-(trifluoromethyl)phenyl)((R)-pyrrolidin-2-yl)methyl)-2-(isopropylamino)-5,6-dihydropyrido[3,4-d]pyrimidine-7(8H)-carboxamide (I-15)

N'-isopropyl-5,6,7,8-tetrahydropyrido[3,4-d]pyrimidin-2-amine hydrochloride (72)

Step a:

To a solution of propan-2-amine (11.6 mL, 136 mmol) and DMF (70 mL) at RT under nitrogen was added DIPEA (23.8 mL, 136 mmol) followed by pyrazole guanadine (20 g, 136 mmol). The reaction was stirred overnight then the flask was fitted with a short path distillation head and the solvent and residual DIPEA were removed under high vacuum at 60° C. Residual DMF was efficiently removed by stirring the oil with chloroform (100 mL). The N-isopropylguanidine oiled out and floated to the top. The CHCl₃ solution was removed with a separatory funnel and discarded. There was obtained 34 g (69, 96% purity, 93% yield) as an orange oil which was a 1:1 chloroform solvate which was concentrated under high vacuum and used without further purification.

Step b:

To a solution of 21 (11.0 g, 43.25 mmol), EtOH (25 mL), and sodium ethoxide (40.37 mL, 108.1 mmol) was added a solution of 2-isopropylguanidine hydrochloride-chloroform (1:1 complex, 11.12 g, 43.25 mmol) in EtOH (150 mL) and the solution stirred at RT for 18 h. The solution was concentrated in vacuo and the residue suspended in water (500 mL) and the aqueous solution neutralized by adding satd. aq. NH$_4$Cl (500 mL). The solution was extracted with EtOAc (3×250 mL). The combined extracts were dried (Na$_2$SO$_4$), filtered and concentrated in vacuo to afford 11.6 g (78%, 85% pure) of tert-butyl 2-(N'-isopropyl-guanidino)-5,8-dihydro-6H-pyrido[3,4-d]pyrimidine-7-carboxylate (70).

Step c:

To a solution of 70 (15.0 g, 43.6 mmol), DCM (40 mL) and MeOH (40 mL) under nitrogen atmosphere was added 4N HCl in dioxane (50.3 mL, 210 mmol) and the resulting solution stirred for 18 h at 40° C. The solution was concentrated in vacuo to afford 11.4 g (90% purity, 95% yield) of 72 as a hard dark red solid: MS m/z (APCI-pos) M+1=193.1.

Step 1:

To a solution of (R)-1-(tert-butoxycarbonyl)pyrrolidine-2-carboxylic acid (11.93 g, 55.42 mmol) and DCM (70 mL) cooled to –15° C. was added a solution of NMM (5.79 g, 57.3 mmol), ethyl carbonochloridate (12.03 g, 110.8 mmol) and DCM (50 mL) and the mixture was stirred for 15 min. Additional NMM (11.59 g, 114.5 mmol) was added followed by portion wise addition of O,N-dimethylhydroxylamine hydrochloride (10.81 g, 110.8 mmol). The reaction was stirred at RT for 18 h. The reaction was poured onto water and extracted with DCM. The organic layer was dried, filtered, and concentrated and the crude residue was purified by SiO$_2$ chromatography eluting with EtOAc/hexane (1:1) to afford 9.74 g (68.03%) of (R)-tert-butyl 2-(methoxy(methyl)carbamoyl)pyrrolidine-1-carboxylate (74).

Step 2:

To a solution of 4-bromo-2-fluoro-1-(trifluoromethyl)benzene (4.854 g, 19.98 mmol) and ether (50 mL) cooled to –78° C. was added butyl lithium (7.990 mL, 19.98 mmol) slowly over 10 min. The reaction was transferred via cannula to a solution of 74 (4.30 g, 16.65 mmol) in THF (50 mL) cooled to –78° C. The reaction was stirred for 10 min after all aryl lithium was added. The reaction was quenched with water and extracted with DCM. The organic layer was concentrated and the crude product purified by SiO$_2$ chromatography eluting with an EtOAc/hexane (1 to 5% EtOAc). A close running impurity was not removed by this purification. A SiO$_2$ column was run eluting with an Et$_2$O/hexane gradient (1 to 3% Et$_2$O). The impurity was still present and the compound was finally purified on a SP4 reverse phase column chromatography eluting with MeCN/water gradient (65 to 100% MeCN) to afford 2.105 g (33.2%) of (R)-tert-butyl 2-(3-fluoro-4-(trifluoromethyl)benzoyl)-pyrrolidine-1-carboxylate (76).

Step 3:

To a solution of 76 (1.797 mg, 0.004973 mmol) and MeOH (50 mL) cooled to 0° C. was added NaBH$_4$ (0.1882 mg, 0.004973 mmol) and reaction was stirred at 0° C. for 1 h. Ice was slowly added to the reaction mixture and the resulting mixture was stirred for 10 min. The mixture was extracted with DCM and concentrated to afford crude (R)-tert-butyl 2-((4-chloro-3-(trifluoromethyl)phenyl)(hydroxy)methyl)pyrrolidine-1-carboxylate (78) which was used without further purification.

Step 4:

(R)-tert-butyl 2-((S)-(1,3-dioxoisoindolin-2-yl)(3-fluoro-4-(trifluoromethyl)phenyl)methyl)pyrrolidine-1-carboxylate (80) was prepared from 78 in accord with the procedure in step 4 of example 10 to afford 1.036 g (42%) of 80.

Step 5:

(R)-tert-butyl 2-((S)-amino(3-fluoro-4-(trifluoromethyl)phenyl)methyl)pyrrolidine-1-carboxylate (82) was prepared from 80 in accord with the procedure described for step 5 of example 10: yield 596 mg (78%).

Step 6:

(R)-tert-butyl 2-((S)-(3-fluoro-4-(trifluoromethyl)phenyl)(2-(isopropylamino)-5,6,7,8-tetrahydropyrido[3,4-d]pyrimidine-7-carboxamido)methyl)pyrrolidine-1-carboxylate (84) was prepared from 82 and 72 in accord with the procedure described in step 6 of example 1 except 26 was replaced with 72 to afford 150 mg (58%) of 84.

Step 7:

To a solution of 84 (149 mg, 0.257 mmol) and DCM (2 mL) was added TFA (19.8 µL, 0.257 mmol) and the reaction was stirred at RT for 7 h. The reaction was concentrated in vacuo and the resulting residue partitioned between DCM and saturated NaHCO$_3$. The mixture was stirred for 15 min. The organic layer was separated, dried, filtered, and concentrated to afford 82 mg (66.5%) of I-15: $^1$H NMR (400 MHz, CDCl$_3$) δ 8.09 (s, 1H), 7.53 (t, 1H), 7.21 (m, 2H), 5.52 (d, 1H), 4.79 (m, 2H), 4.38 (m, 2H), 4.11 (m, 1H), 3.72 (m, 1H), 3.58 (m, 1H), 3.46 (m, 1H), 2.89 (m, 2H), 2.66 (t, 2H), 1.75-1.59 (m, 3H), 1.47 (m, 1H), 1.23 (d, 6H); LCMS (ACPI-pos) m/z 481.2 (M+H)$^+$.

N—((S)-(3,4-dichlorophenyl)((R)-pyrrolidin-2-yl)methyl)-2-(isopropylamino)-5,6-dihydropyrido[3,4-d]pyrimidine-7(8H)-carboxamide (I-49) was prepared analogously except in step 2,4-bromo-2-fluoro-1-(trifluoromethyl)benzene was replaced with 4-bromo-3,4-dichloro-benzene. The product was purified by SiO$_2$ chromatography eluting with DCM/MeOH containing 1% NH$_4$OH (500:30 to 500:50) to afford 0.120 g (29.2%) of I-49: MS m/z (APCI-pos) M+1=463.

N—((S)—((S)-1-acetylpyrrolidin-2-yl)(4-chloro-3-fluorophenyl)methyl)-2-(isopropylamino)-5,6-dihydropyrido[3,4-d]pyrimidine-7(8H)-carboxamide
(I-87)

N—((S)-(4-chloro-3-fluorophenyl)((S)-pyrrolidin-2-yl)methyl)-2-(isopropylamino)-5,6-dihydropyrido[3,4-d]pyrimidine-7(8H)-carboxamide hydrochloride (83) was prepared as described above except in step 2,4-bromo-2-fluoro-1-(trifluoromethyl)benzene was replaced with 4-bromo-1-chloro-2-fluorobenzene.

A solution of 83 and Ac$_2$O (6.45 µL, 0.0683 mmol), TEA (25.9 µL, 0.186 mmol) and DCM (5 mL) was stirred for 1 h then poured into water and extracted with DCM. The combined organic extracts were dried (MgSO$_4$), filtered, and concentrated in vacuo. The crude product was purified by SiO$_2$ chromatography eluting with DCM/MeOH (500:10) to afford 0.020 g (65.9%) of I-87: MS m/z (APCI-pos) M+1=489.

(R)—N-(1-(4-fluorophenyl)ethyl)-2-(isopropylamino)-5,6-dihydropyrido[3,4-d]pyrimidine-7(8H)-carboxamide (I-81)

To a solution of (R)-1-(4-fluorophenyl)ethanamine (0.122 g, 0.874 mmol, CASRN 374898-01-8) and DCM cooled to 0° C. was added sequentially TEA (0.366 mL, 2.62 mmol) and CDI (0.142 g, 0.874 mmol) an the solution stirred for 30 min. The solution was added to a solution of DCM (5 mL), 72 (0.200 g, 0.874 mmol) and TEA (0.366 mL, 2.62 mmol) and stirred for 18 h. The reaction mixture was poured into water and extracted with DCM. The combined organic extracts were dried (MgSO$_4$), filtered, and concentrated in vacuo. The crude product was purified by SiO$_2$ chromatography eluting with DCM/MeOH (20:1) to afford 0.010 g (3.2%) of I-81: MS m/z (APCI-pos) M+1=358.

(R)—N-(1-(3,4-dichlorophenyl)ethyl)-2-(1-methylpiperidin-4-ylamino)-5,6-dihydropyrido[3,4-d]pyrimidine-7(8H)-carboxamide (I-83)

N-(1-methylpiperidin-4-yl)-5,6,7,8-tetrahydropyrido[3,4-d]pyrimidin-2-amine dihydrochloride (73) was in accord with the procedures in steps 3 to 5 of example 1 except in step 3 tetrahydro-2H-pyran-4-amine was replaced with 1-methylpiperidin-4-amine. The title compound was prepared in accord with the procedure in step 6 of example 1 except 28 was replaced by 73 and 22 was replaced by 185. The crude product was purified by SiO$_2$ chromatography with a DCM/MeOH (containing 1% NH$_4$OH) gradient (500:40) to afford 0.300 g (69.1%) of I-81: MS m/z (APCI-pos) M+1=463.

(R)—N-(1-(3,4-dichlorophenyl)ethyl)-2-(2-morpholinoethylamino)-5,6-dihydropyrido[3,4-d]pyrimidine-7(8H)-carboxamide (I-88)

N-(2-morpholinoethyl)-5,6,7,8-tetrahydropyrido[3,4-d]pyrimidin-2-amine dihydrochloride (109) was prepared in accord with the procedures in steps 3 to 5 of example 1 except in step 3, tetrahydro-2H-pyran-4-amin was replaced with by 2-morpholinoethanamine. The title compound was prepared in accord with the procedure in step 6 of example 1 except 28 was replaced by 109 and 22 was replaced by 185. The crude product was purified by SiO$_2$ chromatography with a DCM/MeOH gradient (500:15 to 500:25) to afford 0.120 g (25.0%) of I-88: MS m/z (APCI-pos) M+1=479.

Example 12

(S)—N-(1-(3,4-dichlorophenyl)-2-hydroxyethyl)-2-(isopropylamino)-5,6-dihydropyrido[3,4-d]pyrimidine-7(8H)-carboxamide (I-16)

Step 1:
To a solution of 1-(3,4-dichlorophenyl)-2-hydroxyethanone (11.86 g, 57.843 mmol, CASRN 113337-38-5), imidazole (5.91 g, 86.764 mmol), and DMAP (0.71 g, 5.7843 mmol) in DMF (100 mL) cooled to 0° C. was added slowly tert-butylchlorodimethylsilane (10.898 g, 72.304 mmol) and the reaction was stirred at RT for 18 h. Water was added and the mixture was extracted with ether. The organic layer was dried, filtered, and concentrated. The crude residue was purified by passage through a SiO$_2$ plug eluting with an EtOAc/hexane gradient (10 to 50% EtOAc) to afford 12.15 g (82.0%) of 2-(tert-butyldimethylsilyloxy)-1-(3,4-dichlorophenyl)ethanone (84). Conversion of 84 to (S)-2-(tert-butyldimethylsilyloxy)-1-(4-chloro-3-fluorophenyl)ethanamine (85) was carried out in accord with the procedure in steps 3 to 5 of example 10 except in step 3,2-(tert-butyldimethylsilyloxy)-1-(4-chloro-3-fluorophenyl)ethanone (62) was replaced with 84. The title compound was prepared from 85 in accord with the procedure in steps 6 and 7 of example 10 except in step 6, 72 was used in place of 26 and 85 was used in place of 68 to afford 136 mg (56%) of I-16: $^1$H NMR (400 MHz, CDCl$_3$) δ 8.07 (s, 1H), 7.42 (m, 2H), 7.18 (d, 1H), 5.32 (m, 1H), 4.95 (m, 1H), 4.81 (d, 1H), 4.38 (s, 2H), 4.10 (m, 1H), 3.92 (m, 1H), 3.83 (m, 1H), 3.75-3.60 (m, 2H), 2.67 (t, 2H), 2.55 (bs, 1H), 1.22 (d, 6H); LCMS (ACPI-pos) m/z 426.4 (M+H)$^+$.

Example 13

(S)-3-(4-Chloro-3-fluoro-phenyl)-1-(2-isopropylamino-5,8-dihydro-6H-pyrido[3,4-d]pyrimidin-7-yl)-4-methylamino-butan-1-one (I-17)

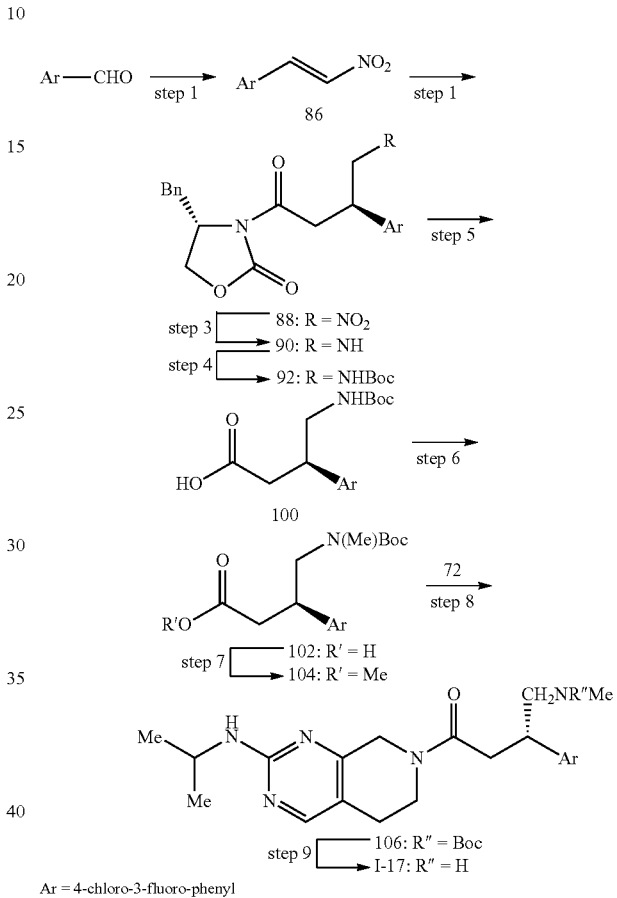

Ar = 4-chloro-3-fluoro-phenyl

Step 1:
To a solution of 4-chloro-3-fluorobenzaldehyde (10 g, 63.07 mmol) and ammonium acetate (4.861 g, 63.07 mmol) in HOAc (50 mL) was added nitromethane (14.12 mL, 252.3 mmol) and the reaction mixture was heated to reflux (120° C. oil bath) for 18 h. The reaction was cooled and diluted with water. The reaction mixture was filtered and solids were purified by SiO$_2$ chromatography eluting with a EtOAc/hexane gradient (0 to 5% EtOAc) to afford 1.736 g (13.65%) of (E)-1-chloro-2-fluoro-4-(2-nitrovinyl)benzene (86).

Step 2:
To a solution of THF solution of LDA (9.70 mL, 17.46 mmol, 1.8 M in THF) and THF (40 mL) cooled to −78° C. was added dropwise a solution of (S)-3-acetyl-4-benzyloxazolidin-2-one (3.827 g, 17.46 mmol) in THF. The reaction was stirred at −78° C. for 1 h. A solution of (E)-1-chloro-2-fluoro-4-(2-nitrovinyl)benzene (3.06 g, 15.18 mmol) in THF (40 mL) was then added dropwise and the reaction was stirred at −78° C. for 1 h. The reaction was quenched with satd. aq. NH$_4$Cl and extracted with DCM. The solution was evaporated and the crude product was purified by SiO$_2$ chromatography eluting with a EtOAc/hexane gradient (20 to 50%

EtOAc) to afford 2.673 g of product. Mixed fractions were combined and rechromatographed using similar conditions to afford another 330 mg of product. The combined batches afford 3.003 g (47.0%) of (S)-4-benzyl-3-((S)-3-(4-chloro-3-fluorophenyl)-4-nitrobutanoyl)oxazolidin-2-one (88).

Step 3:
To a solution of 88 (1.55 g, 3.68 mmol) in EtOAc/EtOH (1:1, 50 mL) was added a Raney Nickel suspension (0.316 g, 3.68 mmol) and the reaction mixture was purged with nitrogen then placed under 40 psi hydrogen for 20 h. A second aliquot of Raney Ni suspension (1 mL) was added and the reaction was placed under hydrogen pressure for another 24 h. A third aliquot of Raney Ni was added (1 mL) and the reaction was placed under hydrogen pressure of 45 psi for 24 h. The reaction was filtered through a plug of CELITE® and the filtrate was concentrated. The crude product was purified by $SiO_2$ chromatography eluting with an EtOAc/hexane gradient (10 to 30% EtOAc) to afford 400 mg (50.8%) of (S)-4-(4-chloro-3-fluorophenyl)pyrrolidin-2-one (90).

Step 4:
A solution of 90 (621 mg, 2.91 mmol), $Boc_2O$ (761 mg, 3.49 mmol), DMAP (35.5 mg, 0.291 mmol) and MeCN (10 mL) was stirred at RT for 1 h. The reaction was concentrated and diluted with $Et_2O$. The organic phase was extracted with 1N HCl followed by brine. The organic layer was dried, filtered and concentrated in vacuo to afford 912 mg (100%) of (S)-tert-butyl 4-(4-chloro-3-fluorophenyl)-2-oxopyrrolidine-1-carboxylate (92) which was used without addition purification.

Step 5:
To a solution of 92 (912 mg, 2.91 mmol) in $THF/H_2O$ (2:1; 15 mL) was added solid LiOH (209 mg, 8.72 mmol). The reaction mixture was stirred at RT for 18 h. The reaction mixture was acidified with 1M HCl to ca. pH 2-3 then twice extracted with EtOAc. The combined EtOAc layers were dried ($Na_2SO_4$), filtered and concentrated to afford 902 mg (93.5%) of (S)-4-(tert-butoxycarbonylamino)-3-(4-chloro-3-fluorophenyl)butanoic acid (100) which was used without further purification.

Step 6:
Powdered KOH (1525 mg, 27.19 mmol) was added to DMSO (3 mL) and the resulting mixture was stirred for 5 min at RT. To this solution was added 100 (902 mg, 2.719 mmol) followed immediately by iodomethane (1.35 mL, 21.75 mmol). The resulting mixture was stirred at RT for 5 h. The reaction mixture was diluted with EtOAc and washed sequentially with $H_2O$, 2M HCl and brine. The organic layer was dried, filtered, and concentrated. The crude product was purified by $SiO_2$ chromatography eluting with 10:1 DCM/EtOAc. The impure product therefrom was rechromatographed under similar conditions to afford 586 mg (59.90%) of (S)-methyl 4-(tert-butoxycarbonyl(methyl)amino)-3-(4-chloro-3-fluorophenyl)butanoate (102).

Step 7:
To a solution of 102 (632 mg, 1.756 mmol) in 4:1 $THF/H_2O$ (5 mL) was added 3M aq. LiOH (5.855 mL, 17.56 mmol). The reaction mixture was stirred at RT for 4 h. The aqueous solution was acidified with 2N HCl to ca. pH 2-3 and then twice extracted with EtOAc. The combined extracts were dried ($Na_2SO_4$), filtered, and concentrated to afford 598 mg (98.46%) of (S)-4-(tert-butoxycarbonyl(methyl)amino)-3-(4-chloro-3-fluorophenyl)butanoic acid (104).

Step 8:
To a solution of 72 (102 mg, 0.401 mmol) and 104 (126 mg, 0.364 mmol) and HATU (152 mg, 0.401 mmol) in DMF (5 mL) was added DIPEA (190 µL, 1.09 mmol). The reaction mixture was stirred at RT for 18 h. The reaction mixture was diluted with EtOAc and washed with 1M HCl, satd. aq. $NaHCO_3$, dried ($Na_2SO_4$), filtered and concentrated. The crude product was purified by reverse phase column chromatography (SP4) eluting with a $MeCN/H_2O$ gradient (5 to 95% MeCN) to afford 102 mg (53.8%) of (S)-tert-butyl 2-(4-chloro-3-fluorophenyl)-4-(2-(isopropylamino)-5,6-dihydropyrido[3,4-d]pyrimidin-7(8H)-yl)-4-oxobutyl(methyl)carbamate (106).

Step 9:
To a solution of 106 (106 mg, 0.204 mmol) in MeOH (2 mL) and a small amount of DCM was added 4 M HCl in dioxane (764 µL, 3.06 mmol). The reaction was stirred at RT for 4 h. The reaction was concentrated and purified by reverse phase column chromatography (SP4) eluting with a $MeCN/H_2O$ gradient (0-80% MeCN) to afford 50.7 mg (54.5%) of I-17: LCMS (ACPI-pos) m/z 420.3 $(M+H)^+$.

Example 14

N-((1S,2S)-1-(2-fluoro-3-(trifluoromethyl)phenyl)-2-hydroxypropyl)-2-(isopropylamino)-5,6-dihydropyrido[3,4-d]pyrimidine-7(8H)-carboxamide (I-18)

Step 1:
(S)-Methyl 2-hydroxypropanoate (30.0 g, 288 mmol) and pyrrolidine (22.5 g, 317 mmol) were stirred at RT for 3 d. The crude product was purified by passing through a $SiO_2$ plug eluting with 80% EtOAc/hexane to afford 41.1 g (99.6%) (S)-2-hydroxy-1-(pyrrolidin-1-yl)propan-1-one (108).

Step 2:
To a solution of 108 (41.1 g, 287.0 mmol), imidazole (29.31 g, 430.6 mmol), and DMAP (3.507 g, 28.70 mmol) in DMF (100 mL) was added slowly tert-butylchlorodimethylsilane (54.08 g, 358.8 mmol) and the reaction was stirred at RT for 18 h. Water was added and mixture was extracted with $Et_2O$. The organic layer was dried, filtered, and concentrated. The resulting residue was purified by passing through a $SiO_2$ plug eluting with an EtOAc/hexane gradient (10 to 50% EtOAc) to afford 56.93 g (77.04%) of (S)-2-(tert-butyldimethylsilyloxy)-1-(pyrrolidin-1-yl)propan-1-one (110).

Step 3:
To a solution of 4-bromo-2-fluoro-1-(trifluoromethyl)benzene (4.93 g, 20.3 mmol) in THF (50 mL) cooled to −78° C. was added slowly over 10 min butyl lithium (8.11 mL, 20.3 mmol, 2.5 M in hexanes). The reaction was transferred via cannula to a cooled solution (−78° C.) of 110 (4.35 g, 16.9 mmol) in THF (50 mL). The reaction was stirred for 10 min after all aryl lithium was added. The reaction was quenched with $H_2O$ and extracted with DCM. The organic layer was concentrated and the resulting residue was purified by $SiO_2$ chromatography eluting with an EtOAc/hexane gradient (1 to 5% EtOAc) to afford impure (S)-2-(tert-butyldimethylsilyloxy)-1-(2-fluoro-3-(trifluoromethyl)phenyl)propan-1-one (112) which was used without further purification.

Step 4:
To a solution of 112 (1.374 g, 3.921 mmol) and $Et_2O$ (20 mL) cooled to 0° C. was added a solution of zinc borohydride (8.46 mL, 1.176 mmol) was added and the reaction was stirred for 2 h. Water was added slowly and the mixture was extracted with ether. The organic layer was washed with water and brine then dried, filtered, and concentrated to afford (1R,2S)-2-(tert-butyldimethylsilyloxy)-1-(2-fluoro-3-(trifluoromethyl)phenyl)propan-1-ol (114) which was used without additional purification.

Step 5:
N-((1S,2R)-2-(tert-butyldimethylsilyloxy)-1-(2-fluoro-3-(trifluoromethyl)phenyl)propyl)-2-(isopropylamino)-5,6-dihydropyrido[3,4-d]pyrimidine-7(8H)-carboxamide (116)

was prepared from 114 in accord with the procedure described in steps 4 to 6 of example 10 except in step 6, 72 was used in place of 28 to afford 116 which was used without additional purification.

Step 6:

To a solution of 116 (533 mg, 0.936 mmol) and THF (10 mL) cooled to 0° C. was added TBAF (1.310 mL, 1.31 mmol) and reaction was stirred at RT for 45 min. The reaction was poured onto water and extracted with DCM. The organic layer was concentrated and the crude product was purified by $SiO_2$ chromatography eluting with 1% MeOH/DCM to afford 269 mg (63.1%) of I-18: LCMS (ACPI-pos) m/z 420.3 $(M+H)^+$.

Example 15

N-((1S,2R)-1-(2-fluoro-3-(trifluoromethyl)phenyl)-2-hydroxypropyl)-2-(isopropylamino)-5,6-dihydropyrido[3,4-d]pyrimidine-7(8H)-carboxamide (I-19)

Step 1:

To a solution of I-18 (30.3 mg, 0.06653 mmol) and THF (50 mL) cooled to 0° C. was added 4-nitrobenzoic acid (22.24 mg, 0.1331 mmol) and $PPh_3$ (26.17 mg, 0.09979 mmol) followed by the dropwise addition of DEAD (39.28 μL, 0.09979 mmol, 40% solution in toluene). The reaction was warmed to RT and stirred for 20 h then concentrated to dryness. The crude product was purified by reverse phase column chromatography eluting with a $MeCN/H_2O$ gradient (5 to 95% MeCN) which afforded an impure product which was used in step 2 without further purification.

Step 2:

To a solution of (1S,2R)-1-(2-fluoro-3-(trifluoromethyl)phenyl)-1-(2-(isopropylamino)-5,6,7,8-tetrahydropyrido[3,4-d]pyrimidine-7-carboxamido)propan-2-yl 4-nitrobenzoate (40 mg, 0.040 mmol) in MeOH (1 mL) was added 2M $K_2CO_3$ (40 μL, 0.079 mmol) at RT. The solution was stirred at RT for 30 min. Water was added and reaction was extracted with DCM. The organic layer was concentrated and the resulting residue was purified by reverse phase column chromatography (SP4) eluting with a $MeCH/H_2O$ gradient (5 to 95% MeCN). The recovered product was further purified by $SiO_2$ chromatography eluting with a MeOH/EtOAc (1 to 3% MeOH) to afford 0.6 mg (3.3%) of I-19: LCMS (ACPI-pos) m/z 420.3 $(M+H)^+$.

Example 16

N—((S)-1-(3-chloro-4-fluorophenyl)-2-hydroxyethyl)-5-hydroxy-2-(isopropylamino)-5,6-dihydropyrido[3,4-d]pyrimidine-7(8H)-carboxamide (I-20)

Step 1:

A solution of ethyl 2-(benzylamino)acetate (40 g, 207 mmol) and $NaHCO_3$ (20.9 g, 248 mmol) in THF (400 mL) and water (30 mL) was heated to 50° C. 1-chloropropan-2-one (23.9 g, 259 mmol) was added and the reaction was stirred at 50° C. for 2 d. Water was added the solution extracted with hexanes. The organic layer was separated, dried, filtered, and concentrated to afford crude ethyl 2-(benzyl(2-oxopropyl)amino)acetate (118) which without further purification Step 2:

A suspension of 118 (51.6 g, 207.0 mmol), $Boc_2O$ (47.43 g, 217.3 mmol), and Pd/C (3.5 g, 32.89 mmol) and IPA (200 mL) and were stirred under hydrogen (15 psi) for 18 h. The reaction was filtered through a pad of CELITE and the filtrate was concentrated. The crude product was purified by passing through a $SiO_2$ plug eluting with an EtOAc/hexane gradient (20 to 25% EtOAc) to afford 26.41 g (49.21%) of ethyl 2-(tert-butoxycarbonyl(2-oxopropyl)amino)acetate (120).

Step 3:

To a cooled solution (0° C.) of potassium tert-butoxide (112.0 mL, 112.0 mmol) was added via addition funnel over 1.5 h, a solution 120 (26.41 g, 101.9 mmol) in ether (200 mL). The mixture was stirred for an additional 3 h. The precipitate was filtered off and washed with ether. The solid was dissolved in water and the pH was adjusted to ca. 4 with HOAc. The solids were filtered, washed with water, and dried to afford 13.16 g (60.6%) of tert-butyl 3,5-dioxopiperidine-1-carboxylate (122).

Step 4:

To a solution of 122 (12.39 g, 58.11 mmol) in toluene (120 mL) was added 1,1-dimethoxy-N,N-dimethylmethanamine (11.62 mL, 87.16 mmol) and the reaction was heated to 80° C. for 30 min then at 50° C. for 1 h. The reaction was concentrated to afford 16.5 g (105%) of crude tert-butyl 4-((dimethylamino)methylene)-3,5-dioxopiperidine-1-carboxylate (124) which was used without additional purification.

Step 5:

To a solution of 124 (1.88 g, 5.04 mmol) and DIPEA (0.905 mL, 5.05 mmol) in toluene (10 mL) was added 69 (1.80 g, 5.04 mmol) was added and stirred at reflux for 1.5 h. The reaction was concentrated and suspended in water (250 mL) and saturated $NH_4Cl$ (250 mL) was added. The mixture was extracted with EtOAc (3×250 mL). The organic layers were combined, dried, filtered and concentrated. The crude product was purified by $SiO_2$ chromatography eluting with 2% MeOH/DCM to afford 0.605 g (27.8%) of tert-butyl 2-(isopropylamino)-5-oxo-5,6-dihydropyrido[3,4-d]pyrimidine-7(8H)-carboxylate (126).

Step 6:

To a solution of 126 (400 mg, 1.31 mmol) in MeOH (1 mL) cooled to 0° C. was added slowly $NaBH_4$ (49.4 mg, 1.31 mmol) and the reaction was stirred at RT for 15 min. The reaction was quenched with water and the mixture was extracted with DCM. The organic layer was dried, filtered and concentrated to afford 400 mg (99%) of tert-butyl 5-hydroxy-2-(isopropylamino)-5,6-dihydropyrido[3,4-d]pyrimidine-7(8H)-carboxylate (128) which was used with out additional purification.

Step 7:

A solution of 128 (400 mg, 1.30 mmol) and 4 N HCl in dioxane (4 mL) was stirred for 1 h. The reaction was concentrated to afford crude 2-(isopropylamino)-5,6,7,8-tetrahydropyrido[3,4-d]pyrimidin-5-ol hydrochloride (130) which was used without additional purification.

Step 8:

N—((S)-2-(tert-butyldimethylsilyloxy)-1-(3-chloro-4-fluorophenyl)ethyl)-5-hydroxy-2-(isopropylamino)-5,6-dihydropyrido[3,4-d]pyrimidine-7(8H)-carboxamide (132) was prepared from 130 in accord with the procedure in step 6 of example 1 except (S)-2-(tert-butyldimethylsilyloxy)-1-(3-chloro-4-fluorophenyl)ethanamine replaced 22 and 72 replaced 28 to afford 170 mg (34.3%) of 132.

Step 9:

To a solution of 132 (35 mg, 0.0650 mmol) in THF (1 mL) cooled to 0° C. was added TBAF (91 μL, 0.0911 mmol) and reaction was stirred at RT for 2 h. The reaction was concentrated and the resulting residue was purified on a reverse phase column (SP4) eluting with a $MeCN/H_2O$ gradient (5 to 95% MeCN) to afford 17.2 mg (62.4%) of I-20: LCMS (ACPI-pos) m/z 424.1 (M+H)+.

Example 17

N—((R)-1-(4-chloro-3-fluorophenyl)ethyl)-2-((S)-1-hydroxypropan-2-ylamino)-5,6-dihydropyrido[3,4-d]pyrimidine-7(8H)-carboxamide (I-21)

Step a:
To a solution of 1H-pyrazole-1-carboximidamide hydrochloride (29.27 g, 199.7 mmol) and DMF (100 mL) at RT under a nitrogen atmosphere was added sequentially DIPEA (46.38 mL, 266.3 mmol) and a DMF (15 mL) solution of (S)-2-aminopropan-1-ol (10.00 g, 133.1 mmol) and the reaction was stirred overnight. $Et_2O$ (150 mL) was added, and stirred for 10 min. The ether was decanted and concentrated in vacuo to afford 19.8 g (98%) of (S)-1-(1-hydroxypropan-2-yl)guanidine (134) as a orange oil which was used without additional purification: MS m/z (APCI-pos) M+1=118.1.

Step b:
A 500 mL scintillation vial was charged with 21 (49.18 g, 131.5 mmol), EtOH (100 mL) and 134 (19.75 g, 131.5 mmol) then stirred at 45° C. for 10 min. When the solution became homogeneous sodium ethoxide (98.18 mL, 263.0 mmol, 21% in EtOH) was added and the reaction stirred at 50° C. for 18 h. The crude was concentrated and resuspended in EtOAc. The organic phase was washed with brine, dried ($Na_2SO_4$), filtered and concentrated to afford 45 g (99%, 90% purity) of (S)-tert-butyl 2-(1-hydroxypropan-2-ylamino)-5,6-dihydropyrido[3,4-d]pyrimidine-7(8H)-carboxylate (136) as an orange solid: MS m/z (APCI-pos) M+1=309.1.

Step c:
To a solution of 136 (39.5 g, 128 mmol), DCM (100 mL) and MeOH (100 mL) was added 4N solution of HCl in dioxane (160 mL, 640 mmol) and stirred for 18 h. The reaction was concentrated to afford a red oil. The residue was taken up in DCM/7N methanolic $NH_3$ (100 mL, 9:1) and the mixture was sonicated for 5 min. The inorganic salt precipitate was removed by filtration and washed with the same solvent. The filtrate was concentrated to afford a viscous red oil. The crude product was purified by $SiO_2$ chromatography (Biotage 40 M) eluting with DCM/7N methanolic $NH_3$ (7:1). The recovered light brown oil crystallized to form 21.2 g (95%) (S)-2-(5,6,7,8-tetrahydropyrido[3,4-d]pyrimidin-2-ylamino)propan-1-ol (138) as a brown solid: MS m/z (APCI-pos) M+1=209.1.

(R)-1-(4-Chloro-3-fluoro-phenyl)-ethylamine (140) was prepared from 1-(4-chloro-3-fluorophenyl)ethanone (CASRN 151945-84-5) in accord with the procedure described in steps 3 to 5 of example 10. Condensation of 140 and 138 was carried out in accord with the procedure in step 6 of example 1, except 138 was substituted for 28 to afford 88 mg (23%) of I-21: $^1H$ NMR (400 MHz, $CDCl_3$) δ 8.08 (s, 1H), 7.34 (t, 1H), 7.12 (dd, 1H), 7.06 (d, 1H), 5.06 (d, 1H), 4.99 (t, 1H), 4.68 (d, 1H), 4.34 (s, 2H), 4.09 (m, 1H), 3.75 (dd, 1H), 3.70-3.58 (m, 3H), 2.66 (t, 2H), 1.48 (d, 3H), 1.25 (d, 3H); LCMS (APCI+) m/z 408.1 (M+H)+.

N—((R)-1-(4-chloro-2,5-difluorophenyl)ethyl)-2-((S)-1-hydroxypropan-2-ylamino)-5,6-dihydropyrido[3,4-d]pyrimidine-7(8H)-carboxamide (I-22) was prepared analogously except (4-chloro-2,5-diphenyl)ethanone was used in place of 1-(4-chloro-3-fluorophenyl)ethanone: yield: 89 mg (26%).

N—((R)-1-(4-chloro-3-fluorophenyl)propyl)-2-((S)-1-hydroxypropan-2-ylamino)-5,6-dihydropyrido[3,4-d]pyrimidine-7(8H)-carboxamide (I-38)

(R)-1-(4-chloro-3-fluorophenyl)propan-1-amine hydrochloride (139) was prepared in accord with procedures described in steps 1 and 2 of example 1, except in step 1, oxazole-5-carbaldehyde was replaced with 4-chloro-3-fluorobenzaldehyde. Condensation of (R)-1-(4-chloro-3-fluorophenyl)propan-1-amine and 138 was carried out in accord with step 6 of example 1 except 28 was replaced with 138 and 22 was replaced with 1-(4-chloro-3-fluorophenyl)propan-1-amine. The crude product was purified by $SiO_2$ chromatography eluting with DCM/MeOH (500:40) to afford 0.30 g (75%) of I-38: $^1H$ NMR (400 MHz, $d_6$-DMSO) δ 8.06 (s, 1H), 7.51-7.47 (t, 1H), 7.34 (d, 1H), 7.17 (d, 1H), 6.95 (d, 1H), 6.53 (d, 1H), 4.64-4.55 (m, 2H), 4.38-4.26 (m, 2H), 3.93-3.90 (m, 1H), 3.59-3.55 (m, 2H), 3.46-3.31 (m, 1H), 3.29-3.24 (m, 1H), 2.55-2.50 (m, 2H), 1.76-1.63 (m, 1H), 1.08 (d, 3H), 0.84 (t, 3H); MS m/z (APCI-pos) M+1=422.

N—((R)-1-(3,4-dichlorophenyl)ethyl)-2-((S)-1-hydroxypropan-2-ylamino)-5,6-dihydropyrido[3,4-d]pyrimidine-7(8H)-carboxamide (I-44)

Condensation of 185 and 138 was carried out in accord with step 6 of example 1 except 28 was replaced with 138 and 22 was replaced with 185. The crude product was purified by $SiO_2$ chromatography eluting with a DCM/MeOH gradient (500:15 to 500:25) to afford 0.004 g (1.31%) of I-44: MS m/z (APCI-pos) M+1=424.

(S)—N-(3,4-dichlorobenzyl)-2-(1-hydroxypropan-2-ylamino)-5,6-dihydropyrido[3,4-d]pyrimidine-7(8H)-carboxamide (I-90) was prepared analogously except 3,4-dichlorobenzylamine for (R)-1-(4-chloro-3-fluorophenyl)propan-1-amine hydrochloride was used in place of 140: $^1H$ NMR (400 MHz, $CDCl_3$) δ 8.03 (s, 1H), 7.37 (m, 2H), 7.14 (m, 1H), 5.37 (dd, 1H), 5.23 (d, 1H), 4.38 (d, 2H), 4.32 (s, 2H), 4.21 (br s, 1H), 4.06 (m, 1H), 3.64 (m, 4H), 2.63 (dd, 2H), 1.21 (d, 3H); MS m/z (APCI-pos) M+1=410.5.

N-(3-chloro-4-cyanobenzyl)-2-(tetrahydro-2H-pyran-4-ylamino)-5,6-dihydropyrido[3,4-d]pyrimidine-7(8H)-carboxamide (I-94) was prepared analogously except 4-(aminomethyl)-2-chlorobenzonitrile hydrochloride (CASRN 202522-15-4) was used in place of 140 and 28 was used in place of 138: $^1H$ NMR (400 MHz, DMSO) δ 8.09 (s, 1H), 7.90 (d, J=8.0 Hz, 1H), 7.59 (s, 1H), 7.47-7.33 (m, 2H), 6.92 (d, J=7.8 Hz, 1H), 4.38-4.28 (m, 4H), 3.85 (d, J=11.2 Hz, 3H), 3.59 (d, J=5.0 Hz, 2H), 3.36 (t, J=11.6 Hz, 2H), 2.57 (s, 2H), 1.80 (d, J=12.1 Hz, 2H), 1.48 (dd, J=20.0, 10.9 Hz, 2H); MS m/z (APCI-pos) M+1=427.1.

(R)—N-(1-phenylpropyl)-2-(tetrahydro-2H-pyran-4-ylamino)-5,6-dihydropyrido[3,4-d]pyrimidine-7(8H)-carboxamide carboxamide (I-95) was prepared analogously except (R)-1-phenylpropan-1-amine was used in place of 140 and 28 was used in place of 138: $^1H$ NMR (400 MHz, DMSO) δ 8.07 (s, 1H), 7.34-7.24 (m, 4H), 7.18 (t, J=6.7, 1H), 6.91 (d, J=8.1, 2H), 4.58 (dd, J=14.8, 8.4, 1H), 4.42-4.23 (m, 2H), 3.88 (dd, J=19.1, 11.1, 3H), 3.65-3.51 (m, 2H), 3.36 (dd, J=9.3, 7.5, 2H), 2.53 (t, J=6.2, 2H), 1.85-1.58 (m, 4H), 1.47 (qd, J=11.9, 4.2, 2H), 0.84 (t, J=7.3, 3H); MS m/z (APCI-pos) M+1=396.2.

(R)-2-(tetrahydro-2H-pyran-4-ylamino)-N-(1-(4-(trifluoromethyl)phenyl)propyl)-5,6-dihydropyrido[3,4-d]pyrimidine-7(8H)-carboxamide (I-96) was prepared analogously except (R)-1-(4-(trifluoromethyl)phenyl)propan-1-amine hydrochloride was used in place of 140 and 28 was used in place of 138: $^1H$ NMR (400 MHz, DMSO) δ 8.07 (s, 1H), 7.65 (d, J=7.8 Hz, 2H), 7.53 (d, J=7.9 Hz, 2H), 7.01 (d, J=7.7 Hz, 1H), 6.88 (d, J=7.9 Hz, 1H), 4.65 (dd, J=14.8, 7.3 Hz, 1H), 4.33 (q, J=18.0 Hz, 2H), 3.85 (d, J=11.9 Hz, 3H), 3.59 (t, J=9.5 Hz, 2H), 3.36 (t, J=11.5 Hz, 2H), 2.53 (d, J=9.9 Hz, 2H), 1.72 (ddd, J=20.4, 18.9, 8.4 Hz, 4H), 1.48 (dd, J=20.4, 11.1 Hz, 2H), 0.87 (t, J=7.2 Hz, 3H); MS m/z (APCI-pos) M+1=464.2.

(R)—N-(1-(4-chlorophenyl)ethyl)-2-(tetrahydro-2H-pyran-4-ylamino)-5,6-dihydropyrido[3,4-d]pyrimidine-7(8H)-carboxamide (I-97) was prepared analogously except (R)-1-(4-chlorophenyl)ethanamine was used in place of 140 and 28 was used in place of 138: $^1$H NMR (400 MHz, DMSO) δ 8.07 (s, 1H), 7.34 (s, 4H), 6.97 (d, J=7.5 Hz, 1H), 6.88 (d, J=7.8 Hz, 1H), 4.83 (t, J=6.9 Hz, 1H), 4.32 (s, 2H), 3.85 (d, J=11.3 Hz, 3H), 3.56 (t, J=5.0 Hz, 2H), 3.36 (t, J=11.7 Hz, 2H), 2.53 (d, J=5.3 Hz, 2H), 1.80 (d, J=11.9 Hz, 2H), 1.57-1.43 (m, 2H), 1.36 (d, J=7.0 Hz, 3H); MS m/z (APCI-pos) M+1=416.1.

(R)-2-(tetrahydro-2H-pyran-4-ylamino)-N-(1-(4-(trifluoromethyl)phenyl)ethyl)-5,6-dihydropyrido[3,4-d]pyrimidine-7(8H)-carboxamide (I-98) was prepared analogously except (R)-1-(4-(trifluoromethyl)phenyl)ethanamine hydrochloride was used in place of 140 and 28 was used in place of 138: $^1$H NMR (400 MHz, DMSO) δ 8.08 (s, 1H), 7.65 (d, J=8.0 Hz, 2H), 7.54 (d, J=8.0 Hz, 2H), 7.07 (d, J=7.5 Hz, 1H), 6.89 (d, J=7.7 Hz, 1H), 4.98-4.84 (m, 1H), 4.41-4.27 (m, 2H), 3.85 (d, J=11.1 Hz, 3H), 3.58 (s, 2H), 3.37 (t, J=9.2 Hz, 2H), 2.55 (s, 2H), 1.80 (d, J=13.1 Hz, 2H), 1.48 (dd, J=21.8, 9.7 Hz, 2H), 1.40 (d, J=7.1 Hz, 3H); MS m/z (APCI-pos) M+1=450.2.

N-(4-cyano-3-(trifluoromethyl)benzyl)-2-(tetrahydro-2H-pyran-4-ylamino)-5,6-dihydropyrido[3,4-d]pyrimidine-7(8H)-carboxamide (I-99) was prepared analogously except 4-cyano-3-trifluoromethyl-benzylamine (prepared from 4-bromo-3-(trifluoromethyl)benzaldehyde, CASRN 101066-58-4) was used in place of 140 and 28 was used in place of 138: $^1$H NMR (400 MHz, DMSO) δ 8.10 (d, J=9.2 Hz, 2H), 7.87 (s, 1H), 7.76 (d, J=7.9 Hz, 1H), 7.44 (t, J=5.4 Hz, 1H), 6.91 (d, J=7.9 Hz, 1H), 4.40 (d, J=5.4 Hz, 2H), 4.34 (s, 2H), 3.85 (d, J=11.3 Hz, 3H), 3.58 (t, J=5.4 Hz, 2H), 3.36 (t, J=11.5 Hz, 2H), 2.57 (t, J=5.4 Hz, 2H), 1.80 (d, J=12.2 Hz, 2H), 1.48 (td, J=15.6, 4.0 Hz, 2H); MS m/z (APCI-pos) M+1=461.1.

(R)—N-(1-(4-fluorophenyl)propyl)-2-(tetrahydro-2H-pyran-4-ylamino)-5,6-dihydropyrido[3,4-d]pyrimidine-7(8H)-carboxamide (I-100) was prepared analogously except (R)-1-(4-fluorophenyl)propan-1-amine (CASRN 374898-01-8) was used in place of 140 and 28 was used in place of 138: $^1$H NMR (400 MHz, DMSO) δ 8.07 (s, 1H), 7.34 (dd, J=8.6, 5.7 Hz, 2H), 7.10 (t, J=8.9 Hz, 2H), 6.91 (d, J=8.0 Hz, 2H), 4.57 (dd, J=15.0, 8.3 Hz, 1H), 4.40-4.25 (m, 2H), 3.95-3.81 (m, 3H), 3.66-3.49 (m, 2H), 3.36 (dd, J=11.9, 10.1 Hz, 2H), 2.56-2.52 (m, 2H), 1.85-1.59 (m, 4H), 1.47 (qd, J=12.3, 4.3 Hz, 2H), 0.83 (t, J=7.3 Hz, 3H); m/z (APCI-pos) M+1=414.2.

(R)—N-(1-(4-fluorophenyl)ethyl)-2-(tetrahydro-2H-pyran-4-ylamino)-5,6-dihydropyrido[3,4-d]pyrimidine-7(8H)-carboxamide (I-101) was prepared analogously except 1-(4-fluorophenyl)ethanamine) was used in place of 140 and 28 was used in place of 138. The enantiomers were separated using chiral SFC chromatography to afford (R)—N-(1-(4-fluorophenyl)ethyl)-2-(tetrahydro-2H-pyran-4-ylamino)-5,6-dihydropyrido[3,4-d]pyrimidine-7(8H)-carboxamide (10% yield) and (S)—N-(1-(4-fluorophenyl)ethyl)-2-(tetrahydro-2H-pyran-4-ylamino)-5,6-dihydropyrido[3,4-d]pyrimidine-7(8H)-carboxamide (15% yield): $^1$H NMR (400 MHz, DMSO) δ 8.08 (s, 1H), 7.35 (dd, J=8.6, 5.7 Hz, 2H), 7.10 (t, J=8.9, 2H), 6.97 (d, J=7.8 Hz, 1H), 6.91 (d, J=7.8 Hz, 1H), 4.84 (p, J=7.1 Hz, 1H), 4.32 (s, 2H), 3.87 (dd, J=16.1, 13.2, 3H), 3.56 (t, J=5.6, 2H), 3.40-3.35 (m, 2H), 2.57-2.52 (m, 2H), 1.79 (d, J=12.6, 2H), 1.56-1.41 (m, 2H), 1.36 (d, J=7.1, 3H); MS m/z (APCI-pos) M+1=400.2.

(R)—N-(1-phenylethyl)-2-(tetrahydro-2H-pyran-4-ylamino)-5,6-dihydropyrido[3,4-d]pyrimidine-7(8H)-carboxamide (I-102) was prepared analogously except (R)-1-phenylethanamine was used in place of 140 and 138 was used in place of 138: $^1$H NMR (400 MHz, DMSO) δ 8.07 (s, 1H), 7.30 (dt, J=15.1, 7.4, 4H), 7.18 (t, J=7.0, 1H), 6.95 (d, J=7.8, 1H), 6.88 (d, J=7.9, 1H), 4.85 (p, J=7.0, 1H), 4.33 (s, 2H), 3.85 (d, J=11.9, 3H), 3.57 (t, J=5.6, 2H), 3.36 (dd, J=12.5, 10.8, 2H), 2.53 (dd, J=10.1, 4.5, 2H), 1.79 (d, J=12.6, 2H), 1.48 (ddd, J=15.7, 12.1, 4.5, 2H), 1.37 (d, J=7.1, 3H); MS m/z (APCI-pos) M+1=382.2.

N—((R)-1-(3-chloro-4-fluorophenyl)ethyl)-2-((S)-1-hydroxypropan-2-ylamino)-5,6-dihydropyrido[3,4-d]pyrimidine-7(8H)-carboxamide (I-147) was prepared analogously except (R)-1-(3-chloro-4-fluorophenyl)ethanamine was used in place of 140. The crude product was purified by $SiO_2$ chromatography eluting with 2.5% MeOH/EtOAc to afford 102 mg (51%) of I-147 as a white solid: $^1$H NMR (400 MHz, CDCl$_3$) δ 7.84 (s, 1H), 7.35-7.38 (m, 1H), 7.18-7.23 (m, 1H), 7.06-7.11 (m, 1H), 6.23 (s, 1H), 4.95-5.02 (m, 1H), 4.62 (d, 1H, J=7.0 Hz), 4.45 (s, 2H), 3.90-3.98 (m, 1H), 3.71-3.75 (m, 1H), 3.52-3.57 (m, 3H), 2.75 (t, 2H, J=5.9 Hz), 1.48 (d, 3H, J=7.1 Hz), 1.22 (d, 3H, J=6.5 Hz); MS (APCI-pos) M+1=407.5.

Example 18

N—((S)-1-(3,4-dichlorophenyl)-2,2,2-trifluoroethyl)-2-((S)-1-hydroxypropan-2-ylamino)-5,6-dihydropyrido[3,4-d]pyrimidine-7(8H)-carboxamide (I-23)

Step 1:

Dichloro {(S)-(−)-2,2'-bis[di(3,5-xylyl)phosphino]-1-1'binaphthyl}[(2S)-(−)-1,1-bis(4-methoxyPh)-3-Me-1,2-butanediamine]Ru(II) (0402 g, 0.0329 mmol) was added to a solution of IPA (80 mL), 1-(3,4-dichlorophenyl)-2,2,2-trifluoroethanone (8.00 g, 32.9 mmol, CASRN 125733-43-9), toluene (15 mL) and potassium tert-butoxide (0.658 ml, 0.658 mmol) in tert-BuOH which had been degassed by bubbling nitrogen into the vial. The beaker was put into an autoclave and it was purged by three vacuum-filling with nitrogen cycles. Hydrogen was introduced into the autoclave at a pressure of 150 psi, then reduced to 20 psi by slowly releasing the stop valve. After this procedure was repeated three times, the autoclave was pressurized to 240 psi (hydrogen was recharged to 200 psi then the pressure dropped to (160 psi). The reaction mixture was vigorously stirred at RT for 64 h. The pressure was released and the solvent was removed. The residue was dissolved in ether (200 mL), washed with brine (100 mL), dried (Na$_2$SO$_4$), filtered and concentrated. The crude product was purified by $SiO_2$ chromatography eluting with EtOAc/hexane (2:1) to afford 7.31 g (90.6%) of solid (R)-1-(3,4-dichlorophenyl)-2,2,2-trifluoroethanol (142).

Step 2:

To a solution of 142 (7.10 g, 29.0 mmol) and 2,6-dimethylpyridine (4.97 g, 46.4 mmol) in cyclohexane (20 mL) and cooled to −10° C. was added trifluoromethanesulfonic anhydride (12.3 g, 43.5 mmol) over 30 min. The reaction was stirred for 90 min at 0° C., quenched with H$_2$O and the mixture was extracted with DCM. The organic layer was dried, filtered and concentrated to afford (R)-1-(3,4-dichlorophenyl)-2,2,2-trifluoroethyl trifluoromethanesulfonate (144) which was used without additional purification.

Step 3:

A solution of 144 (10.9 g, 28.9 mmol), K$_2$CO$_3$ (5.99 g, 43.4 mmol) and (3,4-dimethoxyphenyl)methanamine (6.77 g, 40.5 mmol) in cyclohexane (200 mL) and heated to 65° C. for 24 h. Water was added and the organic layer was concentrated and the crude product was purified by SiO$_2$ chromatography eluting with EtOAc/hexane (5 to 20% EtOAc) to afford 4.11 g (36.1%) of 1-(3,4-dichlorophenyl)-N-(3,4-dimethoxybenzyl)-2,2,2-trifluoroethanamine (146).

Step 4:

To a solution of 146 (4.11 g, 10.43 mmol) in DCM (50 mL) was added TFA (2.410 ml, 31.28 mmol) and reaction was stirred for 18 hr at RT. The reaction mixture was concentrated and dissolved in DCM. A solution of HCl (20 mL, 2M Et$_2$O) was added and the solvent was decanted from the solids. The solids were dissolved in 15% MeOH/DCM and saturated NaHCO$_3$ was added. The organic layer was separated and concentrated. The residue was triturated with EtOAc and allowed to stand. The resulting solids were filtered to afford 1.904 g (74.8%) of 1-(3,4-dichlorophenyl)-2,2,2-trifluoroethanamine (148).

Step 5:

A solution of 148 (1.00 g, 4.01 mmol), 4-nitrophenyl carbonochloridate (0.9085 g, 4.507 mmol) and pyridine (0.7131 g, 9.015 mmol) in DCM (10 mL) were stirred for 30 min. Water was added and the reaction mixture was extracted with DCM. The organic layer was concentrated and purified by SiO$_2$ chromatography eluting with 20% EtOAc/hexane to afford 1.511 g (90.0%) of 4-nitrophenyl 1-(3,4-dichlorophenyl)-2,2,2-trifluoroethylcarbamate (150).

Step 7:

A solution of (S)-2-(5,6,7,8-tetrahydropyrido[3,4-d]pyrimidin-2-ylamino)propan-1-ol (138, 0.215 g, 1.03 mmol), TBDMS-Cl (0.171 g, 1.14 mmol) and TEA (0.216 ml, 1.55 mmol) and DCM (5 mL) were stirred for 18 h, poured into water and extracted with DCM. The combined organic fractions were dried (MgSO$_4$), filtered, and concentrated to give the crude product, which was purified by SiO$_2$ chromatography eluting with DCM/MeOH (500:50) to afford 0.220 g (66.1%) of (S)—N-(1-(tert-butyldimethylsilyloxy)propan-2-yl)-5,6,7,8-tetrahydropyrido[3,4-d]pyrimidin-2-amine (152).

Step 8:

Condensation of (S)—N-(1-(tert-butyldimethylsilyloxy)propan-2-yl)-5,6,7,8-tetrahydropyrido[3,4-d]pyrimidin-2-amine (152) and 150 was carried out in accord with the procedure in step 6 of example 1 except 152 was used in place of 28 and 150 was used in place of 22 to afford 89 mg (72%) of 2-((S)-1-(tert-butyldimethylsilyloxy)propan-2-ylamino)-N—((S)-1-(3,4-dichlorophenyl)-2,2,2-trifluoroethyl)-5,6-dihydropyrido[3,4-d]pyrimidine-7(8H)-carboxamide (154).

Step 9:

To a solution of 154 (111 mg, 0.187 mmol) in DCM and TBAF (187 µL, 0.187 mmol) and the solution was stirred at RT for 3 h. The reaction was quenched with water and extracted with DCM. The organic layer was dried, filtered and concentrated. The crude product was purified on a SP4 reverse phase column chromatography eluting with an MeCN/H$_2$O gradient (5 to 90% MeCN) to afford 26.7 mg (29.8%) of I-23: LCMS (APCI+) m/z 480.5 (M+H)$^+$.

2-((S)-2-Hydroxy-1-methyl-ethylamino)-5,8-dihydro-6H-pyrido[3,4-d]pyrimidine-7-carboxylic acid [(R)-1-(3-fluoro-4-trifluoromethyl-phenyl)-ethyl]-amide (I-64) can be prepared in accord with the procedure described in step 6 of example 1 except 152 was used in place of 28 and 143 was used in place of 22 to afford to afford I-64: MS m/z (APCI-pos) M+1=442. 1-(4-Trifluoromethyl-3-fluorophenyl)ethanone (CASRN 204339-72-0) can be prepared from 4-trifluoromethyl-3-fluorobenzaldehyde in accord with the procedure in steps 1 to 3 of example 1. (R)-1-(4-trifluoromethyl-3-fluoro-phenyl)-ethylamine (143) can be prepared from 1-(4-trifluoromethyl-3-fluorophenyl)ethanone (143a, CASRN 237761-81-8) in accord with the procedure described in steps 3 to 5 of example 10.

2-((S)-2-Hydroxy-1-methyl-ethylamino)-5,8-dihydro-6H-pyrido[3,4-d]pyrimidine-7-carboxylic acid [(R)-1-(3-chloro-5-fluoro-phenyl)-ethyl]-amide (I-65) can be prepared in accord with the procedure described in step 6 of example 1 except 152 was used in place of 28 and 145 was used in place of 22 to afford to afford I-64: MS m/z (APCI-pos) M+1=408. (R)-1-(5-chloro-3-fluoro-phenyl)-ethylamine (145) can be prepared from 1-(5-chloro-3-fluorophenyl)ethanone (CASRN 842140-52-7) in accord with the procedure described in steps 3 to 5 of example 10.

Example 19

N—((R)-1-(3,4-dichlorophenyl)propyl)-2-((S)-1-hydroxypropan-2-ylamino)-5,6-dihydropyrido[3,4-d]pyrimidine-7(8H)-carboxamide (I-24)

Step 1:

To a solution of THF (100 mL) and 2,2'-oxybis(N,N-dimethylethanamine) (9.18 g, 57.3 mmol) cooled to 0° C. was added ethylmagnesium bromide (19.1 mL, 57.3 mmol, 3N in THF) and stirred for 10 min. The solution was cooled to −60° C. and a solution of 3,4-dichlorobenzoyl chloride (10.0 g, 47.7 mmol) in THF (20 mL) was added dropwise over 10 min. The reaction was stirred for 1 h, quenched by adding sat'd. NH$_4$Cl sat. and extracted with EtOAc. The combined extracts were dried with (Na$_2$SO$_4$), filtered and concentrated in vacuo. The crude product was purified by SiO$_2$ chromatography (Biotage 40M) eluting an EtOAc/hexane gradient (2 to 10% EtOAc) to afford 6.0 g (85%, 53% pure) 1-(3,4-dichlorophenyl)propan-1-one (156) as clear oil which was used without additional purification.

Step 2:

A 250 mL round-bottom flask was charged with MTBE (35 mL), a solution of (R)-1-methyl-3,3-diphenylhexahydropyrrolo[1,2-c][1,3,2]oxazaborole (2.51 mL, 2.51 mmol) and borane diethylaniline (4.45 mL, 25.1 mmol) at RT then heated to 40° C. A MTBE (20 mL) solution of 156 (6.00 g, 25.1 mmol) was added dropwise and the reaction was stirred at 40° C. for 3 h. The reaction was cooled to RT and MeOH (5 mL) was then added slowly, followed by 1M HCl and the reaction was stirred for 18 h. The water was removed and the remaining organic phase dried (Na$_2$SO$_4$), filtered and concentrated to get a light gray oil. The crude product was purified by SiO$_2$ chromatography (SNAP 100) eluting with EtOAc/hexane (1:3) to afford 3.45 g (66%) of (S)-1-(3,4-dichlorophenyl)propan-1-ol (158) as a clear oil.

Step 3:

To a solution of 158 (3.45 g, 16.5 mmol) and THF (45 mL) cooled to 0° C. was added isoindoline-1,3-dione (2.67 g, 18.1 mmol) and PPh$_3$ (6.49 g, 24.7 mmol) followed by the dropwise addition of neat DIAD (6.67 g, 33.0 mmol). The reaction was warmed to RT and stirred 18 h. The reaction was stirred with NaOH 2N (50 mL) and DCM (50 mL) for 2 h (emulsion) and then extracted with DCM. The combined organic fractions were dried (Na$_2$SO$_4$), filtered, and concentrated. The residue was triturated with hexane/EtOAc (1:1) and the precipitated POPh$_3$ was filtered. The filtrate was concentrated and chromatographed (Isolera) eluting with hexane/EtOAc (9:1) to afford 2.05 g (32%) of (R)-2-(1-(3,4-dichlorophenyl)propyl)isoindoline-1,3-dione (160)

Step 4:

To a solution of 160 (2.05 g, 5.21 mmol) and THF:MeOH (1:1, 40 mL) at RT was added hydrazine monohydrate (1.31 mL, 26.1 mmol) and the reaction was heated to 50° C. and stirred for 24 h. THF (20 mL) was added and precipitated phthalimide was filtered and discarded. The filtrate was washed with brine, extracted with DCM and the organic phases combined, dried ($Na_2SO_4$), filtered and concentrated to afford 1.18 g (89%) of (R)-1-(3,4-dichloro phenyl)propan-1-amine (162) as a viscous yellow oil. The $^{19}F$ NMR of the Mosher amide indicated an ee of 93% based on peaks at −69.28 and −69.31.

Step 5:

A vial was charged with CDI (0.584 g, 3.60 mmol), 162 (0.735 g, 3.60 mmol), DIPEA (1.88 mL, 10.8 mmol), DCM (7 mL) and DMF (2 mL). The solution was stirred for 30 min and a solution of 138 (0.750 g, 3.60 mmol), DIPEA (1.88 mL, 10.8 mmol) in DCM (3 mL) was added. The reaction mixture was stirred for 18 h, washed with brine (4 mL) and the organic phase concentrated in vacuo. The residue was suspended in EtOAc and washed with brine (2×50 mL) and then concentrated. The crude product was purified on a reverse phase liquid chromatography column (Horizen C18 biotage 40M) eluting with MeCN/$H_2O$ (1:1). The product was eluted at ~50% MeCN/50% water to afford 0.905 g (55%) of I-24 as a light yellow solid: $^1H$ NMR (400 MHz, $CD_3OD$) δ 8.01 (s, 1H), 7.44 (m, 1H), 7.39 (d, 1H), 7.19 (d, 1H), 4.58 (m, 1H), 4.39 (m, 2H), 4.04 (m, 1H), 3.61 (m, 4H), 2.61 (t, 3H), 1.77 (m, 2H), 1.16 (d, 3H), 0.89 (t, 3H); MS m/z (APCI-pos) M+1=438.1.

N—((R)-1-(3,4-dichlorophenyl)-2-methylpropyl)-2-((S)-1-hydroxypropan-2-ylamino)-5,6-dihydropyrido[3,4-d]pyrimidine-7(8H)-carboxamide (I-32) was prepared analogously except in step 1, isopropylmagnesium bromide was used in place of ethylmagnesium bromide to afford 0.70 g (95%) of 1-(3,4-dichlorophenyl)-2-methylpropan-1-amine: m/z (APCI-pos) M+1=217.8.

Condensation of 1-(3,4-dichlorophenyl)-2-methylpropan-1-amine and 138 afforded I-32. The crude product was purified by reverse phase chromatography (SP4 C18 Biotage 40M column eluting with a MeCN/$H_2O$ gradient (eluted at ca. 50% MeCN) to afford (73 mg) of the title compound. Chiral HPLC separation was achieved with a Tech IC column, 4.6 mm×250 mm, 1 mL/min, 220 nM eluting with hexane/EtOH (6:4) at a 1 mL/min flow rate. Peaks eluted at 4.7 min and 5.9 min. The recovered oil was repurified on a SP4 Biotage 25M column eluting with a MeCN/$H_2O$ gradient (0 to 70% MeCN) over 30 column volumes to afford 0.010 g (32%) of I-32 as a white solid: $^1H$ NMR (400 MHz, $CD_3OD$) δ 8.00 (s, 1H), 7.45 (m, 1H), 7.39 (d, 1H), 7.20 (m, 1H), 6.81 (d, 1H), 4.35 (m, 3H), 4.03 (m, 1H), 3.60 (m, 2H), 3.51 (m, 2H), 3.31 (s, 2H), 2.60 (t, 2H), 2.01 (m, 1H), 1.16 (d, 3H), 1.01 (d, 3H), 0.71 (d, 3H); m/z (APCI-pos) M+1=452.1.

Example 20

N-(1-(3,4-dichlorophenyl)-3,3,3-trifluoropropyl)-2-((S)-1-hydroxypropan-2-ylamino)-5,6-dihydropyrido[3,4-d]pyrimidine-7(8H)-carboxamide (I-34)

A 40 mL vial was charged with CDI (0.584 g, 3.60 mmol), 1-(3,4-dichlorophenyl)-3,3,3-trifluoropropan-1-amine (0.929 g, 3.60 mmol), DIPEA (1.88 mL, 10.8 mmol), DCM (7 mL) and DMF (2 mL). The mixture was stirred for 30 min then a solution of 138 (0.750 g, 3.60 mmol) and DIPEA (1.88 mL, 10.8 mmol) in DCM (3 mL) was added and the mixture stirred for 18 h. The reaction mixture was washed with brine (4 mL) and the organic phase isolated and concentrated. The residue was resuspended in EtOAc and washed with brine (2×50 mL) and concentrated in vacuo. The crude product was purified by reverse phase chromatography (Horizen C18 Biotage 40M) eluting with a MeCN/$H_2O$ gradient (eluted at ca. 50% MeCN) to afford 925 mg which was separated by chiral HPLC chromatography and repurified as described in example 19 to afford 0.212 g (23%) of I-34 as a white solid: $^1H$ NMR (400 MHz, $CD_3OD$) δ 8.06 (s, 1H), 7.55 (m, 1H), 7.49 (d, 1H), 7.31 (m, 1H), 5.20 (m, 1H), 4.41 (q, 2H), 4.06 (m, 1H), 3.65 (t, 2H), 3.56 (m, 2H), 2.79 (m, 4H), 1.20 (d, 3H); m/z (APCI-pos) M+1=492.0.

Example 21

N—((R)-1-(3,4-dichloro phenyl)propyl)-2-((1S,3S)-3-hydroxycyclopentylamino)-5,6-dihydropyrido[3,4-d]pyrimidine-7(8H)-carboxamide (I-25)

Step 1:

To a stirred solution of (1S,3S)-3-aminocyclopentanol (9.00 g, 89.0 mmol) (obtained from ASID pharmaceuticals) in DMF (45 mL) at RT under nitrogen was added DIPEA (31.0 mL, 178 mmol) followed by 1H-pyrazole-1-carboximidamide hydrochloride (14.7 g, 133 mmol). After stirring overnight $Et_2O$ (150 mL) was added and the reaction was stirred for 10 min. The $Et_2O$ was decanted and concentrated under high vacuum to afford 21 g (99%) of 1-((1S,3S)-3-hydroxycyclopentyl)guanidine (164) as a dark orange oil: MS m/z (APCI-pos) M+1=144.1

Step 2:

A solution of 21 (10.99 g, 41.90 mmol), EtOH (10 mL) and 1-((1S,3S)-3-hydroxycyclopentyl)guanidine (10.0 g, 41.90 mmol) was stirred at 45° C. for 10 min. When the solution was homogenous sodium ethoxide (31.29 mL, 83.81 mmol, 21% in EtOH) was added and the reaction stirred at 45° C. for 18 h. The crude was concentrated and resuspended in EtOAc. The organic phase was washed with brine, dried ($Na_2SO_4$), filtered and concentrated. The crude product was purified by $SiO_2$ chromatography (Biotage 25 M) eluting with EtOAc/MeOH (9:1) to afford 10.9 g (50%) of tert-butyl 2-((1S,3S)-3-hydroxycyclopentylamino)-5,6-dihydropyrido[3,4-d]pyrimidine-7(8H)-carboxylate (166) as yellow foam: MS m/z (APCI-pos) M+1=335.1.

Step 3:

To a solution of 166 (10.85 g, 21.09 mmol), DCM (100 mL) and MeOH (10 mL) was added HCl/dioxane (26.36 mL, 105.4 mmol, 4N solution in dioxane) and the reaction was stirred for 18 h. The solution was concentrated to afford a red oil. To the residue was added DCM/methanolic $NH_3$ (100 mL, 9:1, 7N) and the mixture sonicated for 5 min. The filtrate was concentrated to afford a thick red oil. The crude product was purified by $SiO_2$ chromatography (Biotage 40 M) eluting with DCM/7N methanolic:$NH_3$ (4:1 then 9:1 solution) to afford 4.1 g (80%) of (1S,3S)-3-(5,6,7,8-tetrahydropyrido[3,4-d]pyrimidin-2-ylamino)cyclopentanol (168) as a light brown oil: MS m/z (APCI-pos) M+1=235.2.

Step 4:

The title compound was prepared in accord with step 6 of example 1 except 22 was replaced with 168. The crude product was purified by preparative TLC (2.0 mm thickness) developed with EtOAc/MeOH (9:1) and the product with an $R_f$ ca. 0.6 was eluted to afford a white solid which afforded 0.026 g (24% yield) of I-25: $^1H$ NMR (400 MHz, $CDCl_3$) δ 8.06 (s, 1H), 7.38 (m, 2H), 7.16 (m, 1H), 5.00 (m, 1H), 4.91 (m, 1H), 4.73 (m, 1H), 4.50 (m, 2H), 4.33 (s, 2H), 3.64 (m, 2H), 3.48 (s, 1H), 2.64 (m, 2H), 2.4-1.4 (m, 8H), 0.91 (t, 3H); MS m/z (APCI-pos) M+1=464.1.

N—((R)-1-(3,4-dichlorophenyl)ethyl)-2-((1S,3S)-3-hydroxycyclopentylamino)-5,6-dihydropyrido[3,4-d]pyrimidine-7(8H)-carboxamide (I-42)

Condensation of 185 and 168 was carried out in accord with step 6 of example 1 except 28 was replaced with 168 and 22 was replaced 185. The crude product was purified by $SiO_2$ chromatography eluting with a DCM/MeOH gradient (500: 15 to 500:30) to afford 0.066 g (61.3%) of I-42: MA m/z (APCI-pos) M+1=450.

N—((R)-1-(3-fluoro-4-(trifluoromethyl)phenyl)propyl)-2-((1S,3S)-3-hydroxycyclopentylamino)-5,6-dihydropyrido[3,4-d]pyrimidine-7(8H)-carboxamide (I-37) (R)-1-(3-fluoro-4-(trifluoromethyl)phenyl)propan-1-amine (167) can be prepared in accord with the procedure described in steps 1 to 4 of example 19, except in step 1,3-fluoro-4-trifluoromethyl-benzoyl chloride was used in place of 3,4-dichlorobenzoyl chloride. Condensation of 167 and 168 was carried out in accord with step 5 of example 19 except 162 was replaced with 167 and 132 was replaced 168. The product was purified on a preparative $SiO_2$ TLC plate (1.0 mm thickness) developed with EtOAc/MeOH (9:1) to afford 0.030 g (48%) of I-42 as a white solid: $^1$H NMR (400 MHz, $CDCl_3$) δ 8.06 (s, 1H), 7.53 (t, 1H), 7.17 (m, 2H), 5.03 (m, 2H), 4.80 (m, 1H), 4.49 (m, 2H), 4.35 (s, 2H), 3.65 (m, 2H), 2.65 (t, 2H), 2.13 (m, 4H), 1.81 (m, 2H), 1.68 (m, 2H), 1.44 (m, 1H), 0.93 (t, 3H); m/z (APCI-pos) M+1=482.1.

N—((R)-1-(3-fluoro-4-(trifluoromethyl)phenyl)ethyl)-2-((1S,3S)-3-hydroxycyclopentylamino)-5,6-dihydropyrido[3,4-d]pyrimidine-7(8H)-carboxamide (I-52) was prepared analogously. The crude product was isolated by reverse phase chromatography (12M Horizen C18 column) eluting with a $MeCN/H_2O$ (the product eluted with ca. 25% MeCN) to afford 0.059 g (48%) of I-52 as a white solid: $^1$H NMR (400 MHz, $CD_3OD$) δ 7.99 (s, 1H), 7.55 (t, 1H), 7.25 (m, 2H), 6.97 (d, 1H), 4.93 (m, 1H), 4.40 (m, 3H), 4.31 (m, 1H), 3.61 (m, 2H), 2.60 (t, 2H), 2.17 (m, 1H), 2.00 (m, 2H), 1.68 (m, 1H), 1.56 (m, 1H), 1.45 (m, 4H); m/z (APCI-pos) M+1=468.2.

Example 22

N—((R)-1-(3,4-dichlorophenyl)ethyl)-2-((1R,4R)-4-hydroxycyclohexylamino)-5,6-dihydropyrido[3,4-d]pyrimidine-7(8H)-carboxamide (I-26)

(1R,4R)-4-(5,6,7,8-tetrahydropyrido[3,4-d]pyrimidin-2-ylamino)cyclohexanol (170) was prepared in accord with steps 1 to 3 of example 21 except (1R,4R)-4-aminocyclohexanol was used in place of (1S,3S)-3-aminocyclopentanol.

N—((R)-1-(3,4-dichlorophenyl)ethyl)-2-((1R,4R)-4-hydroxycyclohexylamino)-5,6-dihydropyrido[3,4-d]pyrimidine-7(8H)-carboxamide (I-26) was prepared from 170 in accord with the procedure described in step 6 of example 1. Yield 29.1 mg (8%); $^1$H NMR (400 MHz, $CDCl_3$) δ 8.07 (s, 1H), 7.40 (m, 2H), 7.17 (dd, 1H), 5.48 (m, 1H), 4.78 (d, 1H), 4.66 (d, 1H), 4.33 (s, 2H), 3.78 (m, 1H), 3.71-3.58 (m, 3H), 2.66 (t, 2H), 2.13 (d, 2H), 2.01 (d, 2H), 1.43 (m, 4H), 1.43 (m, 2H), 1.26 (m, 2H); LCMS (APCI+) m/z 466.5 (M+H)$^+$.

Example 23

(R)—N-(1-(4-(difluoromethoxy)phenyl)propyl)-2-(tetrahydro-2H-pyran-4-ylamino)-5,6-dihydropyrido[3,4-d]pyrimidine-7(8H)-carboxamide (I-27)

(R)-1-(4-(difluoromethoxy)phenyl)propan-1-amine was prepared from 4-(difluoromethoxy)benzaldehyde in accord with the procedures in steps 1 and 2 of example 1. Condensation of (R)-1-(4(difluoromethoxy)phenyl)propan-1-amine and 28 was carried out in accord with step 6 of example 1. The product was purified by reverse phase chromatography (SP4 C18) eluting with a $MeCN/H_2O$ gradient (1 to 60% MeCN) over 30 column volumes, to afford 0.113 g (56%) of I-27: $^1$H NMR (400 MHz, $CDCl_3$) 8.07 (s, 1H), 7.30 (d, 2H), 7.08 (d, 2H), 6.48 (t, 1H), 5.02 (d, 1H), 4.89 (m, 2H), 4.34 (s, 2H), 4.02 (m, 3H), 3.62 (m, 4H), 2.66 (m, 2H), 2.03 (m, 2H), 1.81 (m, 2H), 0.92 (m, 2H), 0.90 (t, 3H)); MS m/z (APCI-pos) M+1=462.1.

Example 24

(R)—N-(1-(3,4-dichlorophenyl)-3-methoxypropyl)-2-(tetrahydro-2H-pyran-4-ylamino)-5,6-dihydropyrido[3,4-d]pyrimidine-7(8H)-carboxamide (I-28)

Step 1:

T a solution of (R)-3-amino-3-(3,4-dichlorophenyl)propanoic acid (10.0 g, 42.7 mmol, CASRN 909709-44-0) and THF (57.0 mL, 42.7 mmol) under a $N_2$ atmosphere and cooled to 0° C. was added dropwise $LiAlH_4$ (32.0 mL, 32.0 mmol, 1M solution in THF) at a rate that maintained the internal temperature at 20° C. (10 min addition). The reaction was stirred at 0° C. for 1 h, then warmed to RT and stirred overnight. The reaction was quenched with 2M HCl (20 mL) then 2M NaOH (30 mL) and brine (50 mL) were added sequentially. The white solids were removed by filtration through CELITE and rinsed with THF (100 mL) and EtOAc (50 mL). The organic phase was dried ($Na_2SO_4$), filtered and concentrated to afford 5.25 g (56%) of (R)-3-amino-3-(3,4-dichlorophenyl)propan-1-ol (172) as a light yellow oil which was used without additional purification: MS m/z (APCI-pos) M+1=220.0.

Step 2:

To a solution of 172 (5.00 g, 22.7 mmol), NaOH (2M aq) (34.1 mL, 68.2 mmol) in THF (50 mL, 22.7 mmol) was added $Boc_2O$ (5.45 g, 25.0 mmol) and the reaction stirred at RT overnight. Additional NaOH (2M aq) (34.1 ml, 68.2 mmol) was added to stabilize the pH at ca. 12. Additional $Boc_2O$ (3.0 g) was added and the pH was maintained at ca. 12. After 3 h $Et_2O$ was added and the organic phase dried ($Na_2SO_4$), filtered and concentrated in vacuo. The crude product was purified by $SiO_2$ chromatography (SNAP 100) eluting with EtOAc/hexane (1:1) to afford 3.40 g (41%) of (R)-tert-butyl 1-(3,4-dichlorophenyl)-3-hydroxypropylcarbamate (174) as a yellow solid: ee ca.90% (chiral HPLC using OJ column).

Step 3:

To a solution of 174 (2.22 g, 6.93 mmol) and THF (30 mL).cooled to 0° C. and maintained under a $N_2$ atmosphere was added NaH (0.333 g, 8.32 mmol, 60% in mineral oil). The ice bath was removed and the solution stirred for 30 min then MeI (0.519 mL, 8.32 mmol) was added and the yellow solution stirred overnight. The reaction was diluted with $H_2O$ and extracted with $Et_2O$. The combined extracts were dried ($Na_2SO_4$), filtered and concentrated in vacuo. The crude product was purified by $SiO_2$ chromatography (SNAP 50) eluting with hexane/EtOAc (4:1) to afford 0.660 g (28%) of (R)-tert-butyl 1-(3,4-dichlorophenyl)-3-methoxypropylcarbamate (176) as a light yellow oil.

Step 4:

Deprotection of 176 was carried out in accord with the procedure in step 5 of example 1 to afford 0.375 g (80%) of (R)-1-(3,4-dichlorophenyl)-3-methoxypropan-1-amine (178): m/z (APCI-pos) M+1=234.0.

Step 5:

Condensation of 178 and 28 was carried out in accord with step 6 of example 1. The crude product was loaded on a SiO$_2$ column and eluted with MeOH/DCM (1:4) then repurified on a reverse phase column (SP4 C18) eluting with a MeCN/H$_2$O gradient (1 to 70% MeCN) to afford 0.013 g (12%) of I-28 as a white solid: $^1$H NMR (400 MHz, CDCl$_3$) δ 8.08 (s, 1H), 7.36 (m, 2H), 7.13 (m, 1H), 6.29 (d, 2H), 4.93 (m, 2H), 4.36 (q, 2H), 3.99 (m, 3H), 3.57 (m, 6H), 3.38 (s, 3H), 2.67 (t, 2H), 2.07 (m, 2H), 1.90 (m, 1H), 1.55 (m, 2H); m/z (APCI-pos) M+1=494.1.

Example 25

(R)—N-(1-(3,4-dichlorophenyl)ethyl)-2-(1-methyl-1H-pyrazol-5-ylamino)-5,6-dihydropyrido[3,4-d]pyrimidine-7(8H)-carboxamide (I-29)

Step 1:

To a stirred solution of (E)-benzyl (1H-pyrazol-1-yl)methanediylidenedicarbamate (1.95 g, 5.15 mmol, CASRN 152120-55-3) in THF (10 mL) at RT under nitrogen was added DIPEA (2.24 mL, 12.9 mmol) via syringe. The mixture was stirred for 2 h then 1-methyl-1H-pyrazol-5-amine (0.500 g, 5.15 mmol) was added and stirred for 3 d. The reaction was diluted to 50 mL with EtOAc and washed sequentially with 2N HCl (2×50 mL), satd. aq. NaHCO$_3$ (2×50 mL) and brine (1×50 mL). The organic phase was isolated, dried (MgSO$_4$), filtered and concentrated to afford 1.00 g (90% purity, 43%) of (Z)-benzyl (benzyloxycarbonylamino)(1-methyl-1H-pyrazol-5-ylamino)methylenecarbamate (180) as a white solid which was used without further purification: MS m/z (APCI-pos) M+1=408.3

Step 2:

To a stirred solution of 180 (1.00 g, 2.45 mmol) in EtOH/THF (1:1, 35 mL) at RT was added Pearlman's Catalyst (0.172 g, 0.245 mmol). The mixture subjected to a vacuum/purge cycle three times with hydrogen gas and then maintained under 1 atmosphere balloon of hydrogen pressure. After stirring overnight and the reaction was filtered through GF/F filter paper with EtOH and the filtrate was concentrated to afford 0.31 g (90%) of 1-(1-methyl-1H-pyrazol-5-yl) guanidine (182) as a clear glass which was used without further purification: MS m/z (APCI-pos) M+1=140.0.

Step 3:

A sealable pressure tube was charged with 182 (0.310 g, 2.23 mmol) in THF/EtOH (1:1, 10 mL) at RT flushed with nitrogen and 21 (0.567 g, 2.23 mmol) was added. The solution was warmed to 100° C. for 24 h. The reaction was cooled to RT and concentrated to afford 0.556 g (70%) of tert-butyl 2-(1-methyl-1H-pyrazol-5-ylamino)-5,6-dihydropyrido[3,4-d]pyrimidine-7(8H)-carboxylate as an white glassy solid: MS m/z (APCI-pos) M+1=331.1.

Step 4:

To a solution of tert-butyl 2-(1-methyl-1H-pyrazol-5-ylamino)-5,6-dihydropyrido[3,4-d]pyrimidine-7(8H)-carboxylate (0.556 g, 1.68 mmol) in DCM/EtOH 5 mL, 1:1) was added 4N HCl in dioxane (4.21 ml, 16.8 mmol) and the solution stirred for 18 h. The reaction was concentrated to afford an orange solid that was neutralized by stirring with 7N NH$_3$/MeOH and washed with DCM. The precipitate was filtered and purified by SiO$_2$ chromatography (SNAP 25) eluting with a MeOH/DCM gradient (0 to 20% MeOH) to afford 0.223 g (75% purity, 44% yield) of N-(1-methyl-1H-pyrazol-5-yl)-5,6,7,8-tetrahydropyrido[3,4-d]pyrimidin-2-amine (184) as a light yellow solid: MS m/z (APCI-pos) M+1=231.2.

Step 5:

A vial was charged with (R)-1-(3,4-dichlorophenyl)ethanamine (185, 0.046 g, 0.24 mmol, CASRN 150520-10-8), CDI (0.040 g, 0.24 mmol), DIPEA (0.085 ml, 0.49 mmol) and DCM (1 mL), sealed and stir for 30 min. A solution of 184 (0.075 g, 0.24 mmol), DIPEA (0.085 ml, 0.49 mmol) and DCM (1 mL) was added. The reaction mixture was stirred for 5 h, washed with brine (4 mL), and loaded on a preparative SiO$_2$ TLC (1.0 mm thickness). The plate was developed with EtOAc/MeOH (95:5) which afforded 0.0041 g (4%) of I-29: $^1$H NMR (400 MHz, CDCl$_3$) δ 8.21 (s, 1H), 7.48 (m, 3H), 7.19 (m, 1H), 6.76 (s, 1H), 6.27 (s, 1H), 4.97 (m, 1H), 4.76 (m, 1H), 4.38 (s, 2H), 3.76 (s, 3H), 3.69 (m, 2H), 2.73 (m, 2H), 1.49 (m, 3H); m/z (APCI-pos) M+1=446.0.

(R)—N-(1-(3,4-dichlorophenyl)ethyl)-2-(1-ethyl-1H-pyrazol-4-ylamino)-5,6-dihydropyrido[3,4-d]pyrimidine-7(8H)-carboxamide (I-30) was prepared analogously except in step 1,1-methyl-1H-pyrazol-5-amine was replaced with 1-ethyl-1H-pyrazol-4-amine. I-30 was purified on a preparative SiO$_2$ TLC (1.0 mm thickness) and developed with EtOAc/MeOH (95:5) to afford 0.0185 g (12%) of product as a clear glass: $^1$H NMR (400 MHz, CDCl$_3$) δ 8.17 (s, 1H), 7.82 (s, 1H), 7.50 (s, 1H), 7.42 (m, 1H), 7.38 (d, 1H), 7.19 (m, 1H), 7.03 (s, 1H), 4.94 (m, 2H), 4.43 (s, 1H), 4.15 (q, 2H), 3.67 (m, 2H), 2.70 (t, 2H), 1.49 (m, 6H); m/z (APCI-pos) M+1=460.1.

(R)—N-(1-(3,4-dichlorophenyl)ethyl)-2-(1-methyl-1H-pyrazol-4-ylamino)-5,6-dihydropyrido[3,4-d]pyrimidine-7(8H)-carboxamide (I-31) was prepared analogously except in step 1,1-methyl-1H-pyrazol-5-amine was replaced with 1-methyl-1H-pyrazol-4-amine. I-31 was purified by SiO$_2$ chromatography (Biotage) eluting with MeOH/EtOAc (5/95) to afford 82 mg (86%) of I-31.

Example 26

N—((R)-1-(3,4-dichlorophenyl)-3-hydroxypropyl)-2-((S)-1-hydroxypropan-2-ylamino)-5,6-dihydropyrido[3,4-d]pyrimidine-7(8H)-carboxamide (I-33)

Step 1:

A round-bottom flask was charged with (R)-3-amino-3-(3,4-dichlorophenyl)propan-1-ol (9.25 g, 42.0 mmol, CASRN 147611-61-8), DMAP (0.513 g, 4.20 mmol) and DCM (84.1 mL) then a solution of TBDMS-Cl (6.65 g, 44.1 mmol) and DCM (10 mL) was added. The reaction was stirred at RT for 2 d. The reaction mixture was poured into water and extracted with DCM. The organic extracts were dried (Na$_2$SO$_4$), filtered and concentrated in vacuo. The crude product was purified by SiO$_2$ chromatography eluting with a DCM/MeOH gradient (500:8 to 500:10) to afford 10.2 g (72%) of (R)-3-(tert-butyl dimethylsilyloxy)-1-(3,4-dichlorophenyl)propan-1-amine (186): m/z (APCI-pos) M+1=334.0.

Chiral ee analysis was carried out with a Mosher amide. (The amine was stirred with mosher acid chloride, DIPEA and CDCl$_3$ for 15 min). $^{19}$F NMR analysis of the peaks at −69.26 and −69.33 compared to racemate indicated an ee of 81%. Obtained (R)-3-(tert-butyl dimethylsilyloxy)-1-(3,4-dichlorophenyl)propan-1-amine 10.2, (100% purity, 72% yield).

Step 2:

A vial was charged with 186 (0.161 g, 0.480 mmol), CDI (0.0779 g, 0.480 mmol), DIPEA (0.167 ml, 0.960 mmol) and DCM (1 mL). The solution was stirred for 30 min then a solution of (S)-2-(5,6,7,8-tetrahydropyrido[3,4-d]pyrimidin-2-ylamino)propan-1-ol (0.100 g, 0.480 mmol), DIPEA (0.167 ml, 0.960 mmol) and DCM (1 mL) was added and the solution stirred overnight. The reaction mixture was washed the reaction with brine (4 mL) and loaded on a preparative SiO₂ TLC (1.0 mm thickness) and developed with DCM/MeOH (9:1). The product was eluted and afforded 83 mg of product as a silyl ether which was diluted with DCM/MeOH (4:1.5 mL) and a 4N HCl/dioxane solution was added and the reaction stirred for 4 h. The volatile solvents were removed and the crude product purified on a preparative SiO₂ plate and developed with eluting with DCM/7M methanolic NH3 (9:1). The recovered material was further purified on a Biotage 12M Horizen C18 column eluting with MeCN/H₂O (~20-25% (H₂O/MeCN) to afford 0.045 g (20%) of I-33: ¹H NMR (400 MHz, CDCl₃) δ 7.99 (s, 1H), 7.46 (m, 1H), 7.38 (d, 1H), 7.23 (m, 1H), 4.91 (m, 1H), 4.79 (s, 2H), 4.36 (q, 2H), 4.03 (m, 1H), 3.53 (m, 6H), 2.59 (m, 2H), 1.94 (m, 2H), 1.16 (d, 3H); m/z (APCI-pos) M+1=454.1.

Example 27

(R)—N-(1-(3,4-dichlorophenyl)ethyl)-2-(2-ethoxypyridin-4-ylamino)-5,6-dihydropyrido[3,4-d]pyrimidine-7(8H)-carboxamide (I-35)

N-(2-ethoxypyridin-4-yl)-5,6,7,8-tetrahydropyrido[3,4-d]pyrimidin-2-amine (186) was prepared in accord with the procedures described in steps 1 to 4 of example 25 except in step 1, 1-methyl-1H-pyrazol-5-amine was replaced with 2-ethoxypyridin-4-amine.

A vial was charged with 185 (0.105 g, 0.553 mmol), CDI (0.0896 g, 0.553 mmol) and DCM (2 mL) and stirred for 30 min. To the solution was added 186 (0.150 g, 0.553 mmol) and DIPEA (0.193 ml, 1.11 mmol) and the resulting reaction stirred for 3 d. The reaction was washed with brine (4 mL), and the organic phase concentrated and loaded on to a preparative SiO₂ plate (1.0 mm thickness) which was developed with EtOAc/MeOH (95:5) and eluted to afford 0.038 g (13%) of I-35: ¹H NMR (400 MHz, CDCl₃) δ 8.23 (s, 1H), 7.96 (d, 1H), 7.73 (s, 1H), 7.44 (m, 1H), 7.35 (d, 1H), 7.29 (m, 1H), 7.20 (m, 1H), 6.95 (m, 1H), 5.40 (d, 1H), 5.00 (m, 1H), 4.49 (s, 1H), 4.36 (q, 2H), 3.68 (m, 2H), 2.72 (d, 2h), 1.49 (d, 3H), 1.39 (t, 3H); m/z (APCI-pos) M+1=487.2.

Example 28

(R)—N-(1-(3,4-dichlorophenyl)ethyl)-2-(2-methylpyridin-4-ylamino)-5,6-dihydropyrido[3,4-d]pyrimidine-7(8H)-carboxamide (I-36)

tert-Butyl 2-amino-5,6-dihydropyrido[3,4-d]pyrimidine-7(8H)-carboxylate (187) was prepared in accord with the procedure described in step 4 of example 1 except 24 was replaced with guanidine.

Step 1:
A tube was charged with 187 (300 mg, 1.20 mmol), Pd(dba)₂ (34.5 mg, 0.0599 mmol), Binap-rac (74.6 mg, 0.120 mmol), 4-chloro-2-methylpyridine (229 mg, 1.80 mmol), and NaO-tert-Bu (230 mg, 2.40 mmol) and toluene (3 mL), sealed, degassed with nitrogen for 5 min then heated to 90° C. for 4 h. The reaction was cooled and filtered through a plug of CELITE®. The filtrate was concentrated and purified by reverse phase column chromatography (SP4) eluting with a MeCN/H₂O gradient (5 to 85% MeCN) to afford 136 mg (33.2%) of tert-butyl 2-(2-methylpyridin-4-ylamino)-5,6-dihydropyrido[3,4-d]pyrimidine-7(8H)-carboxylate (188).

Step 2:
A solution of 188 (136 mg, 0.398 mmol) and TFA (2 mL) was stirred for 15 min. The reaction was concentrated to afford N-(2-methylpyridin-4-yl)-5,6,7,8-tetrahydropyrido[3,4-d]pyrimidin-2-amine (190) which was used without additional purification.

Step 3:
Condensation of 190 and 185 was carried out in accord with the procedure in step 6 of example 1 to afford 70 mg (72%) of I-36: ¹H NMR (400 MHz, CDCl₃) δ 8.35 (d, 1H), 8.29 (s, 1H), 7.44-7.35 (m, 3H), 7.19 (dd, 1H), 7.14 (s, 1H), 5.00 (m, 1H), 4.74 (d, 1H), 4.50 (s, 2H), 3.70 (m, 2H), 2.78 (t, 2H), 2.54 (s, 3H), 1.50 (d, 3H); LCMS (APCI+) m/z 461.1 (M+H)⁺.

Example 29

(S)—N-(1-(3,4-dichlorophenyl)-2-methoxyethyl)-2-(tetrahydro-2H-pyran-4-ylamino)-5,6-dihydropyrido[3,4-d]pyrimidine-7(8H)-carboxamide (I-41)

Step 1:
To a solution of 2-methoxyacetyl chloride (10 g, 92.1 mmol) and DCM (100 mL) cooled to 0° C. was added N,O-dimethylhydroxylamine hydrochloride (9.89 g, 101 mmol) and TEA (38.5 mL, 276 mmol) and the reaction warmed to RT and stirred for 18 h. The reaction mixture was poured into H₂O and extracted with DCM. The combined organic extracts were dried (MgSO₄), filtered, and concentrated to give the crude product, which was purified by SiO₂ chromatography eluting with DCM/MeOH (500:50) to afford 12 g (97.8%) of N,2-dimethoxy-N-methylacetamide.

Step 2:
To a solution of 4-bromo-1,2-dichlorobenzene (2.04 g, 9.01 mmol) and ether (5 mL) cooled to -78° C. was added as a steady stream n-BuLi (3.61 ml, 9.01 mmol) and the reaction was stirred for 10 min then cannulated into a solution of N,2-dimethoxy-N-methylacetamide (1.0 g, 7.51 mmol) and ether (10 mL) which was stirred for an additional 20 min. The reaction was quenched with water and extracted with EtOAc. The organic fractions were dried, filtered and concentrated. The crude product which was purified by SiO₂ chromatography eluting with hexane/EtOAc (9:1) to afford 1.30 g (79.0%) of 1-(3,4-dichlorophenyl)-2-methoxyethanone as a white solid (192).

Step 3:
A solution of (R)-1-methyl-3,3-diphenylhexahydropyrrolo[1,2-c][1,3,2]oxazaborole (0.593 ml, 0.593 mmol) and borane diethylaniline (1.05 ml, 5.93 mmol) and MTBE (15 mL) was prepared at RT and then heated to 40° C. A solution of 192 (1.30 g, 5.93 mmol) and MTBE (15 mL) was then added dropwise to the above solution and the reaction was stirred at 40° C. for 30 min. The reaction was quenched with MeOH followed by the addition of 1M HCl and the resulting mixture poured into water and extracted with DCM. The combined organic fractions were dried (MgSO₄), filtered, and concentrated. The crude product was purified by SiO₂ chromatography eluting with a hexane/EtOAc gradient (6:1 to 4:1) to afford 1.25 g (95.3%) of (R)-1-(3,4-dichlorophenyl)-2-methoxyethanol (194).

Step 4:
To a solution of 194 (1.25 g, 5.65 mmol) and THF (10 mL) at RT was added sequentially isoindoline-1,3-dione (0.915 g, 6.22 mmol) and PPh₃ (2.22 g, 8.48 mmol) followed by the dropwise addition of DEAD (3.34 mL, 8.48 mmol). The reaction was warmed to RT, stirred for 20 h and then concentrated to dryness. Ether (300 mL) was added, and the resulting solid was filtered and discarded. The filtrate was then poured into water, and extracted with DCM. The combined organic fractions were dried (MgSO₄), filtered and concentrated. The crude product was purified by SiO₂ chromatography eluting with DCM to afford 1.9 g (96.0%) of (S)-2-(1-(3,4-dichlorophenyl)-2-methoxyethyl)isoindoline-1,3-dione (196).

Step 5:

To a solution of 196 (2.0 g, 5.7 mmol) and THF:MeOH (1:1, 20 mL) at RT was added hydrazine monohydrate (2.9 g, 57 mmol) and the reaction was heated to 50° C. for 18 h. The reaction was cooled to RT, filtered, and the filtrate was poured into water and extracted with DCM. The combined organic fractions were dried (MgSO₄), filtered, and concentrated. The crude product was purified by SiO₂ chromatography eluting with DCM/MeOH (500:30) to afford 1.1 g (88%) of (S)-1-(3,4-dichlorophenyl)-2-methoxyethanamine as a off-white solid (198).

Step 7:

Condensation of 198 and 28 was carried out in accord with the procedure described in step 6 of example 1 to afford 0.110 g (31%) of I-41. The crude product was purified by SiO₂ chromatography eluting with a DCM/MeOH gradient (500: 10 to 500:15): MS m/z (APCI-pos) M+1=480.

(S)—N-(1-(4-chloro-3-fluorophenyl)-2-methoxyethyl)-2-(tetrahydro-2H-pyran-4-ylamino)-5,6-dihydropyrido[3,4-d]pyrimidine-7(8H)-carboxamide (I-45) was prepared analogously except in step 1,4-bromo-1,2-dichlorobenzene was replaced with 4-bromo-1-chloro-2-fluoro-benzene which afforded (S)-1-(4-chloro-3-fluorophenyl)-2-methoxyethanamine (197). The crude product was purified by SiO₂ chromatography eluting with DCM/MeOH (500:10 to 500:15): MS m/z (APCI-pos) M+1=464.

N—((S)-1-(3,4-dichlorophenyl)-2-methoxyethyl)-2-((S)-1-hydroxypropan-2-ylamino)-5,6-dihydropyrido[3,4-d]pyrimidine-7(8H)-carboxamide (I-48) was prepared analogously except in step 1, except 28 was replaced with 138. The crude product was purified by SiO₂ chromatography eluting with DCM/MeOH (500:15 to 500:25): m/z (APCI-pos) M+1=454.

N—((S)-1-(4-chloro-3-fluorophenyl)-2-methoxyethyl)-2-((S)-1-hydroxypropan-2-ylamino)-5,6-dihydropyrido[3,4-d]pyrimidine-7(8H)-carboxamide (I-55) was prepared analogously except in step 1, except 28 was replaced with 138 and in step 7, 198 was replaced with 197. The crude product was purified by SiO₂ chromatography eluting with DCM/MeOH gradient (500:5 to 500:25) to afford 0.205 g (47.7%) of I-55: MS m/z (APCI-pos) M+1=438.

Example 30

(S)—N-(1-(3-chloro-4-fluorophenyl)-2-hydroxyethyl)-2-(tetrahydro-2H-pyran-4-ylamino)-5,6-dihydropyrido[3,4-d]pyrimidine-7(8H)-carboxamide (I-46)

To a solution of (S)—N-(2-(tert-butyldimethylsilyloxy)-1-(3-chloro-4-fluorophenyl)ethyl)-2-(tetrahydro-2H-pyran-4-ylamino)-5,6-dihydropyrido[3,4-d]pyrimidine-7(8H)-carboxamide (0.250 g, 0.443 mmol) and THF (5 mL) at RT was added TBAF (0.532 mL, 0.532 mmol) and the reaction was stirred for 1 h at RT, poured into water and extracted with DCM. The combined organic fractions were dried (MgSO₄), filtered, and concentrated in vacuo. The crude product was purified by SiO₂ chromatography eluting with a DCM/MeOH gradient (500:20 to 500:30) to afford 0.100 g (50.2%) of I-46: ¹H NMR (400 MHz, d₆-DMSO) δ 8.08 (s, 1H), 7.52 (d, 1H), 7.32 (d, 2H), 6.91-6.86 (m, 2H), 4.85 (br s, 1H), 4.74 (m, 1H), 4.40-4.30 (m, 2H), 3.87-3.84 (m, 3H), 3.58-3.54 (m, 4H), 3.38-3.31 (m, 2H), 2.56-2.54 (m, 2H), 1.81-1.78 (m, 2H), 1.53-1.46 (m, 2H); MS m/z (APCI-pos) M+1=450.

Example 31

(S)-2-(3-chloro-4-fluorophenyl)-2-(2-(tetrahydro-2H-pyran-4-ylamino)-5,6,7,8-tetrahydropyrido[3,4-d]pyrimidine-7-carboxamido)ethyl acetate (I-47)

To a solution of I-46 (0.150 g, 0.333 mmol) and DCM (5 mL) at RT was added sequentially TEA (0.139 mL, 1.00 mmol) and Ac₂O (0.0346 mL, 0.367 mmol) and the reaction was stirred at RT for 1 h and then poured into water, and extracted with DCM. The combined organic fractions were dried (MgSO₄), filtered, and concentrated in vacuo. The crude product was purified by SiO₂ chromatography eluting with DCM/hexane (500:20) to afford 0.150 g (91.5%) of I-47: MS m/z (APCI-pos) M+1=492.

(S)-2-(3-chloro-4-fluorophenyl)-2-(2-(tetrahydro-2H-pyran-4-ylamino)-5,6,7,8-tetrahydropyrido[3,4-d]pyrimidine-7-carboxamido)ethyl pivalate (I-67)

To a solution of I-46 (0.100 g, 0.222 mmol), TEA (0.0929 mL, 0.667 mmol) and DCM (5 mL) at RT was added sequentially pivalic anhydride (0.0496 mL, 0.244 mmol) and DMAP (0.0272 g, 0.222 mmol). The reaction was heated to 50° C. for 5 h and then cooled to RT and then poured into water, and extracted with DCM. The combined organic extracts were dried (MgSO₄), filtered, and concentrated in vacuo. The crude product was purified by SiO₂ chromatography eluting with DCM/MeOH (500:10) to afford 0.060 g (50.5%) of I-67: MS m/z (APCI-pos) M+1=534.

Example 32

(R)—N-(1-(3,4-dichlorophenyl)ethyl)-5,5-difluoro-2-(tetrahydro-2H-pyran-4-ylamino)-5,6-dihydropyrido[3,4-d]pyrimidine-7(8H)-carboxamide (I-50)

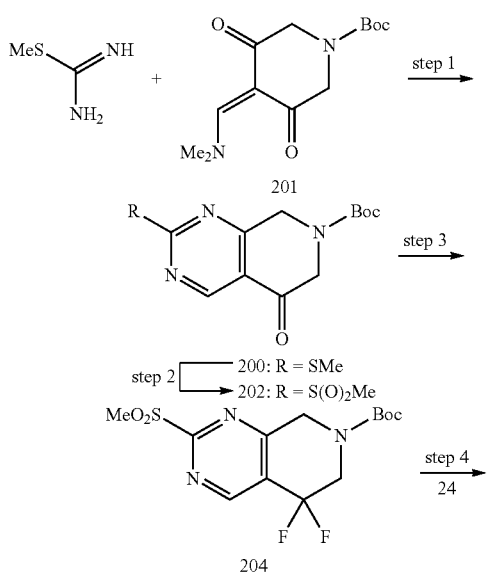

-continued

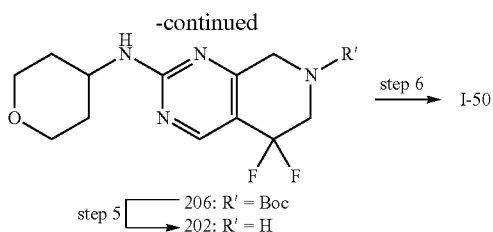

step 5 [ 206: R' = Boc
         202: R' = H

Step 1:

To a stirred suspension of methyl carbamimidothioate hemisulfate (14.72 g, 52.89 mmol, CASRN 867-44-7) in EtOH (105 mL) at RT under nitrogen was added neat via pipet DIPEA (20.10 mL, 115.4 mmol). The mixture was heated to 80° C. for 30 min and a solution of 1,1-dimethylethyl 4-[(dimethylamino)methylene]-3,5-dioxo-1-piperidinecarboxylate (201, 12.90 g, 48.08 mmol, CASRN 478623-90-4) in absolute EtOH (45 mL) was then added via pipet and heating at 80° C. for 3 h. The reaction was then cooled to RT and partially concentrated in a rotovap. The mixture was partitioned between with EtOAc and satd. aq. NaHCO$_3$ (400 mL, 1:1). The layers were separated and the organic phase washed with brine (1×200 mL). The organics layer was isolated, dried (MgSO$_4$), filtered and concentrated in vacuo. The crude product was loaded onto a SiO$_2$ column (Biotage 65M) with DCM and was eluted with EtOAc/hexane (15/85). The product containing fractions were pooled and concentrated to afford 3.3 g (23%) of tert-butyl 2-(methylthio)-5-oxo-5,6-dihydropyrido[3,4-d]pyrimidine-7(8H)-carboxylate (200) as a pale yellow solid.

Step 2:

To a stirred solution of 200 (3.3 g, 11.2 mmol) in DCM (66 mL) at RT under nitrogen was added neat solid MCPBA (6.91 g, 28.0 mmol, technical grade, 65-70% by weight). After 4 h the reaction was quenched with 10% sodium thiosulfate solution (0.63 M, 110 mL) and stirred for 30 min. The mixture was then diluted to 400 mL with DCM satd. aq. NaHCO$_3$ (1:1) and shaken. The layers were separated (emulsions formed) and the aqueous phase was extracted with DCM (2×100 mL). The combined organics were isolated, dried (MgSO$_4$), filtered and concentrated to afford 2.7 g (73%) of tert-butyl 2-(methylsulfonyl)-5-oxo-5,6-dihydropyrido[3,4-d]pyrimidine-7(8H)-carboxylate (202) as a yellow solid.

Step 3:

To a stirred solution of 202 (2.0 g, 6.110 mmol) in DCE (18 mL) at RT in a capped polyethylene vial was added deoxofluor (1.239 mL, 6.721 mmol) neat via syringe. The reaction was warmed to 50° C. and stirred overnight. After cooling to RT, the reaction was poured into ice-cold satd. aq. NaHCO$_3$ (50 mL) with stirring. After 15 min, the pH was still basic (approx. pH=9). The mixture was diluted with DCM (50 mL) and stirred for another 5 min. The layers were separated (emulsions) and the aqueous phase extracted with DCM (1×50 mL). The combined organics were washed with satd. aq. NaHCO$_3$ (1×100 mL), isolated, dried (MgSO$_4$), filtered and concentrated in vacuo. The crude product was purified by SiO$_2$ chromatography (Biotage 40M column). The crude was loaded on the column with DCM and eluted with EtOAc/hexanes (3/7) which afford a pale yellow foam. The foam was triturated with EtOAc/hexane (1/1) and the resulting solid filtered off and dried under high vacuum to afford 850 mg (40%) of tert-butyl 5,5-difluoro-2-(methylsulfonyl)-5,6-dihydropyrido[3,4-d]pyrimidine-7(8H)-carboxylate (204) as a white solid.

Step 4:

To a stirred suspension of 204 (349 mg, 1 mmol) in IPA (3 mL) at RT under nitrogen was added sequentially via syringe neat DIPEA (174 µL, 1 mmol) and neat tetrahydro-2H-pyran-4-amine (101 mg, 1 mmol). The mixture was heated to 90° C. and became homogeneous. Heating was continued for 60 min them cooled to RT, diluted to 30 mL with EtOAc and was washed sequentially with 10% citric acid solution (2×30 mL) and satd. aq. NaHCO$_3$ (2×30 mL). The organic phase was isolated, dried (MgSO$_4$), filtered and concentrated to a clear oil. The oil was triturated with hexane/EtOAc (4/1) with sonication to produce a precipitate that was filtered and rinsed with hexane/EtOAc (4/1). The mother liquor was recovered and re-precipitated. Both precipitated batches were combined to afford 215 mg (58%) of tert-butyl 5,5-difluoro-2-(tetrahydro-2H-pyran-4-ylamino)-5,6-dihydropyrido[3,4-d]pyrimidine-7(8H)-carboxylate (206) as a white solid.

Step 5:

To a stirred solution of 206 (215 mg, 0.5805 mmol) in DCM (4 mL) at RT under nitrogen was added 5M HCl in IPA (1.161 mL, 5.805 mmol) by pipet. After stirring overnight, the reaction was concentrated to dryness by rotovap and high vacuum to afford 106 mg (100%) of 5,5-difluoro-N-(tetrahydro-2H-pyran-4-yl)-5,6,7,8-tetrahydropyrido[3,4-d]pyrimidin-2-amine hydrochloride (208) which was used without additional purification.

Step 6:

Condensation of 208 and 185 were carried out in accord with the procedure in step 5 of example 25. The crude product was loaded onto a small SiO$_2$ gravity column (1×2 cm) with EtOAc/hexane (1/1) and eluted to afford 4 mg (47%) of I-50 as a yellow foam: $^1$H NMR (400 MHz, CDCl$_3$) δ 8.56 (br s, 1H), 7.40 (s, 1H), 7.39 (d, 1H), 7.16 (dd, 1H), 5.28 (br s, 1H), 4.95 (m, 1H), 4.79 (d, 1H), 4.45 (br s, 1H), 4.08 (br s, 1H), 3.98 (m, 4H), 3.94 (m, 2H), 3.55 (m, 2H), 2.01 (m, 2H), 1.55 (m, 2H), 1.48 (d, 3H); m/z (APCI-pos) M+1=487.3.

(S)—N-(1-(4-chloro-3-fluorophenyl)-2-methoxyethyl)-5,5-difluoro-2-(tetrahydro-2H-pyran-4-ylamino)-5,6-dihydropyrido[3,4-d]pyrimidine-7(8H)-carboxamide (I-51) To a solution of 197 (0.0854 g, 0.293 mmol) and DCM (5 mL) was added sequentially TEA (0.123 mL, 0.880 mmol) and CDI (0.0476 g, 0.293 mmol) and the solution was stirred at RT for 30 min. To the solution was added dropwise a solution of TEA (0.123 mL, 0.880 mmol), 208 (0.090 g, 0.293 mmol) and DCM (5 mL). The reaction was stirred for 18 h then poured into water and extracted with DCM. The combined organic extracts were dried (MgSO$_4$), filtered, and concentrated in vacuo. The crude product was purified by SiO$_2$ chromatography eluting with 2% MeOH/DCM to afford 0.060 g (40.9%) of I-51: MS m/z (APCI-pos) M+1=499.

(S)—N-(1-(3-chloro-4-fluorophenyl)-2-hydroxyethyl)-5,5-difluoro-2-(tetrahydro-2H-pyran-4-ylamino)-5,6-dihydropyrido[3,4-d]pyrimidine-7(8H)-carboxamide (I-53)

(S)-2-(tert-butyldimethylsilyloxy)-1-(3-chloro-4-fluorophenyl)ethanamine (210) was prepared in accord with the procedures described in steps 1 to 5 of example 10 except in step 2, (4-chloro-3-fluorophenyl) magnesium bromide was replaced with 3-chloro-4-fluorophenyl) magnesium bromide.

Condensation of 208 and 210 to afford (S)—N-(2-(tert-butyldimethylsilyloxy)-1-(3-chloro-4-fluorophenyl)ethyl)-5,5-difluoro-2-(tetrahydro-2H-pyran-4-ylamino)-5,6-dihydropyrido[3,4-d]pyrimidine-7(8H)-carboxamide (212) were carried out in accord with the procedure in step 6 of example 1, except 28 was replaced with 208 and 22 was replaced with 210. Removal of the silyl protecting group of 212 was carried out in accord with the procedure in step 7 of example 10. The crude product was purified by $SiO_2$ chromatography eluting with a DCM/MeOH gradient (500:30 to 500:40) to afford 0.070 g (86.5%) of I-53: MS m/z (APCI-pos) M+1=486.

Example 33

(S)—((S)-2-(3-chloro-4-fluorophenyl)-2-(2-(tetrahydro-2H-pyran-4-ylamino)-5,6,7,8-tetrahydropyrido[3,4-d]pyrimidine-7-carboxamido)ethyl) 2-amino-3-methylbutanoate (I-54)

Step 1:
To a solution of I-46 (0.100 g, 0.222 mmol) and (S)-2-(tert-butoxycarbonylamino)-3-methylbutanoic acid (0.0531 g, 0.244 mmol) and DCM (5 mL) at RT was added DMAP (0.0543 g, 0.445 mmol) and DCC (0.0504 g, 0.244 mmol) and the reaction was stirred at RT for 1 h and then poured into water, and extracted with DCM. The combined organic fractions were dried ($MgSO_4$), filtered and concentrated in vacuo. The crude product was purified by $SiO_2$ chromatography eluting with DCM/MeOH (500:15) to afford 0.130 g (90.1%) of (S)—((S)-2-(3-chloro-4-fluorophenyl)-2-(2-(tetrahydro-2H-pyran-4-ylamino)-5,6,7,8-tetrahydropyrido[3,4-d]pyrimidine-7-carboxamido)ethyl) 2-(tert-butoxycarbonylamino)-3-methylbutanoate (214).

Step 2:
To a solution of 214 (0.130 g, 0.200 mmol) and DCM (5 mL) was added HCl (0.334 mL, 2.00 mmol) was added, and the reaction was stirred for 2 h, and then poured into satd. aq. $NaHCO_3$ and extracted with DCM. The combined organic fractions were dried ($MgSO_4$), filtered and concentrated in vacuo. The crude product was purified by $SiO_2$ chromatography eluting with a DCM/MeOH gradient (500:40 to 500:50) to afford 0.090 g (81.9%) of I-54: MS m/z (APCI-pos) M+1=549.

(S)-2-(3-chloro-4-fluorophenyl)-2-(2-(tetrahydro-2H-pyran-4-ylamino)-5,6,7,8-tetrahydropyrido[3,4-d]pyrimidine-7-carboxamido)ethyl 2-methoxyacetate (I-56) was prepared analogously except in step 1, and (S)-2-(tert-butoxycarbonylamino)-3-methylbutanoic acid was replaced with 2-methoxyacetic acid and step 2 was omitted. The crude product was purified by $SiO_2$ chromatography eluting with DCM/MeOH (500:15) to afford 0.120 g (76.6%) of I-56: MS m/z (APCI-pos) M+1=522.

Example 34

N—((R)-1-(4-chloro-3-fluorophenyl)propyl)-2-((S)-1-hydroxybutan-2-ylamino)-5,6-dihydropyrido[3,4-d]pyrimidine-7(8H)-carboxamide (I-57)

(S)-2-(5,6,7,8-tetrahydropyrido[3,4-d]pyrimidin-2-ylamino)butan-1-ol hydrochloride (216) was prepared in accord with the process described in steps 1 to 3 of example 17 except in step 1, (S)-2-aminopropan-1-ol was replaced with (S)-2-aminobutan-1-ol. After drying under high vacuum, the process afforded 216 as a hygroscopic solid.

Step 1:
To a solution of 139 (0.173 g, 0.773 mmol) and DCM (5 mL) at RT was added TEA (0.235 g, 2.32 mmol) and CDI (0.125 g, 0.773 mmol) and the reaction was stirred at RT for 30 min. To this solution was added dropwise a solution of 216 (0.200 g, 0.773 mmol), TEA (0.235 g, 2.32 mmol) and DCM (5 mL) and the resulting solution stirred for 4 h then poured into water and extracted with DCM. The combined organic fractions were dried ($MgSO_4$), filtered, and concentrated in vacuo. The crude product was purified by $SiO_2$ chromatography eluting with DCM/MeOH (500:40) to afford 0.050 g (14.8%) of I-57: MS m/z (APCI-pos) M+1=436.

Example 35

N—((R)-1-(3-chloro-4-(trifluoromethoxy)phenyl)propyl)-2-((S)-1-hydroxypropan-2-ylamino)-5,6-dihydropyrido[3,4-d]pyrimidine-7(8H)-carboxamide (I-58)

Step 1:
To a solution of 3-chloro-4-(trifluoromethoxy)benzaldehyde (2.8 g, 12 mmol) and (R)-2-methylpropane-2-sulfinamide (2.7 g, 22 mmol) and THF (25 mL) at RT was added tetraethoxytitanium (9.3 mL, 45 mmol) and the reaction was heated to 65° C. for 12 h. The reaction was cooled to RT, water (100 mL) was added and the solids were filtered and discarded. The filtrate was extracted with EtOAc, the organic fraction was dried, filtered, and concentrated in vacuo. The crude product was purified by $SiO_2$ chromatography eluting with DCM/MeOH (500:10) to afford 3.8 g (98%) of (R,E)-N-(3-chloro-4-(trifluoromethoxy)benzylidene)-2-methylpropane-2-sulfinamide (218).

Step 2:
To a solution of 218 (3.8 g, 12 mmol) and THF (40 mL) cooled to −78° C. was added dropwise a solution of ethylmagnesium bromide (5.8 mL, 17 mmol) in ether and the solution was stirred for 1 h, quenched with water, and extracted with $Et_2O$. The crude product was purified by $SiO_2$ chromatography eluting with an EtOAc/hexane gradient (35 to 40% EtOAc) to afford 3.5 g (84%) of (R)—N—((R)-1-(3-chloro-4-(trifluoromethoxy)phenyl)propyl)-2-methylpropane-2-sulfinamide (220).

Step 3:
To a solution of 220 (3.5 g, 9.8 mmol) and DCM (10 mL) was added 4N HCl in dioxane (17 mL, 68 mmol) and the reaction stirred for 30 min at RT. $Et_2O$ was added, and the reaction stirred for 10 min and filtered, washed with ether and dried to afford 2.5 g (88%) of (R)-1-(3-chloro-4-(trifluoromethoxy)phenyl)propan-1-amine hydrochloride (222) as a white solid.

Step 4:
Condensation of 222 and 138 was carried out in accord with the procedure in step 6 of example 1 except, 22 was replaced with 222 and 28 was replaced with 138. The crude product was purified by $SiO_2$ chromatography eluting with an EtOAc/hexane gradient (45-50% EtOAc) to afford 0.12 g (28.5%) of I-58: MS m/z (APCI-pos) M+1=488.

Example 36

(R)—N-(1-(3-chloro-4-fluorophenyl)-2-cyanoethyl)-2-(tetrahydro-2H-pyran-4-ylamino)-5,6-dihydropyrido[3,4-d]pyrimidine-7(8H)-carboxamide (I-59)

Step 1:
To a solution of (S)-tert-butyl 1-(3-chloro-4-fluorophenyl)-2-hydroxyethylcarbamate (0.75 g, 2.59 mmol) and DCM (15 mL) at RT was added TEA (0.541 mL, 3.88 mmol) and MsCl (0.210 mL, 2.72 mmol). The reaction was stirred at RT for 1 h then poured into water and extracted with DCM. The combined organic extracts were dried ($MgSO_4$), filtered, and concentrated in vacuo. The crude product was purified by $SiO_2$ chromatography eluting with DCM/MeOH (500:5) to afford 0.8 g (84%) of (S)-2-(tert-butoxycarbonylamino)-2-(3-chloro-4-fluorophenyl)ethyl methanesulfonate (224).

Step 2:
To a solution of 224 (1.5 g, 4.1 mmol) and THF/acetone (24 mL, 5:1) was added NaI (3.1 g, 20 mmol) and the reaction was stirred at RT overnight. The reaction mixture was poured into water and extracted with EtOAc. The combined organic fractions were dried ($MgSO_4$), filtered, and concentrated in vacuo to afford 1.6 g (98%) of (S)-tert-butyl 1-(3-chloro-4-fluorophenyl)-2-iodoethylcarbamate which was used without additional purification.

Step 3:
To a solution of the iodide (1.6 g, 4.0 mmol) and DMSO (10 mL) was added NaCN (0.22 g, 4.4 mmol) and the reaction was heated to 80° C. for 18 h. The reaction was cooled to RT, water was added and the solution extracted with EtOAc. The organic fraction was dried, filtered, and concentrated in vacuo. The crude product was purified by $SiO_2$ chromatography eluting with hexane/EtOAc (4:1) to afford 0.75 g (63%) of (R)-tert-butyl 1-(3-chloro-4-fluorophenyl)-2-cyanoethylcarbamate (226).

Step 4:
To a solution of 226 (0.350 g, 1.17 mmol) in dioxane (5 mL) was added 4N HCl in dioxane (2.93 mL, 11.7 mmol) and stirred for 1 h at RT then concentrated to dryness which afforded 0.2 g (72.6%) of (R)-3-amino-3-(3-chloro-4-fluorophenyl)propanenitrile hydrochloride (228), which was used without further purification.

Step 5:
Condensation of 228 and 28 was carried out in accord with the procedure in step 6 of example 1 except, 22 was replaced with 228. The crude product was purified by $SiO_2$ chromatography eluting with 10% MeOH/DCM to afford 0.035 g (8.96%) of I-59: MS m/z (APCI-pos) M+1=488: MS m/z (APCI-pos) M+1=459.

Example 37

N—((S)-1-(3,4-dichlorophenyl)-2-hydroxyethyl)-2-(1-fluoropropan-2-ylamino)-5,6-dihydropyrido[3,4-d]pyrimidine-7(8H)-carboxamide (I-60)

Step 1:
To a solution of phenylmethanamine (5.63 g, 52.6 mmol) and 1-fluoropropan-2-one (4.0 g, 52.6 mmol) and DCE (50 mL) was added NaBH(OAc)$_3$ (15.6 g, 73.6 mmol) and HOAc (3.01 mL, 52.6 mmol) and the reaction was capped and stirred at RT for 3 h. The reaction was then poured into water, and extracted with DCM. The combined organic extracts were dried ($MgSO_4$), filtered, and concentrated in vacuo. The crude product was purified by $SiO_2$ chromatography eluting with a DCM/MeOH gradient (500:5 to 500:10) to afford 6.2 g (70.5%) of N-benzyl-1-fluoropropan-2-amine (230).

Step 2:
A suspension of 230 (2.5 g, 15 mmol), Pd/C (3.2 g, 1.5 mmol) and MeOH (30 mL) was stirred under hydrogen ($H_2$ filled balloon) for 5 h. To the solution was added 6M HCl (12 mL, 75 mmol) in IPA and the reaction stirred for 5 min. The reaction was filtered and concentrated to dryness to afford 1.5 g (88%) of 1-fluoropropan-2-amine hydrochloride (232).

Step 3:
A tube was charged with (Z)-benzyl (1H-pyrazol-1-yl)methylenedicarbamate (4.2 g, 11 mmol), DIPEA (3.9 mL, 22 mmol) and THF (20 mL) then 1-fluoropropan-2-amine hydrochloride (1.4 g, 12 mmol) was added. The reaction was sealed and heated to 60° C. for 2 h and then cooled to RT, poured into water and extracted with DCM. The combined organic extracts were dried ($MgSO_4$), filtered, and concentrated in vacuo. The crude product was purified by $SiO_2$ chromatography eluting with DCM to afford 4.8 g (>100%) of (Z)-benzyl (benzyloxycarbonylamino)(1-fluoropropan-2-ylamino)methylenecarbamate (234).

Step 4:
A suspension of 234 (4.8 g, 12 mmol), Pd(OH)$_2$/C (0.87 g, 1.2 mmol) and EtOH/THF (95%, 1:1, 60 mL) at RT was stirred under a hydrogen atmosphere ($H_2$ filled balloon) for 18 h. The reaction was filtered, washed with THF, and concentrated to afford 1.4 g (95%) of 1-(1-fluoropropan-2-yl)guanidine (236).

Steps 5 and 6:
tert-Butyl 2-(1-fluoropropan-2-ylamino)-5,6,7,8-tetrahydropyrido[3,4-d]pyrimidine-7-carbonylcarbamate (238) can be prepared from 236 and 21 in accord with the procedures described in steps 4 and 5 of example 1.

Step 7:
N—((S)-2-(tert-butyldimethylsilyloxy)-1-(3,4-dichlorophenyl)ethyl)-2-(1-fluoropropan-2-ylamino)-5,6-dihydropyrido[3,4-d]pyrimidine-7(8H)-carboxamide (240) can be prepared from 238 and 185 in accord with the procedure described in step 6 of example 1 except 22 is replaced by 185 and 28 is replaced by 238. The crude product was purified by $SiO_2$ chromatography eluting with DCM/MeOH (500:7).

Step 8:
To a solution of 240 (0.500 g, 0.898 mmol) and DCM (5 mL) at RT was added 6M HCl in IPA (1.50 mL, 8.98 mmol) and the reaction was stirred for 1 h and then concentrated to dryness. The residue was partitioned between aq. $Na_2CO_3$ and DCM. The organic fraction was dried, filtered, and concentrated in vacuo. The crude product was purified by $SiO_2$ chromatography eluting with a DCM/MeOH gradient (500:30 to 500:35) to afford 0.34 g (85.6%) of I-60 as a mixture of diastereomers: MS m/z (APCI-pos) M+1=442. The racemic mixture was resolved by chiral supercritical fluid chromatography.

Example 38

N—((S)-(3,4-dichlorophenyl)((R)-1-methylpyrrolidin-2-yl)methyl)-2-(isopropylamino)-5,6-dihydropyrido[3,4-d]pyrimidine-7(8H)-carboxamide (I-61)

(R)-1-(tert-butoxycarbonyl)pyrrolidine-2-carboxylic acid and be converted to (R)-tert-butyl 2-(3,4-dichlorobenzoyl)-pyrrolidine-1-carboxylate in accord with steps 1 and 2 of example 11, except in step 2,4-bromo-1-(trifluoromethyl)benzene was replaced with 1-bromo-3,4-dichlorobenzene. Reduction of the ketone with (R)-1-methyl-3,3-diphenylhexahydropyrrolo[1,2-c][1,3,2]oxazaborole and condensation with isoindoline-1,3 dione can be carried out in accord with procedures in steps 4 and 5 of example 11 to afford (R)-tert-butyl 2-((S)-(3,4-dichlorophenyl)(1,3-dioxoisoindolin-2-yl)methyl)pyrrolidine-1-carboxylate (242).

Step 1:
To a solution of 242 (0.120 g, 0.252 mmol) and DCM (1 mL) was added 5M HCl in IPA (10 mL) and the reaction was stirred for 1 h and then concentrated to dryness to afford 0.086 g (82.7%) of 2-((S)-(3,4-dichlorophenyl)((R)-pyrrolidin-2-yl)methyl)isoindoline-1,3-dione hydrochloride (242).

Step 2:
To a solution of 242 (0.400 g, 0.972 mmol) and DCE (10 mL) at RT was added TEA (0.295 g, 2.91 mmol) and formaldehyde (0.631 g, 7.77 mmol) and the reaction was stirred for 10 min before NaBH(OAc)$_3$ (0.824 g, 3.89 mmol) was added. The reaction was stirred for 2 h at RT. The reaction was poured into satd. aq. Na₂CO₃ and extracted with DCM. The combined organic extracts were dried (MgSO₄), filtered, and concentrated in vacuo. The crude product was purified by SiO₂ chromatography eluting with a hexane/EtOAc gradient (3:1 to 1:1) to afford 0.3 g (79.3%) of 2-((S)-(3,4-dichlorophenyl)((R)-1-methylpyrrolidin-2-yl)methyl)isoindoline-1,3-dione (244).

Step 3:

To a solution of 244 (0.40 g, 1.03 mmol) and MeOH:THF (1:1, 10 mL) was added hydrazine monohydrate (0.514 g, 10.3 mmol) and the reaction was stirred at 50° C. for 18 h. The reaction mixture was poured into water and extracted with DCM. The combined organic extracts were dried (MgSO₄), filtered, and concentrated in vacuo. The crude product was purified by SiO₂ chromatography eluting with DCM/MeOH (500:50) to afford 0.130 g (48.8%) of (S)-(3,4-dichlorophenyl)((R)-1-methylpyrrolidin-2-yl)methanamine (246).

Step 4:

Condensation of 246 and 138 was carried out in accord with the procedure in step 6 of example 1 except 28 was replaced with 138 and 22 was replaced with 246. The crude product was purified by SiO₂ chromatography eluting with a DCM/MeOH gradient (500:20 to 500:25) to afford 0.100 g (41.8%) of I-61: m/z (APCI-pos) M+1=477.

Example 39

N-((1S,2S)-1-(3,4-dichlorophenyl)-2,3-dihydroxypropyl)-2-(isopropylamino)-5,6-dihydropyrido[3,4-d]pyrimidine-7(8H)-carboxamide (I-62)

Step 1:

To a solution of (S)-2-methylpropane-2-sulfinamide (4.7 g, 39 mmol) and DCM (15 mL) at RT was added anhydrous CuSO₄ (14 g, 85 mmol) followed by a solution of (R)-1,4-dioxaspiro[4.5]decane-2-carbaldehyde (6.0 g, 35 mmol) and DCM (20 mL). The reaction was stirred at RT for 3 d then filtered through CELITE, washed with DCM and concentrated in vacuo. The crude product was purified by SiO₂ chromatography eluting with hexane/EtOAc (9:1 to 7:1) to afford 4.7 g (49%) of (S,Z)—N—((S)-1,4-dioxaspiro[4.5]decan-2-ylmethylene)-2-methylpropane-2-sulfinamide (248).

Step 2:

To a solution of 248 (2.0 g, 7.3 mmol) and toluene (30 mL) cooled to −78° C. was added (3,4-dichlorophenyl)magnesium bromide (29 mL, 15 mmol) and warmed to 0° C. for 30 min. The reaction was poured into water and extracted with DCM. The combined organic extracts were dried (MgSO₄), filtered and concentrated in vacuo. The crude product was purified by SiO₂ chromatography eluting with a hexane/EtOAc gradient (4:1 to 1:1) to afford 1.8 g (59%) of (S)—N—((S)-(3,4-dichlorophenyl)((S)-1,4-dioxaspiro[4.5]decan-2-yl)methyl)-2-methylpropane-2-sulfinamide (250) which appears to be a ca. 10:1 mixture of diastereomers by 1H NMR.

Step 3:

To a solution of 250 (1.8 g, 4.3 mmol) and DCM (5 mL) was added a solution of HCl in IPA (7.1 mL, 43 mmol) and the reaction was stirred for 1 h. The reaction concentrated to dryness and 4M HCl in dioxane (5 eq) and H₂O (1 mL) was added to cleave the cyclohexyl ketal. The reaction was stirred for 1 h and then concentrated to dryness to afford 1.1 g (94%) of (2S,3S)-3-amino-3-(3,4-dichlorophenyl)propane-1,2-diol hydrochloride (252).

Step 4:

To a solution of 252 (0.50 g, 1.83 mmol) and DCM (5 mL) at RT was added TEA (1.28 mL, 9.17 mmol) followed by TBDMSOTf (1.05 mL, 4.59 mmol) and the reaction was stirred for 30 min. The reaction poured into aq. NaHCO₃ and extracted with DCM. The combined extracts were dried (MgSO₄), filtered and concentrated in vacuo. The crude product was purified by SiO₂ chromatography eluting with hexane/EtOAc/DCM (8:1:1) to afford 0.280 g (32.9%) of (1S,2S)-2,3-bis-(tert-butyldimethylsilyloxy)-1-(3,4-dichlorophenyl)propan-1-amine (254).

Step 5:

Condensation of 254 and 138 was carried out in accord with the procedure in step 6 of example 1 except 28 was replaced with 138 and 22 was replaced with 254. The crude product was purified by SiO₂ chromatography eluting with a DCM/MeOH (500:5) to afford 0.240 g (60.5%) of N-((1S,2S)-2,3-bis-(tert-butyldimethylsilyloxy)-1-(3,4-dichlorophenyl)propyl)-2-(isopropylamino)-5,6-dihydropyrido[3,4-d]pyrimidine-7(8H)-carboxamide (256).

Step 6:

To solution of 256 (0.240 g, 0.351 mmol) and DCM (2 mL) was added 6N HCl in IPA (0.586 mL, 3.51 mmol) and the reaction was stirred at RT for 1 h then poured into satd. aq. Na₂CO₃ and extracted with DCM. The combined organic extracts were dried (MgSO₄), filtered, and concentrated in vacuo. The crude product was purified by SiO₂ chromatography eluting with a DCM/MeOH gradient (500:30 to 500:50) to afford 0.078 g (48.8%) of I-62: MS m/z (APCI-pos) M+1=454.

N-((1S,2S)-1-(4-chloro-3-fluorophenyl)-2,3-dihydroxypropyl)-2-(isopropylamino)-5,6-dihydropyrido[3,4-d]pyrimidine-7(8H)-carboxamide (I-63) was prepared analogously except in step 2, (3,4-dichlorophenyl)magnesium bromide was replaced with (3-fluoro-4-chlorophenyl)magnesium bromide to afford I-63: MS m/z (APCI-pos) M+1=438.

Example 40

(S)—N-(1-(3-fluoro-4-(trifluoromethyl)phenyl)-2-(methylamino)ethyl)-2-(isopropylamino)-5,6-dihydropyrido[3,4-d]pyrimidine-7(8H)-carboxamide hydrochloride (I-66)

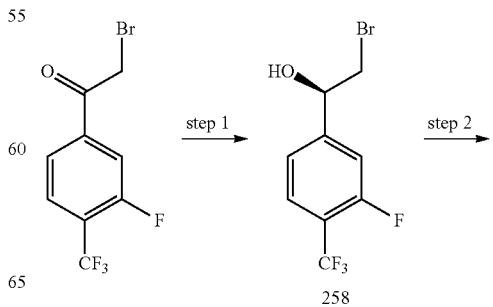

258

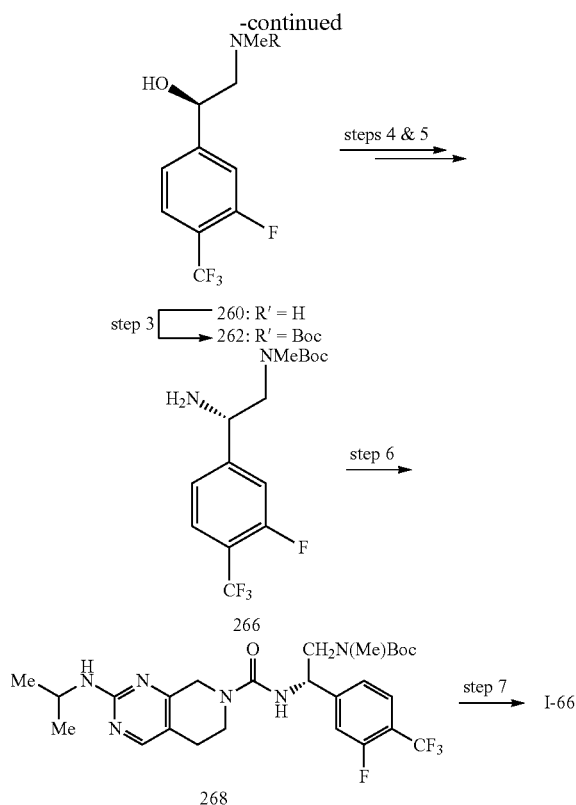

Step 1:

A solution of (R)-1-methyl-3,3-diphenylhexahydropyrrolo[1,2-c][1,3,2]oxazaborole (0.83 mL, 1.4 mmol) and borane diethylaniline (2.5 mL, 14 mmol) in MTBE (25 mL) prepared at RT and heated to 40° C. A solution of 2-bromo-1-(3-fluoro-4-(trifluoromethyl)phenyl)ethanone (143a, 4.0 g, 14 mmol, CASRN 54429-22-3) and MTBE (30 mL) was added dropwise to the above solution and the reaction was stirred at 40° C. for 30 min. The reaction was quenched by adding MeOH followed by 1M HCl and the reaction mixture was then poured into water and extracted with DCM. The combined organic extracts were dried (MgSO$_4$), filtered, and concentrated in vacuo. The crude product was purified by SiO$_2$ chromatography eluting with EtOAc/hexane (9:1) to afford 3.2 g (79%) of (R)-2-bromo-1-(3-fluoro-4-(trifluoromethyl)phenyl)ethanol (258).

Step 2:

To a solution of 258 (1.0 g, 3.5 mmol) and THF (20 mL) at RT was added methylamine (2.7 g, 35 mmol, 40% in water) and the reaction was sealed and stirred for 24 h at RT. The reaction was then concentrated to afford 0.83 g (100%) of (R)-1-(3-fluoro-4-(trifluoromethyl)phenyl)-2-(methylamino)ethanol (260) which was used without further purification.

Step 3:

To a solution of 260 (0.80 g, 3.4 mmol) and THF:H$_2$O (2:1, 18 mL) at RT was added a solution of Boc$_2$O (0.81 g, 3.7 mmol) and THF (5 mL) and the reaction was stirred at RT. K$_2$CO$_3$ (0.47 g, 3.4 mmol) was added until the reaction was complete, then poured into water and extracted with DCM. The combined organic fractions were dried (MgSO$_4$), filtered and concentrated in vacuo. The crude product was purified on a SiO$_2$ chromatography eluting with a hexane/EtOAc gradient (9:1 to 3:1) to afford 0.9 g (79%) of (R)-tert-butyl 2-(3-fluoro-4-(trifluoromethyl)phenyl)-2-hydroxyethyl(methyl)carbamate (262).

Step 4:

To a solution of 262 (0.98 g, 2.91 mmol) and THF (30 mL) cooled to 0° C. was added sequentially isoindoline-1,3-dione (0.470 g, 3.20 mmol) and PPh$_3$ (1.14 g, 4.36 mmol), followed by a solution of DEAD (1.72 mL, 4.36 mmol) and THF (10 mL). The reaction was warmed to RT and stirred overnight. The reaction was concentrated to dryness, Et$_2$O (300 mL) added and the resulting solid was filtered and discarded. The filtrate was then poured into water, and extracted with DCM. The combined organic extracts were dried (MgSO$_4$), filtered, and concentrated in vacuo. The crude product was purified by SiO$_2$ chromatography eluting with DCM:MeOH (500:2) to afford 0.99 g (73.1%) of (S)-tert-butyl 2-(1,3-dioxoisoindolin-2-yl)-2-(3-fluoro-4-(trifluoromethyl)phenyl)ethyl(methyl)carbamate (264).

Step 5:

To a solution of 264 (0.4 g, 0.86 mmol) and THF:MeOH (10 mL, 1:1) was added hydrazine monohydrate (0.43 g, 8.6 mmol) and the reaction was stirred at RT for 48 h. The reaction was then diluted with THF and filtered. The solid was discarded, and the filtrate concentrated to remove THF, then poured into water and extracted with DCM. The combined organic extracts were concentrated in vacuo. The crude product was purified by SiO$_2$ chromatography eluting with DCM/MeOH (500:20) to afford 0.28 g (97%) of (S)-tert-butyl 2-amino-2-(3-fluoro-4-(trifluoromethyl-phenyl)ethyl(methyl)carbamate (266).

Step 6:

(S)-tert-butyl 2-(3-fluoro-4-(trifluoromethyl)phenyl)-2-(2-(isopropylamino)-5,6,7,8-tetrahydropyrido[3,4-d]pyrimidine-7-carboxamido)ethyl(methyl)carbamate (268) was prepared in accord with the procedure described in step 6 of example 1 except 266 was used in place of 28 and 72 was used in place of 22 to afford to afford I-64. The crude product was purified by SiO$_2$ chromatography eluting with DCM/MeOH (500:8) to afford 0.180 g (64.2%) of (S)-tert-butyl 2-(3-fluoro-4-(trifluoromethyl)phenyl)-2-(2-(isopropylamino)-5,6,7,8-tetrahydropyrido[3,4-d]pyrimidine-7-carboxamido)ethyl(methyl)carbamate (268).

Step 7:

To a solution of 268 (0.075 g, 0.14 mmol) and DCM (3 mL) at RT was added TFA (2 mL) and the reaction was stirred at RT for 1 h then concentrated to dryness. The resulting product was next dissolved in minimal DCM (with MeOH to increase solubility) and added with stirring to a solution of 1M HCl in ether. The resulting solid was filtered, washed with ether and dried to afford 0.050 g (75%) of I-66: MS m/z (APCI-pos) M+1=455.

(S)—N-(1-(3-fluoro-4-(trifluoromethyl)phenyl)-2-(methylamino)ethyl)-2-(4-fluorophenylamino)-5,6-dihydropyrido[3,4-d]pyrimidine-7(8H)-carboxamide hydrochloride (I-68)

2-(4-Fluorophenylamino)-5,6-dihydropyrido[3,4-d]pyrimidin-2-amine (270) can be prepared in accord with steps 3 to 5 of example 1 except in step 3, tetrahydro-2H-pyran-4-amine was replaced with 4-fluoro-aniline. Condensation 266 and 270 can be carried out in accord with the procedures in steps 6 and 7 of the present example except in step 6, 270 was used in place 72 to afford I-68: MS m/z (APCI-pos) M+1=507.

Example 41

N—((R)-1-(3-fluoro-4-(trifluoromethyl)phenyl)ethyl)-2-((S)-1-hydroxybutan-2-ylamino)-5,6-dihydropyrido[3,4-d]pyrimidine-7(8H)-carboxamide (I-69)

(S)-2-(5,6,7,8-Tetrahydro-pyrido[3,4-d]pyrimidin-2-ylamino)-butan-1-ol (272) can be prepared in accord with steps 3 to 5 of example 1 except in step 3, tetrahydro-2H-pyran-4-amine was replaced with (S)-1-hydroxybutan-2-yl amine. Condensation 143 and 272 can be carried out in accord with the procedures in steps 6 and 7 of example 40 except in step 6, 272 was used in place of 72 and 143 was used in place of 266 to afford I-69: MS m/z (APCI-pos) M+1=456.

N—((S)-1-(4-chloro-3-fluorophenyl)-2-methoxyethyl)-2-((S)-1-hydroxybutan-2-ylamino)-5,6-dihydropyrido[3,4-d]pyrimidine-7(8H)-carboxamide (I-71) was prepared analogously except 197 was used in place of 143: MS m/z (APCI-pos) M+1=452.

Example 42

N-(1-(3-fluoro-4-(trifluoromethyl)phenyl)-3-hydroxypropyl)-2-(isopropylamino)-5,6-dihydropyrido[3,4-d]pyrimidine-7(8H)-carboxamide (I-70)

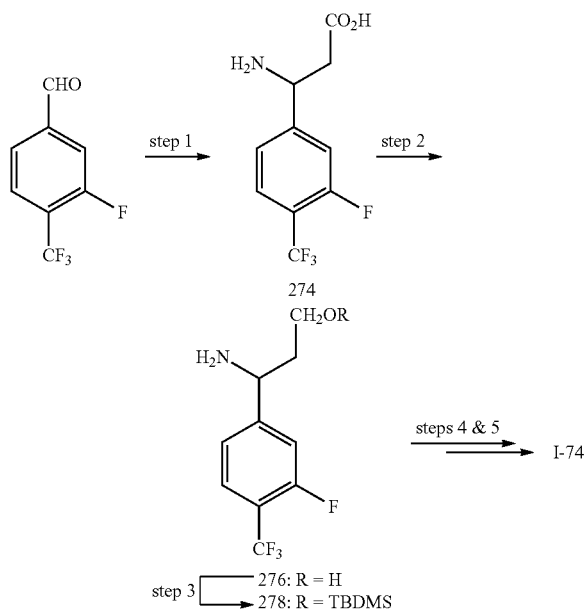

Step 1:
A solution of 3-fluoro-4-(trifluoromethyl)benzaldehyde (4.8 g, 25 mmol), malonic acid (2.6 g, 25 mmol), ammonium acetate (0.85 g, 50 mmol) and EtOH (30 mL) was heated at 80° C. for 18 h. The reaction was cooled, diluted with Et$_2$O (50 mL) and filtered to afford 2.0 g (16%) of 3-amino-3-(3-fluoro-4-(trifluoromethyl)phenyl)propanoic acid (274) as a white solid which was used without further purification.

Step 2:
To a stirred suspension of 274 (2.0 g, 8.0 mmol) and THF (25 mL) under N$_2$ at 0:C was added dropwise 1M LiAlH$_4$ in THF (12 mL, 12 mmol) and the reaction stirred at 0° C. in an ice bath for 1.5 h. The cold reaction mixture was quenched by carefully adding the reaction mixture to a satd. solution of Rochelle's salt (50 mL) that was cooled in an ice bath and adequately vented. The resulting mixture was stirred for 18 h while warming to RT slowly as the ice bath melted. The mixture was diluted with EtOAc (50 mL) and filtered through CELITE to remove solids which were rinsed several times with EtOAc. The phases were separated and the aqueous phase re-extracted with EtOAc (30 mL). The combined organic extracts were washed with brine (50 mL), dried (MgSO$_4$), filtered, and concentrated in vacuo. The crude product was purified by SiO$_2$ chromatography eluting with 5% 7N NH$_3$ in MeOH in DCM (500 mL to pre-wash column, followed by 500 mL of eluent, then 500 mL of 7.5% 7N NH$_3$ in MeOH in DCM) to afford 0.43 g (22%) of 3-amino-3-(3-fluoro-4-(trifluoromethyl)phenyl)propan-1-ol (276).

Step 3:
solution of 276 (0.200 g, 0.843 mmol), TBDMS-Cl (0.153 g, 1.01 mmol), DIPEA (0.294 mL, 1.69 mmol), DMAP (0.0103 g, 0.0843 mmol) and DCM (6 mL) was stirred for 1 h at RT and then poured into H$_2$O, and extracted with DCM. The combined organic fractions were dried (MgSO$_4$), filtered, and concentrated in vacuo. The crude product was purified by SiO$_2$ chromatography eluting with DCM/MeOH (500:5) to afford 0.210 g (70.9%) of 3-(tert-butyldimethylsilyloxy)-1-(3-fluoro-4-(trifluoromethyl)phenyl)propan-1-amine (278).

Step 4:
Condensation of 278 and 72 was carried out in accord with the procedure described in step 6 of example 1 except 278 was used in place of 28 and 72 was used in place of 22. The crude product was purified by SiO$_2$ chromatography eluting with DCM/MeOH (500:5) to afford 0.123 g (28.1%) of N-(3-(tert-butyldimethylsilyloxy)-1-(3-fluoro-4-(trifluoromethyl)phenyl)propyl)-2-(isopropylamino)-5,6-dihydropyrido[3,4-d]pyrimidine-7(8H)-carboxamide (280).

Step 5:
To a solution of 280 (0.100 g, 0.176 mmol) and THF (5 mL) at 0° C. was added TBAF (0.228 mL, 0.228 mmol) and the reaction was stirred at RT for 2 h then poured into water, and extracted with DCM. The combined organic fractions were dried (MgSO$_4$), filtered, and concentrated in vacuo. The crude product was purified by SiO$_2$ chromatography eluting with a DCM/MeOH gradient (500:15 to 500:25) to afford 0.032 g (40.0%) of I-70: MS m/z (APCI-pos) M+1=456.

N-(1-(4-chloro-3-fluorophenyl)-3-hydroxypropyl)-2-(isopropylamino)-5,6-dihydropyrido[3,4-d]pyrimidine-7(8H)-carboxamide (I-74) was prepared analogously except in step 1,3-fluoro-4-trifluoromethylbenzaldehyde was replaced with 4-chloro-3-fluorobenzaldehyde to afford I-74: MS m/z (APCI-pos) M+1=422.

Example 43

(R)—N-(3-amino-1-(3-fluoro-4-(trifluoromethyl)phenyl)propyl)-2-(isopropylamino)-5,6-dihydropyrido[3,4-d]pyrimidine-7(8H)-carboxamide (I-72)

Step 1:
To a solution of 258 (0.8 g, 2.8 mmol) and EtOH:water (4:1) was heated to 50° C. was added NaCN (0.20 g, 4.2 mmol) and the reaction stirred at 50° C. overnight. The reaction was then cooled and concentrated to dryness then partitioned between H$_2$O and EtOAc. The combined organic fractions were dried (MgSO$_4$), filtered and concentrated in vacuo. The crude product was purified by SiO$_2$ chromatography eluting with a hexane/EtOAc gradient (4:1 to 3:1) to afford 0.5 g (77%) of (S)-3-(3-fluoro-4-(trifluoromethyl)phenyl)-3-hydroxypropanenitrile (282).

Step 2:

To a solution of 282 (0.5 g, 2.1 mmol) and THF (10 mL) was added $BH_3$—$SMe_2$ (2.1 mL, 4.3 mmol) and the reaction was stirred at 65° C. for 8 h. The reaction was poured into water and extracted with DCM. The combined organic extracts were dried ($MgSO_4$), filtered, and concentrated in vacuo. The crude product was purified by $SiO_2$ chromatography eluting with EtOAc/MeOH/$NH_4OH$ (90/9/1) to afford 0.48 g (94%) of (S)-3-amino-1-(3-fluoro-4-(trifluoromethyl)phenyl)propan-1-ol (284).

Step 3:

To a solution of 284 (0.48 g, 2.0 mmol) and THF/water (9 mL, 2:1) at RT was added a THF solution (5 mL) of $Boc_2O$ (0.49 g, 2.2 mmol) and the reaction was stirred at RT for 1 h. The reaction was poured into water, and extracted with DCM. The combined organic extracts were dried ($MgSO_4$), filtered, and concentrated in vacuo. The crude product was purified by $SiO_2$ chromatography eluting with DCM/MeOH (500:5) to afford 0.60 g (88%) of (S)-tert-butyl 3-(3-fluoro-4-(trifluoromethyl)phenyl)-3-hydroxypropylcarbamate (286).

Step 4:

To a solution of 286 (0.600 g, 1.78 mmol) and THF (15 mL) cooled to 0° C. was added isoindoline-1,3-dione (0.288 g, 1.96 mmol) and $PPh_3$ (0.700 g, 2.67 mmol) followed by the dropwise addition of a THF (6 mL) solution of DEAD (0.420 mL, 2.67 mmol). The reaction was warmed to RT and stirred for 20 h. The reaction was concentrated, triturated with ether and filtered. The resulting filtrate was poured into water and extracted with DCM. The combined organic extracts were dried ($MgSO_4$), filtered, and concentrated in vacuo. The crude product was purified by $SiO_2$ chromatography eluting with hexane/EtOAc (4:1) to afford 0.350 g (42.4%) of (R)-tert-butyl 3-(1,3-dioxoisoindolin-2-yl)-3-(3-fluoro-4-(trifluoromethyl)phenyl)propylcarbamate (288).

Step 5:

To a solution of 288 (0.350 g, 0.750 mmol) and MeOH:THF (6 mL, 1:1) was added hydrazine monohydrate (0.188 mL, 3.75 mmol) and the reaction was heated to 50° C. for 4 d. The reaction was then poured into water, and extracted with DCM. The combined organic extracts were dried ($MgSO_4$), filtered, and concentrated in vacuo. The crude product was purified by $SiO_2$ chromatography eluting with DCM/MeOH (500:20) to afford 0.150 g (59.4%) of (R)-tert-butyl 3-amino-3-(3-fluoro-4-(trifluoromethyl)phenyl)propylcarbamate (290).

Step 7:

Condensation of 290 and 72 was carried out in accord with the procedure described in step 6 of example 1 except 290 was used in place of 28 and 72 was used in place of 22. The crude product was purified by $SiO_2$ chromatography eluting with DCM/MeOH gradient (500:8 to 500:15) to afford 0.090 g (39.0%) of (R)-tert-butyl 3-(3-fluoro-4-(trifluoromethyl)phenyl)-3-(2-(isopropylamino)-5,6,7,8-tetrahydropyrido[3,4-d]pyrimidine-7-carboxamido)propylcarbamate (292).

Step 8:

To a solution 292 (0.090 g, 0.16 mmol) and DCM (3 mL) at RT was added TFA (1 mL) and the reaction was stirred at RT for 1 h and then concentrated to dryness. The resulting product was next dissolved in minimal DCM (using MeOH to aid solubility) and added to a stirring solution of 1M HCl in ether. The resulting solid was filtered, washed with ether and dried to afford 0.060 g (75%) of I-72: MS m/z (APCI-pos) M+1=455.

(R)—N-(3-acetamido-1-(3-fluoro-4-(trifluoromethyl)phenyl)propyl)-2-(isopropylamino)-5,6-dihydropyrido[3,4-d]pyrimidine-7(8H)-carboxamide (I-85)

To a solution of I-72 (0.048 g, 0.0978 mmol) and DCM (5 mL) at RT was added TEA (0.0409 mL, 0.293 mmol) and $Ac_2O$ (0.0102 mL, 0.108 mmol) and the reaction mixture stirred for 1 h, poured into water, and extracted with DCM. The combined organic extracts were dried ($MgSO_4$), filtered, and concentrated in vacuo. The crude product was purified by $SiO_2$ chromatography eluting with a DCM/MeOH gradient (500:10 to 500:20) to afford 0.020 g (41.2%) of I-85: MS m/z (APCI-pos) M+1=497.

Example 44

(S)—N-(1-(3,4-dichlorophenyl)-2-methyl)-2-(2-hydroxyethylamino)-5,6-dihydropyrido[3,4-d]pyrimidine-7(8H)-carboxamide (I-73)

2-(5,6,7,8-tetrahydropyrido[3,4-d]pyrimidin-2-ylamino) ethanol (294) was prepared in accord with the procedures in steps a to c of example 17 except in step 1, (S)-2-aminopropan-1-ol was replaced with aminoethanol. Condensation of 294 and 198 to afford I-73 was carried out in accord with the procedure in step 6 of example 1 except 28 was replaced by 294 and 22 was replaced by 198: MS m/z (APCI-pos) M+1=440.

Example 45

(R)—N-(1-(3,4-dichlorophenyl)ethyl)-2-(1,3-dihydroxypropan-2-ylamino)-5,6-dihydropyrido[3,4-d]pyrimidine-7(8H)-carboxamide (I-75)

Step 1:

To a solution of 1H-pyrazole-1-carboximidamide hydrochloride (12 g, 82 mmol) and DMF (40 mL) at RT was added DIPEA (19 mL, 110 mmol) and 2-aminopropane-1,3-diol (5.0 g, 55 mmol) and the reaction was stirred overnight. $Et_2O$ (15 mL) was added and the reaction was stirred for 10 min before the reaction was allowed to settle and the ether layer was decanted. The remaining crude oil was concentrated under high vacuum to afford 7.3 g (100%) of 1-(1,3-dihydroxypropan-2-yl)guanidine (296) which contained residual DMF.

Steps 2 and 3:

Tetrahydropyrido[3,4-d]pyrimidin-2-ylamino)propane-1,3-diol hydrochloride (298) was prepared in accord with the procedures described in steps 4 and 5 of example 1 except in step 4, 24 was replaced with 296. The product was concentrated to dryness and dried under vacuum to afford 298 as a hygroscopic solid.

Step 4:

Condensation of 298 and 185 was carried out in accord with the procedure described in step 6 of example 1 except 298 was used in place of 28 and 185 was used in place of 22. The crude product was purified by $SiO_2$ chromatography eluting with DCM/MeOH gradient (500:30-500:50) to afford I-75: MS m/z (APCI-pos) M+1=440.

(R)-2-(1,3-dihydroxypropan-2-ylamino)-N-(1-(3-fluoro-4-(trifluoromethyl)phenyl)ethyl)-5,6-dihydropyrido[3,4-d]pyrimidine-7(8H)-carboxamide (I-82) was prepared analogously except 185 was replaced with 143. The crude product was purified by $SiO_2$ chromatography eluting with a DCM/MeOH gradient (500:20 to 500:30) to afford 0.200 g (57.0%) of I-82: MS m/z (APCI-pos) M+1=458.

Example 46

N—((S)-1-(3,4-dichlorophenyl)-2-hydroxyethyl)-2-(1,1,1-trifluoropropan-2-ylamino)-5,6-dihydropyrido[3,4-d]pyrimidine-7(8H)-carboxamide (I-76)

N-(1,1,1-trifluoropropan-2-yl)-5,6,7,8-tetrahydropyrido[3,4-d]pyrimidin-2-amine (300) was prepared in accord with the procedures in steps 3 to 5 of example 1, except in step 3, tetrahydro-2H-pyran-4-amine was replaced with 1,1,1-trifluoro-2-amino-propane and the bis-CBZ derivative of 1H-pyrazole-1-carboximidamidate to afford racemic N-(2,2,2-Trifluoro-1-methyl-ethyl)-guanidine after deprotection.

Step 1:

To a solution of 85 (0.104 g, 0.325 mmol) and DCM (5 mL) at RT was added TEA (0.136 mL, 0.975 mmol) and CDI (0.0527 g, 0.325 mmol) and the reaction was stirred at RT for 30 min and then added to a solution of 300 (0.080 g, 0.325 mmol), TEA (0.136 ml, 0.975 mmol) and DCM (5 mL) solution and the resulting solution stirred for 4 h. The reaction mixture was poured into water and extracted with DCM. The combined organic extracts were dried (MgSO$_4$), filtered, and concentrated in vacuo. The crude product was purified by SiO$_2$ chromatography eluting with DCM/MeOH (500:7) to afford 0.160 g (83.1%) of N—((S)-2-(tert-butyldimethylsilyloxy)-1-(3,4-dichlorophenyl)ethyl)-2-(1,1,1-trifluoropropan-2-ylamino)-5,6-dihydropyrido[3,4-d]pyrimidine-7(8H)-carboxamide (302).

Step 2:

To a solution of 302 (0.160 g, 0.270 mmol) and DCM (5 mL) at RT was added 6M HCl in IPA (0.450 mL, 2.70 mmol) and the reaction was stirred for 1 h. The reaction was poured into satd. aq. Na$_2$CO$_3$, and extracted with DCM. The combined organic extracts were dried (MgSO$_4$), filtered, and concentrated in vacuo. The crude product was purified by SiO$_2$ chromatography eluting with a DCM/MeOH gradient (500:20 to 500:30) to afford 0.010 g (7.74%) of I-76: MS m/z (APCI-pos) M+1=478.

N-((4-chloro-3-fluorophenyl)(oxazol-5-yl)methyl)-2-((R)-1,1,1-trifluoropropan-2-ylamino)-5,6-dihydropyrido[3,4-d]pyrimidine-7(8H)-carboxamide (I-84)

(4-Chloro-3-fluorophenyl)(oxazol-5-yl)methanamine was prepared in accord with procedures in steps 1 and 2 of example 1 except in step 2, (3,4-dichlorophenyl)magnesium bromide was replaced with 4-chloro-3-fluorophenyl)magnesium bromide. Condensation of 300 and 22 was carried out in accord with the procedure described in step 6 of example 1 except 300 was used in place of 28. The crude product was purified by reverse phase column chromatography eluting with a MeCN/H$_2$O (5 to 95% MeCN) to afford 0.160 g (45.3%) of I-84: MS m/z (APCI-pos) M+1=499.

Example 47

N-(1-(3,4-difluorophenyl)-3-hydroxypropyl)-2-(isopropylamino)-5,6-dihydropyrido[3,4-d]pyrimidine-7(8H)-carboxamide (I-77)

Step 1:

To a stirred suspension of 3-amino-3-(3,4-difluorophenyl)propanoic acid hydrochloride (17 g, 72 mmol, <30% pure) in THF (100 mL) under N$_2$ cooled to 0° C. was added a 1M solution LiAlH$_4$ in THF (215 mL, 215 mmol) in THF dropwise. The reaction was stirred at 0° C. in an ice bath for 1.5 h. To the ice-cold solution was added carefully a ice-cold satd. aq. solution of Rochelle's salt (300 mL). The resulting mixture was stirred for 18 h warming to RT slowly as the ice bath melted. The mixture was diluted with EtOAc (500 mL), and filtered through CELITE to remove solids which were rinsed several times with EtOAc. The phases were separated and the aqueous phase re-extracted with EtOAc (200 mL). The combined organic extracts were washed with brine (200 mL), dried (MgSO$_4$), filtered and concentrated in vacuo. The crude product was purified by SiO$_2$ chromatography (Biotage Flash 65) eluting with 5% MeOH (containing 7N NH$_3$)/DCM (1 L to pre-wash column, followed by 1 L of elution), then 10% MeOH (containing 7N NH$_3$) in DCM (1 L) to afford 0.92 g (6%) of 3-amino-3-(3,4-difluorophenyl)propan-1-ol (304).

Step 2:

A solution of 304 (0.400 g, 2.14 mmol), TBDMS-Cl (0.386 g, 2.56 mmol), DIPEA (0.744 mL, 4.27 mmol), DMAP (0.0261 g, 0.214 mmol) and DCM (10 mL) was stirred at RT for 1 h and then poured into water and extracted with DCM. The combined organic extracts were dried (MgSO$_4$), filtered, and concentrated in vacuo. The crude product was purified by SiO$_2$ chromatography eluting with DCM/MeOH (500:7) to afford 0.45 g (69.9%) of 3-(tert-butyldimethylsilyloxy)-1-(3,4-difluorophenyl)propan-1-amine (306).

Condensation of 306 and 72 was carried out in accord with the procedure described in step 6 of example 1 except 72 was used in place of 28 and 306 was used in place of 22. The crude product was purified by SiO$_2$ chromatography eluting with a DCM/MeOH gradient (500:5 to 500:8) to afford 0.11 g (31.9%) of N-(3-(tert-butyldimethylsilyloxy)-1-(3,4-difluorophenyl)propyl)-2-(isopropylamino)-5,6-dihydropyrido[3,4-d]pyrimidine-7(8H)-carboxamide (308). The silyl group was removed with TBAF in accord with the procedure described in step 5 of example 42. The product was purified by SiO$_2$ chromatography eluting with a DCM/MeOH gradient (500:15-500:25) to afford 0.010 g (12.8%) of I-77: MS m/z (APCI-pos) M+1=406.

Example 48

N-(1-(4-chloro-3-fluorophenyl)-3-(methylamino)propyl)-2-(isopropylamino)-5,6-dihydropyrido[3,4-d]pyrimidine-7(8H)-carboxamide (I-78)

Step 1:

To a solution of I-74 (0.050 g, 0.119 mmol and DCM (5 mL) cooled to 0° C. was added sequentially TEA (0.0496 mL, 0.356 mmol) and MsCl (9.17 µL, 0.119 mmol) and the reaction was stirred at 0° C. for 1 h. The reaction mixture was poured into water and extracted with DCM. The combined organic extracts were dried (MgSO$_4$), filtered and concentrated in vacuo to afford 0.59 g (99.6%) of 3-(4-chloro-3-fluorophenyl)-3-(2-(isopropylamino)-5,6,7,8-tetrahydropyrido[3,4-d]pyrimidine-7-carboxamido)propyl methanesulfonate (310) which was used without further purification.

Step 2:

To a solution of 310 (0.059 g, 0.12 mmol) and THF (3 mL) was added methylamine (0.092 g, 1.2 mmol, 40% aqueous solution) and the reaction was stirred at 45° C. for 1 h. The solution was concentrated, poured into water and extracted with DCM. The combined organic extracts were dried (MgSO$_4$), filtered and concentrated in vacuo. The crude product was purified by SiO$_2$ chromatography eluting with DCM/MeOH (500:30) to afford 3 mg (5.8%) of I-78: MS m/z (APCI-pos) M+1=435.

Example 49

N—((S)-1-(3-fluoro-4-(trifluoromethyl)phenyl)-2-methoxyethyl)-2-((S)-1-hydroxybutan-2-ylamino)-5,6-dihydropyrido[3,4-d]pyrimidine-7(8H)-carboxamide (I-79)

Step 1:

A MTBE (25 mL) solution of (R)-1-methyl-3,3-diphenylhexahydropyrrolo[1,2-c][1,3,2]oxazaborole (0.83 mL, 1.4 mmol) and borane diethylaniline (2.5 mL, 14 mmol) was prepared at RT and heated to 40° C. A solution of 2-bromo-1-(3-fluoro-4-(trifluoromethyl)phenyl)ethanone (4.0 g, 14 mmol) and MTBE (30 mL) was then added dropwise to the above solution and the reaction was stirred at 40° C. for 30 min. MeOH was then added, followed by the addition of 1M HCl and the reaction was poured into water and extracted with DCM. The combined organic fractions were dried (MgSO$_4$), filtered and concentrated to give the crude product, which was purified by SiO$_2$ chromatography eluting with hexane/EtOAc (9:1) to afford 3.2 g (79%) of (R)-2-bromo-1-(3-fluoro-4-(trifluoromethyl)phenyl)ethanol.

Step 2:

A mixture of (R)-2-bromo-1-(3-fluoro-4-(trifluoromethyl)phenyl)ethanol (3.0 g, 10 mmol), K$_2$CO$_3$ (2.9 g, 21 mmol) and acetone (50 mL) and was stirred for 18 h at RT, then poured in H$_2$O and extracted with DCM. The combined organic extracts were dried (MgSO$_4$), filtered and concentrated in vacuo. The crude product was purified by SiO$_2$ chromatography eluting with hexane/EtOAc (9:1) to afford 2.0 g (93%) of (R)-2-(3-fluoro-4-(trifluoromethyl)phenyl)oxirane (312).

Step 3:

To a solution of 312 (0.600 g, 2.91 mmol) and MeOH (1 mL) was added NaOMe (11.6 mL, 5.82 mmol) in MeOH and the reaction was stirred at RT for 3 d, then poured into water and extracted with DCM. The combined organic extractions were dried (MgSO$_4$), filtered, and concentrated in vacuo. The crude product was purified by SiO$_2$ chromatography eluting with DCM/MeOH (500:10) to afford 0.630 g (90.9%) of (R)-1-(3-fluoro-4-(trifluoromethyl)phenyl)-2-methoxyethanol (314) which was contaminated with a small amount of the regioisomeric epoxide ring-opening product.

Steps 4 and 5:

The conversion of 314 (S)-1-(3-fluoro-4-(trifluoromethyl)phenyl)-2-methoxyethanamine (316, 0.630 g, 2.65 mmol) was carried out in analogy to the procedures described in steps 4 and 5 of example 10.

Step 6:

Condensation of 316 and 272 was carried out in accord with the procedure described in step 6 of example 1 except 272 was used in place of 28 and 316 was used in place of 22. The crude product, which was purified by SiO$_2$ chromatography eluting with a DCM/MeOH gradient (500:15 to 500:25) to afford 0.085 g (45.3%) of I-79: MS m/z (APCI-pos) M+1=486.

Example 50

N—((S)-1-(3-fluoro-4-(trifluoromethyl)phenyl)-2-(methylamino)ethyl)-2-((S)-1-hydroxypropan-2-ylamino)-5,6-dihydropyrido[3,4-d]pyrimidine-7(8H)-carboxamide hydrochloride (I-80)

Step 1:

To a solution of (S)-tert-butyl 2-amino-2-(3-fluoro-4-(trifluoromethyl)phenyl)ethyl(methyl)carbamate (0.220 g, 0.654 mmol) and DCM (5 mL) was cooled to 0° C. was added sequentially TEA (0.365 mL, 2.62 mmol) and CDI (0.106 g, 0.654 mmol). The reaction was stirred for 30 min then added to a solution of 138 (0.160 g, 0.654 mmol), TEA (0.365 mL, 2.62 mmol) and DCM (5 mL) at RT and the resulting solution was stirred at RT for 18 h. The solution was poured into water, and extracted with DCM. The combined organic extracts were dried (MgSO$_4$), filtered and concentrated in vacuo. The crude product was purified by SiO$_2$ chromatography eluting with a DCM/MeOH gradient (500:10 to 500:20) to afford 0.100 g (26.8%) of tert-butyl (S)-2-(3-fluoro-4-(trifluoromethyl)phenyl)-2-(2-((S)-1-hydroxypropan-2-ylamino)-5,6,7,8-tetrahydropyrido[3,4-d]pyrimidine-7-carboxamido)ethyl(methyl)carbamate (318).

Step 2:

To a solution of 318 (0.100 g, 0.175 mmol) and DCM (5 mL) at RT was added TFA (2 mL) and the reaction was stirred at RT for 1 h then concentrated to dryness. The crude product was next dissolved in minimal DCM (with MeOH to aid solubility) and added to a stirred solution of 1M HCl in ether. The resulting solid was filtered, washed with ether and dried to afford 0.070 g (78.8%) of I-80: MS m/z (APCI-pos) M+1=471.

Example 51

N—((S)—((S)-5,5-dimethylpyrrolidin-2-yl)(2-fluoro-4-(trifluoromethyl)phenyl)methyl)-2-(tetrahydro-2H-pyran-4-ylamino)-5,6-dihydropyrido[3,4-d]pyrimidine-7(8H)-carboxamide (I-86)

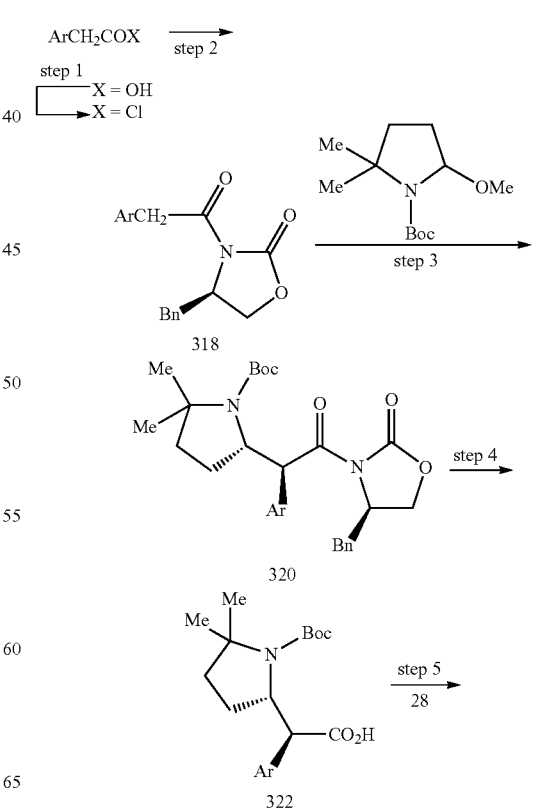

-continued

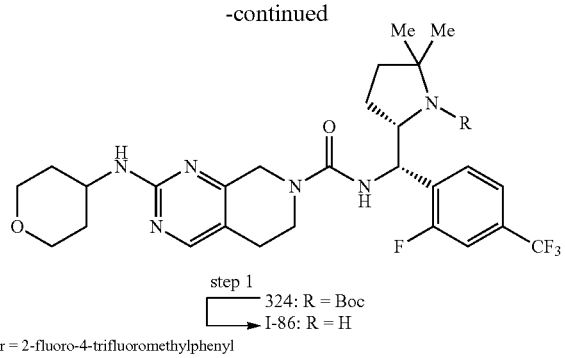

324: R = Boc
I-86: R = H

Ar = 2-fluoro-4-trifluoromethylphenyl

Step 1:
To a solution of 2-(2-fluoro-4-(trifluoromethyl)phenyl)acetic acid (5 g, 22.509 mmol, CASRN 209991-64-0) in DCM (112 mL, 22.509 mmol) was added oxalyl chloride (2.94 mL, 33.8 mmol) and 3 drops of DMF. The solution was stirred at RT overnight and concentrated to dryness to afford 5.2 g (88.2%) of 2-(2-fluoro-4-(trifluoromethyl)phenyl)acetyl chloride.

Step 2:
To a stirred solution of (R)-4-benzyloxazolidin-2-one (4.0615 g, 22.921 mmol) and dry THF (100 mL) at −78° C. was added n-BuLi (15.0 mL, 24.012 mmol). The reaction mixture was stirred for 25 min and then a solution of 2-(2-fluoro-4-(trifluoromethyl)phenyl)acetyl chloride (5.2517 g, 21.829 mmol) in dry THF (50 mL) at −78° C. This solution was stirred for 90 min then quenched with $H_2O$ and diluted with EtOAc. The combined organic extracts were washed with brine, dried ($MgSO_4$), filtered and concentrated in vacuo. The crude product was purified by $SiO_2$ chromatography eluting with an EtOAc/hexane gradient (5-20% EtOAc) to afford 2.5 g (30.8%) of (R)-4-benzyl-3-(2-(2-fluoro-4-(trifluoromethyl)phenyl)acetyl)oxazolidin-2-one (318).

Step 3:
To a solution 318 (12.35 g, 32.39 mmol) and dry DCM (300 mL) cooled to −78° C. was added $TiCl_4$ (34.01 ml, 34.01 mmol). To the cold solution was added DIPEA (0.59 mL, 3.40 mmol). The reaction was stirred at −78° C. for 15 min then a solution of tert-butyl 5-methoxy-2,2-dimethylpyrrolidine-1-carboxylate (13.37 g, 58.3 mmol) in DCM (50 mL) was added. The rxn was warmed to −10° C. (acetone/ice) for 2 h. The reaction was quenched with $NH_4Cl$ and layers separated, dried and concentrated in vacuo. The crude product was purified by $SiO_2$ chromatography eluting with an EtOAc/hexane gradient (5%-10%) to afford 16.21 g (86.5%) of (S)-tert-butyl 5-((S)-2-((R)-4-benzyl-2-oxooxazolidin-3-yl)-1-(2-fluoro-4-(trifluoromethyl)phenyl)-2-oxoethyl)-2,2-dimethylpyrrolidine-1-carboxylate (320).

Step 4:
To a solution of LiOH—$H_2O$ (0.3177 g, 7.570 mmol) in THF/water (2:1, 240 mL) was added 30% $H_2O_2$ (0.91 mL, 9.46 mmol) and the soln stirred at RT for 10 min. The solution was cooled to 0° C. and a solution of 320 (2.19 g, 3.785 mmol) in THF (10 mL) was added. The reaction was stirred at 0° C. for 2 h then warmed to RT and stirred overnight. The reaction was then cooled to 0° C. and treated with 1M $Na_2SO_3$ (10 mL) and stirred for 10 min then warmed to RT and stirred for 10 min. The reaction was concentrated and extracted with EtOAc (2×20 mL). The aqueous phase was acidified with $H_2SO_4$ to pH ca. 1-2 and extracted with DCM (2×20 mL). The organic extracts were concentrated and the crude product purified C18 preparative MPLC (Analogix 200 g C18 column) to afford 1.321 g (83.2%) of (S)-2-((S)-1-(tert-butoxycarbonyl)-5,5-dimethylpyrrolidin-2-yl)-2-(2-fluoro-4-(trifluoromethyl)phenyl)acetic acid (322).

Step 5:
To a solution of 322 (0.341 g, 0.813 mmol) and benzene (8 mL) cooled 0° C. was added TEA (0.154 mL, 1.11 mmol) and diphenylphosphoryl azide (0.239 mL, 1.11 mmol) and the reaction stirred at RT for 1 h then refluxed for 3 h. The reaction was then cooled to RT and a solution of 28 (0.200 g, 0.739 mmol), TEA (0.154 mL, 1.11 mmol) and DMF (3 mL) was added, and stirred at RT for 18 h. The reaction was poured into water and extracted with DCM. The combined organic extracts were dried ($MgSO_4$), filtered, and concentrated in vacuo. The crude product was purified by $SiO_2$ chromatography eluting with DCM/MeOH (500:10) to afford 0.360 g (74.9%) of (S)-tert-butyl 5-((S)-(2-fluoro-4-(trifluoromethyl)phenyl)(2-(tetrahydro-2H-pyran-4-ylamino)-5,6,7,8-tetrahydropyrido[3,4-d]pyrimidine-7-carboxamido)methyl)-2,2-dimethylpyrrolidine-1-carboxylate (324).

Step 6:
To a solution of 324 (0.380 g, 0.584 mmol) and DCM (5 mL). was added 6M HCl in IPA (0.973 mL, 5.84 mmol) and the reaction was stirred for 1 h and then poured into $Na_2CO_3$ and extracted with DCM. The combined organic extracts were dried ($MgSO_4$), filtered, and concentrated in vacuo. The crude product was purified by $SiO_2$ chromatography eluting with a DCM/MeOH gradient (500:40 to 500:50) to afford 0.210 g (65.3%) of I-86: MS m/z (APCI-pos) M+1=551.

Example 52

N-((1S,2R)-1-(3-chloro-4-fluorophenyl)-2-hydroxypropyl)-2-(isopropylamino)-5,6-dihydropyrido[3,4-d]pyrimidine-7(8H)-carboxamide (I-89)

Step 1:
To a stirred solution of (S)-2-amino-2-(3-chloro-4-fluorophenyl)ethanol hydrochloride (1.89 g, 9.97 mmol, CASRN 496856-52-1) in MeOH (18 mL) cooled to 0° C. under nitrogen was added sequentially TEA (4.17 mL, 29.9 mmol) and a solution of $(Boc)_2O$ (2.18 g, 9.97 mmol) in MeOH (2 mL). The reaction was allowed to RT overnight. The solution was partially concentrated, diluted to 50 mL with DCM and washed sequentially with 2N HCl (2×50 mL) and satd. aq. $NaHCO_3$ (2×50 mL). The combined organic extracts were isolated, dried ($MgSO_4$), filtered and concentrated to afford 2.55 g (85%) of (S)-tert-butyl 1-(3-chloro-4-fluorophenyl)-2-hydroxyethylcarbamate (326) as a white solid.

Step 2:
To a stirred solution of 326 (1.134 g, 3.914 mmol) and DCM (8 mL) under nitrogen cooled to 0° C. was added $NaHCO_3$ (0.9864 g, 11.74 mmol) followed by Dess-Martin periodinane (2.490 g, 5.871 mmol) both as solids. After 3 h, the reaction was about 50% complete by TLC. The reaction was warmed to RT for 1 h, then the reaction was diluted with $Et_2O$ (10 mL) and poured into ice cold satd. aq. $NaHCO_3$ (50 mL) containing sodium bisulfite (15 gm). After stirring for 15 min, the layers were separated and the aqueous phase was extracted with $Et_2O$ (2×30 mL). The combined organic extracts were washed sequentially with satd. aq. $NaHCO_3$ (2×50 mL) and brine (1×50 mL), dried ($MgSO_4$), filtered and concentrated to afford 0.814 g (72%) of (S)-tert-butyl 1-(3-chloro-4-fluorophenyl)-2-oxoethylcarbamate (328) as a yellow foam.

Step 3:
To a stirred solution of freshly prepared 328 (1.2 g, 4.171 mmol) in $Et_2O$ (20 mL) cooled to −78° C. under nitrogen was added MeMgBr (2.781 mL, 8.342 mmol, 3M solution in Et₂O) dropwise via syringe. The resulting suspension became viscous as the Grignard addition proceeded and eventually became unstirrable. Et₂O (20 mL) was added to aid stirring and the reaction was warmed to 0° C. The reaction was stirred for 2 h at 0° C. and then poured into a stirred satd. aq. NH₄Cl (50 mL) solution. The layers were separated and the aqueous phase was extracted with Et₂O (1×50 mL). The combined organic extracts were washed brine (1×100 mL), dried (MgSO₄), filtered and concentrated to a clear oil. The crude product was loaded onto a SiO₂ column (Biotage 40M) and eluted with EtOAc/hexane (25/75). The higher $R_f$ material was residual aldehyde. The lower $R_f$ material was isolated and concentrated to afford 354 mg (28%) of a 5:1 mixture (330) of tert-butyl (1S,2S)-1-(3-chloro-4-fluorophenyl)-2-hydroxypropylcarbamate and tert-butyl (1S,2R)-1-(3-chloro-4-fluorophenyl)-2-hydroxypropylcarbamate as clear oil.

Step 4:

To a stirred solution of a 330 (354 mg, 1.165 mmol) in THF (5.5 mL) at RT under nitrogen was added 4-nitrobenzoic acid (194.8 mg, 1.165 mmol) followed by Ph₃P (305.7 mg, 1.165 mmol) and finally neat DIAD (225.7 μL, 1.165 mmol) dropwise via syringe. A mild exotherm was detectable. After 1 h another 0.5 equiv. of 4-nitrobenzoic acid, triphenylphosphine and DIAD were added as before and the reaction stirred for another hour. The reaction mixture was loaded directly onto a SiO₂ column (Biotage 40S) column with a minimum of DCM and eluted with hexane/EtOAc (9/1). The product containing fractions eluted quickly and were impure. The fractions were pooled and concentrated to a yellow solid. The crude product was triturated with Et₂O with sonication to afford a powder that was filtered off and rinsed with ether to afford 300 mg (57%) of the major diastereomer, (1S,2R)-1-(tert-butoxycarbonylamino)-1-(3-chloro-4-fluorophenyl)propan-2-yl 4-nitrobenzoate (332). Chiral HPLC analysis shows two cleanly resolved peaks for the racemic material and only one for the material prepared here with an estimated ee of >95%.

Step 5:

To a stirred solution of 332 (103 mg, 0.227 mmol) in DCM (2.2 mL) at RT under nitrogen was added TFA (1 mL). After 2 h the reaction was concentrated to dryness in a rotovap and high vacuum. The crude presumed TFA salt was redissolved in DCM (5 mL) and stirred rapidly with 10% aqueous Na₂CO₃ (5 mL). After 5 min the organics phase was separated, dried (MgSO₄), filtered and concentrated to afford 80 mg (100%) of (1S,2R)-1-amino-1-(3-chloro-4-fluorophenyl)propan-2-yl 4-nitrobenzoate (334) as a yellow oil which was used without additional purification.

Step 6:

To a stirred solution of 334 (80 mg, 0.227 mmol) in DCM (1.1 mL) at RT under nitrogen was added sequentially neat CDI (40.5 mg, 0.249 mmol) DIPEA (79.0 μL, 0.454 mmol) neat by syringe. After 30 min, 72 (43.6 mg, 0.227 mmol) was added neat as a solid. After stirring overnight, LC/MS shows a major LC and MS peak for the desired product. The reaction was diluted to 30 mL with DCM and washed with 10% citric acid (2×30 mL) and satd. aq. NaHCO₃ (2×30 mL). The organic phase was dried (MgSO₄), filtered and concentrated to afford 116 mg (90%) of (1S,2R)-1-(3-chloro-4-fluorophenyl)-1-(2-(isopropylamino)-5,6,7,8-tetrahydropyrido[3,4-d]pyrimidine-7-carboxamido)propan-2-yl 4-nitrobenzoate (336) as a yellow solid which was used without additional purification.

Step 7:

To a stirred solution of 336 (116 mg, 0.203 mmol) in MeOH (2 mL) at RT under nitrogen was added K₂CO₃ (112 mg, 0.813 mmol) neat as a solid. After 30 min the reaction was diluted to 30 mL with DCM and washed H₂O (1×30 mL). The organic phase was isolated, dried (MgSO₄), filtered and concentrated to a yellow oil that was loaded onto a SiO₂ column (Biotage 12M) and eluted with EtOAc to afford 46 mg (54%) of I-89 as an off white solid.

N-((1S,2R)-1-(3-chloro-4-fluorophenyl)-2-hydroxybutyl)-2-(isopropylamino)-5,6-dihydropyrido[3,4-d]pyrimidine-7(8H)-carboxamide (I-91) was prepared analogously except in step 3, ethyl magnesium bromide was used in place of methyl magnesium bromide: ¹H NMR (400 MHz, CDCl₃) δ 8.06 (s, 1H), 7.42 (dd, 1H), 7.23 (m, 1H), 7.09 (m, 1H), 5.62 (d, 1H), 4.83 (m, 2H), 4.35 (s, 2H), 4.11 (m, 2H), 3.85 (m, 1H), 3.64 (dd, 2H), 2.64 (dd, 2H), 1.39 (m, 1H), 1.22 (d, 6H); MS m/z (APCI-pos) M+1=436.5.

Example 53

N—((R)-1-(3,4-dichlorophenyl)ethyl)-2-(1,1,1-trifluoro-3-hydroxypropan-2-ylamino)-5,6-dihydropyrido[3,4-d]pyrimidine-7(8H)-carboxamide (I-92)

Step 1:

To a stirred solution of 2-amino-3,3,3-trifluoropropanoic acid (250 mg, 1.75 mmol, CASRN 17463-43-3) in dioxane (9 mL) and 1M Na₂CO₃ (9 mL) at 0° C. under nitrogen was added Boc₂O (381 mg, 1.75 mmol) neat as a solid. After 2 h the gel-like mixture was partially concentrated in a rotovap and then diluted with EtOAc (30 mL) and 30 mL of 2N HCl (pH<3). The mixture was stirred briefly and the layers were separated. The organic phase was washed with brine (1×30 mL), dried (MgSO₄), filtered and concentrated to afford 294 mg (69%) of 2-(tert-butoxycarbonylamino)-3,3,3-trifluoropropanoic acid (338) as a clear oil which was used without additional purification.

Step 2:

To a stirred solution of 338 (294 mg, 1.209 mmol) in THF (10 mL) at 0° C. under nitrogen was added sequentially NMM (159.5 μL, 1.451 mmol) neat via syringe and ethyl chloroformate (138.7 μL, 1.451 mmol) neat by syringe. After 45 min the resulting suspension was filtered through GF/F filter paper with THF and the filtrate was isolated and stirred at 0° C. under nitrogen. A solution of NaBH₄ (45.74 mg, 1.209 mmol) in H₂O (2 mL) was added and the cooling bath was removed. After about 15 min, the reaction was concentrated and the residue was resuspended in Et₂O (30 mL) and H₂O (30 mL) with stirring. After stirring for 5 min the layers were separated and the organic phase washed brine (1×30 mL). The organic phase was (MgSO₄), filtered and concentrated to afford 240 mg (86%) of tert-butyl 1,1,1-trifluoro-3-hydroxypropan-2-ylcarbamate (340) as a white solid.

Step 3:

To a stirred solution of 340 (240 mg, 1.047 mmol) in DCM (3 mL) at 0° C. under nitrogen was added solid imidazole (71.29 mg, 1.047 mmol) followed by tert-butylchlorodiphenylsilane (272.3 μL, 1.047 mmol) neat by syringe. After 4 h the reaction was diluted to 30 mL with DCM and was washed 2N HCl (2×30 mL) and satd. aq. NaHCO₃ (2×30 mL). The organic phase was isolated, dried (MgSO₄), filtered and concentrated to afford 460 mg (94%) of tert-butyl 3-(tert-butyldiphenylsilyloxy)-1,1,1-trifluoropropan-2-ylcarbamate a white solid (342).

Step 4:

To a stirred solution of 342 (229 mg, 0.490 mmol) in DCM (3.3 mL) at 0° C. under nitrogen was added TFA (1.6 mL) neat by pipet. After 1 h the reaction was concentrated in a rotovap under a high vacuum and then redissolved in a mixture of DCM (30 mL) and 1M Na₂CO₃ (30 mL). The mixture was stirred for 5 min and the layers were separated. The aqueous phase was extracted with DCM (1×20 mL). The organic extract was dried (MgSO$_4$), filtered and concentrated to afford 180 mg (100%) of 3-(tert-butyldiphenylsilyloxy)-1,1,1-trifluoropropan-2-amine as a yellow oil (344).

Step 5:
To a stirred solution of 344 (180 mg, 0.490 mmol) in THF (1.5 mL) at RT under nitrogen was added solid benzyl (1H-pyrazol-1-yl)methylenedicarbamate (186 mg, 0.490 mmol). After stirring overnight the reaction mixture was diluted to 30 mL with DCM and was washed with 2N HCl (2×30 mL) and satd. aq. NaHCO$_3$ (2×30 mL). The organic phase was dried (MgSO$_4$), filtered and concentrated to a yellow foam. The crude product was purified by SiO$_2$ chromatography (Biotage 25S column) eluting with hexane/EtOAc (4/1) to afford 210 mg (63%) of (Z)-benzyl 11,11-dimethyl-3-oxo-1,10,10-triphenyl-7-(trifluoromethyl)-2,9-dioxa-4,6-diaza-10-sila-dodecan-5-ylidenecarbamate (346) as a clear oil.

Step 6:
To a stirred solution of 346 (210 mg, 0.310 mmol) in 95% EtOH/THF (5 mL, 1:1) was added Pearlman's Catalyst (21.8 mg, 0.0310 mmol). The suspension was put through a vacuum/purge cycle three times with hydrogen gas and then maintained under 1 atmosphere of hydrogen pressure overnight. The mixture was then filtered through GF/F filter paper with 95% ethanol and the filtrate was concentrated to afford 127 mg (100%) of 1-(3-(tert-butyldiphenylsilyloxy)-1,1,1-trifluoropropan-2-yl)guanidine (348) as a white solid.

Step 7:
To a stirred solution of 348 (1.37 g, 3.35 mmol) in absolute EtOH (10 mL) at RT under nitrogen was added solid 21 (0.851 g, 3.35 mmol) neat as a solid. The reaction was sealed in a capped reaction vial, heated to 80° C. and stirred for 60 h. The reaction was cooled to RT and concentrated in a rotovap under high vacuum to afford a yellow foam. The crude product was loaded onto a SiO$_2$ column (Biotage 40M) pre-equilibrated with EtOAc/hexanes (3/7) and eluted. After the first ninhydrin positive spot eluted, the eluant was changed to EtOAc/hexanes (1/1) and the second ninhydrin positive eluted. The product containing fractions were pooled and concentrated separately to afford pale yellow foams. The high R$_f$ ninhydrin positive spot corresponds to the TBDPS protected product and afforded 150 mg (8%) of tert-butyl 2-(3-(tert-butyldiphenylsilyloxy)-1,1,1-trifluoropropan-2-ylamino)-5,6-dihydropyrido[3,4-d]pyrimidine-7(8H)-carboxylate (350) and 250 mg (21%) of tert-butyl 2-(1,1,1-trifluoro-3-hydroxypropan-2-ylamino)-5,6-dihydropyrido[3,4-d]pyrimidine-7(8H)-carboxylate (352).

Step 8:
To a stirred solution of 352 (53 mg, 0.15 mmol) in DCM (750 µL) at RT under nitrogen was added TFA (750 µL). The solution was stirred for 2 h and was then concentrated in a rotovap under high vacuum. The residue was redissolved in DCM (10 mL) and stirred rapidly with 1M Na$_2$CO$_3$ (10 mL) for 5 min. The layers were separated and the aqueous phase was extracted with DCM (2×10 mL). The combined extracts were dried (MgSO$_4$), filtered and concentrated to afford 29 mg (76%) of 3,3,3-trifluoro-2-(5,6,7,8-tetrahydropyrido[3,4-d]pyrimidin-2-ylamino)propan-1-ol (354) as a yellow foam.

Step 9:
To a stirred solution of 185 (21.0 mg, 0.111 mmol) in DCM (1 mL) at RT under nitrogen was added sequentially DIPEA (38.5 µL, 0.221 mmol) neat by syringe followed by CDI (17.9 mg, 0.111 mmol) neat as a solid. After stirring for 30 min, the solution was added by pipet to a flask containing solid 354 (29 mg, 0.111 mmol). The reaction was stirred at RT under nitrogen overnight. The reaction was diluted to 30 mL with DCM and washed sequentially with 2 N HCl (2×30 mL) with 2N HCl and satd. aq. NaHCO$_3$ (2×30 mL). The organics were dried (MgSO$_4$), filtered and concentrated to a yellow foam. The crude product was purified by SiO$_2$ chromatography (Biotage 12S) eluting with EtOAc. The product containing fractions were pooled and concentrated to afford 10 mg (19%) of I-92 as a yellow residue: $^1$H NMR (400 MHz, CDCl$_3$) δ 8.12 (s, 1H), 7.39 (m, 2H), 7.17 (dd, 1H), 5.57 (d, 1H), 4.97 (m, 1H), 4.91 (m, 1H), 4.75 (d, 1H), 4.36 (s, 2H), 3.96 (m, 2H), 3.65 (m, 2H), 2.69 (dd, 2H), 1.48 (d, 6H); MS m/z (APCI-pos) M+1=478.5.

Example 54

N-(4-(3,4-dichlorophenyl)piperidin-4-yl)-2-(isopropylamino)-5,6-dihydropyrido[3,4-d]pyrimidine-7(8H)-carboxamide (I-93)

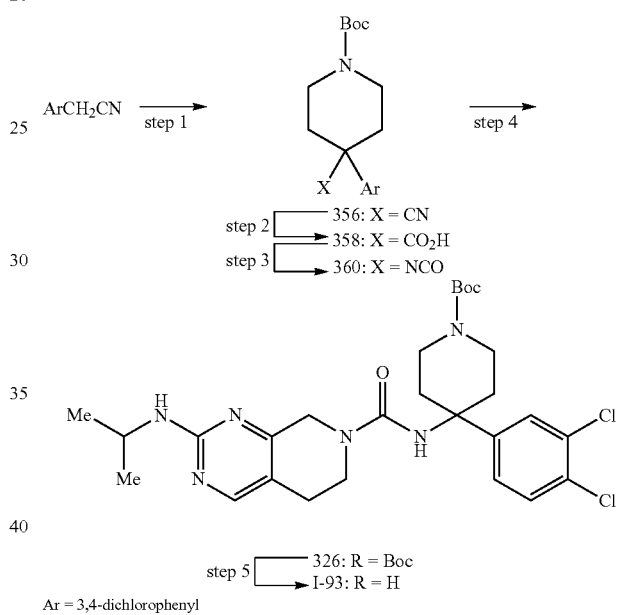

Ar = 3,4-dichlorophenyl

Step 1:
To a stirred solution of 2-(3,4-dichlorophenyl)acetonitrile (3.50 g, 18.8 mmol, CASRN 3218-49-3) and 15-crown-5 (0.414 g, 1.88 mmol) in DMF (75 mL) at 0° C. under nitrogen was added NaH (1.88 g, 47.0 mmol, 60% mineral oil dispersion) in 2 portions. The reaction mixture was warmed to RT and stirred 35 min then re-cooled to 0° C. NaI (2.82 g, 18.8 mmol) was added followed by a solution of freshly prepared tert-butyl bis-(2-chloroethyl)carbamate (4.56 g, 18.8 mmol) in DMF (10 mL) via syringe. The reaction mixture was warmed to RT and stirred overnight. The reaction mixture was then poured into ice cold sat'd. NH$_4$Cl solution (250 mL) with stirring and the mixture was extracted with EtOAc (2×250 mL). The combined extracts were dried (MgSO$_4$), filtered and concentrated. The crude product was loaded onto a SiO$_2$ column (Biotage 40L) and eluted with hexanes/EtOAc (6/1) to afford 4.54 g (68%) of tert-butyl 4-cyano-4-(3,4-dichlorophenyl)piperidine-1-carboxylate (356) as an off white solid.

Step 2:
A solution of 356 (4.54 g, 12.78 mmol) and concentrated HCl (106.5 mL, 1278 mmol) was heated to reflux and stirred over the weekend. The reaction mixture was then cooled to RT, transferred to separatory funnel, and washed with $Et_2O$ (1×200 mL). The aqueous layer was concentrated in a rotovap under high vacuum. The resulting solids were dissolved in 10% NaOH (20.45 g, 51.12 mmol). To the solution was added dioxane (30 mL) followed by $Boc_2O$ (2.929 g, 13.42 mmol). After stirring overnight, the reaction was diluted with $H_2O$ (100 mL) and washed with ether (1×100 mL). The aqueous layer was acidified with solid $KHSO_4$ and then extracted with DCM (200 mL). The combined extracts were dried ($MgSO_4$), filtered, concentrated and dried under high vacuum to afford 1.98 g (41%) of 1-(tert-butoxycarbonyl)-4-(3,4-dichlorophenyl)piperidine-4-carboxylic acid (358) as a white foam.

Step 3:

To a stirred solution of 358 (187 mg, 0.4997 mmol) in DMF (1.5 mL) at RT under nitrogen was added TEA (167.1 µL, 1.199 mmol) neat via syringe followed by DPPA (129.6 µL, 0.5996 mmol) neat by syringe. The solution was stirred for 2 h at RT then warmed to 60° C. After 3 h at 60° C., the reaction was cooled to RT and diluted to 30 mL with EtOAc. The organic extract was washed with $H_2O$ (3×30 mL) and brine (1×30 mL). The organics were dried ($MgSO_4$), filtered and concentrated to afford 170 mg (91%) of tert-butyl 4-(3,4-dichlorophenyl)-4-isocyanatopiperidine-1-carboxylate (360) as a clear oil.

Step 4:

To a stirred solution of 360 (133 mg, 0.358 mmol) in THF (1.8 mL) at RT in a capped reaction vial was added DIPEA (125 µL, 0.716 mmol) followed by solid 72 (81.9 mg, 0.358 mmol). The reaction was initially a suspension but became a brown solution over about 30 min. After stirring overnight the reaction was diluted to 30 mL with EtOAc and washed sequentially with 10% citric acid solution (2×30 mL), aq. satd. $NaHCO_3$ (2×30 mL) and brine (1×30 mL). The organic extract was dried ($MgSO_4$), filtered and concentrated to a clear oil. The crude product was loaded onto a $SiO_2$ column (Biotage 12M) and eluted with EtOAc/hexane (3/2) to afford 102 mg (50%) of tert-butyl 4-(3,4-dichlorophenyl)-4-(2-(isopropylamino)-5,6,7,8-tetrahydropyrido[3,4-d]pyrimidine-7-carboxamido)piperidine-1-carboxylate (362) as a yellow foam.

Step 5:

To a stirred solution of 362 (102 mg, 0.1810 mmol) in DCM (1.8 mL) at RT in a capped flask was added MeOH (180 µL) followed by 4M HCl dioxane solution (452.5 µL, 1.810 mmol). After 2 h the reaction was diluted with $Et_2O$ (5 mL) which produced a coarse yellow precipitate. The solid was filtered off and washed with generous amounts of ether to afford 80 mg (80%) of I-93 as a pale yellow solid which was dried under high vacuum: MS m/z (APCI-pos) M+1=463.4.

Example 55

(R)—N-(3-cyano-1-(3,4-dichlorophenyl)propyl)-2-(tetrahydro-2H-pyran-4-ylamino)-5,6-dihydropyrido[3,4-d]pyrimidine-7(8H)-carboxamide (I-103)

Step 1:

To a stirred solution of 174 (1.327 g, 4.144 mmol) in THF (30 mL) at 0° C. was added TEA (0.6931 mL, 4.973 mmol) and MsCl (0.3528 mL, 4.559 mmol) and the solution stirred for 1 h at 0° C. The mixture was diluted with EtOAc, washed with dilute HCl solution, aq. satd. $NaHCO_3$, and brine, dried ($MgSO_4$) and concentrated to afford 1.51 grams (91%) of (R)-3-(tert-butoxycarbonylamino)-3-(3,4-dichlorophenyl) propyl methanesulfonate (364). The product may contain some of the corresponding chloride.

Step 2:

To a stirred solution of 364 (750 mg, 1.88 mmol) in THF (25 mL) and acetone (5 mL) at RT was added NaI (1411 mg, 9.41 mmol) and stirring was continued overnight. The mixture was poured into water, extracted with EtOAc, washed with brine, dried ($MgSO_4$), and concentrated to afford 810 mgs (100%) of (R)-tert-butyl 1-(3,4-dichlorophenyl)-3-iodopropylcarbamate (366).

Step 3:

To a stirred solution of 366 (810 mg, 1.88 mmol) in DMSO (4 mL) at RT was added NaCN (102 mg, 2.07 mmol) and the resulting mixture was stirred at 80° C. overnight. The mixture was poured into water, extracted with EtOAc, washed with brine, dried ($MgSO_4$), and concentrated. The product was purified by $SiO_2$ chromatography eluting with 20% EtOAc/hexanes to afford 534 mgs (86%) of (R)-tert-butyl 3-cyano-1-(3,4-dichlorophenyl)propylcarbamate (368).

Step 4:

To a stirred solution of 368 (534 mg, 1.62 mmol) in DCM (5 mL) was added 4M HCl (811 µL, 3.24 mmol) in dioxane and stirring was continued for 12 h. The mixture was diluted with ether, filtered and dried to afford 225 mgs (52%) of (R)-4-amino-4-(3,4-dichlorophenyl)butanenitrile hydrochloride (370) as a white solid.

Step 5:

The condensation of 370 and 28 was carried out in accord with the procedure in step 6 of example 1 except 22 was replaced with 370. The crude product was purified by reverse phase chromatography (Biotage SP4 C18) eluting a MeCN/$H_2O$ gradient (5 to 95% MeCN) to afford 49 mgs (46%) of I-103 as off-white solid: $^1H$ NMR (400 MHz, $CDCl_3$) δ 8.08 (s, 1H), 7.45 (d, 1H), 7.40 (s, 1H), 7.17 (d, 1H), 5.00 (dd, 1H), 4.89 (d, 1H), 4.80 (d, 1H), 4.38 (d, 1H), 4.32 (d, 1H), 3.98 (m, 2H), 3.97-4.05 (m, 1H), 3.60 (t, 2H), 3.54 (t, 2H), 2.68 (t, 2H), 2.41 (t, 2H), 2.18 (m, 2H), 2.02 (br d, 2H), 1.53 (m, 2H); MS m/z (APCI-pos) M+1=489.1.

(R)—N-(3-cyano-1-(3,4-dichlorophenyl)propyl)-2-(isopropylamino)-5,6-dihydropyrido[3,4-d]pyrimidine-7(8H)-carboxamide (I-104) was prepared analogously except 72 was used in place of 28. The crude product was purified by reverse phase chromatography (Biotage SP4 C18) eluting MeCN/$H_2O$ gradient (5 to 95% MeCN) to afford 72 mgs (61%) of I-104 as off-white solid: $^1H$ NMR (400 MHz, $CDCl_3$) δ 8.08 (s, 1H), 7.45 (d, 1H), 7.40 (d, 1H), 7.17 (d, 1H), 5.00 (m, 1H), 4.80 (d, 1H), 4.76 (d, 1H), 4.36 (d, 1H), 4.31 (d, 1H), 4.09 (m, 1H), 3.66 (t, 2H), 2.67 (t, 2H), 2.40 (t, 2H), 2.21 (m, 1H), 2.15 (m, 1H), 1.22 (d, 6H); MS m/z (APCI-pos) M+1=447.1.

Example 56

(R)—N-(1-(3,4-dichlorophenyl)-3-(methylsulfonyl) propyl)-2-(tetrahydro-2H-pyran-4-ylamino)-5,6-dihydropyrido[3,4-d]pyrimidine-7(8H)-carboxamide (I-105)

Step 1:

A solution of 366 (810 mg, 1.88 mmol) and sodium methanethiolate (158 mg, 2.26 mmol) in DMSO (4 mL) was stirred at 50° C. overnight. The mixture was poured into water, extracted with EtOAc, washed with brine, dried ($MgSO_4$), and concentrated in vacuo to afford 395 mg (60%) of (R)-tert-butyl 1-(3,4-dichlorophenyl)-3-(methylthio)propylcarbamate (372).

Step 2:

To a stirred solution of 372 (660 mg, 1.88 mmol) in DCM (20 mL) at 0° C. was added MCPBA (1393 mg, 5.65 mmol)

and stirring was continued at RT for 24 h. A dilute solution of NaOH was added and the mixture was twice extracted with DCM, washed with brine, dried (MgSO$_4$), and concentrated in vacuo. The crude product was purified by SiO$_2$ chromatography eluting with 10% EtOAc/hexane to afford 609 mg (84%) of (R)-tert-butyl 1-(3,4-dichlorophenyl)-3-(methylsulfonyl)propylcarbamate (374) as a white solid.

Step 3:

To a stirred solution of 374 (395 mg, 1.03 mmol) in DCM (5 mL) was added a 4M HCl in dioxane (1.03 mL, 4.13 mmol) and stirring was continued overnight. The mixture was diluted with ether, filtered, dried and concentrated to afford 248 mg (75%) of (R)-1-(3,4-dichlorophenyl)-3-(methylsulfonyl)propan-1-amine hydrochloride (376) as white solid.

Step 4:

The condensation of 376 and 28 was carried out in accord with the procedure in step 6 of example 1 except 22 was replaced with 376. The crude product was purified by reverse phase chromatography (Biotage SP4 C18) eluting a MeCN/H$_2$O gradient (5-95% MeCN) to afford I-105 as white solid: $^1$H NMR (400 MHz, CDCl$_3$) δ 8.07 (s, 1H), 7.43 (d, 1H), 7.42 (br s, 1H), 7.17 (dd, 1H), 5.44 (d, 1H), 5.01 (m, 1H), 4.93 (d, 1H), 4.36 (s, 1H), 3.98 (m, 2H), 3.97-4.05 (m, 1H), 3.64 (m, 2H), 3.54 (m, 2H), 3.12 (t, 2H), 2.97 (s, 3H), 2.67 (t, 2H), 2.35 (m, 2H), 2.01 (br d, 2H), 1.53 (m, 2H); MS m/z (APCI-pos) M+1=542.1.

(R)—N-(1-(3,4-dichlorophenyl)-3-(methylsulfonyl)propyl)-2-(isopropylamino)-5,6-dihydropyrido[3,4-d]pyrimidine-7(8H)-carboxamide (I-106) was prepared analogously except 72 was used in place of 28. The crude product was purified by reverse phase chromatography (Biotage SP4 C18) eluting MeCN/H$_2$O gradient (5 to 95% MeCN) to afford 52 mgs (60%) of I-106 as off-white solid: $^1$H NMR (400 MHz, CDCl$_3$) δ 8.07 (s, 1H), 7.41-7.44 (m, 2H), 7.17 (d, 1H), 5.31 (d, 1H), 5.01 (m, 1H), 4.80 (d, 1H), 4.35 (s, 2H), 4.10 (m, 1H), 3.64 (t, 2H), 3.11 (t, 2H), 2.96 (s, 3H), 2.66 (t, 2H), 2.35 (m, 2H), 1.23 (d, 6H); m/z (APCI-pos) M+1=500.1.

Example 57

N-(1-(1H-indol-6-yl)ethyl)-2-(tetrahydro-2H-pyran-4-ylamino)-5,6-dihydropyrido[3,4-d]pyrimidine-7 (8H)-carboxamide (I-107)

The title compound was prepared in accord with the procedure in step 6 of example 1 except 22 was replaced with 1-(1H-indol-6-yl)ethanamine (30.8 mg, 0.192 mmol, Sphinx Scientific). The reaction mixture was purified by SiO$_2$ chromatography eluting with a MeOH/EtOAc gradient (0 to 1% MeOH). The recovered solid was re-purified on reverse phase column chromatography (Biotage SP4 C18) eluting MeCN/H$_2$O gradient (5 to 95% MeCN) to afford 36 mgs (44%) of I-107 as a pink solid: $^1$H NMR (400 MHz, CDCl$_3$) δ 8.44 (br s, 1H) 8.05 (s, 1H), 7.60 (d, 1H), 7.38 (s, 1H), 7.19 (m, 1H), 7.11 (d, 1H), 6.51 (m, 1H), 5.16 (m, 1H), 4.92 (d, 1H), 4.78 (d, 1H), 4.34 (d, 1H), 4.29 (d, 1H), 3.97 (m, 1H), 3.94-4.04 (m, 2H), 3.64 (t, 2H), 3.52 (t, 2H), 2.68 (t, 2H), 2.00 (br d, 2H), 1.58 (d, 3H), 1.51 (m, 2H); m/z (APCI-pos) M+1=421.1.

The enantiomers were separated by chiral hplc to afford (R)—N-(1-(1H-indol-6-yl)ethyl)-2-(tetrahydro-2H-pyran-4-ylamino)-5,6-dihydropyrido[3,4-d]pyrimidine-7(8H)-carboxamide and (S)—N-(1-(1H-indol-6-yl)ethyl)-2-(tetrahydro-2H-pyran-4-ylamino)-5,6-dihydropyrido[3,4-d] pyrimidine-7(8H)-carboxamide.

Example 58

(R)—N-(3-cyano-1-(4-(difluoromethoxy)phenyl) propyl)-2-(tetrahydro-2H-pyran-4-ylamino)-5,6-dihydropyrido[3,4-d]pyrimidine-7(8H)-carboxamide (I-108)

Step 1:

To a stirred solution of 4-(difluoromethoxy)benzaldehyde (10 g, 58 mmol) and (S)-2-methylpropane-2-sulfinamide (13 g, 105 mmol) in THF (50 mL) was added Ti(OEt)$_4$ (43 mL, 209 mmol) and the reaction was stirred at RT overnight. The mixture was poured into brine (400 mL) and stirred for 10 min, filtered, and the filtered solids rinsed with additional THF/EtOAc. The organic layer was separated, and the aqueous layer extracted with additional EtOAc. The combined extracts were washed with brine, dried (MgSO$_4$), and concentrated. The residue was dry loaded and passed through a SiO$_2$ plug eluting with a EtOAc/hexane gradient (10 to 15% EtOAc) to afford 16 g (100%) of (S,E)-N-(4-(difluoromethoxy)benzylidene)-2-methylpropane-2-sulfinamide (378) as pale yellow liquid.

Step 2:

To a stirred solution of diisopropylamine (16.70 mL, 119.1 mmol) in THF (80 mL) at 0° C. was added dropwise 2.5M n-butyllithium (48.82 mL, 122.0 mmol) and stirring was continued for 15 min. The solution was cooled to −78° C. and methyl acetate (9.219 mL, 116.2 mmol) was added dropwise and stirring continued for 30 min. A solution of Ti(O-iPr)$_3$Cl (58.30 mL, 244.1 mmol) in THF (20 mL) was introduced dropwise at −78° C. and stirring was continued for 45 min. A solution of 378 (16 g, 58.12 mmol) in THF (20 mL) was then added dropwise and stirring was continued for 3 h. The reaction was quenched at −78° C. by dropwise addition of satd. aq. NH$_4$Cl and warmed to RT. The mixture was thrice extracted with EtOAc, washed with brine, dried (MgSO$_4$), and concentrated. The crude product was purified by SiO$_2$ chromatography eluting with an EtOAc/hexane gradient (20 to 60% EtOAc) to afford 8.67 g (43%) of (R)-methyl 3-(4-(difluoromethoxy)phenyl)-3-((S)-1,1-dimethylethylsulfinamido) propanoate (380) as a low melting white solid along with 9.67 g impure material.

Step 3:

To a stirred solution of 380 (8.98 g, 25.7 mmol) in MeOH (60 mL) and DCM (30 mL) was added 4M HCl in dioxane (12.9 mL, 51.4 mmol) and stirring was continued for 60 min at RT. HCl was removed with a stream of dry N$_2$ and most of the solvent was removed on in a rotary evaporator. Ether was added to the residue and the precipitated white solid was filtered to afford 7.23 g (100%) of (R)-methyl 3-amino-3-(4-(difluoromethoxy)phenyl)propanoate hydrochloride (382) which was ca. 95% ee by chiral hplc.

Step 4:

To a stirred mixture of 382 (7.2 g, 25.6 mmol) in DCM (50 mL) at RT was added Boc$_2$O (5.86 g, 26.8 mmol) and TEA (3.92 mL, 28.1 mmol) and stirring was continued for 6 h. The mixture was concentrated and the residue purified by SiO$_2$ chromatography eluting with an EtOAc/hexane gradient (10 to 30% EtOAc) to afford 9 g (100% of (R)-methyl 3-(tert-butoxycarbonylamino)-3-(4-(difluoromethoxy)phenyl)propanoate (384) containing a small amount of solvent.

Step 5:

To a stirred mixture of 384 (7.1 g, 20.6 mmol) in THF (150 mL) at −78° C. was added dropwise 1M LiAlH$_4$ (30.8 mL, 30.8 mmol) and stirring was continued for 3 to 4 h. The mixture was diluted with THF, quenched by portion-wise addition of Na$_2$SO$_4$ decahydrate and filtered. Solids were rinsed with additional THF, and the filtrate concentrated. The crude product was purified by SiO₂ chromatography eluting with 50% EtOAc/hexanes to afford 3.58 g (55%) of (R)-tert-butyl 1-(4-(difluoromethoxy)phenyl)-3-hydroxypropylcarbamate (386) as a clear viscous liquid which was ca. 95% ee by chiral HPLC.

Step 6:

To a stirred solution of 386 (550 mg, 1.73 mmol) in DCM (20 mL) at 0° C. was added TEA (290 µL, 2.08 mmol) and MeSO₂Cl (148 µL, 1.91 mmol) and stirring was continued for 1 h at 0° C. The mixture was diluted with EtOAc, washed sequentially with water, dilute HCl solution, aq. satd. NaHCO₃ and brine, dried (MgSO₄), and concentrated to afford 685 mg (100%) of (R)-3-(tert-butoxycarbonylamino)-3-(4-(difluoromethoxy)phenyl)propyl methanesulfonate (388) containing some of the corresponding chloride.

Step 7:

To a stirred solution of 388 in DMSO (5 mL) was added NaCN (92.0 mg, 1.88 mmol) and NaI (25.6 mg, 0.171 mmol) and the mixture heated at 85° C. overnight. After cooling to RT, the mixture was diluted with H₂O (100 mL), stirred for 30 min and filtered to afford a tan solid. The solid was purified by SiO₂ chromatography eluting with an EtOAc/hexane gradient (0 to 25% EtOAc) to afford 261 mg (47%) of (R)-tert-butyl 3-cyano-1-(4-(difluoromethoxy)phenyl)propylcarbamate (390) as a white solid.

Step 8:

To a stirred solution of 390 in DCM (5 mL) was added 4M HCl solution in dioxane (400 µL, 1.60 mmol) and stirring was continued overnight. The mixture was concentrated and triturated with ether to afford 204 mg (87%) of (R)-4-amino-4-(4-(difluoromethoxy)phenyl)butanenitrile hydrochloride (292) giving a white solid.

Step 9:

The condensation of 292 and 28 was carried out in accord with the procedure in step 6 of example 1 except 22 was replaced with 292. The crude product was purified by reverse phase chromatography (Biotage SP4 C18) eluting a MeCN/H₂O gradient (5-95% MeCN) to afford 67 mg (60%) of I-108 as white solid: ¹H NMR (400 MHz, CDCl₃) δ 8.07 (s, 1H), 7.32 (d, 2H), 7.13 (d, 2H), 6.51 (t, 1H), 5.01 (m, 1H), 4.96 (d, 1H), 4.92 (d, 1H), 4.37 (d, 1H), 4.31 (d, 1H), 3.97 (m, 1H), 3.94-4.04 (m, 2H), 3.65 (t, 2H), 3.53 (m, 2H), 2.68 (t, 2H), 2.00 (br d, 2H), 1.58 (d, 3H), 1.51 (m, 2H); m/z (APCI-pos) M+1=487.2.

Example 59

2-((S)-2-Hydroxy-1-methyl-ethylamino)-5,8-dihydro-6H-pyrido[3,4-d]pyrimidine-7-carboxylic acid (2-trifluoromethyl-pyrimidin-5-ylmethyl)-amide (I-109)

(S)-2-(1-hydroxypropan-2-ylamino)-N-((2-(trifluoromethyl)pyrimidin-5-yl)methyl)-5,6-dihydropyrido[3,4-d]pyrimidine-7(8H)-carboxamide (I-109) was prepared by condensing 138 and ((2-(trifluoromethyl)pyrimidin-5-yl)methyl)amine (CASRN 608515-92-0) in accord with the procedure in example 17; MS m/z (APCI-pos) M+1=412.2.

Example 60

N-(3-amino-1-(3,4-dichlorophenyl)propyl)-2-(isopropylamino)-5,6-dihydropyrido[3,4-d]pyrimidine-7(8H)-carboxamide (I-110)

Step 1:

To a solution of 3-(3,4-dichlorophenyl)-3-oxopropanenitrile (5.16 g, 24.1 mmol, CASRN 4640-68-0) in EtOH (115 mL) was added slowly NaBH₄ (0.912 g, 24.1 mmol) over 30 min. The reaction was stirred at RT for 3 h, concentrated to a solid and partitioned between aq. NH₄Cl and EtOAc. The phases were separated and the organic extract was washed with brine, dried, filtered and concentrated. The crude 3-(3,4-dichlorophenyl)-3-hydroxypropanenitrile was taken up in THF (90 mL), cooled in a 0° C. bath and BH₃-THF (1M, 75.5 mL) was added over 30 min. The reaction mixture was heated at reflux for 2.5 h, cooled to 0° C. and quenched with H₂O. The reaction mixture was thrice extracted with DCM and the combined organic phases were dried, filtered and concentrated. The crude product was dissolved in DCM and then 1M HCl/dioxane was added. The solution was diluted with Et₂O and the resulting precipitate was collected by filtration, washed with Et₂O, and dried under high vacuum to afford 4.41 g (72%) of 3-amino-1-(3,4-dichlorophenyl)propan-1-ol hydrochloride (294) as a solid: ¹H NMR (400 MHz, CD₃OD) δ 7.53 (d, 1H), 7.46 (d, 1H), 7.28 (dd, 1H), 4.79 (m, 1H), 3.05 (m, 2H), 1.95 (m, 2H).

Step 2:

To a solution of 294 (4.41 g, 17.2 mmol) in dioxane (40 mL) and 5N NaOH (8.59 mL) at 0° C. was added dropwise via an addition funnel a solution of Boc₂O (5.63 g, 25.8 mmol) in dioxane (40 mL). The reaction was stirred at RT for 4 h then diluted with EtOAc. The phases were separated and the organic phase was washed sequentially with NaHCO₃ then thrice with brine, dried, filtered and concentrated to a clear glass. The crude product was dissolved in THF (100 mL) and isoindoline-1,3-dione (2.78 g, 18.9 mmol) and PPh₃ (7.17 g, 25.8 mmol) were added and the resulting solution cooled to 0° C. To the solution was added dropwise DEAD (4.49 mL, 25.8 mmol), and the reaction warmed to RT with stirring overnight. The mixture was concentrated in vacuo and the residue was purified by SiO₂ chromatography eluting with hexane/EtOAc (4:1) to afford 4.71 g (61%) of tert-butyl 3-(3,4-dichlorophenyl)-3-(1,3-dioxoisoindolin-2-yl)propylcarbamate (296) as a colorless glass: LRMS (APCI pos) m/e=348.9 (M-Boc).

Step 3:

To a solution of 296 (4.71 g, 10.5 mmol) in MeOH was added hydrazine (0.336 g, 10.5 mmol) and the reaction was stirred at RT overnight. The thick white suspension was taken up in hot MeOH, sonicated, filtered and washed with MeOH. The filtrate was concentrated to afford 2.98 g (89%) of tert-butyl 3-amino-3-(3,4-dichlorophenyl)propylcarbamate (298) as a pale yellow foam: LRMS (APCI pos) m/e=319.0 (M+H).

Step 4:

To a solution of 298 (35 mg, 0.11 mmol) in DCM (2 mL) was added DIPEA (0.032 mL, 0.18 mmol) followed by CDI (15 mg, 0.091 mmol) and the mixture stirred 30 min. To the resulting solution was added 72 (21 mg, 0.091 mmol) and the reaction stirred at RT for 5 h. The reaction was diluted with H₂O (15 mL), extracted DCM (2×15 mL), dried (MgSO₄), filtered and concentrated. The crude product was purified by SiO₂ chromatography eluting with MeOH/DCM (5:95) to afford 29 mg (59%) of tert-butyl 3-(3,4-dichlorophenyl)-3-(2-(isopropylamino)-5,6,7,8-tetrahydropyrido[3,4-d]pyrimidine-7-carboxamido)propylcarbamate (300) as a pale yellow solid: LRMS (APCI pos) m/e=537.1 (M+H).

Step 5:

To a solution of 300 (29 mg, 0.0540 mmol) in DCM (2 mL) was added TFA (1 mL, 13.0 mmol). The reaction was stirred at RT 30 min, concentrated, and partitioned between DCM (15 mL) and satd. aq. NaHCO$_3$ (15 mL). The phases were separated and the aqueous phase extracted with DCM (15 mL). The combined organic extracts were dried (MgSO$_4$), filtered and concentrated. The crude product was purified on a preparative SiO$_2$ TLC plate (0.5 mm) developed with MeOH/DCM/NH$_4$OH (9/90/1) to afford 11 mg (47%) of I-110 as a colorless glass: $^1$H NMR (400 MHz, CDCl$_3$) δ 8.07 (s, 1H), 7.63 (br s, 1H), 7.39 (d, 1H), 7.36 (d, J=8.2 Hz, 1H), 7.15 (dd, 1H), 4.97 (m, 1H), 4.83 (d, 1H), 4.38 (m, 2H), 4.10 (m, 1H), 3.70 (m, 1H), 3.60 (m, 1H), 2.89 (br s, 2H), 2.64 (t, 2H) 1.97 (m, 1H), 1.81 (m, 1H), 1.21 (d, 6H); LRMS (APCI pos) m/e=437.1 (M+H).

Example 61

N-((1H-indol-2-yl)methyl)-2-(tetrahydro-2H-pyran-4-ylamino)-5,6-dihydropyrido[3,4-d]pyrimidine-7(8H)-carboxamide (I-114)

To a solution of (1H-indol-2-yl)methanamine hydrochloride (50 mg, 0.27 mmol, CASRN 21109-25-1) and DCM (2.5 mL) at RT were added sequentially TEA (50 μL, 0.36 mmol) and CDI (44 mg, 0.27 mmol) and the reaction was stirred at RT for 30 min. This solution was added to a solution of 28 (55 mg, 0.229 mmol) and TEA (95.7 μL, 0.687 mmol) in DCM (5 mL) and the combined solution was stirred overnight. This solution was loaded directly a SiO$_2$ chromatography column and eluted with a gradient hexane/EtOAc (0 to 10% EtOAc) to afford 57 mg (61.1%) of I-114: $^1$H NMR (400 MHz, CDCl$_3$) δ 9.28 (s, 1H), 8.07 (s, 1H), 7.54 (d, 1H, J=7.8 Hz), 7.34 (d, 1H, J=7.1 Hz), 7.12-7.17 (m, 1H), 7.04-7.08 (m, 1H), 6.31-6.32 (m, 1H), 4.99-5.03 (m, 1H), 4.87 (d, 1H, J=7.7 Hz), 4.50 (d, 2H, J=5.9 Hz), 4.34 (s, 2H), 3.94-4.04 (m, 3H), 3.65-3.69 (m, 2H), 3.49-3.56 (m, 2H), 2.66-2.71 (m, 2H), 1.98-2.04 (m, 2H), 1.46-1.57 (m, 2H); MS (APCI-pos) M+1=407.4.

Example 62

3-(3-chloro-4-fluorophenyl)-4-hydroxy-1-(2-(isopropylamino)-5,6-dihydropyrido[3,4-d]pyrimidin-7(8H)-yl)butan-1-one (I-112)

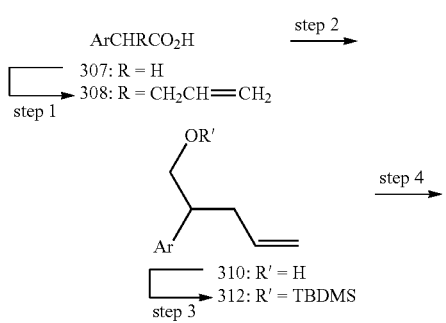

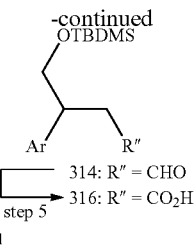

Ar = 3-chloro-4-fluorophenyl

Step 1:

To a solution of 2-(3-chloro-4-fluorophenyl)acetic acid (1 g, 5.303 mmol) in THF (40 mL) cooled in a −10° C. bath was added slowly a 1M solution of lithium bis(trimethylsilyl) amide in THF (11.67 mL, 11.67 mmol). The reaction mixture was stirred 30 min, then allyl bromide (1.147 mL, 13.26 mmol) was added dropwise and the reaction was stirred at RT 2 h. The reaction mixture was partitioned between with 0.5 M HCl (50 mL) and EtOAc (50 mL). The phases were separated, the aqueous phase extracted EtOAc (50 mL), and the combined organic extracts washed satd. aq. NaCl (50 mL), dried (MgSO$_4$), filtered and concentrated to afford 1.28 g (105%) of 2-(3-chloro-4-fluorophenyl)pent-4-enoic acid (308) as a yellow oil: $^1$H NMR (400 MHz, CDCl$_3$) δ 7.38 (dd, 1H), 7.19 (m, 1H), 7.10 (t, 1H), 5.68 (m, 1H), 5.07 (m, 2H), 3.62 (t, 1H), 2.79 (m, 1H), 2.50 (m, 1H).

Step 2:

To a solution of 308 (1.165 g, 5.095 mmol) in THF (40 mL) was added 1M LiAlH$_4$ in THF (10.19 mL, 10.19 mmol) and the reaction stirred under N$_2$ at RT 1 h. The reaction was quenched with H$_2$O (0.4 mL), 1M NaOH (0.4 mL) then H$_2$O (1.2 mL), filtered, rinsed with THF, and concentrated to afford 642 mg (59%) of 2-(3-chloro-4-fluorophenyl)pent-4-en-1-ol (310) as a yellow oil; $^1$H NMR (400 MHz, CDCl$_3$) δ 7.26 (m, 1H), 7.09 (m, 2H), 5.68 (m, 1H), 5.03 (m, 2H), 3.79 (m, 2H), 2.85 (m, 1H), 2.47 (m, 1H), 2.33 (m, 1H).

Step 3:

To a solution of 310 (642 mg, 2.99 mmol) and DIPEA (0.781 mL, 4.49 mmol) in DCM (25 mL) cooled to 0° C. was added TBDMSCl (473 mg, 3.14 mmol) and DMAP (37 mg, 0.30 mmol). After 6 h at RT, the reaction was diluted with H$_2$O (50 mL), the phases separated and the aqueous phase extracted with DCM (50 mL). The combined organic extracts were dried (MgSO$_4$), filtered and concentrated. The crude product was purified by SiO$_2$ chromatography eluting with hexanes to afford 514 mg (52%) of tert-butyl(2-(3-chloro-4-fluorophenyl)pent-4-enyloxy)dimethylsilane as a colorless oil (312): $^1$H NMR (400 MHz, CDCl$_3$) δ 7.24 (m, 1H), 7.04 (m, 2H), 5.67 (m, 1H), 4.98 (m, 2H), 3.67 (d, 2H), 2.77 (m, 1H), 2.54 (m, 1H), 2.31 (m, 1H), 0.85 (s, 9H), −0.05 (d, 2H).

Step 4:

To a solution of 312 (400 mg, 1.22 mmol) in THF (10 mL) and water (10 mL) was added OsO$_4$ (0.762 mL, 0.0608 mmol, 2.5% in tert-BuOH). The reaction was stirred 10 min, then NaIO$_4$ (650 mg, 3.04 mmol) was added and the reaction stirred at RT overnight. The reaction mixture was filtered through CELITE and rinsed with THF. The filtrate was partitioned between EtOAc (50 mL) and H$_2$O (50 mL), the phases separated and the aqueous phase extracted with EtOAc (50 mL). The combined organic extracts were washed with satd. aq. NaCl (50 mL), dried (MgSO$_4$), filtered and concentrated. The crude product was purified by SiO$_2$ chromatography, eluting with 20% EtOAc/hexane to afford 302 mg (75%) of 4-(tert-butyldimethylsilyloxy)-3-(3-chloro-4-fluorophenyl)butanal (314) as a yellow oil: $^1$H NMR (400

MHz, CDCl$_3$) δ 9.74 (s, 1H), 7.28 (m, 1H), 7.08 (m, 2H), 3.74 (m, 1H), 3.61 (m, 1H), 3.38 (m, 1H), 2.94 (m, 1H), 2.70 (m, 1H), 0.87 (s, 9H), −0.02 (s, 6H).

Step 5:

To a solution of 314 (302 mg, 0.913 mmol) in tert-BuOH (20 mL) and H$_2$O (5 mL) was added 2M solution of 2-methyl-2-butene in THF (4.56 mL, 9.13 mmol) then NaH$_2$PO$_4$ (1.204 g, 10.0 mmol). The reaction was stirred 5 min, then NaClO$_2$ (495 mg, 5.48 mmol) was added and the reaction stirred at RT overnight. The reaction was partitioned between EtOAc (50 mL) and 0.5M HCl (30 mL), phases separated and the aqueous phase extracted with EtOAc (50 mL). The combined organic extracts were washed with satd. aq. NaCl (50 mL), dried (MgSO$_4$), filtered and concentrated. The crude product was purified by SiO$_2$ chromatography eluting with 10% EtOAc/hexane to afford 270 mg (85%) of 4-(tert-butyldimethylsilyloxy)-3-(3-chloro-4-fluorophenyl)butanoic acid (316) as a gray crystalline solid: $^1$H NMR (400 MHz, CDCl$_3$) δ 7.27 (dd, J=2.3, 7.1 Hz, 1H), 7.08 (m, 2H), 3.74 (m, 1H), 3.61 (m, 1H), 3.26 (m, 1H), 2.91 (m, 1H), 2.61 (m, 1H), 0.86 (s, 9H), −0.03 (d, J=1.6 Hz, 6H); MS LRMS (APCI neg) m/e=345.1 (M−H).

Step 6:

To a solution of 316 (30 mg, 0.086 mmol) in MeCN (3 mL) was added sequentially 72 (15 mg, 0.079 mmol), NMM (0.026 ml, 0.24 mmol) and HATU (36 mg, 0.094 mmol). The reaction stirred at RT 1 h. The reaction was diluted with DCM (15 mL) and H$_2$O (15 mL), the phases separated and the aqueous phase extracted with DCM (15 mL). The combined organic extracts were dried (MgSO$_4$), filtered and concentrated. The crude product was purified SiO$_2$ chromatography eluting with 5% MeOH/DCM to afford 44 mg (105%) of 4-(tert-butyldimethylsilyloxy)-3-(3-chloro-4-fluorophenyl)-1-(2-(isopropylamino)-5,6-dihydropyrido[3,4-d]pyrimidin-7(8H)-yl)butan-1-one (318) as a colorless residue: LRMS (APCI pos) m/e=521.2 (M+H).

Step 7:

To a solution of 318 (36 mg, 0.069 mmol) in THF (1 mL) was added TBAF hydrate (25 mg, 0.090 mmol) and the reaction stirred at RT 1 h. The reaction was partitioned between DCM (10 mL) and H$_2$O (10 mL), the phases separated and the aqueous phase extracted with DCM (10 mL). The combined organic phases were dried (MgSO$_4$), filtered and concentrated. The crude product was purified on a preparative SiO$_2$ TLC plate (0.5 mm plate) developed with 10% MeOH/DCM to afford 19 mg (68%) I-112 as a colorless gum: $^1$H NMR (400 MHz, CDCl$_3$) δ 8.04 (d, J=11.7 Hz, 1H), 7.29 (m, 1H), 7.13 (m, 1H), 7.07 (m, 1H), 4.92 (dd, 1H), 4.57 (s, 1H), 4.37 (m, 1H), 4.09 (m, 1H), 3.80 (m, 3H), 3.66 (t, 3H), 3.43 (m, 1H), 2.90 (m, 1H), 2.74 (m, 1H), 2.66 (m, 1H), 2.60 (m, 1H), 1.22 (t, 6H); $^{19}$F NMR (376 MHz, CDCl$_3$) δ-118.4; LRMS (APCI pos) m/e=407.0 (M+H).

Example 63

(S)-3-(4-chlorophenyl)-1-(2-(isopropylamino)-5,6-dihydropyrido[3,4-d]pyrimidin-7(8H)-yl)-4-(methylamino)butan-1-one (I-113)

Step 1:

Condensation of (S)-4-(tert-butoxycarbonyl(methyl)amino)-3-(4-chlorophenyl)butanoic acid (320, CASRN 78215-13-1) and 72 was carried out in accord with the procedure described in step 6 of example 62 except 320 was substituted for 316 to afford 28 mg (89%) of (S)-tert-butyl 2-(4-chlorophenyl)-4-(2-(isopropylamino)-5,6-dihydropyrido[3,4-d]pyrimidin-7(8H)-yl)-4-oxobutyl(methyl)carbamate (322) as a pale yellow residue: LRMS (APCI, pos) m/e=502.2 (M+H).

Step 2:

To a solution 322 (28 mg, 0.056 mmol) in MeOH (2 mL) was added 4M HCl in dioxane (0.6 mL, 2.4 mmol) and the reaction stirred at RT 4 h. The reaction was diluted with DCM (25 mL) and satd. aq. NaHCO$_3$ (25 mL), the phases separated and the aqueous phase extracted with 10% MeOH/DCM (25 mL). The combined organic extracts were dried (MgSO$_4$), filtered and concentrated. The crude product was purified on a preparative SiO$_2$ TLC plate (0.5 mm) developed with MeOH/DCM/NH4OH (9/90/1) to afford 6 mg (25%) of I-113 as a pale yellow residue: $^1$H NMR (400 MHz, CDCl$_3$) δ 8.04 (s, 0.6H), 8.02 (s, 0.4H), 7.15-7.30 (m, 4H), 4.80 (m, 1H), 4.52 (s, 1H), 4.34 (m, 1H), 4.09 (m, 1H), 3.74 (m, 1H), 3.59 (m, 1H), 3.47 (m, 1H), 2.79-2.92 (m, 3H), 2.51-2.73 (m, 3H), 2.42 (s, 1.2H), 2.39 (s, 2.8H), 1.87 (br s, 2H), 1.22 (m, 6H); LRMS (M+H) (APCI pos) m/e=402.1.

Example 64

(R)—N-(1-(4-chlorophenyl)-3-hydroxypropyl-2-(isopropylamino)-5,6-dihydropyrido[3,4-d]pyrimidine-7(8H)-carboxamide (I-154)

Step 1:

To a suspension of (R)-3-amino-3-(4-chlorophenyl)propanoic acid (710 mg, 3.56 mmol, CASRN 131690-61-4) in THF (30 mL) under N$_2$ at 0° C. was added slowly 1M LiAlH$_4$ in Et$_2$O (5.33 mL, 5.33 mmol). The reaction was stirred at 0° C. for 90 min. The reaction was quenched with H$_2$O (0.2 mL), 15% NaOH (0.2 mL) then H$_2$O (0.6 mL) and stirred at RT overnight. The mixture was filtered, rinsed with THF, and concentrated to afford 593 mg (90%) of (R)-3-amino-3-(4-chlorophenyl)propan-1-ol (324) as a colorless oil: $^1$H NMR (400 MHz, CDCl$_3$) δ 7.32 (d, 2H), 7.24 (d, 2H), 4.25 (t, 1H), 4.13 (m, 1H), 3.79 (m, 2H), 1.85 (m, 2H), 1.65 (br s, 2H); LRMS (APCI, pos) m/e=185.9 (M+H).

Step 2:

Silylation of 324 was carried out in accord with the procedure described in step 3 of example 62 substituting 324 (243 mg, 1.31 mmol) for 310 to afford 383 mg (98%) of (R)-3-(tert-butyldimethylsilyloxy)-1-(4-chlorophenyl)propan-1-amine (328) as a colorless oil: LRMS (APCI pos) m/e=300.0 (M+H).

Step 3:

Condensation of (S)-4-(tert-butoxycarbonyl(methyl)amino)-3-(4-chlorophenyl)butanoic acid (328) and 72 was carried out in accord with the procedure described in step 6 of example 62 except 328 was substituted for 316 to afford 90 mg (87%) of (R)—N-(3-(tert-butyldimethylsilyloxy)-1-(4-chlorophenyl)propyl)-2-(isopropylamino)-5,6-dihydropyrido[3,4-d]pyrimidine-7(8H)-carboxamide (324) as a yellow viscous oil: LRMS (APCI pos) m/e=518.6 (M+H).

Step 4:

Desilylation of 324 was carried out in accord with the procedure described in step 7 of example 62 to afford 32 mg (46%) of I-154 as a yellow glass: LRMS (APCI pos) m/e=404.3 (M+H). $^1$H NMR (400 MHz, CDCl$_3$) δ 8.07 (s, 1H), 7.31 (d, 2H), 7.26 (d, 2H), 5.47 (m, 1H), 5.12 (m, 1H), 4.94 (m, 1H), 4.34 (s, 2H), 4.09 (m, 1H), 3.59-3.75 (m, 4H), 2.66 (t, 2H), 2.11 (m, 1H), 1.84 (m, 1H), 1.22 (d, 6H).

N-(1-(3,4-dichlorophenyl)-3-hydroxypropyl)-2-(isopropylamino)-5,6-dihydropyrido[3,4-d]pyrimidine-7(8H)-carboxamide (I-115) was prepared analogously except in step 1, (R)-3-amino-3-(4-chlorophenyl)propanoic acid was replaced with 3-amino-3-(3,4-dichlorophenyl)propanoic acid to afford I-115 as a pale yellow foam: $^1$H NMR (400 MHz, CDCl$_3$) δ 8.08 (s, 1H), 7.40 (m, 2H), 7.17 (dd, 1H), 5.69 (d, 1H), 5.09 (m, 1H), 4.37 (m, 2H), 4.12 (m, 1H), 3.60-3.76 (m, 4H), 2.67 (t, 2H), 2.11 (m, 1H), 1.85 (m, 1H), 1.23 (d, 6H); LRMS (APCI pos) m/e=438.4 (M+H).

Example 65

(R)—N-(3-amino-1-(4-chlorophenyl)propyl)-2-(isopropylamino)-5,6-dihydropyrido[3,4-d]pyrimidine-7(8H)-carboxamide (I-116)

Step 1:
(R)-tert-butyl 1-(4-chlorophenyl)-3-hydroxypropylcarbamate (326) was prepared from (R)-3-amino-3-(4-chlorophenyl)propan-1-ol ((S)-isomer is CASRN 886061-26-3) in accord with the procedure in step 2 of example 60. The product was a colorless syrup: $^1$H NMR (400 MHz, CDCl$_3$) δ 7.32 (d, 2H), 7.24 (d, 2H), 5.04 (br m, 1H), 4.88 (br s, 1H), 3.69 (m, 2H), 2.04 (m, 1H), 1.80 (m, 1H), 1.44 (s, 9H); LRMS (APCI pos) m/e=185.9 (M-Boc fragment).

Step 2:
To a solution of 326 (861 mg, 3.013 mmol) in THF (25 mL) at 0° C. were added PPh$_3$ (1.185 g, 4.519 mmol) then DIAD (0.5836 mL, 3.013 mmol) and the solution stirred for 15 min then diphenylphosphoryl azide (0.974 mL, 4.519 mmol) was added. After 22 h at RT the reaction was quenched with satd. aq. NH$_4$Cl (50 mL), the phases separated and the aqueous phase extracted with EtOAc (5 0 mL). The combined organic extracts were washed with satd. aq. NaCl (50 mL), dried (MgSO$_4$), filtered and concentrated. The crude product was purified by SiO$_2$ chromatography eluting with hexanes to afford 720 mg (77%) of (R)-tert-butyl 3-azido-1-(4-chlorophenyl)propylcarbamate (328) as a white solid: $^1$H NMR (400 MHz, CDCl$_3$) δ 7.32 (d, 2H), 7.21 (d, 2H), 4.91 (m, 1H), 4.75 (m, 1H), 3.31 (m, 2H), 1.98 (m, 2H), 1.41 (s, 9H).

Step 3:
To a solution of 328 (620 mg, 1.99 mmol) in DCM (10 ml) was added TFA (5 mL, 64.9 mmol). The reaction mixture was stirred at RT for 45 min, concentrated, partitioned between DCM (15 mL) and satd. aq. NaHCO$_3$ (15 mL), the phases separated and the aqueous phase extracted with 10% MeOH/DCM (15 mL). The combined organic extracts were dried (MgSO$_4$), filtered and concentrated to afford 414 mg of a crude pale yellow oil. A portion of the crude oil (314 mg) was purified by SiO$_2$ chromatography, eluting with 5% MeOH/DCM, to afford 137 mg (33%) of (R)-3-azido-1-(4-chlorophenyl)propan-1-amine (330) as a tan oil: $^1$H NMR (400 MHz, CDCl$_3$) δ 7.32 (d, 2H), 7.26 (d, 2H), 4.04 (t, 1H), 3.36 (m, 1H), 3.22 (m, 1H), 1.89 (m, 2H), 1.55 (br s, 2H); LRMS (APCI pos) m/e=210.9 (M+H).

Step 4:
Condensation of 330 and 72 was carried out in accord with the procedure described in step 6 of example 62 except 330 was substituted for 316 to afford 226 mg (81%) of (R)—N-(3-azido-1-(4-chlorophenyl)propyl)-2-(isopropylamino)-5,6-dihydropyrido[3,4-d]pyrimidine-7(8H)-carboxamide (332) as a yellow solid: LRMS (APCI pos) m/e=429.4 (M+H).

Step 5:
To a solution of 332 (53 mg, 0.12 mmol) in THF (2 mL) and H$_2$O (2 mL, 0.12 mmol) was added PPh$_3$ (65 mg, 0.25 mmol). The reaction was stirred in a 50° C. oil bath for 2 h. The reaction mixture was partially concentrated then purified on a preparative TLC plate (0.5 mm) developed with MeOH/DCM/NH$_4$OH (9/90/1) to afford 32 mg (64%) of I-116 as a pale yellow glass: $^1$H NMR (400 MHz, CDCl$_3$) δ 8.07 (s, 1H), 7.40 (br s, 1H), 7.23-7.29 (m, 4H), 5.01 (m, 1H), 4.79 (d, 1H), 4.37 (m, 2H), 4.10 (m, 1H), 3.69 (m, 1H), 3.61 (m, 1H), 2.85 (m, 2H), 2.64 (t, 2H), 1.95 (m, 1H), 1.80 (m, 1H), 1.22 (d, 6H); LRMS (APCI pos) m/e=403.3 (M+H).

(R)—N-(3-amino-1-(3-chlorophenyl)propyl)-2-(isopropylamino)-5,6-dihydropyrido[3,4-d]pyrimidine-7(8H)-carboxamide (I-118) was prepared analogously except in step 1, (R)-3-amino-3-(4-chlorophenyl)propan-1-ol was replaced with (R)-3-amino-3-(3-chlorophenyl)propan-1-ol which afforded 20 mg (71%) of I-118 as a yellow solid: $^1$H NMR (400 MHz, CDCl$_3$) δ 8.07 (s, 1H), 7.48 (d, 1H), 7.17-7.28 (m, 3H), 5.02 (m, 1H), 4.80 (d, 1H), 4.38 (m, 2H), 4.11 (m, 1H), 3.60-3.72 (m, 2H), 2.85 (m, 2H), 2.65 (t, 2H), 1.96 (m, 1H), 1.85 (br s, 2H), 1.81 (m, 1H), 1.22 (d, 6H); LRMS (APCI pos) m/e=403.2 (M+H).

(R)—N-(3-amino-1-(4-(trifluoromethyl)phenyl)propyl)-2-(isopropylamino)-5,6-dihydropyrido[3,4-d]pyrimidine-7(8H)-carboxamide (I-119) was prepared analogously except in step 1, (R)-3-amino-3-(4-chlorophenyl)propan-1-ol was replaced with (R)-3-amino-3-(4-(trifluoromethyl)phenyl)propan-1-ol which afforded 8 mg (42%) of I-119 as an orange oil: $^1$H NMR (400 MHz, CDCl$_3$) δ 8.07 (s, 1H), 7.64 (d, 1H), 7.56 (d, 2H), 7.42 (d, 2H), 5.07 (m, 1H), 4.82 (d, 1H), 4.39 (m, 2H), 4.10 (m, 1H), 3.57-3.74 (m, 2H), 2.88 (m, 2H), 2.65 (t, 2H), 2.24 (br s, 2H), 2.01 (m, 1H), 1.83 (m, 1H), 1.22 (d, 6H); $^{19}$F NMR (376 MHz, CDCl$_3$) δ −62.8; LRMS (APCI pos) m/e=437.3 (M+H).

Example 66

(R)—N-(1-(4-chlorophenyl)-3-(methylamino)propyl)-2-(isopropylamino)-5,6-dihydropyrido[3,4-d]pyrimidine-7(8H)-carboxamide (I-117)

A suspension of PS—PPh$_3$ (278 mg, 2.28 mmol/g, 0.634 mmol) and THF (5 mL) was was allowed to stand for 5 min then a solution 332 (136 mg, 0.317 mmol) in THF (1 mL) was added. The suspension was stirred at RT for 4 h then MeI (0.0593 mL, 0.951 mmol) was added. The mixture was stirred at RT for 17 h, filtered through a fritted funnel and the resin washed with THF (5×10 mL) and DCM (5×10 mL). The resin was transferred to a pressure tube and suspended in MeOH (8 mL) and a solution of KOH (178 mg, 3.17 mmol) in MeOH (2 mL) was added. The mixture was heated to 65° C. for 4 h, cooled to RT, filtered and the resin washed with DCM (4×3 mL) and MeOH (2×3 mL). The filtrate and washings were combined and concentrated to a white solid. The crude product was partitioned between DCM and dilute aq. NaHCO$_3$ and the aqueous layer extracted with EtOAc. The combined organic extracts were dried (MgSO$_4$), filtered, and concentrated. The crude product was purified on a preparative TLC plate (0.5 mm) developed with MeOH/DCM/NH$_4$OH (9/90/1) to afford 50 mg (38%) of I-117 as a pale yellow foam: $^1$H NMR (400 MHz, CDCl$_3$) δ 8.06 (s, 1H), 7.72 (br s, 1H), 7.22-7.28 (m, 4H), 4.95 (m, 1H), 4.80 (d, 1H), 4.37 (m, 2H), 4.10 (m, 1H), 3.69 (m, 1H), 3.60 (m, 1H), 2.72 (m, 2H), 2.65 (t, 2H), 2.48 (s, 3H), 2.05 (m, 1H), 1.80 (m, 1H), 1.22 (d, 6H); LRMS (APCI pos) m/e=417.4 (M+H).

Example 67

N-(1-(3,4-dichlorophenyl)-3-(methylamino)propyl)-2-(isopropylamino)-5,6-dihydropyrido[3,4-d]pyrimidine-7(8H)-carboxamide (I-111)

To a solution of tert-butyl 3-(3,4-dichlorophenyl)-3-(2-(isopropylamino)-5,6,7,8-tetrahydropyrido[3,4-d]pyrimidine-7-carboxamido)propylcarbamate (89 mg, 0.17 mmol) in THF (5 mL) under $N_2$ was added $BH_3$·THF complex (0.36 mL, 0.36 mmol) and the reaction was heated at reflux under $N_2$ for 19 h. The reaction was cooled to RT, quenched with MeOH (10 mL), and heated at reflux for 1 h. The reaction was concentrated, then partitioned between DCM (25 mL) and sat. aq. $NaHCO_3$ (25 mL). The phases were separated, the aqueous phase extracted with DCM (25 ml). The combined organic extracts were dried ($MgSO_4$), filtered and concentrated. The crude product was purified on a preparative $SiO_2$ TLC (1 mm) plate developed with $MeOH/DCM/NH_4OH$ (9/90/1) to afford 11 mg (15%) of I-111 as a white solid: $^1H$ NMR (400 MHz, $CDCl_3$) δ 8.07 (s, 1H), 7.36 (m, 2H), 7.13 (dd, 1H), 4.91 (m, 1H), 4.80 (d, 1H), 4.37 (m, 2H), 4.10 (m, 1H), 3.69 (m, 1H), 3.61 (m, 1H), 2.64-2.75 (m, 4H), 2.48 (s, 3H), 2.02 (m, 1H), 1.73 (m, 1H), 1.22 (dd, 6H); LRMS (APCI pos) m/e=451.1 (M+H).

Example 68

N-((3S,4R)-4-(3-fluoro-4-(trifluoromethyl)phenyl) pyrrolidin-3-yl)-2-(isopropylamino)-5,6-dihydropyrido[3,4-d]pyrimidine-7(8H)-carboxamide (I-148)

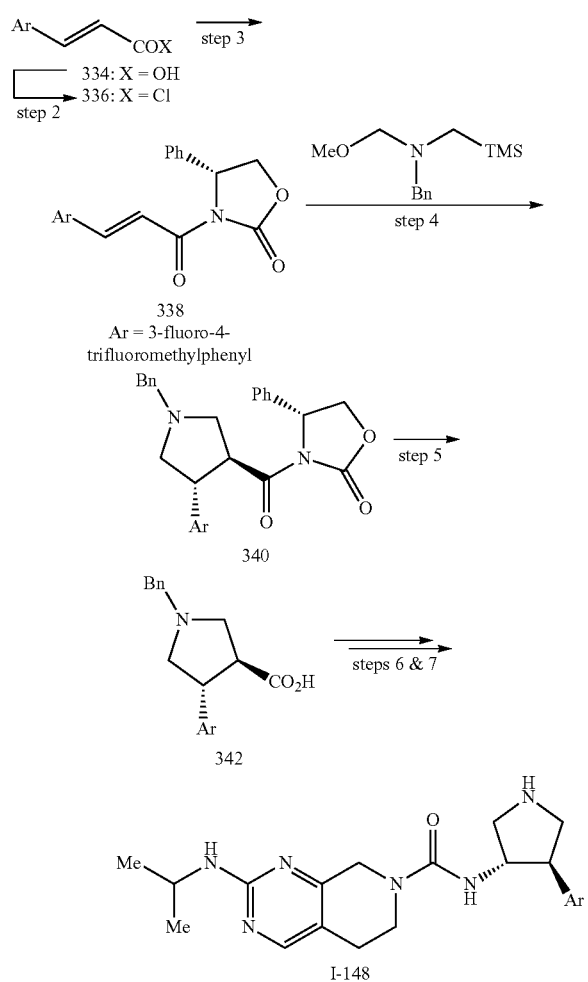

Step 1:

A mixture of 3-fluoro-4-(trifluoromethyl)benzaldehyde (12.8 g, 66.9 mmol), malonic acid (7.65 g, 73.5 mmol) and pyridine (8.11 mL, 100 mmol) was heated to 100° C. and agitated 6 h. Upon cooling the residue was agitated with 3M HCl (100 mL) for 1 h and the precipitate was filtered, washed with $H_2O$ and dried to afford 14.1 g (90.2%) of (E)-3-(3-fluoro-4-(trifluoromethyl)phenyl)acrylic acid (334) as white solid which was used without further purification. Used without purification.

Step 2:

To a suspension of 334 (2.07 g, 8.84 mmol), toluene (25 mL) and oxalyl chloride (1.54 mL, 17.7 mmol) was added one drop of DMF. The mixture was agitated overnight and evaporated to afford 2.23 g (99.9%) of (E)-3-(3-fluoro-4-(trifluoromethyl)phenyl)acryloyl chloride (336) as amber oil which was used without purification.

Step 3:

To a solution of (R)-4-phenyloxazolidin-2-one (1.40 g, 8.58 mmol) and dry THF (25 mL) cooled to −78° C. in dry ice/acetone bath was added dropwise over 15 min 1M lithium bis-(trimethylsilyl)amide in THF (8.75 mL, 8.75 mmol) and the mixture was agitated for 15 min at −78° C. To the resulting solution was added slowly a solution of 336 (2.23 g, 8.83 mmol) and THF (5 mL) and the mixture agitated for 1 h at −78° C. then warmed to RT. After stirring for additional 2 h, the reaction was quenched with satd. aq. $NaHCO_3$ (50 mL) and stirred for 1 h. The mixture was diluted with EtOAc (200 mL), washed sequentially with $H_2O$ and EtOAc, dried ($MgSO_4$), filtered and evaporated to afford 3.18 g (97.7%) of crude (R,E)-3-(3-(3-fluoro-4-(trifluoromethyl)phenyl)acryloyl)-4-phenyloxazolidin-2-one (338) as tan solid which was used without purification.

Step 4:

To a solution of 338 (2.10 g, 5.54 mmol) and N-(methoxymethyl)-N-(trimethylsilylmethyl)benzylamine (1.98 mL, 7.75 mmol) dissolved in toluene (25 mL) and cooled to 0° C. A solution of TFA (0.0427 mL, 0.554 mmol) and benzene (1 mL) was added slowly over 15 min and the mixture was stirred for 4 h. The mixture was washed sequentially with satd. aq. $NaHCO_3$, twice with water, dried, filtered and evaporated. The crude residue was purified by $SiO_2$ chromatography eluting with an EtOAc/hexane gradient (20-40% EtOAc) to afford 1.62 g (57.1%) of (R)-3-((3S,4R)-1-benzyl-4-(3-fluoro-4-(trifluoromethyl)phenyl)pyrrolidine-3-carbonyl)-4-phenyloxazolidin-2-one (340) as white foamy solid.

Step 5:

To a 1M LiOH solution (8.20 mL, 8.20 mmol) cooled to 0° C. was added 30% hydrogen peroxide (1.06 mL, 10.2 mmol). The mixture was stirred for 10 min at 0° C. and then added to solution of 340 (2.10 g, 4.10 mmol) in THF (15 mL) cooled to 0° C. over 15 min. The mixture was stirred for 4 h at 0° C. then 2M sodium sulfite (10 mL) was added and the mixture stirred for 30 min. The pH was adjusted to ca. 5-6 with 2M $KHSO_4$ and the mixture was thrice extracted with 50 mL portions of 3:1 $CHCl_3$/IPA. The combined organic extracts were combined, washed with brine, dried ($MgSO_4$), filtered and evaporated. The crude product was purified by $SiO_2$ chromatography eluting with a MeOH/DCM gradient (5 to 10% MeOH) to afford 1.28 g (85.0%) of (3S,4R)-1-benzyl-4-(3-fluoro-4-(trifluoromethyl)phenyl)pyrrolidine-3-carboxylic acid (342) as white solid: MS m/z (APCI-neg) M−1=366.

Step 6:

To a solution of 342 (0.175 g, 0.476 mmol) and toluene (5 mL) was added DIPEA (0.166 mL, 0.953 mmol) followed by diphenylphosphoryl azide (0.154 mL, 0.715 mmol). The mixture was stirred at RT for 30 min then slowly heated to 100° C. and stirred for 3 h. 72 (109 mg, 0.476 mmol) was added to the cooled mixture and the mixture was stirred overnight. The crude product was loaded on a SiO₂ column and eluted with a MeOH/DCM gradient (1 to 3% MeOH) to afford 0.160 g (60.3%) of N-((3S,4R)-1-benzyl-4-(3-fluoro-4-(trifluoromethyl)phenyl)pyrrolidin-3-yl)-2-(isopropylamino)-5,6-dihydropyrido[3,4-d]pyrimidine-7(8H)-carboxamide (344) as tan solid.

Step 7:

To a solution of 344 (0.160 g, 0.287 mmol) and MeOH (10 mL) was added Pd/C (10% Degussa, 50% wet, 100 mg). The mixture was stirred under a hydrogen atmosphere overnight (H₂ filled balloon). The catalyst was filtered and the filtrate evaporated to afford 0.130 (97%) of I-148: MS m/z (APCI-pos) M+1=467.

Example 69

N-((3S,4R)-4-(3-fluoro-4-(trifluoromethyl)phenyl)-1-methylpyrrolidin-3-yl)-2-(isopropylamino)-5,6-dihydropyrido[3,4-d]pyrimidine-7(8H)-carboxamide (I-120)

To a solution of I-148 (0.045 g, 0.0965 mmol) and MeOH (2 mL) was added formaldehyde (0.0359 mL, 0.482 mmol). The mixture was stirred for 1 h then a 1M NaBH4 solution in THF (0.579 mL, 0.579 mmol) was added slowly over 10 min. The mixture was stirred for 2 h then quenched by addition of 1M NaOH solution. After stirring for 15 min the mixture was twice extracted twice with CHCl₃/IPA (3:1) mixture. The combined extracts were washed with satd. aq. NaHCO₃, dried (MgSO₄), filtered and evaporated. The residue was purified by SiO₂ chromatography eluting a MeOH/DCM gradient (5 to 10%) with addition of 0.1M of ammonia to afford 0.020 g (43.1%) of I-120 as white solid: ¹H NMR (400 MHz, CDCl₃) 8.07 (s, 1H), 7.52 (t, 1H), 7.20 (m, 2H), 4.98 (d, 1H), 4.81 (d, 1H), 4.41 (m, 1H), 4.31 (s, 2H), 4.09 (m, 1H), 3.63 (m, 2H), 3.25 (m, 2H), 2.85-2.63 (m, 4H), 2.40-2.37 (m, 4H), 1.22 (d, 6H); MS m/z (APCI-pos) M+1=481.

N-((3S,4R)-4-(3,4-difluorophenyl)-1-methylpyrrolidin-3-yl)-2-(isopropylamino)-5,6-dihydropyrido[3,4-d]pyrimidine-7(8H)-carboxamide (I-121) was prepared in accord with the procedures in examples 68 and 69 except in step 1 of example 68, 3-fluoro-4-(trifluoromethyl)benzaldehyde was replaced with 3,4-difluoro-benzaldehyde to afford I-121: ¹H NMR (400 MHz, CDCl₃) δ 8.06 (s, 1H), 7.16-7.03 (m, 3H), 5.00 (d, 1H), 4.84 (d, 1H), 4.37 (m, 1H), 4.31 (s, 2H), 4.10 (m, 1H), 3.63 (m, 2H), 3.26-3.14 (m, 2H), 2.77 (m, 2H), 2.64 (m, 2H), 2.38 (s, 3H), 2.32 (t, 1H), 1.22 (d, 6H); MS m/z (APCI-pos) M+1=431.

N-((3S,4R)-4-(3-fluorophenyl)-1-methylpyrrolidin-3-yl)-2-(isopropylamino)-5,6-dihydropyrido[3,4-d]pyrimidine-7(8H)-carboxamide (I-122) was prepared in accord with the procedures in examples 68 and 69 except in step 1 of example 68, 3-fluoro-4-(trifluoromethyl)benzaldehyde was replaced with 3-fluoro-benzaldehyde to afford I-121: ¹H NMR (400 MHz, CDCl₃) δ 8.06 (s, 1H), 7.26 (m, 1H), 7.09-6.90 (m, 3H), 5.02 (d, 1H), 4.82 (d, 1H), 4.43 (s, 1H), 4.31 (s, 2H), 4.10 (m, 1H), 3.62 (m, 2H), 3.32-3.20 (m, 2H), 2.84 (m, 2H), 2.64 (m, 2H), 2.40 (s, 3H), 2.37 (t, 1H), 1.22 (d, 6H); MS m/z (APCI-pos) M+1=413.

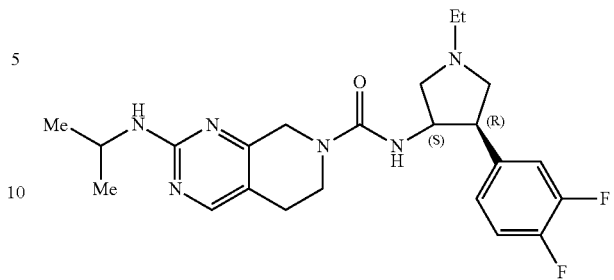

(I-123)

N-((3S,4R)-4-(3,4-difluorophenyl)-1-ethylpyrrolidin-3-yl)-2-(isopropylamino)-5,6-dihydropyrido[3,4-d]pyrimidine-7(8H)-carboxamide (I-123) was prepared in accord with the procedures in examples 68 and 69 except in step 1 of example 68, 3-fluoro-4-(trifluoromethyl)benzaldehyde was replaced with 3,4-difluoro-benzaldehyde and in the procedure in example 69, formaldehyde was replaced with acetaldehyde to afford I-123: ¹H NMR (400 MHz, CDCl₃) δ 8.05 (s, 1H), 7.15-7.02 (m, 3H), 5.64 (d, 1H), 4.87 (d, 1H), 4.48 (m, 1H), 4.34 (s, 2H), 4.10 (m, 1H), 3.63 (m, 2H), 3.42 (m, 1H), 3.28 (m, 1H), 3.01 (m, 1H), 2.86 (m, 1H), 2.68-2.56 (m, 4H), 2.38 (t, 1H), 2.07 (s, 1H), 1.22 (d, 6H), 1.17 (t, 3H); MS m/z (APCI-pos) M+1=445.

N-((3S,4R)-4-(4-chloro-3-fluorophenyl)-1-methylpyrrolidin-3-yl)-2-(tetrahydro-2H-pyran-4-ylamino)-5,6-dihydropyrido[3,4-d]pyrimidine-7(8H)-carboxamide (I-124) was prepared in accord with the procedures in examples 68 and 69 except in step 6 of example 68, 72 was replaced with 28 and in step 1 of example 68, 3-fluoro-4-(trifluoromethyl)benzaldehyde was replaced with 3-fluoro-4-chloro-benzaldehyde to afford I-124: ¹H NMR (400 MHz, CDCl₃) δ 8.06 (s, 1H), 7.28 (t, 1H), 7.11 (d, 1H), 7.04 (d, 1H), 5.04-4.96 (m, 2H), 4.39 (bs, 1H), 4.32 (s, 2H), 3.98 (m, 3H), 3.64-3.50 (m, 4H), 3.28-3.16 (m, 2H), 2.78 (m, 2H), 2.65 (m, 2H), 2.38 (s, 3H), 2.32 (t, 1H), 2.02 (d, 2H), 1.54 (m, 2H); MS m/z (APCI-pos) M+1=489.

N-((3S,4R)-4-(3-fluoro-4-(trifluoromethyl)phenyl)-1-methylpyrrolidin-3-yl)-2-(tetrahydro-2H-pyran-4-ylamino)-5,6-dihydropyrido[3,4-d]pyrimidine-7(8H)-carboxamide (I-125) was prepared in accord with the procedures in examples 68 and 69 except in step 6 of example 68, 72 was replaced with 28 to afford I-124: ¹H NMR (400 MHz, CDCl₃) δ 8.07 (s, 1H), 7.52 (t, 1H), 7.20 (m, 2H), 5.01-4.89 (m, 2H), 4.42 (bs, 1H), 4.32 (s, 2H), 3.99 (m, 3H), 3.65-3.51 (m, 4H), 3.28-3.22 (m, 2H), 2.80 (m, 2H), 2.65 (m, 2H), 2.40 (s, 3H), 2.36 (t, 1H), 2.02 (d, 2H), 1.54 (m, 2H); MS m/z (APCI-pos) M+1=523.

N-((3S,4R)-4-(3,4-difluorophenyl)-1-methylpyrrolidin-3-yl)-2-(tetrahydro-2H-pyran-4-ylamino)-5,6-dihydropyrido[3,4-d]pyrimidine-7(8H)-carboxamide (I-126) was prepared in accord with the procedures in examples 68 and 69 except in step 6 of example 68, 72 was replaced with 28 and in step 1 of example 68, 3-fluoro-4-(trifluoromethyl)benzaldehyde was replaced with 3,4-difluoro-benzaldehyde to afford I-124: ¹H NMR (400 MHz, CDCl₃) δ 8.07 (s, 1H), 7.16-7.02 (m, 3H), 4.89 (m, 2H), 4.37 (m, 1H), 4.32 (s, 2H), 3.99 (m, 3H), 3.64-3.50 (m, 4H), 3.25 (m, 1H), 3.15 (m, 1H), 2.78 (m, 2H), 2.65 (m, 2H), 2.38 (s, 3H), 2.31 (t, 1H), 2.02 (d, 2H), 1.52 (m, 2H); MS m/z (APCI-pos) M+1=473.

N-((3S,4R)-4-(3-fluorophenyl)-1-methylpyrrolidin-3-yl)-2-(tetrahydro-2H-pyran-4-ylamino)-5,6-dihydropyrido[3,4-d]pyrimidine-7(8H)-carboxamide (I-127) was prepared in accord with the procedures in examples 68 and 69 except in step 6 of example 68, 72 was replaced with 28 and in step 1 of example 68, 3-fluoro-4-(trifluoromethyl)benzaldehyde was replaced with 3-fluoro-benzaldehyde to afford I-127: $^1$H NMR (400 MHz, CDCl$_3$) δ 8.06 (s, 1H), 7.25 (m, 1H), 7.09-6.88 (m, 3H), 5.02-4.93 (m, 2H), 4.23 (m, 1H), 4.32 (s, 2H), 3.98 (m, 3H), 3.64-3.50 (m, 4H), 3.30-3.18 (m, 2H), 2.78 (m, 2H), 2.65 (m, 2H), 2.38 (s, 3H), 2.32 (t, 1H), 2.00 (d, 2H), 1.54 (m, 2H); MS m/z (APCI-pos) M+1=455.

N—((S)-1,1,1-trifluoropropan-2-yl)-5,6,7,8-tetrahydropyrido[3,4-d]pyrimidin-2-amine ((S)-300) and N—((R)-1,1-trifluoropropan-2-yl)-5,6,7,8-tetrahydropyrido[3,4-d]pyrimidin-2-amine ((R)-300) were prepared in accord with the procedures in steps 3 to 5 of example 1, except in step 3, tetrahydro-2H-pyran-4-amine was replaced with (S)-1,1,1-trifluoro-2-amino-propane (CASRN 125278-10-6) and with (R)-1,1,1-trifluoro-2-amino-propane (CASRN 779303-24-1) respectively.

N-((3S,4R)-4-(4-chloro-3-fluorophenyl)-1-methylpyrrolidin-3-yl)-2-((S)-1,1,1-trifluoropropan-2-ylamino)-5,6-dihydropyrido[3,4-d]pyrimidine-7(8H)-carboxamide (I-128) was prepared in accord with the procedures in examples 68 and 69 except in step 6 of example 68, 72 was replaced with (S)-300 and in step 1 of example 68, 3-fluoro-4-(trifluoromethyl)benzaldehyde was replaced with 4-chloro-3-fluorobenzaldehyde to afford I-128: $^1$H NMR (400 MHz, CDCl$_3$) δ 8.10 (s, 1H), 7.30 (t, 1H), 7.11 (d, 1H), 7.04 (d, 1H), 5.27 (d, 1H), 5.01 (d, 1H), 4.92 (m, 1H), 4.38 (m, 1H), 4.33 (s, 2H), 3.63 (t, 2H), 3.25 (t, 1H), 3.17 (m, 1H), 2.78 (m, 2H), 2.65 (m, 2H), 2.38 (s, 3H), 2.32 (t, 1H), 1.38 (d, 3H); MS m/z (APCI-pos) M+1=501.

N-((3S,4R)-4-(4-chloro-3-fluorophenyl)-1-methylpyrrolidin-3-yl)-2-((R)-1,1,1-trifluoropropan-2-ylamino)-5,6-dihydropyrido[3,4-d]pyrimidine-7(8H)-carboxamide (I-129) was prepared in accord with the procedures in examples 68 and 69 except in step 6 of example 68, 72 was replaced with (R)-300 and in step 1 of example 68, 3-fluoro-4-(trifluoromethyl)benzaldehyde was replaced with 4-chloro-3-fluoro-benzaldehyde to afford I-129: $^1$H NMR (400 MHz, CDCl$_3$) δ 8.10 (s, 1H), 7.30 (t, 1H), 7.11 (d, 1H), 7.04 (d, 1H), 5.08 (d, 1H), 4.95 (d, 1H), 4.92 (m, 1H), 4.38 (m, 1H), 4.34 (s, 2H), 3.63 (m, 2H), 3.25 (t, 1H), 3.17 (m, 1H), 2.78 (m, 2H), 2.67 (t, 2H), 2.38 (s, 3H), 2.32 (t, 1H), 1.38 (d, 3H); MS m/z (APCI-pos) M+1=501.

Example 70

(S)-(2-phenylpyrrolidin-1-yl)(2-(tetrahydro-2H-pyran-4-ylamino)-5,6-dihydropyrido[3,4-d]pyrimidin-7(8H)-yl)methanone (I-130)

To a solution of triphosgene (0.0127 g, 0.0427 mmol) and THF and cooled to 0° C. was added DIPEA (0.0446 mL, 0.256 mmol) and the reaction was stirred for 5 min at 0° C. To the solution was added a slurry of 28 (0.020 g, 0.0854 mmol) and DIPEA (0.0446 mL, 0.256 mmol) in THF and the reaction stirred at 0° C. for 20 min. (S)-2-phenylpyrrolidine hydrochloride (0.0157 g, 0.0854 mmol, CASRN 56523-58-1) was added and the reaction was stirred at RT for 24 h. The solution was partitioned between EtOAc and 0.1N HCl and the aqueous layer was extracted with EtOAc. The combined extracts were washed sequentially with water (twice), brine, dried (Na$_2$SO$_4$), filtered and concentrated to an oil. The crude product was purified by SiO$_2$ chromatography to afford 0.014 g (41%) of (I-130) as a solid: MS m/z (APCI-pos) M+1=408.2.

(R)-(2-phenylpyrrolidin-1-yl)(2-(tetrahydro-2H-pyran-4-ylamino)-5,6-dihydropyrido[3,4-d]pyrimidin-7(8H)-yl) methanone (I-131) was prepared analogously except (S)-2-phenylpyrrolidine hydrochloride was replaced with (R)-2-phenylpyrrolidine hydrochloride (CASRN 56523-48-9): MS m/z (APCI-pos) M+1=408.2.

(2-(4-chlorophenyl)pyrrolidin-1-yl)(2-(tetrahydro-2H-pyran-4-ylamino)-5,6-dihydropyrido[3,4-d]pyrimidin-7(8H)-yl)methanone (I-132) was prepared analogously except (S)-2-phenylpyrrolidine hydrochloride was replaced with 2-(4-chlorophenyl)pyrrolidine (CASRN 38944-14-3): MS m/z (APCI-pos) M+1=442.2, 444.2.

(2-(3-chlorophenyl)pyrrolidin-1-yl)(2-(tetrahydro-2H-pyran-4-ylamino)-5,6-dihydropyrido[3,4-d]pyrimidin-7(8H)-yl)methanone (I-132) was prepared analogously except (S)-2-phenylpyrrolidine hydrochloride was replaced with 2-(3-chlorophenyl)pyrrolidine (CASRN 298690-74-1): MS m/z (APCI-pos) M+1=442.2, 444.2.

(2-(4-fluorophenyl)pyrrolidin-1-yl)(2-(tetrahydro-2H-pyran-4-ylamino)-5,6-dihydropyrido[3,4-d]pyrimidin-7(8H)-yl)methanone (I-134) was prepared analogously except (S)-2-phenylpyrrolidine hydrochloride was replaced with 2-(4-fluorophenyl)pyrrolidine (CASRN 72215-06-9): MS m/z (APCI-pos) M+1=426.2.

(2-phenylazetidin-1-yl)(2-(tetrahydro-2H-pyran-4-ylamino)-5,6-dihydropyrido[3,4-d]pyrimidin-7(8H)-yl) methanone (I-135) was prepared analogously except (S)-2-phenylpyrrolidine hydrochloride was replaced with 2-phenylazetidine (CASRN 473443-15-1): MS m/z (APCI-pos) M+1=394.2.

(R)-(2-(2,5-difluorophenyl)pyrrolidin-1-yl)(2-(tetrahydro-2H-pyran-4-ylamino)-5,6-dihydropyrido[3,4-d]pyrimidin-7(8H)-yl)methanone (I-136) was prepared analogously except (S)-2-phenylpyrrolidine hydrochloride was replaced with (R)-2-(2,5-difluorophenyl)pyrrolidine (CASRN 1218935-60-4): MS m/z (APCI-pos) M+1=444.2.

(2-benzylpyrrolidin-1-yl)(2-(tetrahydro-2H-pyran-4-ylamino)-5,6-dihydropyrido[3,4-d]pyrimidin-7(8H)-yl) methanone (I-137) was prepared analogously except (S)-2-phenylpyrrolidine hydrochloride was replaced with 2-benzyl-pyrrolidine (CASRN 3584091-6): MS m/z (APCI-pos) M+1=422.2.

(2-(pyridin-3-yl)pyrrolidin-1-yl)(2-(tetrahydro-2H-pyran-4-ylamino)-5,6-dihydropyrido[3,4-d]pyrimidin-7(8H)-yl)methanone (I-138) was prepared analogously except (S)-2-phenylpyrrolidine hydrochloride was replaced with 2-(3-pyridin-2-yl)pyrrolidine (CASRN 67209-89-6): MS m/z (APCI-pos) M+1=422.2.

(2-(tetrahydro-2H-pyran-4-ylamino)-5,6-dihydropyrido[3,4-d]pyrimidin-7(8H)-yl)(2-(thiazol-2-yl)pyrrolidin-1-yl) methanone (I-139) was prepared analogously except (S)-2-phenylpyrrolidine hydrochloride was replaced with 2-(thiazol-2-yl)pyrrolidine (CASRN 524674-17-7): MS m/z (APCI-pos) M+1=415.0.

(2-Phenyl-piperidin-1-yl)-[2-(tetrahydro-pyran-4-ylamino)-5,8-dihydro-6H-pyrido[3,4-d]pyrimidin-7-yl]-methanone (I-140) was prepared analogously except (S)-2-phenylpyrrolidine hydrochloride was replaced with 2-phenyl-piperidine (CASRN 3466-80-6): MS m/z (APCI-pos) M+1=422.3.

(2-Phenylpiperazin-1-yl)(2-(tetrahydro-2H-pyran-4-ylamino)-5,6-dihydropyrido[3,4-d]pyrimidin-7(8H)-yl) methanone (I-141) was prepared analogously except (S)-2-phenylpyrrolidine hydrochloride was replaced with tert-butyl 3-phenylpiperazine-1-carboxylate (CASRN 502649-25-4). tert-Butyl 3-phenyl-4-(2-(tetrahydro-2H-pyran-4-ylamino)-5,6,7,8-tetrahydropyrido[3,4-d]pyrimidine-7-carbonyl)piperazine-1-carboxylate (0.0446 g, 0.0853 mmol) was dissolved in 3:1 DCM/TFA at 0° C. and then stirred for 45 minutes at room temperature. The solution was concentrated, 0.1 mL of 7N NH₃/MeOH was added and the solution was concentrated. DCM was added and the solids were removed by filtration. The mother liquor was concentrated to provide (2-phenylpiperazin-1-yl)(2-(tetrahydro-2H-pyran-4-ylamino)-5,6-dihydropyrido[3,4-d]pyrimidin-7(8H)-yl)methanone:MS m/z (APCI-pos) M+1=423.4.

(3-phenylmorpholino)(2-(tetrahydro-2H-pyran-4-ylamino)-5,6-dihydropyrido[3,4-d]pyrimidin-7(8H)-yl)methanone (I-142) was prepared analogously except (S)-2-phenylpyrrolidine hydrochloride was replaced with 2-phenyl-morpholine (CASRN 138713-44-7): MS m/z (APCI-pos) M+1=424.3.

(2-Phenylpiperazin-1-yl)(2-(tetrahydro-2H-pyran-4-ylamino)-5,6-dihydropyrido[3,4-d]pyrimidin-7(8H)-yl)methanone (I-143)

Step 1:
To a solution of (R)-tert-butyl 2-(2-oxoethyl)pyrrolidine-1-carboxylate (A. Furstner and J. W. L. Kennedy, Chem.— Eur. J. 2006 12(28):7398-7410) in THF cooled to −78° C. was added (3-chloro-4-fluorophenyl)magnesium bromide (0.720 mL, 0.360 mmol) and the reaction was warmed to RT for 1 h. The reaction was quenched with water and extracted with EtOAc. The organic layer was washed with water and brine, dried (Na₂SO₄), filtered and concentrated to afford an oil which was purified by SiO₂ chromatography to afford 0.0745 g (72%) of (2R)-tert-butyl 2-(2-(3-chloro-4-fluorophenyl)-2-hydroxyethyl)pyrrolidine-1-carboxylate (301) as a clear oil.

Step 2:
To a solution of 301 (0.0754 g, 0.219 mmol), isoindoline-1,3-dione (0.0387 g, 0.263 mmol) and PPh₃ (0.127 g, 0.482 mmol) in THF cooled to 0° C. was added DEAD (0.0760 mL, 0.482 mmol) and the reaction warmed to RT and stirred overnight. The reaction was quenched with water and extracted with EtOAc. The organic layer was washed with water and brine, dried (Na₂SO₄) filtered and concentrated to an oil. The crude oil was purified by SiO₂ chromatography to afford 0.0507 g (49%) of (2R)-tert-butyl 2-(2-(3-chloro-4-fluorophenyl)-2-(1,3-dioxoisoindolin-2-yl)ethyl)pyrrolidine-1-carboxylate (303) as a clear oil.

Step 3:
To a solution of 303 (0.0507 g, 0.1072 mmol) and THF/MeOH (1:1) was added hydrazine monohydrate (0.080 mL, 1.072 mmol) and the reaction stirred at RT 3 d. A thick white precipitate formed which was filtered through CELITE. The solution was concentrated and purified by SiO₂ chromatography to afford 0.0214 g (58%) of (2R)-tert-butyl 2-(2-amino-2-(3-chloro-4-fluorophenyl)ethyl)pyrrolidine-1-carboxylate (305) as a clear oil.

Step 4:
(2R)-tert-Butyl 2-(2-(3-chloro-4-fluorophenyl)-2-(2-(tetrahydro-2H-pyran-4-ylamino)-5,6,7,8-tetrahydropyrido[3,4-d]pyrimidine-7-carboxamido)ethyl)pyrrolidine-1-carboxylate (309) was prepared as described in example 70 except (S)-2-phenylpyrrolidine hydrochloride was replaced with 305 and crude product used without purification.

Step 5:
A solution of 309 and DCM/TFA (3:1) at 0° C. was stirred for 45 min at RT. The solution was concentrated, 0.1 mL of 7N NH₃/MeOH was added and the solution was re-concentrated. DCM was added and the solids were removed by filtration. The mother liquor was concentrated to afford 0.0193 g (62% for two steps) of I-143 as a clear oil: MS m/z (APCI-pos) M+1=503.4, 505.4.

Example 71

N—((R)-(4-chloro-3-fluorophenyl)((R)-morpholin-2-yl)methyl)-2-(tetrahydro-2H-pyran-4-ylamino)-5,6-dihydropyrido[3,4-d]pyrimidine-7(8H)-carboxamide and N—((S)-(4-chloro-3-fluorophenyl)((S)-morpholin-2-yl)methyl)-2-(tetrahydro-2H-pyran-4-ylamino)-5,6-dihydropyrido[3,4-d]pyrimidine-7(8H)-carboxamide mixture (I-144)

Step 1:
To a solution of NMM (300 µL) in DCM (10 mL) cooled in ice/salt was added ethyl chloroformate (0.5210 mL, 5.449 mmol). To this solution was added slowly 4-(tert-butoxycarbonyl)morpholine-2-carboxylic acid (0.63 g, 2.724 mmol). The reaction mixture was stirred with cooling for 20 min then NMM (600 µL) was added followed by slow addition of N-methylmethoxylamine hydrochloride (0.5315 g, 5.449 mmol) to the cooled stirred solution. The mixture was warmed to RT and stirred overnight then diluted with DCM and washed with water. The DCM was dried (MgSO₄), filtered, and evaporated to yield 1.1 g impure tert-butyl 2-(methoxy(methyl)carbamoyl)morpholine-4-carboxylate (302) as a colorless oil which was used without additional purification.

Step 2:
To crude 302 (1.1 g, 4.0 mmol) in THF (10 mL) cooled to −78° C. was added slowly a 0.5 M THF solution of (4-chloro-3-fluorophenyl)magnesium bromide (8.0 mL, 4.0 mmol). The mixture was slowly warmed to RT. After 1 h the reaction mixture was diluted with water and extracted with EtOAc. The EtOAc was washed with brine, dried (MgSO₄), filtered, and evaporated to yield 1.15 g of a yellow oil. The crude product was purified by SiO₂ chromatography (Biotage 50 g SNAP column) eluting with hexane/EtOAc (4:1) to afford 0.70 g (51%) of tert-butyl 2-(4-chloro-3-fluorobenzoyl)morpholine-4-carboxylate (304) as a colorless oil containing minor impurities.

Step 3:
To a solution of 304 (0.70 g, 2.0 mmol) in MeOH (20 mL) cooled in ice, was added NaBH₄ (0.077 g, 2.0 mmol) and the solution stirred at 0° C. After 20 min, the reaction mixture was diluted with H₂O and extracted with DCM. The DCM was washed with brine, dried (MgSO₄), filtered, and evaporated to yield 0.68 g of a colorless oil. The crude product was purified by SiO₂ chromatography (50 g Biotage SNAP column) eluting with hexane/EtOAc (2:1). Fractions 30-36 contained 0.10 g (14.3%) of a white solid tentatively assigned as a mixture of (R)-tert-butyl 2-((S)-(4-chloro-3-fluorophenyl)(hydroxy)methyl)morpholine-4-carboxylate and (S)-tert-butyl 2-((R)-(4-chloro-3-fluorophenyl)(hydroxy)methyl)morpholine-4-carboxylate (306a). Fractions 42-50 contained 0.23 g (32.9%) of a colorless oil tentatively assigned as a mixture of (S)-tert-butyl 2-((S)-(4-chloro-3-fluorophenyl)(hydroxy)methyl)morpholine-4-carboxylate and (R)-tert-butyl 2-((R)-(4-chloro-3-fluorophenyl)(hydroxy)methyl)morpholine-4-carboxylate (306b).

Step 4:
To a solution of 306b (0.10 g, 0.2892 mmol) in THF (5 mL) cooled in ice was added phthalimide (0.04680 g, 0.3181 mmol) and PS-triphenylphosphine (0.22 g, 0.4338 mmol, 1.99 mmol/g) followed by dropwise addition of DEAD (68.31 µL, 0.4338 mmol) at 0° C. After 5 h the reaction mixture was diluted with EtOAc, filtered, washed sequentially with water and brine, dried (MgSO₄), filtered, and evaporated to afford 0.19 g (138.3%) an impure mixture of (R)-tert-butyl 2-((R)-(4-chloro-3-fluorophenyl)(1,3-dioxoisoindolin-2-yl)methyl)morpholine-4-carboxylate and (S)- tert-butyl 2-((S)-(4-chloro-3-fluorophenyl)(1,3-dioxoisoindolin-2-yl)methyl)morpholine-4-carboxylate (308b) as a colorless oil that solidified.

Step 5:

To a mixture of 308b in THF/MeOH (5 mL, 1:1) was added hydrazine monohydrate (0.1399 mL, 2.885 mmol). The mixture was stirred at RT for 2.5 d. The reaction mixture was filtered and the residue washed with some THF. The filtrate was evaporated to yield 0.15 g of a pale yellow semi-solid which was triturated with EtOAc and filtered. The filtrate was concentrated and purified by $SiO_2$ chromatography (10 g Biotage SNAP column) eluting with DCM/MeOH (10:1). Fractions 5-8 contained 0.10 g impure product which was dissolved in EtOAc and washed sequentially with 2 portions water, brine then dried ($MgSO_4$), filtered and evaporated to afford 82 mg (82.44%) of a mixture of (R)-tert-butyl 2-((R)-amino(4-chloro-3-fluorophenyl)methyl)morpholine-4-carboxylate and (S)-tert-butyl 2-((S)-amino(4-chloro-3-fluorophenyl)methyl)morpholine-4-carboxylate (310b) as a colorless film contaminated with DEAD byproduct.

Step 6:

To a mixture of 310b (0.082 g, 0.238 mmol) in DCM (3 mL) cooled in ice, was added TEA (99.4 µL, 0.713 mmol) and CDI (0.0386 g, 0.238 mmol). The mixture was stirred 20 min, then a solution of 28 (0.0557 g, 0.238 mmol) in DCM (3 mL) was added and mixture stirred overnight at RT. The reaction mixture was partitioned between water and DCM. The DCM was washed with brine, dried ($MgSO_4$), filtered, and evaporated to yield 0.13 g of a colorless film. The crude product was purified by $SiO_2$ chromatography (10 g Biotage SNAP column) eluting with DCM/MeOH (10:1). Fractions 3-6 contained 0.084 g (58.4%) of a mixture of (R)-tert-butyl 2-((R)-(4-chloro-3-fluorophenyl)(2-(tetrahydro-2H-pyran-4-ylamino)-5,6,7,8-tetrahydropyrido[3,4-d]pyrimidine-7-carboxamido)methyl)morpholine-4-carboxylate and (S)-tert-butyl 2-((S)-(4-chloro-3-fluorophenyl)(2-(tetrahydro-2H-pyran-4-ylamino)-5,6,7,8-tetrahydropyrido[3,4-d]pyrimidine-7-carboxamido)methyl)morpholine-4-carboxylate (312b) as a yellow oil.

Step 7:

To a mixture of 312b (0.084 g, 0.139 mmol) in DCM (2 mL) was added TFA (0.30 mL, 0.389 mmol). The mixture was stirred at RT for 30 min. The reaction mixture was evaporated and the residue treated with satd. aq. $NaHCO_3$ and extracted with DCM. The aqueous layer was extracted with another portion of DCM. The combined DCM extracts were dried ($MgSO_4$), filtered, and evaporated to afford 76 mg pale yellow solid. The crude product was purified by $SiO_2$ chromatography (10 g Biotage SNAP column) eluting with DCM/MeOH/$NH_4OH$ (90/10/1). Fractions 7-10 contained a mixture of 0.281 g (40.1%) of I-144 as a yellow film. $^1H$ NMR (400 MHz, $CD_3OD$) δ 8.06 (s, 1H), 7.45-7.36 (m, 1H), 7.31-7.26 (m, 1H), 7.18-7.15 (m, 1H), 4.79-4.76 (m, 1H), 4.43 (dd, 2H), 4.00-3.87 (m, 5H), 3.78-3.47 (m, 5H), 2.81-2.72 (m, 1H), 2.68-2.63 (m, 2H), 2.60-2.56 (m, 2H), (2.42-2.53 (m, 1H), 1.98-1.92 (m, 2H), 1.61-1.50 (m, 2H); MS m/z 505.3 (LC/MS positive ionization) [M+1].

A mixture of N—((R)-(4-chloro-3-fluorophenyl)((S)-morpholin-2-yl)methyl)-2-(tetrahydro-2H-pyran-4-ylamino)-5,6-dihydropyrido[3,4-d]pyrimidine-7(8H)-carboxamide and N—((S)-(4-chloro-3-fluorophenyl)((R)-morpholin-2-yl)methyl)-2-(tetrahydro-2H-pyran-4-ylamino)-5,6-dihydropyrido[3,4-d]pyrimidine-7(8H)-carboxamide mixture was prepared analogously from 306a to afford the title compound 0.0683 g (51.2%) as a yellow film: $^1H$ NMR (400 MHz, $CD_3OD$) δ 8.05 (s, 1H), 7.39-7.35 (m, 1H), 7.28-7.25 (m, 1H), 7.17-7.13 (m, 1H), 4.79-4.77 (d, 1H), 4.45-4.36 (m, 2H), 4.00-3.93 (m, 3H), 3.84-3.79 (m, 1H), 3.76-3.71 (m, 1H), 3.65-3.62 (m, 2H), 3.55-3.47 (m, 3H), 3.01-2.97 (m, 1H), 2.74-2.70 (m, 2H), 2.66-2.62 (m, 2H), 2.47-2.41 (m, 1H), 1.97-1.91 (m, 2H), 1.61-1.50 (m, 2H); MS m/z 505.3 (LC/MS positive ionization) [M+1].

Example 72

N-((3S,4R)-4-(4-chloro-3-fluorophenyl)-1-methylpyrrolidin-3-yl)-2-(4-fluoro-2-methylphenylamino)-5,6-dihydropyrido[3,4-d]pyrimidine-7(8H)-carboxamide (I-145)

Step 1:

A solution of (Z)-benzyl (1H-pyrazol-1-yl)methanediylidenedicarbamate (9.071 g, 23.97 mmol), 4-fluoro-2-methylaniline (2.664 mL, 23.97 mmol), TEA (0.3341 mL, 2.397 mmol) and THF (15 mL) was stirred at 45° C. for 12 h. The reaction mixture was diluted with THF (30 mL) and treated with MeOH (250 mL) with vigorous stirring. The resulting precipitate was filtered and thrice washed with MeOH (50 mL) to afford 8.4 g (80.5%) of (Z)-benzyl (benzyloxycarbonylamino)(4-fluoro-2-methylphenylamino)methylenecarbamate (314) as a white powder.

Step 2:

To a solution of 314 (8.4 g, 19.3 mmol) in THF (160 mL) and MeOH (40 mL) was added 5% Pd/C (6.16 g, 2.89 mmol). The reaction was purged with $N_2$ several times, then filled with $H_2$ and stirred for 24 h. The reaction mixture was then filtered and the filtrate concentrated to afford 1.98 g (69.4%) of 1-(4-fluoro-2-methylphenyl)guanidine (316) as a white solid: MS (APCI-pos) M+1=168.1.

Step 3:

A solution of 316 (1.98 g, 11.8 mmol) and 21 (4.52 g, 17.8 mmol) and n-butanol (24 mL) was heated on 80° C. for 20 h. The reaction mixture was concentrated in vacuo, then dissolved in DCM and purified by $SiO_2$ chromatography eluting with DCM to afford 2.08 g (49.0%) of tert-butyl 2-(4-fluoro-2-methylphenylamino)-5,6-dihydropyrido[3,4-d]pyrimidine-7(8H)-carboxylate (318) as a white solid: MS (APCI-pos) M+1=359.0.

Step 4:

To a solution 318 (2.08 g, 5.80 mmol) in DCM (1 mL) was added a 4M solution of HCl in dioxane (14.5 mL, 58.0 mmol) and stirred for 1 h. The reaction mixture was then concentrated in vacuo to afford 1.8 g (96%) of N-(4-fluoro-2-methylphenyl)-5,6,7,8-tetrahydropyrido[3,4-d]pyrimidin-2-amine hydrochloride (320): MS (APCI-pos) M+1=259.2.

Step 5:

A solution of 320 (86 mg, 0.23 mmol) and TEA (98 µL, 0.70 mmol) in THF (1 mL) was treated with a solution of (3R,4S)-tert-butyl 3-(4-chloro-3-fluorophenyl)-4-isocyanatopyrrolidine-1-carboxylate (80 mg, 0.23 mmol, in toluene (1 mL). The reaction mixture was stirred at RT for 48 h. After concentrating in vacuo, the residue was purified by $SiO_2$ chromatography eluting with a DCM/EtOAc gradient (0 to 50% EtOAc) to afford (3R,4S)-tert-butyl 3-(4-chloro-3-fluorophenyl)-4-(2-(4-fluoro-2-methylphenylamino)-5,6,7,8-tetrahydropyrido[3,4-d]pyrimidine-7-carboxamido)pyrrolidine-1-carboxylate (322).

Step 6:

A solution of 322 (70 mg, 0.117 mmol) in DCM (810 µL) was treated with TFA (90.0 µL, 1.17 mmol) and stirred at RT for 2 h. The reaction mixture was then concentrated in vacuo and diluted with DCM (1 mL) and washed with satd. aq. $NaHCO_3$ (1 mL) then directly purified by $SiO_2$ chromatography and eluting a MeOH/EtOAc gradient (0 to 10% MeOH)

to afford 50 mg (86%) of N-((3S,4R)-4-(4-chloro-3-fluorophenyl)pyrrolidin-3-yl)-2-(4-fluoro-2-methylphenylamino)-5,6-dihydropyrido[3,4-d]pyrimidine-7(8H)-carboxamide (324): MS (APCI-pos) M+1=499.1.

Step 7:

To a solution of 324 (20 mg, 0.0401 mmol) in MeOH (1 mL) was added aqueous formaldehyde (11.9 µL, 0.160 mmol). After stirring for 1 h, a solution of sodium triacetoxyborohydride (42.5 mg, 0.200 mmol) in THF (1 mL) was added dropwise over 15 min. After stirring for 1 h the mixture was diluted with EtOAc (3 mL) then washed with satd. aq. NaHCO₃ (2 mL). The organic layer was concentrated in vacuo, then purified by SiO₂ chromatography eluting with a MeOH/EtOAc gradient (0 to 10% MeOH) to afford 18 mg (83%) of I-145: 1H NMR (CDCl₃) δ 8.17 (s, 1H), 7.76-7.81 (m, 1H), 7.28-7.33 (m, 1H), 7.10-7.14 (m, 1H), 7.03-7.07 (m, 1H), 6.92-6.96 (m, 2H), 6.57 (s, 1H), 4.92 (d, 1H, J=7.83 Hz), 4.35-4.41 (m, 3H), 3.61-3.72 (m, 2H), 3.22-3.28 (m, 1H), 3.12-3.19 (m, 1H), 2.69-2.82 (m, 4H), 2.38 (s, 3H), 2.31-2.35 (m, 1H), 2.29 (s, 3H); MS (APCI-pos) M+1=513.2.

Example 73

2-(4-fluoro-2-methylphenylamino)-N-((3S,4R)-4-(3-fluorophenyl)-1-methylpyrrolidin-3-yl)-5,6-dihydropyrido[3,4-d]pyrimidine-7(8H)-carboxamide (I-146)

The title compound was prepared in accord with the procedure in example 72 except N-(3S,4R)-1-benzyl-4-(3-fluorophenyl)pyrrolidine-3-carboxylic acid was used in place of the N-boc analogue in example 72. Debenzylation of the pyrrolidine was carried out in accord with the procedures in step 7 of example 68 and N-methylation of the pyrrolidine was carried out in accord with the procedure in example 69. The crude product was purified by SiO₂ chromatography eluting with a MeOH/DCM gradient (3 to 5% MeOH to afford 0.048 g (66.6%) of I-146 of as clear glassy solid: ¹H NMR (CDCl₃) δ 8.16 (s, 1H), 7.74-7.79 (m, 1H), 7.22-7.28 (m, 1H), 7.06-7.09 (m, 1H), 6.98-7.03 (m, 1H), 6.87-6.95 (m, 3H), 6.67 (s, 1H), 5.01 (d, 1H, J=7.8 Hz), 4.40-4.46 (m, 1H), 4.38 (s, 2H), 3.60-3.71 (m, 2H), 3.25-3.31 (m, 1H), 3.15-3.22 (m, 1H), 2.75-2.83 (m, 2H), 2.67-2.72 (m, 2H), 2.38 (s, 3H), 2.30-2.35 (m, 1H), 2.28 (s, 3H); MS (APCI-pos) M+1=479.2.

Example 74

N—((R)-1-(3,4-dichlorophenyl)ethyl)-7-((S)-1-hydroxypropan-2-ylamino)-3,4-dihydro-2,6-naphthyridine-2(1H)-carboxamide (I-149)

Step 1:

A vial was charged with tert-butyl 7-chloro-3,4-dihydro-2,6-naphthyridine-2(1H)-carboxylate (175 mg, 0.651 mmol, CASRN 1060816-50-3), Pd₂(dba)₃ (29.8 mg, 0.0326 mmol), Binap-rac (40.5 mg, 0.0651 mmol), (S)-2-aminopropan-1-ol (97.8 mg, 1.30 mmol), and NaO-tert-Bu (125 mg, 1.30 mmol) and toluene (3 mL), sealed, degassed with nitrogen for 5 min then heated to 90° C. for 4 h. The reaction was cooled and filtered through a plug of CELITE. The filtrate was concentrated and the resulting residue was purified by reverse phase chromatography (SP4) eluting with a MeCN/H₂O gradient (5-95% ACN) to afford 56 mg (28%) of (S)-tert-butyl 7-(1-hydroxypropan-2-ylamino)-3,4-dihydro-2,6-naphthyridine-2(1H)-carboxylate (326).

Step 2:

A solution of 326 (56 mg, 0.18 mmol) and TFA (2 mL) and was stirred at RT for 45 min. The reaction was concentrated to provide crude (S)-2-(5,6,7,8-tetrahydro-2,6-naphthyridin-3-ylamino)propan-1-ol 2,2,2-trifluoroacetate (328) which was used in the nest step without further purification.

Step 3:

N—((R)-1-(3,4-dichlorophenyl)ethyl)-7-((S)-1-hydroxypropan-2-ylamino)-3,4-dihydro-2,6-naphthyridine-2(1H)-carboxamide was prepared from 328 in accord with the procedure in step 6 of example 1 except (R)-1-(3,4-dichlorophenyl)ethanamine was used in place of 22 to afford 32 mg (41%) of I-149: ¹H NMR (400 MHz, CDCl₃) δ 7.85 (s, 1H), 7.40 (m, 2H), 7.17 (m, 1H), 6.23 (s, 1H), 4.98 (m, 1H), 4.62 (m, 1H), 4.45 (s, 2H), 4.40 (bs, 1H), 3.94 (m, 1H), 3.73 (dd, 1H), 3.55 (m, 3H), 2.75 (m, 2H), 1.48 (d, 3H), 1.23 (d, 3H); m/z (APCI-pos) M+1=423.3.

Example 75

(R)—N—((S)-1-(4-chloro-3-fluorophenyl)-2-hydroxyethyl)-2-(tetrahydro-2H-pyran-4-ylamino)-6,7-dihydro-5H-pyrano[2,3-d]pyrimidine-7-carboxamide (I-150) (SCHEME E)

(S)-ethyl 2-hydroxy-4-iodobutanoate

To a solution of (S)-3-hydroxydihydrofuran-2(3H)-one (10 g, 98.0 mmol), EtOH (4.51 g, 98.0 mmol) and DCM (70 mL) cooled to 0° C. under N₂ was added TMS-I (19.6 g, 98.0 mmol) over 20 min via addition funnel. The reaction was stirred for 1 h at 0° C. then warmed to RT for 3 h. The mixture was partitioned between H₂O (100 mL) and DCM. The organic extract was washed sequentially with NaHCO₃, 1% NaHSO₃ and brine, dried (Na₂SO₄), filtered and concentrated. The crude product was purified by SiO₂ chromatography (SNAP 50) eluting first hexane/EtOAc (1:1) then EtOAc (100%) to afford 18.3 g (65%) of (S)-ethyl 2-hydroxy-4-iodobutanoate (392) as a light yellow oil.

(S)-ethyl 4-iodo-2-(triethylsilyloxy)butanoate

To a solution of 392 (15.5 g, 60.1 mmol), 2,6-lutidine (21.0 ml, 180 mmol) and DCM (125 mL) cooled to 0° C. and maintained under N₂ was added dropwise triethylsilyl trifluoromethanesulfonate (17.5 g, 66.1 mmol). The reaction was stirred at 0° C. for 1 h then warmed to RT and stirred for 18 h. The reaction was quenched by adding satd. aq. NH₄Cl and extracted with DCM. The organic extract was washed organic with brine, dried (Na₂SO₄), filtered and concentrated. The crude product was purified by SiO₂ chromatography (SNAP 100) eluting with EtOAc/hexane (9:1) to afford 18.9 g (76%) of (S)-ethyl 4-iodo-2-(triethylsilyloxy)butanoate (396) as a yellow oil.

Step 1:

A solution of dimethyl malonate (6.155 ml, 53.72 mmol), (S)-ethyl 4-iodo-2-(triethylsilyloxy)butanoate (10.00 g, 26.86 mmol) and THF (100 mL), dimethyl malonate, (S)-ethyl 4-iodo-2-(triethylsilyloxy)butanoate (10.00 g, 26.86 mmol) was cooled to −78° C. and maintained under N₂. To the solution was added sodium hydride (2.149 g, 53.72 mmol, 60% dispersion in mineral oil) portion wise over 5 min and the resulting mixture stirred at −78° C. for 3 h. The reaction was warmed to RT and stirred for 48 h. The reaction was quenched by adding H₂O and extracted with EtOAc. The organic extract was dried (Na₂SO₄), filtered and concentrated in vacuo. The crude product was purified by SiO₂ chromatography eluting with EtOAc/hexane (4:1) to afford 4.2 g, (41%) of (S)-4-ethyl 1,1-dimethyl 4-(triethylsilyloxy)butane-1,1,4-tricarboxylate (398).

Step 2:

A solution of 398 (3.75 g, 9.46 mmol), 24 (1.63 g, 11.4 mmol), EtOH (30 mL) and NaOEt (3.86 g, 11.4 mmol) was heated to 85° C. and stirred overnight. The reaction was cooled to RT and quenched reaction by addition of 4N HCl in dioxane (2.37 mL, 9.46 mmol) and the solution concentrated. The crude product was purified by reverse phase chromatography (Biotage 40 M C18 using a C18 samplet loaded using water) eluting with a MeCH/$H_2O$ chromatography (0-60% MeCN) over 30 column volumes to afford 1.25 g (37%) of (S)-ethyl-4-(4,6-dihydroxy-2-(tetrahydro-2H-pyran-4-ylamino) pyrimidin-5-yl)-2-hydroxybutanoate (400): MS m/z (APCI-pos) M+1=342.1.

Step 3:

A flask was charged with $PPh_3$ (0.807 g, 3.08 mmol), anhydrous THF (20 mL) and DEAD (0.655 g, 3.08 mmol). The solution was stirred for 10 min under $N_2$ then a solution of 400, THF (5 mL) and DMF (5 mL) was added and solution stirred 18 h. The solution was concentrated in vacuo to afford an orange oil. The crude product was purified by reverse phase chromatography (SP4 biotage 40M C18 using a C18 Biotage 40 samplet) and eluted with a MeCN/$H_2O$ gradient (0-60% MeCN) to afford a light yellow oil which solidified under high vacuum. The crude product was re-purified by $SiO_2$ chromatography (SNAP 25) eluting with DCM/MeOH (95:5) to afford 0.42 g (60%) of Obtained (R)-ethyl 4-hydroxy-2-(tetrahydro-2H-pyran-4-ylamino)-6,7-dihydro-5H-pyrano[2,3-d]pyrimidine-7-carboxylate (402) as a clear oil: m/z (APCI-pos) M+1=324.0

Step 4:

A solution of 402 (0.500 g, 1.55 mmol) and $POCl_3$ (2.83 mL, 30.9 mmol) was heated to 100° C. for 3 h then concentrated under highvac to remove excess $POCl_3$. Water was added and the resulting mixture sonicated for 2 min. The mixture was extracted with DCM, dried ($Na_2SO_4$), filtered and concentrated to 0.52 g (78%) of (R)-ethyl 4-chloro-2-(tetrahydro-2H-pyran-4-ylamino)-6,7-dihydro-5H-pyrano [2,3-d]pyrimidine-7-carboxylate (404): MS m/z (APCI-pos) M+1=342.0.

Step 5:

A solution of 404 (0.525 g, 1.23 mmol) and EtOAc (15 mL) was subjected to vacuum/nitrogen purge cycles then Pd/C (0.392 g, 0.369 mmol, 10% Degussa) was added and the solution stirred for 2 h under $H_2$ ($H_2$ balloon). The mixture was filtered and the solid washed with EtOAc and the filterate passed through a 0.45 micron frit and then concentrated. The crude product was purified by $SiO_2$ chromatography eluting with MeOH/DCM (5:95) to afford 0.32 g (77%) of (R)-ethyl 2-(tetrahydro-2H-pyran-4-ylamino)-6,7-dihydro-5H-pyrano [2,3-d]pyrimidine-7-carboxylate (406) as a clear oil: MS m/z (APCI-pos) M+1=308.1.

Step 6:

A solution of 406 (0.310 g, 1.01 mmol), THF (5 mL), LiOH.$H_2O$ (0.0508 g, 1.21 mmol) and water (1 mL) was stirred for 3 h. To the solution was added 4N HCl in dioxane (0.303 mL, 1.21 mmol) and concentrated to afford 0.31 g (95%) of (R)-2-(tetrahydro-2H-pyran-4-ylamino)-6,7-dihydro-5H-pyrano[2,3-d]pyrimidine-7-carboxylic acid (408) which was used without further purification: MS m/z (APCI-pos) M+1=280.1.

Step 7:

A vial was charged 408 (0.050 g, 0.15 mmol), HATU (0.069 g, 0.18 mmol), 68 (0.055 g, 0.18 mmol), DIPEA (1 mL), DCM (2 mL) and DMF (1 mL) and stirred for 18 h. To the solution was added satd. aq. $Na_2CO_3$ (5 mL), and the mixture stirred for 5 min. The organic phase was washed with brine, dried ($Na_2SO_4$), filtered and concentrated in vacuo.

The crude product was purified by $SiO_2$ chromatography (SNAP 25) eluting with DCM/MeOH (95:5) to afford 0.041 g (43%) of (R)—N—((S)-2-(tert-butyldimethylsilyloxy)-1-(4-chloro-3-fluorophenyl)ethyl)-2-(tetrahydro-2H-pyran-4-ylamino)-6,7-dihydro-5H-pyrano[2,3-d]pyrimidine-7-carboxamide (410): MS m/z (APCI-pos) M+1=565.0.

Step 8:

A solution of 410 (0.041 g, 0.071 mmol), DCM/MeOH (4:1, 3 mL) and 4N HCl in dioxane (1 mL) was stirred for 10 min. The reaction was quenched by addition of satd. aq. $Na_2CO_3$ (5 mL) and the solution stirred for 5 min. The organic phase was dried ($Na_2SO_4$), filtered and concentrated in vacuo. The crude product was purified by reverse phase chromatography (SP4 C18 loading with a Biotage 12M samplet) and eluted with a MeCH/$H_2O$ gradient (0-60% MeCN) over 30 column volumes to afford 0.017 g (52%) of I-150: $^1H$ NMR (400 MHz, $CDCl_3$) δ 7.96 (s, 1H), 7.54 (d, 1H), 7.35 (t, 1H), 7.17 (m, 1H), 7.09 (m, 1H), 5.14 (d, 1H), 5.07 (m, 1H), 4.71 (m, 1H), 3.96 (m, 3H), 3.88 (m, 2H), 3.53 (m, 2H), 2.67 (m, 2H), 2.46 (m, 1H), 2.01 (m, 3H), 1.51 (m, 2H). $^{19}F$ NMR (400 MHz, $CDCl_3$) δ –114.8 (m); MS m/z (APCI-pos) M+1=451.0.

Example 76

2-(tetrahydro-pyran-4-ylamino)-5,8-dihydro-6H-pyrido[3,4-d]pyrimidine-7-carboxylic acid [4-(4-chloro-3-fluoro-phenoxy)-1-methyl-pyrrolidin-3-yl]-amide (I-151) (SCHEME F)

Step 1:

To a solution of tert-butyl 2H-pyrrole-1(5H)-carboxylate (25.0 g, 0.148 mol, CASRN 73286-70-1) and DCM (300 mL) was added MCPBA (38.2 g, 0.221 mol). The mixture was stirred at RT for 12 h. The mixture was washed sequentially with $Na_2HSO_3$ (10%, 500 mL) and sat. $NaHCO_3$ (3×200 mL). The organic phases were dried ($Na_2SO_4$), filtered and concentrated in vacuo to afford 25 g (81%) of tert-6-oxa-3-aza-bicyclo[3.1.0]hexane-3-carboxylate (412) as a brown oil.

Step 2:

A mixture of 412 (2.4 g, 13 mmol), 4-chloro-3-fluorophenol (3.8 g, 26 mmol), $Cs_2CO_3$ (10.6 g, 32.5 mmol), 18-crown-6 (20 mg) and EtOH (25 mL) was heated at reflux for 12 h. The solvent was removed in vacuo and the residue partitioned between $H_2O$ (100 mL) and EtOAc (3×100 mL). The combined organic phases were washed with water (3×100 mL), dried ($Na_2SO_4$) and concentrated. The residue was purified by $SiO_2$ chromatography eluting with EtOAc/petroleum ether (1:2) to afford 1.9 g (54%) of trans-(±)-tert-butyl 3-(4-chloro-3-fluorophenoxy)-4-hydroxypyrrolidine-1-carboxylate (414) as a white solid: LC-MS (ESI) m/z 276 (M+H-56).

Step 3:

To a solution of 414 (0.200 g, 0.603 mmol) and EtOAc (20 mL) was added 2-iodoxybenzoic acid (0.675 g, 2.41 mmol) and the resulting solution heated at reflux overnight. The reaction was cooled to RT and the white solid was filtered off and the filtrated was concentrated in vacuo to afford 0.16 g (80%) of tert-butyl 3-(4-chloro-3-fluorophenoxy)-4-oxo-pyrrolidine-1-carboxylate (416): LC-MS (ESI) m/z 274 (M+H-56).

Step 4:

To a solution of 416 (1.6 g, 4.9 mmol) and anhydrous THF (50 mL) cooled to –78° C. was added dropwise L-selectride (1.0 M, 15 mL) and the reaction was stirred at –78° C. for 3 h. The reaction was quenched with $H_2O$ (30 mL). The mixture was extracted with EtOAc (3×100 mL) and the extract was washed with brine (3×30 mL). The organic phases were dried (Na₂SO₄), filtered and concentrated. LC-MS indicated about 9:1 of two isomers. The residue was purified by reverse phase column chromatography using a MeCN/5% aqueous NH₄OH (0 to 35%) to afford 0.56 g (35%) of cis-(±)-tert-butyl 3-(4-chloro-3-fluorophenoxy)-4-hydroxy-pyrrolidine-1-carboxylate (418). LC-MS (ESI) m/z 276 (M+H-56).

Step 5:

To a solution of 418 (0.560 g, 1.69 mmol) and MeOH (10 mL) was added a methanolic HCl solution (4 N, 5 mL). The mixture was stirred at RT for 3 h and the solvent was removed in vacuo. The residue was neutralized with satd. aq. NaHCO₃ (20 mL) and extracted with DCM/IPA (3:1, 3×100 mL) to afford 0.35 g (90%) of cis-(±)-4-(4-chloro-3-fluorophenoxy) pyrrolidin-3-ol (420) as a yellow oil.

Step 6:

To a solution of 420 (0.35 g, 1.52 mmol) and MeOH (5 mL) was added HCHO (37% in water, 0.42 mL, 15.2 mmol). The mixture was stirred at RT for 2 h and then NaCNBH₃ (1.43 g, 22.8 mmol) was added. The reaction was stirred at RT for 3 h. The reaction was quenched with aqueous NH₄OH (50 mL) and the mixture was extracted with EtOAc (3×10 mL). The combined organic phases were washed with water (3×50 mL), dried (Na₂SO₄) and concentrated in vacuo to afford 0.830 g of cis-(±)-4-(4-chloro-3-fluorophenoxy)-1-methylpyrrolidin-3-ol as a brown oil (422) which used for next step without further purification: LC-MS (ESI) m/z 246 (M+H).

Step 7:

To a solution of 422 (0.830 g, 3.38 mmol) and DCM (10 mL) was added TEA (1.2 mL, 8.1 mmol). The solution was cooled to 0° C. and MsCl (0.300 mL, 4.05 mmol) was added dropwise and the mixture was stirred at RT for 3 h. The reaction was diluted with DCM (50 mL) and then quenched with H₂O (50 mL). The mixture was extracted with DCM (3×50 mL) and the extract was washed sequentially with H₂O (3×50 mL) and brine (30 mL). The organic phase were dried and concentrated in vacuo to afford 400 mg of crude cis-(±)-4-(4-chloro-3-fluorophenoxy)-1-methylpyrrolidin-3-yl methanesulfonate (424) which was used for next step without further purification: LC-MS (ESI) m/z 324 (M+H).

Step 8:

To a solution of 424 (400 mg, 1.24 mmol) and DMF (2.0 mL) was added sodium azide (0.806 g, 12.4 mmol). The mixture was heated at 90° C. overnight. The mixture was cooled, diluted with H₂O (30 mL) and extracted with EtOAc (3×50 mL). The combined extracts were washed with water (3×30 mL), dried (Na₂SO₄), filtered and concentrated in vacuo to afford 300 mg of trans-(±)-3-azido-4-(4-chloro-3-fluorophenoxy)-1-methylpyrrolidine (426) which was used for next step without further purification: LC-MS (ESI) m/z 271 (M+H).

Step 9:

To a solution of 426 (0.480 g, 1.77 mmol), PPh₃ (0.930 g, 3.54 mmol) and THF (10 mL) was added H₂O (1.0 mL). The resultant mixture was heated at 55° C. for 3 h. The solvent was removed in vacuo. The residue was purified by SiO₂ chromatography eluting with DCM/MeOH (5:1 DCM/MeOH then 1:1) to afford 85 mg (21% over 5 steps) of trans-(±)-4-(4-chloro-3-fluorophenoxy)-1-methylpyrrolidin-3-amine (428): LC-MS (ESI) m/z 245 (M+H).

Step 10:

To a solution of 428 (0.085 g, 0.347 mmol) and DCM (15 mL) was added TEA (1 mL) and CDI (0.149 g, 0.919 mmol). The mixture was stirred at RT for 1 h and then 28 (0.081 g, 0.35 mmol) was added. The reaction was stirred at RT for 2 h. The solvent was removed in vacuo and the residue was purified by preparative reverse HPLC to afford 31 mg (28%) of I-151 as a white solid: LC-MS (ESI) m/z 505 (M+H).

Example 77

2-((2S,4S)-2-Hydroxymethyl-tetrahydro-pyran-4-ylamino)-5,8-dihydro-6H-pyrido[3,4-d]pyrimidine-7-carboxylic acid [(R)-1-(4-chloro-3-fluoro-phenyl)-ethyl]-amide (I-155)

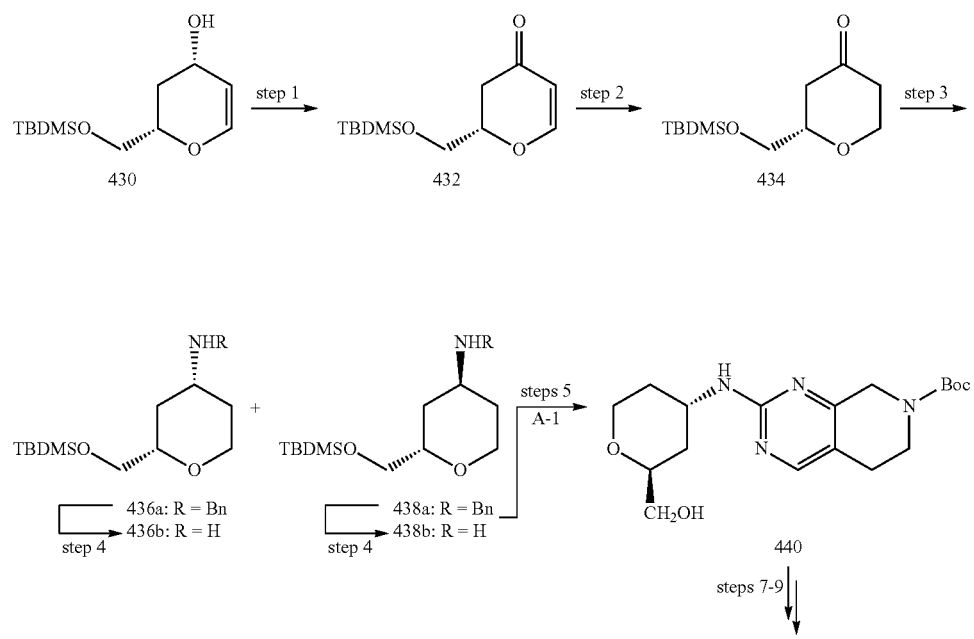

-continued

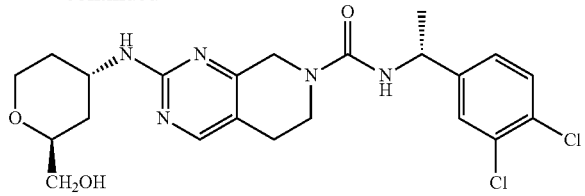

I-155

Step 1:

To a solution of (2S,4S)-2-((tert-butyldimethylsilyloxy)methyl)-3,4-dihydro-2H-pyran-4-ol (430, 3.565 g, 14.59 mmol) (prepared from (2R,3S,4R)-2-(hydroxymethyl)-3,4-dihydro-2H-pyran-3,4-diol according to the procedures in S. V. Govindan and P. L. Fuchs, *J. Org. Chem.* 1988 53:2953-2959) and DCM (25 mL) was added 4 Å molecular sieves (7 g) followed by N-methyl morpholine N-oxide (3.418 g, 29.17 mmol) and tetrapropylammonium perruthenate (0.2563 g, 0.7293 mmol). The reaction was stirred for 1.5 h at RT. The mixture was passed through a plug of $SiO_2$ and eluted with DCM. The filtrate was concentrated and the resulting residue was purified by $SiO_2$ chromatography eluting with 25% EtOAc/hexane to afford 3.097 g (87.6%) of 432.

Step 2:

A suspension of 432 (3.097 g, 12.78 mmol), Pd/C (0.5439 g, 0.2555 mmol) and EtOAc (30 mL) and was stirred and maintained under hydrogen balloon pressure for 18 h. The reaction was filtered through a plug of CELITE and concentrated. The resulting residue was purified by SiO2 chromatography eluting with 20% EtOAc/hexane to afford 2.035 g (65.17%) of 434.

Step 3:

To a solution of 434 (1.885 g, 7.713 mmol) and phenylmethanamine (0.9470 mL, 8.484 mmol) and DCE (40 mL) was added $NaBH(OAc)_3$ (2.288 g, 10.80 mmol) and the reaction stirred for 1 h. The reaction mixture was poured into water and extracted with DCM. The combined organic extracts were washed with $NaHCO_3$, dried ($MgSO_4$), filtered and concentrated. The resulting residue was purified by $SiO_2$ eluting with a DCM/MeOH gradient (0 to 3% MeOH) to afford a mixture of (2S,4S)—N-benzyl-2-((tert-butyldimethylsilyloxy)methyl)tetrahydro-2H-pyran-4-amine (438a, 1.686 g, 65.15% yield) and the trans (2S,4R)—N-benzyl-2-((tert-butyldimethylsilyloxy)methyl)tetrahydro-2H-pyran-4-amine (436a, 1.04 g, 40.18% yield).

Step 4:

To a solution of 436a (1.04 g, 3.10 mmol) and EtOH (20 mL) was Pd/C (0.660 g, 0.310 mmol) and the reaction was stirred and maintained under balloon hydrogen pressure for 18 h. The mixture was filtered through a zap cap membrane filter. The filtrate was concentrated to afford 664 mg (87.3%) of 436b which was used without further purification.

The conversion of 438a to (2S,4S)-2-((tert-butyldimethylsilyloxy)methyl)tetrahydro-2H-pyran-4-amine (438b) was carried out analogously.

Step 5:

Condensation of 438b and 21 can be carried out in accord with the procedure described in step 1 of example 1 to afford 440. Hydrolysis of the Boc (step 6) to afford 440 and condensation with (S)-(4-chloro-3-fluorophenyl)(1-methyl-1H-pyrazol-4-yl)methanamine (140) can be carried out in accord with the procedure example 17 to afford I-155.

Example 78

N—((S)-(3,4-dichlorophenyl)(oxazol-5-yl)methyl)-2-((3S,4S)-3-fluorotetrahydro-2H-pyran-4-ylamino)-5,6-dihydropyrido[3,4-d]pyrimidine-7(8H)-carboxamide (I-156)

Step 1:

To a solution of 1-chloromethyl-4-fluoro-1,4-diazoniabicyclo[2.2.2]octane bis-tetrafluoroborate (147 g, 414 mmol, Selectfluor) and $MeCN/H_2O$ (1:1, 800 mL) cooled to 0° C. in a 3 L round-bottom flask was added dropwise a solution of 4-methoxy-3,6-dihydro-2H-pyran (446, 45.0 g, 394 mmol, CASRN 17327-22-9) and MeCN (120 mL). The reaction was stirred for 30 min in an ice bath before the bath was removed and the reaction was stirred for an additional 1 h. Solid NaCl (200 g) was then added to the reaction along with DCM (300 mL). A saturated $Na_2CO_3$ solution was then added slowly until pH=10. The mixture was transferred into a 4 L sep. funnel and thrice extracted into DCM. The aqueous layer was then placed in a continuous liquid-liquid extractor with DCM and heated to 58° C. for 18 h. The combined organic extracts were dried ($MgSO_4$), filtered and concentrated at 20° C. on the rotovap. The crude product was purified by $SiO_2$ chromatography eluting with DCM/MeOH gradient (500:3 to 500:5 DCM:MeOH) to afford 30 g (64.4%) of 3-fluorodihydro-2H-pyran-4(3H)-one (448).

Step 2:

To a solution of 448 (30 g, 254 mmol) and DCE (800 mL) cooled to 0° C. was added phenylmethanamine (29.8 ml, 267 mmol) and the solution was stirred for 10 min. To the reaction mixture was added $NaBH(OAc)_3$ (75.4 g, 356 mmol) followed by the dropwise addition of glacial HOAc (14.5 mL, 254 mmol). The reaction was stirred for 2 h and then poured into 1M NaOH and extracted with DCM. The combined organic fractions were dried (MgSO4), filtered and concentrated. The crude product was purified by reverse phase column chromatography using a MeCN/H2O gradient (0 to 40% MeCN) to afford 39 g (73.4%) of the racemic cis product [(3S,4S)- and (3R,4R)—N-benzyl-3-fluorotetrahydro-2H-pyran-4-amine 450a and 450b respectively].

The enantiomers can be separated by chromatography on a Chiralpak IC, 5×25 cm column eluting with 10% IPA (0.1% $NH_4OH$)/90% $CO_2$ at a flow rate of 300 mL/min and a temperature of 40° C. The back pressure was 100 Bar.

Step 3:

To a solution of 450a (3.7 g, 18 mmol) and MeOH (40 mL) at RT was added Pd/C (3.8 g, 1.8 mmol) and the resulting suspension stirred under $H_2$ for 18 h. The catalyst was filtered, washed with MeOH. The solvent was concentrated to afford 2.1 g (100%) (3S,4S)-3-fluorotetrahydro-2H-pyran-4-amine (452): $H^1$ NMR (400 MHz, $CDCl_3$) δ 4.58-4.44 (m, 1H), 4.19-4.09 (m, 1H), 4.05-3.95 (m, 1H), 3.56-3.38 (m, 2H), 2.96-2.84 (m, 1H), 1.88-1.77 (m, 1H), 1.72-1.65 (m, 1H).

N—((S)-(3,4-dichlorophenyl)(oxazol-5-yl)methyl)-2-((3S,4S)-3-fluorotetrahydro-2H-pyran-4-ylamino)-5,6-dihydropyrido[3,4-d]pyrimidine-7(8H)-carboxamide can be prepared in accord with the procedure in example 1 except in step 3 tetrahydro-2H-pyran-4-amine is replaced with 452 to afford I-156.

Example 79

ERK-2 Enzymatic Assay

Compounds were tested in an enzymatic assay using human ERK-2 (Mitogen Activated Kinase 1), recombinantly expressed as an n-terminal 6-His fusion protein in *E. coli* and corresponding to aa 8-360. The substrate used was the fluorescent Omnia peptide S/T17 (Invitrogen of Carlsbad, Calif.; Cat. KNZ1171C). Test compounds were diluted in DMSO in 3-fold serial dilutions at 100× final concentrations. In addition to compound, the assay contained 50 mM HEPES [pH 7.3], 10 mM $MgCl_2$, 1 mM DTT, 0.005% Triton-X100, 5 nM ERK-2 enzyme, 6.25 µM S/T17 peptide substrate and 25 µM ATP (corresponding to the observed $K_m$) for a total reaction volume of 25 µL. The assay was run at ambient temperature in a white 384-well polypropylene plate (Nunc, Inc of Naperville, Ill.; Cat. 267462) collecting data every 50 seconds for approximately 30 minutes on an Envision plate reader (PerkinElmer, Inc. of Waltham, Mass.); Excitation 340 nm/Emission 495 nm. The data collected from each well was fit to a straight line and the resulting rates were used to calculate percent of control. Percent of control was plotted against compound concentration and $IC_{50}$ values were determined using a four-parameter fit. Table 2 contains representative data for compounds disclosed herein. Representative date is in TABLE 2 (infra).

Example 80

Cell Proliferation/Viability Assay

Viable cells after a 3-day (72-hour) incubation with ERK compounds were quantified using the Cell Titer-Blue Cell Viability Assay from Promega.

Materials and Methods: HCT116 cells were plated in 96 well micro-plates at a density of 1,000 cells/well. The cells were allowed to attach to micro-plate overnight at 37° C./5% $CO_2$. After overnight attachment, diluted compounds were then added to the cells at a final concentration of 0.5% DMSO. After 3 days (72 hours) at 37° C./5% $CO_2$, the number of viable cells was determined using the Cell Titer-Blue Cell Viability Assay from Promega. Briefly, Cell Titer-Blue reagent were added to the cells and incubated for 1 hour. Fluorescense (560 $nm_{excitation}$/590 $nm_{emission}$) was then read using a fluorescence micro-plate reader. Background from high concentration ERK-inhibited wells was subtracted. Representative date is in TABLE III (infra).

Example 81

Cellular P90RSK(Ser380) Phosphorylation Assay

Inhibition of PMA-stimulated P90RSK(Ser380) phosphorylation was determined by the following in vitro cellular mechanistic assay, which comprises incubating cells with a compound for 1.5 hours and quantifying fluorescent pP90RSK(Ser380) signal on fixed cells and normalizing to GAPDH signal.

Materials and Methods: HepG2 cells were obtained from ATCC and grown in DMEM supplemented with 10% fetal bovine serum. Cells were plated in 96-well plates at 35,000 cells/well and allowed to attach overnight at 37° C./5% $CO_2$. Diluted compounds were then added at a final concentration of 0.5% DMSO. After 1.5 hour compound incubation, cells were stimulated with the addition of PMA (phorbol 12-myristate 13-acetate) at a final concentration of 100 ng/mL; the PMA stimulation was a 30-minute incubation at 37° C./5% $CO_2$. After the 30-minute PMA stimulation, cells were washed with PBS and fixed in 3.7% formaldehyde in PBS at room temperature for 15-20 minutes. This was followed by another wash in PBS and then permeabilization in 100% MeOH at room temperature for 10-15 minutes. Following the permeabilization incubation, cells were washed in PBS/0.05% Tween-20, followed by a block in Odyssey blocking buffer (LI-COR Biosciences) for at least 1 hour. Antibodies to phosphorylated P90RSK(Ser380) (Cell Signaling #9335, rabbit monoclonal) and GAPDH (Fitzgerald 10R-G109a, mouse monoclonal) were added to the cells and incubated overnight at 4° C. pP90RSK(Ser380) antibody was used at a 1:250 dilution; GAPDH was used at a 1:10,000 dilution. After washing with PBS/0.05% Tween-20, the cells were incubated with fluorescently-labeled secondary antibodies (Anti-rabbit-Alexa Flour680, Invitrogen Cat#A21109; Anti-mouse-IRDye800CW, Rockland Inc. Cat#610-131-121) for 1 hour. Both secondary antibodies were used at a 1:1000 dilution. Cells were then washed and analyzed for fluorescence at both wavelengths using the Odyssey Infrared Imaging System (LI-COR Biosciences). Phosphorylated P90RSK(Ser380) signal was normalized to GAPDH signal. Representative date is in TABLE III (infra).

TABLE III

| Cpd. No. | ERK Inhibition[1] $IC_{50}$ (µM) | Cell Assay[2] $IC_{50}$ (µm) | Cell Proliferation[3] $IC_{50}$ (µM) |
|---|---|---|---|
| I-1 | 0.0011 | 0.00455 | 0.301 |
| I-3 | 0.0038 | 0.101 | |
| I-5 | 0.0014 | 0.0473 | |
| I-7 | 0.0015 | 0.0435 | |
| I-9 | 0.0024 | 0.0717 | |
| I-12 | 0.0040 | 0.235 | |
| I-15 | 0.0011 | 0.0373 | 0.625 |
| I-16 | 0.0011 | 0.0524 | 2.1 |
| I-17 | 0.0032 | 0.281 | |
| I-21 | 0.0016 | 0.0552 | |
| I-23 | 0.0032 | 0.493 | |
| I-27 | 0.0015 | 0.0269 | 0.628 |
| I-28 | 0.0016 | 0.0328 | 1.9 |
| I-33 | 0.0011 | 0.055 | 1.9 |
| I-35 | 0.0056 | 0.0913 | |
| I-37 | 0.0048 | 0.093 | |
| I-50 | 0.0016 | 0.0283 | |
| I-52 | 0.0027 | 0.057 | 1.4 |
| I-56 | 0.0053 | 0.0662 | |
| I-59 | 0.0006 | 0.0855 | |
| I-60 | 0.0033 | 0.1 | |
| I-61 | 0.0029 | 0.093 | |
| I-62 | 0.0024 | 0.109 | |
| I-66 | 0.0041 | 0.132 | |
| I-68 | 0.0023 | 0.146 | |
| I-73 | 0.0098 | 0.241 | |
| I-75 | 0.0056 | 0.314 | |
| I-83 | 0.1128 | 2.5 | |
| I-86 | 0.1478 | 3.6 | |
| I-87 | 0.1951 | 5.1 | |
| I-90 | 0.0021 | 0.103 | |
| I-93 | 0.0038 | 6.2 | |
| I-104 | 0.0022 | 0.0586 | 1.6 |
| I-105 | 0.0026 | 0.101 | |
| I-107 | 0.0027 | 0.03 | |

TABLE III-continued

| Cpd. No. | ERK Inhibition[1] IC$_{50}$ (µM) | Cell Assay[2] IC$_{50}$ (µm) | Cell Proliferation[3] IC$_{50}$ (µM) |
|---|---|---|---|
| I-109 | 0.0927 | 3.3 | |
| I-114 | 0.0232 | 0.0254 | 1.5 |
| I-119 | 0.0018 | 0.694 | |
| I-120 | 0.0016 | 0.0378 | 0.557 |
| I-124 | 0.0023 | 0.00595 | 0.0475 |
| I-130 | 0.1231 | 10 | |
| I-134 | 0.0204 | 1.2 | |
| I-139 | 0.2636 | | |
| I-141 | 0.1085 | | |
| I-144 | 0.0023 | 0.0913 | |
| I-149 | 0.0030 | 0.0757 | 4.1 |
| II-7 | 0.0019 | 50 | |
| II-10 | 0.061 | 20.8 | |
| II-17 | 0.0041 | 1.1 | |
| II-24 | 0.244 | 50 | |
| II-26 | 0.0866 | 12.2 | |
| II-34 | 0.0259 | 13.2 | |
| II-35 | 0.0215 | 0.16 | |
| II-40 | 0.00323 | 0.0873 | |
| II-41 | 0.0154 | 1.9 | |
| II-43 | 0.0071 | 0.917 | |
| II-50 | 0.00443 | 1 | |
| II-51 | 0.0024 | 0.435 | |
| II-61 | 0.21 | 21.3 | |
| II-64 | 0.0383 | 3.1 | |
| II-72 | 0.0072 | 0.208 | |
| II-78 | 0.0177 | 1.4 | |
| II-95 | 0.0243 | 0.551 | |
| II-99 | 0.144 | 5.6 | |
| II-102 | 0.409 | | |
| II-111 | 0.0047 | 0.693 | |
| II-116 | 0.00233 | 0.13 | |
| II-126 | 0.0069 | 0.141 | |
| II-136 | 0.0022 | 0.464 | |
| II-151 | 0.0528 | 10 | |
| II-171 | 0.0007 | 10 | |
| II-195 | 0.0066 | 0.281 | |
| II-200 | 0.411 | 1 | |
| II-223 | 0.0057 | 0.186 | |
| II-267 | 0.0201 | 28 | |
| II-287 | 0.0023 | 0.0913 | |
| II-288 | 0.0627 | 9.5 | |
| II-341 | 0.004 | 0.371 | |
| II-355 | 0.0075 | 0.97 | |
| II-359 | 0.0024 | 0.030 | |
| II-366 | 0.00239 | 0.091 | |
| II-371 | 0.00315 | 0.090 | |
| II-399 | 0.00303 | 0.287 | |
| II-400 | 0.109 | 1.3 | |
| II-415 | 0.0023 | 0.0395 | |

[1] Example 79
[2] Example 80
[3] Example 81

Example 82

Pharmaceutical compositions of the subject Compounds for administration via several routes were prepared as described in this Example.

Composition for Oral Administration (A)

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
|---|---|
| Active ingredient | 20.0% |
| Magnesium stearate | 0.5% |
| Croscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (D)

| Ingredient | % wt./wt. |
|---|---|
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation (F)

| Ingredients | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |

-continued

| Ingredients | grams |
|---|---|
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:
1. A compound according to formula I

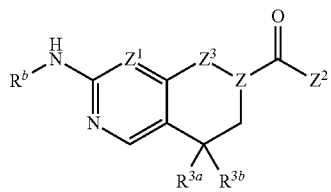

(I)

wherein:
Z is N and $Z^3$ is $CH_2$ or C=O; or, Z is $CR^g$ and $Z^3$ is O;
$Z^1$ is independently CH or N;

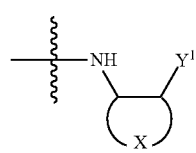

(II)

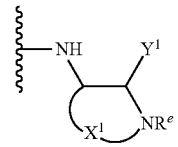

(IIc)

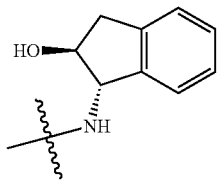

(III)

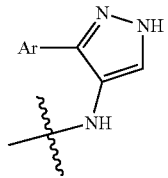

(IV)

$Z^2$ is (a) $NR^aCR^1R^2Y$; (b) formula II wherein X is O, $(CH_2)_{1-3}$ or $CH_2NR^eCH_2$; (c) $CH_2CR^1R^2Y$; (d) formula III; (e) $CH_2CH(NR^hR^i)Ar$; (f) $CH_2NR^jAr$ wherein $R^j$ is $C_{1-6}$ alkyl or $C_{1-6}$ hydroxyalkyl and Ar is optionally substituted phenyl; (g) formula IV; (h) $CH_2NR^hR^i$ or (i) formula IIc wherein $X^1$ is $(CH_2)_{2-3}$;

$R^e$ is hydrogen, $C_{1-3}$ alkyl, $C_{1-3}$ hydroxyalkyl, $C_{1-3}$ alkoxy-$C_{1-3}$ alkyl, $C_{1-3}$ haloalkyl, $C_{1-3}$ acyl, benzyl, $C_{1-3}$ cyanoalkyl or $C_{1-3}$ alkylsulfonyl;

Y is $C_{3-6}$ cycloalkyl, aryl, $C_{1-3}$ aralkyl, phenoxymethyl, or heteroaryl wherein said heteroaryl is selected from the group consisting of benzoxazolyl, benzothiazolyl, benzimidazolyl, indolyl, N—$C_{1-3}$ alkyl-indolyl, pyrimidinyl, pyridinyl, oxazolyl and thiazolyl;

$Y^1$ is —Ar, —OAr, —$S(O)_{0-2}$Ar or —$NR^gAr$ wherein Ar is optionally substituted phenyl;

$R^1$ and $R^2$ are independently selected from the group consisting of (a) hydrogen, (b) $C_{1-10}$ alkyl, (c) $C_{1-6}$ haloalkyl, (d) $C_{3-7}$ cycloalkyl, (e) $C_{1-10}$ heteroalkyl optionally further substituted by aryl or benzyl, (f) $(CH_2)_{1-3}OC(=O)R^f$ wherein $R^f$ is $C_{1-6}$ alkyl, $C_{1-6}$ heteroalkyl or $C_{1-3}$ alkoxy-$C_{1-3}$ alkyl, (g) $(CH_2)_{1-3}NR^cR^d$ wherein $R^c$ and $R^d$ are independently hydrogen, $C_{1-6}$ alkyl, $C(=O)R^g$, $S(=O)_2C_{1-3}$ alkyl, $C_{2-4}$ hydroxyalkyl, $C_{1-3}$ alkoxy-$C_{1-3}$ alkyl, $C_{3-7}$ cycloalkyl-$C_{1-3}$ alkyl, pyridinyl, or pyrimidinyl, (h) cyano-$C_{1-3}$ alkyl, (i) $C_{1-3}$ alkylsulfonyl-$C_{1-3}$ alkyl, (j) carbamoyl, (k) N—$C_{1-3}$ alkyl-carbamoyl, (l) N,N—$C_{1-3}$ alkylcarbamoyl; (m) optionally substituted heteroaryl or heteroaryl-$C_{1-3}$ alkyl wherein said heteroaryl is selected from the group consisting of pyridinyl, 2-oxo-1,2-dihydropyridinyl, 6-oxo-1,6-dihydropyridinyl, pyrimidinyl, pyrazinyl, pyridazinyl, pyrazolyl, N—$C_{1-3}$ alkyl-pyrazolyl, imidazolyl, oxazolyl, isoxazolyl, thiazolyl, isothiazolyl, oxadiazolyl, indolyl, benzoxazolyl, benzothiazolyl, triazolyl, N—$C_{1-3}$ alkyl-triazolyl and triazinyl, (n) heterocycle or heterocyclyl-$C_{1-3}$ alkyl said heterocyclyl selected from the group consisting of pyrrolidinyl, N—$C_{1-3}$ alkyl-pyrrolidinyl, N—$C_{1-3}$ acyl-pyrrolidinyl, azetidinyl, N—$C_{1-3}$ alkyl-azetidinyl, morpholinyl, piperidinyl and N—$C_{1-3}$ alkyl-piperidinyl and wherein said heterocycle is optionally substituted by 1 to 3 groups independently selected from $C_{1-6}$ alkyl, halogen, hydroxyl, phenyl and oxo, and (o) (2-methoxyethoxy) methyl;

or $R^1$ and $R^2$ together with the carbon to which they are attached form a cyclic amine optionally substituted by 1 to 3 $C_{1-6}$ alkyl groups;

or $R^1$ and $R^a$ together with the atoms to which they are attached form a cyclic amine in which one carbon atom can be optionally replaced by $NR^g$, O or S and the cyclic amine is optionally substituted by 1 to 3 groups independently selected from $C_{1-6}$ alkyl, halogen, hydroxyl phenyl, benzyl or oxo;

$R^{3a}$ and $R^{3b}$ are independently hydrogen, halogen or hydroxyl;

$R^a$ is (a) hydrogen or $C_{1-3}$ alkyl or (b) $R^1$ and $R^a$ together with the atoms to which they are attached form a cyclic amine optionally substituted by 1 to 3 groups independently selected from $C_{1-6}$ alkyl, halogen, hydroxyl, phenyl, benzyl or oxo;

$R^b$ is selected from the group consisting of (a) hydrogen, (b) $C_{1-10}$ alkyl, (c) $C_{1-6}$ haloalkyl, (d) optionally substituted aryl or aryl-$C_{1-6}$ alkyl, (e) optionally substituted heteroaryl or heteroaryl-$C_{1-6}$ alkyl wherein said heteroaryl is selected from the group consisting of isoxazole, pyridinyl, pyridone, N—$C_{1-3}$ alkyl-pyridone, pyrimidinyl, pyrazinyl, pyrazole, N-alkyl-pyrazolyl, N-benzylpyrazolyl, thiazolyl, N—$C_{1-6}$ alkyl triazolyl and 2-oxo-tetrahydroquinolin-6-yl, (f) heterocyclyl or heterocyclyl-$C_{1-6}$ alkyl wherein said heterocyclyl is selected from the group consisting of tetrahydropyranyl, tetrahydrofuranyl, oxetanyl, piperidinyl, pyrrolidinyl, morpholinyl, N—$C_{1-6}$ alkyl piperidinyl and N—$C_{1-6}$ alkyl-2-oxo-pyrrolidinyl, (g) $C_{3-7}$ cycloalkyl or $C_{3-7}$ cycloalkyl-$C_{1-6}$ alkyl wherein said cycloalkyl is optionally substituted by hydroxyl or halo, (h) $C_{1-6}$ heteroalkyl, (i) $C_{1-6}$ acyl and (j) $C_{1-6}$ hydroxyalkyl;

each $R^g$ is independently hydrogen or $C_{1-3}$ alkyl;

each $R^h$ and $R^i$ together with the nitrogen atom to which they are attached form a pyrrolidinyl, piperidinyl, piperazinyl, N-methyl-piperazinyl or morpholinyl ring each optionally substituted with phenyl ring which phenyl ring is optionally substituted with halogen or $C_{1-3}$ haloalkyl;

wherein:

each said aryl and each said heteroaryl is optionally substituted by 1 to 5 groups independently selected from $C_{1-6}$ alkyl, $C_{1-6}$ haloalkyl, $C_{1-6}$ alkoxy, $C_{3-6}$ cycloalkyl, halogen, hydroxyl, $C_{1-6}$ haloalkoxy, $C_{1-6}$ alkylthio, $C_{1-6}$ haloalkylthio, $C_{1-6}$ acylamino, cyano, nitro, optionally substituted aryloxy or $C_{1-3}$ cyanoalkyl;

each said heterocyclyl is optionally substituted with $C_{1-6}$ alkyl, $C_{1-6}$ haloalkyl, $C_{1-3}$ hydroxyalkyl or halogen;

each said cycloalkyl is optionally substituted by one to four groups independently selected from $C_{1-6}$ alkyl, $C_{1-6}$ alkoxy, halogen, cyano or oxo;

each said heteroalkyl is optionally substituted by phenyl, benzyl or $C_{1-3}$ haloalkyl; or, a tautomer, stereoisomer or pharmaceutically acceptable salt thereof.

2. The compound according to claim 1 wherein:
Z and $Z^1$ are N;
$Z^2$ is $NR^aCR^1R^2Ar$;
$Z^3$ is $CH_2$;
$R^1$, $R^{3a}$, $R^{3b}$ and $R^a$ are hydrogen;
Ar is optionally substituted phenyl;
$R^2$ is hydrogen, $C_{1-10}$ alkyl, $C_{1-6}$ haloalkyl, $C_{1-6}$ hydroxyalkyl, $C_{1-3}$ alkoxy-$C_{1-6}$ alkyl, $(CH_2)_{1-3}NR^cR^d$, pyrrolidin-2-yl, N—$C_{1-3}$ alkyl, pyrrolidin-2-yl or heteroaryl; and,
$R^b$ is $C_{1-10}$ alkyl, $C_{1-10}$ haloalkyl, $C_{1-6}$ hydroxyalkyl, $C_{4-6}$ cycloalkyl optionally substituted by a hydroxy or heterocyclyl.

3. The compound according to claim 2 wherein $R^2$ is pyrazolyl, N—$C_{1-3}$ alkyl pyrazolyl, oxadiazolyl, triazolyl or N—$C_{1-3}$ triazolyl.

4. The compound according to claim 3 wherein $R^b$ is tetrahydropyranyl, $C_{1-6}$ hydroxyalkyl or $C_{1-6}$ haloalkyl.

5. The compound according to claim 2 wherein $R^1$ is hydrogen and $R^2$ is pyrrolidinyl or N—$C_{1-3}$ alkyl-pyrrolidinyl.

6. The compound according to claim 5 wherein $R^b$ is tetrahydropyranyl, $C_{1-6}$ hydroxyalkyl or $C_{1-6}$ haloalkyl.

7. The compound according to claim 1 wherein:
Z and $Z^1$ are N;
$Z^3$ is $CH_2$;
$Z^2$ is $NR^aCR^1R^2Ar$;
$R^1$ and $R^a$ are hydrogen;
Ar is optionally substituted heteroaryl;
$R^2$ is hydrogen, $C_{1-10}$ alkyl, $C_{1-6}$ haloalkyl, $C_{1-6}$ hydroxyalkyl, $C_{1-3}$ alkoxy-$C_{1-6}$ alkyl, $(CH_2)_{1-3}NR^cR^d$, pyrrolidin-2-yl, N—$C_{1-3}$ alkyl-pyrrolidin-2-yl or heteroaryl;
$R^{3a}$ and $R^{3b}$ are hydrogen; and,
$R^b$ is $C_{1-10}$ alkyl, $C_{1-10}$ haloalkyl, $C_{1-6}$ hydroxyalkyl, $C_{4-6}$ cycloalkyl optionally substituted by a hydroxy or heterocyclyl.

8. The compound according to claim 1 wherein:
Z and $Z^1$ are N;
$Z^2$ is H;
$Z^3$ is $CH_2$;
$R^{3a}$ and $R^{3b}$ are hydrogen; and,
$R^b$ is $C_{1-10}$ alkyl, $C_{1-10}$ haloalkyl, $C_{1-6}$ hydroxyalkyl, $C_{4-6}$ cycloalkyl optionally substituted by a hydroxy, or heterocyclyl.

9. The compound according to claim 8 wherein X is $CH_2NR^eCH_2$, $Y^1$ is Ar and Ar is optionally substituted phenyl.

10. The compound according to claim 9 wherein $R^b$ is tetrahydropyranyl, $C_{1-6}$ hydroxyalkyl, or $C_{1-6}$ haloalkyl.

11. The compound according to claim 8 wherein X is $CH_2NR^eCH_2$, $Y^1$ is —OAr and Ar is optionally substituted phenyl.

12. The compound according to claim 11 wherein $R^b$ is tetrahydropyranyl, $C_{1-6}$ hydroxyalkyl, or $C_{1-6}$ haloalkyl.

13. The compound according to claim 8 wherein X is $(CH_2)_3$, $Y^1$ is Ar and Ar is optionally substituted phenyl.

14. The compound according to claim 8 wherein X is $(CH_2)_3$, $Y^1$ is OAr and Ar is optionally substituted phenyl.

15. The compound according to claim 1 wherein Z is N and $Z^1$ is CH.

16. The compound according to claim 15 wherein:
$Z^2$ is $NR^aCR^1R^2Ar$;
$R^1$, $R^a$, $R^{3a}$ and $R^{3b}$ are hydrogen;
$R^2$ is $C_{1-10}$ alkyl, $C_{1-6}$ haloalkyl or $C_{1-6}$ hydroxyalkyl;
Ar is optionally substituted phenyl; and,
$R^b$ is $C_{1-10}$ alkyl, $C_{1-10}$ haloalkyl, $C_{1-6}$ hydroxyalkyl, $C_{4-6}$ cycloalkyl optionally substituted by a hydroxy, or heterocyclyl.

17. The compound according to claim 16 wherein $R^b$ is tetrahydropyranyl, $C_{1-6}$ hydroxyalkyl or $C_{1-6}$ haloalkyl.

18. The compound of claim 1 wherein $Z^3$ is O and $R^{3a}$ and $R^{3b}$ are hydrogen.

19. The compound according to claim 1 selected from the group consisting of:

2-(Tetrahydro-pyran-4-ylamino)-5,8-dihydro-6H-pyrido[3,4-d]pyrimidine-7-carboxylic acid [(S)-(3,4-dichloro-phenyl)-oxazol-5-yl-methyl]-amide, 2-(Tetrahydro-pyran-4-ylamino)-5,8-dihydro-6H-pyrido[3,4-d]pyrimidine-7-carboxylic acid [(S)-(4-chloro-3-fluoro-phenyl)-oxazol-5-yl-methyl]-amide, 2-(Tetrahydro-pyran-4-ylamino)-5,8-dihydro-6H-pyrido[3,4-d]pyrimidine-7-carboxylic acid [(4-chloro-3-fluoro-phenyl)-(1-methyl-1H-pyrazol-3-yl)-methyl]-amide, 2-(Tetrahydro-pyran-4-ylamino)-5,8-dihydro-6H-pyrido[3,4-d]pyrimidine-7-carboxylic acid [(S)-(4-chloro-3-fluoro-phenyl)-(1-methyl-1H-pyrazol-3-yl)-methyl]-amide, 2-(Tetrahydro-pyran-4-ylamino)-5,8-dihydro-6H-pyrido[3,4-d]pyrimidine-7-carboxylic acid [(4-chloro-3-fluoro-phenyl)-(1-methyl-1H-pyrazol-4-yl)-methyl]-amide, 2-(Tetrahydro-pyran-4-ylamino)-5,8-dihydro-6H-pyrido[3,4-d]pyrimidine-7-carboxylic acid [(S)-(4-chloro-3-fluoro-phenyl)-(1-methyl-1H-pyrazol-4-yl)-methyl]-amide, 2-(Tetrahydro-pyran-4-ylamino)-5,8-dihydro-6H-pyrido[3,4-d]pyrimidine-7-carboxylic acid [(4-chloro-3-fluoro-phenyl)-(1H-pyrazol-4-yl)-methyl]-amide, 2-(Tetrahydro-pyran-4-ylamino)-5,8-dihydro-6H-pyrido[3,4-d]pyrimidine-7-carboxylic acid [(S)-(4-chloro-3-fluoro-phenyl)-(1H-pyrazol-4-yl)-methyl]-amide, 2-(Tetrahydro-pyran-4-ylamino)-5,8-dihydro-6H-pyrido[3,4-d]pyrimidine-7-carboxylic acid [(4-chloro-3-fluoro-phenyl)-[1,3,4]oxadiazol-2-yl-methyl]-amide, 2-(Tetrahydro-pyran-4-ylamino)-5,8-dihydro-6H-pyrido[3,4-d]pyrimidine-7-carboxylic acid [(R)-(3,4-dichloro-phenyl)-(2H-pyrazol-3-yl)-methyl]-amide, 2-(Tetrahydro-pyran-4-ylamino)-5,8-dihydro-6H-pyrido[3,4-d]pyrimidine-7-carboxylic acid [(S)-(4-chloro-3-fluoro-phenyl)-(2-methyl-2H-pyrazol-3-yl)-methyl]-amide, 2-(Tetrahydro-pyran-4-ylamino)-5,8-dihydro-6H-pyrido[3,4-d]pyrimidine-7-carboxylic acid [(4-chloro-3-fluoro-phenyl)-isoxazol-5-yl-methyl]-amide, 2-(Tetrahydro-pyran-4-ylamino)-5,8-dihydro-6H-pyrido[3,4-d]pyrimidine-7-carboxylic acid [(R)-(3-fluoro-4-trifluoromethyl-phenyl)-oxazol-5-yl-methyl]-amide, 2-(Tetrahydro-pyran-4-ylamino)-5,8-dihydro-6H-pyrido[3,4-d]pyrimidine-7-carboxylic acid [(S)-1-(4-chloro-3-fluoro-phenyl)-2-hydroxy-ethyl]-amide, 2-Isopropylamino-5,8-dihydro-6H-pyrido[3,4-d]pyrimidine-7-carboxylic acid [(S)-(3-fluoro-4-trifluoromethyl-phenyl)-(R)-pyrrolidin-2-yl-methyl]-amide, 2-Isopropylamino-5,8-dihydro-6H-pyrido[3,4-d]pyrimidine-7-carboxylic acid [(S)-1-(3,4-dichloro-phenyl)-2-hydroxy-ethyl]-amide, (S)-3-(4-Chloro-3-fluoro-phenyl)-1-(2-isopropylamino-5,8-dihydro-6H-pyrido[3,4-d]pyrimidin-7-yl)-4-methylamino-butan-1-one, 2-Isopropylamino-5,8-dihydro-6H-pyrido[3,4-d]pyrimidine-7-carboxylic acid [(1S,2S)-1-(2-fluoro-3-trifluoromethyl-phenyl)-2-hydroxy-propyl]-amide, 2-Isopropylamino-5,8-dihydro-6H-pyrido[3,4-d]pyrimidine-7-carboxylic acid [(1S,2R)-1-(2-fluoro-3-trifluoromethyl-phenyl)-2-hydroxy-propyl]-amide, 5-Hydroxy-2-isopropylamino-5,8-dihydro-6H-pyrido[3,4-d]pyrimidine-7-carboxylic acid [1-(3-chloro-4-fluoro-phenyl)-2-hydroxy-ethyl]-amide, 2-((S)-2-Hydroxy-1-methyl-ethylamino)-5,8-dihydro-6H-pyrido[3,4-d]pyrimidine-7-carboxylic acid [(R)-1-(4-chloro-3-fluoro-phenyl)-ethyl]-amide, 2-((S)-2-Hydroxy-1-methyl-ethylamino)-5,8-dihydro-6H-pyrido[3,4-d]pyrimidine-7-carboxylic acid [(R)-1-(4-chloro-2,5-difluoro-phenyl)-ethyl]-amide, 2-((S)-2-Hydroxy-1-methyl-ethylamino)-5,8-dihydro-6H-pyrido[3,4-d]pyrimidine-7-carboxylic acid [(S)-1-(3,4-dichloro-phenyl)-2,2,2-trifluoro-ethyl]-amide, 2-((S)-2-Hydroxy-1-methyl-ethylamino)-5,8-dihydro-6H-pyrido[3,4-d]pyrimidine-7-carboxylic acid [(R)-1-(3,4-dichloro-phenyl)-propyl]-amide, 2-((1S,3S)-3-Hydroxy-cyclopentylamino)-5,8-dihydro-6H-pyrido[3,4-d]pyrimidine-7-carboxylic acid [(R)-1-(3,4-dichloro-phenyl)-propyl]-amide, 2-(4-Hydroxy-cyclohexylamino)-5,8-dihydro-6H-pyrido[3,4-d]pyrimidine-7-carboxylic acid [(R)-1-(3,4-dichloro-phenyl)-ethyl]-amide, 2-(Tetrahydro-pyran-4-ylamino)-5,8-dihydro-6H-pyrido[3,4-d]pyrimidine-7-carboxylic acid [(R)-1-(4-difluoromethoxy-phenyl)-propyl]-amide, 2-(Tetrahydro-pyran-4-ylamino)-5,8-dihydro-6H-pyrido[3,4-d]pyrimidine-7-carboxylic acid [(R)-1-(3,4-dichloro-phenyl)-3-methoxy-propyl]-amide, 2-(2-Methyl-2H-pyrazol-3-ylamino)-5,8-dihydro-6H-pyrido[3,4-d]pyrimidine-7-carboxylic acid [(R)-1-(3,4-dichloro-phenyl)-ethyl]-amide, 2-(1-Ethyl-1H-pyrazol-4-ylamino)-5,8-dihydro-6H-pyrido[3,4-d]pyrimidine-7-carboxylic acid [(R)-1-(3,4-dichloro-phenyl)-ethyl]-amide, 2-(1-Methyl-1H-pyrazol-4-ylamino)-5,8-dihydro-6H-pyrido[3,4-d]pyrimidine-7-carboxylic acid [(R)-1-(3,4-dichloro-phenyl)-ethyl]-amide, 2-((S)-2-Hydroxy-1-methyl-ethylamino)-5,8-dihydro-6H-pyrido[3,4-d]pyrimidine-7-carboxylic acid [(R)-1-(3,4-dichloro-phenyl)-2-methyl-propyl]-amide, 2-((S)-2-Hydroxy-1-methyl-ethylamino)-5,8-dihydro-6H-pyrido[3,4-d]pyrimidine-7-carboxylic acid [(R)-1-(3,4-dichloro-phenyl)-3-hydroxy-propyl]-amide, 2-((S)-2-Hydroxy-1-methyl-ethylamino)-5,8-dihydro-6H-pyrido[3,4-d]pyrimidine-7-carboxylic acid [1-(3,4-dichloro-phenyl)-3,3,3-trifluoro-propyl]-amide, 2-(2-Ethoxy-pyridin-4-ylamino)-5,8-dihydro-6H-pyrido[3,4-d]pyrimidine-7-carboxylic acid [(R)-1-(3,4-dichloro-phenyl)-ethyl]-amide, 2-(2-Methyl-pyridin-4-ylamino)-5,8-dihydro-6H-pyrido[3,4-d]pyrimidine-7-carboxylic acid [(R)-1-(3,4-dichloro-phenyl)-ethyl]-amide, 2-((1S,3S)-3-Hydroxy-cyclopentylamino)-5,8-dihydro-6H-pyrido[3,4-d]pyrimidine-7-carboxylic acid [(R)-1-(3-fluoro-4-trifluoromethyl-phenyl)-propyl]-amide, 2-((S)-2-Hydroxy-1-methyl-ethylamino)-5,8-dihydro-6H-pyrido[3,4-d]pyrimidine-7-carboxylic acid [(R)-1-(4-chloro-3-fluoro-phenyl)-propyl]-amide, 2-(Tetrahydro-pyran-4-ylamino)-5,8-dihydro-6H-pyrido[3,4-d]pyrimidine-7-carboxylic acid [(R)-1-(3,4-dichloro-phenyl)-ethyl]-amide, 2-(Tetrahydro-pyran-4-ylamino)-5,8-dihydro-6H-pyrido[3,4-d]pyrimidine-7-carboxylic acid [(R)-1-(4-chloro-3-fluoro-phenyl)-ethyl]-amide, 2-(Tetrahydro-pyran-4-ylamino)-5,8-dihydro-6H-pyrido[3,4-d]pyrimidine-7-carboxylic acid [(S)-1-(3,4-dichloro-phenyl)-2-methoxy-ethyl]-amide, 2-((1S,3S)-3-Hydroxy-cyclopentylamino)-5,8-dihydro-6H-pyrido[3,4-d]pyrimidine-7-carboxylic acid [(R)-1-(3,4-dichloro-phenyl)-ethyl]-amide, 2-(Tetrahydro-pyran-4-ylamino)-5,8-dihydro-6H-pyrido[3,4-d]pyrimidine-7-carboxylic acid [(S)-1-(3,4-dichloro-phenyl)-2-hydroxy-ethyl]-amide, 2-((S)-2-Hydroxy-1-methyl-ethylamino)-5,8-dihydro-6H-pyrido[3,4-d]pyrimidine-7-carboxylic acid [(R)-1-(3,4-dichloro-phenyl)-ethyl]-amide, 2-(Tetrahydro-pyran-4-ylamino)-5,8-dihydro-6H-pyrido[3,4-d]pyrimidine-7-carboxylic acid [(S)-1-(4-chloro-3-fluoro-phenyl)-2-methoxy-ethyl]-amide, 2-(Tetrahydro-pyran-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide, Acetic acid (S)-2-(3-chloro-4-fluoro-phenyl)-2-{[2-(tetrahydro-pyran-4-ylamino)-5,8-dihydro-6H-pyrido[3,4-d]pyrimidine-7-carbonyl]-amino}-ethyl ester, 2-((S)-2-Hydroxy-1-methyl-ethylamino)-5,8-dihydro-6H-pyrido[3,4-d]pyrimidine-7-carboxylic acid [(S)-1-(3,4-dichloro-phenyl)-2-methoxy-ethyl]-amide, 2-Isopropylamino-5,8-dihydro-6H-pyrido[3,4-d]pyrimidine-7-carboxylic acid [(S)-(3,4-dichloro-phenyl)-(R)-pyrrolidin-2-yl-methyl]-amide, 5,5-Difluoro-2-(tetrahydro-pyran-4-ylamino)-5,8-dihydro-6H-pyrido[3,4-d]pyrimidine-7-carboxylic acid [(R)-1-(3,4-dichloro-phenyl)-ethyl]-amide, 5,5-Difluoro-2-(tetrahydro-pyran-4-ylamino)-5,8-dihydro-6H-pyrido[3,4-d]pyrimidine-7-carboxylic acid [(S)-1-(4-chloro-3-fluoro-phenyl)-2-methoxy-ethyl]-amide, 2-((1S,3S)-3-Hydroxy-cyclopentylamino)-5,8-dihydro-6H-pyrido[3,4-d]pyrimidine-7-carboxylic acid [(R)-1-(3-fluoro-4-trifluoromethyl-phenyl)-ethyl]-amide, 5,5-Difluoro-2-(tetrahydro-pyran-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide, (S)-2-Amino-3-methyl-butyric acid (S)-2-(3-chloro-4-fluoro-phenyl)-2-{[2-(tetrahydro-pyran-4-ylamino)-5,8-dihydro-6H-pyrido[3,4-d]pyrimidine-7-carbonyl]-amino}-ethyl ester, 2-((S)-2-Hydroxy-1-methyl-ethylamino)-5,8-dihydro-6H-pyrido[3,4-d]pyrimidine-7-carboxylic acid [(S)-1-(4-chloro-3-fluoro-phenyl)-2-methoxy-ethyl]-amide, Methoxy-acetic acid (S)-2-(3-chloro-4-fluoro-phenyl)-2-{[2-(tetrahydro-pyran-4-ylamino)-5,8-dihydro-6H-pyrido[3,4-d]pyrimidine-7-carbonyl]amino}-ethyl ester, 2-((S)-1-Hydroxymethyl-propylamino)-5,8-dihydro-6H-pyrido[3,4-d]pyrimidine-7-carboxylic acid [(R)-1-(4-chloro-3-fluoro-phenyl)-propyl]-amide, 2-((S)-2-Hydroxy-1-methyl-ethylamino)-5,8-dihydro-6H-pyrido[3,4-d]pyrimidine-7-carboxylic acid [(R)-1-(3-chloro-4-trifluoromethoxy-phenyl)-propyl]-amide, 2-(Tetrahydro-pyran-4-ylamino)-5,8-dihydro-6H-pyrido[3,4-d]pyrimidine-7-carboxylic acid [(R)-1-(3-chloro-4-fluoro-phenyl)-2-cyano-ethyl]-amide, 2-((R)-2-Fluoro-1-methyl-ethylamino)-5,8-dihydro-6H-pyrido[3,4-d]pyrimidine-7-carboxylic acid [(S)-1-(3,4-dichloro-phenyl)-2-hydroxy-ethyl]-amide, 2-Isopropylamino-5,8-dihydro-6H-pyrido[3,4-d]pyrimidine-7-carboxylic acid [(S)-(3,4-dichloro-phenyl)-((R)-1-methyl-pyrrolidin-2-yl)-methyl]-amide, 2-Isopropylamino-5,8-dihydro-6H-pyrido[3,4-d]pyrimidine-7-carboxylic acid [(1S,2S)-1-(3,4-dichloro-phenyl)-2,3-dihydroxy-propyl]-amide, 2-Isopropylamino-5,8-dihydro-6H-pyrido[3,4-d]pyrimidine-7-carboxylic acid [(1S,2S)-1-(4-chloro-3-fluoro-phenyl)-2,3-dihydroxy-propyl]-amide, 2-((S)-2-Hydroxy-1-methyl-ethylamino)-5,8-dihydro-6H-pyrido[3,4-d]pyrimidine-7-carboxylic acid [(R)-1-(3-fluoro-4-trifluoromethyl-phenyl)-ethyl]-amide, 2-((S)-2-Hydroxy-1-methyl-ethylamino)-5,8-dihydro-6H-pyrido[3,4-d]pyrimidine-7-carboxylic acid [(R)-1-(3-chloro-5-fluoro-phenyl)-ethyl]-amide, 2-Isopropylamino-5,8-dihydro-6H-pyrido[3,4-d]pyrimidine-7-carboxylic acid [(S)-1-(3-fluoro-4-trifluoromethyl-phenyl)-2-methylamino-ethyl]-amide, 2,2-Dimethyl-propionic acid (S)-2-(3-chloro-4-fluoro-phenyl)-2-{[2-(tetrahydro-pyran-4-ylamino)-5,8-dihydro-6H-pyrido[3,4-d]pyrimidine-7-carbonyl]-amino}-ethyl ester, 2-(4-Fluoro-phenylamino)-5,8-dihydro-6H-pyrido[3,4-d]pyrimidine-7-carboxylic acid [(S)-1-(3-fluoro-4-trifluoromethyl-phenyl)-2-methylamino-ethyl]-amide, 2-((S)-1-Hydroxymethyl-propylamino)-5,8-dihydro-6H-pyrido[3,4-d]pyrimidine-7-carboxylic acid [(R)-1-(3-fluoro-4-trifluoromethyl-phenyl)-ethyl]-amide, 2-Isopropylamino-5,8-dihydro-6H-pyrido[3,4-d]pyrimidine-7-carboxylic acid [1-(3-fluoro-4-trifluoromethyl-phenyl)-3-hydroxy-propyl]-amide, 2-((S)-1-Hydroxymethyl-propylamino)-5,8-dihydro-6H-pyrido[3,4-d]pyrimidine-7-carboxylic acid [(S)-1-(4-chloro-3-fluoro-phenyl)-2-methoxy-ethyl]-amide, 2-Isopropylamino-5,8-dihydro-6H-pyrido[3,4-d]pyrimidine-7-carboxylic acid [(R)-3-amino-1-(3-fluoro-4-trifluoromethyl-phenyl)-propyl]-amide, 2-(2-Hydroxy-ethylamino)-5,8-dihydro-6H-pyrido[3,4-d]pyrimidine-7-carboxylic acid [(S)-1-(3,4-dichloro-phenyl)-2-methoxy-ethyl]-amide, 2-Isopropylamino-5,8-dihydro-6H-pyrido[3,4-d]pyrimidine-7-carboxylic acid [1-(4-chloro-3-fluoro-phenyl)-3-hydroxy-propyl]-amide, 2-(2-Hydroxy-1-hydroxymethyl-ethylamino)-5,8-dihydro-6H-pyrido[3,4-d]pyrimidine-7-carboxylic acid [(R)-1-(3,4-dichloro-phenyl)-ethyl]-amide, 2-(2,2,2-Trifluoro-1-methyl-ethylamino)-5,8-dihydro-6H-pyrido[3,4-d]pyrimidine-7-carboxylic acid [1-(3,4-dichloro-phenyl)-2-hydroxy-ethyl]-amide, 2-Isopropylamino-5,8-dihydro-6H-pyrido[3,4-d]pyrimidine-7-carboxylic acid [1-(3,4-difluoro-phenyl)-3-hydroxy-propyl]-amide, 2-Isopropylamino-5,8-dihydro-6H-pyrido[3,4-d]pyrimidine-7-carboxylic acid [1-(4-chloro-3-fluoro-phenyl)-3-methylamino-propyl]-amide, 2-((S)-1-Hydroxymethyl-propylamino)-5,8-dihydro-6H-pyrido[3,4-d]pyrimidine-7-carboxylic acid [(S)-1-(3-fluoro-4-trifluoromethyl-phenyl)-2-methoxy-ethyl]-amide, 2-((S)-2-Hydroxy-1-methyl-ethylamino)-5,8-dihydro-6H-pyrido[3,4-d]pyrimidine-7-carboxylic acid [(S)-1-(3-fluoro-4-trifluoromethyl-phenyl)-2-methylamino-ethyl]-amide, 2-Isopropylamino-5,8-dihydro-6H-pyrido[3,4-d]pyrimidine-7-carboxylic acid [(R)-1-(4-fluoro-phenyl)-ethyl]-amide, 2-(2-Hydroxy-1-hydroxymethyl-ethylamino)-5,8-dihydro-6H-pyrido[3,4-d]pyrimidine-7-carboxylic acid [(R)-1-(3-fluoro-4-trifluoromethyl-phenyl)-ethyl]-amide, 2-(1-Methyl-piperidin-4-ylamino)-5,8-dihydro-6H-pyrido[3,4-d]pyrimidine-7-carboxylic acid [(R)-1-(3,4-dichloro-phenyl)-ethyl]-amide, 2-(2,2,2-Trifluoro-1-methyl-ethylamino)-5,8-dihydro-6H-pyrido[3,4-d]pyrimidine-7-carboxylic acid [(4-chloro-3-fluoro-phenyl)-oxazol-5-yl-methyl]-amide, 2-Isopropylamino-5,8-dihydro-6H-pyrido[3,4-d]pyrimidine-7-carboxylic acid [(R)-3-acetylamino-1-(3-fluoro-4-trifluoromethyl-phenyl)-propyl]-amide,
2-(Tetrahydro-pyran-4-ylamino)-5,8-dihydro-6H-pyrido[3,4-d]pyrimidine-7-carboxylic acid [(S)—((S)-5,5-dimethyl-pyrrolidin-2-yl)-(2-fluoro-4-trifluoromethyl-phenyl)-methyl]-amide,
2-Isopropylamino-5,8-dihydro-6H-pyrido[3,4-d]pyrimidine-7-carboxylic acid [(S)—((S)-1-acetyl-pyrrolidin-2-yl)-(4-chloro-3-fluoro-phenyl)-methyl]-amide,
2-(2-Morpholin-4-yl-ethylamino)-5,8-dihydro-6H-pyrido[3,4-d]pyrimidine-7-carboxylic acid [(R)-1-(3,4-dichloro-phenyl)-ethyl]-amide,
2-Isopropylamino-5,8-dihydro-6H-pyrido[3,4-d]pyrimidine-7-carboxylic acid [(1S,2S)-1-(3-chloro-4-fluoro-phenyl)-2-hydroxy-propyl]-amide,
2-((S)-2-Hydroxy-1-methyl-ethylamino)-5,8-dihydro-6H-pyrido[3,4-d]pyrimidine-7-carboxylic acid 3,4-dichloro-benzylamide,
2-Isopropylamino-5,8-dihydro-6H-pyrido[3,4-d]pyrimidine-7-carboxylic acid [(1S,2R)-1-(3-chloro-4-fluoro-phenyl)-2-hydroxy-butyl]-amide,
2-(2,2,2-Trifluoro-1-hydroxymethyl-ethylamino)-5,8-dihydro-6H-pyrido[3,4-d]pyrimidine-7-carboxylic acid [1-(3,4-dichloro-phenyl)-ethyl]-amide,
2-Isopropylamino-5,8-dihydro-6H-pyrido[3,4-d]pyrimidine-7-carboxylic acid [4-(3,4-dichloro-phenyl)-piperidin-4-yl]-amide,
2-(Tetrahydro-pyran-4-ylamino)-5,8-dihydro-6H-pyrido[3,4-d]pyrimidine-7-carboxylic acid 3-chloro-4-cyano-benzylamide,
2-(Tetrahydro-pyran-4-ylamino)-5,8-dihydro-6H-pyrido[3,4-d]pyrimidine-7-carboxylic acid ((R)-1-phenyl-propyl)-amide,
2-(Tetrahydro-pyran-4-ylamino)-5,8-dihydro-6H-pyrido[3,4-d]pyrimidine-7-carboxylic acid [(R)-1-(4-trifluoromethyl-phenyl)-propyl]-amide,
2-(Tetrahydro-pyran-4-ylamino)-5,8-dihydro-6H-pyrido[3,4-d]pyrimidine-7-carboxylic acid [(R)-1-(4-chloro-phenyl)-ethyl]-amide,
2-(Tetrahydro-pyran-4-ylamino)-5,8-dihydro-6H-pyrido[3,4-d]pyrimidine-7-carboxylic acid [(R)-1-(4-trifluoromethyl-phenyl)-ethyl]-amide,
2-(Tetrahydro-pyran-4-ylamino)-5,8-dihydro-6H-pyrido[3,4-d]pyrimidine-7-carboxylic acid 4-cyano-3-trifluoromethyl-benzylamide,
2-(Tetrahydro-pyran-4-ylamino)-5,8-dihydro-6H-pyrido[3,4-d]pyrimidine-7-carboxylic acid [(R)-1-(4-fluoro-phenyl)-propyl]-amide,
2-(Tetrahydro-pyran-4-ylamino)-5,8-dihydro-6H-pyrido[3,4-d]pyrimidine-7-carboxylic acid [(R)-1-(4-fluoro-phenyl)-ethyl]-amide,
2-(Tetrahydro-pyran-4-ylamino)-5,8-dihydro-6H-pyrido[3,4-d]pyrimidine-7-carboxylic acid ((R)-1-phenyl-ethyl)-amide,
2-(Tetrahydro-pyran-4-ylamino)-5,8-dihydro-6H-pyrido[3,4-d]pyrimidine-7-carboxylic acid [(R)-3-cyano-1-(3,4-dichloro-phenyl)-propyl]-amide,
2-Isopropylamino-5,8-dihydro-6H-pyrido[3,4-d]pyrimidine-7-carboxylic acid [(R)-3-cyano-1-(3,4-dichloro-phenyl)-propyl]-amide,
2-(Tetrahydro-pyran-4-ylamino)-5,8-dihydro-6H-pyrido[3,4-d]pyrimidine-7-carboxylic acid [(R)-1-(3,4-dichloro-phenyl)-3-methanesulfonyl-propyl]-amide,
2-Isopropylamino-5,8-dihydro-6H-pyrido[3,4-d]pyrimidine-7-carboxylic acid [(R)-1-(3,4-dichloro-phenyl)-3-methanesulfonyl-propyl]-amide,
2-(Tetrahydro-pyran-4-ylamino)-5,8-dihydro-6H-pyrido[3,4-d]pyrimidine-7-carboxylic acid [1-(1H-indol-6-yl)-ethyl]-amide,
2-(Tetrahydro-pyran-4-ylamino)-5,8-dihydro-6H-pyrido[3,4-d]pyrimidine-7-carboxylic acid [(R)-3-cyano-1-(4-difluoromethoxy-phenyl)-propyl]-amide,
2-((S)-2-Hydroxy-1-methyl-ethylamino)-5,8-dihydro-6H-pyrido[3,4-d]pyrimidine-7-carboxylic acid (2-trifluoromethyl-pyrimidin-5-ylmethyl)-amide,
2-Isopropylamino-5,8-dihydro-6H-pyrido[3,4-d]pyrimidine-7-carboxylic acid [3-amino-1-(3,4-dichloro-phenyl)-propyl]-amide,
2-Isopropylamino-5,8-dihydro-6H-pyrido[3,4-d]pyrimidine-7-carboxylic acid [1-(3,4-dichloro-phenyl)-3-methylamino-propyl]-amide,
3-(3-Chloro-4-fluoro-phenyl)-4-hydroxy-1-(2-isopropylamino-5,8-dihydro-6H-pyrido[3,4-d]pyrimidin-7-yl)-butan-1-one,
(S)-3-(4-Chloro-phenyl)-1-(2-isopropylamino-5,8-dihydro-6H-pyrido[3,4-d]pyrimidin-7-yl)-4-methylamino-butan-1-one,
2-(Tetrahydro-pyran-4-ylamino)-5,8-dihydro-6H-pyrido[3,4-d]pyrimidine-7-carboxylic acid (1H-indol-2-ylmethyl)-amide,
2-Isopropylamino-5,8-dihydro-6H-pyrido[3,4-d]pyrimidine-7-carboxylic acid [1-(3,4-dichloro-phenyl)-3-hydroxy-propyl]-amide,
2-Isopropylamino-5,8-dihydro-6H-pyrido[3,4-d]pyrimidine-7-carboxylic acid [(R)-3-amino-1-(4-chloro-phenyl)-propyl]-amide,
2-Isopropylamino-5,8-dihydro-6H-pyrido[3,4-d]pyrimidine-7-carboxylic acid [(R)-1-(4-chloro-phenyl)-3-methylamino-propyl]-amide,
2-Isopropylamino-5,8-dihydro-6H-pyrido[3,4-d]pyrimidine-7-carboxylic acid [(R)-3-amino-1-(3-chloro-phenyl)-propyl]-amide,
2-Isopropylamino-5,8-dihydro-6H-pyrido[3,4-d]pyrimidine-7-carboxylic acid [(R)-3-amino-1-(4-trifluoromethyl-phenyl)-propyl]-amide,
2-Isopropylamino-5,8-dihydro-6H-pyrido[3,4-d]pyrimidine-7-carboxylic acid [(3S,4R)-4-(3-fluoro-4-trifluoromethyl-phenyl)-1-methyl-pyrrolidin-3-yl]-amide,
2-Isopropylamino-5,8-dihydro-6H-pyrido[3,4-d]pyrimidine-7-carboxylic acid [(3S,4R)-4-(3,4-difluoro-phenyl)-1-methyl-pyrrolidin-3-yl]-amide,
2-Isopropylamino-5,8-dihydro-6H-pyrido[3,4-d]pyrimidine-7-carboxylic acid [(3S,4R)-4-(3-fluoro-phenyl)-1-methyl-pyrrolidin-3-yl]-amide,
2-Isopropylamino-5,8-dihydro-6H-pyrido[3,4-d]pyrimidine-7-carboxylic acid [(3S,4R)-4-(3,4-difluoro-phenyl)-1-ethyl-pyrrolidin-3-yl]-amide,
2-(Tetrahydro-pyran-4-ylamino)-5,8-dihydro-6H-pyrido[3,4-d]pyrimidine-7-carboxylic acid [(3S,4R)-4-(4-chloro-3-fluoro-phenyl)-1-methyl-pyrrolidin-3-yl]-amide,
2-(Tetrahydro-pyran-4-ylamino)-5,8-dihydro-6H-pyrido[3,4-d]pyrimidine-7-carboxylic acid [(3S,4R)-4-(3-fluoro-4-trifluoromethyl-phenyl)-1-methyl-pyrrolidin-3-yl]-amide,
2-(Tetrahydro-pyran-4-ylamino)-5,8-dihydro-6H-pyrido[3,4-d]pyrimidine-7-carboxylic acid [(3S,4R)-4-(3,4-difluoro-phenyl)-1-methyl-pyrrolidin-3-yl]-amide,
2-(Tetrahydro-pyran-4-ylamino)-5,8-dihydro-6H-pyrido[3,4-d]pyrimidine-7-carboxylic acid [(3S,4R)-4-(3-fluoro-phenyl)-1-methyl-pyrrolidin-3-yl]-amide,
2-((S)-2,2,2-Trifluoro-1-methyl-ethylamino)-5,8-dihydro-6H-pyrido[3,4-d]pyrimidine-7-carboxylic acid

[(3S,4R)-4-(4-chloro-3-fluoro-phenyl)-1-methyl-pyrrolidin-3-yl]-amide, 2-((R)-2,2,2-Trifluoro-1-methyl-ethylamino)-5,8-dihydro-6H-pyrido[3,4-d]pyrimidine-7-carboxylic acid [(3S,4R)-4-(4-chloro-3-fluoro-phenyl)-1-methyl-pyrrolidin-3-yl]-amide, ((S)-2-Phenyl-pyrrolidin-1-yl)-[2-(tetrahydro-pyran-4-ylamino)-5,8-dihydro-6H-pyrido[3,4-d]pyrimidin-7-yl]-methanone, ((R)-2-Phenyl-pyrrolidin-1-yl)-[2-(tetrahydro-pyran-4-ylamino)-5,8-dihydro-6H-pyrido[3,4-d]pyrimidin-7-yl]-methanone,

[2-(4-Chloro-phenyl)-pyrrolidin-1-yl]-[2-(tetrahydro-pyran-4-ylamino)-5,8-dihydro-6H-pyrido[3,4-d]pyrimidin-7-yl]-methanone,

[2-(3-Chloro-phenyl)-pyrrolidin-1-yl]-[2-(tetrahydro-pyran-4-ylamino)-5,8-dihydro-6H-pyrido[3,4-d]pyrimidin-7-yl]-methanone, [2-(4-Fluoro-phenyl)-pyrrolidin-1-yl]-[2-(tetrahydro-pyran-4-ylamino)-5,8-dihydro-6H-pyrido[3,4-d]pyrimidin-7-yl]-methanone, (2-Phenyl-azetidin-1-yl)-[2-(tetrahydro-pyran-4-ylamino)-5,8-dihydro-6H-pyrido[3,4-d]pyrimidin-7-yl]-methanone,

[(R)-2-(2,5-Difluoro-phenyl)-pyrrolidin-1-yl]-[2-(tetrahydro-pyran-4-ylamino)-5,8-dihydro-6H-pyrido[3,4-d]pyrimidin-7-yl]-methanone, (2-Benzyl-pyrrolidin-1-yl)-[2-(tetrahydro-pyran-4-ylamino)-5,8-dihydro-6H-pyrido[3,4-d]pyrimidin-7-yl]-methanone, (2-Pyridin-3-yl-pyrrolidin-1-yl)-[2-(tetrahydro-pyran-4-ylamino)-5,8-dihydro-6H-pyrido[3,4-d]pyrimidin-7-yl]-methanone,

[2-(Tetrahydro-pyran-4-ylamino)-5,8-dihydro-6H-pyrido[3,4-d]pyrimidin-7-yl]-(2-thiazol-2-yl-pyrrolidin-1-yl)-methanone, (2-Phenyl-piperidin-1-yl)-[2-(tetrahydro-pyran-4-ylamino)-5,8-dihydro-6H-pyrido[3,4-d]pyrimidin-7-yl]-methanone, (2-Phenyl-piperazin-1-yl)-[2-(tetrahydro-pyran-4-ylamino)-5,8-dihydro-6H-pyrido[3,4-d]pyrimidin-7-yl]-methanone, (3-Phenyl-morpholin-4-yl)-[2-(tetrahydro-pyran-4-ylamino)-5,8-dihydro-6H-pyrido[3,4-d]pyrimidin-7-yl]-methanone, 2-(Tetrahydro-pyran-4-ylamino)-5,8-dihydro-6H-pyrido[3,4-d]pyrimidine-7-carboxylic acid [1-(3-chloro-4-fluoro-phenyl)-2-pyrrolidin-2-yl-ethyl]-amide, 2-(Tetrahydro-pyran-4-ylamino)-5,8-dihydro-6H-pyrido[3,4-d]pyrimidine-7-carboxylic acid [(R)-(4-chloro-3-fluoro-phenyl)-(R)-morpholin-2-yl-methyl]-amide, 2-(4-Fluoro-2-methyl-phenylamino)-5,8-dihydro-6H-pyrido[3,4-d]pyrimidine-7-carboxylic acid [(3S,4R)-4-(4-chloro-3-fluoro-phenyl)-1-methyl-pyrrolidin-3-yl]-amide, 2-(4-Fluoro-2-methyl-phenylamino)-5,8-dihydro-6H-pyrido[3,4-d]pyrimidine-7-carboxylic acid [(3S,4R)-4-(3-fluoro-phenyl)-1-methyl-pyrrolidin-3-yl]-amide, 2-((S)-2-Hydroxy-1-methyl-ethylamino)-5,8-dihydro-6H-pyrido[3,4-d]pyrimidine-7-carboxylic acid [(R)-1-(3-chloro-4-fluoro-phenyl)-ethyl]-amide, 2-Isopropylamino-5,8-dihydro-6H-pyrido[3,4-d]pyrimidine-7-carboxylic acid [(3S,4R)-4-(3-fluoro-4-trifluoromethyl-phenyl)-pyrrolidin-3-yl]-amide, 7-((S)-2-Hydroxy-1-methyl-ethylamino)-3,4-dihydro-1H-[2,6]naphthyridine-2-carboxylic acid [(R)-1-(3,4-dichloro-phenyl)-ethyl]-amide, (R)-2-(Tetrahydro-pyran-4-ylamino)-6,7-dihydro-5H-pyrano[2,3-d]pyrimidine-7-carboxylic acid [(S)-1-(4-chloro-3-fluoro-phenyl)-2-hydroxy-ethyl]-amide, 2-(Tetrahydro-pyran-4-ylamino)-5,8-dihydro-6H-pyrido[3,4-d]pyrimidine-7-carboxylic acid [4-(4-chloro-3-fluoro-phenoxy)-1-methyl-pyrrolidin-3-yl]-amide, 2-(Tetrahydro-pyran-4-ylamino)-5,8-dihydro-6H-pyrido[3,4-d]pyrimidine-7-carboxylic acid [4-(3-chloro-4-fluoro-phenoxy)-1-methyl-pyrrolidin-3-yl]-amide, 2-(Tetrahydro-pyran-4-ylamino)-5,8-dihydro-6H-pyrido[3,4-d]pyrimidine-7-carboxylic acid [4-(3,4-difluoro-phenoxy)-1-methyl-pyrrolidin-3-yl]-amide, 2-Isopropylamino-5,8-dihydro-6H-pyrido[3,4-d]pyrimidine-7-carboxylic acid [(R)-1-(4-chloro-phenyl)-3-hydroxy-propyl]-amide, N—((R)-1-(3,4-dichlorophenyl)ethyl)-2-((2S,4R)-2-(hydroxymethyl)tetrahydro-2H-pyran-4-ylamino)-5,6-dihydropyrido[3,4-d]pyrimidine-7(8H)-carboxamide, N—((S)-(3,4-dichlorophenyl)(oxazol-5-yl)methyl)-2-((3S,4S)-3-fluorotetrahydro-2H-pyran-4-ylamino)-5,6-dihydropyrido[3,4-d]pyrimidine-7(8H)-carboxamide, 4-Amino-3-(4-chloro-phenyl)-1-(2-isopropylamino-5,8-dihydro-6H-pyrido[3,4-d]pyrimidin-7-yl)-butan-1-one, 2-Isopropylamino-5,8-dihydro-6H-pyrido[3,4-d]pyrimidine-7-carboxylic acid [(S)-1-(3-chloro-4-fluoro-phenyl)-2-hydroxy-ethyl]-amide, 2-(2-Oxo-1,2,3,4-tetrahydro-quinolin-6-ylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-((S)-1-Hydroxymethyl-propylamino)-5,8-dihydro-6H-pyrido[3,4-d]pyrimidine-7-carboxylic acid [(S)-1-(3-chloro-4-fluoro-phenyl)-2-hydroxy-ethyl]-amide, (S)-4-Amino-3-(4-chloro-phenyl)-1-(2-isopropylamino-5,8-dihydro-6H-pyrido[3,4-d]pyrimidin-7-yl)-butan-1-one, 2-Isopropylamino-5,8-dihydro-6H-pyrido[3,4-d]pyrimidine-7-carboxylic acid (4-phenyl-piperidin-4-yl)-amide, 2-Isopropylamino-5,8-dihydro-6H-pyrido[3,4-d]pyrimidine-7-carboxylic acid [(S)-2-amino-1-(3-chloro-4-fluoro-phenyl)-ethyl]-amide, 2-Isopropylamino-5,8-dihydro-6H-pyrido[3,4-d]pyrimidine-7-carboxylic acid [1-(3,4-dichloro-phenyl)-3-methylamino-propyl]-amide, 2-[2-(2-Fluoro-phenyl)-ethylamino]-5,8-dihydro-6H-pyrido[3,4-d]pyrimidine-7-carboxylic acid [(S)-1-(3-chloro-4-fluoro-phenyl)-2-hydroxy-ethyl]-amide, 2-[2-(6-Methyl-pyridin-2-yl)-ethylamino]-5,8-dihydro-6H-pyrido[3,4-d]pyrimidine-7-carboxylic acid [(S)-1-(3-chloro-4-fluoro-phenyl)-2-hydroxy-ethyl]-amide, 2-(2-Pyridin-3-yl-ethylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-[2-(3-Chloro-phenyl)-ethylamino]-5,8-dihydro-6H-pyrido[3,4-d]pyrimidine-7-carboxylic acid [(S)-1-(3-chloro-4-fluoro-phenyl)-2-hydroxy-ethyl]-amide, 2-(2-Hydroxy-ethylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-Isopropylamino-5,8-dihydro-6H-pyrido[3,4-d]pyrimidine-7-carboxylic acid [(S)-1-(3-chloro-4-fluoro-phenyl)-2-methylamino-ethyl]-amide, 3-(4-Fluoro-phenyl)-1-(2-isopropylamino-5,8-dihydro-6H-pyrido[3,4-d]pyrimidin-7-yl)-propan-1-one, 2-Isopropylamino-5,8-dihydro-6H-pyrido[3,4-d]pyrimidine-7-carboxylic acid [4-(4-chloro-3-fluoro-phenyl)-piperidin-4-yl]-amide, 2-((S)-1-Hydroxymethyl-2-phenyl-ethylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-Cyclopentylamino-5,8-dihydro-6H-pyrido[3,4-d]pyrimidine-7-carboxylic acid [(S)-1-(3-chloro-4-fluoro-phenyl)-2-hydroxy-ethyl]-amide, 2-((R)-2-Hydroxy-1-methyl-ethylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-tert-Butylamino-5,8-dihydro-6H-pyrido[3,4-d]pyrimidine-7-carboxylic acid [(S)-1-(3-chloro-4-fluoro-phenyl)-2-hydroxy-ethyl]-amide, 3-(3-Fluoro-phenyl)-1-(2-isopropylamino-5,8-dihydro-6H-pyrido[3,4-d]pyrimidin-7-yl)-propan-1-one, 3-(4-Chloro-2-fluoro-phenyl)-1-(2-isopropylamino-5,8-dihydro-6H-pyrido[3,4-d]pyrimidin-7-yl)-propan-1-one, 3-(3,4-Dichloro-phenyl)-1-(2-isopropylamino-5,8-dihydro-6H-pyrido[3,4-d]pyrimidin-7-yl)-propan-1-one, 3-(2,4-Dichloro-phenyl)-1-(2-isopropylamino-5,8-dihydro-6H-pyrido[3,4-d]pyrimidin-7-yl)-propan-1-one, 3-(3,4-Difluoro-phenyl)-1-(2-isopropylamino-5,8-dihydro-6H-pyrido[3,4-d]pyrimidin-7-yl)-propan-1-one, 2-Isopropylamino-5,8-dihydro-6H-pyrido[3,4-d]pyrimidine-7-carboxylic acid [(3-chloro-4-fluoro-phenyl)-methylcarbamoyl-methyl]-amide, 2-Isopropylamino-5,8-dihydro-6H-pyrido[3,4-d]pyrimidine-7-carboxylic acid [(S)-1-(3-chloro-4-fluoro-phenyl)-2-ethylamino-ethyl]-amide, 2-Isopropylamino-5,8-dihydro-6H-pyrido[3,4-d]pyrimidine-7-carboxylic acid [(S)-1-(3-chloro-4-fluoro-phenyl)-2-(2-hydroxy-ethylamino)-ethyl]-amide, 2-Isopropylamino-5,8-dihydro-6H-pyrido[3,4-d]pyrimidine-7-carboxylic acid [(S)-1-(3-chloro-4-fluoro-phenyl)-2-isobutylamino-ethyl]-amide, 2-Methylamino-5,8-dihydro-6H-pyrido[3,4-d]pyrimidine-7-carboxylic acid [(S)-1-(3-chloro-4-fluoro-phenyl)-2-hydroxy-ethyl]-amide, 2-[2-(4-Chloro-phenyl)-1-methyl-ethylamino]-5,8-dihydro-6H-pyrido[3,4-d]pyrimidine-7-carboxylic acid [1-(3-chloro-4-fluoro-phenyl)-2-hydroxy-ethyl]-amide, 2-Isobutylamino-5,8-dihydro-6H-pyrido[3,4-d]pyrimidine-7-carboxylic acid [(S)-1-(3-chloro-4-fluoro-phenyl)-2-hydroxy-ethyl]-amide, 2-((S)-2-Methoxy-1-methyl-ethylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-(3,5-Dimethyl-isoxazol-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-(4-Fluoro-phenylamino)-5,8-dihydro-6H-pyrido[3,4-d]pyrimidine-7-carboxylic acid [(S)-1-(3-chloro-4-fluoro-phenyl)-2-methylamino-ethyl]-amide, 2-(4-Fluoro-phenylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-(4-Fluoro-phenylamino)-5,8-dihydro-6H-pyrido[3,4-d]pyrimidine-7-carboxylic acid [3-amino-1-(3,4-dichloro-phenyl)-propyl]-amide, 2-(3,5-Dimethyl-isoxazol-4-ylamino)-5,8-dihydro-6H-pyrido[3,4-d]pyrimidine-7-carboxylic acid [3-amino-1-(3,4-dichloro-phenyl)-propyl]-amide, 2-(3,5-Dimethyl-isoxazol-4-ylamino)-5,8-dihydro-6H-pyrido[3,4-d]pyrimidine-7-carboxylic acid [(S)-1-(3-chloro-4-fluoro-phenyl)-2-methylamino-ethyl]-amide, 2-Isopropylamino-5,8-dihydro-6H-pyrido[3,4-d]pyrimidine-7-carboxylic acid [(1S,2S)-1-(3-chloro-4-fluoro-phenyl)-2-hydroxy-propyl]-amide, 2-Isopropylamino-5,8-dihydro-6H-pyrido[3,4-d]pyrimidine-7-carboxylic acid [(S)-1-(3-chloro-4-fluoro-phenyl)-2-(2-methoxy-ethylamino)-ethyl]-amide, 2-Isopropylamino-5,8-dihydro-6H-pyrido[3,4-d]pyrimidine-7-carboxylic acid [(S)-2-acetylamino-1-(3-chloro-4-fluoro-phenyl)-ethyl]-amide, 2-Isopropylamino-5,8-dihydro-6H-pyrido[3,4-d]pyrimidine-7-carboxylic acid [(S)-1-(3-chloro-4-fluoro-phenyl)-2-methanesulfonylamino-ethyl]-amide, 2-Isopropylamino-5,8-dihydro-6H-pyrido[3,4-d]pyrimidine-7-carboxylic acid [(S)-1-(3-chloro-4-fluoro-phenyl)-2-(cyclopropylmethyl-amino)-ethyl]-amide, 2-Acetylamino-5,8-dihydro-6H-pyrido[3,4-d]pyrimidine-7-carboxylic acid [(S)-1-(3-chloro-4-fluoro-phenyl)-2-hydroxy-ethyl]-amide, 2-((S)-2-Hydroxy-propylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-Amino-5,8-dihydro-6H-pyrido[3,4-d]pyrimidine-7-carboxylic acid [(S)-1-(3-chloro-4-fluoro-phenyl)-2-hydroxy-ethyl]-amide, 4-Amino-3-(4-chloro-3-fluoro-phenyl)-1-(2-isopropylamino-5,8-dihydro-6H-pyrido[3,4-d]pyrimidin-7-yl)-butan-1-one, 4-Amino-3-(3-chloro-4-fluoro-phenyl)-1-(2-isopropylamino-5,8-dihydro-6H-pyrido[3,4-d]pyrimidin-7-yl)-butan-1-one, 2-Isopropylamino-5,8-dihydro-6H-pyrido[3,4-d]pyrimidine-7-carboxylic acid [(S)-1-(3-chloro-4-fluoro-phenyl)-2-(pyrimidin-2-ylamino)-ethyl]-amide, 2-Isopropylamino-5,8-dihydro-6H-pyrido[3,4-d]pyrimidine-7-carboxylic acid [(S)-1-(3-chloro-4-fluoro-phenyl)-2-(pyrimidin-4-ylamino)-ethyl]-amide, 2-(4-Fluoro-phenylamino)-5,8-dihydro-6H-pyrido[3,4-d]pyrimidine-7-carboxylic acid [(1S,2S)-1-(3-chloro-4-fluoro-phenyl)-2-hydroxy-propyl]-amide, 2-Isopropylamino-5,8-dihydro-6H-pyrido[3,4-d]pyrimidine-7-carboxylic acid [(S)-(4-chloro-3-fluoro-phenyl)-(S)-pyrrolidin-2-yl-methyl]-amide, 2-Isopropylamino-5,8-dihydro-6H-pyrido[3,4-d]pyrimidine-7-carboxylic acid [(R)-1-(4-fluoro-phenyl)-3-hydroxy-propyl]-amide, 2-(2-Methyl-pyridin-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-(4-Chloro-pyridin-2-ylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-(2-Methyl-pyridin-3-ylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-(Tetrahydro-pyran-4-ylamino)-5,8-dihydro-6H-pyrido[3,4-d]pyrimidine-7-carboxylic acid [(S)-(3,4-dichloro-phenyl)-(2H-pyrazol-3-yl)-methyl]-amide, 2-Isopropylamino-5,8-dihydro-6H-pyrido[3,4-d]pyrimidine-7-carboxylic acid [(S)-1-(3-chloro-4-fluoro-phenyl)-2-methoxy-ethyl]-amide, 2-(3-Chloro-4-fluoro-phenylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-(4-Chloro-3-fluoro-phenylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-Isopropylamino-5,8-dihydro-6H-pyrido[3,4-d]pyrimidine-7-carboxylic acid [(R)-1-(3,4-dichloro-phenyl)-3-methylamino-propyl]-amide, 2-Isopropylamino-5,8-dihydro-6H-pyrido[3,4-d]pyrimidine-7-carboxylic acid [(S)-1-(3,4-dichloro-phenyl)-3-methylamino-propyl]-amide, 2-(4-Fluoro-phenylamino)-5,8-dihydro-6H-pyrido[3,4-d]pyrimidine-7-carboxylic acid [3-(4-chloro-phenyl)-pyrrolidin-3-yl]-amide, 2-((S)-2-Hydroxy-1-methyl-ethylamino)-5,8-dihydro-6H-pyrido[3,4-d]pyrimidine-7-carboxylic acid [(S)-1-(3-chloro-4-fluoro-phenyl)-2-methoxy-ethyl]-amide, 2-(4-Methyl-pyrimidin-5-ylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-Isopropylamino-5,8-dihydro-6H-pyrido[3,4-d]pyrimidine-7-carboxylic acid ((1S,2S)-2-hydroxy-indan-1-yl)-amide, 2-Isopropylamino-5,8-dihydro-6H-pyrido[3,4-d]pyrimidine-7-carboxylic acid [1-(3-chloro-4-fluoro-phenyl)-2-hydroxy-2-methyl-propyl]-amide, 2-Isopropylamino-5,8-dihydro-6H-pyrido[3,4-d]pyrimidine-7-carboxylic acid [(S)-1-(3-chloro-4-fluoro-phenyl)-2-(2-methoxy-ethoxy)-ethyl]-amide, 2-((S)-2-Hydroxy-1-methyl-ethylamino)-5,8-dihydro-6H-pyrido[3,4-d]pyrimidine-7-carboxylic acid [(R)-1-(3-fluoro-4-trifluoromethyl-phenyl)-ethyl]-amide, 2-Isopropylamino-5,8-dihydro-6H-pyrido[3,4-d]pyrimidine-7-carboxylic acid [(R)-1-(3,4-dichloro-phenyl)-3-hydroxy-propyl]-amide, 2-Isopropylamino-5,8-dihydro-6H-pyrido[3,4-d]pyrimidine-7-carboxylic acid [(R)-1-(3-fluoro-4-trifluoromethyl-phenyl)-3-hydroxy-propyl]-amide, 2-Isopropylamino-5,8-dihydro-6H-pyrido[3,4-d]pyrimidine-7-carboxylic acid [(S)-1-(3,4-dichloro-phenyl)-3-hydroxy-propyl]-amide, 2-Isopropylamino-5,8-dihydro-6H-pyrido[3,4-d]pyrimidine-7-carboxylic acid [(S)-1-(3-fluoro-4-trifluoromethyl-phenyl)-3-hydroxy-propyl]-amide, 2-(Pyrimidin-5-ylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-(1-Methyl-1H-pyrazol-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-Isopropylamino-5,8-dihydro-6H-pyrido[3,4-d]pyrimidine-7-carboxylic acid ((S)-1-hydroxymethyl-2-phenyl-ethyl)-amide, 2-((S)-2-Hydroxy-1-methyl-ethylamino)-5,8-dihydro-6H-pyrido[3,4-d]pyrimidine-7-carboxylic acid [(S)-1-(3-chloro-4-fluoro phenyl)-2-(2-methoxy-ethoxy)-ethyl]-amide, 2-Isopropylamino-5,8-dihydro-6H-pyrido[3,4-d]pyrimidine-7-carboxylic acid [(S)-2-(4-chloro-phenyl)-1-hydroxymethyl-ethyl]-amide, 2-Isopropylamino-5,8-dihydro-6H-pyrido[3,4-d]pyrimidine-7-carboxylic acid [(S)-(3-fluoro-4-trifluoromethyl-phenyl)-(S)-pyrrolidin-2-yl-methyl]-amide, 1-(2-Isopropylamino-5,8-dihydro-6H-pyrido[3,4-d]pyrimidin-7-yl)-3-(4-trifluoromethyl-phenyl)-butan-1-one, 1-[2-(2-Hydroxy-1-methyl-ethylamino)-5,8-dihydro-6H-pyrido[3,4-d]pyrimidin-7-yl]-3-(4-trifluoromethyl-phenyl)-butan-1-one, 2-Isopropylamino-5,8-dihydro-6H-pyrido[3,4-d]pyrimidine-7-carboxylic acid [(S)-2-(3,4-dichloro-phenyl)-1-hydroxymethyl-ethyl]-amide, 2-(2-Hydroxy-1-methyl-ethylamino)-5,8-dihydro-6H-pyrido[3,4-d]pyrimidine-7-carboxylic acid [1-(3,4-dichloro-phenyl)-3-hydroxy-propyl]-amide, 2-(2-Hydroxy-1-methyl-ethylamino)-5,8-dihydro-6H-pyrido[3,4-d]pyrimidine-7-carboxylic acid [1-(3-fluoro-4-trifluoromethyl-phenyl)-propyl]-amide, 2-Isopropylamino-5,8-dihydro-6H-pyrido[3,4-d]pyrimidine-7-carboxylic acid [1-(3-fluoro-4-trifluoromethyl-phenyl)-propyl]-amide, 7-Isopropylamino-3,4-dihydro-1H-[2,6]naphthyridine-2-carboxylic acid [(S)-1-(3-chloro-4-fluoro-phenyl)-2-hydroxy-ethyl]-amide, 7-(4-Fluoro-phenylamino)-3,4-dihydro-1H-[2,6]naphthyridine-2-carboxylic acid [(S)-1-(3-chloro-4-fluoro-phenyl)-2-hydroxy-ethyl]-amide, 2-(3-Hydroxy-cyclopentylamino)-5,8-dihydro-6H-pyrido[3,4-d]pyrimidine-7-carboxylic acid [1-(3,4-dichloro-phenyl)-3-hydroxy-propyl]-amide, 2-((1S,3S)-3-Hydroxy-cyclopentylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-((S)-1-Hydroxymethyl-propylamino)-5,8-dihydro-6H-pyrido[3,4-d]pyrimidine-7-carboxylic acid [1-(4-fluoro-phenyl)-1-methyl-ethyl]-amide, 2-((1S,3S)-3-Hydroxy-cyclopentylamino)-5,8-dihydro-6H-pyrido[3,4-d]pyrimidine-7-carboxylic acid [(S)-1-(3-chloro-4-fluoro-phenyl)-2-ethoxy-ethyl]-amide, 2-((S)-2-Hydroxy-1-methyl-ethylaminio)-5,8-dihydro-6H-pyrido[3,4-d]primidine-7-carboxylic acid [(S)-1-(3-chloro-4-fluoro-phenyl)-2-isopropoxy-ethyl]-amide, 2-((S)-2-Hydroxy-1-methyl-ethylamino)-5,8-dihydro-6H-pyrido[3,4-d]pyrimidine-7-carboxylic acid [(S)-1-(3-chloro-4-fluoro-phenyl)-2-ethoxy-ethyl]-amide, 2-((1S,3S)-3-Hydroxy-cyclopentylamino)-5,8-dihydro-6H-pyrido[3,4-d]pyrimidine-7-carboxylic acid [(S)-1-(3-chloro-4-fluoro-phenyl)-2-isopropoxy-ethyl]-amide, 2-Isopropylamino-8-oxo-5,8-dihydro-6H-pyrido[3,4-d]pyrimidine-7-carboxylic acid [(S)-(4-chloro-3-fluoro-phenyl)-(S)-pyrrolidin-2-yl-methyl]-amide, 3-(3-Fluoro-4-trifluoromethyl-phenyl)-1-[2-(2-hydroxy-1-methyl-ethylamino)-5,8-dihydro-6H-pyrido[3,4-d]pyrimidin-7-yl]-hexan-1-one, 3-(3-Fluoro-4-trifluoromethyl-phenyl)-1-(2-isopropylamino-5,8-dihydro-6H-pyrido[3,4-d]pyrimidin-7-yl)-hexan-1-one, 2-Isopropylamino-5,8-dihydro-6H-pyrido[3,4-d]pyrimidine-7-carboxylic acid [(S)-(3-fluoro-4-trifluoromethyl-phenyl)-(6-oxo-1,6-dihydro-pyridin-2-yl)-methyl]-amide, 2-Isopropylamino-5,8-dihydro-6H-pyrido[3,4-d]pyrimidine-7-carboxylic acid [(S)-(3-fluoro-4-trifluoromethyl-phenyl)-(6-methoxy-pyridin-2-yl)-methyl]-amide, 2-Isopropylamino-5,8-dihydro-6H-pyrido[3,4-d]pyrimidine-7-carboxylic acid [(S)-1-(3-fluoro-4-trifluoromethyl-phenyl)-2-pyrrolidin-1-yl-ethyl]-amide, 2-Isopropylamino-5,8-dihydro-6H-pyrido[3,4-d]pyrimidine-7-carboxylic acid [(S)-2-(3-fluoro-4-trifluoromethyl-phenyl)-2-pyrrolidin-1-yl-ethyl]-amide, 2-((1S,3S)-3-Hydroxy-cyclopentylamino)-5,8-dihydro-6H-pyrido[3,4-d]pyrimidine-7-carboxylic acid [(R)-(3-chloro-4-fluoro-phenyl)-cyclopropyl-methyl]-amide, 2-((1S,3S)-3-Hydroxy-cyclopentylamino)-5,8-dihydro-6H-pyrido[3,4-d]pyrimidine-7-carboxylic acid [(R)-(3-chloro-4-fluoro-phenyl)-cyclopentyl-methyl]-amide, 7-(3-Hydroxy-cyclopentylamino)-3,4-dihydro-1H-[2,6]naphthyridine-2-carboxylic acid [1-(3,4-dichloro-phenyl)-ethyl]-amide, 2-(2,2,2-Trifluoro-1-methyl-ethylamino)-5,8-dihydro-6H-pyrido[3,4-d]pyrimidine-7-carboxylic acid [1-(3-chloro-4-fluoro-phenyl)-2-hydroxy-ethyl]-amide, 2-((1S,3S)-3-Hydroxy-cyclopentylamino)-5,8-dihydro-6H-pyrido[3,4-d]pyrimidine-7-carboxylic acid [(R)-1-(3-fluoro-4-trifluoromethyl-phenyl)-2-methyl-propyl]-amide, 2-[(3-Chloro-4-fluoro-phenyl)-(2-hydroxy-ethyl)-amino]-1-(2-isopropylamino-5,8-dihydro-6H-pyrido[3,4-d]pyrimidin-7-yl)-ethanone, 2-((1S,3S)-3-Hydroxy-cyclopentylamino)-5,8-dihydro-6H-pyrido[3,4-d]pyrimidine-7-carboxylic acid [(R)-1-(3,4-dichloro-phenyl)-3-hydroxy-propyl]-amide, 7-(2-Cyclopropyl-pyridin-4-ylamino)-3,4-dihydro-1H-[2,6]naphthyridine-2-carboxylic acid [(R)-1-(3,4-dichloro-phenyl)-ethyl]-amide, 2-((S)-1-Hydroxymethyl-2-phenyl-ethylamino)-5,8-dihydro-6H-pyrido[3,4-d]pyrimidine-7-carboxylic acid [(R)-1-(3,4-dichloro-phenyl)-ethyl]-amide, 3-(3,4-Dichloro-phenyl)-1-[2-(3-hydroxy-cyclopentylamino)-5,8-dihydro-6H-pyrido[3,4-d]pyrimidin-7-yl]-butan-1-one, 7-(2-Methyl-pyridin-4-ylamino)-3,4-dihydro-1H-[2,6]naphthyridine-2-carboxylic acid [(R)-1-(3,4-dichloro-phenyl)-ethyl]-amide, 2-((S)-2-Hydroxy-1-methyl-ethylamino)-8-oxo-5,8-dihydro-6H-pyrido[3,4-d]pyrimidine-7-carboxylic acid [(R)-1-(3,4-dichloro-phenyl)-ethyl]-amide, 2-((S)-2-Hydroxy-1-methyl-ethylamino)-5,8-dihydro-6H-pyrido[3,4-d]pyrimidine-7-carboxylic acid [(R)-1-(3,4-difluoro-phenyl)-ethyl]-amide, 2-((S)-3,3-Difluoro-cyclopentylamino)-5,8-dihydro-6H-pyrido[3,4-d]pyrimidine-7-carboxylic acid [(R)-1-(3,4-dichloro-phenyl)-ethyl]-amide, 2-(2-Hydroxy-1-methyl-ethylamino)-5,8-dihydro-6H-pyrido[3,4-d]pyrimidine-7-carboxylic acid [1-(3,4-dichloro-phenyl)-3,3,3-trifluoro-propyl]-amide, 2-(2-Ethyl-2H-pyrazol-3-ylamino)-5,8-dihydro-6H-pyrido[3,4-d]pyrimidine-7-carboxylic acid [(R)-1-(3,4-dichloro-phenyl)-ethyl]-amide, 2-(1-Benzyl-1H-pyrazol-4-ylamino)-5,8-dihydro-6H-pyrido[3,4-d]pyrimidine-7-carboxylic acid [(R)-1-(3,4-dichloro-phenyl)-ethyl]-amide, 2-((S)-2-Hydroxy-1-methyl-ethylamino)-5,8-dihydro-6H-pyrido[3,4-d]pyrimidine-7-carboxylic acid [(R)-1-(3,4,5-trifluoro-phenyl)-ethyl]-amide, 2-(2-Hydroxy-1-methyl-ethylamino)-5,8-dihydro-6H-pyrido[3,4-d]pyrimidine-7-carboxylic acid [(3,4-dichloro-phenyl)-(2H-pyrazol-3-yl)-methyl]-amide, 7-(1-Methyl-1H-pyrazol-4-ylamino)-3,4-dihydro-1H-[2,6]naphthyridine-2-carboxylic acid [(R)-1-(3,4-dichloro-phenyl)-ethyl]-amide, 2-(3-Hydroxy-cyclopentylamino)-5,8-dihydro-6H-pyrido[3,4-d]pyrimidine-7-carboxylic acid [1-(3,4-dichloro-phenyl)-3,3,3-trifluoro-propyl]-amide, 7-(2-Hydroxy-1-methyl-ethylamino)-3,4-dihydro-1H-[2,6]naphthyridine-2-carboxylic acid [1-(3,4-dichloro-phenyl)-3,3,3-trifluoro-propyl]-amide, 7-((S)-2-Hydroxy-1-methyl-ethylamino)-3,4-dihydro-1H-[2,6]naphthyridine-2-carboxylic acid [(R)-1-(3,4-dichloro-phenyl)-propyl]-amide, 2-(2-Methyl-pyrimidin-4-ylamino)-5,8-dihydro-6H-pyrido[3,4-d]pyrimidine-7-carboxylic acid [(R)-1-(3,4-dichloro-phenyl)-ethyl]-amide, 2-(2-Hydroxy-1-methyl-ethylamino)-5,8-dihydro-6H-pyrido[3,4-d]pyrimidine-7-carboxylic acid [1-(3,4-dichloro-phenyl)-2-methyl-propyl]-amide, 7-((S)-2-Hydroxy-1-methyl-ethylamino)-3,4-dihydro-1H-[2,6]naphthyridine-2-carboxylic acid [(S)-1-(3,4-dichloro-phenyl)-2-methoxy-ethyl]-amide, 2-((S)-2-Hydroxy-1-methyl-ethylamino)-5,8-dihydro-6H-pyrido[3,4-d]pyrimidine-7-carboxylic acid [(R)-1-(3,4-dichloro-phenyl)-3,3,3-trifluoro-propyl]-amide, 2-((S)-2-Hydroxy-1-methyl-ethylamino)-5,8-dihydro-6H-pyrido[3,4-d]pyrimidine-7-carboxylic acid [(S)-1-(3,4-dichloro-phenyl)-3,3,3-trifluoro-propyl]-amide, 7-((S)-2-Hydroxy-1-methyl-ethylamino)-3,4-dihydro-1H-[2,6]naphthyridine-2-carboxylic acid [(R)-1-(3,4-dichloro-phenyl)-3-hydroxy-propyl]-amide, 2-(2-Hydroxy-1-methyl-ethylamino)-5,8-dihydro-6H-pyrido[3,4-d]pyrimidine-7-carboxylic acid [2-(4-chloro-3-fluoro-phenyl)-1-methyl-ethyl]-amide, 2-(2-Hydroxy-1-methyl-ethylamino)-5,8-dihydro-6H-pyrido[3,4-d]pyrimidine-7-carboxylic acid 4-chloro-3-trifluoromethoxy-benzylamide, 2-((S)-2-Hydroxy-1-methyl-ethylamino)-5,8-dihydro-6H-pyrido[3,4-d]pyrimidine-7-carboxylic acid [(1S,2S)-1-(3-chloro-4-fluoro-phenyl)-2-hydroxy-propyl]-amide, 7-((S)-2-Hydroxy-1-methyl-ethylamino)-3,4-dihydro-1H-[2,6]naphthyridine-2-carboxylic acid [(1S,2S)-1-(3-chloro-4-fluoro-phenyl)-2-hydroxy-propyl]-amide, 2-(2-Hydroxy-1-methyl-ethylamino)-5,8-dihydro-6H-pyrido[3,4-d]pyrimidine-7-carboxylic acid [2-(4-chloro-phenyl)-1-methyl-ethyl]-amide, 2-((S)-2-Hydroxy-1-methyl-ethylamino)-5,8-dihydro-6H-pyrido[3,4-d]pyrimidine-7-carboxylic acid [(R)-1-(2,4-dichloro-phenyl)-ethyl]-amide, 7-((S)-2-Hydroxy-1-methyl-ethylamino)-3,4-dihydro-1H-[2,6]naphthyridine-2-carboxylic acid [(S)-1-(4-chloro-3-fluoro-phenyl)-2-methoxy-ethyl]-amide, 2-((S)-2-Hydroxy-1-methyl-ethylamino)-5,8-dihydro-6H-pyrido[3,4-d]pyrimidine-7-carboxylic acid 4-chloro-3-trifluoromethyl-benzylamide, 2-((S)-2-Hydroxy-1-methyl-ethylamino)-5,8-dihydro-6H-pyrido[3,4-d]pyrimidine-7-carboxylic acid 3-trifluoromethyl-benzylamide, 2-((S)-2-Hydroxy-1-methyl-ethylamino)-5,8-dihydro-6H-pyrido[3,4-d]pyrimidine-7-carboxylic acid 3-chloro-benzylamide, 2-((S)-2-Hydroxy-1-methyl-ethylamino)-5,8-dihydro-6H-pyrido[3,4-d]pyrimidine-7-carboxylic acid 4-chloro-2-fluoro-benzylamide, 2-((S)-2-Hydroxy-1-methyl-ethylamino)-5,8-dihydro-6H-pyrido[3,4-d]pyrimidine-7-carboxylic acid 2,4-dichloro-benzylamide, 2-((S)-2-Hydroxy-1-methyl-ethylamino)-5,8-dihydro-6H-pyrido[3,4-d]pyrimidine-7-carboxylic acid 2,3-dichloro-benzylamide, 2-((S)-2-Hydroxy-1-methyl-ethylamino)-5,8-dihydro-6H-pyrido[3,4-d]pyrimidine-7-carboxylic acid 4-chloro-3-fluoro-benzylamide, 2-((S)-2-Hydroxy-1-methyl-ethylamino)-5,8-dihydro-6H-pyrido[3,4-d]pyrimidine-7-carboxylic acid 3-chloro-4-trifluoromethoxy-benzylamide, 7-((S)-2-Hydroxy-1-methyl-ethylamino)-3,4-dihydro-1H-[2,6]naphthyridine-2-carboxylic acid [(R)-1-(3-chloro-4-fluoro-phenyl)-ethyl]-amide 7-Isopropylamino-3,4-dihydro-1H-[2,6]naphthyridine-2-carboxylic acid [(R)-1-(3,4-dichloro-phenyl)-3-hydroxy-propyl]-amide, 2-(1-Methyl-6-oxo-1,6-dihydro-pyridin-3-ylamino)-5,8-dihydro-6H-pyrido[3,4-d]pyrimidine-7-carboxylic acid [(R)-1-(3,4-dichloro-phenyl)-ethyl]-amide, 2-(1-Methyl-6-oxo-1,6-dihydro-pyridin-3-ylamino)-5,8-dihydro-6H-pyrido[3,4-d]pyrimidine-7-carboxylic acid [(R)-1-(3-fluoro-4-trifluoromethyl-phenyl)-ethyl]-amide, 2-((S)-2-Hydroxy-1-methyl-ethylamino)-5,8-dihydro-6H-pyrido[3,4-d]pyrimidine-7-carboxylic acid (benzooxazol-2-ylmethyl)-amide, 2-((S)-2-Hydroxy-1-methyl-ethylamino)-5,8-dihydro-6H-pyrido[3,4-d]pyrimidine-7-carboxylic acid (benzothiazol-2-ylmethyl)-amide, 2-((S)-2-Hydroxy-1-methyl-ethylamino)-5,8-dihydro-6H-pyrido[3,4-d]pyrimidine-7-carboxylic acid [(S)-1-(3,4-dichloro-phenyl)-2-methyl-propyl]-amide, 2-((S)-2-Hydroxy-1-methyl-ethylamino)-5,8-dihydro-6H-pyrido[3,4-d]pyrimidine-7-carboxylic acid [(S)-(3-fluoro-4-trifluoromethyl-phenyl)-(S)-pyrrolidin-2-yl-methyl]-amide, 2-((S)-2-Hydroxy-1-methyl-ethylamino)-5,8-dihydro-6H-pyrido[3,4-d]pyrimidine-7-carboxylic acid [(S)-(4-chloro-3-fluoro-phenyl)-(S)-pyrrolidin-2-yl-methyl]-amide, 2-(2-Hydroxy-1-methyl-ethylamino)-5,8-dihydro-6H-pyrido[3,4-d]pyrimidine-7-carboxylic acid (2-phenyl-cyclopropyl)-amide, 2-Isopropylamino-5,8-dihydro-6H-pyrido[3,4-d]pyrimidine-7-carboxylic acid (2-phenyl-cyclopropyl)-amide, 8-Fluoro-7-((S)-2-hydroxy-1-methyl-ethylamino)-3,4-dihydro-1H-[2,6]naphthyridine-2-carboxylic acid [(R)-1-(3,4-dichloro-phenyl)-ethyl]-amide, 2-((S)-2-Hydroxy-1-methyl-ethylamino)-5,8-dihydro-6H-pyrido[3,4-d]pyrimidine-7-carboxylic acid 3-chloro-4-trifluoromethyl-benzylamide, 2-((S)-2-Hydroxy-1-methyl-ethylamino)-5,8-dihydro-6H-pyrido[3,4-d]pyrimidine-7-carboxylic acid 2-chloro-4-trifluoromethyl-benzylamide, 2-((S)-2-Hydroxy-1-methyl-ethylamino)-5,8-dihydro-6H-pyrido pyrimidine-7-carboxylic acid 4-chloro-3-methyl-benzylamide, 2-((S)-2-Hydroxy-1-methyl-ethylamino)-5,8-dihydro-6H-pyrido[3,4-d]pyrimidine-7-carboxylic acid 4-trifluoromethylsulfanyl-benzylamide, 2-((S)-2-Hydroxy-1-methyl-ethylamino)-5,8-dihydro-6H-pyrido pyrimidine-7-carboxylic acid 3-chloro-4-methoxy-benzylamide, 2-((S)-2-Hydroxy-1-methyl-ethylamino)-5,8-dihydro-6H-pyrido[3,4-d]pyrimidine-7-carboxylic acid 3-chloro-4-methyl-benzylamide, 2-((S)-2-Hydroxy-1-methyl-ethylamino)-5,8-dihydro-6H-pyrido[3,4-d]pyrimidine-7-carboxylic acid 4-difluoromethoxy-benzylamide, 2-((S)-2-Hydroxy-1-methyl-ethylamino)-5,8-dihydro-6H-pyrido[3,4-d]pyrimidine-7-carboxylic acid 3-acetylamino-benzylamide, 2-((S)-2-Hydroxy-1-methyl-ethylamino)-5,8-dihydro-6H-pyrido[3,4-d]pyrimidine-7-carboxylic acid 4-cyano-benzylamide, 2-((S)-2-Hydroxy-1-methyl-ethylamino)-5,8-dihydro-6H-pyrido pyrimidine-7-carboxylic acid 4-methylsulfanyl-benzylamide, 2-((S)-2-Hydroxy-1-methyl-ethylamino)-5,8-dihydro-6H-pyrido[3,4-d]pyrimidine-7-carboxylic acid (1H-indol-6-ylmethyl)-amide, 2-((S)-2-Hydroxy-1-methyl-ethylamino)-5,8-dihydro-6H-pyrido[3,4-d]pyrimidine-7-carboxylic acid (1H-benzoimidazol-2-ylmethyl)-amide, 2-(2-Hydroxy-1-methyl-ethylamino)-5,8-dihydro-6H-pyrido[3,4-d]pyrimidine-7-carboxylic acid [4-(4-trifluoromethyl-phenyl)-pyrrolidin-3-yl]-amide, 2-(2-Hydroxy-1-methyl-ethylamino)-5,8-dihydro-6H-pyrido[3,4-d]pyrimidine-7-carboxylic acid [4-(4-chloro-phenyl)-pyrrolidin-3-yl]-amide, 7-(Tetrahydro-pyran-4-ylamino)-3,4-dihydro-1H-[2,6]naphthyridine-2-carboxylic acid [(R)-1-(3,4-dichloro-phenyl)-3-hydroxy-propyl]-amide, 2-(2-Hydroxy-1-methyl-ethylamino)-5,8-dihydro-6H-pyrido[3,4-d]pyrimidine-7-carboxylic acid [4-(3,4-dichloro-phenyl)-pyrrolidin-3-yl]-amide, 2-Isopropylamino-5,8-dihydro-6H-pyrido[3,4-d]pyrimidine-7-carboxylic acid [4-(3,4-dichloro-phenyl)-pyrrolidin-3-yl]-amide, 7-(Tetrahydro-pyran-4-ylamino)-3,4-dihydro-1H-[2,6]naphthyridine-2-carboxylic acid [(S)-1-(3-chloro-4-fluoro-phenyl)-2-hydroxy-ethyl]-amide, 2-Isopropylamino-5,8-dihydro-6H-pyrido[3,4-d]pyrimidine-7-carboxylic acid [1-(1H-benzoimidazol-2-yl)-ethyl]-amide, 2-Isopropylamino-5,8-dihydro-6H-pyrido[3,4-d]pyrimidine-7-carboxylic acid (1-benzothiazol-2-yl-ethyl)-amide, 7-Isopropylamino-3,4-dihydro-1H-[2,6]naphthyridine-2-carboxylic acid [(S)-1-(3,4-dichloro-phenyl)-2-hydroxy-ethyl]-amide, 2-Isopropylamino-5,8-dihydro-6H-pyrido[3,4-d]pyrimidine-7-carboxylic acid [4-(3,4-difluoro-phenyl)-pyrrolidin-3-yl]-amide, 2-Isopropylamino-5,8-dihydro-6H-pyrido[3,4-d]pyrimidine-7-carboxylic acid [4-(4-trifluoromethyl-phenyl)-pyrrolidin-3-yl]-amide, 2-Isopropylamino-5,8-dihydro-6H-pyrido[3,4-d]pyrimidine-7-carboxylic acid [1-methyl-4-(4-trifluoromethyl-phenyl)-pyrrolidin-3-yl]-amide, 7-Isopropylamino-3,4-dihydro-1H-[2,6]naphthyridine-2-carboxylic acid [4-(4-trifluoromethyl-phenyl)-pyrrolidin-3-yl]-amide, 2-(4-Fluoro-phenylamino)-5,8-dihydro-6H-pyrido[3,4-d]pyrimidine-7-carboxylic acid (1-benzothiazol-2-yl-ethyl)-amide, 2-(1-Methyl-1H-pyrazol-3-ylamino)-5,8-dihydro-6H-pyrido[3,4-d]pyrimidine-7-carboxylic acid [(R)-1-(3,4-dichloro-phenyl)-ethyl]-amide, 2-(4-Fluoro-phenylamino)-5,8-dihydro-6H-pyrido[3,4-d]pyrimidine-7-carboxylic acid [1-(1H-benzoimidazol-2-yl)-ethyl]-amide, 2-Isopropylamino-5,8-dihydro-6H-pyrido[3,4-d]pyrimidine-7-carboxylic acid [(R)-(4-chloro-3-fluoro-phenyl)-oxazol-4-yl-methyl]-amide, 2-Isopropylamino-5,8-dihydro-6H-pyrido[3,4-d]pyrimidine-7-carboxylic acid [(S)-(4-chloro-3-fluoro-phenyl)-oxazol-4-yl-methyl]-amide, 2-((S)-2-Hydroxy-1-methyl-ethylamino)-5,8-dihydro-6H-pyrido[3,4-d]pyrimidine-7-carboxylic acid 3-fluoro-4-methoxy-benzylamide, 2-((S)-2-Hydroxy-1-methyl-ethylamino)-5,8-dihydro-6H-pyrido[3,4-d]pyrimidine-7-carboxylic acid 4-methyl-3-trifluoromethyl-benzylamide, 2-((S)-2-Hydroxy-1-methyl-ethylamino)-5,8-dihydro-6H-pyrido[3,4-d]pyrimidine-7-carboxylic acid [(R)-1-(3,4-dichloro-phenyl)-3-methoxy-propyl]-amide,
2-((S)-2-Hydroxy-1-methyl-ethylamino)-5,8-dihydro-6H-pyrido[3,4-d]pyrimidine-7-carboxylic acid 4-(cyano-dimethyl-methyl)-benzylamide,
2-(4-Methyl-thiazol-2-ylamino)-5,8-dihydro-6H-pyrido[3,4-d]pyrimidine-7-carboxylic acid [(R)-1-(3,4-dichloro-phenyl)-ethyl]-amide,
2-((S)-2-Hydroxy-1-methyl-ethylamino)-5,8-dihydro-6H-pyrido[3,4-d]pyrimidine-7-carboxylic acid 4-chloro-3-methoxy-benzylamide,
2-Isopropylamino-5,8-dihydro-6H-pyrido[3,4-d]pyrimidine-7-carboxylic acid (1H-indol-2-ylmethyl)-amide,
2-(Tetrahydro-pyran-4-ylamino)-5,8-dihydro-6H-pyrido[3,4-d]pyrimidine-7-carboxylic acid [(R)-(3,4-dichloro-phenyl)-oxazol-5-yl-methyl]-amide,
7-(Tetrahydro-pyran-4-ylamino)-3,4-dihydro-1H-[2,6]naphthyridine-2-carboxylic acid [(S)-1-(3,4-dichloro-phenyl)-2-hydroxy-ethyl]-amide,
2-(Tetrahydro-pyran-4-ylamino)-5,8-dihydro-6H-pyrido[3,4-d]pyrimidine-7-carboxylic acid 4-difluoromethoxy-benzylamide,
2-((S)-2-Hydroxy-1-methyl-ethylamino)-5,8-dihydro-6H-pyrido[3,4-d]pyrimidine-7-carboxylic acid (1H-indol-5-ylmethyl)-amide,
2-((S)-2-Hydroxy-1-methyl-ethylamino)-5,8-dihydro-6H-pyrido[3,4-d]pyrimidine-7-carboxylic acid (1H-indol-7-ylmethyl)-amide,
2-((S)-2-Hydroxy-1-methyl-ethylamino)-5,8-dihydro-6H-pyrido[3,4-d]pyrimidine-7-carboxylic acid (1-methyl-1H-indol-6-ylmethyl)-amide,
2-Isopropylamino-5,8-dihydro-6H-pyrido[3,4-d]pyrimidine-7-carboxylic acid (1H-indol-6-ylmethyl)-amide,
2-(1-Methyl-1H-[1,2,4]triazol-3-ylamino)-5,8-dihydro-6H-pyrido[3,4-d]pyrimidine-7-carboxylic acid [(R)-1-(3,4-dichloro-phenyl)-ethyl]-amide,
2-Isopropylamino-5,8-dihydro-6H-pyrido[3,4-d]pyrimidine-7-carboxylic acid [(3S,4R)-1-benzyl-4-(3,4-difluoro-phenyl)-pyrrolidin-3-yl]-amide,
2-(2-Hydroxy-1-methyl-ethylamino)-5,8-dihydro-6H-pyrido[3,4-d]pyrimidine-7-carboxylic acid [1-(5-chloro-pyrimidin-2-yl)-ethyl]-amide,
2-Isopropylamino-5,8-dihydro-6H-pyrido[3,4-d]pyrimidine-7-carboxylic acid [(3,4-dichloro-phenyl)-(2H-pyrazol-3-yl)-methyl]-amide,
2-((S)-2-Hydroxy-1-methyl-ethylamino)-5,8-dihydro-6H-pyrido[3,4-d]pyrimidine-7-carboxylic acid [(1R,2R)-1-(3,4-dichloro-phenyl)-2-methoxy-propyl]-amide,
2-(Tetrahydro-pyran-4-ylamino)-5,8-dihydro-6H-pyrido[3,4-d]pyrimidine-7-carboxylic acid [(S)-1-(4-difluoromethoxy-phenyl)-propyl]-amide,
2-(Tetrahydro-pyran-4-ylamino)-5,8-dihydro-6H-pyrido[3,4-d]pyrimidine-7-carboxylic acid [(3S,4R)-4-(3,4-difluoro-phenyl)-1-methyl-pyrrolidin-3-yl]-amide,
2-Isopropylamino-5,8-dihydro-6H-pyrido[3,4-d]pyrimidine-7-carboxylic acid [(3S,4R)-4-(3,4-difluoro-phenyl)-1-(2-hydroxy-ethyl)-pyrrolidin-3-yl]-amide,
2-Isopropylamino-5,8-dihydro-6H-p[3,4-d]pyrimidine-7-carboxylic acid [1-(5-chloro-pyrimidin-2-yl)-ethyl]-amide,
2-Isopropylamino-5,8-dihydro-6H-pyrido[3,4-d]pyrimidine-7-carboxylic acid [(S)-(3,4-dichloro-phenyl)-(2H-pyrazol-3-yl)-methyl]-amide,
2-(Tetrahydro-pyran-4-ylamino)-5,8-dihydro-6H-pyrido[3,4-d]pyrimidine-7-carboxylic acid [(S)-1-(4-chloro-3-fluoro-phenyl)-2-hydroxy-ethyl]-amide,
7-(Tetrahydro-pyran-4-ylamino)-3,4-dihydro-1H-[2,6]naphthyridine-2-carboxylic acid [(S)-1-(4-chloro-3-fluoro-phenyl)-2-hydroxy-ethyl]-amide,
2-((S)-2-Hydroxy-1-methyl-ethylamino)-5,8-dihydro-6H-pyrido[3,4-d]pyrimidine-7-carboxylic acid [(1S,2R)-1-(3,4-dichloro-phenyl)-2-methoxy-propyl]-amide,
2-Isopropylamino-5,8-dihydro-6H-pyrido[3,4-d]pyrimidine-7-carboxylic acid [(R)-(3,4-dichloro-phenyl)-(2H-pyrazol-3-yl)-methyl]-amide,
2-Isopropylamino-5,8-dihydro-6H-pyrido[3,4-d]pyrimidine-7-carboxylic acid [(3S,4R)-4-(3,4-difluoro-phenyl)-1-(2,2,2-trifluoro-ethyl)-pyrrolidin-3-yl]-amide,
2-Isopropylamino-5,8-dihydro-6H-pyrido[3,4-d]pyrimidine-7-carboxylic acid [(3S,4R)-1-(2,2-difluoro-ethyl)-4-(3,4-difluoro-phenyl)-pyrrolidin-3-yl]-amide,
2-(4-Fluoro-phenylamino)-5,8-dihydro-6H-pyrido[3,4-d]pyrimidine-7-carboxylic acid [(3S,4R)-4-(3-fluoro-4-trifluoromethyl-phenyl)-pyrrolidin-3-yl]-amide,
2-o-Tolylamino-5,8-dihydro-6H-pyrido[3,4-d]pyrimidine-7-carboxylic acid [(3S,4R)-4-(3,4-difluoro-phenyl)-pyrrolidin-3-yl]-amide,
2-((S)-2-Hydroxy-1-methyl-ethylamino)-5,8-dihydro-6H-pyrido[3,4-d]pyrimidine-7-carboxylic acid {(R)-1-[4-(4-fluoro-phenoxy)-phenyl]ethyl}-amide,
2-(Tetrahydro-pyran-4-ylamino)-5,8-dihydro-6H-pyrido[3,4-d]pyrimidine-7-carboxylic acid [(3,4-dichloro-phenyl)-oxazol-5-yl-methyl]-amide,
2-(Tetrahydro-pyran-4-ylamino)-5,8-dihydro-6H-pyrido[3,4-d]pyrimidine-7-carboxylic acid (1H-indol-6-ylmethyl)-amide,
2-(Tetrahydro-pyran-4-ylamino)-5,8-dihydro-6H-pyrido[3,4-d]pyrimidine-7-carboxylic acid [(R)-1-(3-fluoro-4-trifluoromethoxy-phenyl)-propyl]-amide,
2-(Tetrahydro-pyran-4-ylamino)-5,8-dihydro-6H-pyrido[3,4-d]pyrimidine-7-carboxylic acid [(4-chloro-3-fluoro-phenyl)-(2-methyl-2H-pyrazol-3-yl)-methyl]-amide,
2-(Tetrahydro-pyran-4-ylamino)-5,8-dihydro-6H-pyrido[3,4-d]pyrimidine-7-carboxylic acid [(3,4-dichloro-phenyl)-(2H-pyrazol-3-yl)-methyl]-amide,
2-((R)-2-Fluoro-1-methyl-ethylamino)-5,8-dihydro-6H-pyrido[3,4-d]pyrimidine-7-carboxylic acid [(S)-1-(3,4-dichloro-phenyl)-2-hydroxy-ethyl]-amide,
2-((S)-2-Fluoro-1-methyl-ethylamino)-5,8-dihydro-6H-pyrido[3,4-d]pyrimidine-7-carboxylic acid [(S)-1-(3,4-dichloro-phenyl)-2-hydroxy-ethyl]-amide,
2-(Tetrahydro-pyran-4-ylamino)-5,8-dihydro-6H-pyrido[3,4-d]pyrimidine-7-carboxylic acid (5-fluoro-1H-indol-2-ylmethyl)-amide,
2-Isopropylamino-5,8-dihydro-6H-pyrido[3,4-d]pyrimidine-7-carboxylic acid (5-fluoro-1H-indol-2-ylmethyl)-amide,
2-Isopropylamino-5,8-dihydro-6H-pyrido[3,4-d]pyrimidine-7-carboxylic acid [(S)-(3,4-dichloro-phenyl)-(S)-pyrrolidin-2-yl-methyl]-amide,
2-(Tetrahydro-pyran-4-ylamino)-5,8-dihydro-6H-pyrido[3,4-d]pyrimidine-7-carboxylic acid [(S)-(3,4-dichloro-phenyl)-(S)-pyrrolidin-2-yl-methyl]-amide,
2-(4-Fluoro-2-methyl-phenylamino)-5,8-dihydro-6H-pyrido[3,4-d]pyrimidine-7-carboxylic acid [(S)-1-(4-chloro-3-fluorophenyl)-2-hydroxy-ethyl]-amide, 2-(Tetrahydro-pyran-4-ylamino)-5,8-dihydro-6H-pyrido[3,4-d]pyrimidine-7-carboxylic acid [(4-chloro-3-fluoro-phenyl)-isoxazol-5-yl-methyl]-amide,
2-(Tetrahydro-pyran-4-ylamino)-5,8-dihydro-6H-pyrido[3,4-d]pyrimidine-7-carboxylic acid (pyridin-3-ylmethyl)-amide,
2-(Tetrahydro-pyran-4-ylamino)-5,8-dihydro-6H-pyrido[3,4-d]pyrimidine-7-carboxylic acid (pyridin-2-ylmethyl)-amide,
2-(Tetrahydro-pyran-4-ylamino)-5,8-dihydro-6H-pyrido[3,4-d]pyrimidine-7-carboxylic acid (oxazol-5-ylmethyl)-amide,
2-(Tetrahydro-pyran-4-ylamino)-5,8-dihydro-6H-pyrido[3,4-d]pyrimidine-7-carboxylic acid 4-cyano-3-fluoro-benzylamide,
2-(Tetrahydro-pyran-4-ylamino)-5,8-dihydro-6H-pyrido[3,4-d]pyrimidine-7-carboxylic acid (pyridin-4-ylmethyl)-amide,
2-(4-Fluoro-2-methyl-phenylamino)-5,8-dihydro-6H-pyrido[3,4-d]pyrimidine-7-carboxylic acid [(3S,4R)-4-(3-fluoro-phenyl)-pyrrolidin-3-yl]-amide,
2-o-Tolylamino-5,8-dihydro-6H-pyrido[3,4-d]pyrimidine-7-carboxylic acid [(S)-1-(4-chloro-3-fluoro-phenyl)-2-hydroxy-ethyl]-amide,
2-(Tetrahydro-pyran-4-ylamino)-5,8-dihydro-6H-pyrido[3,4-d]pyrimidine-7-carboxylic acid [(4-chloro-3-fluoro-phenyl)-oxazol-5-yl-methyl]-amide,
2-(Tetrahydro-pyran-4-ylamino)-5,8-dihydro-6H-pyrido[3,4-d]pyrimidine-7-carboxylic acid benzylamide,
2-(Tetrahydro-pyran-4-ylamino)-5 8-dihydro-6H-pyrido[3,4-d]pyrimidine-7-carboxylic acid [(R)-(4-chloro-3-fluoro-phenyl)-oxazol-5-yl-methyl]-amide,
2-(2-Chloro-phenylamino)-5,8-dihydro-6H-pyrido[3,4-d]pyrimidine-7-carboxylic acid [(S)-1-(4-chloro-3-fluoro-phenyl)-2-hydroxy-ethyl]-amide,
2-(Tetrahydro-pyran-4-ylamino)-5,8-dihydro-6H-pyrido[3,4-d]pyrimidine-7-carboxylic acid [(3-fluoro-4-trifluoromethoxy-phenyl)-oxazol-5-yl-methyl]-amide,
2-(Tetrahydro-pyran-4-ylamino)-5,8-dihydro-6H-pyrido[3,4-d]pyrimidine-7-carboxylic acid ((S)-1-phenyl-ethyl)-amide,
2-(Tetrahydro-pyran-4-ylamino)-5,8-dihydro-6H-pyrido[3,4-d]pyrimidine-7-carboxylic acid 4-fluoro-3-methoxy-benzylamide,
2-(Tetrahydro-pyran-4-ylamino)-5,8-dihydro-6H-pyrido[3,4-d]pyrimidine-7-carboxylic acid (6-methoxy-pyridin-3-ylmethyl)-amide
2-(Tetrahydro-pyran-4-ylamino)-5,8-dihydro-6H-pyrido[3,4-d]pyrimidine-7-carboxylic acid (5-fluoro-pyridin-3-ylmethyl)-amide
2-(Tetrahydro-pyran-4-ylamino)-5,8-dihydro-6H-pyrido[3,4-d]pyrimidine-7-carboxylic acid (pyrimidin-5-ylmethyl)-amide,
2-(Tetrahydro-pyran-4-ylamino)-5,8-dihydro-6H-pyrido[3,4-d]pyrimidine-7-carboxylic acid (6-trifluoromethyl-pyridin-3-ylmethyl)-amide,
2-(Tetrahydro-pyran-4-ylamino)-5,8-dihydro-6H-pyrido[3,4-d]pyrimidine-7-carboxylic acid [(R)-1-(3,4-dichloro-phenyl)-2-(4H-[1,2,4]triazol-3-yl)-ethyl]-amide,
2-(2-Chloro-4-fluoro-phenylamino)-5,8-dihydro-6H-pyrido[3,4-d]pyrimidine-7-carboxylic acid [(S)-1-(4-chloro-3-fluoro-phenyl)-2-hydroxy-ethyl]-amide,
2-Isopropylamino-5,8-dihydro-6H-pyrido[3,4-d]pyrimidine-7-carboxylic acid 4-cyano-3-fluoro-benzylamide,
2-((S)-2-Hydroxy-1-methyl-ethylamino)-5,8-dihydro-6H-pyrido[3,4-d]pyrimidine-7-carboxylic acid 4-cyano-3-fluoro-benzylamide,
2-(Tetrahydro-pyran-4-ylamino)-5,8-dihydro-6H-pyrido[3,4-d]pyrimidine-7-carboxylic acid (6-methoxy-pyridin-2-ylmethyl)-amide,
2-(Tetrahydro-pyran-4-ylamino)-5,8-dihydro-6H-pyrido[3,4-d]pyrimidine-7-carboxylic acid [(R)-(4-chloro-3-fluoro-phenyl)-(1-methyl-1H-pyrazol-4-yl)-methyl]-amide,
2-((S)-2-Hydroxy-1-methyl-ethylamino)-5,8-dihydro-6H-pyrido[3,4-d]pyrimidine-7-carboxylic acid [(R)-1-(4-difluoromethoxy-phenyl)-propyl]-amide,
2-((S)-2-Hydroxy-1-methyl-ethylamino)-5,8-dihydro-6H-pyrido[3,4-d]pyrimidine-7-carboxylic acid [(R)-1-(3-fluoro-4-trifluoromethoxy-phenyl)-propyl]-amide,
2-(Tetrahydro-pyran-4-ylamino)-5,8-dihydro-6H-pyrido[3,4-d]pyrimidine-7-carboxylic acid [(R)-(4-chloro-3-fluoro-phenyl)-(2-methyl-2H-pyrazol-3-yl)-methyl]-amide,
2-((S)-2-Hydroxy-1-methyl-ethylamino)-5,8-dihydro-6H-pyrido[3,4-d]pyrimidine-7-carboxylic acid ((R)-1-phenyl-ethyl)-amide,
2-Isopropylamino-5,8-dihydro-6H-pyrido[3,4-d]pyrimidine-7-carboxylic acid ((R)-1-phenyl-ethyl)-amide,
2-(Tetrahydro-pyran-4-ylamino)-5,8-dihydro-6H-pyrido[3,4-d]pyrimidine-7-carboxylic acid 3-cyano-4-fluoro-benzylamide,
2-(Tetrahydro-pyran-4-ylamino)-5,8-dihydro-6H-pyrido[3,4-d]pyrimidine-7-carboxylic acid [(R)-1-(6-methyl-pyridin-3-yl)-ethyl]-amide,
2-(Tetrahydro-pyran-4-ylamino)-5,8-dihydro-6H-pyrido[3,4-d]pyrimidine-7-carboxylic acid [(S)-1-(6-methyl-pyridin-3-yl)-ethyl]-amide,
2-(1-Methyl-5-oxo-pyrrolidin-3-ylamino)-5,8-dihydro-6H-pyrido[3,4-d]pyrimidine-7-carboxylic acid [1-(4-chloro-3-fluoro-phenyl)-ethyl]-amide,
2-(1-Methyl-5-oxo-pyrrolidin-3-ylamino)-5,8-dihydro-6H-pyrido[3,4-d]pyrimidine-7-carboxylic acid [1-(4-chloro-3-fluoro-phenyl)-2-hydroxy-ethyl]-amide,
2-(Cyclopropylmethyl-amino)-5,8-dihydro-6H-pyrido[3,4-d]pyrimidine-7-carboxylic acid [(S)-1-(4-chloro-3-fluoro-phenyl)-2-hydroxy-ethyl]-amide,
2-(Tetrahydro-pyran-4-ylamino)-5,8-dihydro-6H-pyrido[3,4-d]pyrimidine-7-carboxylic acid [(R)-1-(1H-indol-6-yl)-ethyl]-amide,
2-(Tetrahydro-pyran-4-ylamino)-5,8-dihydro-6H-pyrido[3,4-d]pyrimidine-7-carboxylic acid [(S)-1-(1H-indol-6-yl)-ethyl]-amide,
2-((S)-2-Hydroxy-1-methyl-ethylamino)-5,8-dihydro-6H-pyrido[3,4-d]pyrimidine-7-carboxylic acid ((R)-1-phenyl-propyl)-amide,
2-((S)-2-Hydroxy-1-methyl-ethylamino)-5,8-dihydro-6H-pyrido[3,4-d]pyrimidine-7-carboxylic acid [(S)-1-(4-fluoro-phenyl)-ethyl]-amide,
2-((S)-2-Hydroxy-1-methyl-ethylamino)-5,8-dihydro-6H-pyrido[3,4-d]pyrimidine-7-carboxylic acid [(R)-1-(4-fluoro-phenyl)-ethyl]-amide,
2-((S)-2-Hydroxy-1-methyl-ethylamino)-5,8-dihydro-6H-pyrido[3,4-d]pyrimidine-7-carboxylic acid 3-cyano-benzylamide,
2-((S)-2-Hydroxy-1-methyl-ethylamino)-5,8-dihydro-6H-pyrido[3,4-d]pyrimidine-7-carboxylic acid cyclohexylmethyl-amide,
2-((S)-2-Hydroxy-1-methyl-ethylamino)-5,8-dihydro-6H-pyrido[3,4-d]pyrimidine-7-carboxylic acid ((R)-1-cyclohexyl-ethyl)-amide, 2-(Tetrahydro-pyran-4-ylamino)-5,8-dihydro-6H-pyrido[3,4-d]pyrimidine-7-carboxylic acid [(R)-(4-chloro-3-fluoro-phenyl)-(1-methyl-1H-pyrazol-3-yl)-methyl]-amide,
2-(Cyclopropylmethyl-amino)-5,8-dihydro-6H-pyrido[3,4-d]pyrimidine-7-carboxylic acid [(R)-1-(4-chloro-3-fluoro-phenyl)-ethyl]-amide,
2-(Tetrahydro-pyran-4-ylamino)-5,8-dihydro-6H-pyrido[3,4-d]pyrimidine-7-carboxylic acid [(R)-1-(4-fluoro-phenyl)-ethyl]-amide,
2-(Tetrahydro-pyran-4-ylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide,
2-(Tetrahydro-pyran-4-ylamino)-5,8-dihydro-6H-pyrido[3,4-d]pyrimidine-7-carboxylic acid [(S)-1-(4-fluoro-phenyl)-propyl]-amide,
2-(5-Chloro-pyrazin-2-ylamino)-5,8-dihydro-6H-pyrido[3,4-d]pyrimidine-7-carboxylic acid [(R)-1-(3,4-dichloro-phenyl)-ethyl]-amide,
2-(2-Hydroxy-1-methyl-ethylamino)-5,8-dihydro-6H-pyrido[3,4-d]pyrimidine-7-carboxylic acid [(4-chloro-3-fluoro-phenyl)-(1-methyl-1H-pyrazol-4-yl)-methyl]-amide,
2-(Tetrahydro-pyran-4-ylamino)-5,8-dihydro-6H-pyrido[3,4-d]pyrimidine-7-carboxylic acid [(S)-(3-fluoro-4-trifluoromethoxy-phenyl)-oxazol-5-yl-methyl]-amide,
7-(Tetrahydro-pyran-4-ylamino)-3,4-dihydro-1H-[2,6]naphthyridine-2-carboxylic acid [(3S,4R)-4-(4-chloro-3-fluoro-phenyl)-pyrrolidin-3-yl]-amide,
2-(Tetrahydro-pyran-4-ylamino)-5,8-dihydro-6H-pyrido[3,4-d]pyrimidine-7-carboxylic acid [(4-chloro-3-fluoro-phenyl)-morpholin-2-yl-methyl]-amide,
(2-Pyridin-2-yl-pyrrolidin-1-yl)-[2-(tetrahydro-pyran-4-ylamino)-5,8-dihydro-6H-pyrido[3,4-d]pyrimidin-7-yl]-methanone,
2-(4-Fluoro-2-methyl-phenylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide,
2-(4-Fluoro-2-trifluoromethyl-phenylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide,
2-(Tetrahydro-pyran-4-ylamino)-5,8-dihydro-6H-pyrido[3,4-d]pyrimidine-7-carboxylic acid [(4-chloro-3-fluoro-phenyl)-(2-methyl-oxazol-5-yl)-methyl]-amide,
2-(Tetrahydro-pyran-4-ylamino)-5,8-dihydro-6H-pyrido[3,4-d]pyrimidine-7-carboxylic acid [(R)-(4-chloro-3-fluoro-phenyl)-(R)-piperidin-2-yl-methyl]-amide,
2-(Tetrahydro-pyran-4-ylamino)-5,8-dihydro-6H-pyrido[3,4-d]pyrimidine-7-carboxylic acid [(R)-1-(4-chloro-3-fluoro-phenyl)-2-(R)-piperidin-2-yl-ethyl]-amide,
2-Isopropylamino-5,8-dihydro-6H-pyrido[3,4-d]pyrimidine-7-carboxylic acid [(R)-(4-chloro-3-fluoro-phenyl)-(R)-piperidin-2-yl-methyl]-amide,
2-Isopropylamino-5,8-dihydro-6H-pyrido[3,4-d]pyrimidine-7-carboxylic acid [(R)-1-(4-chloro-3-fluoro-phenyl)-2-(R)-piperidin-2-yl-ethyl]-amide,
2-(Tetrahydro-pyran-4-ylamino)-5,8-dihydro-6H-pyrido[3,4-d]pyrimidine-7-carboxylic acid [(3-chloro-4-fluoro-phenyl)-piperidin-4-yl-methyl]-amide,
2-(Tetrahydro-pyran-4-ylamino)-5,8-dihydro-6H-pyrido[3,4-d]pyrimidine-7-carboxylic acid [(4-chloro-3-fluoro-phenyl)-morpholin-2-yl-methyl]-amide,
2-(5-Chloro-pyrazin-2-ylamino)-5,8-dihydro-6H-pyrido[3,4-d]pyrimidine-7-carboxylic acid [(S)-1-(3-chloro-4-fluoro-phenyl)-2-hydroxy-ethyl]-amide,
3-{1-[2-(Tetrahydro-pyran-4-ylamino)-5,8-dihydro-6H-pyrido[3,4-d]pyrimidine-7-carbonyl]-pyrrolidin-2-yl}-benzonitrile,
2-((S)-2-Hydroxy-1-methyl-ethylamino)-5,8-dihydro-6H-pyrido[3,4-d]pyrimidine-7-carboxylic acid [(R)-1-(4-chloro-3-fluoro-phenyl)-2-(R)-piperidin-2-yl-ethyl]-amide,
2-((R)-2,2,2-Trifluoro-1-methyl-ethylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide,
2-Ethylamino-5,8-dihydro-6H-pyrido[3,4-d]pyrimidine-7-carboxylic acid [(S)-1-(4-chloro-3-fluoro-phenyl)-2-hydroxy-ethyl]-amide,
2-(5-Chloro-pyrazin-2-ylamino)-5,8-dihydro-6H-pyrido[3,4-d]pyrimidine-7-carboxylic acid [(S)-1-(4-chloro-3-fluoro-phenyl)-2-hydroxy-ethyl]-amide,
2-Ethylamino-5,8-dihydro-6H-pyrido[3,4-d]pyrimidine-7-carboxylic acid [(S)-1-(3-chloro-4-fluoro-phenyl)-2-hydroxy-ethyl]-amide,
2-(Tetrahydro-pyran-4-ylamino)-5,8-dihydro-6H-pyrido[3,4-d]pyrimidine-7-carboxylic acid {(R)-1-[4-(2,2,2-trifluoro-ethoxy)-phenyl]-propyl}-amide,
2-(Tetrahydro-pyran-4-ylamino)-5,8-dihydro-6H-pyrido[3,4-d]pyrimidine-7-carboxylic acid methyl-(1-phenyl-ethyl)-amide,
2-(6-Methyl-pyrimidin-4-ylamino)-5,8-dihydro-6H-pyrido[3,4-d]pyrimidine-7-carboxylic acid [(S)-1-(4-chloro-3-fluoro-phenyl)-2-hydroxy-ethyl]-amide,
2-(6-Methyl-pyrimidin-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide,
2-(Tetrahydro-pyran-4-ylamino)-5,8-dihydro-6H-pyrido[3,4-d]pyrimidine-7-carboxylic acid [(S)-1-(4-difluoromethoxy-phenyl)-2-hydroxy-ethyl]-amide,
2-((S)-2-Hydroxy-1-methyl-ethylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide,
2-((S)-2-Hydroxy-1-methyl-ethylamino)-5,8-dihydro-6H-pyrido[3,4-d]pyrimidine-7-carboxylic acid [(3S,4R)-4-(4-chloro-3-fluoro-phenyl)-1-methyl-pyrrolidin-3-yl]-amide,
2-((S)-2,2,2-Trifluoro-1-methyl-ethylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide,
2-(2-Chloro-4-fluoro-phenylamino)-5,8-dihydro-6H-pyrido[3,4-d]pyrimidine-7-carboxylic acid [(3S,4R)-4-(4-chloro-3-fluoro-phenyl)-pyrrolidin-3-yl]-amide,
2(2-Chloro-4-fluoro-phenylamino)-5,8-dihydro-6H-pyrido[3,4-d]pyrimidine-7-carboxylic acid [(3S,4R)-4-(4-chloro-3-fluoro-phenyl)-1-methyl-pyrrolidin-3-yl]-amide,
2-(2,2,2-Trifluoro-1-hydroxymethyl-ethylamino)-5,8-dihydro-6H-pyrido[3,4-d]pyrimidine-7-carboxylic acid [1-(4-chloro-3-fluoro-phenyl)-2-hydroxy-ethyl]-amide,
2-(2-Fluoro-1-fluoromethyl-ethylamino)-5,8-dihydro-6H-pyrido[3,4-d]pyrimidine-7-carboxylic acid [(S)-1-(4-chloro-3-fluoro-phenyl)-2-hydroxy-ethyl]-amide,
2-(Tetrahydro-pyran-4-ylamino)-5,8-dihydro-6H-pyrido[3,4-d]pyrimidine-7-carboxylic acid [(S)-(4-chloro-3-fluoro-phenyl)-(2-methyl-oxazol-5-yl)-methyl]-amide,
2-(Tetrahydro-pyran-4-ylamino)-5,8-dihydro-6H-pyrido[3,4-d]pyrimidine-7-carboxylic acid [(R)-(4-chloro-3-fluoro-phenyl)-(2-methyl-oxazol-5-yl)-methyl]-amide, 2-(Tetrahydro-pyran-4-ylamino)-5,8-dihydro-6H-pyrido[3,4-d]pyrimidine-7-carboxylic acid ((R)-1-cyclohexyl-ethyl)-amide, 2-(Tetrahydro-pyran-4-ylamino)-5,8-dihydro-6H-pyrido[3,4-d]pyrimidine-7-carboxylic acid 4-fluoro-benzylamide, 2-(Tetrahydro-pyran-4-ylamino)-5,8-dihydro-6H-pyrido[3,4-d]pyrimidine-7-carboxylic acid 4-chloro-benzylamide, 2-(Tetrahydro-pyran-4-ylamino)-5,8-dihydro-6H-pyrido[3,4-d]pyrimidine-7-carboxylic acid 4-trifluoromethyl-benzylamide, 2-(Tetrahydro-furan-3-ylamino)-5,8-dihydro-6H-pyrido[3,4-d]pyrimidine-7-carboxylic acid [1-(4-chloro-3-fluoro-phenyl)-2-hydroxy-ethyl]-amide, 2-(Tetrahydro-furan-3-ylamino)-5,8-dihydro-6H-pyrido[3,4-d]pyrimidine-7-carboxylic acid [1-(3-chloro-4-fluoro-phenyl)-2-hydroxy-ethyl]-amide, 2-((S)-2-Hydroxy-1-methyl-ethylamino)-5,8-dihydro-6H-pyrido[3,4-d]pyrimidine-7-carboxylic acid [(R)-1-(4-fluoro-phenyl)-propyl]-amide, 2-((S)-2,2,2-Trifluoro-1-methyl-ethylamino)-5,8-dihydro-6H-pyrido[3,4-d]pyrimidine-7-carboxylic acid [(S)-1-(4-chloro-3-fluoro-phenyl)-2-hydroxy-ethyl]-amide, 2-(2,2,2-Trifluoro-ethylamino)-5,8-dihydro-6H-pyrido[3,4-d]pyrimidine-7-carboxylic acid [(S)-1-(4-chloro-3-fluoro-phenyl)-2-hydroxy-ethyl]-amide, 2-(2,2,2-Trifluoro-ethylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-(2,2,2-Trifluoro-ethylamino)-5,8-dihydro-6H-pyrido[3,4-d]pyrimidine-7-carboxylic acid [(R)-1-(3,4-dichloro-phenyl)-ethyl]-amide, 2-((S)-2,2,2-Trifluoro-1-methyl-ethylamino)-5,8-dihydro-6H-pyrido[3,4-d]pyrimidine-7-carboxylic acid [(R)-1-(4-difluoromethoxy-phenyl)-propyl]-amide, 2-(4-Cyano-2-fluoro-phenylamino)-5,8-dihydro-6H-pyrido[3,4-d]pyrimidine-7-carboxylic acid [(S)-1-(4-chloro-3-fluoro-phenyl)-2-hydroxy-ethyl]-amide, 2-(3,3,3-Trifluoro-propylamino)-5,8-dihydro-6H-pyrido[3,4-d]pyrimidine-7-carboxylic acid [(R)-1-(4-difluoromethoxy-phenyl)-propyl]-amide, 2-(Tetrahydro-pyran-3-ylamino)-5,8-dihydro-6H-pyrido[3,4-d]pyrimidine-7-carboxylic acid [1-(4-chloro-3-fluoro-phenyl)-2-hydroxy-ethyl]-amide, 2-(Tetrahydro-furan-3-ylamino)-5,8-dihydro-6H-pyrido[3,4-d]pyrimidine-7-carboxylic acid [1-(4-(3-fluoro-4-trifluoromethyl-phenyl)-1-methyl-pyrrolidin-3-yl]-amide, 2-(Tetrahydro-pyran-3-ylamino)-5,8-dihydro-6H-pyrido[3,4-d]pyrimidine-7-carboxylic acid [1-(3-chloro-4-fluoro-phenyl)-2-hydroxy-ethyl]-amide, 2-((S)-2,2,2-Trifluoro-1-methyl-ethylamino)-5,8-dihydro-6H-pyrido[3,4-d]pyrimidine-7-carboxylic acid (2-phenoxy-ethyl)-amide, 2-(Tetrahydro-pyran-4-ylamino)-5,8-dihydro-6H-pyrido[3,4-d]pyrimidine-7-carboxylic acid [(4-chloro-3-fluoro-phenyl)-(3-methyl-[1,2,4]oxadiazol-5-yl)-methyl]-amide, 2-(Tetrahydro-pyran-4-ylamino)-5,8-dihydro-6H-pyrido[3,4-d]pyrimidine-7-carboxylic acid [(4-chloro-3-fluoro-phenyl)-(5-methyl-[1,3,4]oxadiazol-2-yl)-methyl]-amide, 2-(4,4-Difluoro-cyclohexylamino)-5,8-dihydro-6H-pyrido[3,4-d]pyrimidine-7-carboxylic acid [(S)-1-(4-chloro-3-fluoro-phenyl)-2-hydroxy-ethyl]-amide, 2-(4,4-Difluoro-cyclohexylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-(Tetrahydro-pyran-4-ylamino)-5,8-dihydro-6H-pyrido[3,4-d]pyrimidine-7-carboxylic acid [(3S,4R)-1-cyanomethyl-4-(3,4-difluoro-phenyl)-pyrrolidin-3-yl]-amide 2-((S)-2-Hydroxy-1-methyl-ethylamino)-5,8-dihydro-6H-pyrido[3,4-d]pyrimidine-7-carboxylic acid [(R)-1-(3,4-difluoro-phenyl)-propyl]-amide, 2-(2-Methyl-pyrimidin-4-ylamino)-5,8-dihydro-6H-pyrido[3,4-d]pyrimidine-7-carboxylic acid [(S)-1-(4-chloro-3-fluoro-phenyl)-2-hydroxy-ethyl]-amide, 2-(2-Methyl-pyrimidin-4-ylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-(2-Chloro-4-fluoro-phenylamino)-5,8-dihydro-6H-pyrido[3,4-d]pyrimidine-7-carboxylic acid [(S)-(4-chloro-3-fluoro-phenyl)-(S)-pyrrolidin-2-yl-methyl]-amide, 2-(Tetrahydro-pyran-4-ylamino)-5,8-dihydro-6H-pyrido[3,4-d]pyrimidine-7-carboxylic acid [(R)-1-(3-chloro-4-cyano-phenyl)-ethyl]-amide, 2-(Tetrahydro-pyran-4-ylamino)-5,8-dihydro-6H-pyrido[3,4-d]pyrimidine-7-carboxylic acid [(R)-1-(3-chloro-4-cyano-phenyl)-propyl]-amide, 2-(Tetrahydro-pyran-4-ylamino)-5,8-dihydro-6H-pyrido[3,4-d]pyrimidine-7-carboxylic acid [(R)-1-(4-cyano-3-fluoro-phenyl)-ethyl]-amide, 2-(Tetrahydro-pyran-4-ylamino)-5,8-dihydro-6H-pyrido[3,4-d]pyrimidine-7-carboxylic acid [(R)-1-(4-cyano-3-fluoro-phenyl)-propyl]-amide, 2-(Tetrahydro-pyran-4-ylamino)-5,8-dihydro-6H-pyrido[3,4-d]pyrimidine-7-carboxylic acid [(R)-1-(4-cyano-2-fluoro-phenyl)-propyl]-amide, 2-(Tetrahydro-pyran-4-ylamino)-5,8-dihydro-6H-pyrido[3,4-d]pyrimidine-7-carboxylic acid [(R)-1-(4-cyano-3-methyl-phenyl)-ethyl]-amide, 2-(Tetrahydro-pyran-4-ylamino)-5,8-dihydro-6H-pyrido[3,4-d]pyrimidine-7-carboxylic acid [(R)-1-(4-cyano-3-methyl-phenyl)-propyl]-amide, 2-((S)-2-Hydroxy-1-methyl-ethylamino)-5,8-dihydro-6H-pyrido[3,4-d]pyrimidine-7-carboxylic acid [(R)-1-(3-chloro-4-cyano-phenyl)-propyl]-amide, 2-((S)-2-Hydroxy-1-methyl-ethylamino)-5,8-dihydro-6H-pyrido[3,4-d]pyrimidine-7-carboxylic acid [(R)-1-(4-cyano-3-fluoro-phenyl)-propyl]-amide, 2-(3,3-Difluoro-cyclobutylamino)-5,8-dihydro-6H-pyrido[3,4-d]pyrimidine-7-carboxylic acid [(R)-1-(3,4-dichloro-phenyl)-ethyl]-amide, 2-Isopropylamino-5,8-dihydro-6H-pyrido[3,4-d]pyrimidine-7-carboxylic acid [4-(3,4-dichloro-phenyl)-1-methyl-piperidin-4-yl]-amide, 2-((S)-2-Hydroxy-1-methyl-ethylamino)-5,8-dihydro-6H-pyrido[3,4-d]pyrimidine-7-carboxylic acid [(R)-1-(3-chloro-4-methoxy-phenyl)-propyl]-amide, 2-((S)-2-Hydroxy-1-methyl-ethylamino)-5,8-dihydro-6H-pyrido[3,4-d]pyrimidine-7-carboxylic acid [(R)-1-(3-fluoro-4-methoxy-phenyl)-propyl]-amide, 2-(Tetrahydro-pyran-4-ylamino)-5,8-dihydro-6H-pyrido[3,4-d]pyrimidine-7-carboxylic acid [(R)-(4-chloro-3-fluoro-phenyl)-[1,3,4]oxadiazol-2-yl-methyl]-amide, 2-(Tetrahydro-pyran-4-ylamino)-5,8-dihydro-6H-pyrido[3,4-d]pyrimidine-7-carboxylic acid [(S)-(4-chloro-3-fluoro-phenyl)-[1,3,4]oxadiazol-2-yl-methyl]-amide, 2-(2-Methyl-tetrahydro-pyran-4-ylamino)-5,8-dihydro-6H-pyrido[3,4-d]pyrimidine-7-carboxylic acid [1-(3-chloro-4-fluoro-phenyl)-2-hydroxy-ethyl]-amide, 2-(2-Methyl-tetrahydro-pyran-4-ylamino)-5,8-dihydro-6H-pyrido[3,4-d]pyrimidine-7-carboxylic acid [1-(3,4-dichloro-phenyl)-ethyl]-amide, 2-((S)-2,2,2-Trifluoro-1-methyl-ethylamino)-5,8-dihydro-6H-pyrido[3,4-d]pyrimidine-7-carboxylic acid [(3S,4R)-4-(3,4-difluoro-phenyl)-pyrrolidin-3-yl]-amide, 2-((S)-2,2,2-Trifluoro-1-methyl-ethylamino)-5,8-dihydro-6H-pyrido[3,4-d]pyrimidine-7-carboxylic acid [(3S,4R)-4-(3,4-difluoro-phenyl)-1-methyl-pyrrolidin-3-yl]-amide, 2-(3,3-Difluoro-cyclobutylamino)-5,8-dihydro-6H-pyrido[3,4-d]pyrimidine-7-carboxylic acid [(S)-1-(4-chloro-3-fluoro-phenyl)-2-hydroxy-ethyl]-amide, 2-(2-Methyl-tetrahydro-pyran-4-ylamino)-5,8-dihydro-6H-pyrido[3,4-d]pyrimidine-7-carboxylic acid [1-(4-chloro-3-fluoro-phenyl)-2-hydroxy-ethyl]-amide, 2-(3,3-Difluoro-cyclobutylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-(Tetrahydro-pyran-4-ylamino)-5,8-dihydro-6H-pyrido[3,4-d]pyrimidine-7-carboxylic acid [3-(3-chloro-4-cyano-phenyl)-1H-pyrazol-4-yl]-amide, 2-(Tetrahydro-pyran-4-ylamino)-5,8-dihydro-6H-pyrido[3,4-d]pyrimidine-7-carboxylic acid [4-(4-fluoro-phenoxy)-tetrahydro-furan-3-yl]-amide, 2-(3-Hydroxy-cyclobutylamino)-5,8-dihydro-6H-pyrido[3,4-d]pyrimidine-7-carboxylic acid [1-(3-chloro-4-fluoro-phenyl)-2-hydroxy-ethyl]-amide, 2-((1S,3S)-3-Hydroxy-cyclobutylamino)-5,8-dihydro-6H-pyrido[3,4-d]pyrimidine-7-carboxylic acid [(R)-1-(3,4-dichloro-phenyl)-ethyl]-amide, 2-((1R,3R)-3-Hydroxy-cyclobutylamino)-5,8-dihydro-6H-pyrido[3,4-d]pyrimidine-7-carboxylic acid [(R)-1-(3,4-dichloro-phenyl)-ethyl]-amide, 2-(4-Methyl-2-phenyl-piperazin-1-yl)-1-[2-(tetrahydro-pyran-4-ylamino)-5,8-dihydro-6H-pyrido[3,4-d]pyrimidin-7-yl]-ethanone, 2-(4-Methyl-2-phenyl-piperazin-1-yl)-1-[2-(tetrahydro-pyran-4-ylamino)-5,8-dihydro-6H-pyrido[3,4-d]pyrimidin-7-yl]-ethanone, 2-[2-(4-Fluoro-phenyl)-piperidin-1-yl]-1-[2-(tetrahydro-pyran-4-ylamino)-5,8-dihydro-6H-pyrido[3,4-d]pyrimidin-7-yl]-ethanone, 2-[2-(4-Chloro-phenyl)-piperazin-1-yl]-1-[2-(tetrahydro-pyran-4-ylamino)-5,8-dihydro-6H-pyrido[3,4-d]pyrimidin-7-yl]-ethanone, 2-[2-(4-Fluoro-phenyl)-piperidin-1-yl]-1-[2-(tetrahydro-pyran-4-ylamino)-5,8-dihydro-6H-pyrido[3,4-d]pyrimidin-7-yl]-ethanone, (R)-2-(Tetrahydro-pyran-4-ylamino)-6,7-dihydro-5H-pyrano[2,3-d]pyrimidine-7-carboxylic acid [(R)-1-(4-chloro-3-fluoro-phenyl)-propyl]-amide, 2-(2,2-Dimethyl-tetrahydro-pyran-4-ylamino)-5,8-dihydro-6H-pyrido[3,4-d]pyrimidine-7-carboxylic acid [1-(4-chloro-3-fluoro-phenyl)-2-hydroxy-ethyl]-amide, 2-(3-Hydroxy-cyclobutylamino)-5,8-dihydro-6H-pyrido[3,4-d]pyrimidine-7-carboxylic acid [1-(4-chloro-3-fluoro-phenyl)-2-hydroxy-ethyl]-amide, (R)-2-(Tetrahydro-pyran-4-ylamino)-6,7-dihydro-5H-pyrano[2,3-d]pyrimidine-7-carboxylic acid [(R)-1-(3-fluoro-4-trifluoromethoxy-phenyl)-propyl]-amide, (R)-2-(Tetrahydro-pyran-4-ylamino)-6,7-dihydro-5H-pyrano[2,3-d]pyrimidine-7-carboxylic acid [(S)-1-(4-difluoromethoxy-phenyl)-2-hydroxy-ethyl]-amide, 2-(2-Fluoro-1-methyl-ethylamino)-5,8-dihydro-6H-pyrido[3,4-d]pyrimidine-7-carboxylic acid [4-(4-chloro-3-fluoro-phenyl)-1-methyl-pyrrolidin-3-yl]-amide, 2-(2,2-Difluoro-1-methyl-ethylamino)-5,8-dihydro-6H-pyrido[3,4-d]pyrimidine-7-carboxylic acid [4-(4-chloro-3-fluoro-phenyl)-1-methyl-pyrrolidin-3-yl]-amide, 2-(2,2-Dimethyl-tetrahydro-pyran-4-ylamino)-5,8-dihydro-6H-pyrido[3,4-d]pyrimidine-7-carboxylic acid [1-(3-chloro-4-fluoro-phenyl)-2-hydroxy-ethyl]-amide, (R)-2-(Tetrahydro-pyran-4-ylamino)-6,7-dihydro-5H-pyrano[2,3-d]pyrimidine-7-carboxylic acid [(S)-(4-chloro-3-fluoro-phenyl)-(R)-pyrrolidin-2-yl-methyl]-amide, 2-((S)-3-Phenyl-morpholin-4-yl)-1-[2-(tetrahydro-pyran-4-ylamino)-5,8-dihydro-6H-pyrido[3,4-d]pyrimidin-7-yl]-ethanone, 2-((R)-3-Phenyl-morpholin-4-yl)-1-[2-(tetrahydro-pyran-4-ylamino)-5,8-dihydro-6H-pyrido[3,4-d]pyrimidin-7-yl]-ethanone, 1-[2-(Tetrahydro-pyran-4-ylamino)-5,8-dihydro-6H-pyrido[3,4-d]pyrimidin-7-yl]-2-[2-(4-trifluoromethyl-phenyl)-pyrrolidin-1-yl]-ethanone, 1-[2-(Tetrahydro-pyran-4-ylamino)-5,8-dihydro-6H-pyrido[3,4-d]pyrimidin-7-yl]-2-[2-(4-trifluoromethyl-phenyl)-pyrrolidin-1-yl]-ethanone, 2-(2,2-Difluoro-1-methyl-ethylamino)-5,8-dihydro-6H-pyrido[3,4-d]pyrimidine-7-carboxylic acid [4-(4-difluoromethoxy-phenyl)-1-methyl-pyrrolidin-3-yl]-amide, 2-((S)-2,2,2-Trifluoro-1-methyl-ethylamino)-5,8-dihydro-6H-pyrido[3,4-d]pyrimidine-7-carboxylic acid [(3S,4R)-4-(4-difluoromethoxy-phenyl)-1-methyl-pyrrolidin-3-yl]-amide, 2-(2-Methyl-tetrahydro-pyran-4-ylamino)-5,8-dihydro-6H-pyrido[3,4-d]pyrimidine-7-carboxylic acid [1-(4-chloro-3-fluoro-phenyl)-2-hydroxy-ethyl]-amide, 2-(2-Methyl-tetrahydro-pyran-4-ylamino)-5,8-dihydro-6H-pyrido[3,4-d]pyrimidine-7-carboxylic acid [1-(4-chloro-3-fluoro-phenyl)-2-hydroxy-ethyl]-amide, 2-(Tetrahydro-pyran-4-ylamino)-5,8-dihydro-6H-pyrido[3,4-d]pyrimidine-7-carboxylic acid [2-(3,4-difluoro-phenyl)-1-methyl-pyrrolidin-3-yl]-amide, 2-(Tetrahydro-pyran-4-ylamino)-5,8-dihydro-6H-pyrido[3,4-d]pyrimidine-7-carboxylic acid [4-(3-chloro-4-cyano-phenoxy)-1-methyl-pyrrolidin-3-yl]-amide, 2-((S)-1-Hydroxymethyl-3-methoxy-propylamino)-5,8-dihydro-6H-pyrido[3,4-d]pyrimidine-7-carboxylic acid [(S)-1-(4-chloro-3-fluoro-phenyl)-2-hydroxy-ethyl]-amide, 2-((S)-1-Hydroxymethyl-3-methoxy-propylamino)-5,8-dihydro-6H-pyrido[3,4-d]pyrimidine-7-carboxylic acid [(S)-1-(3-chloro-4-fluoro-phenyl)-2-hydroxy-ethyl]-amide, 2-((S)-1-Hydroxymethyl-3-methoxy-propylamino)-5,8-dihydro-6H-pyrido[3,4-d]pyrimidine-7-carboxylic acid [(R)-1-(3,4-dichloro-phenyl)-ethyl]-amide, (R)-2-((R)-1-Cyclopropyl-ethylamino)-6,7-dihydro-5H-pyrano[2,3-d]pyrimidine-7-carboxylic acid [(S)-1-(4-difluoromethoxy-phenyl)-2-hydroxy-ethyl]-amide, (R)-2-((R)-1-Cyclopropyl-ethylamino)-6,7-dihydro-5H-pyrano[2,3-d]pyrimidine-7-carboxylic acid [(R)-3-cyano-1-(4-difluoromethoxy-phenyl)-propyl]-amide, (S)-2-((R)-1-Cyclopropyl-ethylamino)-6,7-dihydro-5H-pyrano[2,3-d]pyrimidine-7-carboxylic acid [(S)-1-(4-difluoromethoxy-phenyl)-2-hydroxy-ethyl]-amide,
2-(Tetrahydro-pyran-4-ylamino)-5,8-dihydro-6H-pyrido[3,4-d]pyrimidine-7-carboxylic acid [4-(4-chloro-3-fluoro-phenoxy)-pyrrolidin-3-yl]-amide,
2-(Tetrahydro-pyran-4-ylamino)-5,8-dihydro-6H-pyrido[3,4-d]pyrimidine-7-carboxylic acid [4-(3-chloro-4-cyano-phenoxy)-pyrrolidin-3-yl]-amide,
2-(2-Hydroxymethyl-tetrahydro-pyran-4-ylamino)-5,8-dihydro-6H-pyrido[3,4-d]pyrimidine-7-carboxylic acid [1-(4-chloro-3-fluoro-phenyl)-2-hydroxy-ethyl]-amide,
2-(2-Hydroxymethyl-tetrahydro-pyran-4-ylamino)-5,8-dihydro-6H-pyrido[3,4-d]pyrimidine-7-carboxylic acid [1-(3-chloro-4-fluoro-phenyl)-2-hydroxy-ethyl]-amide,
2-(2-Hydroxymethyl-tetrahydro-pyran-4-ylamino)-5,8-dihydro-6H-pyrido[3,4-d]pyrimidine-7-carboxylic acid [1-(3,4-dichloro-phenyl)-ethyl]-amide,
2-(Tetrahydro-pyran-4-ylamino)-5,8-dihydro-6H-pyrido[3,4-d]pyrimidine-7-carboxylic acid [2-(3,4-difluoro-phenyl)-1-(2-methoxy-ethyl)-pyrrolidin-3-yl]-amide,
2-((S)-2,2,2-Trifluoro-1-methyl-ethylamino)-5,8-dihydro-6H-pyrido[3,4-d]pyrimidine-7-carboxylic acid [(3S,4R)-4-(4-fluoro-3-methoxy-phenyl)-1-methyl-pyrrolidin-3-yl]-amide,
2-(Tetrahydro-pyran-4-ylamino)-5,8-dihydro-6H-pyrido[3,4-d]pyrimidine-7-carboxylic acid [(3S,4R)-4-(4-fluoro-3-methoxy-phenyl)-1-methyl-pyrrolidin-3-yl]-amide,
(R)-2-(Tetrahydro-pyran-4-ylamino)-6,7-dihydro-5H-pyrano[2,3-d]pyrimidine-7-carboxylic acid [(R)-3-cyano-1-(4-difluoromethoxy-phenyl)-propyl]-amide,
2-(Tetrahydro-pyran-4-ylamino)-5,8-dihydro-6H-pyrido[3,4-d]pyrimidine-7-carboxylic acid (1-methyl-4-phenyl-pyrrolidin-3-yl)-amide,
2-(Tetrahydro-pyran-4-ylamino)-5,8-dihydro-6H-pyrido[3,4-d]pyrimidine-7-carboxylic acid [1-(3-cyano-4-fluoro-phenyl)-propyl]-amide,
2-(2-Hydroxy-1-methyl-ethylamino)-5,8-dihydro-6H-pyrido[3,4-d]pyrimidine-7-carboxylic acid [1-(3-chloro-4-ethoxy-phenyl)-propyl]-amide,
2-(2-Hydroxy-1-methyl-ethylamino)-5,8-dihydro-6H-pyrido[3,4-d]pyrimidine-7-carboxylic acid [1-(3-fluoro-4-methoxy-phenyl)-butyl]-amide,
2-(2-Hydroxymethyl-tetrahydro-pyran-4-ylamino)-5,8-dihydro-6H-pyrido[3,4-d]pyrimidine-7-carboxylic acid [1-(3-fluoro-4-methoxy-phenyl)-propyl]-amide,
2-(Tetrahydro-pyran-4-ylamino)-5,8-dihydro-6H-pyrido[3,4-d]pyrimidine-7-carboxylic acid [1-(3-cyano-4-methoxy-phenyl)-propyl]-amide,
(R)-2-((S)-2,2,2-Trifluoro-1-methyl-ethylamino)-6,7-dihydro-5H-pyrano[2,3-d]pyrimidine-7-carboxylic acid [(R)-3-cyano-1-(4-difluoromethoxy-phenyl)-propyl]-amide,
(R)-2-((S)-2,2,2-Trifluoro-1-methyl-ethylamino)-6,7-dihydro-5H-pyrano[2,3-d]pyrimidine-7-carboxylic acid [(S)-1-(4-difluoromethoxy-phenyl)-2-hydroxy-ethyl]-amide,
(R)-2-(Tetrahydro-pyran-4-ylamino)-6,7-dihydro-5H-pyrano[2,3-d]pyrimidine-7-carboxylic acid [(S)-(3-fluoro-4-trifluoromethyl-phenyl)-(S)-pyrrolidin-2-yl-methyl]-amide,
(R)-2-(Tetrahydro-pyran-4-ylamino)-6,7-dihydro-5H-pyrano[2,3-d]pyrimidine-7-carboxylic acid [(3S,4R)-4-(3,4-difluoro-phenyl)-pyrrolidin-3-yl]-amide,
2-(Tetrahydro-pyran-4-ylamino)-5,8-dihydro-6H-pyrido[3,4-d]pyrimidine-7-carboxylic acid [4-(4-chloro-3-fluoro-phenyl)-1-methyl-pyrrolidin-3-yl]-amide, (R)-2-((S)-2-Hydroxy-1-methyl-ethylamino)-6,7-dihydro-5H-pyrano[2,3-d]pyrimidine-7-carboxylic acid [(R)-1-(3-fluoro-4-methoxy-phenyl)-propyl]-amide,
2-(Tetrahydro-pyran-4-ylamino)-5,8-dihydro-6H-pyrido[3,4-d]pyrimidine-7-carboxylic acid [(S)-(3-chloro-4-fluoro-phenyl)-(1-methyl-1H-pyrazol-4-yl)-methyl]-amide,
2-(Tetrahydro-pyran-4-ylamino)-5,8-dihydro-6H-pyrido[3,4-d]pyrimidine-7-carboxylic acid [4-(3,4-difluoro-phenyl)-1-methyl-pyrrolidin-3-yl]-amide,
2-(Tetrahydro-pyran-4-ylamino)-5,8-dihydro-6H-pyrido[3,4-d]pyrimidine-7-carboxylic acid [4-(3-chloro-4-fluoro-phenyl)-1-methyl-pyrrolidin-3-yl]-amide,
2-(Tetrahydro-pyran-4-ylamino)-5,8-dihydro-6H-pyrido[3,4-d]pyrimidine-7-carboxylic acid [(S)-(3-chloro-4-methoxy-phenyl)-(1-methyl-1H-pyrazol-4-yl)-methyl]-amide,
(R)-2-(Tetrahydro-pyran-4-ylamino)-6,7-dihydro-5H-pyrano[2,3-d]pyrimidine-7-carboxylic acid [(S)-(3-fluoro-4-methoxy-phenyl)-((R)-1-methyl-pyrrolidin-2-yl)-methyl]-amide,
2-(Tetrahydro-pyran-4-ylamino)-5,8-dihydro-6H-pyrido[3,4-d]pyrimidine-7-carboxylic acid [(R)-(4-cyano-3-fluoro-phenyl)-(1-methyl-1H-pyrazol-4-yl)-methyl]-amide,
2-(Tetrahydro-pyran-4-ylamino)-5,8-dihydro-6H-pyrido[3,4-d]pyrimidine-7-carboxylic acid [(3-cyano-4-methoxy-phenyl)-(1-methyl-1H-pyrazol-4-yl)-methyl]-amide,
2-(Tetrahydro-pyran-4-ylamino)-5,8-dihydro-6H-pyrido[3,4-d]pyrimidine-7-carboxylic acid [(3-cyano-4-methoxy-phenyl)-(1-methyl-1H-pyrazol-4-yl)-methyl]-amide and
2-(Tetrahydro-pyran-4-ylamino)-5,8-dihydro-6H-pyrido[3,4-d]pyrimidine-7-carboxylic acid [(R)-(3-chloro-4-cyano-phenyl)-(1-methyl-1H-pyrazol-4-yl)-methyl]-amide
and pharmaceutically acceptable salts thereof.

20. A composition comprising a compound according to claim 1 or a tautomer, stereoisomer or pharmaceutically acceptable salt thereof and at least one pharmaceutically acceptable carrier, excipient or diluent.

* * * * *